(12) United States Patent
Berdini et al.

(10) Patent No.: US 10,045,982 B2
(45) Date of Patent: *Aug. 14, 2018

(54) SUBSTITUTED PYRIDO[2,3-B]PYRAZINES AS FGFR KINASE INHIBITORS

(71) Applicant: ASTEX THERAPEUTICS LIMITED, Cambridge (GB)

(72) Inventors: Valerio Berdini, Cambridge (GB); Gordon Saxty, Zagreb (HR); Patrick Rene Angibaud, Fontaine-Bellenger (FR); Olivier Alexis Georges Querolle, Saint-Vigor (FR); Virginie Sophie Poncelet, Le Manoir (FR); Bruno Roux, Montmain (FR); Lieven Meerpoel, Beerse (BE)

(73) Assignee: ASTEX THERAPEUTICS LTD, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/019,563

(22) Filed: Feb. 9, 2016

(65) Prior Publication Data

US 2016/0235744 A1  Aug. 18, 2016

Related U.S. Application Data

(63) Continuation of application No. 14/354,832, filed as application No. PCT/GB2012/052672 on Oct. 26, 2012, now Pat. No. 9,309,242.

(60) Provisional application No. 61/552,888, filed on Oct. 28, 2011.

(30) Foreign Application Priority Data

Oct. 28, 2011 (GB) .................................. 1118656.6

(51) Int. Cl.
| C07D 471/04 | (2006.01) |
| A61K 31/4985 | (2006.01) |
| A61K 31/506 | (2006.01) |
| A61K 31/5377 | (2006.01) |

(52) U.S. Cl.
CPC ........ A61K 31/4985 (2013.01); A61K 31/506 (2013.01); A61K 31/5377 (2013.01); C07D 471/04 (2013.01)

(58) Field of Classification Search
CPC .................................................. C07D 471/04
USPC ............................ 544/350; 548/335.1, 364.7
See application file for complete search history.

(56) References Cited

U.S. PATENT DOCUMENTS

| 2,940,972 A | 6/1960 | Roch |
| 4,666,828 A | 5/1987 | Gusella |
| 4,683,202 A | 7/1987 | Mullis |
| 4,801,531 A | 1/1989 | Frossard |
| 5,192,659 A | 3/1993 | Simons |
| 5,272,057 A | 12/1993 | Smulson et al. |
| 5,700,823 A | 12/1997 | Hirth et al. |
| 5,882,864 A | 3/1999 | An et al. |
| 6,218,529 B1 | 4/2001 | An et al. |
| 6,271,231 B1 | 8/2001 | Bergstrand et al. |
| 6,331,555 B1 | 12/2001 | Hirth et al. |
| 7,432,279 B2 | 10/2008 | Green et al. |
| 8,895,601 B2 | 11/2014 | Saxty et al. |
| 9,145,367 B2 | 9/2015 | Tazi et al. |
| 9,221,804 B2 | 12/2015 | Leonard et al. |
| 9,290,478 B2 | 3/2016 | Saxty et al. |
| 9,303,029 B2 | 4/2016 | Woodhead et al. |
| 9,303,030 B2 | 4/2016 | Angibaud et al. |
| 9,309,241 B2 | 4/2016 | Angibaud et al. |
| 9,309,242 B2 | 4/2016 | Berdini et al. |

(Continued)

FOREIGN PATENT DOCUMENTS

| CA | 2524525 | 12/2004 |
| CA | 2524948 | 12/2004 |

(Continued)

OTHER PUBLICATIONS

International Search Report for PCT/GB2012/052672 dated Jan. 7, 2013.
GB Search Report for GB1118656.6 dated Feb. 27, 2012.
Yan, Lin et al. "An efficient synthesis of quinoxaline derivatives from 4-chloro-4-deoxy-α-D-galactose and their cytotoxic activities", Bioorganic & Medicinal Chemistry Letters, vol. 17, No. 3, 2006, pp. 609-612.
Thompson, Andrew M. et al. "Synthesis and Structure—Activity Relationships of 7-Substituted 3-(2,6-Dichlorophenyl)-1,6-napthyridin-2(1H)-ones as Selective Inhibitors of pp60$^{c\text{-}src}$", Journal of Medicinal Chemistry, vol. 43, No. 16, 2000, pp. 3134-3147.
Berge, Stephen M. et al. "Pharmaceutical Salts", Journal of Pharmaceutical Sciences, vol. 66, No. 1, 1977, pp. 1-19.
Deady, Leslie W. "Ring Nitrogen Oxidation of Amino Substituted Nitrogen Heterocycles with m-Chloroperbenzoic Acid", Synthetic Communications, vol. 7(8), 1977, pp. 509-514.

(Continued)

Primary Examiner — Douglas M Willis
(74) Attorney, Agent, or Firm — Heslin Rothenberg Farley & Mesiti P.C.

(57) ABSTRACT

The invention relates to new pyridopyrazine derivative compounds of formula (I-A) or formula (I-B):

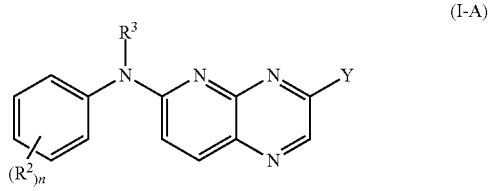

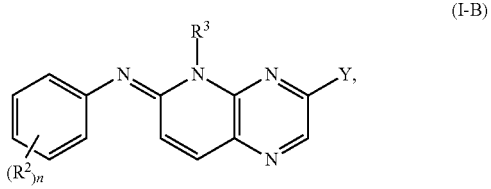

to pharmaceutical compositions comprising said compounds, to processes for the preparation of said compounds and to the use of said compounds in the treatment of diseases, e.g. cancer.

33 Claims, No Drawings

(56) References Cited

U.S. PATENT DOCUMENTS

| | | |
|---|---|---|
| 9,439,896 B2 | 9/2016 | Berdini et al. |
| 9,447,098 B2 | 9/2016 | Saxty et al. |
| 9,464,071 B2 | 10/2016 | Saxty et al. |
| 9,493,426 B2 | 11/2016 | Angibaud et al. |
| 9,527,844 B2 | 12/2016 | Angibaud et al. |
| 9,737,544 B2 | 8/2017 | Angibaud et al. |
| 9,757,364 B2 | 9/2017 | Angibaud et al. |
| 9,850,228 B2 | 12/2017 | Saxty et al. |
| 9,856,236 B2 | 1/2018 | Saxty et al. |
| 9,902,714 B2 | 2/2018 | Vermeulen |
| 2003/0207886 A1 | 11/2003 | Plucker et al. |
| 2005/0261307 A1 | 11/2005 | Cai et al. |
| 2005/0272728 A1 | 12/2005 | Altenbach et al. |
| 2005/0272736 A1 | 12/2005 | Altenbach et al. |
| 2007/0123494 A1 | 5/2007 | Seipelt et al. |
| 2007/0149484 A1 | 6/2007 | Claus et al. |
| 2008/0116789 A1 | 5/2008 | Yamaguchi et al. |
| 2009/0054304 A1 | 2/2009 | Herbert et al. |
| 2009/0118261 A1 | 5/2009 | Aquila et al. |
| 2009/0221591 A1 | 9/2009 | Hartmann et al. |
| 2010/0228026 A1 | 9/2010 | Yoshida et al. |
| 2010/0234347 A1 | 9/2010 | Dollinger et al. |
| 2011/0123545 A1 | 5/2011 | Marsh et al. |
| 2013/0072457 A1 | 3/2013 | Saxty et al. |
| 2013/0267525 A1 | 10/2013 | Saxty et al. |
| 2014/0288053 A1 | 9/2014 | Berdini et al. |
| 2014/0296236 A1 | 10/2014 | Berdini et al. |
| 2015/0031669 A1 | 1/2015 | Woodhead et al. |
| 2015/0031703 A1 | 1/2015 | Suzuki et al. |
| 2015/0057293 A1 | 2/2015 | Angibaud et al. |
| 2015/0105368 A1 | 4/2015 | Saxty et al. |
| 2015/0203589 A1 | 7/2015 | Iavarone et al. |
| 2015/0239883 A1 | 8/2015 | Angibaud et al. |
| 2015/0291589 A1 | 10/2015 | Saxty et al. |
| 2016/0031856 A1 | 2/2016 | Saxty et al. |
| 2016/0075666 A1 | 3/2016 | Angibaud et al. |
| 2016/0108034 A1 | 4/2016 | Angibaud et al. |
| 2016/0213677 A1 | 7/2016 | Angibaud et al. |
| 2016/0220564 A1 | 8/2016 | Woodhead et al. |
| 2016/0287699 A1 | 10/2016 | Karkera et al. |
| 2016/0311800 A1 | 10/2016 | Saxty et al. |
| 2017/0000781 A1 | 1/2017 | Berdini et al. |
| 2017/0000796 A1 | 1/2017 | Saxty et al. |
| 2017/0100406 A1 | 4/2017 | Jovcheva et al. |
| 2017/0101396 A1 | 4/2017 | Vermeulen et al. |
| 2017/0105978 A1 | 4/2017 | Angibaud et al. |
| 2017/0119763 A1 | 5/2017 | Jovcheva et al. |
| 2018/0021332 A1 | 1/2018 | Broggini |
| 2018/0127397 A1 | 5/2018 | Saxty et al. |

FOREIGN PATENT DOCUMENTS

| | | |
|---|---|---|
| CN | 1128496A A | 8/1996 |
| CN | 102036963 A | 4/2011 |
| EP | 0544445 A2 | 6/1993 |
| EP | 1001946 | 5/2000 |
| EP | 1990342 | 11/2008 |
| EP | 2332939 | 6/2011 |
| EP | 2650293 A1 | 10/2013 |
| JP | 2003213463 A | 7/2003 |
| JP | 2006516561 A | 7/2006 |
| JP | 2008530030 A | 8/2008 |
| JP | 2008540535 A | 11/2008 |
| JP | 2010514693 A | 5/2010 |
| RU | 2377241 C2 | 12/2009 |
| WO | 94/26723 A2 | 11/1994 |
| WO | 95/19169 A2 | 7/1995 |
| WO | 98/54156 A1 | 12/1998 |
| WO | 99/17759 A2 | 4/1999 |
| WO | 00/42026 A1 | 7/2000 |
| WO | 01/19825 A1 | 2/2001 |
| WO | 01/68047 A2 | 9/2001 |
| WO | 02/076985 A1 | 10/2002 |
| WO | 03/051833 A2 | 6/2003 |
| WO | 03/055491 A1 | 7/2003 |
| WO | 03/086394 A1 | 10/2003 |
| WO | 2004/006355 A2 | 1/2004 |
| WO | 2004/030635 A2 | 4/2004 |
| WO | 2004/043950 A1 | 5/2004 |
| WO | 2004/056822 A1 | 7/2004 |
| WO | 2004065378 A1 | 8/2004 |
| WO | 2004/098494 A2 | 11/2004 |
| WO | 2004/110350 A2 | 12/2004 |
| WO | 2005/007099 A2 | 1/2005 |
| WO | 2005/009437 A1 | 2/2005 |
| WO | 2005/012288 A1 | 2/2005 |
| WO | 2005/039587 A1 | 5/2005 |
| WO | 2005/047244 A2 | 5/2005 |
| WO | 2005/054201 A1 | 6/2005 |
| WO | 2005054231 A1 | 6/2005 |
| WO | 2005/061463 A1 | 7/2005 |
| WO | 2006/040052 A1 | 4/2006 |
| WO | 2006/066361 A1 | 6/2006 |
| WO | 2006084338 A1 | 8/2006 |
| WO | 2006/092430 A1 | 9/2006 |
| WO | 2006124354 A2 | 11/2006 |
| WO | 2007/003419 A1 | 1/2007 |
| WO | 2007/023186 A1 | 3/2007 |
| WO | 2007054556 A1 | 5/2007 |
| WO | 2007/075567 A1 | 7/2007 |
| WO | 2007/125405 A2 | 11/2007 |
| WO | 2007/132227 A1 | 11/2007 |
| WO | 2008/003702 A2 | 1/2008 |
| WO | 2008/076278 A1 | 6/2008 |
| WO | 2008/078091 A1 | 7/2008 |
| WO | 2008/082198 A1 | 7/2008 |
| WO | 2008079988 A2 | 7/2008 |
| WO | 2008080015 A2 | 7/2008 |
| WO | 2008/138878 A2 | 11/2008 |
| WO | 2008/141065 A1 | 11/2008 |
| WO | 2008/148867 A2 | 12/2008 |
| WO | 2008/150827 A1 | 12/2008 |
| WO | 2008/155378 A1 | 12/2008 |
| WO | 2009/019518 A1 | 2/2009 |
| WO | 2009/021083 A1 | 2/2009 |
| WO | 2009/064835 A1 | 5/2009 |
| WO | 2009/137378 A1 | 11/2009 |
| WO | 2009/141386 A1 | 11/2009 |
| WO | 2010059771 A1 | 5/2010 |
| WO | 2010/084152 A1 | 7/2010 |
| WO | 2010088177 A1 | 8/2010 |
| WO | 2010129570 A1 | 11/2010 |
| WO | 2011/026579 A1 | 3/2011 |
| WO | 2011/028947 A2 | 3/2011 |
| WO | 2011/064250 A1 | 6/2011 |
| WO | 2011/126903 A2 | 10/2011 |
| WO | 2011/135376 A1 | 11/2011 |
| WO | 2011/146591 A1 | 11/2011 |
| WO | 2011/149937 A1 | 12/2011 |
| WO | 2012/073017 A1 | 6/2012 |
| WO | 2012/104776 A1 | 8/2012 |
| WO | 2012/118492 A1 | 9/2012 |
| WO | 2012/148540 A1 | 11/2012 |
| WO | 2013/032951 A1 | 3/2013 |
| WO | 2013/040515 A1 | 3/2013 |
| WO | 2013/043935 A1 | 3/2013 |
| WO | 2013/052699 A2 | 4/2013 |
| WO | 2013/061074 A1 | 5/2013 |
| WO | 2013/061077 A1 | 5/2013 |
| WO | 2013/061080 A1 | 5/2013 |
| WO | 2013/061081 A1 | 5/2013 |
| WO | 2013/061305 A1 | 5/2013 |
| WO | 2013/063217 A1 | 5/2013 |
| WO | 2013/179033 A1 | 12/2013 |
| WO | 2013/179034 A1 | 12/2013 |
| WO | 2014/174307 A1 | 10/2014 |
| WO | 2015144803 A1 | 10/2015 |
| WO | 2015144804 A1 | 10/2015 |
| WO | 2015144808 A1 | 10/2015 |

(56) References Cited

FOREIGN PATENT DOCUMENTS

| WO | 2016128411 A1 | 8/2016 |
|---|---|---|
| WO | 2016/161239 A1 | 10/2016 |

OTHER PUBLICATIONS

Knights, Victoria et al. "De-regulated FGF receptors as therapeutic targets in cancer", *Pharmacology & Therapeutics*, 2010; vol. 125(1), pp. 105-117.

Korc, M. et al. "The Role of Fibroblast Growth Factors in Tumor Growth", *Current Cancer Drug Targets*, vol. 9(5), 2009, pp. 639-651.

Angerer, Lynne M. et al. "Demonstration of Tissue-Specific Gene Expression by in Situ Hybridization", *Methods in Enzymology*, vol. 152, 1987, pp. 649-661.

Deprimo, Samuel E. et al. "Expression profiling of blood samples from an SU5416 Phase III metastatic colorectal cancer clinical trial: a novel strategy for biomarker identification", *BMC Cancer*, vol. 3, 2003; pp. 1-12.

Orre, Maxine and Rogers, Peter A.W. "VEGF, VEGFR-1, VEGFR-2, Microvessel Density and Endothelial Cell Proliferation in Tumours of the Ovary", *Int. J. Cancer (Pred. Oncol.)*, vol. 84(2), 1999, pp. 101-108.

Zhou, Wenjun et al., "A Structure-Guided Approach to Creating Covalent FGFR Inhibitors", *Chemistry & Biology*, vol. 17, pp. 285-295 (2010).

Avendaño, C., et al., "Drugs That Inhibit Signalling Pathways for Tumor Cell Growth and Proliferation", *Medicinal Chemistry of Anticancer Drugs*, pp. 251-305 (2008).

Garuti, L., et al., Irreversible Protein Kinase Inhibitors, *Current Medicinal Chemistry*, vol. 18, No. 20, Jul. 1, 2011, pp. 2981-2994.

Vippagunta, S.R. et al., Crystalline Solids, *Advanced Drug Delivery Reviews*, vol. 48, pp. 3-26 (2001).

Jordan, V.C., Tamoxifen: A Most Unlikely Pioneering Medicine, *Nature Reviews: Drug Discovery*, vol. 2, pp. 205-213 (2003).

Hackam, D.G., et al., Translation of Research Evidence From Animals to Humans, *JAMA*, vol. 14, pp. 1731-1732 (2006).

"Himicheskaja jenciklopedija" tom 4, str. 990-993, izdatel'stvo "Sovetskaja jencklopedija", Moskva, 1988 (In English: Chemical Encyclopedia, vol. 4, pp. 990-993, Publishing House "Soviet encyclopedia", Moscow, 1988).

V. Hikkinvottom, "Reakcii Organicheskih Soedinenij" Gosudarstvennoe ob#eninennoe nauchno-technicheskoe izdatel'stvo, Redakcija himicheskoj literatury, Moskva, stranicy 360-362, 1939 (In English: V. Hikkinbottom, "Reactions of Organic Compounds", State Associated Scientific-Technical Publishing House, Editor Office of Chemical Literature, pp. 360-362, Moscow, 1939).

"Himicheskaja jenciklopedija" tom. 1, stranicy 242-243, izdatel'stvo "Sovetskaja jencklopedija", Moskva, 1988 (In English: Chemical Encyclopedia (thesaurus), vol. 1, pp. 242-243, publishing house "Soviet encyclopedia", Moscow, 1988).

Dorwald, F.Z., Side Reactions in Organic Synthesis: A Guide to Successful Synthesis Design, Weinheim:WILEY-VCH Verlag GmbH & Co. KGaA, 2005, ISBN: 3-527-31021.5.

Lima, L.M., et al., "Bioisosterism: A Useful Strategy for Molecular Modification and Drug Design", *Current Medical Chemistry*, vol. 12(1), pp. 23-49 (2005).

Patani, G.A., et al., "Bioisosterism: A Rational Approach in Drug Design", *Chem. Rev.* vol. 96, pp. 3147-3176 (1996).

Dieci, M.V., et al., Fibroblast Growth Factor Receptor Inhibitors as a Cancer Treatment: From a Biologic Rationale to Medical Perspectives, *Cancer Discovery*, vol. 3, No. 3, pp. 264-279 (Feb. 2013).

Gallick, G.E., et al., Small-molecule protein tyrosine kinase inhibitors for the treatment of metastatic prostate cancer, *Future Medicinal Chemistry*, vol. 4, No. 1, pp. 107-119 (Jan. 2012).

Study to Assess the Relative Bioavailability of Orally Administered JNJ-42756493 Tablet Versus JNJ-42756493 Capsule in Healthy Participants, ClinicalTrials.gov, pp. 1-4 (2014).

Matsuda, Y., et al., Fibroblast Growth Factor Receptor-2 IIIc as a Novel Molecular Target in Colorectal Cancer, *Current Colorectal Cancer Reports*, vol. 10, No. 1, pp. 20-26 (2014).

Carneiro, B.A., et al., Emerging therapeutic targets in bladder cancer, *Cancer Treatment Reviews*, vol. 41, No. 2, pp. 170-178 (2015).

Fujita, M., et al., Generation of Formaldehyde by Pharmaceutical Excipients and Its Absorption by Meglumine, *Chem. Pharm. Bull*, vol. 57, No. 10, pp. 1096-1099 (2009).

Adcock, J., et al., Diversity oriented synthesis: substitution at C5 in unreactive pyrimidines by Claisen rearrangement and reactivity in nucleophilic substitution at C2 and C4 in pteridines and pyrido [2,3-d]pyrimidines, *Tetrahedron*, vol. 67, pp. 3226-3237 (2011).

Database Caplus, Grina, et al., Preparation of oxohydroquinazolinylaminophenylpropanesulfonamide derivatives and analogs for use as Raf inhibitors, Document No. 157:465574, Accession No. 2012:1301209 (2012).

Liang, G., et al., "Small molecule inhibition of fibroblast growth factor receptors in cancer", *Cytokine & Growth Factor Reviews*, vol. 24, pp. 467-475 (2013).

Golub, T.R., et al., "Molecular Classification of Cancer: Class Discovery and Class Prediction by Gene Expression Monitoring", *Science*, vol. 286, pp. 531-537 (1999).

Greulich, H., et al., "Targeting mutant fibroblast growth factor receptors in cancer", *Trends in Molecular Medicine*, vol. 17, No. 5, pp. 283-292 (2011).

Freshney, R.I., "Culture of Animal Cells, A Manual of Basic Technique", Published by Alan R. Liss, Inc, New York, pp. 1-6 (1983).

Cohen, P., "The development and therapeutic potential of protein kinase inhibitors", *Current Opinion in Chemical Biology*, vol. 3, pp. 459-465 (1999).

Cecil Textbook of Medicine, edited by Bennet, J.C., and Plum, F., 20th edition, vol. 1, pp. 1004-1010 (1996).

Hynes, N.E., et al., "Potential for Targeting the Fibroblast Growth Factor Receptors in Breast Cancer", *Cancer Research*, vol. 70, pp. 5199-5202 (2010).

Neidle, S., "Cancer Drug Design and Discovery", Elsevier/Academic Press, pp. 427-431 (2008).

Dermer, G.B., "Another Anniversary for the War on Cancer", *Biotechnology*, vol. 12, p. 320 (1994).

Katoh, Y., et al., "FGFR2-related pathogenesis and FGFR2-targeted therapeutics (Review)", *International Journal of Molecular Medicine*, vol. 23, pp. 307-311 (2009).

Jain, V.K., et al., "Challenges and opportunities in the targeting of fibroblast growth factor receptors in breast cancer", *Breast Cancer Research*, vol. 14, No. 208, pp. 1-9 (2012).

Ho, H.K., et al, "Current strategies for inhibiting FGFR activities in clinical applications: opportunities, challenges and toxicological considerations", *Drug Discovery Today*, vol. 19, Issue 1, pp. 51-62 (2014).

Sonpavde, G., et al., "Fibroblast growth factor receptors as therapeutic targets in clear-cell renal cell carcinoma", *Expert Opinion on Investigational Drugs*, vol. 23, Issue 3, pp. 305-315 (2014).

Rodriguez-Vida, A., et al., "Complexity of FGFR signaling in metastatic urothelial cancer", *Journal of Hematology & Oncology*, vol. 8, p. 119 et seq. (2015).

SUBSTITUTED PYRIDO[2,3-B]PYRAZINES AS FGFR KINASE INHIBITORS

CROSS REFERENCE TO RELATED APPLICATIONS

This application is a continuation of U.S. application Ser. No. 14/354,832, filed on Apr. 28, 2014, which is a national stage filing under Section 371 of International Application No. PCT/GB2012/052672 filed on Oct. 26, 2012, and published in English as WO 2013/061080 A1 on May 2, 2013, and claims priority to British Application No. 1118656.6 filed on Oct. 28, 2011 and to U.S. Provisional Application No. 61/552,888 filed on Oct. 28, 2011. The entire disclosures of each of the prior applications are hereby incorporated herein by reference.

FIELD OF THE INVENTION

The invention relates to new pyridopyrazine derivative compounds, to pharmaceutical compositions comprising said compounds, to processes for the preparation of said compounds and to the use of said compounds in the treatment of diseases, e.g. cancer.

SUMMARY OF THE INVENTION

According to a first aspect of the invention there is provided compounds of formula (I):

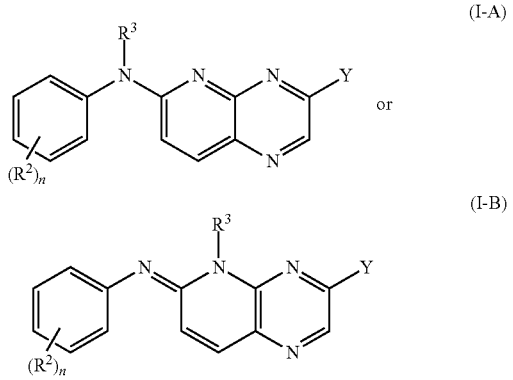

(I-A)

or (I-B)

including any tautomeric or stereochemically isomeric form thereof, wherein
each $R^2$ is independently selected from hydroxyl, halogen, cyano, $C_{1-4}$alkyl, $C_{2-4}$alkenyl, $C_{2-4}$alkynyl, $C_{1-4}$alkoxy, hydroxyC$_{1-4}$alkyl, hydroxyC$_{1-4}$alkoxy, haloC$_{1-4}$alkyl, haloC$_{1-4}$alkoxy, hydroxyhaloC$_{1-4}$alkyl, hydroxyhaloC$_{1-4}$alkoxy, C$_{1-4}$alkoxyC$_{1-4}$alkyl, haloC$_{1-4}$alkoxyC$_{1-4}$alkyl, C$_{1-4}$alkoxyC$_{1-4}$alkyl wherein each C$_{1-4}$alkyl may optionally be substituted with one or two hydroxyl groups, hydroxyhaloC$_{1-4}$alkoxyC$_{1-4}$alkyl, $R^{13}$, C$_{1-4}$alkyl substituted with $R^{13}$, C$_{1-4}$alkyl substituted with —C(=O)—$R^{13}$, C$_{1-4}$alkoxy substituted with $R^{13}$, C$_{1-4}$alkoxy substituted with —C(=O)—$R^{13}$, —C(=O)—$R^{13}$, C$_{1-4}$alkyl substituted with —NR$^7$R$^8$, C$_{1-4}$alkyl substituted with —C(=O)—NR$^7$R$^8$, C$_{1-4}$alkoxy substituted with —NR$^7$R$^8$, C$_{1-4}$alkoxy substituted with —C(=O)—NR$^7$R$^8$, —NR$^7$R$^8$ and —C(=O)—NR$^7$R$^8$; or when two $R^2$ groups are attached to adjacent carbon atoms they may be taken together to form a radical of formula:

—O—(C(R$^{17}$)$_2$)$_p$—O—;

—X—CH=CH—; or

—X—CH=N—;

wherein $R^{17}$ represents hydrogen or fluorine, p represents 1 or 2 and X represents O or S;
Y represents —CR$^{18}$=N—OR$^{19}$ or -E-D;
D represents a 3 to 12 ring membered monocyclic or bicyclic carbocyclyl or a 3 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups;
E represents a bond, —(CR$^{22}$R$^{23}$)$_n$—, C$_{2-4}$alkenediyl optionally substituted with R$^{22}$, C$_{2-4}$alkynediyl optionally substituted with R$^{22}$, —CO—(CR$^{22}$R$^{23}$)$_s$—, —(CR$^{22}$R$^{23}$)$_s$—CO—, —NR$^{22}$—(CR$^{22}$R$^{23}$)$_s$—, —(CR$^{22}$R$^{23}$)$_s$—NR$^{22}$—, —O—(CR$^{22}$R$^{23}$)$_s$—, —(CR$^{22}$R$^{23}$)$_s$—O—, —S(O)$_m$—(CR$^{22}$R$^{23}$)$_s$—, —(CR$^{22}$R$^{23}$)$_s$—S(O)$_m$—, —(CR$^{22}$R$^{23}$)$_s$—CO—NR$^{22}$—(CR$^{22}$R$^{23}$)$_s$— or —(CR$^{22}$R$^{23}$)$_s$—NR$^{22}$—CO—(CR$^{22}$R$^{23}$)$_s$—;
$R^1$ represents hydrogen, halo, cyano, C$_{1-6}$alkyl, C$_{1-6}$alkoxy, —C(=O)—O—C$_{1-6}$alkyl, C$_{2-4}$alkenyl, hydroxyC$_{1-6}$alkyl, haloC$_{1-6}$alkyl, hydroxyhaloC$_{1-6}$alkyl, cyanoC$_{1-4}$alkyl, C$_{1-6}$alkoxyC$_{1-6}$alkyl wherein each C$_{1-6}$alkyl may optionally be substituted with one or two hydroxyl groups, —NR$^4$R$^5$, C$_{1-6}$alkyl substituted with —O—C(=O)—C$_{1-6}$alkyl, C$_{1-6}$alkyl substituted with —NR$^4$R$^5$, —C(=O)—NR$^4$R$^5$, —C(=O)—C$_{1-6}$alkyl-NR$^4$R$^5$, C$_{1-6}$alkyl substituted with —C(=O)—NR$^4$R$^5$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$ alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl, C$_{1-6}$alkyl substituted with —NR$^{12}$—S(=O)$_2$—NR$^{14}$R$^{15}$, R$^6$, C$_{1-6}$alkyl substituted with R$^6$, —C(=O)—R$^6$, C$_{1-6}$alkyl substituted with —C(=O)—R$^6$, hydroxyC$_{1-6}$alkyl substituted with R$^6$, C$_{1-6}$alkyl substituted with —Si(CH$_3$)$_3$, C$_{1-6}$alkyl substituted with —P(=O)(OH)$_2$ or C$_{1-6}$alkyl substituted with —P(=O)(OC$_{1-6}$alkyl)$_2$;
$R^3$ represents hydroxyl, C$_{1-6}$alkoxy, hydroxyC$_{1-6}$alkoxy, C$_{1-6}$alkoxy substituted with —NR$^{10}$R$^{11}$, C$_{1-6}$alkyl, C$_{2-6}$alkenyl, C$_{2-6}$alkynyl, haloC$_{1-6}$alkyl optionally substituted with —O—C(=O)—C$_{1-6}$alkyl, hydroxyC$_{1-6}$alkyl optionally substituted with —O—C(=O)—C$_{1-6}$alkyl, hydroxyC$_{2-6}$alkenyl, hydroxyC$_{2-6}$alkynyl, hydroxyhaloC$_{1-6}$alkyl, cyanoC$_{1-6}$alkyl, C$_{1-6}$alkyl substituted with carboxyl, C$_{1-6}$alkyl substituted with —C(=O)—C$_{1-6}$alkyl, C$_{1-6}$alkyl substituted with —C(=O)—O—C$_{1-6}$alkyl, C$_{1-6}$alkyl substituted with C$_{1-6}$alkoxyC$_{1-6}$alkyl-O—C(=O)—, C$_{1-6}$alkyl substituted with C$_{1-6}$alkoxyC$_{1-6}$alkyl-C(=O)—, C$_{1-6}$alkyl substituted with —O—C(=O)—C$_{1-6}$alkyl, C$_{1-6}$alkoxyC$_{1-6}$alkyl wherein each C$_{1-6}$alkyl may optionally be substituted with one or two hydroxyl groups or with —O—C(=O)—C$_{1-6}$alkyl, C$_{2-6}$alkenyl substituted with C$_{1-6}$alkoxy, C$_{2-6}$alkynyl substituted with C$_{1-6}$alkoxy, C$_{1-6}$alkyl substituted with $R^9$ and optionally substituted with —O—C(=O)—C$_{1-6}$alkyl, C$_{1-6}$alkyl substituted with —C(=O)—$R^9$, C$_{1-6}$alkyl substituted with hydroxyl and $R^9$, C$_{2-6}$alkenyl substituted with $R^9$, C$_{2-6}$alkynyl substituted with $R^9$, C$_{1-6}$alkyl substituted with —NR$^{10}$R$^{11}$, C$_{2-6}$alkenyl substituted with —NR$^{10}$R$^{11}$, C$_{2-6}$alkynyl substituted with —NR$^{10}$R$^{11}$, C$_{1-6}$alkyl substituted with hydroxyl and —NR$^{10}$R$^{11}$, C$_{1-6}$alkyl substituted with one or two halogens and —NR$^{10}$R$^{11}$, —C$_{1-6}$alkyl-C(R$^{12}$)=N—O—R$^{12}$, C$_{1-6}$alkyl substituted with —C(=O)—NR$^{10}$R$^{11}$, C$_{1-6}$alkyl substituted with —O—C(=O)—

NR$^{10}$R$^{11}$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$ —C$_{1-6}$alkyl, C$_{1-6}$alkyl substituted with —S(=O)$_2$-haloC$_6$alkyl, C$_{1-6}$alkyl substituted with —S(=O)$_2$—NR$^{14}$R$^{15}$, C$_{1-6}$alkyl substituted with —NR$^{12}$—S(=O)$_2$—C$_{1-6}$alkyl, C$_{1-6}$alkyl substituted with —NH—S(=O)$_2$-haloC$_{1-6}$alkyl, C$_{1-6}$alkyl substituted with —NR$^{12}$—S(=O)$_2$ —NR$^{14}$R$^{15}$, R$^{13}$, C$_{1-6}$alkyl substituted with —P(=O)(OH)$_2$ or C$_{1-6}$alkyl substituted with —P(=O)(OC$_{1-6}$alkyl)$_2$;

R$^4$ and R$^5$ each independently represent hydrogen, C$_{1-6}$alkyl, C$_{1-6}$alkyl substituted with —NR$^{14}$R$^{15}$, hydroxyC$_{1-6}$alkyl, haloC$_{1-6}$alkyl, hydroxyhaloC$_{1-6}$alkyl, C$_{1-6}$alkoxyC$_{1-6}$alkyl wherein each C$_{1-6}$alkyl may optionally be substituted with one or two hydroxyl groups, —S(=O)$_2$—C$_{1-6}$alkyl, —S(=O)$_2$-haloC$_{1-6}$alkyl, —S(=O)$_2$—NR$^{14}$R$^{15}$, —C(=O)—NR$^{14}$R$^{15}$, —C(=O)—O—C$_{1-6}$alkyl, —C(=O)—R$^{13}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl, C$_{1-6}$alkyl substituted with —NH—S(=O)$_2$—NR$^{14}$R$^{15}$, R$^{13}$ or C$_{1-6}$alkyl substituted with R$^{13}$;

R$^6$ represents C$_{3-8}$cycloalkyl, C$_{3-8}$cycloalkenyl, phenyl, 4 to 7-membered monocyclic heterocyclyl containing at least one heteroatom selected from N, O or S; said C$_{3-8}$cycloalkyl, C$_{3-8}$cycloalkenyl, phenyl, 4 to 7-membered monocyclic heterocyclyl, optionally and each independently being substituted by 1, 2, 3, 4 or 5 substituents, each substituent independently being selected from cyano, C$_{1-6}$alkyl, cyanoC$_{1-6}$alkyl, hydroxyl, carboxyl, hydroxyC$_{1-6}$alkyl, halogen, haloC$_{1-6}$alkyl, hydroxyhaloC$_{1-6}$alkyl, C$_{1-6}$alkoxy, C$_{1-6}$alkoxyC$_{1-6}$alkyl, C$_{1-6}$alkyl-O—C(=O)—, —NR$^{14}$R$^{15}$, —C(=O)—NR$^{14}$R$^{15}$, C$_{1-6}$alkyl substituted with —NR$^{14}$R$^{15}$, C$_{1-6}$alkyl substituted with —C(=O)—NR$^{14}$R$^{15}$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$ —C$_{1-6}$alkyl, C$_{1-6}$alkyl substituted with —S(=O)$_2$-haloC$_{1-6}$ alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl or C$_{1-6}$alkyl substituted with —NH—S(=O)$_2$—NR$^{14}$R$^{15}$;

R$^7$ and R$^8$ each independently represent hydrogen, C$_{1-6}$alkyl, hydroxyC$_{1-6}$alkyl, haloC$_{1-6}$alkyl, hydroxyhaloC$_{1-6}$ alkyl or C$_{1-6}$alkoxyC$_{1-6}$alkyl;

R$^9$ represents C$_{3-8}$cycloalkyl, C$_{3-8}$cycloalkenyl, phenyl, naphthyl, or 3 to 12 membered monocyclic or bicyclic heterocyclyl containing at least one heteroatom selected from N, O or S, said C$_{3-8}$cycloalkyl, C$_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, C$_{1-4}$alkyl, hydroxyl, carboxyl, hydroxyC$_{1-4}$alkyl, cyano, cyanoC$_{1-4}$alkyl, C$_{1-4}$alkyl-O—C(=O)—, C$_{1-4}$alkyl substituted with C$_{1-4}$alkyl-O—C(=O)—, C$_{1-4}$alkyl-C(=O)—, C$_{1-4}$alkoxyC$_{1-4}$alkyl wherein each C$_{1-4}$alkyl may optionally be substituted with one or two hydroxyl groups, halogen, haloC$_{1-4}$alkyl, hydroxyhaloC$_{1-4}$alkyl, —NR$^{14}$R$^{15}$, —C(=O)—NR$^{14}$R$^{15}$, C$_{1-4}$alkyl substituted with —NR$^{14}$R$^{15}$, C$_{1-4}$alkyl substituted with —C(=O)—NR$^{14}$R$^{15}$, C$_{1-4}$alkoxy, —S(=O)$_2$—C$_{1-4}$alkyl, —S(=O)$_2$-haloC$_{1-4}$alkyl, —S(=O)$_2$—NR$^{14}$R$^{15}$, C$_{1-4}$alkyl substituted with —S(=O)$_2$—NR$^{14}$R$^{15}$, C$_{1-4}$alkyl substituted with —NH—S(=O)$_2$—C$_{1-4}$alkyl, C$_{1-4}$alkyl substituted with —NH—S(=O)$_2$-haloC$_{1-4}$alkyl, C$_{1-4}$alkyl substituted with —NH—S(=O)$_2$—NR$^{14}$R$^{15}$, R$^{13}$, —C(=O)—R$^{13}$, C$_{1-4}$alkyl substituted with R$^{13}$, phenyl optionally substituted with R$^{16}$, phenylC$_{1-6}$alkyl wherein the phenyl is optionally substituted with R$^{16}$, a 5 or 6-membered aromatic monocyclic heterocyclyl containing at least one heteroatom selected from N, O or S wherein said heterocyclyl is optionally substituted with R$^{16}$;

or when two of the substituents of R$^9$ are attached to the same atom, they may be taken together to form a 4 to 7-membered saturated monocyclic heterocyclyl containing at least one heteroatom selected from N, O or S;

R$^{10}$ and R$^{11}$ each independently represent hydrogen, carboxyl, C$_{1-6}$alkyl, cyanoC$_6$alkyl, C$_{1-6}$alkyl substituted with —NR$^{14}$R$^{15}$, C$_{1-6}$alkyl substituted with —C(=O)—NR$^{14}$R$^{15}$, haloC$_{1-6}$alkyl, hydroxyC$_{1-6}$alkyl, hydroxyhaloC$_6$alkyl, C$_{1-6}$alkoxy, C$_{1-6}$alkoxyC$_{1-6}$alkyl wherein each C$_{1-6}$alkyl may optionally be substituted with one or two hydroxyl groups, R$^6$, C$_{1-6}$alkyl substituted with R$^6$, —C(=O)—R$^6$, —C(=O)—C$_{1-6}$alkyl, —C(=O)-hydroxyC$_6$alkyl, —C(=O)-haloC$_{1-6}$alkyl, —C(=O)-hydroxyhaloC$_6$alkyl, C$_{1-6}$alkyl substituted with —Si(CH$_3$)$_3$, —S(=O)$_2$—C$_{1-6}$alkyl, —S(=O)$_2$-haloC$_{1-6}$alkyl, —S(=O)$_2$ —NR$^{14}$R$^{15}$, C$_{1-6}$alkyl substituted with —S(=O)$_2$ —C$_{1-6}$ alkyl, C$_{1-6}$alkyl substituted with —S(=O)$_2$-haloC$_6$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$ alkyl, C$_{1-6}$alkyl substituted with —NH—S(=O)$_2$-haloC$_{1-6}$ alkyl, C$_{1-6}$alkyl substituted with carboxyl, or C$_{1-6}$alkyl substituted with —NH—S(=O)$_2$—NR$^{14}$R$^{15}$;

R$^{12}$ represents hydrogen or C$_{1-4}$alkyl optionally substituted with C$_{1-4}$alkoxy;

R$^{13}$ represents C$_{3-8}$cycloalkyl or a saturated 4 to 6-membered monocyclic heterocyclyl containing at least one heteroatom selected from N, O or S, wherein said C$_{3-8}$cycloalkyl or monocyclic heterocyclyl is optionally substituted with 1, 2 or 3 substituents each independently selected from halogen, hydroxyl, C$_{1-6}$alkyl, haloC$_{1-6}$alkyl, =O, cyano, —C(=O)—C$_{1-6}$alkyl, C$_{1-6}$alkoxy, or —NR$^{14}$R$^{15}$;

R$^{14}$ and R$^{15}$ each independently represent hydrogen, or haloC$_{1-4}$alkyl, or C$_{1-4}$alkyl optionally substituted with a substituent selected from hydroxyl, C$_{1-4}$alkoxy, amino or mono- or di(C$_{1-4}$alkyl)amino;

R$^{16}$ represents hydroxyl, halogen, cyano, C$_{1-4}$alkyl, C$_{1-4}$alkoxy, —NR$^{14}$R$^{15}$ or —C(=O)NR$^{14}$R$^{15}$;

R$^{18}$ represents hydrogen, C$_{1-6}$ alkyl, C$_{3-8}$ cycloalkyl, C$_{1-4}$alkyl substituted with C$_{3-8}$ cycloalkyl;

R$^{19}$ represents hydrogen; C$_{1-6}$ alkyl; C$_{3-8}$ cycloalkyl; C$_{1-6}$alkyl substituted with —O—R$^{20}$; —(CH$_2$)$_r$—CN; —(CH$_2$)$_r$—CONR$^{20}$R$^{21}$; —(CH$_2$)$_{r1}$—NR$^{20}$R$^{21}$; —(CH$_2$)$_{r1}$—NR$^{20}$COR$^{21}$; —(CH$_2$)$_{r1}$—NR$^{20}$—(CH$_2$)$_s$—SO$_2$—R$^{21}$; —(CH$_2$)$_{r1}$—NH—SO$_2$—NR$^{20}$R$^{21}$; —(CH$_2$)$_{r1}$—NR$^{20}$CO$_2$R$^{21}$; —(CH$_2$)$_r$SO$_2$NR$^{20}$R$^{21}$; phenyl optionally substituted with 1, 2, 3, 4 or 5 substituents each independently selected from halogen, C$_{1-4}$alkyl, C$_{1-4}$alkyloxy, cyano or amino; a 5- or 6-membered aromatic monocyclic heterocycle containing at least one heteroatom selected from N, O or S, said heterocycle being optionally substituted with 1, 2, 3 or 4 substituents each independently selected from halogen, C$_{1-4}$alkyl, C$_{1-4}$alkyloxy, cyano or amino; wherein said C$_{1-6}$ alkyl and C$_{3-8}$ cycloalkyl, may be optionally substituted by one or more R$^{20}$ groups R$^{20}$ and R$^{21}$ independently represent hydrogen, C$_{1-6}$ alkyl, C$_{1-6}$ alkanol —(CH$_2$)$_n$—O—C$_{1-6}$alkyl, or when attached to a nitrogen atom R$^{20}$ and R$^{21}$ can be taken together to form with the nitrogen atom to which they are attached a monocyclic saturated 4, 5 or 6-membered ring which optionally contains a further heteroatom selected from O, S or N;

$R^{22}$ and $R^{23}$ independently represent hydrogen, $C_{1-6}$ alkyl, or hydroxy$C_{1-6}$alkyl; m independently represents an integer equal to 0, 1 or 2;

n independently represents an integer equal to 0, 1, 2, 3 or 4;

s independently represents an integer equal to 0, 1, 2, 3 or 4;

r independently represent an integer equal to 1, 2, 3, or 4;

r1 independently represent an integer equal to 2, 3 or 4;

the N-oxides thereof, the pharmaceutically acceptable salts thereof or the solvates thereof.

WO 1999/17759, WO2006/092430, WO2008/003702, WO01/68047, WO2005/007099, WO2004/098494, WO2009/141386, WO 2004/030635, WO 2008/141065, WO 2011/026579, WO 2011/028947, WO 00/42026, WO2008/138878, WO2004/104003, WO2004/104002, WO2007/079999, WO2007/054556, WO2010/084152, US2005/0272736, US2005/0272728, US2007/0123494, WO2011/135376 which each disclose a series of heterocyclyl derivatives.

DETAILED DESCRIPTION OF THE INVENTION

Unless the context indicates otherwise, references to formula (I) in all sections of this document (including the uses, methods and other aspects of the invention) include references to all other sub-formula (e.g. I-A, I-B, I-C, I-D), sub-groups, preferences, embodiments and examples as defined herein.

The prefix "$C_{x-y}$" (where x and y are integers) as used herein refers to the number of carbon atoms in a given group. Thus, a $C_{1-6}$alkyl group contains from 1 to 6 carbon atoms, a $C_3$-6cycloalkyl group contains from 3 to 6 carbon atoms, a $C_{1-4}$alkoxy group contains from 1 to 4 carbon atoms, and so on.

The term 'halo' or 'halogen' as used herein refers to a fluorine, chlorine, bromine or iodine atom.

The term '$C_{1-4}$alkyl', or '$C_{1-6}$alkyl' as used herein as a group or part of a group refers to a linear or branched saturated hydrocarbon group containing from 1 to 4 or 1 to 6 carbon atoms. Examples of such groups include methyl, ethyl, n-propyl, isopropyl, n-butyl, isobutyl, sec-butyl, tert-butyl, n-pentyl, isopentyl, neopentyl or hexyl and the like.

The term '$C_{2-4}$alkenyl' or '$C_{2-6}$alkenyl' as used herein as a group or part of a group refers to a linear or branched hydrocarbon group containing from 2 to 4 or 2 to 6 carbon atoms and containing a carbon carbon double bond.

The term '$C_{2-4}$alkynyl' or '$C_{2-6}$alkynyl' as used herein as a group or part of a group refers to a linear or branched hydrocarbon group having from 2 to 4 or 2 to 6 carbon atoms and containing a carbon carbon triple bond.

The term '$C_{1-4}$alkoxy' or '$C_{1-6}$alkoxy' as used herein as a group or part of a group refers to an —O—$C_{1-4}$alkyl group or an —O—$C_{1-6}$alkyl group wherein $C_{1-4}$alkyl and $C_{1-6}$alkyl are as defined herein. Examples of such groups include methoxy, ethoxy, propoxy, butoxy, and the like.

The term '$C_{1-4}$alkoxy$C_{1-4}$alkyl' or '$C_{1-6}$alkoxy$C_{1-6}$alkyl' as used herein as a group or part of a group refers to a $C_{1-4}$alkyl-O—$C_{1-4}$alkyl group or a $C_{1-6}$alkyl-O—$C_{1-6}$alkyl group wherein $C_{1-4}$alkyl and $C_{1-6}$alkyl are as defined herein. Examples of such groups include methoxyethyl, ethoxyethyl, propoxymethyl, butoxypropyl, and the like.

The term '$C_{3-8}$cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term '$C_{3-8}$cycloalkenyl' as used herein refers to a monocyclic hydrocarbon ring of 3 to 8 carbon atoms having a carbon carbon double bond.

The term 'hydroxy$C_{1-4}$alkyl' or 'hydroxy$C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group. The terms 'hydroxy$C_{1-4}$alkyl' or 'hydroxy$C_{1-6}$alkyl' therefore include monohydroxy$C_{1-4}$alkyl, monohydroxy$C_{1-6}$alkyl and also polyhydroxy$C_{1-4}$alkyl and polyhydroxy$C_{1-6}$alkyl. There may be one, two, three or more hydrogen atoms replaced with a hydroxyl group, so the hydroxy$C_{1-4}$ alkyl or hydroxy$C_{1-6}$alkyl may have one, two, three or more hydroxyl groups. Examples of such groups include hydroxymethyl, hydroxyethyl, hydroxypropyl and the like.

The term 'halo$C_{1-4}$alkyl' or 'halo$C_{1-6}$alkyl' as used herein as a group or part of a group refers to a $C_{1-4}$alkyl or $C_{1-6}$alkyl group as defined herein wherein one or more than one hydrogen atom is replaced with a halogen. The term 'halo$C_{1-4}$ alkyl' or 'halo$C_{1-6}$alkyl' therefore include monohalo$C_{1-4}$ alkyl, monohalo$C_{1-6}$alkyl and also polyhalo$C_{1-4}$alkyl and polyhalo$C_{1-6}$alkyl. There may be one, two, three or more hydrogen atoms replaced with a halogen, so the halo$C_{1-4}$ alkyl or halo$C_{1-6}$alkyl may have one, two, three or more halogens. Examples of such groups include fluoroethyl, fluoromethyl, trifluoromethyl or trifluoroethyl and the like.

The term 'hydroxyhalo$C_{1-4}$alkyl' or 'hydroxyhalo$C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group and one or more than one hydrogen atom is replaced with a halogen. The term 'hydroxyhalo$C_{1-4}$alkyl' or 'hydroxyhalo$C_{1-6}$alkyl' therefore refers to a $C_{1-4}$alkyl or $C_{1-6}$alkyl group wherein one, two, three or more hydrogen atoms are replaced with a hydroxyl group and one, two, three or more hydrogen atoms are replaced with a halogen.

The term 'hydroxy$C_{1-4}$alkoxy' or 'hydroxy$C_{1-6}$alkoxy' as used herein as a group or part of a group refers to an —O—$C_{1-4}$alkyl group or an —O—$C_{1-6}$alkyl group wherein the $C_{1-4}$alkyl and $C_{1-6}$alkyl group is as defined above and one or more than one hydrogen atom of the $C_{1-4}$alkyl or $C_{1-6}$alkyl group is replaced with a hydroxyl group. The term 'hydroxy$C_{1-4}$alkoxy' or 'hydroxy$C_{1-6}$alkoxy' therefore include monohydroxy$C_{1-4}$alkoxy, monohydroxy$C_{1-6}$alkoxy and also polyhydroxy$C_{1-4}$alkoxy and polyhydroxy$C_{1-6}$alkoxy. There may be one, two, three or more hydrogen atoms replaced with a hydroxyl group so the hydroxy$C_{1-4}$alkoxy or hydroxy$C_{1-6}$alkoxy may have one, two, three or more hydroxyl groups. Examples of such groups include hydroxymethoxy, hydroxyethoxy, hydroxypropoxy and the like.

The term 'halo$C_{1-4}$alkoxy' or 'halo$C_{1-6}$alkoxy' as used herein as a group or part of a group refers to a —O—$C_{1-4}$ alkyl group or a —O—$C_{1-6}$ alkyl group as defined herein wherein one or more than one hydrogen atom is replaced with a halogen. The terms 'halo$C_{1-4}$alkoxy' or 'halo$C_{1-6}$alkoxy' therefore include monohalo$C_{1-4}$alkoxy, monohalo $C_{1-6}$alkoxy and also polyhalo$C_{1-4}$alkoxy and polyhalo$C_{1-6}$alkoxy. There may be one, two, three or more hydrogen atoms replaced with a halogen, so the halo$C_{1-4}$alkoxy or halo$C_{1-6}$alkoxy may have one, two, three or more halogens. Examples of such groups include fluoroethyloxy, difluoromethoxy or trifluoromethoxy and the like.

The term 'hydroxyhaloC$_{1-4}$alkoxy' as used herein as a group or part of a group refers to an —O—C$_{1-4}$alkyl group wherein the C$_{1-4}$alkyl group is as defined herein and wherein one or more than one hydrogen atom is replaced with a hydroxyl group and one or more than one hydrogen atom is replaced with a halogen. The term 'hydroxyhaloC$_{1-4}$alkoxy' therefore refers to a —O—C$_{1-4}$alkyl group wherein one, two, three or more hydrogen atoms are replaced with a hydroxyl group and one, two, three or more hydrogen atoms are replaced with a halogen.

The term 'haloC$_{1-4}$alkoxyC$_{1-4}$alkyl' as used herein as a group or part of a group refers to a C$_{1-4}$alkyl-O—C$_{1-4}$alkyl group wherein C$_{1-4}$alkyl is as defined herein and wherein in one or both of the C$_{1-4}$alkyl groups one or more than one hydrogen atom is replaced with a halogen. The term 'haloC$_{1-4}$ alkoxyC$_{1-4}$alkyl' therefore refers to a C$_{1-4}$alkyl-O—C$_{1-4}$alkyl group wherein in one or both of the C$_{1-4}$alkyl groups one, two, three or more hydrogen atoms are replaced with a halogen and wherein C$_{1-4}$ alkyl is as defined herein. Preferably, in one of the C$_{1-4}$alkyl groups one or more than one hydrogen atom is replaced with a halogen. Preferably, haloC$_{1-4}$alkoxyC$_{1-4}$alkyl means C$_{1-4}$alkyl substituted with haloC$_{1-4}$alkoxy.

The term 'hydroxyhaloC$_{1-4}$alkoxyC$_{1-4}$alkyl' as used herein refers to a C$_{1-4}$alkyl-O—C$_{1-4}$alkyl group wherein C$_{1-4}$alkyl is as defined herein and wherein in one or both of the C$_{1-4}$alkyl groups one or more than one hydrogen atom is replaced with a hydroxyl group and one or more than one hydrogen atom is replaced with a halogen. The terms 'hydroxyhaloC$_{1-4}$alkoxyC$_{1-4}$alkyl' therefore refers to a C$_{1-4}$alkyl-O—C$_{1-4}$alkyl group wherein in one or both of the C$_{1-4}$alkyl groups one, two, three or more hydrogen atoms are replaced with a hydroxyl group and one, two, three or more hydrogen atoms are replaced with a halogen and wherein C$_{1-4}$alkyl is as defined herein.

The term 'hydroxyC$_{2-6}$alkenyl' as used herein refers to a C$_{2-6}$alkenyl group wherein one or more than one hydrogen atom is replaced with a hydroxyl group and wherein C$_{2-6}$alkenyl is as defined herein.

The term 'hydroxyC$_{2-6}$alkynyl' as used herein refers to a C$_{2-6}$alkynyl group wherein one or more than one hydrogen atom is replaced with a hydroxyl group and wherein C$_{2-6}$alkynyl is as defined herein.

The term phenylC$_{1-6}$alkyl as used herein refers to a C$_{1-6}$alkyl group as defined herein which is substituted with one phenyl group.

The term cyanoC$_{1-4}$alkyl or cyanoC$_{1-6}$alkyl as used herein refers to a C$_{1-4}$alkyl or C$_{1-6}$alkyl group as defined herein which is substituted with one cyano group.

The term "heterocyclyl" as used herein shall, unless the context indicates otherwise, include both aromatic and non-aromatic ring systems. Thus, for example, the term "heterocyclyl group" includes within its scope aromatic, non-aromatic, unsaturated, partially saturated and fully saturated heterocyclyl ring systems. In general, unless the context indicates otherwise, such groups may be monocyclic or bicyclic and may contain, for example, 3 to 12 ring members, more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, and preferably 5, 6 or 7 ring members, more preferably 5 or 6 ring members. Examples of bicyclic groups are those containing 8, 9, 10, 11 and 12 ring members, and more usually 9 or 10 ring members. Where reference is made herein to heterocyclyl groups, the heterocyclyl ring can, unless the context indicates otherwise, be optionally substituted (i.e. unsubstituted or substituted) by one or more substituents as discussed herein.

The heterocyclyl groups can be heteroaryl groups having from 5 to 12 ring members, more usually from 5 to 10 ring members. The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. Each ring may contain up to about five heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 0, 1, 2 or 3 ring heteroatoms;
c) a pyrimidine ring fused to a 5- or 6-membered ring containing 0, 1 or 2 ring heteroatoms;
d) a pyrrole ring fused to a 5- or 6-membered ring containing 0, 1, 2 or 3 ring heteroatoms;
e) a pyrazole ring fused to a 5- or 6-membered ring containing 0, 1 or 2 ring heteroatoms;
f) an imidazole ring fused to a 5- or 6-membered ring containing 0, 1 or 2 ring heteroatoms;
g) an oxazole ring fused to a 5- or 6-membered ring containing 0, 1 or 2 ring heteroatoms;
h) an isoxazole ring fused to a 5- or 6-membered ring containing 0, 1 or 2 ring heteroatoms;
i) a thiazole ring fused to a 5- or 6-membered ring containing 0, 1 or 2 ring heteroatoms;
j) an isothiazole ring fused to a 5- or 6-membered ring containing 0, 1 or 2 ring heteroatoms;
k) a thiophene ring fused to a 5- or 6-membered ring containing 0, 1, 2 or 3 ring heteroatoms;
l) a furan ring fused to a 5- or 6-membered ring containing 0, 1, 2 or 3 ring heteroatoms;
m) a cyclohexyl ring fused to a 5- or 6-membered ring containing 1, 2 or 3 ring heteroatoms; and n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic heteroaryl groups containing an aromatic ring and a non-aromatic ring include, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), indoline and indane groups.

A nitrogen-containing heteroaryl ring must contain at least one ring nitrogen atom. Each ring may, in addition, contain up to about four other heteroatoms typically selected from nitrogen, sulphur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazole, benzthiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic group" embraces, unless the context indicates otherwise, unsaturated ring systems without aromatic character, partially saturated and fully saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated heterocyclyl groups include piperidine, morpholine, thiomorpholine, piperazine. Partially saturated heterocyclyl groups include pyrazolines, for example 2-pyrazoline and 3-pyrazoline.

Examples of non-aromatic heterocyclyl groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclyl groups include saturated groups such as piperidine, pyrrolidine, azetidine, morpholine, piperazine and N-alkyl piperazines.

In a nitrogen-containing non-aromatic heterocyclyl ring the ring must contain at least one ring nitrogen atom. The heterocylic groups can contain, for example cyclic amine moieties (e.g. as in pyrrolidine), cyclic amides (such as a pyrrolidinone, piperidone or caprolactam), cyclic sulphonamides (such as an isothiazolidine 1,1-dioxide, [1,2]thiazinane 1,1-dioxide or [1,2]thiazepane 1,1-dioxide) and combinations thereof. Particular examples of nitrogen-containing non-aromatic heterocyclyl groups include aziridine, morpholine, thiomorpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, dihydrothiazole, imidazoline, imidazolidinone, oxazoline, thiazoline, 6H-1,2,5-thiadiazine, 2-pyrazoline, 3-pyrazoline, pyrazolidine, piperazine, and N-alkyl piperazines such as N-methyl piperazine.

The heterocyclyl groups can be polycyclic fused ring systems or bridged ring systems such as the oxa- and aza analogues of bicycloalkanes, tricycloalkanes (e.g. adamantane and oxa-adamantane). For an explanation of the distinction between fused and bridged ring systems, see *Advanced Organic Chemistry*, by Jerry March, 4$^{th}$ Edition, Wiley Interscience, pages 131-133, 1992.

The heterocyclyl groups can each be unsubstituted or substituted by one or more substituent groups. For example, heterocyclyl groups can be unsubstituted or substituted by 1, 2, 3 or 4 substituents. Where the heterocyclyl group is monocyclic or bicyclic, typically it is unsubstituted or has 1, 2 or 3 substituents.

The term "carbocyclyl" as used herein shall, unless the context indicates otherwise, include both aromatic and non-aromatic ring systems. Thus, for example, the term "carbocyclyl group" includes within its scope aromatic, non-aromatic, unsaturated, partially saturated and fully saturated carbocyclyl ring systems. In general, unless the context indicates otherwise, such groups may be monocyclic or bicyclic and may contain, for example, 3 to 12 ring members, more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, and preferably 5, 6 or 7 ring members, more preferably 5 or 6 ring members. Examples of bicyclic groups are those containing 8, 9, 10, 11 and 12 ring members, and more usually 9 or 10 ring members. Where reference is made herein to carbocyclyl groups, the carbocyclyl ring can, unless the context indicates otherwise, be optionally substituted (i.e. unsubstituted or substituted) by one or more substituents as discussed herein.

The term carbocyclyl comprises aryl, $C_{3-8}$cycloalkyl, $C_{3-8}$cycloalkenyl.

The term aryl as used herein refers to carbocyclyl aromatic groups including phenyl, naphthyl, indenyl, and tetrahydronaphthyl groups.

Whenever used hereinbefore or hereinafter that substituents can be selected each independently out of a list of numerous definitions, all possible combinations are intended which are chemically possible. Whenever used hereinbefore or hereinafter that a particular substituent is further substituted with two or more groups, such as for example hydroxyhalo$C_{1-4}$alkyl, hydroxyhalo$C_{1-4}$alkoxy, all possible combinations are intended which are chemically possible.

In one embodiment, the invention relates to a compound of formula (I-A).

In one embodiment, the invention relates to a compound of formula (I-B).

In one embodiment, Y represents —$CR^{18}$=N—$OR^{19}$. In particular wherein $R^{18}$ and $R^{19}$ represent $C_{1-6}$alkyl.

In one embodiment, Y represents -E-D wherein E represents a bond.

In one embodiment, Y represents a 3 to 12 ring membered monocyclic or bicyclic carbocyclyl or a 3 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups.

In one embodiment, Y represents a 5 to 12 ring membered monocyclic or bicyclic carbocyclyl or a 5 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups.

In one embodiment, Y represents an aromatic 3 to 12, in particular an aromatic 5 to 12, ring membered monocyclic or bicyclic carbocyclyl or an aromatic 3 to 12, in particular an aromatic 5 to 12, ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups.

In one embodiment, Y represents an aromatic 3 to 12 (e.g. 5 to 10) ring membered monocyclic or bicyclic carbocyclyl, wherein said carbocyclyl may be optionally substituted by one or more (e.g. 1, 2 or 3) $R^1$ groups.

In one embodiment, Y represents phenyl or naphthyl, wherein said phenyl or naphthyl may each be optionally substituted by one or more (e.g. 1, 2 or 3) $R^1$ groups.

In one embodiment, Y represents a 5 to 12 ring membered monocyclic or bicyclic heterocyclyl containing at least one heteroatom selected from N, O or S, wherein said heterocyclyl may each be optionally substituted by one or more (e.g. 1, 2 or 3) $R^1$ groups.

In one embodiment, Y represents an aromatic 5 to 12 ring membered monocyclic heterocyclyl containing at least one heteroatom selected from N, O or S, wherein said heterocyclyl group may each be optionally substituted by one or more (e.g. 1, 2 or 3) $R^1$ groups.

In one embodiment, Y represents a 5 or 6 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, Y represents an aromatic 5 or 6 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, Y represents a 5 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, Y represents a 5 ring membered monocyclic aromatic heterocyclyl containing at least one heteroatom selected from N, O or S, wherein said heterocyclyl may each be optionally substituted by one or more (e.g. 1, 2 or 3) $R^1$ groups.

In one embodiment, Y represents pyrazolyl (e.g. pyrazol-4yl), wherein said pyrazolyl may each be optionally substituted by one or more (e.g. 1, 2 or 3) $R^1$ groups.

In one embodiment, Y represents a 6 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, Y represents a 6 ring membered monocyclic aromatic heterocyclyl containing at least one heteroatom selected from N, O or S, wherein said heterocyclyl may each be optionally substituted by one or more (e.g. 1, 2 or 3) $R^1$ groups.

In one embodiment, Y represents a 12 ring membered bicyclic heterocyclyl containing at least one heteroatom selected from N, O or S, wherein said heterocyclyl may each be optionally substituted by one or more (e.g. 1, 2 or 3) $R^1$ groups.

In one embodiment, Y represents a 12 ring membered bicyclic aromatic heterocyclyl containing at least one heteroatom selected from N, O or S, wherein said heterocyclyl may each be optionally substituted by one or more (e.g. 1, 2 or 3) $R^1$ groups.

In one embodiment Y represents

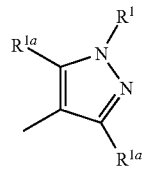

wherein $R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, cyano$C_{1-4}$alkyl, $C_{1-6}$alkoxy$C_{1-6}$alkyl wherein each C$_{1-6}$alkyl may optionally be substituted with one or two hydroxyl groups, C$_{1-6}$alkyl substituted with —NR$^4$R$^5$, C$_{1-6}$alkyl substituted with —C(=O)—NR$^4$R$^5$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl, C$_{1-6}$alkyl substituted with —NR$^{12}$—S(=O)$_2$—NR$^{14}$R$^{15}$, R$^6$, C$_{1-6}$alkyl substituted with R$^6$, C$_{1-6}$alkyl substituted with —C(=O)—R$^6$, hydroxyC$_{1-6}$alkyl substituted with R$^6$, C$_{1-6}$alkyl substituted with —Si(CH$_3$)$_3$, C$_{1-6}$alkyl substituted with —P(=O)(OH)$_2$ or C$_{1-6}$alkyl substituted with —P(=O)(OC$_{1-6}$alkyl)$_2$; and each R$^{1a}$ is independently selected from hydrogen, C$_{1-4}$alkyl, hydroxyC$_{1-4}$alkyl, C$_{1-4}$alkyl substituted with amino or mono- or di(C$_{1-4}$alkyl)amino or —NH(C$_{3-8}$cycloalkyl), cyanoC$_{1-4}$alkyl, C$_{1-4}$alkoxyC$_{1-4}$alkyl, and C$_{1-4}$alkyl substituted with one or more fluoro atoms. In one embodiment, R$^{1a}$ is independently selected from hydrogen and C$_{1-4}$alkyl. In one embodiment, R$^{1a}$ is hydrogen.

In one embodiment, Y represents

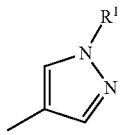

wherein R$^1$ represents hydrogen, C$_{1-6}$alkyl, C$_{2-4}$alkenyl, hydroxyC$_{1-6}$alkyl, haloC$_{1-6}$alkyl, hydroxyhaloC$_{1-6}$alkyl, C$_{1-6}$alkoxyC$_{1-6}$alkyl wherein each C$_{1-6}$alkyl may optionally be substituted with one or two hydroxyl groups, C$_{1-6}$alkyl substituted with —NR$^4$R$^5$, C$_{1-6}$alkyl substituted with —C(=O)—NR$^4$R$^5$, —S(=O)$_2$—C$_{1-6}$alkyl, —S(=O)$_2$-halo C$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl, C$_{1-6}$alkyl substituted with —NR$^{12}$—S(=O)$_2$—NR$^{14}$R$^{15}$, R$^6$, C$_{1-6}$alkyl substituted with R$^6$, C$_{1-6}$alkyl substituted with —C(=O)—R$^6$, hydroxyC$_{1-6}$alkyl substituted with R$^6$, C$_{1-6}$alkyl substituted with —Si(CH$_3$)$_3$, C$_{1-6}$alkyl substituted with —P(=O)(OH)$_2$ or C$_{1-6}$alkyl substituted with —P(=O)(OC$_{1-6}$alkyl)$_2$.

In one embodiment, E represents a bond, C$_{2-4}$alkenediyl optionally substituted with R$^{22}$, CO—(CR$^{22}$R$^{23}$)$_s$—, (CR$^{22}$R$^{23}$)$_s$—, —(CR$^{22}$R$^{23}$)$_s$—CO—, —NR$^{22}$—(CR$^{22}$R$^{23}$)$_s$—, —(CR$^{22}$R$^{23}$)$_s$—NR$^{22}$—, —O—(CR$^{22}$R$^{23}$)$_s$—, —(CR$^{22}$R$^{23}$)$_s$—CO—NR$^{22}$—(CR$^{22}$R$^{23}$)$_s$—, or —(CR$^{22}$R$^{23}$)$_s$—NR$^{22}$—CO—(CR$^{22}$R$^{23}$)$_s$—.

In one embodiment, E represents a bond, C$_{2-4}$alkenediyl, —CO—(CR$^{22}$R$^{23}$)$_s$—, —(CR$^{22}$R$^{23}$)$_s$—CO—, —NR$^{22}$—(CR$^{22}$R$^{23}$)$_s$—, —(CR$^{22}$R$^{23}$)$_s$—NR$^{22}$—, —(CR$^{22}$R$^{23}$)$_s$—CO—NR$^{22}$—(C$^{22}$R$^{23}$)$_s$— or —(CR$^{22}$R$^{23}$)$_s$—NR$^{22}$—CO—(CR$^{22}$R$^{23}$)$_s$—.

In one embodiment, E represents C$_{2-4}$alkenediyl, —CO—(CR$^{22}$R$^{23}$)$_s$—, —(CR$^{22}$R$^{23}$)$_s$—CO—, —NR$^{22}$—(CR$^{22}$R$^{23}$)$_s$—, —(CR$^{22}$R$^{23}$)$_s$—NR$^{22}$—, —(CR$^{22}$R$^{23}$)$_s$—CO—NR$^{22}$—(C$^{22}$R$^{23}$)$_s$— or —(CR$^{22}$R$^{23}$)$_s$—NR$^{22}$—CO—(CR$^{22}$R$^{23}$)$_s$—.

In one embodiment, E represents a bond.

In one embodiment, Y represents -E-D, wherein E is other than a bond.

In one embodiment, Y represents -E-D, wherein E is other than a bond and D represents any one of the following:
a 3 to 12 ring membered monocyclic or bicyclic carbocyclyl or a 3 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) R$^1$ groups;
a 5 to 12 ring membered monocyclic or bicyclic carbocyclyl or a 5 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) R$^1$ groups;
phenyl or naphthyl, wherein said phenyl or naphthyl may each be optionally substituted by one or more (e.g. 1, 2 or 3) R$^1$ groups;
a 5 to 12 ring membered monocyclic or bicyclic heterocyclyl containing at least one heteroatom selected from N, O or S, wherein said heterocyclyl may each be optionally substituted by one or more (e.g. 1, 2 or 3) R$^1$ groups;
a 5 or 6 ring membered monocyclic heterocyclyl containing at least one heteroatom selected from N, O or S, wherein said heterocyclyl may each be optionally substituted by one or more (e.g. 1, 2 or 3) R$^1$ groups;
a 5 ring membered monocyclic heterocyclyl containing at least one heteroatom selected from N, O or S, wherein said heterocyclyl may each be optionally substituted by one or more (e.g. 1, 2 or 3) R$^1$ groups;
a 5 ring membered monocyclic aromatic heterocyclyl containing at least one heteroatom selected from N, O or S, wherein said heterocyclyl group may each be optionally substituted by one or more (e.g. 1, 2 or 3) R$^1$ groups;
a 6 ring membered monocyclic heterocyclyl containing at least one heteroatom selected from N, O or S, wherein said heterocyclyl may each be optionally substituted by one or more (e.g. 1, 2 or 3) R$^1$ groups;
a 6 ring membered monocyclic aromatic heterocyclyl containing at least one heteroatom selected from N, O or S, wherein said heterocyclyl may each be optionally substituted by one or more (e.g. 1, 2 or 3) R$^1$ groups;
a 12 ring membered bicyclic heterocyclyl containing at least one heteroatom selected from N, O or S, wherein said heterocyclyl may each be optionally substituted by one or more (e.g. 1, 2 or 3) R$^1$ groups;
a 12 ring membered bicyclic aromatic heterocyclyl containing at least one heteroatom selected from N, O or S, wherein said heterocyclyl may each be optionally substituted by one or more (e.g. 1, 2 or 3) R$^1$ groups;

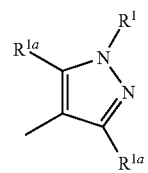

wherein R$^1$ represents hydrogen, C$_{1-6}$alkyl, C$_{2-4}$alkenyl, hydroxyC$_{1-6}$alkyl, haloC$_{1-6}$alkyl, hydroxyhaloC$_{1-6}$alkyl, cyanoC$_{1-4}$alkyl, C$_{1-6}$alkoxyC$_{1-6}$alkyl wherein each $C_{1-6}$alkyl may optionally be substituted with one or two hydroxyl groups, $C_{1-6}$alkyl substituted with —NR$^4$R$^5$, $C_{1-6}$alkyl substituted with —C(=O)—NR$^4$R$^5$, —S(=O)$_2$—$C_{1-6}$alkyl, —S(=O)$_2$-halo$C_{1-6}$alkyl, —S(=O)$_2$—NR$^{14}$R$^{15}$, $C_{1-6}$alkyl substituted with —S(=O)$_2$—$C_{1-6}$ alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NR$^{12}$—S(=O)$_2$—NR$^{14}$R$^{15}$, R$^6$, $C_{1-6}$alkyl substituted with R$^6$, $C_{1-6}$alkyl substituted with —C(=O)—R$^6$, hydroxy$C_{1-6}$alkyl substituted with R$^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$; and each R$^{1a}$ is independently selected from hydrogen, $C_{1-4}$alkyl, hydroxy$C_{1-4}$alkyl, $C_{1-4}$alkyl substituted with amino or mono- or di($C_{1-6}$alkyl)amino or —NH(C$_{3-8}$cycloalkyl), cyano$C_{1-4}$alkyl, $C_{1-4}$alkoxy$C_{1-4}$alkyl, and $C_{1-4}$alkyl substituted with one or more fluoro atoms;

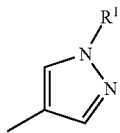

wherein R$^1$ represents hydrogen, $C_{1-6}$alkyl, $C_{2-4}$alkenyl, hydroxy$C_{1-6}$alkyl, halo$C_{1-6}$alkyl, hydroxyhalo$C_6$alkyl, $C_{1-6}$alkoxy$C_{1-6}$alkyl wherein each $C_{1-6}$alkyl may optionally be substituted with one or two hydroxyl groups, $C_{1-6}$alkyl substituted with —NR$^4$R$^5$, $C_{1-6}$alkyl substituted with —C(=O)—NR$^4$R$^5$, —S(=O)$_2$—$C_{1-6}$alkyl, —S(=O)$_2$-ha-loC$_1$. 6alkyl, —S(=O)$_2$—NR$^{14}$R$^{15}$, $C_{1-6}$alkyl substituted with —S(=O)$_2$—$C_{1-6}$alkyl, $C_{1-6}$alkyl substituted with —S(=O)$_2$-halo$C_6$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NR$^{12}$—S(=O)$_2$—NR$^{14}$R$^{15}$, R$^6$, $C_{1-6}$alkyl substituted with R$^6$, $C_{1-6}$alkyl substituted with —C(=O)—R$^6$, hydroxy$C_{1-6}$alkyl substituted with R$^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$.

In one embodiment, D is other than pyrazolyl, in particular D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrolidinyl, thiadiazolyl, oxadiazolyl, said rings being optionally substituted. Said optional substituents may represent halo, cyano, $C_{1-6}$alkyl, $C_{1-6}$alkoxy, —C(=O)—O—$C_{1-6}$alkyl, hydroxy$C_{1-6}$alkyl, —NR$^4$R$^5$, $C_{1-6}$alkyl substituted with —O—C(=O)—$C_{1-6}$alkyl, $C_{1-6}$alkyl substituted with —NR$^4$R$^5$, —C(=O)—NR$^4$R$^5$, —C(=O)—$C_{1-6}$alkyl-NR$^4$R$^5$, R$^6$, $C_{1-6}$alkyl substituted with R$^6$.

In one embodiment, E is other than a bond and D is other than pyrazolyl, in particular D is piperidinyl, pyridinyl, phenyl, pyrrolyl, imidazolyl, triazolyl, pyrrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrrolidinyl, thiadiazolyl, oxadiazolyl, said rings being optionally substituted.

In one embodiment, E is a bond and D is optionally substituted 4-pyrazolyl. In one embodiment, E is a bond and D is 4-pyrazolyl substituted at the 1 position with $C_{1-6}$alkyl for example methyl.

In one embodiment, E is a bond and D is 1-pyrazolyl or 2-pyrazolyl, both may optionally be substituted.

In one embodiment, E is other than a bond and D is 1-pyrazolyl or 2-pyrazolyl, both may optionally be substituted.

In one embodiment, E is other than a bond and D is optionally substituted pyrazolyl.

In one embodiment, E is a bond and D is an optionally substituted 6 membered carbocyclyl or an optionally substituted 5 or 6 membered saturated or aromatic heterocyclyl, such as for example an optionally substituted phenyl, pyrazolyl, pyrrolyl, pyridinyl, morpholino, piperazinyl or piperidinyl; more in particular D is an optionally substituted pyrazolyl; even more in particular D is pyrazolyl substituted with $C_{1-6}$alkyl.

In one embodiment R$^1$ represents hydrogen, $C_{1-6}$alkyl, $C_{2-4}$alkenyl, hydroxy$C_{1-6}$alkyl, halo$C_{1-6}$alkyl, hydroxyhalo$C_6$alkyl, cyano$C_{1-4}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —NR$^4$R$^5$, $C_{1-6}$alkyl substituted with —C(=O)—NR$^4$R$^5$, —S(=O)$_2$—$C_{1-6}$alkyl, —S(=O)$_2$-halo$C_{1-6}$alkyl, —S(=O)$_2$—NR$^{14}$R$^{15}$, $C_{1-6}$alkyl substituted with —S(=O)$_2$—$C_{1-6}$ alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NR$^{12}$—S(=O)$_2$—NR$^{14}$R$^{15}$, R, $C_{1-6}$alkyl substituted with R$^6$, $C_{1-6}$alkyl substituted with —C(=O)—R$^6$, hydroxy$C_{1-6}$alkyl substituted with R$^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$.

In one embodiment R$^1$ represents hydrogen, $C_{1-6}$alkyl, $C_{2-4}$alkenyl, hydroxy$C_{1-6}$alkyl, halo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —NR$^4$R$^5$, $C_{1-6}$alkyl substituted with —C(=O)—NR$^4$R$^5$, —S(=O)$_2$—$C_{1-6}$alkyl, —S(=O)$_2$—NR$^{14}$R$^{15}$, $C_{1-6}$alkyl substituted with —S(=O)$_2$—$C_{1-6}$alkyl, $C_{1-6}$alkyl substituted with —NH—S(=O)$_2$—$C_{1-6}$alkyl, R$^6$, $C_{1-6}$alkyl substituted with R$^6$, $C_{1-6}$alkyl substituted with —C(=O)—R$^6$, hydroxy$C_{1-6}$alkyl substituted with R$^6$, or $C_{1-6}$alkyl substituted with —Si(CH$_3$)$_3$.

In one embodiment R$^1$ represents hydrogen.

In one embodiment R$^1$ represents $C_{1-6}$alkyl, hydroxy$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —NR$^4$R$^5$, $C_{1-6}$alkyl substituted with —S(=O)$_2$—$C_{1-6}$alkyl, R$^6$, $C_{1-6}$alkyl substituted with R$^6$, more in particular R$^1$ represents $C_{1-6}$alkyl. In one embodiment R$^1$ represents methyl.

In one embodiment each R$^2$ is independently selected from hydroxyl, halogen, cyano, $C_{1-4}$alkyl, $C_{2-4}$alkenyl, $C_{1-4}$alkoxy, hydroxy$C_{1-4}$alkyl, hydroxy$C_{1-4}$alkoxy, halo$C_{1-4}$alkyl, halo$C_{1-4}$alkoxy, $C_{1-4}$alkoxy$C_{1-4}$alkyl, R$^{13}$, $C_{1-4}$alkoxy substituted with R$^{13}$, —C(=O)—R$^{13}$, $C_{1-4}$alkyl substituted with NR$^7$R$^8$, $C_{1-4}$alkoxy substituted with NR$^7$R$^8$, —NR$^7$R$^8$ and —C(=O)—NR$^7$R$^8$; or when two R$^2$ groups are attached to adjacent carbon atoms they may be taken together to form a radical of formula —O—(C(R$^{17}$)$_2$)$_p$—O— wherein R$^{17}$ represents hydrogen or fluorine and p represents 1 or 2.

In one embodiment each $R^2$ is independently selected from hydroxyl, halogen, cyano, $C_{1-4}$alkyl, $C_{2-4}$alkenyl, $C_{1-4}$alkoxy, hydroxy$C_{1-4}$alkyl, hydroxy$C_{1-4}$alkoxy, halo$C_{1-4}$alkoxy, $C_{1-4}$alkoxy$C_{1-4}$alkyl, $R^{13}$, $C_{1-4}$alkoxy substituted with $R^{13}$, —C(=O)—$R^{13}$, $C_{1-4}$alkyl substituted with $NR^7R^8$, $C_{1-4}$alkoxy substituted with $NR^7R^8$, —$NR^7R^8$ or —C(=O)—$NR^7R^8$.

In one embodiment one or more $R^2$ represents $C_{1-4}$alkoxy, for example $CH_3O$—, halogen, for example fluoro or chloro, hydroxyl, $C_{1-4}$alkyl, for example methyl, or —C(=O)—$NR^7R^8$, in particular one or more $R^2$ represents $C_{1-4}$alkoxy, for example $CH_3O$—, or halogen, for example fluoro.

In one embodiment one or more $R^2$ represents $C_{1-4}$alkoxy, for example $CH_3O$—.

In one embodiment n is equal to 0. In one embodiment n is equal to 1. In one embodiment n is equal to 2. In one embodiment n is equal to 3. In one embodiment n is equal to 4.

In one embodiment, n is equal to 2, 3 or 4, in particular n is equal to 3 or 4.

In one embodiment n is equal to 2 and one $R^2$ is present at the 3-position and the other is present at the 5-position.

In one embodiment n is equal to 2 and one $R^2$ is present at the 3-position and the other is present at the 5-position and each $R^2$ represents $C_{1-4}$alkoxy, for example each $R^2$ represents $CH_3O$—.

In one embodiment n is equal to 3 and one $R^2$ is present at the 2-position, one $R^2$ is present at the 3-position and one $R^2$ is present at the 5-position.

In one embodiment n is equal to 3 and one $R^2$ is present at the 3-position and represents $C_{1-4}$alkoxy, for example $CH_3O$—; one $R^2$ is present at the 5-position and represents $C_{1-4}$alkoxy, for example $CH_3O$—; one $R^2$ is present at the 2-position and represents halogen, for example fluoro.

In one embodiment n is equal to 4 and one $R^2$ is present at the 2-position, one $R^2$ is present at the 3-position, one $R^2$ is present at the 5-position and one $R^2$ is present at the 6-position.

In one embodiment n is equal to 4 and one $R^2$ is present at the 3-position and represents $C_{1-4}$alkoxy, for example $CH_3O$—; one $R^2$ is present at the 5-position and represents $C_{1-4}$alkoxy, for example $CH_3O$—; one $R^2$ is present at the 2-position and represents halogen, for example fluoro, and one $R^2$ is present at the 6-position and represents halogen, for example fluoro.

In one embodiment, $R^3$ represents $C_{1-6}$alkyl, hydroxy$C_{1-6}$alkyl, hydroxyhalo$C_{1-6}$alkyl, hydroxy$C_{2-6}$alkynyl, halo$C_{1-6}$alkyl, halo$C_{1-6}$alkyl optionally substituted (e.g. substituted) with —O—C(=O)—$C_{1-6}$alkyl, $C_{1-6}$alkyl substituted with —C(=O)—$C_6$alkyl, $C_{1-6}$alkoxy$C_{1-6}$alkyl wherein each $C_{1-6}$alkyl may optionally be substituted with one or two hydroxyl groups, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{1-6}$alkyl substituted with $R^9$, $C_{1-6}$alkyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, $C_{1-6}$alkyl substituted with —C(=O)—O—$C_{1-6}$alkyl, $C_{1-6}$alkyl substituted with —C(=O)—$NR^{10}R^{11}$, $C_{1-6}$alkyl substituted with carboxyl, $C_{1-6}$alkyl substituted with —O—C(=O)—$NR^{10}R^{11}$, $C_{1-6}$alkyl substituted with —$NR^{12}$—S(=O)$_2$—$C_{1-6}$alkyl, $C_{1-6}$alkyl substituted with —$NR^{12}$—S(=O)$_2$—$NR^{14}R^{15}$, $C_{1-6}$alkyl substituted with $R^9$ and optionally substituted with —O—C(=O)—$C_{1-6}$alkyl, $C_{1-6}$alkyl substituted with hydroxyl and $R^9$, —$C_{1-6}$alkyl-C($R^{12}$)=N—O—$R^{12}$, —S(=O)$_2$—$NR^{14}R^{15}$, $C_{1-6}$alkyl substituted with —S(=O)$_2$—$C_{1-6}$alkyl, $C_{1-6}$alkyl substituted with —C(=O)—$NR^{10}R^{11}$, $C_{1-6}$alkyl substituted with —C(=O)—$R^9$, $C_{2-6}$alkenyl substituted with $R^9$, $C_{2-6}$alkynyl substituted with $R^9$, hydroxy$C_{1-6}$alkoxy, $C_{2-6}$alkenyl, $C_{2-6}$alkynyl, $R^{13}$, $C_{1-6}$alkyl substituted with $C_{1-6}$alkoxy$C_{1-6}$alkyl-C(=O)— or $C_{1-6}$alkyl substituted with —P(=O)(O$C_{1-6}$alkyl)$_2$.

In one embodiment $R^3$ represents $C_{1-6}$alkyl, hydroxy$C_{1-6}$alkyl, hydroxyhalo$C_{1-6}$alkyl, halo$C_{1-6}$alkyl, $C_{1-6}$alkyl substituted with —C(=O)—$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with $R^9$, $C_{1-6}$alkyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, $C_{1-6}$alkyl substituted with —C(=O)—O—$C_{1-6}$alkyl, $C_{1-6}$alkyl substituted with —C(=O)—$NR^{10}R^{11}$, $C_{1-6}$alkyl substituted with carboxyl, $C_{1-6}$alkyl substituted with —O—C(=O)—$NR^{10}R^{11}$, $C_{1-6}$alkyl substituted with —$NR^{12}$—S(=O)$_2$—$C_{1-6}$alkyl, $C_{1-6}$alkyl substituted with —$NR^{12}$—S(=O)$_2$—$NR^{14}R^{15}$, $C_{1-6}$alkyl substituted with hydroxyl and $R^9$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —C(=O)—$R^9$, $C_{2-6}$alkynyl substituted with $R^9$, hydroxy$C_{1-6}$alkoxy, $C_{2-6}$alkenyl, $C_{2-6}$alkynyl, $R^{13}$ or $C_{1-6}$alkyl substituted with $C_{1-6}$alkoxy$C_{1-6}$alkyl-C(=O)—.

In one embodiment $R^3$ represents $C_{1-6}$alkyl, hydroxy$C_{1-6}$alkyl, halo$C_{1-6}$alkyl, halo$C_{1-6}$alkyl optionally substituted with —O—C(=O)—$C_{1-6}$alkyl, hydroxyhalo$C_6$alkyl, hydroxy$C_{2-6}$alkynyl, $C_{1-6}$alkyl substituted with —C(=O)—$C_{1-6}$alkyl, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{1-6}$alkyl substituted with $R^9$, cyano$C_{1-6}$alkyl, $C_{1-6}$alkyl substituted with —$NR^{10}R^{11}$, $C_{1-6}$alkyl substituted with hydroxyl and —$NR^{10}R^{11}$, $C_{1-6}$alkyl substituted with one or two halo atoms and —$NR^{10}R^{11}$, $C_{1-6}$alkyl substituted with —C(=O)—O—$C_{1-6}$alkyl, $C_{1-6}$alkyl substituted with $C_{1-6}$alkoxy$C_{1-6}$alkyl-C(=O)—, $C_{1-6}$alkyl substituted with —C(=O)—$NR^{10}R^{11}$, $C_{1-6}$alkyl substituted with —C(=O)—$NR^{14}R^{15}$, $C_{1-6}$alkyl substituted with carboxyl, $C_{1-6}$alkyl substituted with —O—C(=O)—$NR^{10}R^{11}$, $C_{1-6}$alkyl substituted with —$NR^{12}$—S(=O)$_2$—$C_{1-6}$alkyl, $C_{1-6}$alkyl substituted with —$NR^{12}$—S(=O)$_2$—$NR^{14}R^{15}$, $C_{1-6}$alkyl substituted with $R^9$ and substituted with —O—C(=O)—$C_{1-6}$alkyl, $C_{1-6}$alkyl substituted with hydroxyl and $R^9$, —$C_{1-6}$alkyl-C($R^{12}$)=N—O—$R^{12}$, —S(=O)$_2$—$NR^{14}R^{15}$, $C_{1-6}$alkyl substituted with —S(=O)$_2$—$C_{1-6}$alkyl, $C_{1-6}$alkyl substituted with —C(=O)—$R^9$, $C_{2-6}$alkenyl substituted with $R^9$, $C_{2-6}$alkynyl substituted with $R^9$, $C_{1-6}$alkyloxy$C_{1-6}$alkyl wherein each $C_{1-6}$alkyl may optionally be substituted with one or two hydroxyl groups, $C_{2-6}$alkenyl, $C_{2-6}$alkynyl, $R^{13}$, or $C_{1-6}$alkyl substituted with —P(=O)(O$C_{1-6}$alkyl)$_2$.

In one embodiment, $R^3$ represents $C_{1-6}$alkyl, hydroxy$C_{1-6}$alkyl, hydroxyhalo$C_{1-6}$alkyl, halo$C_{1-6}$alkyl, $C_{1-6}$alkyl substituted with —C(=O)—$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with $R^9$, $C_{1-6}$alkyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, $C_{1-6}$alkyl substituted with —C(=O)—O—$C_{1-6}$alkyl, $C_{1-6}$alkyl substituted with —O—C(=O)—$NR^{10}R^{11}$, $C_{1-6}$alkyl substituted with carboxyl, $C_{1-6}$alkyl substituted with —$NR^{12}$—S(=O)$_2$—$C_{1-6}$alkyl, $C_{1-6}$alkyl substituted with —$NR^{12}$—S(=O)$_2$—$NR^{14}R^{15}$, $C_{1-6}$alkyl substituted with hydroxyl and $R^9$, —$C_{1-6}$ alkyl-C($R^{12}$)=N—O—$R^{12}$, $C_{1-6}$alkyl substituted with —C(=O)—$NR^{10}R^{11}$, $C_{1-6}$alkyl substituted with —C(=O)—R$^9$, C$_{2-6}$alkynyl substituted with R$^9$, hydroxyC$_{1-6}$alkoxy, C$_{2-6}$alkenyl, C$_{2-6}$alkynyl or R$^{13}$.

In one embodiment R$^3$ represents C$_{2-6}$alkynyl, haloC$_{1-6}$alkyl optionally substituted with —O—C(=O)—C$_{1-6}$alkyl, hydroxyC$_{1-6}$alkyl optionally substituted with —O—C(=O)—C$_{1-6}$alkyl, hydroxyhaloC$_6$alkyl, C$_{1-6}$alkoxyC$_{1-6}$alkyl wherein each C$_{1-6}$alkyl may optionally be substituted with one or two hydroxyl groups or with —O—C(=O)—C$_{1-6}$alkyl, C$_{1-6}$alkyl substituted with R$^9$, C$_{2-6}$alkynyl substituted with R$^9$, C$_{1-6}$alkyl substituted with —NR$^{10}$R$^{11}$, or C$_{1-6}$alkyl substituted with —O—C(=O)—NR$^{10}$R$^{11}$.

In one embodiment R$^3$ represents hydroxyC$_{1-6}$alkyl, hydroxyhaloC$_{1-6}$alkyl, C$_{1-6}$alkyl substituted with R$^9$, C$_{1-6}$alkyl substituted with —NR$^{10}$R$^{11}$, C$_{2-6}$alkynyl substituted with R$^9$, or C$_{2-6}$alkynyl.

In one embodiment R$^3$ represents C$_{1-6}$alkyl, hydroxyC$_{1-6}$alkyl, hydroxyhaloC$_{1-6}$alkyl, cyanoC$_6$alkyl, C$_{1-6}$alkyl substituted with carboxyl, C$_{1-6}$alkyl substituted with —C(=O)—O—C$_{1-6}$alkyl, C$_{1-6}$alkyl substituted with R$^9$, C$_{1-6}$alkyl substituted with —C(=O)—R$^9$, C$_{1-6}$alkyl substituted with hydroxyl and R$^9$, C$_{1-6}$alkyl substituted with —NR$^{10}$R$^{11}$, C$_{1-6}$alkyl substituted with —C(=O)—NR$^{10}$R$^{11}$, C$_{1-6}$alkyl substituted with —S(=O)$_2$—C$_{1-6}$alkyl, C$_{1-6}$alkoxyC$_{1-6}$alkyl wherein each C$_{1-6}$alkyl may optionally be substituted with one or two hydroxyl groups or with —O—C(=O)—C$_{1-6}$alkyl, C$_{2-6}$alkynyl substituted with R$^9$, or C$_{2-6}$alkynyl. In one embodiment, R$^3$ represents hydroxyC$_{1-6}$alkyl, haloC$_{1-6}$alkyl, C$_{1-6}$alkyl substituted with R$^9$, C$_{1-6}$alkyl substituted with —NR$^{10}$R$^{11}$, C$_{1-6}$alkoxyC$_{1-6}$alkyl, or C$_{2-6}$alkynyl.

In one embodiment R$^3$ represents hydroxyC$_{1-6}$alkyl, hydroxyhaloC$_{1-6}$alkyl, C$_{1-6}$alkyl substituted with R$^9$, C$_{1-6}$alkyl substituted with —NR$^{10}$R$^{11}$, C$_{1-6}$alkoxyC$_{1-6}$alkyl wherein each C$_{1-6}$alkyl may optionally be substituted with one or two hydroxyl groups or with —O—C(=O)—C$_{1-6}$alkyl, C$_{2-6}$alkynyl substituted with R$^9$, or C$_{2-6}$alkynyl.

In one embodiment R$^3$ represents hydroxyC$_{1-6}$alkyl, hydroxyC$_{1-6}$alkoxyl, hydroxyhaloC$_{1-6}$alkyl, C$_{1-6}$alkyl substituted with R$^9$, C$_{1-6}$alkyl substituted with —NR$^{10}$R$^{11}$, C$_{2-6}$alkynyl or C$_{2-6}$alkynyl substituted with R$^9$.

In one embodiment R$^3$ represents C$_{2-6}$alkynyl. R$^3$ may represent CH$_2$—C≡C—H.

In one embodiment when R$^3$ represents C$_{1-6}$alkyl (e.g. C$_{1-4}$alkyl) substituted with R$^9$. R$^9$ represents an optionally substituted aromatic 5 or 6 membered monocyclic heterocyclyl, for example optionally substituted imidazolyl, pyrimidinyl, or pyrazinyl.

In one embodiment when R$^3$ represents C$_{1-6}$alkyl (e.g. C$_{1-4}$alkyl) substituted with R$^9$, wherein R$^9$ represents an optionally substituted aromatic 6 membered monocyclic heterocyclyl containing one or two nitrogen heteroatom, for example pyrimidinyl or pyrazinyl.

In one embodiment when R$^3$ represents C$_{1-4}$alkyl (e.g. methyl) substituted with R$^9$, wherein R$^9$ represents unsubstituted imidazolyl (e.g. imidazol-2-yl), unsubstituted pyrimidinyl (e.g. pyrimidin-2-yl), unsubstituted pyrazinyl, or imidazolyl substituted with —S(O)$_2$—N(CH$_3$)$_2$.

In one embodiment R$^3$ represents C$_{2-6}$alkynyl (e.g. —CH$_2$—C≡C—) substituted with R$^9$. R$^9$ may represent an optionally substituted aromatic 6-membered monocyclic heterocycle containing one or two nitrogen heteroatoms, for example pyridinyl. The heterocyclyl may be substituted, for example substituted with one C$_{1-4}$alkoxy substituent, for example —OCH$_3$. R$^3$ may represent —CH$_2$—C≡C—(3-methoxy-pyridin-2-yl).

In one embodiment R$^3$ represents C$_{1-6}$alkyl substituted with hydroxyl, halo and/or —NR$^{10}$R$^{11}$. In one embodiment R$^3$ represents C$_{1-6}$alkyl substituted with hydroxyl, halo or NR$^{10}$R$^{11}$, wherein the C$_{1-6}$alkyl group is a straight chain alkyl group e.g. 2-ethyl, n-propyl, n-butyl. In a further embodiment R$^3$ represents C$_{1-6}$alkyl substituted with hydroxyl or —NR$^{10}$R$^{11}$.

In one embodiment R$^3$ represents hydroxyC$_{1-6}$alkyl. R$^3$ may represent —CH$_2$CH$_2$OH or —CH$_2$CH$_2$CH$_2$OH.

In one embodiment R$^3$ represents hydroxyhaloC$_{1-6}$alkyl, for example R$^3$ may represent —CH$_2$CHOHCF$_3$.

In one embodiment R$^3$ represents C$_{1-6}$alkoxyC$_{1-6}$alkyl wherein each C$_{1-6}$alkyl may optionally be substituted with one or two hydroxyl groups, for example R$^3$ may represent —CH$_2$CHOHCH$_2$OCH$_3$.

In one embodiment R$^3$ represents C$_{1-6}$alkyl (e.g. C$_{1-4}$alkyl) substituted with R$^9$ or C$_{1-6}$alkyl substituted with —NR$^{10}$R$^{11}$. In particular, R$^3$ represents C$_{1-6}$alkyl (e.g. C$_{1-4}$alkyl) substituted with R$^9$ wherein R$^9$ represents an optionally substituted 5 membered saturated heterocycle, such as for example pyrrolidinonyl or oxazolidinonyl, or an optionally substituted 5 membered aromatic heterocycle, such as for example imidazolyl or triazolyl, or R$^3$ represents C$_{1-6}$alkyl substituted with —NR$^{10}$R$^{11}$ wherein R$^{10}$ and R$^{11}$ each independently represent hydrogen, —C(=O)—C$_{1-6}$alkyl or R$^6$.

In a yet further embodiment R$^3$ represents C$_{1-6}$alkyl substituted with —NR$^{10}$R$^{11}$. In one embodiment R$^3$ represents C$_{1-4}$alkyl substituted with —NR$^{10}$R$^{11}$. In one embodiment R$^3$ represents C$_{1-4}$alkyl substituted —NR$^{10}$R$^{11}$, wherein the C$_{1-4}$alkyl group is a straight chain alkyl group e.g. 2-ethyl, n-propyl. In one embodiment R$^3$ represents C$_{1-4}$alkyl substituted with —NR$^{10}$R$^{11}$, wherein the C$_{1-4}$alkyl group is an ethylene group (—CH$_2$CH$_2$—).

In one embodiment when R$^3$ represents C$_{1-6}$alkyl (e.g. 2-ethyl, n-propyl) substituted with —NR$^{10}$R$^{11}$, wherein R$^{10}$ and R$^{11}$ are independently selected from hydrogen, C$_{1-6}$alkyl and haloC$_{1-6}$alkyl (e.g. hydrogen, iso-propyl or —CH$_2$CF$_3$).

In one embodiment when R$^3$ represents C$_{1-6}$alkyl substituted with —NR$^{10}$R$^{11}$, and one of R$^{10}$ and R$^{11}$ represents hydrogen and the other represents C$_{1-6}$alkyl, for example —CH$_3$ or —CH(CH$_3$)$_2$. R$^3$ may represent —CH$_2$CH$_2$NHCH$_3$ or —CH$_2$CH$_2$NHCH(CH$_3$)$_2$;

In one embodiment R$^3$ represents —CH$_2$CH$_2$NHCH(CH$_3$)$_2$.

In one embodiment, R$^9$ is selected from:
an optionally substituted C$_{3-8}$cycloalkyl,
an optionally substituted aromatic 5 membered monocyclic heterocyclyl,
an optionally substituted saturated 6 membered monocyclic heterocyclyl.
a saturated or an aromatic 3, 4, 5 or 6 membered monocyclic heterocyclyl containing one or two oxygen heteroatoms,
an optionally substituted 4 membered heterocyclyl containing one oxygen heteroatom,
an optionally substituted aromatic 6 membered monocyclic heterocycle containing one or two nitrogen heteroatoms,
a partially saturated 6 membered monocyclic heterocyclyl containing one nitrogen heteroatom which may optionally be substituted,
an optionally substituted saturated 4 membered monocyclic heterocyclyl containing one nitrogen heteroatom,
a saturated 5 membered monocyclic heterocyclyl containing one nitrogen heteroatom,
a saturated 6 membered monocyclic heterocyclyl containing one nitrogen heteroatom, a bicyclic heterocyclyl containing a benzene ring fused to a 5- or 6-membered ring containing 1, 2 or 3 ring heteroatoms, a 4, 5 or 6 membered monocyclic saturated heterocycle substituted with two substituents which are attached to the same atom and which are taken together to form a 4 to 7-membered saturated monocyclic heterocyclyl containing at least one heteroatom selected from N, O or S, an optionally substituted aromatic 5 membered monocyclic heterocyclyl containing one sulphur heteroatom, an optionally substituted aromatic 5 membered monocyclic heterocyclyl containing one sulphur and one nitrogen heteroatom, a saturated 6 membered monocyclic heterocyclyl containing two nitrogen heteroatoms, an aromatic 5 membered monocyclic heterocyclyl containing four nitrogen heteroatoms, an aromatic 5 membered monocyclic heterocyclyl containing one oxygen and two nitrogen heteroatoms, an optionally substituted aromatic 5 membered monocyclic heterocyclyl containing two nitrogen heteroatoms, an optionally substituted aromatic 5 membered monocyclic heterocyclyl containing three nitrogen heteroatoms, a saturated 5 membered monocyclic heterocyclyl containing one nitrogen and one oxygen heteroatom, a saturated 6 membered monocyclic heterocyclyl containing one nitrogen and one sulphur heteroatom, a saturated 7 membered monocyclic heterocyclyl containing two nitrogen heteroatoms, a saturated 7 membered monocyclic heterocyclyl containing one nitrogen and one oxygen heteroatom, and phenyl or naphthyl, in particular phenyl.

In one embodiment, $R^9$ represents an optionally substituted 4 membered saturated heterocycle, such as for example oxetanyl; an optionally substituted 5 membered saturated heterocycle, such as for example pyrrolidinonyl, tetrahydrofuranyl or oxazolidinonyl; an optionally substituted 5 membered aromatic heterocycle, such as for example imidazolyl, oxadiazolyl, isoxazolyl, triazolyl, tetrazolyl, or pyrazolyl; an optionally substituted 6 membered saturated heterocycle, such as for example tetrahydropyranyl or morpholino; an optionally substituted 6 membered aromatic heterocycle, such as for example pyridyl, pyrimidinyl or pyrazinyl; an optionally substituted bicyclic heterocycle, such as for example benzimidazolyl or imidazotetrahydropyridinyl (3H imidazo[4,5-c]4,5,6,7-tetrahydropyridinyl); or $C_{3-6}$cycloalkyl, such as for example cyclopropyl. In one embodiment, $R^9$ represents an optionally substituted 5 membered aromatic heterocycle, such as for example imidazolyl, or an optionally substituted 6 membered aromatic heterocycle, such as for example pyridyl, pyrimidinyl or pyrazinyl. Optional substituents may represent $C_{1-4}$alkoxy or —S(=O)$_2$—NR$^{14}$R$^{15}$.

In one embodiment $R^9$ represents an optionally substituted 5 membered saturated heterocycle, such as for example pyrrolidonyl or oxazolidinonyl, or an optionally substituted 5 membered aromatic heterocycle, such as for example imidazolyl or triazolyl.

In one embodiment, $R^9$ represents an optionally substituted 5 membered aromatic heterocycle, such as for example imidazolyl. Optional substituents may represent —S(=O)$_2$—NR$^{14}$R$^{15}$.

In one embodiment, $R^9$ represents an optionally substituted 6 membered aromatic heterocycle, such as for example pyridinyl or pyrimidinyl. Optional substituents may represent $C_{1-4}$alkoxy.

In one embodiment, $R^9$ represents an optionally substituted 5 membered aromatic or saturated heterocycle, such as for example imidazolyl, pyrolidinyl, oxazolidinyl. Optional substituents may represent =O, a 5 or 6-membered aromatic monocyclic heterocyclyl containing at least one heteroatom selected from N, O or S wherein said heterocyclyl is optionally substituted with $R^{16}$; or —S(=O)$_2$—NR$^{14}$R$^{15}$.

In one embodiment, $R^9$ represents $C_{3-6}$cycloalkyl, such as for example cyclopropyl, a 3 membered saturated heterocyclyl, such as for example oxiranyl, an optionally substituted 5 membered saturated heterocycle, such as for example pyrolidinonyl, an optionally substituted 6 membered aromatic or saturated heterocycle, such as for example pyridyl, pyrimidinyl, pyrazinyl, piperazinyl, or morpholinyl, an optionally substituted bicyclic heterocycle, such as for example 1H-isoindol-1,3-dione. Optional substituents may represent =O, $C_{1-4}$alkoxy, $C_{1-4}$alkyl substituted with —NR$^{14}$R$^{15}$, hydroxy$C_{1-4}$alkyl, or $C_{1-4}$alkyl-C(=O)—.

In one embodiment, optional substituents of $R^9$ are hydroxyl, oxo, $C_{1-4}$alkyl, for example methyl, hydroxy$C_{1-4}$alkyl, $C_{1-4}$alkoxy$C_{1-4}$alkyl, halogen, —NR$^{14}$R$^{15}$, $C_{1-4}$alkyl substituted with —NR$^{14}$R$^{15}$, $C_{1-4}$alkoxy, —S(=O)$_2$—NR$^{14}$R$^{15}$, in particular oxo. In one embodiment $R^{10}$ represents hydrogen or $C_{1-6}$alkyl.

In one embodiment $R^{10}$ is hydrogen.

In one embodiment $R^{11}$ represents hydrogen, $C_{1-6}$alkyl, halo$C_{1-6}$alkyl, —C(=O)—$C_{1-6}$alkyl, —S(=O)$_2$—$C_{1-6}$alkyl, —S(=O)$_2$—NR$^{14}$R$^{15}$, hydroxy$C_{1-6}$alkyl, —C(=O)-hydroxyhalo$C_{1-6}$alkyl, —C(=O)—$R^6$, cyano$C_{1-6}$ alkyl, $R^6$, —C(=O)—$R^6$, $C_{1-6}$alkyl substituted with $R^6$, —C(=O)-halo$C_{1-6}$alkyl, $C_{1-6}$alkyl substituted with —Si(CH$_3$)$_3$, $C_{1-6}$alkyl substituted with —NR$^{14}$R$^{15}$, $C_{1-6}$alkyl substituted with —C(=O)—NR$^{14}$R$^{15}$, $C_{1-6}$alkoxy, hydroxyhalo$C_{1-6}$alkyl, carboxyl, or $C_{1-6}$alkoxy$C_{1-6}$alkyl.

In one embodiment $R^{10}$ and $R^{11}$ represent hydrogen, $C_{1-6}$alkyl, hydroxy$C_{1-6}$alkyl, —C(=O)—$C_{1-6}$alkyl, or $R^6$. In one embodiment $R^{10}$ and $R^{11}$ represent hydrogen or $C_{1-6}$alkyl.

In one embodiment, $R^6$ represents a 6-membered monocyclic saturated heterocyclyl which is optionally substituted. For example piperazinyl or morpholinyl or tetrahydropyranyl, optionally substituted with halogen, $C_{1-6}$alkyl, or $C_{1-6}$alkyl-O—C(=O)—.

In one embodiment, $R^6$ represents a 6-membered monocyclic aromatic heterocyclyl which is optionally substituted. For example pyridinyl, optionally substituted with halogen, $C_{1-6}$alkyl, or $C_{1-6}$alkyl-O—C(=O)—.

In one embodiment, $R^6$ represents a 4 membered monocyclic saturated heterocycle, such as for example oxetanyl; or a 6-membered monocyclic saturated heterocyclyl, such as for example piperidinyl, or a 5-membered monocyclic aromatic heterocycle, such as for example imidazolyl.

In one embodiment, $R^4$ and $R^5$ represent hydrogen.

In one embodiment, $R^7$ and $R^8$ each independently represent hydrogen or $C_{1-6}$alkyl, for example methyl.

In one embodiment, $R^{12}$ represents hydrogen or $C_{1-4}$alkyl optionally substituted with $C_{1-4}$alkyloxy.

In one embodiment, $R^{13}$ represents a saturated 4 to 6-membered monocyclic heterocyclyl containing at least one heteroatom selected from N or O.

In one embodiment, $R^{14}$ and $R^{15}$ each independently represent hydrogen or $C_{1-4}$alkyl optionally substituted with hydroxyl. In one embodiment, $R^{14}$ and $R^{15}$ each independently represent hydrogen or $C_{1-4}$alkyl.

In one embodiment, $R^{22}$ and $R^{23}$ each independently represent hydrogen.

In one embodiment of the invention, n represents an integer equal to 2, 3 or 4; and each $R^2$ represents $C_{1-4}$alkoxy, for example $CH_3O$—, or halogen, for example fluoro; $R^3$ represents hydroxy$C_{1-6}$alkyl, hydroxyhalo$C_{1-6}$alkyl, $C_{1-6}$alkyl substituted with $R^9$, $C_{1-6}$alkyl substituted with —$NR^{10}R^{11}$, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{2-6}$alkynyl substituted with $R^9$, $C_{2-6}$alkynyl; Y represents -E-D wherein E represents a bond and D represents optionally substituted pyrazolyl.

In one embodiment of the invention, n represents an integer equal to 2, 3 or 4; and each $R^2$ represents $C_{1-4}$alkoxy, for example $CH_3O$—, or halogen, for example fluoro; $R^3$ represents hydroxy$C_{1-6}$alkyl, hydroxyhalo$C_{1-6}$alkyl, $C_{1-6}$alkyl substituted with $R^9$, $C_{1-6}$alkyl substituted with —$NR^{10}R^{11}$, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{2-6}$alkynyl substituted with $R^9$, $C_{2-6}$alkynyl; Y represents -E-D wherein E represents a bond and D represents pyrazolyl substituted with $C_{1-6}$alkyl; $R^{10}$ and $R^{11}$ represent hydrogen or $C_{1-6}$alkyl; $R^9$ represents an optionally substituted 5 membered aromatic heterocycle, such as for example imidazolyl, or an optionally substituted 6 membered aromatic heterocycle, such as for example pyridyl, pyrimidinyl or pyrazinyl.

In one embodiment of the invention, n represents an integer equal to 2, 3 or 4; and each $R^2$ represents $C_{1-4}$alkoxy, for example $CH_3O$—, halogen, for example fluoro or chloro, hydroxyl, $C_{1-4}$alkyl, for example methyl, or —C(=O)—$NR^7R^8$, for example —C(=O)—NH—$CH_3$; $R^3$ represents $C_{1-6}$alkyl, for example methyl or ethyl, hydroxy$C_{1-6}$alkyl, hydroxyhalo$C_{1-6}$alkyl, cyano$C_{1-6}$alkyl, $C_{1-6}$alkyl substituted with carboxyl, $C_{1-6}$alkyl substituted with —C(=O)—O—$C_{1-6}$alkyl, $C_{1-6}$alkyl substituted with $R^9$, $C_{1-6}$alkyl substituted with —C(=O)—$R^9$, $C_{1-6}$alkyl substituted with hydroxyl and $R^9$, $C_{1-6}$alkyl substituted with —$NR^{10}R^{11}$, $C_{1-6}$alkyl substituted with —C(=O)—$NR^{10}R^{11}$, $C_{1-6}$alkyl substituted with —S(=O)$_2$—$C_{1-6}$alkyl, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{2-6}$alkynyl substituted with $R^9$, $C_{2-6}$alkynyl; Y represents -E-D wherein E represents a bond and D represents an optionally substituted monocyclic 6 membered carbocyclyl, for example phenyl, or an optionally substituted 5 or 6 membered monocyclic heterocyclyl, for example an optionally substituted 5 or 6 membered saturated or aromatic heterocyclyl, such as for example pyrazolyl, pyrrolyl, pyridinyl, morpholino, piperazinyl or piperdininyl, in particularly D represents pyrazolyl optionally substituted with $C_{1-6}$alkyl, more in particular D represents pyrazolyl substituted with $C_{1-6}$alkyl.

In one embodiment of the invention, n represents an integer equal to 2, 3 or 4; and each $R^2$ represents $C_{1-4}$alkoxy, for example $CH_3O$—, halogen, for example fluoro or chloro, hydroxyl, $C_{1-4}$alkyl, for example methyl, or —C(=O)—$NR^7R^8$, for example —C(=O)—NH—$CH_3$; $R^3$ represents $C_{1-6}$alkyl, for example methyl or ethyl, hydroxy$C_{1-6}$alkyl, hydroxyhalo$C_{1-6}$alkyl, cyano$C_{1-6}$alkyl, $C_{1-6}$alkyl substituted with carboxyl, $C_{1-6}$alkyl substituted with —C(=O)—O—$C_{1-6}$alkyl, $C_{1-6}$alkyl substituted with $R^9$, $C_{1-6}$alkyl substituted with —C(=O)—$R^9$, $C_{1-6}$alkyl substituted with hydroxyl and $R^9$, $C_{1-6}$alkyl substituted with —$NR^{10}R^{11}$, $C_{1-6}$alkyl substituted with —C(=O)—$NR^{10}R^{11}$, $C_{1-6}$alkyl substituted with —S(=O)$_2$—$C_{1-6}$alkyl, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{2-6}$alkynyl substituted with $R^9$, $C_{2-6}$alkynyl; Y represents -E-D wherein E represents a bond and D represents an optionally substituted monocyclic 6 membered carbocyclyl, for example phenyl, or an optionally substituted 5 or 6 membered monocyclic heterocyclyl, for example an optionally substituted 5 or 6 membered saturated or aromatic heterocyclyl, such as for example pyrazolyl, pyrrolyl, pyridinyl, morpholino, piperazinyl or piperidinyl, in particularly D represents pyrazolyl optionally substituted with $C_{1-6}$alkyl, more in particular D represents pyrazolyl substituted with $C_{1-6}$alkyl; $R^1$ represents $C_{1-6}$alkyl, hydroxy$C_{1-6}$alkyl, hydroxyhalo$C_6$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —S(=O)$_2$—$C_{1-6}$alkyl, $R^6$, $C_{1-6}$alkyl substituted with $R^6$, more in particular $R^1$ represents $C_{1-6}$alkyl, for example methyl; $R^9$ represents an optionally substituted 4 membered saturated heterocycle, such as for example oxetanyl; an optionally substituted 5 membered saturated heterocycle, such as for example pyrrolidinonyl, tetrahydrofuranyl or oxazolidinonyl; an optionally substituted 5 membered aromatic heterocycle, such as for example imidazolyl, oxadiazolyl, isoxazolyl, triazolyl, tetrazolyl, or pyrazolyl; an optionally substituted 6 membered saturated heterocycle, such as for example tetrahydropyranyl or morpholino; an optionally substituted 6 membered aromatic heterocycle, such as for example pyridyl, pyrimidinyl or pyrazinyl; an optionally substituted bicyclic heterocycle, such as for example benzimidazolyl or imidazotetrahydropyridinyl (3H imidazo[4,5-c]4,5,6,7-tetrahydropyridinyl); or $C_{3-6}$cycloalkyl, such as for example cyclopropyl, more in particular $R^9$ represents an optionally substituted 5 membered saturated heterocycle, such as for example pyrrolidinonyl or oxazolidinonyl, or an optionally substituted 5 membered aromatic heterocycle, such as for example imidazolyl or triazolyl; $R^{10}$ and $R^{11}$ represent hydrogen, $C_{1-6}$alkyl, hydroxy$C_{1-6}$alkyl, —C(=O)—$C_{1-6}$alkyl, or $R^6$; in particular $R^{10}$ and $R^{11}$ represent hydrogen, —C(=O)—$C_{1-6}$alkyl, or $R^6$; $R^6$ represents a 4 membered monocyclic saturated heterocycle, such as for example oxetanyl; or a 6-membered monocyclic saturated heterocyclyl, such as for example piperidinyl; or a 5-membered monocyclic aromatic heterocycle, such as for example imidazolyl; $R^4$ and $R^5$ represent hydrogen; $R^7$ and $R^8$ each independently represent hydrogen or $C_{1-6}$alkyl, for example methyl, $R^{14}$ and $R^{15}$ each independently represent hydrogen or $C_{1-4}$alkyl optionally substituted with hydroxyl.

In one embodiment, Y is -E-D, wherein E is a bond and D is a 5 or 6 membered monocyclic aromatic heterocyclyl, wherein said heterocyclyl may optionally be substituted by one or more (e.g. 1, 2 or 3) $R^1$ groups, and wherein one or more of the following applies:

n is 2;
$R^2$ is $C_{1-6}$alkyloxy;
$R^2$ is placed in position 3 and 5.

In one embodiment, Y is -E-D, wherein E is a bond and D is piperidinyl, pyridinyl, phenyl, pyrrolyl, imidazolyl, triazolyl, pyrrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrrolidinyl, thiadiazolyl, oxadiazolyl, said rings being optionally substituted, more in particular D is piperidinyl, pyridinyl, phenyl, pyrrolyl, imidazolyl, triazolyl, pyrrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrrolidinyl, thiadiazolyl, oxadiazolyl, said rings being optionally substituted and n is 2, even more in particular D is piperidinyl, pyridinyl, phenyl, pyrrolyl, imidazolyl, triazolyl, pyrrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrrolidinyl, thiadiazolyl, oxadiazolyl, said rings being optionally substituted; n is 2, $R^2$ is $C_{1-6}$alkyloxy, even further in particular D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrrolidinyl, thiadiazolyl, oxadiazolyl, said rings being optionally substituted; n is 2, $R^2$ is $C_{1-6}$alkyloxy and said $R^2$ is placed in position 3 and 5.

In one embodiment there is provided compounds of formula (I):

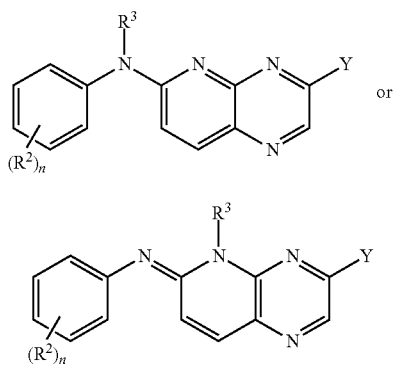

(I-A)

or (I-B)

including any tautomeric or stereochemically isomeric form thereof, wherein each $R^2$ is independently selected from $C_{1-4}$alkoxy, for example $CH_3O$—, or halogen, for example fluoro;

Y represents -E-D;

D represents a 3 to 12 ring membered monocyclic or bicyclic carbocyclyl or a 3 to 12 ring membered monocyclic or bicyclic heterocyclyl containing at least one heteroatom selected from N, O or S, for example pyrazolyl, wherein said carbocyclyl and heterocyclyl may each be optionally substituted by one or more (e.g. 1, 2 or 3) $R^1$ groups;

E represents a bond;

$R^1$ represents $C_{1-6}$alkyl, for example methyl;

$R^3$ represents hydroxy$C_{1-6}$alkyl, for example —$CH_2CH_2OH$ or —$CH_2CH_2CH_2OH$, hydroxyhalo$C_{1-6}$alkyl, for example —$CH_2CHOHCF_3$, $C_{1-6}$alkyl substituted with $R^9$, for example —$CH_2$— substituted with imidazol-2-yl, —$CH_2$— substituted with imidazol-2-yl substituted in the 1 position with —$S(O)_2$—$N(CH_3)_2$, —$CH_2$— substituted with pyrimidin-2-yl, —$CH_2$— substituted with pyrazin-2-yl, $C_{1-6}$alkyl substituted with —$NR^{10}R^{11}$, for example —$CH_2CH_2NHCH_3$ or —$CH_2CH_2NHCH(CH_3)_2$, $C_{1-6}$alkoxy$C_6$alkyl wherein each $C_{1-6}$alkyl may optionally be substituted with one or two hydroxyl groups, for example —$CH_2CHOHCH_2OCH_3$, $C_{2-6}$alkynyl substituted with $R^9$, for example —$CH_2$—C≡C— (3-methoxy-pyridin-2-yl), or $C_{2-6}$alkynyl, for example —$CH_2$—C≡C—H; and n independently represents an integer equal to 2, 3 or 4;

the N-oxides thereof, the pharmaceutically acceptable salts thereof or the solvates thereof.

In one embodiment there is provided compounds of formula (I)

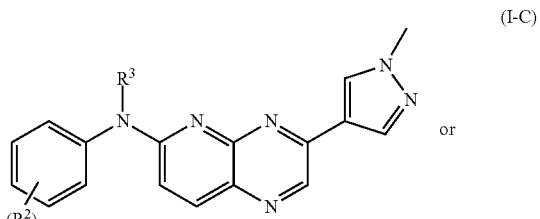

(I-C)

or

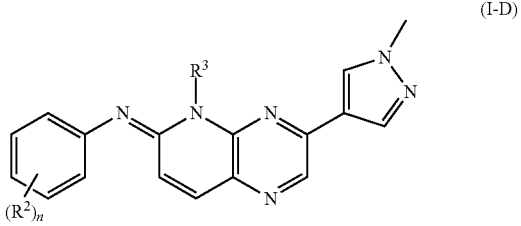

(I-D)

including any tautomeric or stereochemically isomeric form thereof;

wherein n, $R^2$ and $R^3$ are as defined herein;

the N-oxides thereof, the pharmaceutically acceptable salts thereof or the solvates thereof.

In one embodiment there is provided compounds of formula (I-C) or Formula (I-D) including any tautomeric or stereochemically isomeric form thereof, wherein:

$R^2$ represents $C_{1-4}$alkoxy (for example $CH_3O$—) or halogen (for example fluoro); and $R^3$ represents hydroxy$C_{1-6}$alkyl (e.g. —$CH_2CH_2OH$ or —$CH_2CH_2CH_2OH$), $C_{1-6}$alkoxy$C_{1-6}$alkyl wherein each $C_{1-6}$alkyl may optionally be substituted with one or two hydroxyl groups (e.g. —$CH_2CHOHCH_2OCH_3$), hydroxyhalo$C_{1-6}$alkyl (e.g. —$CH_2CHOHCF_3$), $C_{1-6}$alkyl (e.g. $C_{1-4}$alkyl) substituted with $R^9$ (e.g. wherein $R^9$ represents an optionally substituted aromatic 5 or 6 membered monocyclic heterocyclyl, for example optionally substituted imidazolyl, pyrimidinyl, or pyrazinyl), $C_{1-6}$alkyl (e.g. $C_{1-4}$alkyl) substituted with —$NR^{10}R^{11}$ wherein $R^{10}$ and $R^{11}$ are independently selected from hydrogen, $C_{1-6}$alkyl and halo$C_{1-6}$alkyl (e.g. hydrogen, iso-propyl or —$CH_2CF_3$), $C_{2-6}$alkynyl (e.g. —$CH_2$—C≡C—H) or $C_{2-6}$alkynyl (e.g. —$CH_2$—C≡C—) substituted with $R^9$ (e.g. $R^9$ represents an optionally substituted aromatic 6-membered monocyclic heterocycle containing one or two nitrogen heteroatoms, for example pyridinyl);

the N-oxides thereof, the pharmaceutically acceptable salts thereof or the solvates thereof.

In one embodiment there is provided compounds of formula (I-C) or Formula (I-D) including any tautomeric or stereochemically isomeric form thereof, wherein:

$R^2$ represents $C_{1-4}$alkoxy (for example $CH_3O$—) or halogen (for example fluoro); and $R^3$ represents hydroxy$C_{1-6}$alkyl (e.g. —$CH_2CH_2OH$ or —$CH_2CH_2CH_2OH$), $C_{1-6}$alkoxy$C_{1-6}$alkyl wherein each $C_{1-6}$alkyl may optionally be substituted with one or two hydroxyl groups (e.g. —$CH_2CHOHCH_2OCH_3$), hydroxyhalo$C_{1-6}$alkyl (e.g. —$CH_2CHOHCF_3$), $C_{1-4}$alkyl (e.g. methyl) substituted with $R^9$ (e.g. wherein $R^9$ represents an optionally substituted aromatic 5 or 6 membered monocyclic heterocyclyl, for example unsubstituted imidazolyl (e.g. imidazol-2-yl), unsubstituted pyrimidinyl (e.g. pyrimidin-2-yl), unsubstituted pyrazinyl, or imidazolyl substituted with —S(O)$_2$—N(CH$_3$)$_2$), C$_{1-4}$alkyl (e.g. —CH$_2$CH$_2$—) substituted with —NR$^{10}$R$^{11}$ wherein one of R$^{10}$ and R$^{11}$ represents hydrogen and the other represents C$_{1-6}$alkyl, for example —CH$_3$ or —CH(CH$_3$)$_2$ (e.g. R$^3$ represents —CH$_2$CH$_2$NHCH$_3$ or —CH$_2$CH$_2$NHCH(CH$_3$)$_2$), C$_{2-6}$alkynyl (e.g. —CH$_2$—C≡C—H) or C$_{2-6}$alkynyl (e.g. —CH$_2$—C≡C—) substituted with R$^9$ (e.g. —CH$_2$—C≡C—(3-methoxy-pyridin-2-yl); the N-oxides thereof, the pharmaceutically acceptable salts thereof or the solvates thereof.

In one embodiment there is provided compounds of formula (I-C) or Formula (I-D) including any tautomeric or stereochemically isomeric form thereof, wherein:

R$^2$ represents C$_{1-4}$alkoxy (for example CH$_3$O—) or halogen (for example fluoro) or hydroxyl; R$^3$ represents C$_{1-4}$alkyl (e.g. —CH$_2$— or —CH$_2$—CH$_2$—CH$_2$—) substituted with R$^9$ (e.g. wherein R$^9$ represents an optionally substituted aromatic 5 membered monocyclic heterocyclyl, for example unsubstituted imidazolyl (e.g. imidazol-2-yl), or unsubstituted triazolyl (e.g. triazol-3-yl) or R$^9$ represents an optionally substituted saturated 5 membered monocyclic heterocyclyl, for example 2-pyrrolidinonyl (e.g. 2-pyrrolidinon-5-yl or 2-pyrrolidinon-1-yl) or 2-oxazolidinonyl (e.g. 2-oxazolidinon-5-yl)) or R$^3$ represents C$_{1-4}$alkyl (e.g. —CH$_2$CH$_2$—) substituted with —NR$^{10}$R$^{11}$ wherein one of R$^{10}$ and R$^{11}$ represents hydrogen and the other represents C$_{1-6}$alkyl, for example —CH$_3$ or —CH(CH$_3$)$_2$ (e.g. R$^3$ represents —CH$_2$CH$_2$NHCH$_3$ or —CH$_2$CH$_2$NHCH(CH$_3$)$_2$), or —C(=O)—C$_{1-6}$alkyl, for example —C(=O)—CH$_3$ (e.g. R$^3$ represents —CH$_2$CH$_2$NH—C(=O)—CH$_3$), or R$^6$ (e.g. wherein R$^6$ represents an optionally substituted 4 membered saturated heterocycle (e.g. oxetanyl));

n is 2, 3, or 4;

the N-oxides thereof, the pharmaceutically acceptable salts thereof or the solvates thereof.

In one embodiment there is provided compounds of formula (I-C) including any tautomeric or stereochemically isomeric form thereof, wherein:

R$^2$ represents C$_{1-4}$alkoxy (for example CH$_3$O—) or halogen (for example fluoro); R$^3$ represents C$_{1-4}$alkyl (e.g. —CH$_2$—) substituted with R$^9$ (e.g. wherein R$^9$ represents an optionally substituted aromatic 5 membered monocyclic heterocyclyl, for example unsubstituted imidazolyl (e.g. imidazol-2-yl)) or R$^3$ represents C$_{1-4}$alkyl (e.g. —CH$_2$CH$_2$—) substituted with —NR$^{10}$R$^{11}$ wherein one of R$^{10}$ and R$^{11}$ represents hydrogen and the other represents C$_{1-6}$alkyl, for example —CH$_3$ (e.g. R$^3$ represents —CH$_2$CH$_2$NHCH$_3$); in particular R$^3$ represents C$_{1-4}$alkyl (e.g. —CH$_2$—) substituted with R$^9$ (e.g. wherein R$^9$ represents an optionally substituted aromatic 5 membered monocyclic heterocyclyl, for example unsubstituted imidazolyl (e.g. imidazol-2-yl); n is 2, 3, or 4, in particular 3; the N-oxides thereof, the pharmaceutically acceptable salts thereof or the solvates thereof.

In one embodiment there is provided compounds of formula (I-C) including any tautomeric or stereochemically isomeric form thereof, wherein:

R$^2$ represents C$_{1-4}$alkoxy (for example CH$_3$O—) or halogen (for example fluoro); and R$^3$ represents hydroxyC$_{1-6}$alkyl (e.g. —CH$_2$CH$_2$OH or —CH$_2$CH$_2$CH$_2$OH), C$_{1-6}$alkoxyC$_{1-6}$alkyl wherein each C$_{1-6}$alkyl may optionally be substituted with one or two hydroxyl groups (e.g. —CH$_2$CHOHCH$_2$OCH$_3$), hydroxyhaloC$_{1-6}$alkyl (e.g. —CH$_2$CHOHCF$_3$), C$_{1-6}$alkyl (e.g. C$_{1-4}$alkyl) substituted with R$^9$ (e.g. wherein R$^9$ represents an optionally substituted aromatic 5 or 6 membered monocyclic heterocyclyl, for example optionally substituted imidazolyl, pyrimidinyl, or pyrazinyl), C$_{1-6}$alkyl (e.g. C$_{1-4}$alkyl) substituted with —NR$^{10}$R$^{11}$ wherein R$^{10}$ and R$^{11}$ are independently selected from hydrogen, C$_{1-6}$alkyl and haloC$_{1-6}$alkyl (e.g. hydrogen, iso-propyl or —CH$_2$CF$_3$), C$_{2-6}$alkynyl (e.g. —CH$_2$—C≡C—H) or C$_{2-6}$alkynyl (e.g. —CH$_2$—C≡C—) substituted with R$^9$ (e.g. R$^9$ represents an optionally substituted aromatic 6-membered monocyclic heterocycle containing one or two nitrogen heteroatoms, for example pyridinyl);

the N-oxides thereof, the pharmaceutically acceptable salts thereof or the solvates thereof.

In one embodiment there is provided compounds of Formula (I-D) including any tautomeric or stereochemically isomeric form thereof, wherein:

R$^2$ represents C$_{1-4}$alkoxy (for example CH$_3$O—) or halogen (for example fluoro); and R$^3$ represents C$_{1-6}$alkyl (e.g. C$_{1-4}$alkyl) substituted with —NR$^{10}$R$^{11}$ wherein R$^{10}$ and R$^{11}$ are independently selected from hydrogen, C$_{1-6}$alkyl and haloC$_{1-6}$alkyl (e.g. hydrogen, iso-propyl or —CH$_2$CF$_3$) (e.g. R$^3$ represents —CH$_2$CH$_2$NHCH$_3$ or —CH$_2$CH$_2$NHCH(CH$_3$)$_2$); the N-oxides thereof, the pharmaceutically acceptable salts thereof or the solvates thereof.

In one embodiment the compound of formula (I) is a compound of formula (I-C):

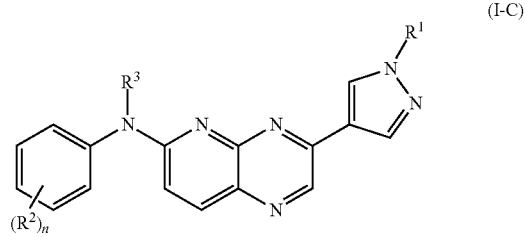

(I-C)

wherein n, R$^1$, R$^2$ and R$^3$ are as defined herein.

In one embodiment the compound of formula (I) is a compound of formula (I-C):

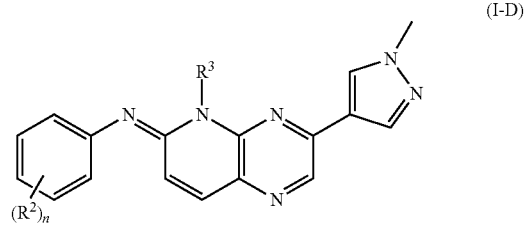

(I-D)

wherein n, R$^1$, R$^2$ and R$^3$ are as defined herein.

In one embodiment, the present invention relates to any one of the following compounds

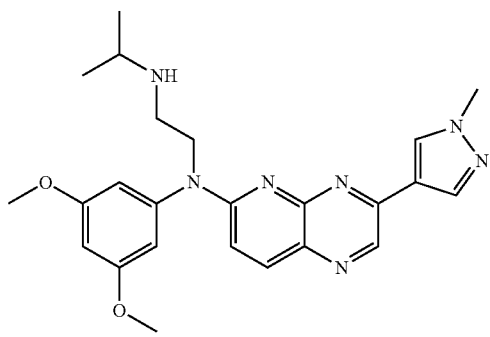

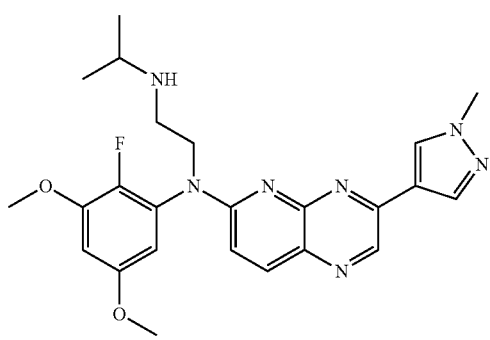

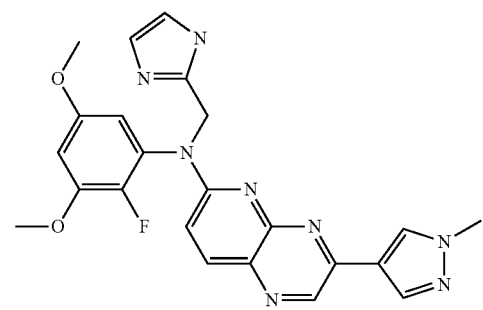

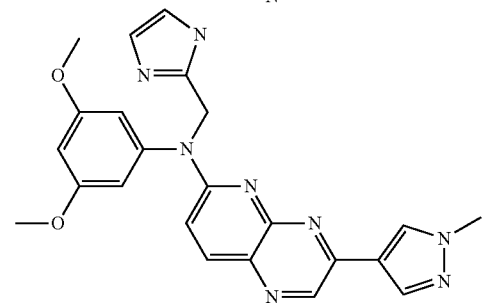

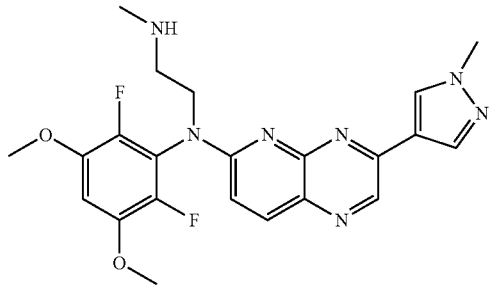

a N-oxide thereof, a pharmaceutically acceptable salt thereof or a solvate thereof.

In one embodiment, the present invention relates to any one of the following compounds

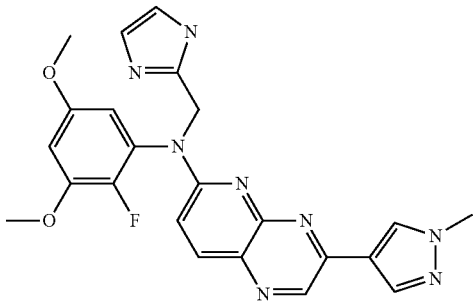

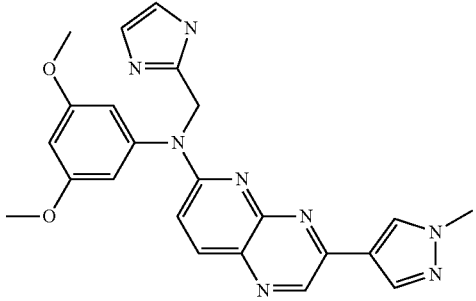

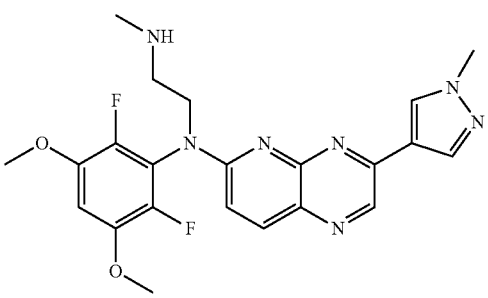

a N-oxide thereof, a pharmaceutically acceptable salt thereof or a solvate thereof.

In one embodiment, the present invention relates to any one of the following compounds

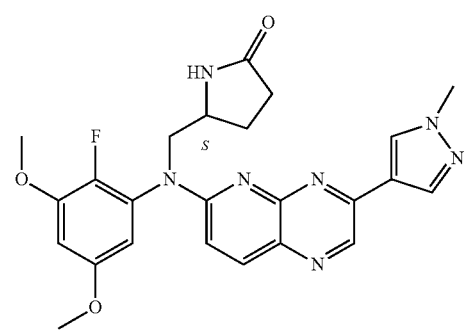

-continued

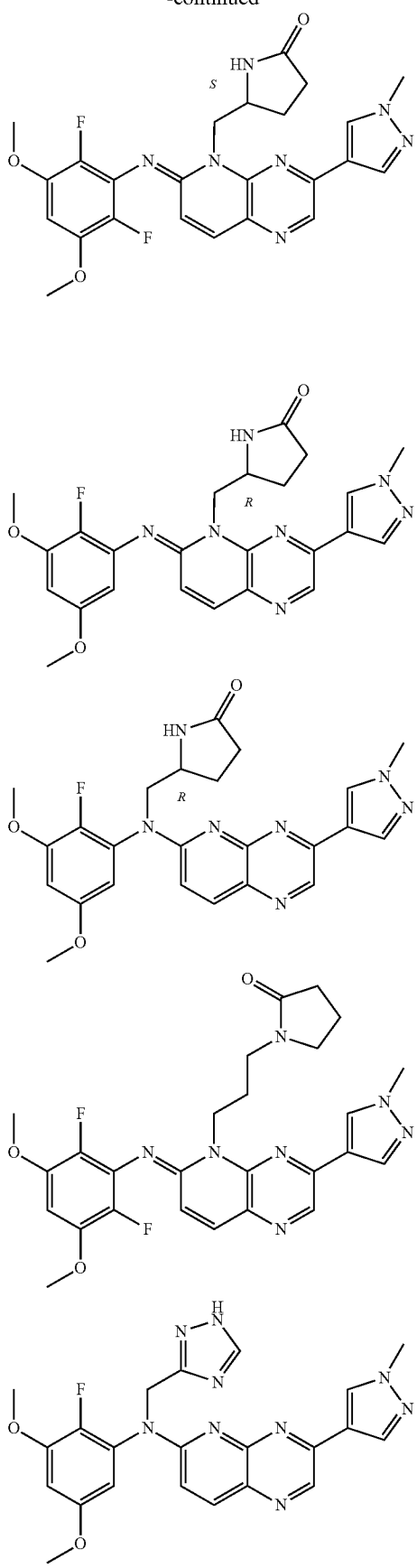

-continued

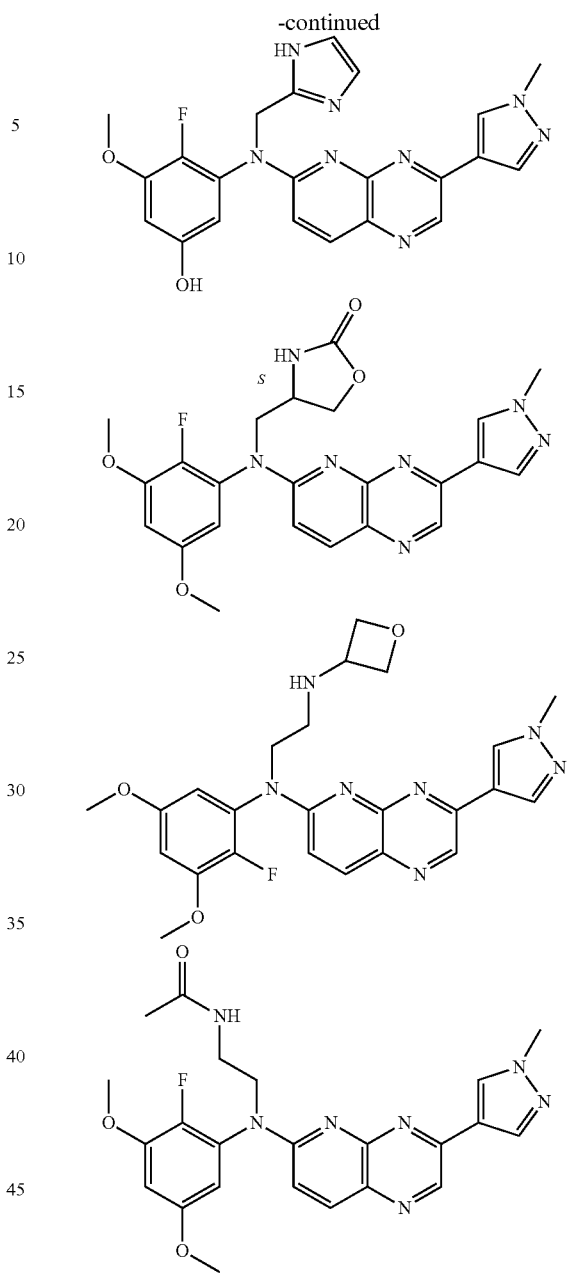

a N-oxide thereof, a pharmaceutically acceptable salt thereof or a solvate thereof.

For the avoidance of doubt, it is to be understood that each general and specific preference, embodiment and example for one substituent may be combined, whenever possible, with each general and specific preference, embodiment and example for one or more, preferably, all other substituents as defined herein and that all such embodiments are embraced by this application.

Methods for the Preparation of Compounds of Formula (I)

In this section, as in all other sections of this application unless the context indicates otherwise, references to formula (I) also include all other sub-groups and examples thereof as defined herein.

In general, compounds of formula (I-A) wherein Y is D (E is a bond), said compounds being represented by formula (I-Aa), can be prepared according to the following reaction Scheme 1.

Scheme 1
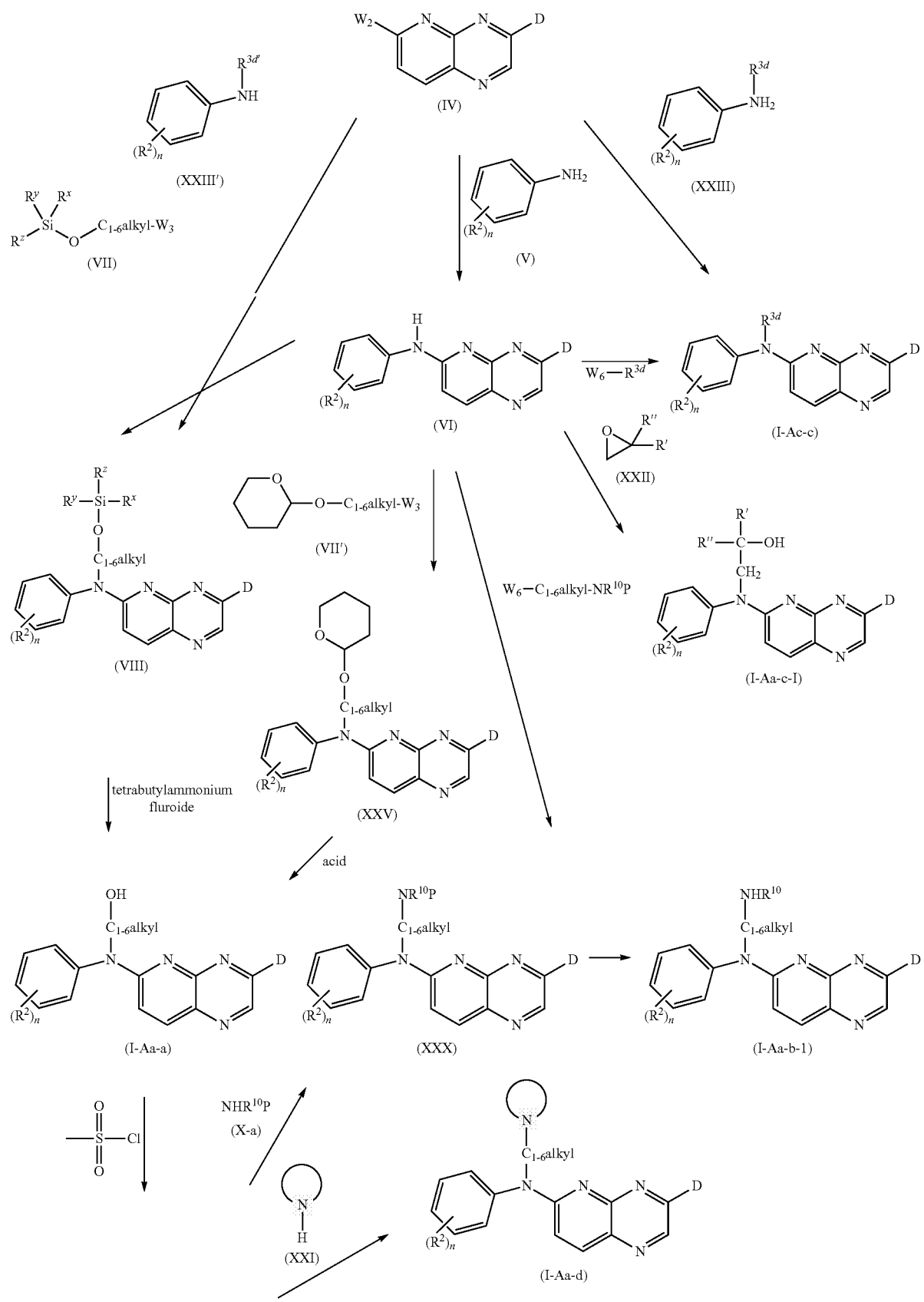

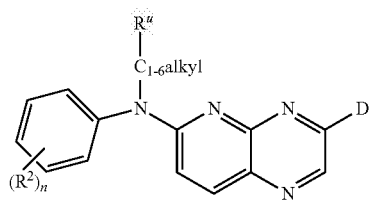 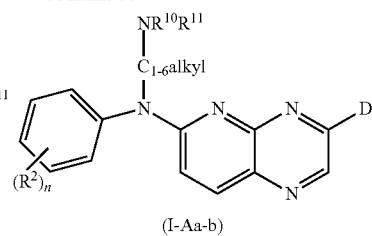

(IX): $R^u$ is —O—S(=O)$_2$—CH$_3$
(IX'): $R^u$ is —Cl (I-Aa-b)

In scheme 1, an intermediate of formula (IV) is reacted with an intermediate of formula (V) in the presence of a suitable catalyst, such as for example palladium (II) acetate, a suitable base, such as sodium tert-butoxide or C$_2$CO$_3$, a suitable ligand, such as for example 1,1'-[1,1'-binaphthalene]-2,2'-diylbis[1,1-diphenylphosphine], and a suitable solvent or solvent mixture, such as for example dioxane or ethylene glycol dimethylether and water or N-methyl-pyrrolidone or dioxane and N-methyl-pyrrolidone, resulting in an intermediate of formula (VI). Or alternatively an intermediate of formula (IV) is reacted with an intermediate of formula (V) in the presence of a suitable solvent, such as for example an alcohol, e.g. n-propanol, and optionally in the presence of a suitable acid, such as for example hydrochloric acid. Or alternatively, an intermediate of formula (IV) is reacted with an intermediate of formula (V) in the presence of potassium bis(trimethylsilyl)amide in the presence of a suitable solvent such as for example tetrahydrofuran or N,N-dimethylformamide. Said intermediate of formula (VI) can then be reacted with an intermediate of formula (VII) wherein W$_3$ represents a suitable leaving group, such as for example halo, e.g. bromo and wherein $R^x$ and $R^y$ represent C$_{1-4}$alkyl, and $R^z$ represent C$_{1-4}$alkyl or phenyl, for instance $R^x$ and $R^y$ represent CH$_3$ and $R^z$ represents C(CH$_3$)$_3$ or phenyl, in the presence of a suitable base, such as for example sodium hydride, and a suitable solvent, such as for example N,N-dimethylformamide or N,N-dimethylacetamide, resulting in an intermediate of formula (VIII). This type of reaction can also be performed to introduce a —C$_{1-6}$alkyl-O—Si($R^x$)($R^y$)($R^z$) group on an appropriate $R^9$ ring within the $R^3$ definition or on an appropriate D moiety. The resulting intermediate can then react with tetrabutylammonium fluoride in the presence of a suitable solvent, such as for example tetrahydrofuran, to result in a compound of formula (I) wherein the appropriate $R^9$ ring is substituted with hydroxyC$_{1-6}$alkyl or the appropriate D moiety is substituted with hydroxyC$_{1-6}$alkyl. Intermediates of formula (VIII) or intermediates of formula (VIII) wherein the $R^1$ substituent carries a suitable protective group can also be prepared by reacting an intermediate of formula (IV) or an intermediate of formula (IV) wherein the $R^1$ substituent carries a suitable protective group with an intermediate of formula (XXIII') wherein $R^{3a'}$ represent —C$_{1-6}$alkyl-O—Si($R^x$)($R^y$)($R^z$) in the presence of a suitable catalyst, such as for example palladium (II) acetate, a suitable ligand, such as for example racemic-2,2'-bis(diphenylphosphino)-1,1'-binaphthyl or 2-dicyclohexylphosphino-2',4',6'-triisopropyl-1,1'-biphenyl, a suitable base, such as for example Cs$_2$CO$_3$, and a suitable solvent, such as for example 1,2-dimethoxyethane or dioxane. Intermediates of formula (VIII) can be converted into a compound of formula (I) wherein $R^3$ represents —C$_{1-6}$alkyl-OH, said compounds being represented by formula (I-Aa-a) or compounds of formula (I-Aa) wherein the $R^1$ substituent carries a suitable protective group, by reaction with tetrabutylammonium fluoride in the presence of a suitable solvent, such as for example tetrahydrofuran. This type of reaction can also be performed in the presence of a suitable acid, such as for example acetic acid or HCl, and a suitable solvent, such as for example tetrahydrofurane or dioxane. Alternatively, an intermediate of formula (VI) can react with an intermediate of formula (VII') wherein W$_3$ represents a suitable leaving group, such as for example halo, e.g. bromo and the like, in the presence of a suitable base, such as for example sodium hydride, and a suitable solvent, such as for example N,N-dimethylformamide or N,N-dimethylacetamide, resulting in an intermediate of formula (XXV) which can then be deprotected in the presence of a suitable acid, such as for example HCl, and a suitable solvent, such as for example an alcohol, e.g. methanol or isopropanol, to give a compound of formula (I-Aa-a). The compounds of formula (I-Aa-a) or compounds of formula (I-Aa-a) wherein the $R^1$ substituent carries a suitable protective group can be reacted with methanesulfonyl chloride in the presence of a suitable base, such as for example triethylamine, diisopropylethanamine or N,N-dimethyl-4-aminopyridine, and a suitable solvent, such as for example dichloromethane or tetrahydrofuran, to result in an intermediate of formula (IX) (mesylate derivative) or an intermediate of formula (IX') (chloride derivative) or intermediates of formula (IX) or (IX') wherein the $R^1$ substituent carries a suitable protective group. In particular, this type of reaction is used to prepare intermediates of formula (IX) or (IX') wherein C$_{1-6}$alkyl represents C$_{3-6}$alkyl. For some variants of intermediates of formula (IX) or (IX'), e.g. wherein C$_{1-6}$alkyl represents C$_{1-2}$alkyl it might be preferred to perform the reaction in non basic conditions. Intermediates of formula (IX) or (IX') can then be reacted with an intermediate of formula (X) to obtain a compound of formula (Ia) wherein $R^3$ represents C$_{1-6}$alkyl substituted with NR$^{10}$R$^{11}$, said compounds being represented by formula (I-Aa-b) or compounds of formula (I-Aa-b) wherein the $R^1$ substituent carries a suitable protective group. This reaction may optionally be performed in the presence of a suitable base, such as for example triethylamine, K$_2$CO$_3$, Na$_2$CO$_3$ or sodium hydride and optionally a suitable solvent, such as for example acetonitrile, tetrahydrofuran, dioxane, N,N-dimethylformamide, 1-methyl-pyrrolidinone, a suitable alcohol, e.g. 1-butanol and the like. This type of reaction can also be performed with a suitable salt of the intermediate of formula (X), e.g. HCl salt of intermediate of formula (X), or may be performed in the presence of potassium iodide. In this way compounds wherein $R^3$ represents iodoC$_{1-6}$alkyl can be obtained. Compounds of formula (Ia-b) wherein the $R^1$ substituent carries a suitable protective group can be converted in a compound of formula (I-Aa-b) by reaction with a suitable acid, such as for example trifluoroacetic acid, in the presence of a suitable solvent, such as for example dichloromethane.

Intermediates of formula (IX) can also react with a suitable nitrogen containing ring within the definition of R⁹, said ring being represented by formula (XXI) or a suitable salt of an intermediate of formula (XXI), in the presence of a suitable solvent, such as for example acetonitrile, 1-methyl-2-pyrrolidinone, or an alcohol, e.g. 1-butanol, optionally in the presence of potassium iodide or a suitable base, such as for example $Na_2CO_3$, $K_2CO_3$ or triethylamine, resulting in a compound of formula (I-Aa-d). Intermediates of formula (IX) can also react with an intermediate of formula (X-a) wherein P represents a suitable protective group, such as for example —C(=O)—O—C(CH₃)₃, in the presence of a suitable base, such as for example sodium hydride, and a suitable solvent, such as for example dimethylacetamide, resulting in an intermediate of formula (XXX) which can be deprotected to a compound of formula (I-Aa-b-1) in the presence of a suitable acid, such as for example HCl or trifluoroacetic acid, and a suitable solvent, such as for example dichloromethane or an alcohol, e.g. methanol. Intermediates of formula (XXX) can also be prepared by reacting an intermediate of formula (VI) with an intermediate of formula $W_6$—$C_{1-6}$alkyl-NR¹⁰P wherein $W_6$ represents a suitable leaving group, such as for example halo, e.g. bromo and the like, or —O—S(=O)₂—CH₃, and P is as defined above, in the presence of a suitable base, such as for example sodium hydride, and a suitable solvent, e.g. N,N-dimethylformamide or N,N-dimethylacetamide. Alternatively compounds of formula (I-Aa-d) or (I-Aa-b-1) can also be prepared by reacting respectively an intermediate of formula (VI) with an intermediate of formula $W_6$—$C_{1-6}$alkyl-Ncycle or $W_6$—$C_{1-6}$alkyl-NHR¹⁰ wherein $W_6$ is as defined above.

Intermediates of formula (VI) can react with $W_6$—$R^{3d}$ wherein $W_6$ represents a suitable leaving group, such as for example halo, e.g. bromo, chloro, and the like, or —O—S(=O)₂—CH₃ or p-toluenesulfonate, and $R^{3d}$ represents optionally substituted $C_{1-6}$alkyl, such as for example —CH₂—C₃H₅, in the presence of a suitable base, such as for example sodium hydride, $Cs_2CO_3$, potassium tert-butoxyde or potassium hydroxide, optionally a suitable phase transfer agent, such as for example tetrabutylammonium bromide, and a suitable solvent, such as for example N,N-dimethylformamide, N,N-dimethylacetamide, 2-methyltetrahydrofuran, tetrahydrofuran, water or acetonitrile, resulting in a compound of formula (I-Aa-c). In this way, compounds of formula (I-Aa-c) wherein R³ represents —S(=O)₂—N(CH₃)₂ can also be prepared by reacting an intermediate of formula (VI) with dimethylsulfamoyl chloride, in the presence of a suitable base, such as for example NaH, and a suitable solvent, such as for example N,N-dimethylformamide. This type of reaction can also be used to prepare an intermediate wherein the $R^{3d}$ moiety is protected by an appropriate protective group, such as for example triphenylmethyl or —CH₂—O—CH₂—CH₂—Si(CH₃) 3, which can then be deprotected to a compound of formula (I-Aa-c) in the presence of a suitable acid, such as for example HCl or trifluoroacetic acid, in a suitable solvent, such as for example dichloromethane or acetonitrile, or by reaction with a suitable phase transfer agent, such as for example tetrabutylammonium fluoride in the presence of a suitable solvent, such as for example tetrahydrofuran. This type of reaction can also be used to prepare a compound of formula (I-Ba) (see hereinafter).

Compounds of formula (I-Aa-c) wherein $R^{3d}$ represents —CH₂—C(OH)(R')(R") wherein R' represents optionally substituted $C_{1-4}$alkyl and R¹¹ represents hydrogen or optionally substituted $C_{1-4}$alkyl, said compounds being represented by formula (I-Aa-c-1), can be prepared by reacting the intermediate of formula (VI) with an intermediate of formula (XXII) in the presence of a suitable base, such as for example sodium hydride, $Cs_2CO_3$, or potassium hydroxide, and a suitable solvent, such as for example N,N-dimethylformamide, N,N-dimethylacetamide, acetonitrile or water. This type of reaction can also be used to prepare a compound of formula (I-Bb).

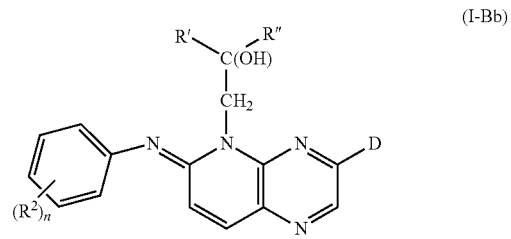

(I-Bb)

This type of reaction can also be used to introduce a —CH₂—C(OH)(R')(R¹¹) group on a D moiety.

Compounds of formula (I-Aa-b) wherein R¹¹ is $C_{1-6}$alkyl substituted with amino, said compounds being represented by formula (I-Aa-b-2), can also be prepared according to the following reaction Scheme 1A.

Scheme 1A

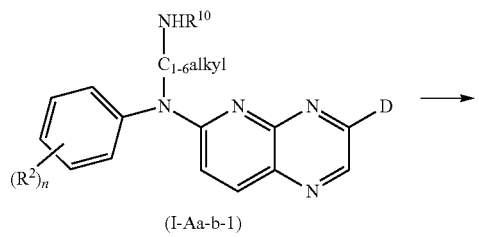

(I-Aa-b-1)

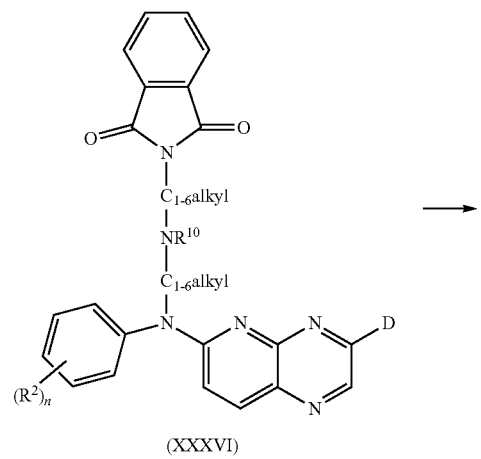

(XXXVI)

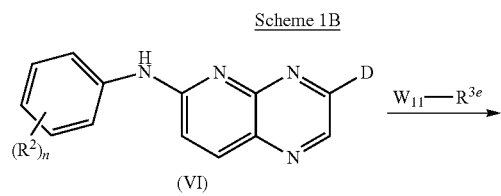

(I-Aa-b-2)

In Scheme 1A, a compound of formula (I-Aa-b-1) is reacted with N-(haloC$_{1-6}$alkyl)phthalimide in the presence of a suitable base, such as for example potassium carbonate, and a suitable solvent, such as for example acetonitrile, resulting in an intermediate of formula (XXXVI) which can be converted into a compound of formula (I-Aa-b-2) by reaction with hydrazine in the presence of a suitable solvent, such as for example an alcohol, e.g. ethanol.

Compounds of formula (I-Aa) wherein R$^3$ represents optionally substituted C$_{2-6}$alkynyl, said compounds being represented by formula (I-Aa-k), can be prepared according to reaction Scheme 1B.

Scheme 1B

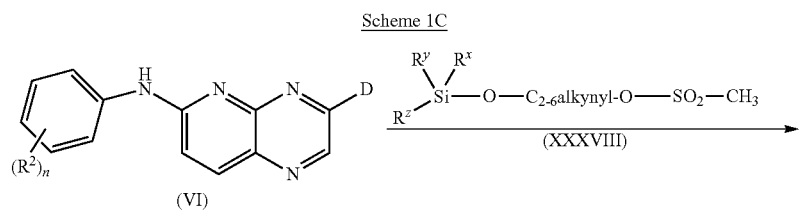

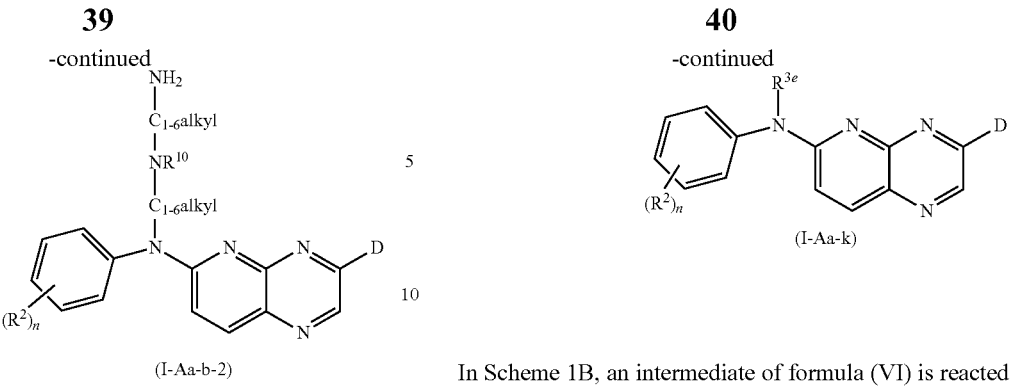

(I-Aa-k)

In Scheme 1B, an intermediate of formula (VI) is reacted with an intermediate of formula W$_{11}$—R$^{3e}$ wherein R$^{3e}$ represents optionally substituted C$_{2-6}$alkynyl and W$_{11}$ represents a suitable leaving group such as for example halo, e.g. chloro, or —O—S(═O)$_2$—CH$_3$, in the presence of a suitable base, such as for example NaH, and a suitable solvent, such as for example N,N-dimethylformamide. The intermediate W$_{11}$—R$^{3e}$ wherein W$_{11}$ represents —O—S(═O)$_2$—CH$_3$, can be prepared by reacting the corresponding alcohol derivative with methanesulfonyl chloride in the presence of a suitable base, such as for example triethylamine or 4-dimethylaminopyridine, and a suitable solvent, such as for example dichloromethane.

Compounds of formula (I-Aa-k), wherein R$^{3e}$ represents C$_{2-6}$alkynyl substituted with hydroxyl, said compounds being represented by formula (I-Aa-k-1), can be prepared according to the following reaction Scheme 1C.

Scheme 1C

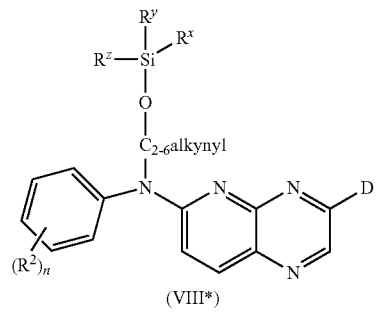

(VIII*)

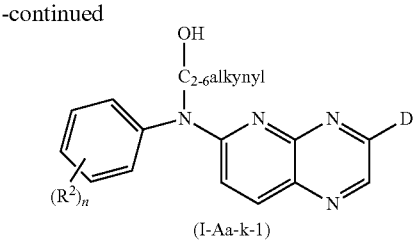

(I-Aa-k-1)

In Scheme 1C, an intermediate of formula (VI) is reacted with an intermediate of formula (XXXVIII) in the presence of a suitable base, such as for example NaH, and a suitable solvent, such as for example N,N-dimethylformamide, resulting in an intermediate of formula (VIII'), which is converted into a compound of formula (I-Aa-k-1) by reaction with a suitable acid, such as for example trifluoroacetic acid, in the presence of a suitable solvent, such as for example tetrahydrofuran. This reaction can also be performed with tetrabutyl ammonium fluoride in the presence of a suitable solvent such as for example tetrahydrofuran.

Alternatively, instead of an intermediate of formula (XXXVIII), halo-$C_{2-6}$alkynyl-O—Si($R^x$)($R^y$)($R^z$) can also be used.

Compounds of formula (I-Aa-k), wherein $R^{3e}$ represents $C_{2-6}$alkynyl, said compounds being represented by formula (I-Aa-k-2), can be prepared according to the following reaction Scheme 1D.

Scheme 1D

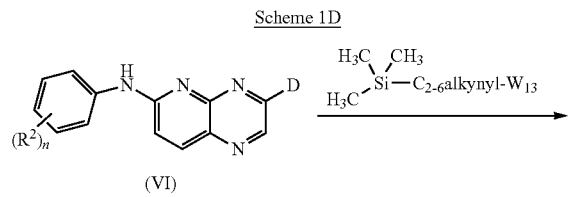

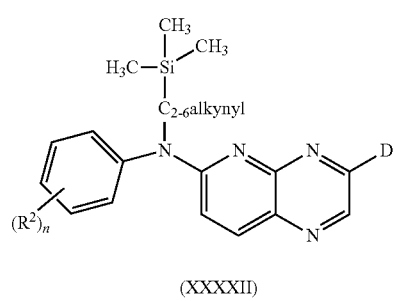

(XXXXII)

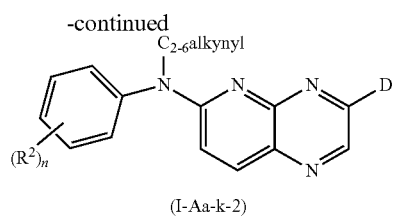

(I-Aa-k-2)

In Scheme 1D, a compound of formula (I-Aa-k-2) is prepared by deprotecting an intermediate of formula (XXXXII) in the presence of a suitable base, such as for example $K_2CO_3$, and a suitable solvent, such as for example an alcohol, e.g. methanol and the like. Said intermediate of formula (XXXXII) can be prepared by reacting an intermediate of formula (VI) with $W_{13}$—$C_{2-6}$alkynyl-Si($CH_3$)$_3$ wherein $W_{13}$ is a suitable leaving group, such as for example halogen, in the presence of a suitable base, such as for example NaH, and a suitable solvent, such as for example N,N-dimethylformamide.

Compounds of formula (I-Aa), wherein $R^3$ represents ethyl substituted with —P(=O)(O$C_{1-6}$alkyl)$_2$, said compounds being represented by formula (I-Aa-I), can be prepared according to the following reaction Scheme 1E.

Scheme 1E

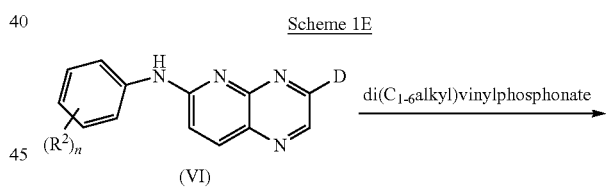

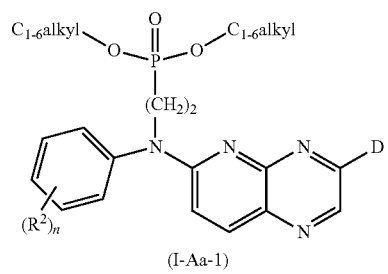

(I-Aa-1)

In scheme 1E, an intermediate of formula (VI) is reacted with di($C_{1-6}$alkyl)vinylphosphonate in the presence of a suitable catalyst, such as for example tri-N-butylphosphine, and a suitable solvent, such as for example acetonitrile resulting in a compound of formula (Ia-I).

Intermediates of formula (IV) can be prepared according to the following reaction Scheme 2.

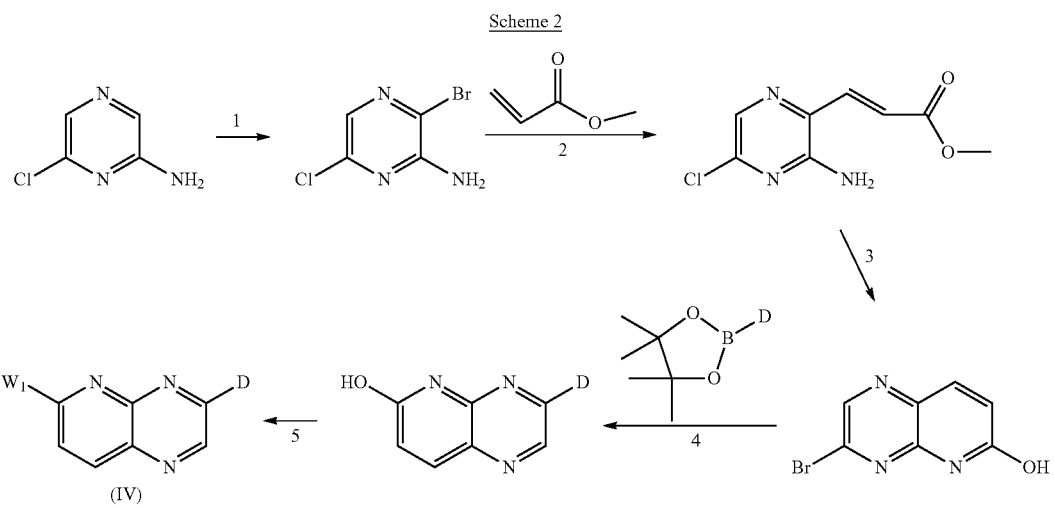

In Scheme 2, the following reaction conditions apply:

1: in the presence of a suitable leaving group introducing agent, such as for example N-bromosuccinimide, and a suitable solvent, such as for example chloroform ($W^a$ represents a suitable leaving group, such as for example a halo, e.g. chloro.

2: in the presence of a suitable catalyst, such as for example bis(tri-tert-butyl-phosphine)palladium(0), a suitable base, such as for example triethylamine, and a suitable solvent, such as for example N,N-dimethylformamide.

3: in the presence of a suitable acid, such as for example HBr/acetic acid.

4: in the presence of a suitable catalyst, such as for example tetrakis(triphenylphosphine)palladium, a suitable base, such as for example $Na_2CO_3$, and a suitable solvent, such as for example 1,2-dimethoxyethane and water.

5: in the presence of a suitable leaving group introducing agent, such as for example $POCl_3$.

Intermediates of formula (IV) can also be prepared according to the following reaction Scheme 2A.

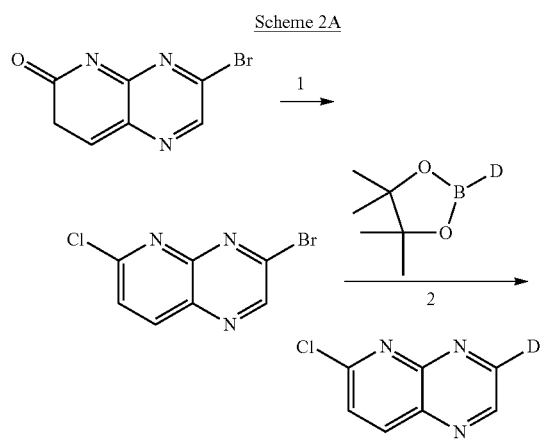

-continued

In Scheme 2A, the following reaction conditions apply:

1: in the presence of $POCl_3$ and a suitable solvent, such as for example N,N-dimethylformamide or 1,2-dichloroethane.

2: in the presence of a suitable catalyst, such as for example tetrakis(triphenylphosphine)palladium, a suitable base, such as for example $Na_2CO_3$, and a suitable solvent, such as for example 1,2-dimethoxyethane and water, dimethylether. Or 3: in the presence of a suitable base, such as for example triethylamine, and a suitable solvent, such as for example dichloromethane.

In general, compounds of formula (I-B) wherein Y is D (E is a bond), said compounds being represented by formula (I-Ba), can be prepared according to the following reactions in Scheme 3.

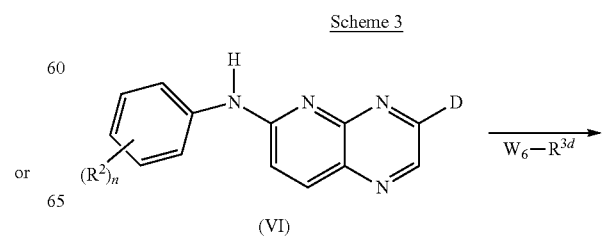

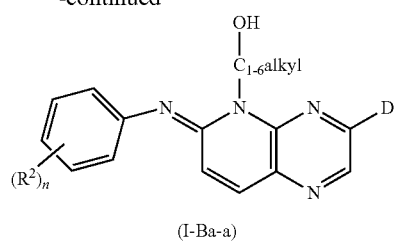

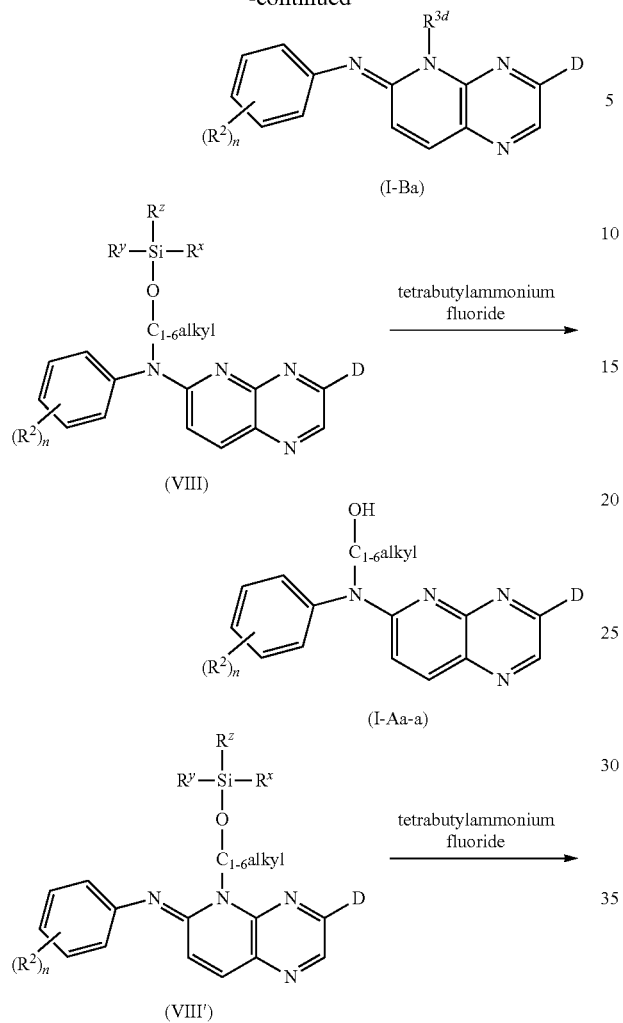

In Scheme 3, an intermediate of formula (VI) can react with $W_6$—$R^3$ wherein $W_6$ represents a suitable leaving group, such as for example halo, e.g. bromo and the like, or —O—S(=O)$_2$—CH$_3$ or p-toluenesulfonate, in the presence of a suitable base, such as for example potassium hydroxide or sodium hydride, and optionally a suitable phase transfer agent, such as for example tetrabutylammonium bromide and, and a suitable solvent, such as for example 2-methyl-tetrahydrofuran and water or N,N-dimethylformamide, resulting in a compound of formula (I-Ba).

Intermediates of formula (VIII) can react with tetrabutylammonium fluoride, in the presence of a suitable solvent, such as for example tetrahydrofuran, resulting in a compound of formula (I-Aa-a). This type of reaction can also be used to prepare a compound of formula (I-Ba-a).

Intermediates of formula (VIII') wherein D is a ring moiety containing a nitrogen atom, can be further reacted according to the following reaction Scheme 4.

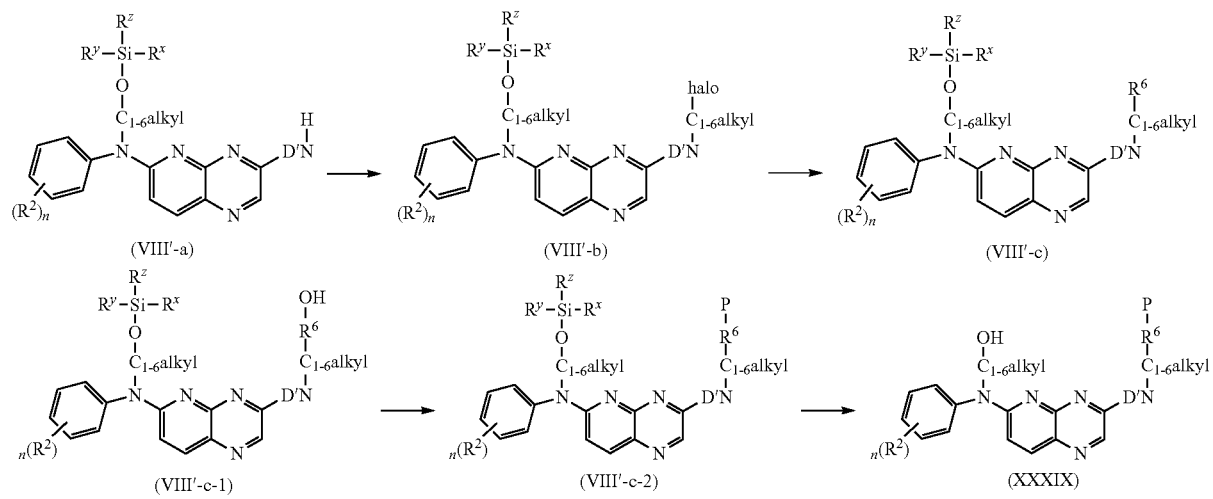

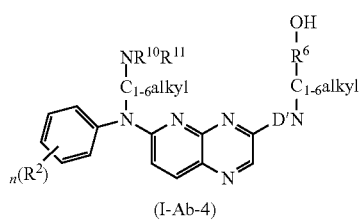 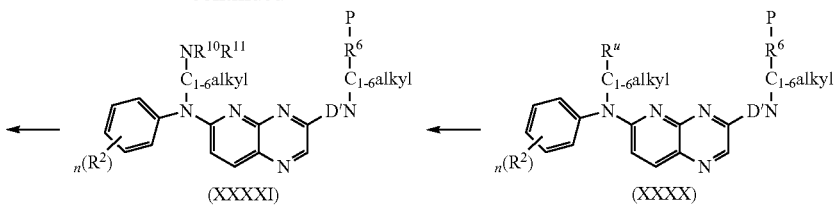

In Scheme 4, the D'N moiety represents a -D moiety wherein the D ring moiety contains a nitrogen atom. Intermediates of formula (VIII') wherein D represents D'NH, said intermediates being represented by formula (VIII'-a), can be converted into an intermediate of formula (VIII'-b) by reaction with $W_{12}$—$C_{1-6}$alkyl-halo wherein $W_{12}$ represents a suitable leaving group, such as for example halo, e.g. chloro, in the presence of a suitable base, such as for example NaH, and a suitable solvent, such as for example N,N-dimethylformamide. Said intermediates of formula (VIII'-b) can be converted into an intermediate of formula (VIII'-c) by reaction with $R^6$ in the presence of a suitable base, such as for example $K_2CO_3$, and a suitable solvent, such as for example acetonitrile. When in an intermediate of formula (VIII'-c) the $R^6$ carries a hydroxyl group as in an intermediate of formula (VIII'-c-1), then said hydroxyl group can be protected by a suitable protective group P, such as for example —O—C(═O)—$C_{1-6}$alkyl, by reaction with $C_{1-6}$alkyl-C(═O)—$W_{12}$, in the presence of a suitable base, such as for example triethylamine, 4-dimethylaminopyridine, and a suitable solvent, such as for example dichloromethane, resulting in an intermediate of formula (VIII'-c-2) which can be converted into an intermediate of formula (XXXIX) by reaction with tetrabutylammonium fluoride in the presence of a suitable solvent, such as for example tetrahydrofuran. Said intermediate of formula (XXXIX) can be converted into an intermediate of formula (XXXX) wherein $R^u$ represents —$SO_2CH_3$, by reaction with methane sulfonyl chloride in the presence of a suitable base, such as for example triethylamine, and a suitable solvent, such as for example dichloromethane. In particular, this type of reaction is used to prepare intermediates of formula (XXXX) wherein $C_{1-6}$alkyl represents $C_{3-6}$alkyl. For some variants of intermediates of formula (XXXX), e.g. wherein $C_{1-6}$alkyl represents $C_{1-2}$alkyl, it might be preferred to perform the reaction in non basic conditions. Intermediates of formula (XXXX) can be converted into an intermediate of formula (XXXXI) by reaction with an intermediate of formula (X) in a suitable solvent, such as for example acetonitrile. Said intermediate of formula (XXXXI) can then be deprotected into a compound of formula (I-Aa-b-4) in the presence of a suitable base, such as for example $K_2CO_3$, and a suitable solvent, such as for example an alcohol, e.g. methanol and the like. It is considered to be within the knowledge of the person skilled in the art to recognize for which other D ring moieties the described reactions also apply. Intermediates of formula (VIII') can also be reacted to prepare compounds of the present invention according to the reaction schemes as presented in Scheme 1. It is considered to be within the knowledge of the skilled person to recognize in which condition and for which definitions of $R^1$ on the D ring moiety a protective group may be appropriate for the reactions to be carried out. For instance, a hydroxyl group within the definition of $R^1$ may be protected with a tert. butyldimethylsilyl moiety; a NH group within the definition of $R^1$ may be protected with a —C(═O)—O—C(CH$_3$)$_3$ group.

It is also considered to be within the knowledge of the skilled person to recognize appropriate deprotection reactions.

Compounds of formula (I-Aa-c) can alternatively also be prepared according to the below reaction Scheme 5.

Scheme 5

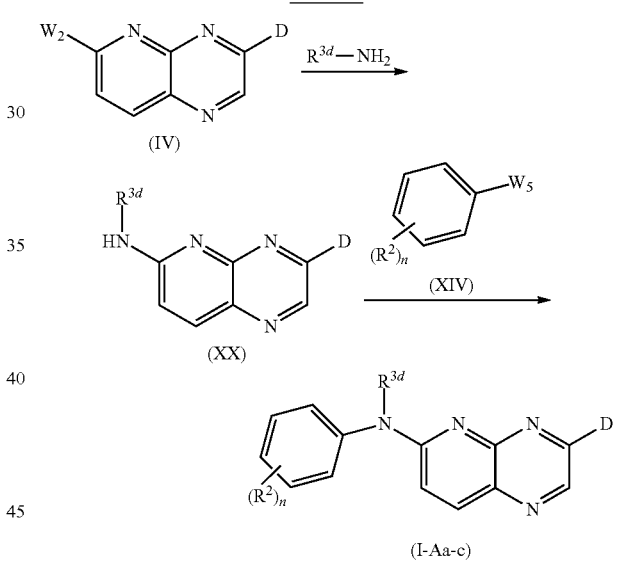

In Scheme 5, an intermediate of formula (IV) is reacted with $R^{3d}$—NH$_2$ in the presence of a suitable catalyst, such as for example palladium (II) acetate, a suitable base, such as for example sodium tert-butoxide, and a suitable ligand, such as for example 1,1'-[1,1'-binaphthalene]-2,2'-diylbis[1,1-diphenylphosphine], resulting in an intermediate of formula (XX) which is reacted in a next step with an intermediate of formula (XIV) in the presence of a suitable catalyst, such as for example palladium (II) acetate or Pd$_2$(dba)$_3$ (tris(dibenzylidene acetone) dipalladium (0)), a suitable ligand such as for example 2-dicyclohexylphosphino-tris-isopropyl-biphenyl or 1,1'-[1,1'-binaphthalene]-2,2'-diylbis[1,1-diphenylphosphine], a suitable base, such as for example sodium tert-butoxide, and a suitable solvent, such as for example ethylene glycol dimethylether.

Compounds of formula (I) wherein $R^3$ is $C_{1-6}$alkyl substituted with 5-amino-1,3,4-oxadiazolyl or with 1,3,4-oxadiazolyl or with 2(3H)-1,3,4-oxadiazolonyl can be prepared according to the below reaction Scheme 6.

Scheme 6

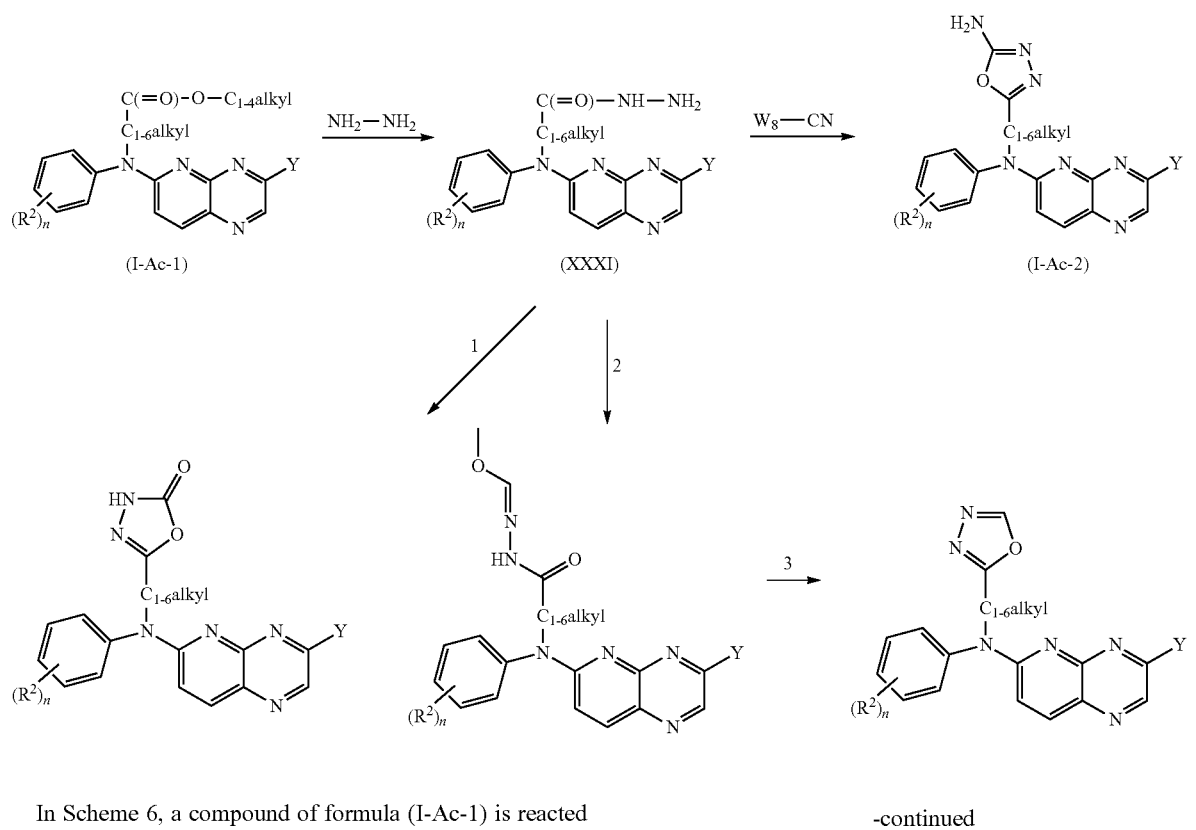

In Scheme 6, a compound of formula (I-Ac-1) is reacted with NH$_2$—NH$_2$ in the presence of a suitable solvent, such as for example an alcohol, e.g. ethanol resulting in an intermediate of formula (XXXI) which is then reacted in a next step with W$_8$—CN, wherein W$_8$ represents a suitable leaving group, such as for example halo, e.g. bromo, in the presence of a suitable base, such as for example NaHCO$_3$, and a suitable solvent, such as for example water or dioxane. Intermediates of formula (XXXI) can further be reacted as described in step 1 in the above scheme in the presence of 1,1'-carbonyldiimidazole and a suitable solvent, such as for example dioxane. Or intermediates of formula (XXXI) can be reacted as described in step 2 in the above scheme in the presence of trimethylorthoformate. The resulting intermediate can further be reacted as described in step 3 in the above scheme in the presence of xylene.

Reaction Schemes 6 A describes the preparation of compounds of formula (I) wherein R$^3$ is C$_{1-6}$alkyl substituted with 5-methyl-1,2,4-oxadiazolyl.

Scheme 6A

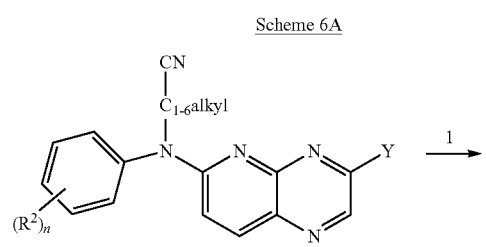

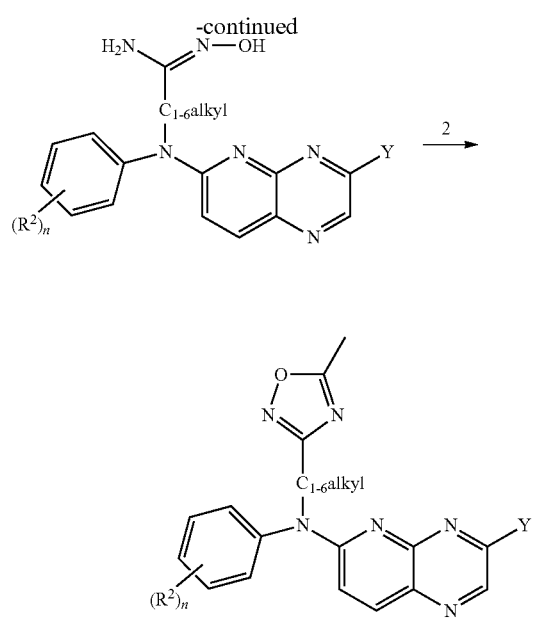

In Scheme 6A, the following reaction conditions apply:

1: in the presence of hydroxylamine HCl, a suitable base, such as for example triethylamine, and a suitable solvent, such as for example an alcohol, e.g. ethanol.

2; in the presence of sodium ethoxide and a suitable solvent, such as for example an alcohol, e.g. ethanol.

Compounds of formula (I) wherein R$^3$ is C$_{1-6}$alkyl substituted with 3,3-dimethyl-morpholine can be prepared according to the below reaction Scheme 7.

Scheme 7

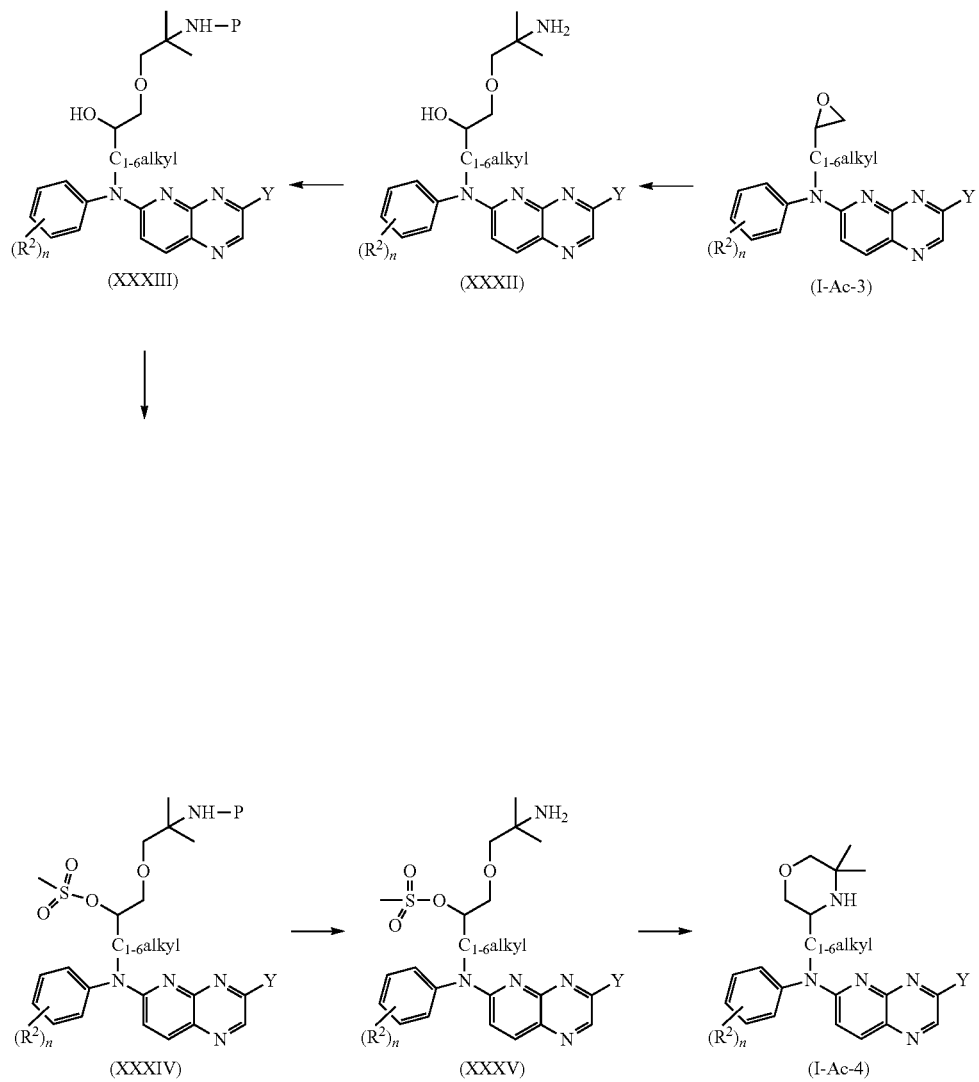

In Scheme 7, a compound of formula (I-Ac-3) is reacted with 2-amino-2-methyl-1-propanol in the presence of a suitable base, such as for example NaH and in the presence of a suitable solvent, such as for example N,N-dimethylformamide resulting in an intermediate of formula (XXXII) of which the $NH_2$ moiety is protected by a suitable protecting group P, such as for example —C(=O)—O—C(CH$_3$)$_3$, by reaction with for instance di-tert-butyl dicarbonate in the presence of a suitable solvent, such as for example dioxane, and a suitable base, such as for example NaHCO$_3$, resulting in an intermediate of formula (XXXIII). In a next step, said intermediate is reacted with methanesulfonyl chloride in the presence of a suitable solvent, such as for example dichloromethane, and a suitable base, such as for example triethylamine resulting in an intermediate of formula (XXXIV). In particular, this type of reaction is used to prepare intermediates of formula (XXXIV) wherein $C_{1-6}$alkyl represents $C_{3-6}$alkyl. For some variants of intermediates of formula (XXXIV), e.g. wherein $C_{1-6}$alkyl represents $C_{1-2}$alkyl it might be preferred to perform the reaction in non basic conditions. Intermediates of formula (XXXIV) are converted into an intermediate of formula (XXXV) by reaction with a suitable acid, such as for example trifluoroacetic acid, in the presence of a suitable solvent, such as for example dichloromethane. The intermediate of formula (XXXV) is converted into a compound of formula (I-Ac-4) by reaction with a suitable base, such as for example N,N-diisopropylethylamine and triethylamine in the presence of a suitable solvent, such as for example an alcohol, e.g. methanol.

As already shown above, compounds of formula (I) or some of the above-described intermediates can be prepared by deprotecting the corresponding protected compounds. Other protection-deprotection reactions are shown in the following reaction Scheme 8.

Scheme 8

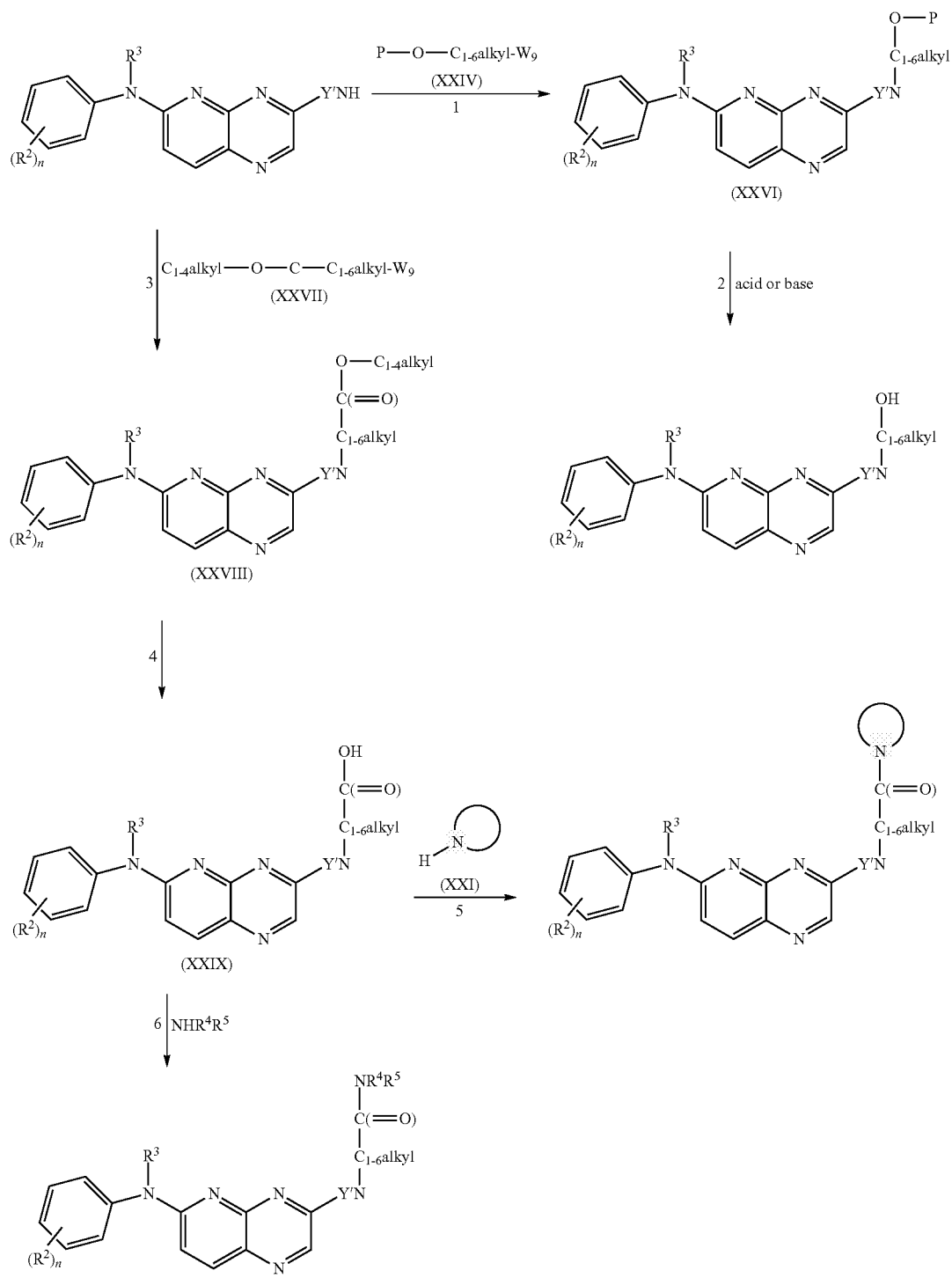

In Scheme 8, the Y'N moiety represents an -E-D moiety wherein the D ring moiety contains a nitrogen atom. Compounds of formula (I) wherein $R^1$ represents hydroxy$C_{1-6}$alkyl can be prepared by deprotecting an intermediate of formula (XXVI) in the presence of a suitable acid, such as for example HCl or trifluoroacetic acid, or a suitable desilylating agent, such as for example tetrabutyl ammonium fluoride, and a suitable solvent, such as an alcohol, e.g. methanol, or tetrahydrofuran (step 2). Intermediates of formula (XXVI) can be prepared by reacting a compound of formula (I) wherein $R^1$ is hydrogen with an intermediate of formula (XXIV) wherein $W_9$ represents a suitable leaving group, such as for example halo, e.g. bromo and the like, and P represents a suitable protective group, such as for example —Si(CH$_3$)$_2$(C(CH$_3$)$_3$) or

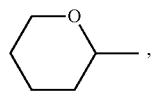

in the presence of a suitable base, such as for example sodium hydride or K$_2$CO$_3$, and a suitable solvent, such as for example N,N-dimethylformamide or acetonitrile (step 1). Compounds of formula (I) wherein R$^1$ represents C$_{1-6}$alkyl substituted with —C(=O)—R$^6$ wherein R$^6$ is an appropriate nitrogen containing ring linked to the C(=O) moiety via the nitrogen atom can be prepared by reacting an intermediate of formula (XXIX) with an intermediate of formula (XXI) in the presence of suitable peptide coupling reagents such as, 1-hydroxy-benzotriazole and 1-(3-dimethylaminopropyl)-3-ethyl carbodiimide HCl (step 5). Intermediates of formula (XXIX) can be prepared by reacting an intermediate of formula (XXVIII) with LiOH in the presence of a suitable solvent, such as for example tetrahydrofuran or water (step 4). Intermediates of formula (XXVIII) can be prepared by as depicted in step 3 with an intermediate of formula (XXVII) wherein W$_9$ is as defined above, in the presence of a suitable base, such as for example sodium hydride, and a suitable solvent, such as for example N,N-dimethylformamide.

Step 6 depicts the preparation of compounds of formula (I) starting from an intermediate of formula (XXIX) by reaction with NHR$^4$R$^5$ in the presence of suitable peptide coupling reagents such as 1-hydroxy-benzotriazole and 1-(3-dimethylaminopropyl)-3-ethyl carbodiimide HCl and a suitable base, such as triethylamine, and a suitable solvent, such as for example dichloromethane.

Further protection-deprotection reactions can also be used as outlined in the following reaction Scheme 9.

Scheme 9

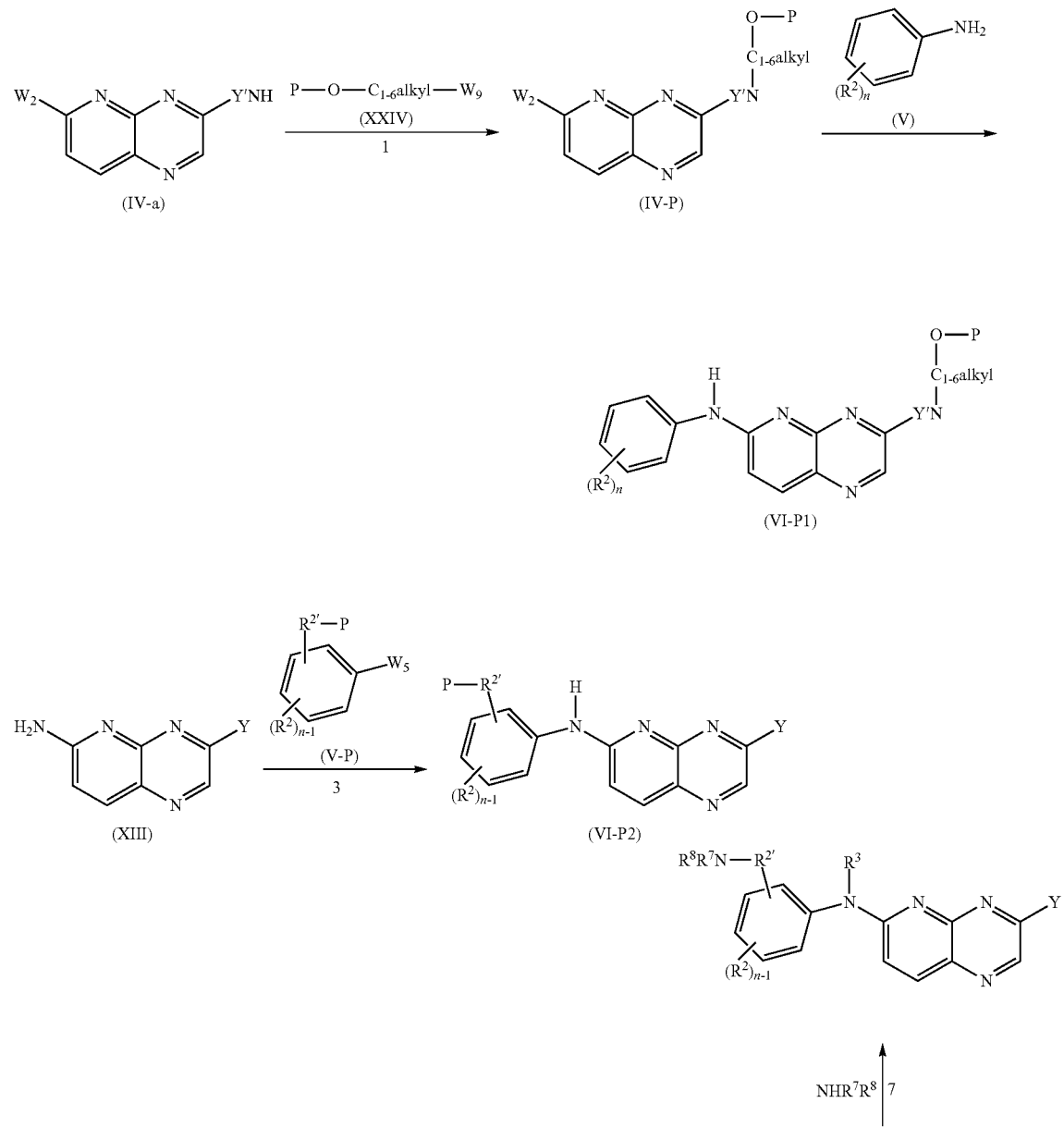

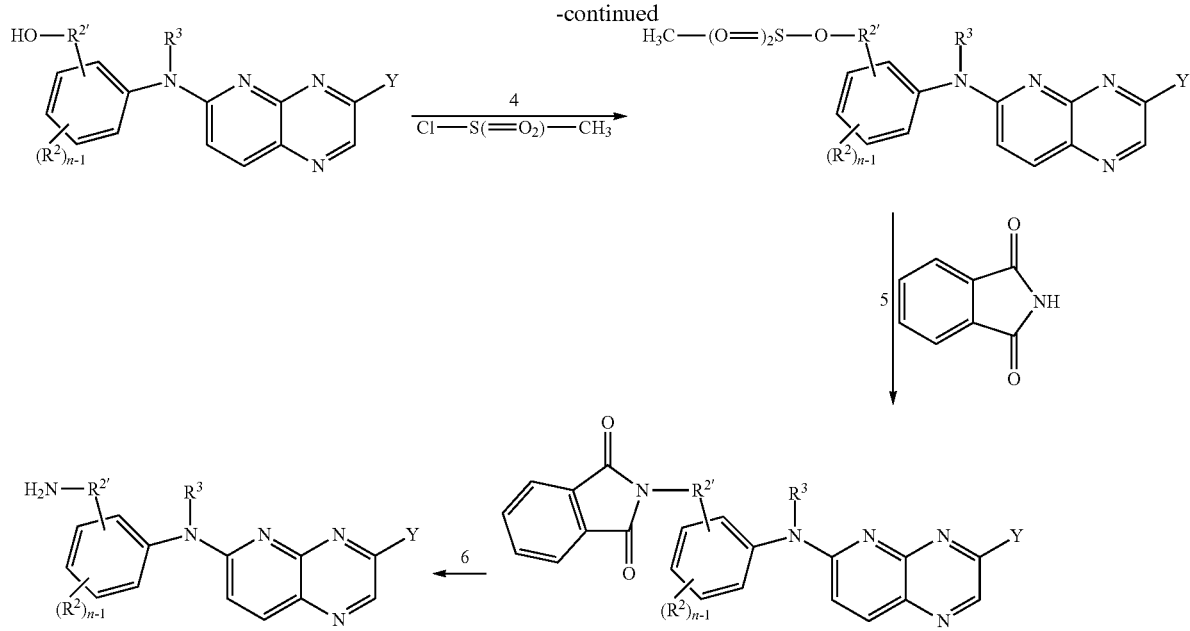

In Scheme 9, the following reaction conditions apply:

1; in the presence of a suitable base, such as for example sodium hydride, and a suitable solvent, such as for example N,N-dimethylformamide.

2: in the presence of a suitable catalyst, such as for example palladium (II)acetate, a suitable base, such as for example sodium tert-butoxide, a suitable ligand, such as for example 1,1'-[1,1'-binaphthalene]-2,2'-diylbis[1,1-diphenylphosphine], and a suitable solvent, such as for example dioxane or ethylene glycol dimethylether.

3: in the presence of a suitable catalyst, such as for example palladium (II)acetate, a suitable base, such as for example sodium tert-butoxide, a suitable ligand, such as for example 1,1'-[1,1'-binaphthalene]-2,2'-diylbis[1,1-diphenylphosphine], and a suitable solvent, such as for example dioxane or ethylene glycol dimethylether.

4: in the presence of a suitable base, such as for example triethylamine, and a suitable solvent, such as for example dichloromethane.

5: in the presence of a suitable base, such as for example $K_2CO_3$, and a suitable solvent, such as for example 1-methyl-2-pyrrolidinone.

6: in the presence of hydrazine monohydrate, and a suitable solvent, such as for example an alcohol, e.g. ethanol.

7: in the presence of a suitable base, such as for example $K_2CO_3$, and a suitable solvent, such as for example tetrahydrofuran.

Compounds of formula (I-A) can also be prepared as outlined in the following reaction Scheme 10.

Scheme 10

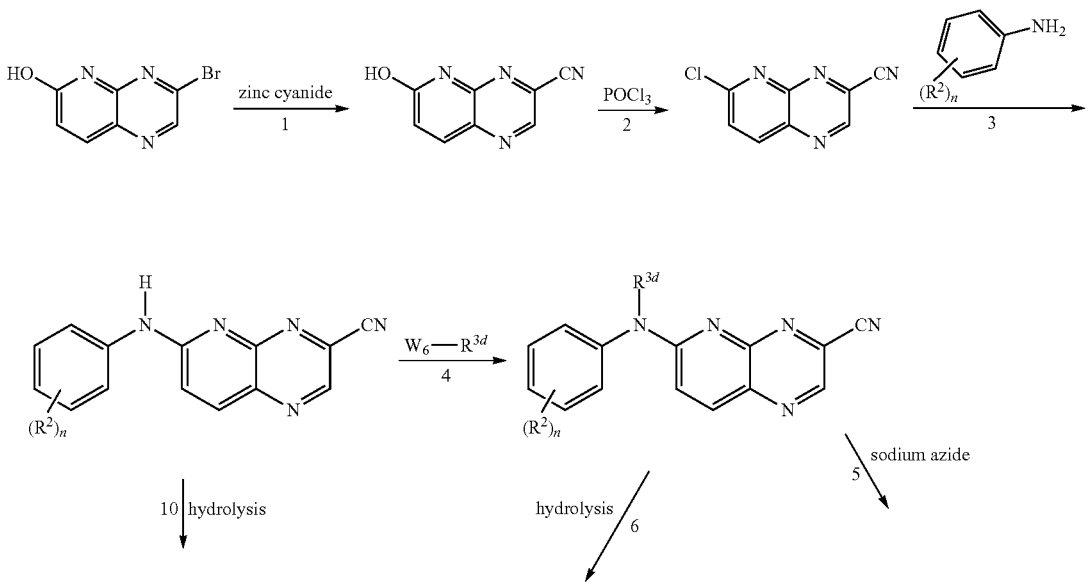

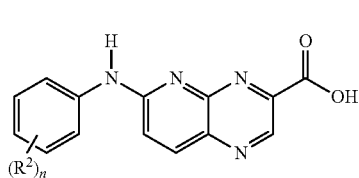
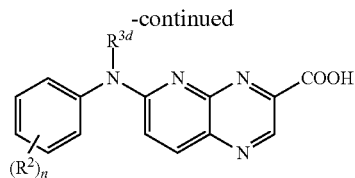
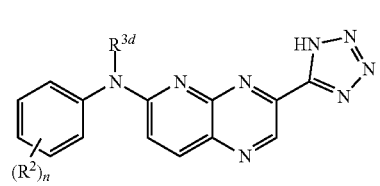

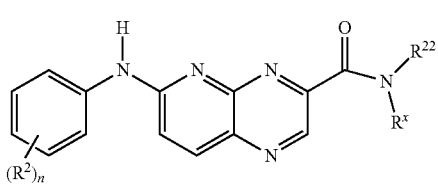
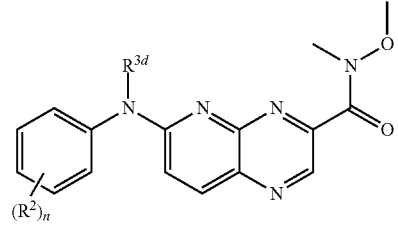

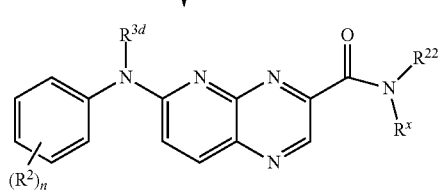
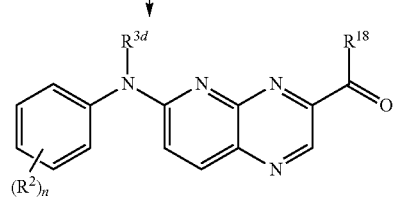

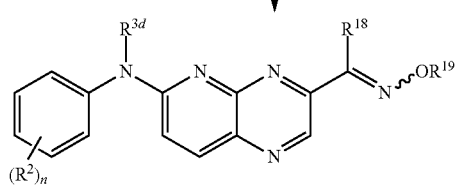

In Scheme 10, the following reaction conditions apply:

1: in the presence of zinc cyanide, a suitable catalyst such as for example tetrakis(triphenylphosphine)palladium, a suitable ligand, such as for example triphenylphosphine, and a suitable solvent, such as for example acetonitrile 2: in the presence of a chlorinating agent such as for example POCl$_3$ 3: in the presence of a suitable solvent, such as for example an alcohol, e.g. n-propanol 4: in the presence of a suitable base, such as for example sodium hydride, Cs$_2$CO$_3$, or potassium hydroxide and a suitable phase transfer agent, such as for example tetrabutylammonium bromide, and a suitable solvent, such as for example N,N-dimethylformamide, N,N-dimethylacetamide, 2-methyltetrahydrofuran, water or acetonitrile 5: in the presence of ammonium chloride and a suitable solvent, such as for example N,N-dimethylformamide 6-7: first hydrolysis of the CN to the acid according to art-known methods, followed by reacting the resulting acid with NH(CH$_3$)(OCH$_3$) in the presence of a suitable coupling agent, such as for example N-3-(ethylcarbonimidoyl)-N1,N1-dimethyl-1,3-ropanediamine, hydrochloride (1:1), a suitable peptide coupling agent such as for example hydroxybenzotriazole, and a suitable solvent, such as for example tetrahydrofuran or dichloromethane 8: reaction with a suitable Grignard reagent in the presence of a suitable solvent, such as for example tetrahydrofuran 9: in the presence of pyridine and a suitable solvent, such as for example an alcohol, e.g. ethanol 10: hydrolysis of the CN to the acid according to art-known methods 11: in the presence of a suitable coupling agent, such as for example N-3-(ethylcarbonimidoyl)-N1,N1-dimethyl-1,3-propanediamine, hydrochloride (1:1), a suitable peptide coupling agent such as for example hydroxybenzotriazole, and a suitable solvent, such as for example tetrahydrofuran or dichloromethane. R$^x$ represents —(CR$^{22}$R$^{23}$)$_s$-D.

12: in the presence of a suitable base, such as for example sodium hydride, Cs$_2$CO$_3$, or potassium hydroxide and a suitable phase transfer agent, such as for example tetrabutylammonium bromide, and a suitable solvent, such as for example N,N-dimethylformamide, N,N-dimethylacetamide, 2-methyltetrahydrofuran, water or acetonitrile Compounds of formula (I-A) can also be prepared as outlined in the following reaction Scheme 11.

4; in the presence of a suitable base, such as for example sodium hydride, Cs$_2$CO$_3$, or potassium hydroxide and a suitable phase transfer agent, such as for example tetrabutylammonium bromide, and a suitable solvent, such as for Scheme 11

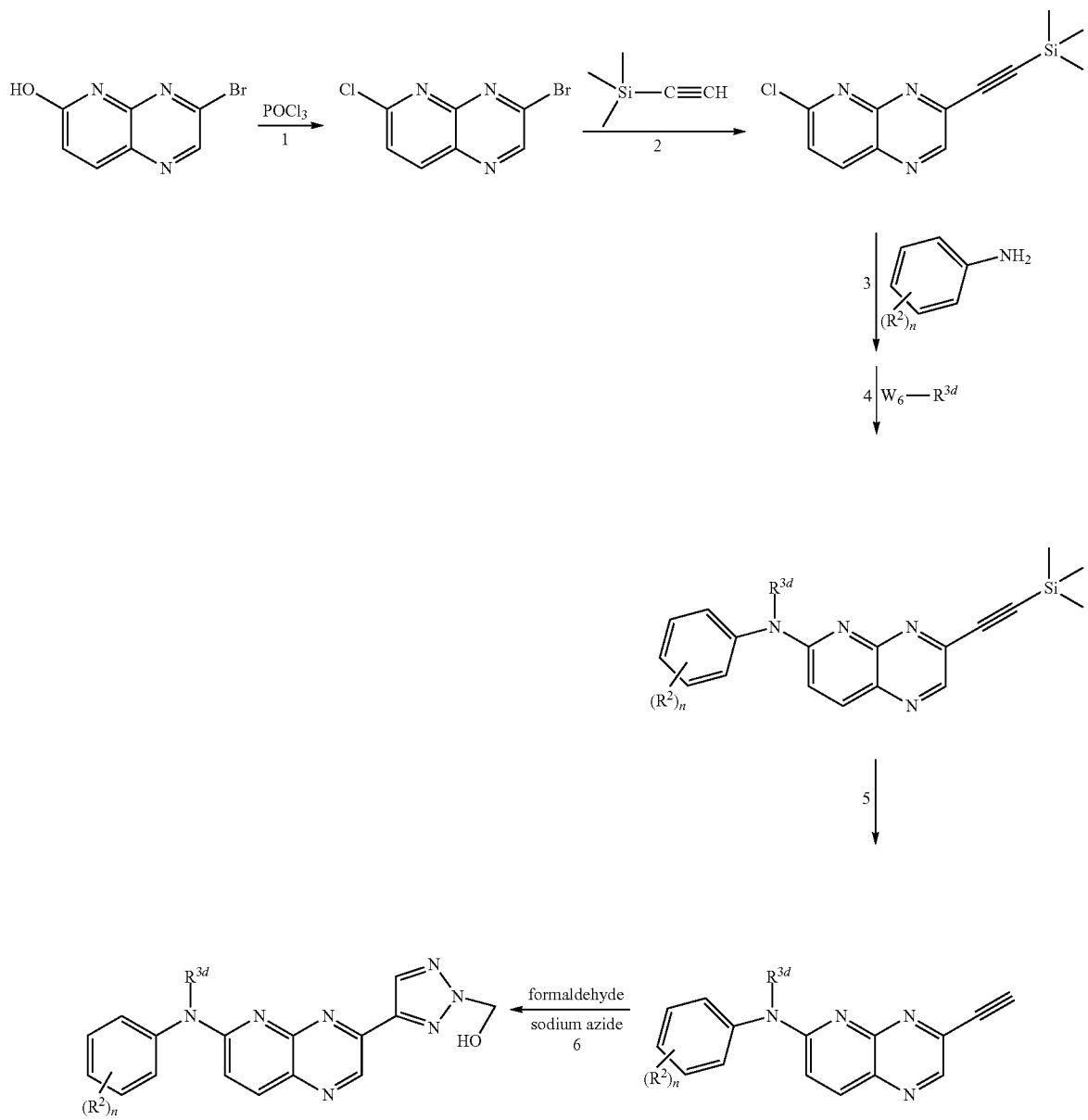

In Scheme 11, the following reaction conditions apply:

1: in the presence of a chlorinating agent such as for example POCl$_3$

2: in the presence of a suitable catalyst, such as for example dichlorobis(triphenylphosphine) palladium (II) and copper iodide, optionally a suitable ligand, such as for example triphenylphosphine, a suitable base, such as for example triethylamine, and a suitable solvent, such as for example N,N-dimethylformamide 3: in the presence of a suitable solvent, such as for example an alcohol, e.g. n-propanol example N,N-dimethylformamide, N,N-dimethylacetamide, 2-methyltetrahydrofuran, water or acetonitrile 5: in the presence of a suitable base, such as for example sodium hydroxide, and a suitable solvent, such as for example an alcohol, e.g. methanol.

6: in the presence of a suitable catalyst, such as for example copper sulfate and sodium L ascorbate, and a suitable solvent, such as for example dioxane and acetic acid Compounds of formula (I-A) can also be prepared as outlined in the following reaction Scheme 12.

Scheme 12

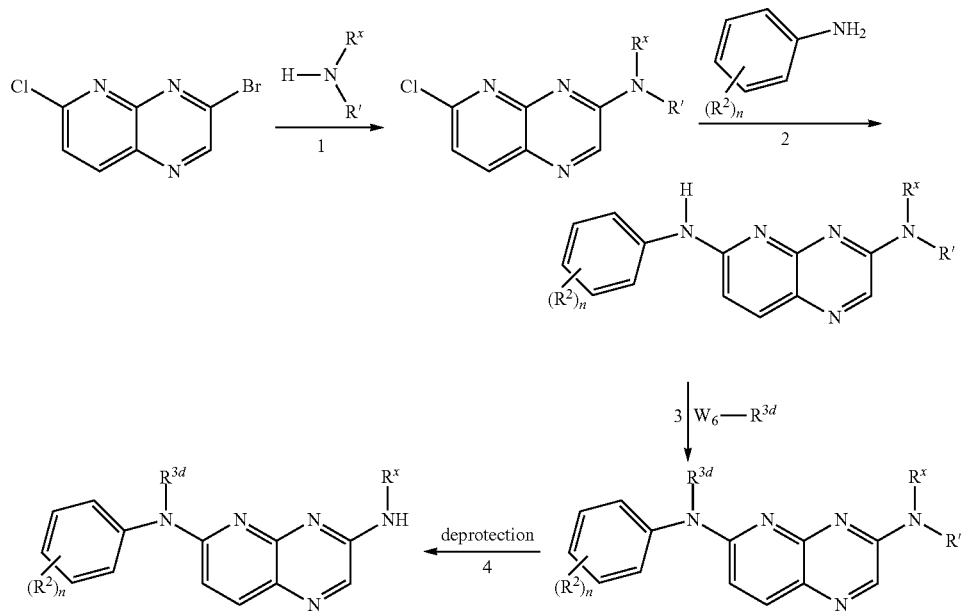

In Scheme 12, the following reaction conditions apply: $R^x$ represents —$(CR^{22}R^{23})_s$-D, and R' represents $R^{22}$ or a suitable protecting group, such as for example benzyl 1: in the presence of a suitable base, such as for example cesium carbonate, and a suitable solvent, such as for example N,N-dimethylformamide 2; in the presence of a suitable solvent, such as for example an alcohol, e.g. n-propanol. Alternatively such reaction could also be performed in the presence of a suitable catalyst, such as for example palladium (II) acetate, a suitable base, such as sodium tert-butoxide or $Cs_2CO_3$, a suitable ligand, such as for example 1,1'-[1,1'-binaphthalene]-2,2'-diylbis[1,1-diphenylphosphine], and a suitable solvent or solvent mixture, such as for example dioxane or ethylene glycol dimethylether and water or N-methyl-pyrrolidone 3: in the presence of a suitable base, such as for example sodium hydride, $Cs_2CO_3$, or potassium hydroxide and a suitable phase transfer agent, such as for example tetrabutylammonium bromide, and a suitable solvent, such as for example N,N-dimethylformamide, N,N-dimethylacetamide, 2-methyltetrahydrofuran, water or acetonitrile 4: deprotection according to art-known methods in case R' is a suitable protecting group.

It is to be considered to be within the knowledge of the person skilled in the art to recognize which of the reactions described above for compounds of (I-A) are also applicable for compounds of formula (I-B).

It is considered to be within the knowledge of the person skilled in the art to recognize in which condition and on which part of the molecule a protective group may be appropriate. For instance, protective group on the $R^1$ substituent or on the D moiety, or protective group on the $R^3$ substituent or on the $R^2$ substituent or combinations thereof.

The skilled person is also considered to be able to recognize the most feasible protective group, such as for example —C(=O)—O—$C_{1-4}$alkyl or

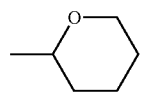

or —$Si(CH_3)_2(C(CH_3)_3)$ or —$CH_2$—O—$CH_2CH_2$—O—$CH_3$ or —$CH_2$—O—$CH_2$—$CH_2$—$Si(CH_3)_3$. The skilled person is also considered to be able to recognize the most feasible deprotection reaction conditions, such as for example suitable acids, e.g. trifluoroacetic acid, hydrochloric acid, or suitable salts, such as for example tetrabutylammonium fluoride. Reference herefore is also made to the examples described in the Experimental Part hereinafter.

The skilled person is also considered to be able to recognize that when $R^1$ represents C(=O)-morpholinyl, said $R^1$ can be prepared from —C(=O)—NH—$CH_2$—$CH_2$—O—$CH_2$—$CH_2$—O—$SO_2$-4-methylphenyl, in the presence of sodium hydride, and a suitable solvent, such as for example N,N-dimethylformamide. Or that when $R^1$ represents —NH—C(=O)-morpholinyl, said $R^1$ can be prepared from —NH—C(=O)—O—$C(CH_3)_3$ in the presence of morpholine, and a suitable solvent, such as for example 1-methyl-2-pyrrolidinone. Or that when $R^1$ represents hydroxyl$C_{1-6}$alkyl, e.g. —$CH_2$—$CH_2$—OH, said $R^1$ can be prepared from the corresponding alkoxycarbonyl intermediate, e.g. —$CH_2$—C(=O)—O—$CH_2$—$CH_3$, in the presence of Dibal-H 1M in hexane, and a suitable solvent, such as for example tetrahydrofuran.

The present invention also comprises deuterated compounds. These deuterated compounds may be prepared by using the appropriate deuterated intermediates during the synthesis process. For instance an intermediate of formula (IV-a)

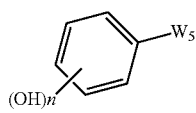

can be converted into an intermediate of formula (IV-b)

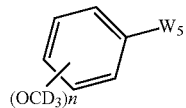

by reaction with iodomethane-D3 in the presence of a suitable base, such as for example cesium carbonate, and a suitable solvent, such as for example acetonitrile.

The compounds of formula (I) may also be converted into each other via art-known reactions or functional group transformations.

For instance, compounds of formula (I) wherein $R^1$ represents tetrahydropyranyl can be converted into a compound of formula (I) wherein $R^1$ represents hydrogen, by reaction with a suitable acid, such as for example HCl or trifluoroacetic acid, in the presence of a suitable solvent, such as for example dichloromethane, dioxane, or an alcohol, e.g. methanol, isopropanol and the like.

Compounds of formula (I) wherein $R^1$ or $R^3$ represent monohaloalkyl, can be converted into a compound of formula (I) wherein $R^1$ or $R^3$ represent $C_{1-6}$alkyl substituted with a ring moiety as defined hereinabove by the intermediate of formula (XXI) and linked to the $C_{1-6}$alkyl moiety by the nitrogen atom, by reaction with an intermediate of formula (XXI) optionally in the presence of a suitable base, such as for example triethylamine or $K_2CO_3$ or sodium hydride, and optionally in the presence of a suitable solvent, such as for example acetonitrile, N,N-dimethylformamide or 1-methyl-2-pyrrolidinone. For the $R^3$ moiety, this type of reaction is in particular used to prepare compounds wherein $C_{1-6}$alkyl represents $C_{3-6}$alkyl. For some variants of the compounds, e.g. wherein $C_{1-6}$alkyl represents $C_{1-2}$alkyl, it might be preferred to perform the reaction in non basic conditions.

Compounds of formula (I) wherein $R^1$ or $R^3$ represents $C_{1-6}$alkyl-OH, can be converted into a compound of formula (I) wherein $R^1$ or $R^3$ represent $C_{1-6}$alkyl-F by reaction with diethylaminosulfur trifluoride in the presence of a suitable solvent, such as for example dichloromethane and in the presence of catalytic amounts of an alcohol, such as for example ethanol. Likewise, a compound of formula (I) wherein $R^1$ or $R^3$ represent $C_{1-6}$alkyl substituted with $R^6$ or $R^9$ wherein said $R^6$ or $R^9$ is substituted with OH, can be converted into a compound of formula (I) wherein $R^1$ or $R^3$ represent $C_{1-6}$alkyl substituted with $R^6$ or $R^9$ wherein said $R^6$ or $R^9$ is substituted with F, by reaction with diethylaminosulfur trifluoride in the presence of a suitable solvent, such as for example dichloromethane.

Compounds of formula (I) wherein $R^1$ or $R^3$ represent $C_{1-6}$alkyl substituted with $R^6$ or $R^9$ wherein said $R^6$ or $R^9$ is substituted with —C(=O)—O—$C_{1-6}$alkyl, can be converted into a compound of formula (I) wherein $R^1$ or $R^3$ represent $C_{1-6}$alkyl substituted with $R^6$ or $R^9$ wherein said $R^6$ or $R^9$ is substituted with —CH$_2$—OH, by reaction with LiAlH$_4$ in the presence of a suitable solvent, such as for example tetrahydrofuran.

Compounds of formula (I) wherein $R^3$ represents $C_{1-6}$alkyl substituted with 1,3-dioxo-2H-isoindol-2-yl, can be converted into a compound of formula (I) wherein $R^3$ represents $C_{1-6}$alkyl substituted with amino, by reaction with hydrazine monohydrate in the presence of a suitable solvent, such as for example an alcohol, e.g. ethanol.

Compounds of formula (I) wherein $R^1$ or $R^3$ represent $C_{1-6}$alkyl substituted with amino, can be converted into a compound of formula (I) wherein $R^1$ or $R^3$ represents $C_{1-6}$alkyl substituted with —NH—S(=O)$_2$—$C_{1-6}$alkyl, by reaction with Cl—S(=O)$_2$—$C_{1-6}$alkyl in the presence of a suitable base, such as for example triethylamine, and a suitable solvent, such as for example dichloromethane.

Compounds of formula (I) wherein $R^1$ or $R^3$ represents $C_{1-6}$alkyl substituted with halo, can be converted into a compound of formula (I) wherein $R^1$ or $R^3$ represent $C_{1-6}$alkyl substituted with NR$^4$R$^5$ or NR$^{10}$R$^{11}$, by reaction with NHR$^4$R$^5$ or NHR$^{10}$R$^{11}$, either using such amino in large excess or in the presence of a suitable base, such as for example $K_2CO_3$, and a suitable solvent, such as for example acetonitrile, N,N-dimethylacetamide or 1-methyl-pyrrolidinone. For the $R^3$ moiety, this type of reaction is in particular used to prepare compounds wherein $C_{1-6}$alkyl represents $C_{3-6}$alkyl. For some variants of the compounds, e.g. wherein $C_{1-6}$alkyl represents $C_{1-2}$alkyl, it might be preferred to perform the reaction in non basic conditions.

Compounds of formula (I) wherein $R^1$ represents hydrogen, can be converted into a compound of formula (I) wherein $R^1$ represents polyhalo$C_{1-6}$alkyl or polyhydroxy$C_{1-6}$ alkyl or $C_{1-6}$alkyl or —S(=O)$_2$—NR$^{14}$R$^{15}$ or —S(=O)$_2$ —$C_{1-6}$alkyl, by reaction with polyhalo$C_{1-6}$ alkyl-W or polyhydroxy$C_{1-6}$alkyl-W or $C_{1-6}$alkyl-W or W—S(=O)$_2$—NR$^{14}$R$^{15}$ or W—S(=O)$_2$—$C_{1-6}$alkyl, wherein W represents a suitable leaving group, such as for example halo, e.g. bromo and the like, in the presence of a suitable base, such as for example sodium hydride or $K_2CO_3$ or triethylamine or 4-dimethylamino-pyridine or diisopropylamine, and a suitable solvent, such as for example N,N-dimethylformamide or acetonitrile or dichloromethane. Compounds of formula (I) wherein $R^1$ represents hydrogen can also be converted into a compound of formula (I) wherein $R^1$ represents $C_{1-6}$alkyl-OH, by reaction with W—$C_{1-6}$alkyl-O—Si(CH$_3$)$_2$ (C(CH$_3$)$_3$) in the presence of a suitable base, such as for example sodium hydride, and a suitable solvent, such as for example N,N-dimethylformamide. Compounds of formula (I) wherein $R^1$ represents hydrogen, can also be converted into compound of formula (I) wherein $R^1$ represents ethyl substituted with —S(=O)$_2$ —$C_{1-6}$alkyl, by reaction with $C_{1-6}$alkyl-vinylsulfone, in the presence of a suitable base, such as for example triethylamine, and a suitable solvent, such as for example an alcohol, e.g. methanol or by reaction with $C_{1-6}$alkyl-2-bromoethylsulfone in the presence of a suitable deprotonating agent, such as for example NaH, and a suitable solvent, such as for example dimethyformamide.

Compounds of formula (I) wherein $R^1$ represents hydrogen can also be converted into a compound of formula (I) wherein $R^1$ represents —$CH_2$—CHOH—$CH_2$

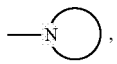

by reaction with

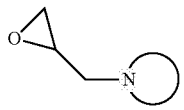

in the presence of a suitable base, such as for example sodium hydride, and a suitable solvent, such as for example N,N-dimethylformamide, wherein

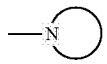

represents a suitable nitrogen containing ring within the definition of $R^6$. Compounds of formula (I) wherein $R^1$ represents $C_{1-6}$alkyl substituted with $R^6$ wherein said $R^6$ is substituted with —C(=O)—O—$C_6$alkyl or —S(=O)$_2$—$NR^{14}R^{15}$ or wherein $R^3$ represents $C_{1-6}$alkyl substituted with $R^9$ wherein said $R^9$ is substituted with —C(=O)—O—$C_{1-6}$alkyl or —S(=O)$_2$—$NR^{14}R^{15}$, can be converted into a compound of formula (I) wherein the $R^6$ or $R^9$ is unsubstituted, by reaction with a suitable acid, such as for example HCl and a suitable solvent, such as for example dioxane, acetonitrile or an alcohol, e.g. isopropylalcohol. Compounds of formula (I) wherein $R^1$ represents $C_{1-6}$alkyl substituted with $R^6$ wherein said $R^6$ is a ring moiety comprising a nitrogen atom which is substituted with —$CH_2$—OH or wherein $R^3$ represents $C_{1-6}$alkyl substituted with $R^9$ wherein said $R^9$ is a ring moiety comprising a nitrogen atom which is substituted with —$CH_2$—OH, can be converted into a compound of formula (I) wherein the $R^6$ or $R^9$ is unsubstituted, by reaction with sodium hydroxide, in the presence of a suitable solvent, such as for example tetrahydrofuran.

Compounds of formula (I) wherein $R^1$ represents $C_{1-6}$alkyl substituted with $R^6$ or $R^3$ represents $C_{1-6}$alkyl substituted with $R^9$, wherein said $R^6$ or said $R^9$ is unsubstituted, can be converted into a compound of formula (I) wherein said $R^6$ or said $R^9$ is substituted with $C_{1-6}$alkyl, by reaction with W—$C_{1-6}$alkyl wherein W is as defined above, in the presence of a suitable base. Such as for example sodium hydride, and a suitable solvent, such as for example N,N-dimethylformamide.

Compounds of formula (I) wherein $R^1$ or $R^3$ represent hydroxy$C_{1-6}$alkyl, can be converted into the corresponding carbonyl compound, by reaction with dess-Martin-periodinane, in the presence of a suitable solvent, such as for example dichloromethane.

Compounds of formula (I) wherein $R^1$ represents $C_{1-6}$alkyl substituted with $R^6$ or $R^3$ represents $C_{1-6}$alkyl substituted with $R^9$, wherein said $R^6$ or said $R^9$ is substituted with $C_{1-6}$alkyl-halo, can be converted into a compound of formula (I) wherein said $R^6$ or said $R^9$ is substituted with $C_{1-6}$alkyl-CN, by reaction with sodium cyanide, in the presence of a suitable solvent, such as for example water or an alcohol, e.g. ethanol.

Compounds of formula (I) wherein $R^1$ represents $C_{1-6}$alkyl substituted with $R^6$ wherein said $R^6$ is unsubstituted or wherein $R^3$ represents $C_{1-6}$alkyl substituted with $R^9$ wherein said $R^9$ is unsubstituted, can be converted into a compound of formula (I) wherein $R^6$ or $R^9$ is substituted with —$CH_3$ or —$CH(CH_3)_2$, by reaction with formaldehyde or acetone and $NaBH_3CN$, in the presence of a suitable solvent, such as for example tetrahydrofuran or an alcohol, e.g. methanol.

Compounds of formula (I) wherein $R^1$ contains a $R^6$ substituent substituted with OH or wherein $R^3$ contains a $R^9$ substituent substituted with OH, can be converted into a compound of formula (I) wherein the $R^6$ or $R^9$ substituent is substituted with $C_{1-6}$alkyloxy, by reaction with W—$C_{1-6}$alkyl, in the presence of a suitable base, such as for example sodium hydride, and a suitable solvent, such as for example N,N-dimethylformamide. Compounds of formula (I) wherein $R^1$ contains a $R^6$ substituent substituted with $C_{1-6}$alkyloxy or wherein $R^3$ contains a $R^9$ substituent substituted with $C_{1-6}$alkyloxy, can be converted into a compound of formula (I) wherein the $R^6$ or $R^9$ substituent is substituted with —OH by reaction with a suitable acid, such as for example hydrochloric acid. Compounds of formula (I) wherein $R^1$ contains a $R^6$ substituent substituted with halo or wherein $R^3$ contains a $R^9$ substituent substituted with halo can be converted into a compound of formula (I) wherein the $R^6$ or $R^9$ substituent is substituted with —$NR^{14}R^{15}$ by reaction with $NHR^{14}R^{15}$ in a suitable solvent, such as for example 1-methyl-pyrrolidinone. Compounds of formula (I) wherein $R^3$ represents $C_{1-6}$alkyl substituted with —C(=O)—O—$C_{1-6}$alkyl, can be converted into a compound of formula (I) wherein $R^3$ represents $C_{1-6}$alkyl substituted with COOH, by reaction with LiOH in the presence of a suitable solvent, such as for example tetrahydrofuran. Said compounds of formula (I) wherein $R^3$ represents $C_{1-6}$alkyl substituted with COOH, can be converted into a compound of formula (I) wherein $R^3$ represents $C_{1-6}$alkyl substituted with —C(=O)—$NH_2$ or —C(=O)—$NHCH_3$ or —C(=O)$NR^{10}R^{11}$, by reaction with $NH(Si(CH_3)_3)_2$ or $MeNH_3^+Cl^-$ or $NHR^{10}R^{11}$ in the presence of suitable peptide coupling reagents such as for example 1-(3-dimethylaminopropyl)-3-ethylcarbodiimide HCl and 1-hydroxybenzotriazole, a suitable base, such as for example triethylamine and a suitable solvent such as for example dichloromethane or N,N-dimethylformamide. Compounds of formula (I) wherein $R^3$ represents $C_{1-6}$alkyl substituted with —C(=O)—O—$C_{1-6}$alkyl, can also be converted into a compound of formula (I) wherein $R^3$ represents $C_{1-6}$alkyl substituted with 4,5-dihydro-imidazol-2-yl, by reaction under $N_2$ with ethylenediamine and trimethylaluminium in the presence of a suitable solvent, such as for example toluene and heptane. Compounds of formula (I) wherein $R^3$ represents $C_{1-6}$alkyl substituted with COOH, can also be converted into a compound of formula (I) wherein $R^3$ represents $C_{1-6}$alkyl substituted with —C(=O)—N($CH_3$)(O$CH_3$) by reaction with dimethylhydroxylamine, in the presence of carbonyldiimidazole and a suitable solvent, such as for example dichloromethane. Compounds of formula (I) wherein $R^3$ represents $C_{1-6}$alkyl substituted with

can be converted into a compound of formula (I) wherein $R^3$ represents $C_{1-6}$alkyl substituted with 2 OH's, by reaction with a suitable acid, such as for example trifluoroacetic acid, and a suitable solvent, such as for example dioxane or water. These compounds of formula (I) wherein $R^3$ represents $C_{1-6}$alkyl substituted with

can also be converted into a compound of formula (I) wherein $R^3$ represents $C_{1-6}$alkyl substituted with OH and $NR^{10}R^{11}$, by reaction with $NH_2R^{10}R^{11}$ optionally in salt form, such as for example $NHR^{10}R^{11+}Cl^-$, optionally in the presence of a suitable base, such as for example sodium hydride or $Na_2CO_3$ or triethylamine, a suitable additive such as for example KI, and in the presence of a suitable solvent, such as for example N,N-dimethylformamide or an alcohol, e.g. 1-butanol or ethanol.

Compounds of formula (I) wherein $R^3$ represents $C_{1-3}$alkyl substituted with —C(=O)—O—$C_{1-6}$alkyl, can be converted into a compound of formula (I) wherein $R^3$ represents $C_{1-3}$alkyl substituted with —C(CH3)$_2$—OH, by reaction with iodomethane and Mg powder, in the presence of a suitable solvent, such as for example diethylether or tetrahydrofuran.

Compounds of formula (I) wherein $R^3$ represents $C_{1-5}$alkyl substituted with —C(=O)—O—$C_{1-6}$alkyl, can be converted into a compound of formula (I) wherein $R^3$ represents $C_{1-6}$alkyl substituted with —OH, by reaction with $LiAlH_4$ in a suitable solvent, such as for example tetrahydrofuran.

Compounds of formula (I) wherein $R^3$ represents $C_{1-5}$alkyl substituted with —OH, can be converted into a compound of formula (I) wherein $R^3$ represents $C_{1-6}$alkyl substituted with —O—C(=O)—$C_{1-6}$alkyl by reaction with Cl—C(=O)—$C_{1-6}$alkyl in the presence of a suitable base, such as for example NaH, and a suitable solvent, such as for example tetrahydrofuran.

Compounds of formula (I) wherein $R^3$ represents —$CH_2$—CH=$CH_2$, can be converted into a compound of formula (I) wherein $R^3$ represents —$CH_2$—CHOH—$CH_2$—OH, by reaction with potassium permanganate, and a suitable solvent, such as for example acetone or water.

Compounds of formula (I) wherein $R^3$ represents $C_{1-6}$alkyl substituted with —C(=O)—$C_{1-6}$alkyl, can be converted into a compound of formula (I) wherein $R^3$ represents $C_{1-6}$alkyl substituted with —C($C_{1-4}$alkyl)=N—OH, by reaction with hydroxylamine, in the presence of a suitable base, such as for example pyridine, and a suitable solvent, such as for example an alcohol, e.g. ethanol.

Compounds of formula (I) wherein $R^3$ represents $C_{1-6}$alkyl substituted with $NH_2$, can be converted into a compound of formula (I) wherein $R^3$ represents $C_{1-6}$alkyl substituted with —NH—C(=O)—$R^6$ or with —NH—C(=O)—$C_{1-6}$alkyl or with —NH—C(=O)-polyhydroxy$C_{1-6}$alkyl or with —NH—C(=O)-polyhalo$C_{1-6}$alkyl or with —NH—C(=O)-polyhydroxypolyhalo$C_{1-6}$alkyl, by reaction with the corresponding COOH analogue, e.g. $R^6$—COOH or $CF_3$—C($CH_3$)(OH)—COOH and the like, in the presence of suitable peptide coupling reagents such as 1-hydroxy-benzotriazole and 1-(3-dimethylamino)propyl) carbodiimide optionally in the presence of a suitable base, such as for example triethylamine. Said compounds of formula (I) wherein $R^3$ represents $C_{1-6}$alkyl substituted with $NH_2$, can also be converted into a compound of formula (I) wherein $R^3$ represents $C_{1-6}$alkyl substituted with —NH—C(=O)—$CF_3$, by reaction with trifluoroacetic anhydride, in the presence of a suitable base, such as for example triethylamine, and a suitable solvent, such as for example tetrahydrofuran. Said compounds of formula (I) wherein $R^3$ represents $C_{1-6}$alkyl substituted with $NH_2$, can also be converted into a compound of formula (I) wherein $R^3$ represents $C_{1-6}$alkyl substituted with —NH-polyhalo$C_6$alkyl, e.g. —NH—$CH_2$—$CH_2$—F, by reaction with polyhalo$C_{1-6}$alkyl-W, with W as defined above, e.g. iodo-2-fluoroethane, in the presence of a suitable base, such as for example $K_2CO_3$, and a suitable solvent, such as for example N,N-dimethylformamide or dioxane. Said compounds of formula (I) wherein $R^3$ represents $C_{1-6}$alkyl substituted with $NH_2$ can also be converted into a compound of formula (I) wherein $R^3$ represents $C_{1-6}$alkyl substituted with —NH—$R^6$ or —N($R^6$)$_2$ wherein $R^6$ represents for example oxetane, by reaction with the appropriate $R^6$ in the presence of a suitable reducing agent, such as for example sodium triacetoxyborohydride, a suitable acid, such as for example acetic acid, and a suitable solvent, such as for example 1,2-dichloroethane.

Compounds of formula (I) wherein $R^3$ represents $C_{1-6}$alkyl substituted with cyano, can be converted into a compound of formula (I) wherein $R^3$ represents $C_{1-6}$alkyl substituted with tetrazolyl by reaction with sodium azide, and $NH_4^+Cl^-$ in the presence of a suitable solvent, such as for example N,N-dimethylformamide.

Compounds of formula (I) wherein $R^3$ represents —CH2-C≡CH, can be converted into a compound of formula (I) wherein $R^3$ represents

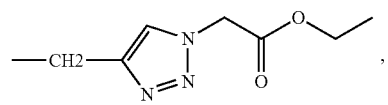

by reaction with ethyl azidoacetate in the presence of CuI and a suitable base, such as for example diisopropylamine, and a suitable solvent, such as for example tetraydrofuran. Compounds of formula (I) wherein $R^3$ represents —CH2-C≡CH, can be converted into a compound of formula (I) wherein $R^3$ represents

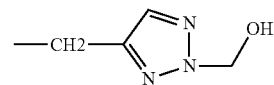

by reaction with sodium azide and formaldehyde, in the presence of a suitable catalyst, such as for example $CuSO_4$ and sodium L ascorbate, a suitable acid, such as for example acetic acid, and a suitable solvent, such as for example dioxane.

Compounds of formula (I) wherein $R^3$ represent $C_{2-6}$alkynyl, can be converted into a compound of formula (I) wherein $R^3$ represents $C_{2-6}$alkynyl substituted with $R^9$, by reaction with W—$R^9$ wherein W is as defined above, in the presence of a suitable catalyst, such as for example dichlorobis(triphenylphosphine)palladium, a suitable co-catalyst such as CuI, a suitable base, such as for example triethylamine, and a suitable solvent, such as for example dimethylsulfoxide.

Compounds of formula (I) wherein $R^3$ comprises $R^9$ substituted with halo, can be converted into a compound of formula (I) wherein $R^3$ comprises $R^9$ substituted with —$NR^{14}R^{15}$ by reaction with $NHR^{14}R^{15}$ in the presence of a suitable solvent, such as for example 1-methyl-2-pyrrolidinone.

Compounds of formula (I) wherein $R^3$ comprises $C_{2-6}$alkynyl, can be hydrogenated into a compound of formula (I) wherein $R^3$ comprises $C_{2-6}$alkyl in the presence of a suitable catalyst, such as for example palladium on charcoal, and a suitable solvent, such as for example ethylacetate.

Compounds of formula (I) wherein $R^3$ comprises $C_{2-6}$alkynyl, can be hydrogenated into a compound of formula (I) wherein $R^3$ comprises $C_{2-6}$alkenyl in the presence of a suitable catalyst, such as for example Lindlar catalyst, and a suitable solvent, such as for example ethylacetate.

Compounds of formula (I) wherein $R^3$ represents $C_{1-6}$alkyl substituted with —$P(=O)(OC_{1-6}alkyl)_2$ can be converted into a compound of formula (I) wherein $R^3$ represents $C_{1-6}$alkyl substituted with —$P(=O)(OH)_2$ by reaction with bromotrimethylsilane in the presence of a suitable solvent, such as for example dichloromethane.

Compounds of formula (I) wherein the $R^9$ substituent is substituted with =O, can be converted into the corresponding reduced $R^9$ substituent by reaction with a suitable reducing agent, such as for example $LiAlH_4$ in a suitable solvent, such as for example tetrahydrofuran.

Compounds of formula (I) wherein $R^3$ represents $C_{1-6}$alkyl substituted with —$C(=O)$—$R^9$ can be converted into a compound of formula (I) wherein $R^3$ represents $C_{1-6}$alkyl substituted with hydroxyl and $R^9$ by reaction with a suitable reducing agent, such as for example sodium borohydride, in the presence of a suitable solvent, such as for example an alcohol, e.g. methanol.

Compounds of formula (I) wherein $R^3$ comprises —$NHR^{10}$ can be converted into a compound of formula (I) wherein $R^3$ comprises —$NR^{10}$—(C=O)-optionally substituted $C_{1-6}$alkyl, by reaction with the corresponding W—(C=O)-optionally substituted $C_{1-6}$alkyl wherein W represents a suitable leaving group, such as for example halo, e.g. chloro and the like, in the presence of a suitable base, such as for example triethylamine, and a suitable solvent, such as for example acetonitrile or dichloromethane.

Compounds of formula (I) wherein $R^3$ represents $C_{1-6}$alkyl substituted with $NR^{10}$ (benzyl) can be converted into a compound of formula (I) wherein $R^3$ represents $C_{1-6}$alkyl substituted with $NHR^{10}$, by reaction with 1-chloroethylchloroformate in the presence of a suitable solvent, such as for example dichloromethane Compounds of formula (I) wherein $R^1$ represents unsubstituted piperidine, can be converted into a compound of formula (I) wherein $R^1$ represents 1-methyl-piperidine, by reaction with iodomethane in the presence of a suitable base, such as for example potassium carbonate, and a suitable solvent, such as for example acetonitrile. Compounds of formula (I) wherein $R^1$ represents hydrogen can be converted into a compound of formula (I) wherein $R^1$ represents optionally substituted $C_{1-6}$alkyl, by reaction with optionally substituted $C_{1-6}$alkyl-W wherein W represents a suitable leaving group, such as for example halo, e.g. bromo and the like, in the presence of a suitable base, such as for example potassium carbonate, and a suitable solvent, such as for example acetonitrile.

Compounds of formula (I) wherein $R^2$ represents halo, e.g. bromo, can be converted into a compound of formula (I) wherein $R^2$ represents cyano, by reaction with zinc cyanide, in the presence of a suitable catalyst, such as for example $Pd_2(dba)_3$ and a suitable ligand, such as for example 1,1-bis(diphenylphosphino)ferrocene, in the presence of a suitable solvent, such as for example N,N-dimethylformamide.

Said $R^2$ substituent being cyano can be converted into —$CH_2$—$NH_2$ by hydrogenation in the presence of $NH_3$ and Nickel.

Compounds of formula (I) wherein $R^2$ represents —$OCH_3$ can be converted into a compounds of formula (I) wherein $R^2$ represents —OH by reaction with boron tribromide in the presence of a suitable solvent, such as for example dichloromethane.

Compounds of formula (I) wherein $R^2$ represents —OH can be converted into a compounds of formula (I) wherein $R^2$ represents —$OCH_3$ by reaction with methyl iodine in the presence of a suitable base, such as for example potassium carbonate, and a suitable solvent, such as for example N,N-dimethylformamide.

Compounds of formula (I) wherein $R^2$ represents hydrogen, can be converted into a compound of formula (I) wherein $R^2$ represents —CHOH—$CF_3$ by reaction with trifluoroacetaldehyde methyl hemiketal.

For the conversion reactions, reference is also made to the examples described in the Experimental Part hereinafter.

A further aspect of the invention is a process for the preparation of a compound of formula (I) as defined herein, which process comprises:

(i) deprotecting a compound of formula (XXX) wherein P represents a suitable protective group, such as for example a butyloxycarbonyl-group (—$CO_2C(CH_3)_3$) in the presence of a suitable acid, such as for example HCl or trifluoroacetic acid;

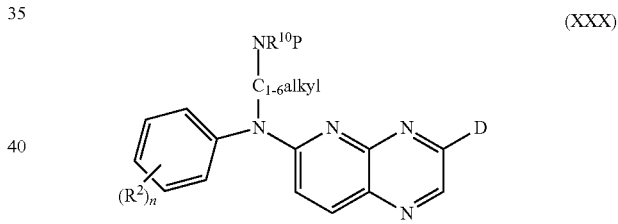

(XXX)

(ii) the reaction of a compound of the formula (IX) or (IX'):

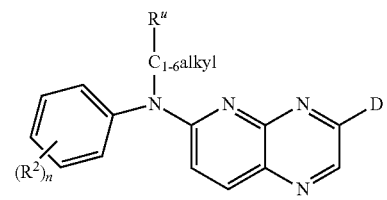

(IX): $R^u$ is —O—(S=O)$_2$—$CH_3$   (IX'): $R^u$ is Cl or a protected form thereof, with an appropriately substituted amine or a reactive derivative thereof, such as for example $NHR^{10}R^{11}$ (X), $NHR^{10}P$ (X-a) or

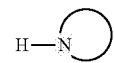

(XXI), for example in a sealed vessel, in the presence of a suitable base, such as for example sodium hydride and/or in the presence or absence of a solvent such as acetonitrile, N,N-dimethylformamide or N,N-dimethylacetamide; or (iii) the reaction of a compound of the formula (VI):

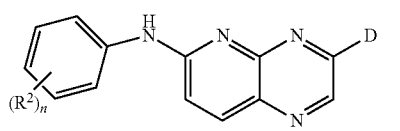

(VI)

or a protected form thereof, with a compound of formula $W_6$—$C_{1-6}$alkyl-$NR^{10}P$ wherein P represents a suitable protective group and $W_6$ represents a suitable leaving group, such as for example halo, e.g. bromo and the like, or —O—S(=O)$_2$—CH$_3$, in the presence of a suitable base, such as for example sodium hydride, and a suitable solvent, e.g. N,N-dimethylformamide or N,N-dimethylacetamide, followed by removing P and optionally removing any further protecting group present; or (iv) the reaction of a compound of the formula (VI):

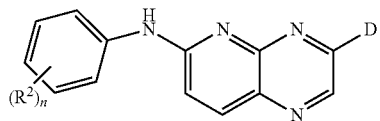

(VI)

or a protected thereof, with a compound of formula $W_6$—$C_{1-6}$ alkyl-$NHR^{10}$ wherein $W_6$ represents a suitable leaving group, such as for example halo, e.g. bromo and the like, or —O—S(=O)$_2$—CH$_3$, in the presence of a suitable base, such as for example sodium hydride, and a suitable solvent, e.g. N,N-dimethylformamide or N,N-dimethylacetamide; (v) the reaction of a compound of formula (XXXVI)

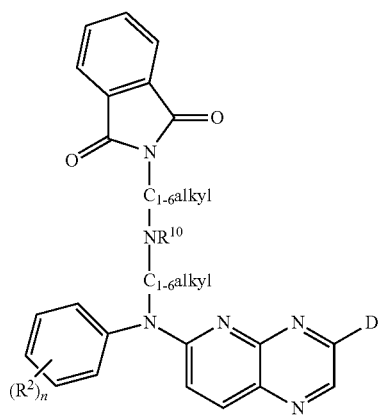

(XXXVI)

with hydrazine in the presence of a suitable solvent, such as for example an alcohol, e.g. ethanol;

(vi) the reaction of a compound of formula (IX-1) wherein $R^u$ represents —O—S(=O)$_2$—CH$_3$,

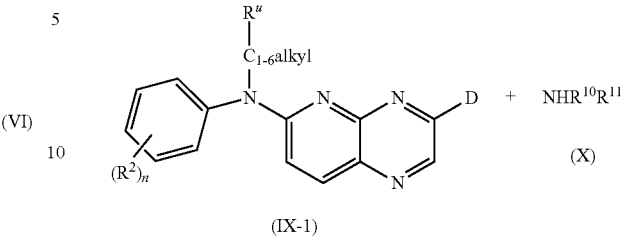

(IX-1)

with an intermediate of formula (X) in the presence of a suitable solvent, such as for example acetonitrile;

(vii) the reaction of a compound of formula (VI)

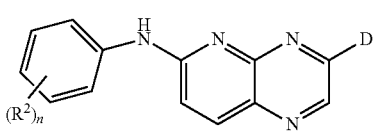

(VI)

with an intermediate of formula $W_{11}$—$R^{3b}$ wherein $R^{3b}$ represents optionally substituted $C_{2-6}$alkynyl and $W_{11}$ represents a suitable leaving group such as for example halo, e.g. chloro, or —O—S(=O)$_2$—CH$_3$, in the presence of a suitable base, such as for example NaH, and a suitable solvent, such as for example N,N-dimethylformamide;

(viii) the reaction of a compound of formula (VIII') wherein $R^x$ and $R^y$ represent $C_{1-4}$alkyl, and $R^z$ represent $C_{1-4}$alkyl or phenyl,

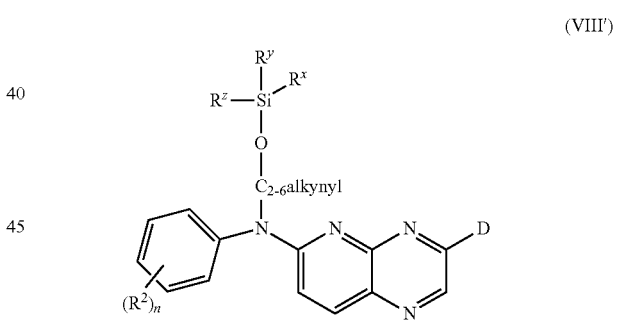

(VIII')

with a suitable acid, such as for example trifluoroacetic acid, in the presence of a suitable solvent, such as for example tetrahydrofuran;

(viii) deprotecting a compound of formula (XXXXII)

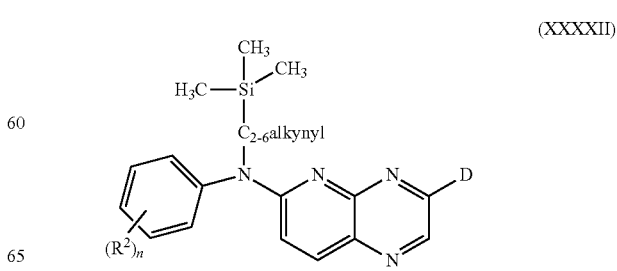

(XXXXII)

in the presence of a suitable base, such as for example K₂CO₃, and a suitable solvent, such as for example an alcohol, e.g. methanol and the like;

(ix) the reaction of a compound of formula (VI)

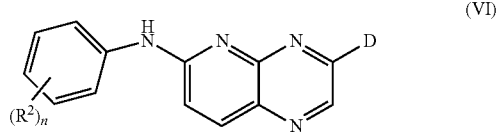
(VI)

with di(C₁₋₆alkyl)vinylphosphonate in the presence of a suitable catalyst, such as for example tri-N-butylphosphine, and a suitable solvent, such as for example acetonitrile;

(x) deprotecting a compound of formula (XXXXI) wherein the D'N moiety represents a D moiety wherein the D moiety contains a nitrogen atom

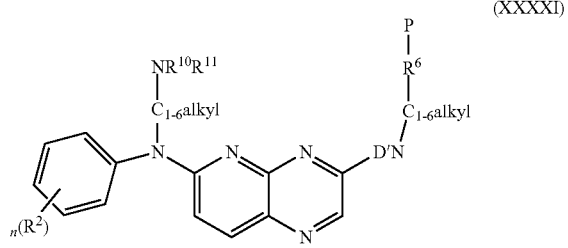
(XXXXI)

in the presence of a suitable base, such as for example K₂CO₃, and a suitable solvent, such as for example an alcohol, e.g. methanol and the like;

(xi) the reaction of a compound of formula (XXXI)

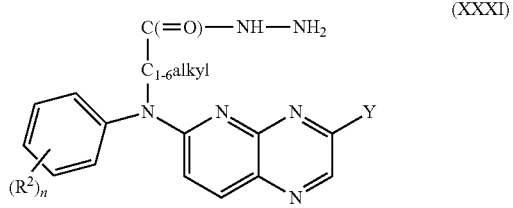
(XXXI)

with W₈—CN, wherein W₈ represents a suitable leaving group, such as for example halo, e.g. bromo, in the presence of a suitable base, such as for example NaHCO₃, and a suitable solvent, such as for example water or dioxane;

(xii) the reaction of a compound of formula (XXXV)

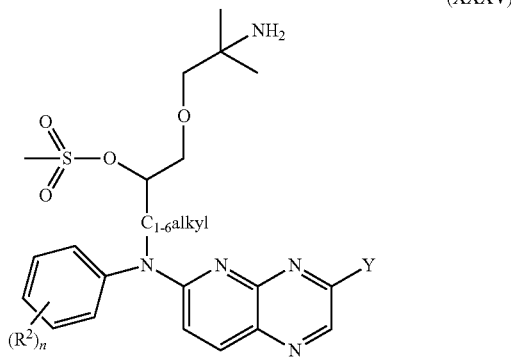
(XXXV)

with a suitable base, such as for example N,N-diisopropylethylamine and triethylamine, in the presence of a suitable solvent, such as for example an alcohol, e.g. methanol;

(xiii) deprotecting a compound of formula (XXVI) wherein P represents a suitable protective group such as for example —O—Si(CH₃)₂(C(CH₃)₃) or

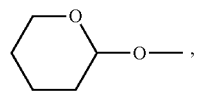

wherein Y'N represents an -E-D moiety wherein the D ring moiety contains a nitrogen atom

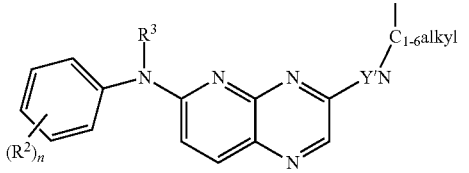
(XXVI)

in the presence of a suitable acid, such as for example HCl or trifluoroacetic acid, or a suitable de-silylating agent, such as for example tetrabutyl ammonium fluoride, and a suitable solvent, such as an alcohol, e.g. methanol, or tetrahydrofuran;

(xiv) the reaction of a compound of formula (XXIX) wherein Y'N represents an -E-D moiety wherein the D ring moiety contains a nitrogen atom, with a compound of formula (XXI)

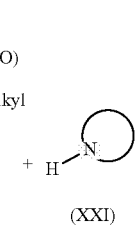
(XXI)

(XXIX)

in the presence of suitable peptide coupling reagents such as, 1-hydroxy-benzotriazole and 1-(3-dimethylaminopropyl)-3-ethyl carbodiimide HCl;

(xv) the reaction of a compound of formula (XXIX) wherein Y'N represents an -E-D moiety wherein the D ring moiety contains a nitrogen atom

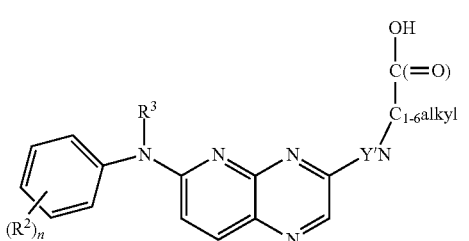
(XXIX)

with NHR⁴R⁵ in the presence of suitable peptide coupling reagents such as 1-hydroxy-benzotriazole and 1-(3-dimethylaminopropyl)-3-ethyl carbodiimide HCl and a suitable base, such as triethylamine, and a suitable solvent, such as for example dichloromethane;

(xvi) reacting the below compound

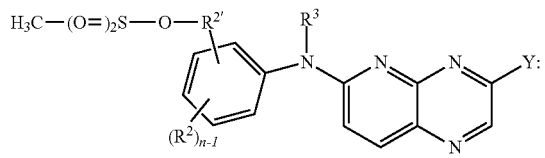

with NHR⁷R⁸ in the presence of a suitable base, such as for example K₂CO₃, and a suitable solvent, such as for example tetrahydrofuran;

(xvii) deprotecting the below compound

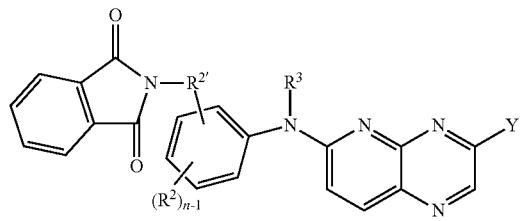

in the presence of hydrazine monohydrate, and a suitable solvent, such as for example an alcohol, e.g. ethanol;

(xvii) reacting an intermediate of formula (VI)

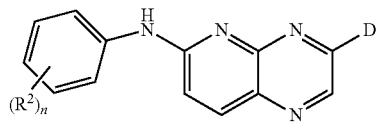

with W₆—R³ᵈ wherein W₆ represents a suitable leaving group, such as for example halo, e.g. bromo, chloro, and the like, or —O—S(=O)₂—CH₃ or p-toluenesulfonate, and R³ᵈ represents optionally substituted $C_{1-6}$alkyl, such as for example —CH₂—C₃H₅, in the presence of a suitable base, such as for example sodium hydride, Cs₂CO₃, potassium tert-butoxyde or potassium hydroxide, optionally a suitable phase transfer agent, such as for example tetrabutylammonium bromide, and a suitable solvent, such as for example N,N-dimethylformamide, N,N-dimethylacetamide, 2-methyltetrahydrofuran, tetrahydrofuran, water or acetonitrile.

wherein the variables are as defined herein; and optionally thereafter converting one compound of the formula (I) into another compound of the formula (I).

A further embodiment is a process for synthesis of a compound of formula (VI) wherein:

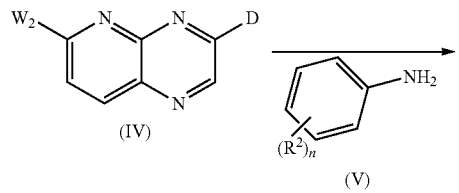

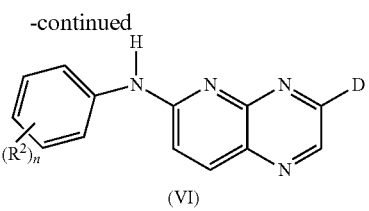

a compound of formula (IV) is reacted with an intermediate of formula (V) in the presence of a suitable catalyst, such as for example palladium (11) acetate, a suitable base, such as sodium tert-butoxide or Cs₂CO₃, a suitable ligand, such as for example 1,1'-[1,1'-binaphthalene]-2,2'-diylbis[1,1-diphenylphosphine], and a suitable solvent or solvent mixture, such as for example dioxane or ethylene glycol dimethylether and water.

Alternatively a compound of formula (IV) is reacted with an intermediate of formula (V) in the presence of a suitable solvent such as for example an alcohol, e.g. isopropanol, and optionally in the presence of a suitable acid such as for example hydrochloric acid.

Alternatively a compound of formula (IV) is reacted with an intermediate of formula (V) in the presence of a suitable deprotonating agent such as for example lithium bis(trimethylsilyl)amide, in the presence of a suitable solvent such as for example N<N-dimethylformamide or tetrahydrofuran.

In a further embodiment the invention provides a novel intermediate. In one embodiment the invention provides a novel intermediate as described herein. In another embodiment the invention provides a novel intermediate of formula (VI) or formula (IX).

In one embodiment, the present invention also relates to a compound having the following formula:

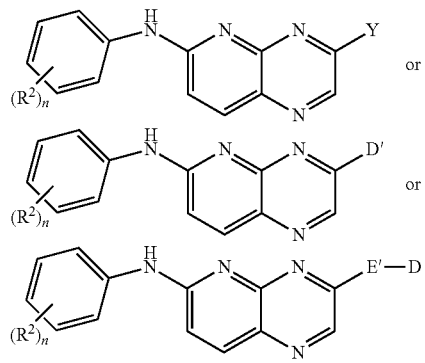

including any stereochemically isomeric form thereof;
wherein Y represents —CR¹⁸=N—OR¹⁹ or -D' or -E'-D;
D' represents a 3 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) R¹ groups;
wherein E' represents —(CR²²R²³)ₙ—, $C_{2-4}$alkenediyl optionally substituted with R²², $C_{2-4}$alkynediyl optionally substituted with R²², —CO—(CR²²R²³)ₛ—, —(CR²²R²³)ₛ—CO—, —NR²²—(CR²²R²³)ₛ—, —(CR²²R²³)ₛ—NR²²—, —O—(CR²²R²³)ₛ—, —(CR²²R²³)ₛ—O—, —S(O)ₘ—(CR²²R²³)ₛ—, —(CR²²R²³)ₛ—S(O)ₘ—, —(CR²²R²³)ₛ—CO—NR²²—(CR²²R²³)ₛ— or —(CR²²R²³)ₛ—NR²²—CO—(CR²²R²³)ₛ—; and wherein D, R² and n are as defined for a compound of formula (I) above; a N-oxide thereof, a pharmaceutically acceptable salt thereof or a solvate thereof.

Pharmaceutically Acceptable Salts, Solvates or Derivatives Thereof

In this section, as in all other sections of this application, unless the context indicates otherwise, references to formula (I) include references to all other sub-groups, preferences, embodiments and examples thereof as defined herein.

Unless otherwise specified, a reference to a particular compound also includes ionic forms, salts, solvates, isomers, tautomers, N-oxides, esters, prodrugs, isotopes and protected forms thereof, for example, as discussed below; preferably, the ionic forms, or salts or tautomers or isomers or N-oxides or solvates thereof; and more preferably, the ionic forms, or salts or tautomers or solvates or protected forms thereof, even more preferably the salts or tautomers or solvates thereof. Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. It will be appreciated that references to "derivatives" include references to ionic forms, salts, solvates, isomers, tautomers, N-oxides, esters, prodrugs, isotopes and protected forms thereof.

According to one aspect of the invention there is provided a compound as defined herein or a salt, tautomer, N-oxide or solvate thereof. According to a further aspect of the invention there is provided a compound as defined herein or a salt or solvate thereof. References to compounds of the formula (I) and sub-groups thereof as defined herein include within their scope the salts or solvates or tautomers or N-oxides of the compounds.

The salt forms of the compounds of the invention are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts.

Such non-pharmaceutically acceptable salts forms, which may be useful, for example, in the purification or separation of the compounds of the invention, also form part of the invention.

The salts of the present invention can be synthesized from the parent compound that contains a basic or acidic moiety by conventional chemical methods such as methods described in Pharmaceutical Salts: Properties, Selection, and Use, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The compounds of the invention may exist as mono- or di-salts depending upon the pKa of the acid from which the salt is formed.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, pyruvic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

If the compound is anionic, or has a functional group which may be anionic (e.g., —COOH may be —COO—), then a salt may be formed with a suitable cation. Examples of suitable inorganic cations include, but are not limited to, alkali metal ions such as Na⁺ and K⁺, alkaline earth metal cations such as $Ca^{2+}$ and $Mg^{2+}$, and other cations such as Al3+. Examples of suitable organic cations include, but are not limited to, ammonium ion (i.e., $NH_4^+$) and substituted ammonium ions (e.g., $NH_3R+$, $NH_2R_2^+$, $NHR_{3+}$, $NR_4+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I). Compounds of the formula (I) containing an amine function may also form N-oxides. A reference herein to a compound of the formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4*th* Edition, Wiley Interscience, pages. More particularly, N-oxides can be made by the procedure of L. W. Deady (*Syn. Comm.* (1977), 7, 509-514) in which the amine compound is reacted with m-chloroperoxybenzoic acid (MCPBA), for example, in an inert solvent such as dichloromethane.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed. Also encompassed by formula (I) are any complexes (e.g. inclusion complexes or clathrates with compounds such as cyclodextrins, or complexes with metals) of the compounds.

Furthermore, the compounds of the present invention may have one or more polymorph (crystalline) or amorphous forms and as such are intended to be included in the scope of the invention.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I). Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

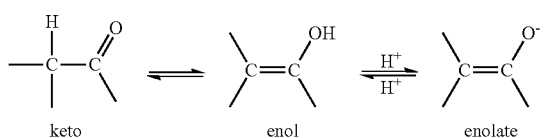

Where compounds of the formula (I) contain one or more chiral centres, and can exist in the form of two or optical isomers, references to compounds of the formula (I) include all optical isomeric forms thereof (e.g. enantiomers, epimers and diastereoisomers), either as individual optical isomers, or mixtures (e.g. racemic mixtures) of two or more optical isomers, unless the context requires otherwise. The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog (1966) *Angew. Chem. Int. Ed. Engl.*, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer). When a specific isomeric form is identified (e.g. S configuration, or E isomer), this means that said isomeric form is substantially free of the other isomer(s), i.e. said isomeric form is present in at least 55%, 60%, 65%, 70%, 75%, 80%, 85%, 90%, 95%, 99% or more (e.g. substantially all) of the total amount of the compound of the invention.

The compounds of the invention include compounds with one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by formula (I). In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group. Examples of esters are compounds containing the group —C(=O)OR, wherein R is an ester substituent, for example, a $C_{1-6}$ alkyl group, a heterocyclyl group, or a $C_{5-20}$ aryl group, preferably a $C_{1-6}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

For example, some prodrugs are esters of the active compound (e.g., a physiologically acceptable metabolically labile ester). By "prodrugs" is meant for example any compound that is converted in vivo into a biologically active compound of the formula (I). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is: $C_{1-6}$alkyl (e.g., -Me, -Et, -nPr, -iPr, -nBu, -sBu, -iBu, -tBu); $C_{1-6}$aminoalkyl [e.g., aminoethyl; 2-(N,N-diethylamino)ethyl; 2-(4-morpholino)ethyl); and acyloxy-$C_{1-7}$alkyl [e.g., acyloxymethyl; acyloxyethyl; pivaloyloxymethyl; acetoxymethyl; 1-acetoxyethyl; 1-(1-methoxy-1-methyl)ethyl-carbonyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl]. Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT) and ligand-directed enzyme pro-drug therapy (LIDEPT) etc.). For example, the prodrug may be a sugar derivative or other glycoside conjugate, or may be an amino acid ester derivative.

Protein Tyrosine Kinases (PTK)

The compounds of the invention described herein inhibit or modulate the activity of certain tyrosine kinases, and thus the compounds will be useful in the treatment or prophylaxis, in particular the treatment, of disease states or conditions mediated by those tyrosine kinases, in particular FGFR.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signalling molecules which act as autocrine as well as paracrine factors. Autocrine FGF signalling may be particularly important in the progression of steroid hormone-dependent cancers to a hormone independent state. FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signalling in human pancreatic cancer (Knights et al., Pharmacology and Therapeutics 2010 125:1 (105-117); Korc M. et al Current Cancer Drug Targets 2009 9:5 (639-651)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4).

Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway. Rhabdomyosarcoma (RMS) is the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes. FGFR1 has also been linked to squamous lung cancer, colorectal cancer, glioblastoma, astrocytomas, prostate cancer, small cell lung cancer, melanoma, head and neck cancer, thyroid cancer, uterine cancer.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembranous bone formation. For example, in Apert (AP) syndrome, characterized by premature cranial suture ossification, most cases are associated with point mutations engendering gain-of-function in fibroblast growth factor receptor 2. In addition, mutation screening in patients with syndromic craniosynostoses indicates that a number of recurrent FGFR2 mutations accounts for severe forms of Pfeiffer syndrome. Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene, and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signalling and suggests that the severe phenotypes of these disease syndromes result from ectopic ligand-dependent activation of fibroblast growth factor receptor 2.

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas. Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC). Increased expression was associated with mutation (85% of mutant tumors showed high-level expression) but also 42% of tumors with no detectable mutation showed over-expression, including many muscle-invasive tumors. FGFR3 is also linked to endometrial and thyroid cancer.

Over expression of FGFR4 has been linked to poor prognosis in both prostate and thyroid carcinomas. In addition a germline polymorphism (Gly388Arg) is associated with increased incidence of lung, breast, colon, liver (HCC) and prostate cancers. In addition, a truncated form of FGFR4 (including the kinase domain) has also been found to be present in 40% of pituitary tumours but not present in normal tissue. FGFR4 overexpression has been observed in liver, colon and lung tumours. FGFR4 has been implicated in colorectal and liver cancer where expression of its ligand FGF19 is frequently elevated. FGFR4 is also linked to astrocytomas, rhabdomyosarcoma.

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis. TGFβ1 and PDGF have been reported to be involved in the fibrogenic process and further published work suggests the elevation of FGF's and consequent increase in fibroblast proliferation, may be in response to elevated TGF31. The potential therapeutic benefit of targeting the fibrotic mechanism in conditions such as idiopathic pulmonary fibrosis (IPF) is suggested by the reported clinical effect of the anti-fibrotic agent pirfenidone. Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

Vascular Endothelial Growth Factor (VEGFR)

Chronic proliferative diseases are often accompanied by profound angiogenesis, which can contribute to or maintain an inflammatory and/or proliferative state, or which leads to tissue destruction through the invasive proliferation of blood vessels.

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage. In diabetes (and in many different eye diseases), new vessels invade the macula or retina or other ocular structures, and may cause blindness. The process of atherosclerosis has been linked to angiogenesis. Tumor growth and metastasis have been found to be angiogenesis-dependent.

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis, ocular diseases, arthritis and hemangioma.

Vascular endothelial growth factor (VEGF), a polypeptide, is mitogenic for endothelial cells in vitro and stimulates angiogenic responses in vivo. VEGF has also been linked to inappropriate angiogenesis. VEGFR(s) are protein tyrosine kinases (PTKs). PTKs catalyze the phosphorylation of specific tyrosine residues in proteins involved in cell function thus regulating cell growth, survival and differentiation.

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction. Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis.

Inhibition at the kinase domain binding site of VEGFR-2 would block phosphorylation of tyrosine residues and serve to disrupt initiation of angiogenesis.

Angiogenesis is a physiologic process of new blood vessel formation mediated by various cytokines called angiogenic factors. Although its potential pathophysiologic role in solid tumors has been extensively studied for more than 3 decades, enhancement of angiogenesis in chronic lymphocytic leukemia (CLL) and other malignant hematological disorders has been recognized more recently. An increased level of angiogenesis has been documented by various experimental methods both in bone marrow and lymph nodes of patients with CLL. Although the role of angiogenesis in the pathophysiology of this disease remains to be fully elucidated, experimental data suggest that several angiogenic factors play a role in the disease progression. Biologic markers of angiogenesis were also shown to be of prognostic relevance in CLL. This indicates that VEGFR inhibitors may also be of benefit for patients with leukemia's such as CLL.

In order for a tumour mass to get beyond a critical size, it must develop an associated vasculature. It has been proposed that targeting a tumor vasculature would limit tumor expansion and could be a useful cancer therapy. Observations of tumor growth have indicated that small tumour masses can persist in a tissue without any tumour-specific vasculature. The growth arrest of nonvascularized tumors has been attributed to the effects of hypoxia at the center of the tumor. More recently, a variety of proangiogenic and antiangiogenic factors have been identified and have led to the concept of the "angiogenic switch," a process in which disruption of the normal ratio of angiogenic stimuli and inhibitors in a tumor mass allows for autonomous vascularization. The angiogenic switch appears to be governed by the same genetic alterations that drive malignant conversion: the activation of oncogenes and the loss of tumour suppressor genes. Several growth factors act as positive regulators of angiogenesis. Foremost among these are vascular endothelial growth factor (VEGF), basic fibroblast growth factor (bFGF), and angiogenin. Proteins such as thrombospondin (Tsp-1), angiostatin, and endostatin function as negative regulators of angiogenesis.

Inhibition of VEGFR2 but not VEGFR1 markedly disrupts angiogenic switching, persistent angiogenesis, and initial tumor growth in a mouse model. In late-stage tumors, phenotypic resistance to VEGFR2 blockade emerged, as tumors regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition.

There is evidence for normalization of glioblastoma blood vessels in patients treated with a pan-VEGF receptor tyrosine kinase inhibitor, AZD2171, in a phase 2 study. MRI determination of vessel normalization in combination with circulating biomarkers provides for an effective means to assess response to antiangiogenic agents.

PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. A growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation.

Advantages of a Selective Inhibitor

Development of FGFR kinase inhibitors with a differentiated selectivity profile provides a new opportunity to use these targeted agents in patient sub-groups whose disease is driven by FGFR deregulation. Compounds that exhibit reduced inhibitory action on additional kinases, particularly VEGFR2 and PDGFR-beta, offer the opportunity to have a differentiated side-effect or toxicity profile and as such allow for a more effective treatment of these indications. Inhibitors of VEGFR2 and PDGFR-beta are associated with toxicities such as hypertension or oedema respectively. In the case of VEGFR2 inhibitors this hypertensive effect is often dose limiting, may be contraindicated in certain patient populations and requires clinical management.

Biological Activity and Therapeutic Uses

The compounds of the invention, and subgroups thereof, have fibroblast growth factor receptor (FGFR) inhibiting or modulating activity and/or vascular endothelial growth factor receptor (VEGFR) inhibiting or modulating activity, and/or platelet derived growth factor receptor (PDGFR) inhibiting or modulating activity, and which will be useful in preventing or treating disease states or conditions described herein. In addition the compounds of the invention, and subgroups thereof, will be useful in preventing or treating diseases or condition mediated by the kinases. References to the preventing or prophylaxis or treatment of a disease state or condition such as cancer include within their scope alleviating or reducing the incidence of cancer.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper-(or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, the compounds of the invention may be useful in alleviating or reducing the incidence of cancer.

More particularly, the compounds of the formulae (I) and sub-groups thereof are inhibitors of FGFRs. For example, compounds of the invention have activity against FGFR1, FGFR2, FGFR3, and/or FGFR4, and in particular FGFRs selected from FGFR1, FGFR2 and FGFR3; or in particular the compounds of formula (I) and sub-groups thereof are inhibitors of FGFR4.

Preferred compounds are compounds that inhibit one or more FGFR selected from FGFR1, FGFR2, FGFR3, and FGFR4. Preferred compounds of the invention are those having $IC_{50}$ values of less than 0.1 μM.

Compounds of the invention also have activity against VEGFR.

In addition many of the compounds of the invention exhibit selectivity for the FGFR 1, 2, and/or 3, and/or 4 compared to VEGFR (in particular VEGFR2) and/or PDGFR and such compounds represent one preferred embodiment of the invention. In particular, the compounds exhibit selectivity over VEGFR2. For example, many compounds of the invention have $IC_{50}$ values against FGFR1, 2 and/or 3 and/or 4 that are between a tenth and a hundredth of the $IC_{50}$ against VEGFR (in particular VEGFR2) and/or PDGFR B. In particular preferred compounds of the invention have at least 10 times greater activity against or inhibition of FGFR in particular FGFR1, FGFR2, FGFR3 and/or FGFR4 than VEGFR2. More preferably the compounds of the invention have at least 100 times greater activity against or inhibition of FGFR in particular FGFR1, FGFR2, FGFR3 and/or FGFR4 than VEGFR2. This can be determined using the methods described herein.

As a consequence of their activity in modulating or inhibiting FGFR, and/or VEGFR kinases, the compounds will be useful in providing a means of preventing the growth or inducing apoptosis of neoplasias, particularly by inhibiting angiogenesis. It is therefore anticipated that the compounds will prove useful in treating or preventing proliferative disorders such as cancers. In addition, the compounds of the invention could be useful in the treatment of diseases in which there is a disorder of proliferation, apoptosis or differentiation.

In particular tumours with activating mutants of VEGFR or upregulation of VEGFR and patients with elevated levels of serum lactate dehydrogenase may be particularly sensitive to the compounds of the invention. Patients with activating mutants of any of the isoforms of the specific RTKs discussed herein may also find treatment with the compounds of the invention particularly beneficial. For example, VEGFR overexpression in acute leukemia cells where the clonal progenitor may express VEGFR. Also, particular tumours with activating mutants or upregulation or overexpression of any of the isoforms of FGFR such as FGFR1, FGFR2 or FGFR3 or FGFR4 may be particularly sensitive to the compounds of the invention and thus patients as discussed herein with such particular tumours may also find treatment with the compounds of the invention particularly beneficial. It may be preferred that the treatment is related to or directed at a mutated form of one of the receptor tyrosine kinases, such as discussed herein. Diagnosis of tumours with such mutations could be performed using techniques known to a person skilled in the art and as described herein such as RTPCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma. In particular, squamous lung cancer, breast cancer, colorectal cancer, glioblastoma, astrocytomas, prostate cancer, small cell lung cancer, melanoma, head and neck cancer, thyroid cancer, uterine cancer, gastric cancer, hepatocellular cancer, cervix cancer, multiple myeloma, bladder cancer, endometrial cancer, urothelial cancer, colon cancer, rhabdomyosarcoma, pituitary gland cancer.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukaemia or AML.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis. A further haematological disorder is hypereosinophilic syndrome. T-cell lymphoproliferative diseases include those derived from natural Killer cells.

In addition the compounds of the invention can be used to gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate and thyroid carcinomas, lung, breast, and colon cancers.

A further subset of cancers includes multiple myeloma, bladder, hepatocellular, oral squamous cell carcinoma and cervical carcinomas.

The compound of the invention, having FGFR such as FGFR1 inhibitory activity, may be particularly useful in the treatment or prevention of breast cancer in particular Classic Lobular Carcinomas (CLC).

As the compounds of the invention have FGFR4 activity they will also be useful in the treatment of prostate or pituitary cancers, or they will be useful in the treatment of breast cancer, lung cancer, prostate cancer, liver cancer (HCC) or lung cancer.

In particular the compounds of the invention as FGFR inhibitors, are useful in the treatment of multiple myeloma, myeloproliferatoive disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the compounds of the invention are useful in the treatment of multiple myeloma (in particular multiple myeloma with t(4; 14) translocation or overexpressing FGFR3), prostate cancer (hormone refractory prostrate carcinomas), endometrial cancer (in particular endometrial tumours with activating mutations in FGFR2) and breast cancer (in particular lobular breast cancer).

In particular the compounds are useful in the treatment of lobular carcinomas such as CLC (Classic lobular carcinoma).

As the compounds have activity against FGFR3 they will be useful in the treatment of multiple myeloma and bladder cancer.

In particular the compounds are useful for the treatment of t(4; 14) translocation positive multiple myeloma.

In one embodiment the compounds may be useful for the treatment of sarcoma. In one embodiment the compounds may be useful for the treatment of lung cancer, e.g. squamous cell carcinoma.

As the compounds have activity against FGFR2 they will be useful in the treatment of endometrial, ovarian, gastric, hepatocellular, uterine, cervix and colorectal cancers. FGFR2 is also overexpressed in epithelial ovarian cancer, therefore the compounds of the invention may be specifically useful in treating ovarian cancer such as epithelial ovarian cancer.

In one embodiment, the compounds may be useful for the treatment of lung cancer, in particular NSCLC, squamous cell carcinoma, liver cancer, kidney cancer, breast cancer, colon cancer, colorectal cancer, prostate cancer.

In one embodiment, the compounds may be useful for the treatment of prostate cancer, bladder cancer, lung cancer such as NSCLC, breast cancer, gastric cancer, and liver cancer (HCC (hepatocellular cancer)).

Compounds of the invention may also be useful in the treatment of tumours pre-treated with VEGFR2 inhibitor or VEGFR2 antibody (e.g. Avastin).

In particular the compounds of the invention may be useful in the treatment of VEGFR2-resistant tumours. VEGFR2 inhibitors and antibodies are used in the treatment of thyroid and renal cell carcinomas, therefore the compounds of the invention may be useful in the treatment of VEGFR2-resistant thyroid and renal cell carcinomas.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR or VEGFR signalling may be determined by means of a cell growth assay as set out below or by a method as set out in the section headed "Methods of Diagnosis".

The compounds of the invention, and in particular those compounds having FGFR, or VEGFR inhibitory activity, may be particularly useful in the treatment or prevention of cancers of a type associated with or characterised by the presence of elevated levels of FGFR, or VEGFR, for example the cancers referred to in this context in the introductory section of this application.

The compounds of the present invention may be useful for the treatment of the adult population. The compounds of the present invention may be useful for the treatment of the pediatric population.

It has been discovered that some FGFR inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

The compounds of the invention may be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions that the compounds of the invention may be useful consists of inflammatory diseases, cardiovascular diseases and wound healing.

FGFR, and VEGFR are also known to play a role in apoptosis, angiogenesis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

The compound of the invention, having FGFR such as FGFR2 or FGFR3 inhibitory activity, may be particularly useful in the treatment or prevention of the skeletal diseases. Particular skeletal diseases are achondroplasia or thanatophoric dwarfism (also known as thanatophoric dysplasia).

The compound of the invention, having FGFR such as FGFR1, FGFR2 or FGFR3 inhibitory activity, may be particularly useful in the treatment or prevention in pathologies in which progressive fibrosis is a symptom. Fibrotic conditions in which the compounds of the inventions may be useful in the treatment of include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the compounds of the inventions may also be useful in the treatment of lung fibrosis in particular in idiopathic pulmonary fibrosis.

The over-expression and activation of FGFR and VEGFR in tumor-associated vasculature has also suggested a role for compounds of the invention in preventing and disrupting initiation of tumor angiogenesis. In particular the compounds of the invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

The activity of the compounds of the invention as inhibitors of FGFR1-4, VEGFR and/or PDGFR A/B can be measured using the assays set forth in the examples below and the level of activity exhibited by a given compound can be defined in terms of the $IC_{50}$ value.

Preferred compounds of the present invention are compounds having an $IC_{50}$ value of less than 1 µM, more preferably less than 0.1 µM.

The invention provides compounds that have FGFR inhibiting or modulating activity, and which may be useful in preventing or treating disease states or conditions mediated by FGFR kinases.

In one embodiment, there is provided a compound as defined herein for use in therapy, for use as a medicine. In a further embodiment, there is provided a compound as defined herein for use in the prophylaxis or treatment, in particular in the treatment, of a disease state or condition mediated by a FGFR kinase.

Thus, for example, the compounds of the invention may be useful in alleviating or reducing the incidence of cancer. Therefore, in a further embodiment, there is provided a compound as defined herein for use in the prophylaxis or treatment, in particular the treatment, of cancer. In one embodiment, the compound as defined herein is for use in the prophylaxis or treatment of FGFR-dependent cancer. In one embodiment, the compound as defined herein is for use in the prophylaxis or treatment of cancer mediated by FGFR kinases.

Accordingly, the invention provides inter alia:

A method for the prophylaxis or treatment of a disease state or condition mediated by a FGFR kinase, which method comprises administering to a subject in need thereof a compound of the formula (I) as defined herein.

A method for the prophylaxis or treatment of a disease state or condition as described herein, which method comprises administering to a subject in need thereof a compound of the formula (I) as defined herein.

A method for the prophylaxis or treatment of cancer, which method comprises administering to a subject in need thereof a compound of the formula (I) as defined herein.

A method for alleviating or reducing the incidence of a disease state or condition mediated by a FGFR kinase, which method comprises administering to a subject in need thereof a compound of the formula (I) as defined herein.

A method of inhibiting a FGFR kinase, which method comprises contacting the kinase with a kinase-inhibiting compound of the formula (I) as defined herein.

A method of modulating a cellular process (for example cell division) by inhibiting the activity of a FGFR kinase using a compound of the formula (I) as defined herein.

A compound of formula (I) as defined herein for use as a modulator of a cellular process (for example cell division) by inhibiting the activity of a FGFR kinase.

A compound of formula (I) as defined herein for use in the prophylaxis or treatment of cancer, in particular the treatment of cancer.

A compound of formula (I) as defined herein for use as a modulator (e.g. inhibitor) of FGFR.

The use of a compound of formula (I) as defined herein for the manufacture of a medicament for the prophylaxis or treatment of a disease state or condition mediated by a FGFR kinase, the compound having the formula (I) as defined herein.

The use of a compound of formula (I) as defined herein for the manufacture of a medicament for the prophylaxis or treatment of a disease state or condition as described herein.

The use of a compound of formula (I) as defined herein for the manufacture of a medicament for the prophylaxis or treatment, in particular the treatment, of cancer.

The use of a compound of formula (I) as defined herein for the manufacture of a medicament for modulating (e.g. inhibiting) the activity of FGFR.

Use of a compound of formula (I) as defined herein in the manufacture of a medicament for modulating a cellular process (for example cell division) by inhibiting the activity of a FGFR kinase.

The use of a compound of the formula (I) as defined herein for the manufacture of a medicament for prophylaxis or treatment of a disease or condition characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of a cancer, the cancer being one which is characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of cancer in a patient selected from a sub-population possessing a genetic aberrations of FGFR3 kinase.

The use of a compound of the formula (I) as defined herein for the manufacture of a medicament for the prophylaxis or treatment of cancer in a patient who has been diagnosed as forming part of a sub-population possessing a genetic aberrations of FGFR3 kinase.

A method for the prophylaxis or treatment of a disease or condition characterised by up-regulation of a FGFR kinase (e.g. FGFR1 or FGFR2 or FGFR3 or FGFR4), the method comprising administering a compound of the formula (I) as defined herein.

A method for alleviating or reducing the incidence of a disease or condition characterised by up-regulation of a FGFR kinase (e.g. FGFR1 or FGFR2 or FGFR3 or FGFR4), the method comprising administering a compound of the formula (I) as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberrations of FGFR3 gene; and (ii) where the patient does possess the said variant, thereafter administering to the patient a compound of the formula (I) as defined herein having FGFR3 kinase inhibiting activity.

A method for the prophylaxis or treatment of (or alleviating or reducing the incidence of) a disease state or condition characterised by up-regulation of an FGFR kinase (e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of a FGFR kinase, thereafter administering to the patient a compound of the formula (I) as defined herein having FGFR kinase inhibiting activity.

In one embodiment, the disease mediated by FGFR kinases is a oncology related disease (e.g. cancer). In one embodiment, the disease mediated by FGFR kinases is a non-oncology related disease (e.g. any disease disclosed herein excluding cancer). In one embodiment the disease mediated by FGFR kinases is a condition described herein. In one embodiment the disease mediated by FGFR kinases is a skeletal condition described herein. Particular abnormalities in human skeletal development, include abnormal ossification of cranial sutures (craniosynostosis), Apert (AP) syndrome, Crouzon syndrome, Jackson-Weiss syndrome, Beare-Stevenson cutis gyrate syndrome, Pfeiffer syndrome, achondroplasia and thanatophoric dwarfism (also known as thanatophoric dysplasia).

Mutated Kinases

Drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme.

A study in gastric cancer patient samples showed the presence of two mutations in FGFR2, Ser167Pro in exon IIIa and a splice site mutation 940-2A-G in exon IIIc. These mutations are identical to the germline activating mutations that cause craniosynotosis syndromes and were observed in 13% of primary gastric cancer tissues studied. In addition activating mutations in FGFR3 were observed in 5% of the patient samples tested and overexpression of FGFRs has been correlated with a poor prognosis in this patient group.

In addition there are chromosomal translocations or point mutations that have been observed in FGFR which give rise to gain-of-function, over-expressed, or constitutively active biological states.

The compounds of the invention would therefore find particular application in relation to cancers which express a mutated molecular target such as FGFR. Diagnosis of tumours with such mutations could be performed using techniques known to a person skilled in the art and as described herein such as RTPCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1 V561M showed that this mutation conferred resistance to a tyrosine kinase inhibitor compared to that of the wild type.

Methods of Diagnosis

Prior to administration of a compound of the formula (I), a patient may be screened to determine whether a disease or condition from which the patient is or may be suffering is one which would be susceptible to treatment with a compound having activity against FGFR, and/or VEGFR.

For example, a biological sample taken from a patient may be analysed to determine whether a condition or disease, such as cancer, that the patient is or may be suffering from is one which is characterised by a genetic abnormality or abnormal protein expression which leads to up-regulation of the levels or activity of FGFR, and/or VEGFR or to sensitisation of a pathway to normal FGFR, and/or VEGFR activity, or to upregulation of these growth factor signalling pathways such as growth factor ligand levels or growth factor ligand activity or to upregulation of a biochemical pathway downstream of FGFR, and/or VEGFR activation.

Examples of such abnormalities that result in activation or sensitisation of the FGFR, and/or VEGFR signal include loss of, or inhibition of apoptotic pathways, up-regulation of the receptors or ligands, or presence of mutant variants of the receptors or ligands e.g PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions. In particular activating mutations in FGFR2 have been identified in 10% of endometrial tumours.

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas. A particular mutation T6741 of the PDGF receptor has been identified in imatinib-treated patients. In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway.

Alternatively, a biological sample taken from a patient may be analysed for loss of a negative regulator or suppressor of FGFR or VEGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR, and/or VEGFR. The term diagnosis includes screening. By marker we include genetic markers including, for example, the measurement of DNA composition to identify mutations of FGFR, and/or VEGFR. The term marker also includes markers which are characteristic of up regulation of FGFR and/or VEGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR, and/or VEGFR may mean that the patient would be particularly suitable for treatment with a FGFR, and/or VEGFR inhibitor. Tumours may preferentially be screened for presence of a FGFR, and/or VEGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR or VEGFR2, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radio-isotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), BMC Cancer, 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR, and/or VEGFR, or detection of FGFR, and/or VEGFR variants or mutants could be applicable in the present case.

Abnormal levels of proteins such as FGFR or VEGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR or VEGFR including the isoforms thereof, include the measurement of microvessel density. This can for example be measured using methods described by Orre and Rogers (Int J Cancer (1999), 84(2) 101-8). Assay methods also include the use of markers, for example, in the case of VEGFR these include CD31, CD34 and CD105.

Therefore all of these techniques could also be used to identify tumours particularly suitable for treatment with the compounds of the invention.

The compounds of the invention are particular useful in treatment of a patient having a mutated FGFR. The G697C mutation in FGFR3 is observed in 62% of oral squamous cell carcmonas and causes constitutive activation of the kinase activity. Activating mutations of FGFR3 have also been identified in bladder carcinoma cases. These mutations were of 6 kinds with varying degrees of prevelence: R248C, S249C, G372C, S373C, Y375C, K652Q. In addition, a Gly388Arg polymorphism in FGFR4 has been found to be associated with increased incidence and aggressiveness of prostate, colon, lung, liver (HCC) and breast cancer.

Therefore in a further aspect the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y375C, K652Q mutations in FGFR3 and Gly388Arg polymorphism in FGFR4.

In another aspect the invention includes a compound of the invention for use in the prophylaxis or treatment of cancer in a patient selected from a sub-population possessing a variant of the FGFR gene (for example G697C mutation in FGFR3 and Gly388Arg polymorphism in FGFR4).

MRI determination of vessel normalization (e.g. using MRI gradient echo, spin echo, and contrast enhancement to measure blood volume, relative vessel size, and vascular permeability) in combination with circulating biomarkers (circulating progenitor cells (CPCs), CECs, SDF1, and FGF2) may also be used to identify VEGFR2-resistant tumours for treatment with a compound of the invention.

Pharmaceutical Compositions and Combinations

In view of their useful pharmacological properties, the subject compounds may be formulated into various pharmaceutical forms for administration purposes.

In one embodiment the pharmaceutical composition (e.g. formulation) comprises at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. The pharmaceutical compositions can be in any form suitable for oral, parenteral, topical, intranasal, ophthalmic, otic, rectal, intravaginal, or transdermal administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage.

Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to exert its anti-tumour activity.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

- platinum coordination compounds for example cisplatin optionally combined with amifostine, carboplatin or oxaliplatin;
- taxane compounds for example paclitaxel, paclitaxel protein bound particles (Abraxane™) or docetaxel;
- topoisomerase I inhibitors such as camptothecin compounds for example irinotecan, SN-38, topotecan, topotecan hcl;
- topoisomerase II inhibitors such as anti-tumour epipodophyllotoxins or podophyllotoxin derivatives for example etoposide, etoposide phosphate or teniposide;
- anti-tumour *vinca* alkaloids for example vinblastine, vincristine or vinorelbine;
- anti-tumour nucleoside derivatives for example 5-fluorouracil, leucovorin, gemcitabine, gemcitabine hcl, capecitabine, cladribine, fludarabine, nelarabine;
- alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;
- anti-tumour anthracycline derivatives for example daunorubicin, doxorubicin optionally in combination with dexrazoxane, doxil, idarubicin, mitoxantrone, epirubicin, epirubicin hcl, valrubicin;
- molecules that target the IGF-1 receptor for example picropodophilin;
- tetracarcin derivatives for example tetracarcin A;
- glucocorticoiden for example prednisone;
- antibodies for example trastuzumab (HER$^2$ antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
- estrogen receptor antagonists or selective estrogen receptor modulators or inhibitors of estrogen synthesis for example tamoxifen, fulvestrant, toremifene, droloxifene, faslodex, raloxifene or letrozole;
- aromatase inhibitors such as exemestane, anastrozole, letrazole, testolactone and vorozole;
- differentiating agents such as retinoids, vitamin D or retinoic acid and retinoic acid metabolism blocking agents (RAMBA) for example accutane;
- DNA methyl transferase inhibitors for example azacytidine or decitabine;
- antifolates for example premetrexed disodium;
- antibiotics for example antinomycin D, bleomycin, mitomycin C, dactinomycin, carminomycin, daunomycin, levamisole, plicamycin, mithramycin;
- antimetabolites for example clofarabine, aminopterin, cytosine arabinoside or methotrexate, azacitidine, cytarabine, floxuridine, pentostatin, thioguanine;
- apoptosis inducing agents and antiangiogenic agents such as Bcl-2 inhibitors for example YC 137, BH 312, ABT 737, gossypol, HA 14-1, TW 37 or decanoic acid;
- tubuline-binding agents for example combrestatin, colchicines or nocodazole;
- kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
- farnesyltransferase inhibitors for example tipifarnib;
- histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;
- Inhibitors of the ubiquitin-proteasome pathway for example PS-341, MLN 0.41 or bortezomib;
- Yondelis;
- Telomerase inhibitors for example telomestatin;
- Matrix metalloproteinase inhibitors for example batimastat, marimastat, prinostat or metastat.
- Recombinant interleukins for example aldesleukin, denileukin diftitox, interferon alfa 2a, interferon alfa 2b, peginterferon alfa 2b
- MAPK inhibitors Retinoids for example alitretinoin, bexarotene, tretinoin
Arsenic trioxide
Asparaginase
Steroids for example dromostanolone propionate, megestrol acetate, nandrolone (decanoate, phenpropionate), dexamethasone
Gonadotropin releasing hormone agonists or antagonists for example abarelix, goserelin acetate, histrelin acetate, leuprolide acetate
Thalidomide, lenalidomide
Mercaptopurine, mitotane, pamidronate, pegademase, pegaspargase, rasburicase
BH3 mimetics for example ABT-737
MEK inhibitors for example PD98059, AZD6244, CI-1040
colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl;
bisphosphonate; palifermin.
a steroidal cytochrome P450 17alpha-hydroxylase-17,20-lyase inhibitor (CYP17), e.g. abiraterone, abiraterone acetate.

The compounds of the present invention also have therapeutic applications in sensitising tumour cells for radiotherapy and chemotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the one or more other medicinal agent and the compound according to the present invention may be formulated into various pharmaceutical forms for administration purposes. The components may be formulated separately in individual pharmaceutical compositions or in a unitary pharmaceutical composition containing all components.

The present invention therefore also relates to a pharmaceutical composition comprising the one or more other medicinal agent and the compound according to the present invention together with a pharmaceutical carrier.

The present invention further relates to the use of a combination according to the invention in the manufacture of a pharmaceutical composition for inhibiting the growth of tumour cells.

The present invention further relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour *vinca* alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter ($mg/m^2$) of body surface area, or as known in the art, if different. Trastuzumab is advantageously administered in a dosage of 1 to 5 mg per square meter ($mg/m^2$) of body surface area, particularly 2 to 4 $mg/m^2$ per course of treatment. These dosages may be administered for example once, twice or more per course of treatment, which may be repeated for example every 7, 14, 21 or 28 days.

The compounds of formula (I), the pharmaceutically acceptable addition salts, in particular pharmaceutically acceptable acid addition salts, and stereoisomeric forms thereof can have valuable diagnostic properties in that they can be used for detecting or identifying the formation of a complex between a labelled compound and other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}I$, $^{131}I$, $^{3}H$ and $^{14}C$. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

General Synthetic Routes

The following examples illustrate the present invention but are examples only and are not intended to limit the scope of the claims in any way.

Experimental Part Hereinafter, the term 'CH$_3$CN' or 'ACN' means acetonitrile, 'DCM' or 'CH$_2$Cl$_2$' means dichloromethane, 'K$_2$CO$_3$' means potassium carbonate, 'Na$_2$CO$_3$' means sodium carbonate, 'Cs$_2$CO$_3$' means cesium carbonate, 'MgSO$_4$' means magnesium sulphate, 'MeOH' or 'CH$_3$OH' means methanol, 'EtOAc' means ethyl acetate, 'EtOH' means ethanol, 'Et$_3$N' means triethylamine, 'THF' means tetrahydrofuran, 'POCl$_3$' means phosphoric trichloride, 'NH$_4$Cl' means ammonium chloride, 'NaCl' means sodium chloride, 'NaOH' means sodium hydroxide, 'KOH' means potassium hydroxide, 'DMF' means N,N-dimethylformamide, 'NaH' means sodium hydride 60% in mineral oil, 'NaHCO$_3$' means sodium hydrogen carbonate, 'TFA' means trifluoroacetic acid, 'DMAP' means 4-dimethylaminopyridine, 'NaBH$_4$' means sodium borohydride, 'LiCl' means lithium chloride, 'Pd(PPh$_3$)$_4$' or 'tetrakis' means tetrakis(triphenylphosphine)palladium, 'PdCl$_2$(dppf).DCM' means 1,1'-Bis(diphenylphosphino)ferrocene-palladium(II) dichloride dichloromethane complex, 'NH$_4$OH' means ammonium hydroxide, 'iPrOH' means 2-propanol, 'DiPE' means diisopropylethyl ether, 'CO$_2$' means carbon dioxide, 'Et$_2$O' means diethyl ether, 'HCl' means hydrochloric acid, 'BBr$_3$' means boron tribromide, 'SiO$_2$' or 'SiOH' means silica, 'N$_2$' means nitrogen, 'LiAlH$_4$' means lithium aluminium hydride, 'M.P.' means melting point, 'rt' means room temperature, 'Boc$_2$O' means di-tert-butyl dicarbonate, 'H$_2$O' means water, 'NH$_4$HCO$_3$' means ammonium bicarbonate, 'DME' means ethylene glycol dimethylether, 'pH' means potential hydrogen, 'nBuLi' means n-butyllithium, 'NMP' means 1-methyl-2-pyrrolidinone, 'CHCl$_3$' means chloroform, 'SFC' means supercritical fluid chromatography, 'Pd(PtBu$_3$)$_2$' means bis(tri-tert-butyl-phosphine)palladium(0), 'DIPEA' means N,N-diisopropylethylamine, 'DCE' means 1,2-dichloroethane, 'HOBT' means 1-hydroxybenzotriazole, 'EDCl means 1-Ethyl-3-(3-dimethylaminopropyl)carbodiimide hydrochloride, 'XPhos' means 2-Dicyclohexylphosphino-2',4',6'-triisopropylbiphenyl, 'Pd$_2$(dba)$_3$' means Tris(dibenzylideneacetone)dipalladium and 'DSC' means differential scanning calorimetry.

Some compounds of the present invention were obtained as salt forms or hydrates or contain some amounts of solvent. Hereinafter, these compounds are reported as determined based on elemental analysis.

A. Preparation of the Intermediates

Example A1

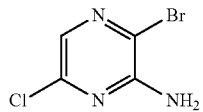

a) Preparation of Intermediate 1

Under N$_2$ flow, N-bromosuccinimide (121 g; 679 mmol) was added dropwise to a mixture of 6-chloro-2-pyrazinamine (88 g; 679 mmol) in CHCl$_3$ (1000 ml) at 0° C. The reaction mixture was stirred at room temperature overnight then was poured out onto water and DCM was added. The organic layer was washed, dried over MgSO$_4$, filtered and evaporated. The residue was purified by chromatography over silica gel (mobile phase: 91% petroleum ether, 9% EtOAc). The pure fractions were collected and the solvent was evaporated to afford 40 g (28%) of intermediate 1.

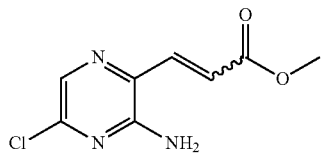

b) Preparation of Intermediate 2

Under N$_2$ flow, Pd(PtBu$_3$)$_2$ (3 g; 5.9 mmol) was added to a mixture of intermediate 1 (41.6 g; 200 mmol), acrylic acid methyl ester (20.6 g; 240 mmol) in triethylamine (50 ml) and N,N-dimethylformamide (300 ml). The reaction mixture was stirred at reflux for 2 hours then was poured out onto water and EtOAc was added. The organic layer was washed, dried over MgSO$_4$, filtered and evaporated. The residue was purified by chromatography over silica gel (mobile phase: 80% petroleum, 20% EtOAc). The pure fractions were collected and the solvent was evaporated to afford 25 g (59%) of intermediate 2.

Intermediate 2 was also prepared according to the following procedure: 2-Amino-3-bromo-6-chloropyrazine (212779-21-0) (39.78 g; 191 mmol) was diluted in dry dioxane (400 mL) and DiPEA (53.3 mL; 305 mmol). The solution was degassed with N$_2$. Then, tris(dibenzylideneacetone)dipalladium(0) (3.50 g; 3.82 mmol), tri-tert-butylphosphonium tetrafluoroborate (2.77 g; 9.54 mmol) and methyl acrylate (34.23 mL; 382 mmol) were added. The mixture was heated at 120° C. for 5h30. The reaction mixture was cooled down to room temperature and a saturated aqueous solution of NaHCO$_3$ and EtOAc were added. Then the mixture was decanted. The organic layer was dried over MgSO$_4$, filtered and concentrated to dryness. The residue was taken up with diisopropylether. The precipitate was filtered off to give 35.67 g (87%, brown solid) of intermediate 2.

c) Preparation of Intermediate 3

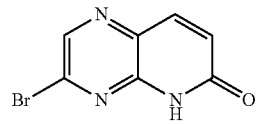

A mixture of intermediate 2 (1.56 g; 7.32 mmol) in a solution of bromidic acid in acetic acid (20 ml) was heated at 45° C. for 3 hours. The reaction mixture was evaporated to give 1.66 g of intermediate 3 which was used in the next step without further purification. Alternatively, in a round bottom flask, intermediate 2 (100 g; 468.1 mmol) was diluted in a 33% solution of bromidic acid in acetic acid (7 L). The mixture was stirred at 40-50° C. for 3 hours. The solvent was evaporated and the residue was washed with methyl ter-butyl ether to give 110 g (92%) of intermediate 3.

d) Preparation of intermediate 4

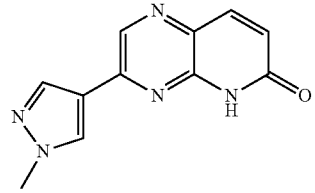 [SMILES: Cn1cc(-c2cnc3ccc(=O)[nH]c3n2)cn1]

Under N$_2$ flow, tetrakis(triphenylphosphine)palladium (0.9 g, 0.75 mmol) was added to a mixture of the intermediate 3 (1.7 g, 7.4 mmol), 1-methylpyrazole-4-boronic acid pinacol ester (1.7 g, 8.1 mmol), sodium carbonate (1.6 g, 14.7 mmol) in DME (40 ml) and water (10 ml). The mixture was heated at 100° C. overnight. The solvent was evaporated then the residue was triturated with methyl-tert-butyl ether, filtered and dried step to give 1.45 g (87%) of intermediate 4. It was used without further purification in the next step.

e) Preparation of Intermediate 5

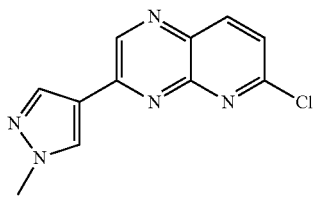 [SMILES: Cn1cc(-c2cnc3ccc(Cl)nc3n2)cn1]

A mixture of intermediate 4 (1.56 g, 6.38 mmol) in POCl$_3$ (15 ml) was stirred and heated at 70° C. for 1 hour. The solvent was evaporated till dryness and the residue was purified by chromatography over silica gel (mobile phase 50% DCM, 50% EtOAc) The desired fractions were collected and the solvent was evaporated to give 0.72 g (45%) of intermediate 5.

Intermediate 5 was also prepared according to the following procedure: POCl$_3$ (6.4 mL; 68.65 mmol) was added drop wise over a 10 minute period to a suspension of intermediate 4 (3.9 g; 17.16 mmol) and DMF (2.66 mL; 34.33 mmol) in 1,2-dichloroethane (75 mL) at 80° C. The reaction mixture was heated at 80° C. for 3 hours and cooled to room temperature. The reaction mixture was slowly poured onto a 10% aqueous solution of K$_2$CO$_3$ and extracted with DCM/MeOH. The organic layer was decanted, washed with water, dried over MgSO$_4$, filtered and dried to dryness yielding 3.1 g (73%) of intermediate 5.

Intermediate 5 was also prepared according to the following procedure: A mixture of 6-chloropyridine-2,3-diamine (CAS 40851-95-4) (10 g; 69.65 mmol), 2-bromo-1-(1-methyl-1H-pyrazol-4-yl)ethan-1-one (CAS 706819-66-1) (14.1 g; 69.65 mmol) and DIPEA (24 mL; 139.3 mmol) in ACN (280 mL) was heated at 90° C. for 18 hours. The heating was stopped and MnO$_2$ (18.2 g; 208.95 mmol) was added portion wise (carefully) and the reaction mixture was stirred at room temperature for 15 minutes. MnO$_2$ was removed by filtration through a pad of Celite® and the filtrate was concentrated. The precipitate was filtered, washed with Et$_2$O and dried to give 10.4 g (61%) of intermediate 5.

Intermediate 5 was also prepared according to the following procedure:

a) Preparation of Intermediate 5a

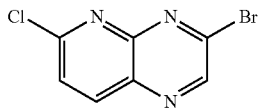 [SMILES: Clc1ccc2ncc(Br)nc2n1]

POCl$_3$ (18.3 mL; 195.47 mmol) was added drop wise to a suspension of intermediate 3 (15 g; 48.87 mmol) and DMF (7.57 mL; 97.74 mmol) in 1,2-dichloroethane (561 mL) previously heated at 80° C. The reaction mixture was heated at 80° C. for 3 hours and cooled to room temperature. The reaction mixture was slowly poured onto a saturated aqueous solution of NaHCO$_3$. DCM was added and the 2 layers were separated. The aqueous layer was extracted with DCM/MeOH (8/2). The organic layer was decanted, washed with water, dried over MgSO$_4$, filtered and evaporated to dryness. The residue was taken up with Et$_2$O. The precipitate was filtered and dried affording 9.05 g (76%) of intermediate 5a which was directly used in the next step without any further purification.

b) A solution of intermediate 5a (20 g; 81.81 mmol), 1-methylpyrazole-4-boronic acid pinacol ester (13.6 g; 65.45 mmol), 2M aqueous Na$_2$CO$_3$ (205 mL) in 1,2-dimethoxyethane (798 mL) were degassed under N$_2$. Pd(PPh$_3$)$_4$ (4.73 g; 4.09 mmol) was added and the reaction mixture was heated at reflux for 2 hours. The mixture was poured into ice and extracted with EtOAc. The mixture was filtered through a pad of Celite® which was washed with DCM. The organic layers were dried over MgSO$_4$, filtered and the solvent was evaporated. The residue was taken up with ACN, filtered and dried to give 15.32 g (76%) of intermediate 5.

Intermediate 5 was also prepared according to the following procedure:

A solution of 3,6-dichloropyrido[2,3,b]pyrazine (CAS: 1350925-22-2) (12 g; 60 mmol), 1-methylpyrazole-4-boronic acid pinacol ester (12.40 g; 60 mmol), in aqueous 2M sodium carbonate (90 mL) and 1,2-dimethoxyethane (400 mL) was degassed with N$_2$ for 15 minutes. Then Pd(PPh$_3$)$_4$ (3.5 g; 3 mmol) was added and the reaction mixture was refluxed for 2 hours, then cooled to room temperature, poured onto a saturated aqueous NaHCO$_3$ solution and EtOAc was added. The resulting mixture was filtered through a pad of Celite®. The filtrate was extracted twice with EtOAc and the organic layer was washed with brine, dried over MgSO$_4$, filtered and evaporated to dryness.

The residue was crystallized from ACN. The precipitate was filtered off, washed with Et$_2$O and dried yielding 5 g (34%) of intermediate 5.

The filtrate was evaporated to dryness then, taken-up with a mixture of ACN/Et$_2$O. The precipitate was filtered off to give additional 2.3 g (16%) of intermediate 5.

Example A2

Preparation of Intermediate 6

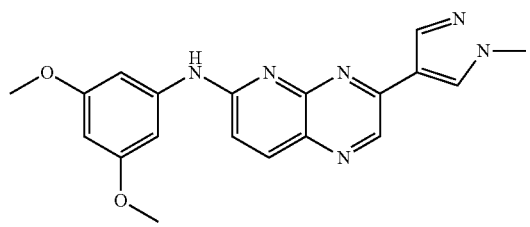

To a solution of intermediate 5 (2 g, 8.14 mmol) in n-propanol (70 ml) was added 3,5-dimethoxyaniline (2.5 g, 16.3 mmol) and the reaction mixture was heated at 100° C. for 4 hours. The reaction mixture was cooled down and poured out onto ice water. The reaction mixture was extracted with EtOAc, washed with brine, dried over MgSO$_4$, filtered and concentrated under reduced pressure. The residue (3.6 g) was purified by chromatography over silica gel (15-40 μm 80 g, mobile phase gradient 97.5% DCM, 2.5% MeOH, 0.1% NH$_4$OH to 97% DCM, 3% MeOH, 0.1% NH$_4$OH). The pure fractions were collected and evaporated till dryness to afford 2.76 g of intermediate 6 (MP: 174° C. (Kofler)).

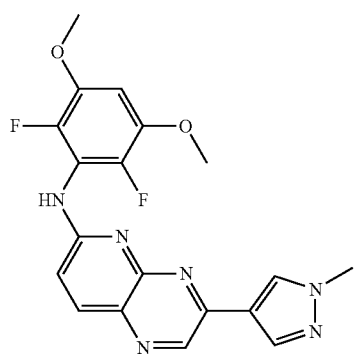

Analogous Preparation of Intermediate 12

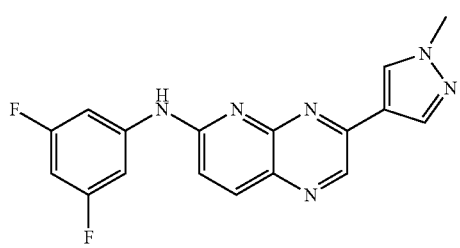 [SMILES: Cn1cc(-c2cnc3ccc(Nc4cc(F)cc(F)c4)nc3n2)cn1]

Analogous Preparation of Intermediate 14
Analogous Preparation of Intermediate 16

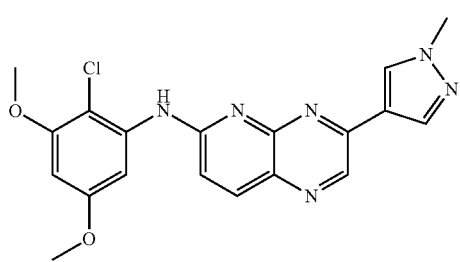 [SMILES: COc1cc(Nc2ccc3ncc(-c4cnn(C)c4)nc3n2)c(Cl)c(OC)c1]

Analogous Preparation of Intermediate 17

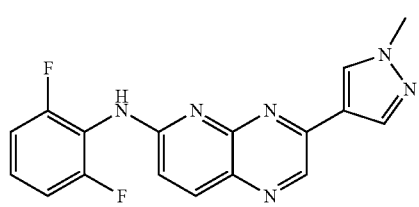 [SMILES: Cn1cc(-c2cnc3ccc(Nc4c(F)cccc4F)nc3n2)cn1]

Analogous Preparation of Intermediate 26

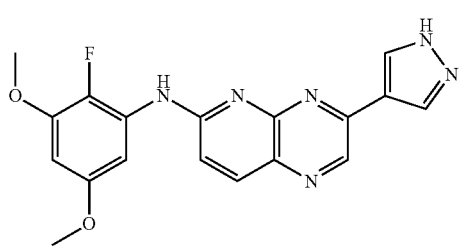 [SMILES: COc1cc(Nc2ccc3ncc(-c4cn[nH]c4)nc3n2)c(F)c(OC)c1]

Starting from Intermediate 27.
Analogous Preparation of Intermediate 54

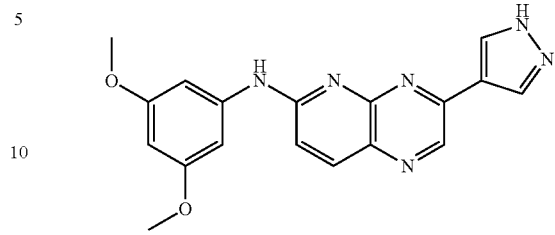

Starting from Intermediate 27
Analogous Preparation of Intermediate 54

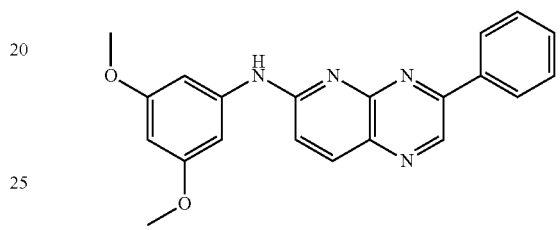

Starting from Intermediate 55
Analogous Preparation of Intermediate 61

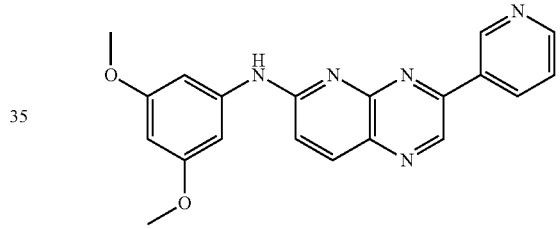

Starting from Intermediate 62
Analogous Preparation of Intermediate 68

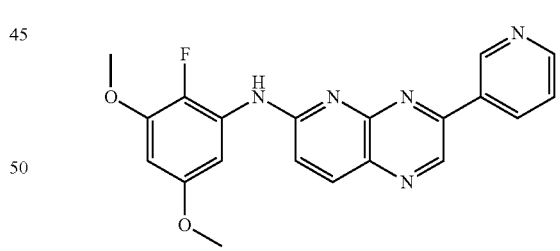

Starting from Intermediate 62
Analogous Preparation of Intermediate 71

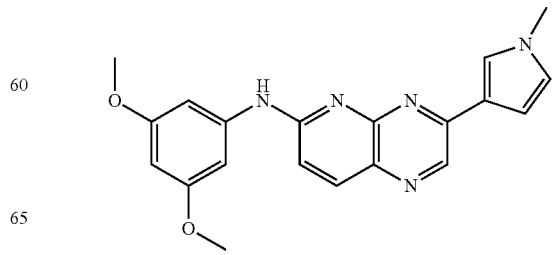

Starting from Intermediate 72
  Analogous Preparation of Intermediate 73

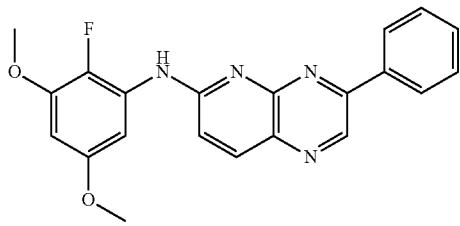 [SMILES: COc1cc(Nc2ccc3ncc(-c4ccccc4)nc3n2)c(F)c(OC)c1]

Starting from Intermediate 55
  Analogous Preparation of Intermediate 74

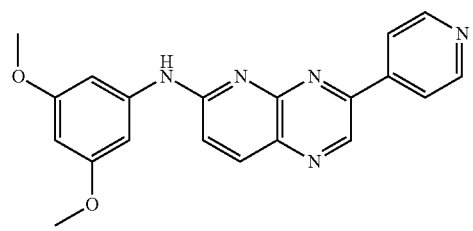 [SMILES: COc1cc(Nc2ccc3ncc(-c4ccncc4)nc3n2)cc(OC)c1]

Starting from Intermediate 75
  Analogous Preparation of Intermediate 86

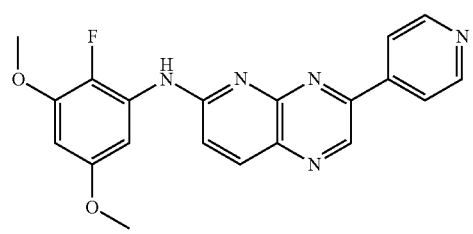 [SMILES: COc1cc(Nc2ccc3ncc(-c4ccncc4)nc3n2)c(F)c(OC)c1]

Starting from Intermediate 75

Analogous Preparation of Intermediate 95

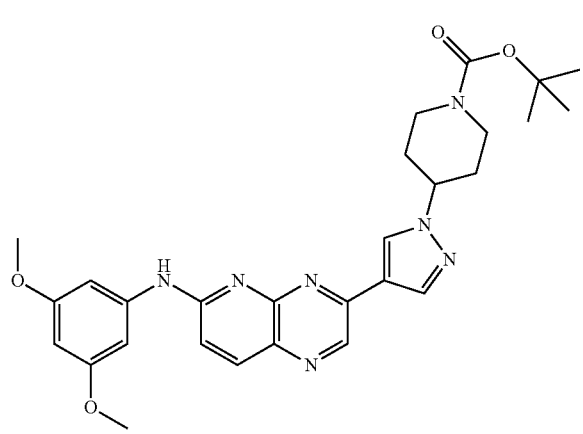 [SMILES: COc1cc(Nc2ccc3ncc(-c4cnn(C5CCN(C(=O)OC(C)(C)C)CC5)c4)nc3n2)cc(OC)c1]

Starting from Intermediate 96
  Analogous Preparation of Intermediate 117

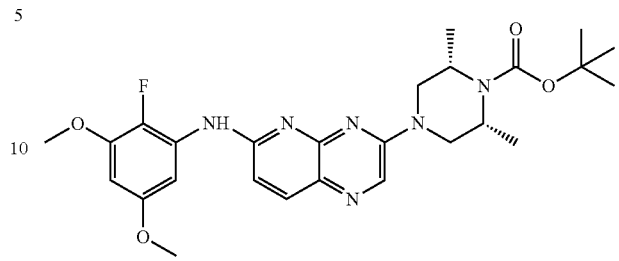

(cis) Starting from Intermediate 119
  Analogous Preparation of Intermediate 134

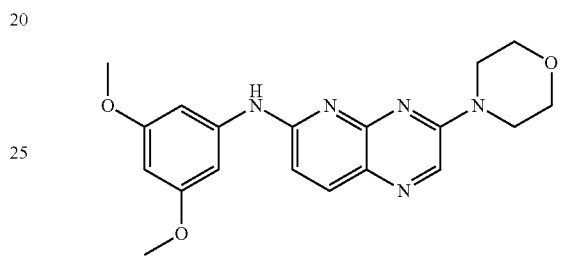

Starting from Intermediate 90

Example A2A

Preparation of Intermediate 129

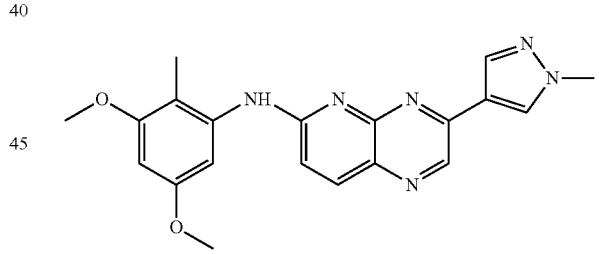

A solution of HCl 4N in 1,4-dioxane (0.2 ml; 0.8 mmol) was added to a solution of intermediate 5 (1.96 g; 7.97 mmol) and 3,5-dimethoxy-2-methyl-aniline (2 g; 11.96 mmol) in n-propanol (49 mL). The reaction mixture was heated at 100° C. overnight and cooled to room temperature. A 10% aqueous solution of $K_2CO_3$ was added and the reaction mixture was extracted with DCM (4 times). The organic layer was decanted, dried over MgSO4, filtered and evaporated to dryness. The residue was crystallized from ACN. The precipitate was filtered, washed with $Et_2O$ and dried to give 2.29 g (76%) of intermediate 129. M.P.: 146° C. (kofler).

115

Preparation of Intermediate 7

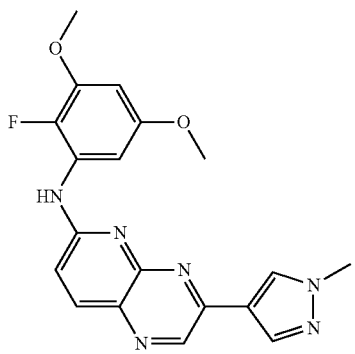 [SMILES: COc1cc(Nc2ccc3ncc(-c4cnn(C)c4)nc3n2)c(F)c(OC)c1]

The reaction was performed twice on the same quantities of intermediate 5 (7.5 g; 30.53 mmol):

To a solution of intermediate 5 (15 g; 61.06 mmol) in n-propanol (375 mL) was added 2-fluoro-3,5-dimethoxyaniline (10.45 g; 61.06 mmol), then HCl 4M in 1,4-dioxane (1.53 mL; 6.11 mmol) and the reaction mixture was heated at 100° C. overnight. The reaction mixture was cooled down, and the precipitate was filtered, washed with Et$_2$O and dried. The precipitate was taken up in a 10% aqueous solution of K$_2$CO$_3$ and stirred overnight. The precipitate was filtered off, washed with water three times, dried, dissolved with DCM/MeOH (8/2) and evaporated to dryness. The residue was taken up in ACN. The precipitate was filtered, washed with Et$_2$O and dried yielding 19.58 g (84%) of intermediate 7.

Analogous Preparation of Intermediate 133

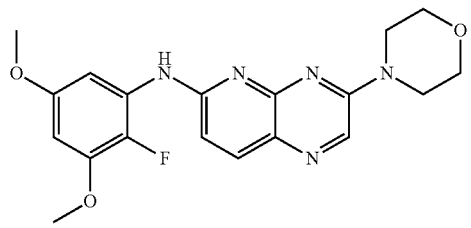 [SMILES: COc1cc(Nc2ccc3ncc(N4CCOCC4)nc3n2)c(F)c(OC)c1]

Starting from Intermediate 90

Example A3

Preparation of Intermediate 7

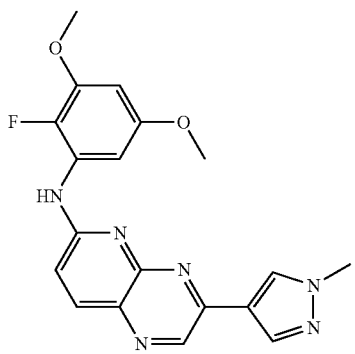 [SMILES: COc1cc(Nc2ccc3ncc(-c4cnn(C)c4)nc3n2)c(F)c(OC)c1]

116

To a solution of intermediate 5 (1.3 g; 5.29 mmol) in n-propanol (60 ml) was added 2-fluoro-3,5-dimethoxybenzenamine (1.8 g; 10.6 mmol) and the reaction mixture was heated at 100° C. for 4 hours. The reaction mixture was cooled down, poured out onto ice-water and the reaction mixture was extracted with EtOAc. The organic layer was washed with brine, dried (MgSO$_4$), filtered and concentrated under reduced pressure. The obtained residue was purified by chromatography over silica gel (15-40 μm 300 g, mobile phase: 98% DCM, 2% MeOH). The desired product fractions were collected and concentrated to afford 800 mg (43%) of intermediate 7 (MP: 212° C. (DSC)).

Example A4

Preparation of Intermediate 8

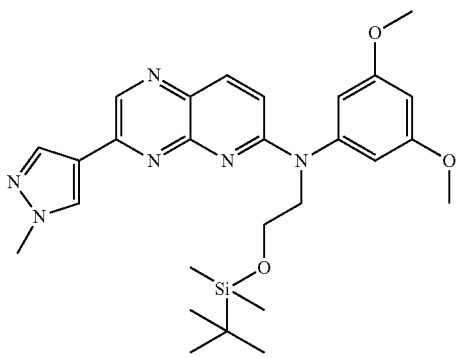 [SMILES: COc1cc(OC)cc(N(CCO[Si](C)(C)C(C)(C)C)c2ccc3ncc(-c4cnn(C)c4)nc3n2)c1]

Under N$_2$ flow, NaH (0.037 g, 0.94 mmol, 60% in mineral oil) was added portionwise to a solution of intermediate 6 (0.17 g, 0.47 mmol) in N,N-dimethylformamide (5 ml) at 5° C. The reaction mixture was stirred at 5° C. for 30 minutes. Then a solution of (2-bromoethoxy)-tert-butyldimethylsilane (0.2 ml, 0.94 mmol) was added dropwise at 5° C. The reaction was stirred at room temperature for 15 hours. The reaction was poured out onto ice water and EtOAc was added. The organic layer was separated, washed with brine, dried (MgSO$_4$), filtered and the solvent was evaporated to dryness to give 0.22 g (91%) of intermediate 8.

Analogous Preparation of Intermediate 11

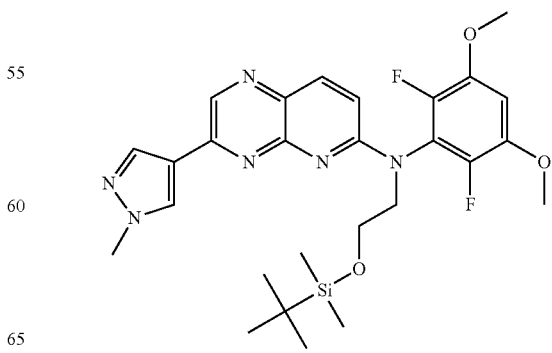

Starting from Intermediate 12
  Analogous Preparation of Intermediate 15

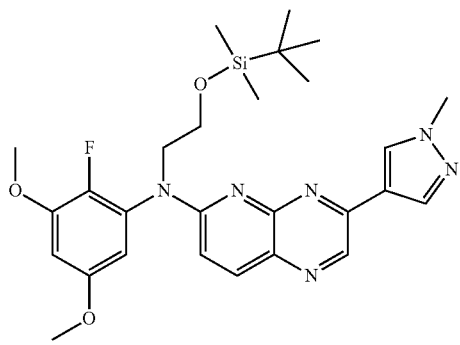 [SMILES: COc1cc(OC)c(F)c(N(CCO[Si](C)(C)C(C)(C)C)c2ccc3ncc(-c4cnn(C)c4)nc3n2)c1]

Starting from Intermediate 7
  Analogous Preparation of Intermediate 88

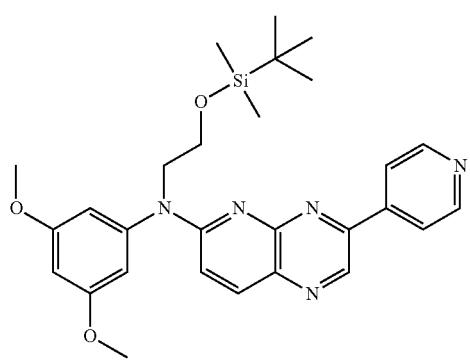 [SMILES: COc1cc(OC)cc(N(CCO[Si](C)(C)C(C)(C)C)c2ccc3ncc(-c4ccncc4)nc3n2)c1]

Starting from Intermediate 74
  Preparation of Intermediate 9a

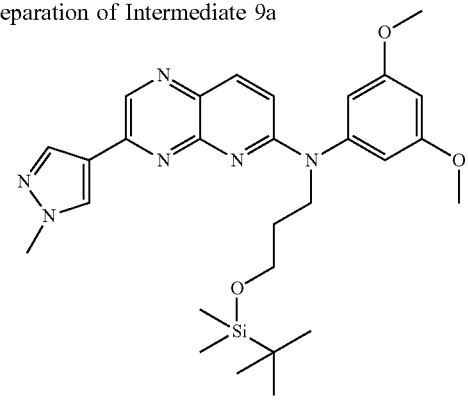

And Intermediate 9b

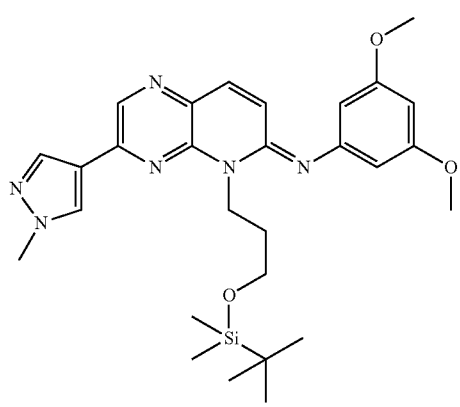 [SMILES: COc1cc(/N=c2\ccc3ncc(-c4cnn(C)c4)nc3n2CCCO[Si](C)(C)C(C)(C)C)cc(OC)c1]

Under N₂ flow, NaH (0.127 g, 3.2 mmol, 60% in mineral oil) was added portionwise to a solution of intermediate 6 (0.5 g, 1.4 mmol) in N,N-dimethylformamide (15 ml) at 5° C. The reaction mixture was stirred at 5° C. for 30 minutes. Then a solution of (3-bromopropoxy)-tert-butyldimethylsilane (0.66 ml, 2.8 mmol) was added dropwise at 5° C. The reaction was allowed to reach room temperature and stirred at for overnight. The reaction was poured out onto ice water and EtOAc was added. The organic layer was separated, washed with brine, dried (MgSO₄), filtered and the solvent was evaporated till dryness to give 887 mg of a mixture of intermediate 9a and 9b. The mixture was used without further purification in the next step.

Analogous Preparation of Intermediate 10a

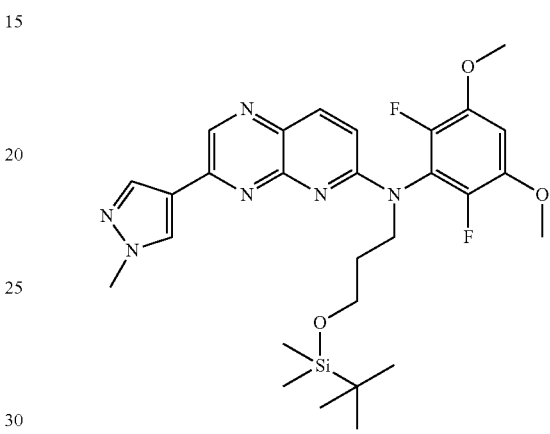

And Intermediate 10b

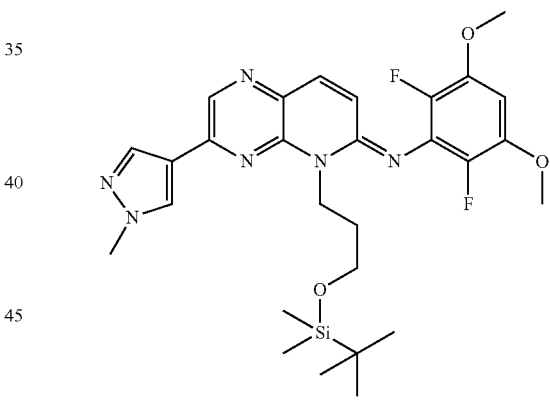

Starting from Intermediate 12

Example A5

Alternative Preparation of Intermediate 12

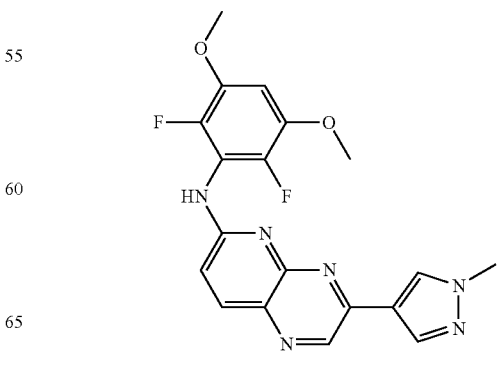

A solution of intermediate 5 (200 mg; 0.81 mmol), 2,6-difluoro-3,5-dimethoxybenzeneamine (308 mg; 1.63 mmol) and Cs₂CO₃ (1.33 g; 4.07 mmol) in NMP (1.2 mL) and dioxane (12 mL) was degassed at room temperature under N₂ flow. After 10 minutes, [+-]-2,2'-bis[diphenylphosphino]-1,1'-binaphthalene (105 mg; 0.16 mmol) and palladium(II) acetate (18 mg; 0.081 mmol) were added and the reaction mixture was heated at 150° C. for 30 minutes using microwave power. The reaction mixture was poured out onto ice water and EtOAc. The solution was filtered through a pad of Celite®, extracted with EtOAc, washed with water, dried (MgSO₄) and concentrated under reduced pressure. The obtained residue was purified by chromatography over silica gel (15-40 µm 24 g, mobile phase gradient from 97.5% DCM, 2.5% MeOH, 0.1% NH₄OH to 97% DCM, 2% MeOH, 0.1% NH₄OH). The desired product fractions were collected and the solvent was evaporated to afford 35 mg (11%) of intermediate 12.

Example A6

Preparation of Intermediate 18

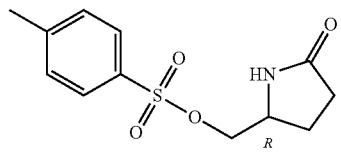

Et₃N (6 mL; 41.69 mmol), p-toluenesulfonyl chloride (7.95 g; 41.69 mmol) and DMAP (424 mg; 3.47 mmol) were added successively to a solution of (R)-(−)5-(hydroxymethyl)-2-pyrrolidinone (CAS 66673-40-3) (4 g; 34.743 mmol) in DCM (60 mL) at 5° C. under N₂ flow and the reaction mixture was stirred at room temperature for 2 hours. An aqueous solution of HCl 1N was added. The mixture was extracted with DCM (3 times). The organic layer was dried over MgSO₄, filtered and the solvent was evaporated to dryness. The residue was purified by chromatography over silica gel (Irregular SiOH, 20-45 µm, 80 g; mobile phase: 98% DCM, 2% MeOH, 0.2% NH₄OH). The pure fractions were collected and evaporated to give 6.8 g (72%) of intermediate 18.

Example A7

Preparation of Intermediate 19

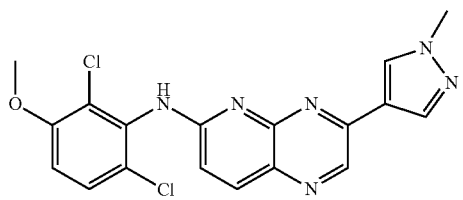 [SMILES: COc1ccc(Cl)c(Nc2ccc3ncc(-c4cnn(C)c4)nc3n2)c1Cl]

A solution of potassium bis(trimethylsilyl)amide 0.5M in toluene (12.2 mL; 6.11 mmol) was added drop wise to a solution of 2,6-chloro-3-methoxyphenylamine (0.78 g; 4.07 mmol) in THF (20 mL) at 0° C. The reaction mixture was stirred at 0° C. at for 1 hour. Then, intermediate 5 (1 g; 4.07 mmol) was added portion wise at 0° C., after 30 minutes DMF (20 mL) was added and the reaction mixture was stirred at room temperature for hours. The reaction mixture was poured into ice water, brine then EtOAc was added and the reaction mixture was stirred at room temperature for 30 minutes. The organic layer was separated, extracted with EtOAc, washed with brine then dried over MgSO₄, filtered and evaporated to dryness. The residue was purified by chromatography on silica gel (Spherical Silica, 5 µm, 150× 30.0 mm; mobile phase: gradient from 0.1% NH₄OH, 97% DCM, 3% MeOH). The product fractions were collected and evaporated to give 0.85 g (52%) of intermediate 19.

Preparation of Intermediate 12

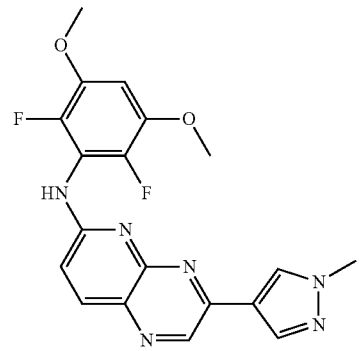 [SMILES: COc1cc(OC)c(F)c(Nc2ccc3ncc(-c4cnn(C)c4)nc3n2)c1F]

Potassium bis(trimethylsilyl)amide 1M in THF (71 mL; 70 mmol) was added drop wise at 0° C. to a solution of 2,6-difluoro-3,5-dimethoxyphenylamine (8.9 g; 46.9 mmol) in DMF (220 mL). The reaction mixture was stirred at 0° C. for 1 hour. Then; intermediate 5 (12 g; 39 mmol) was added portion wise at 0° C. and the reaction mixture was stirred at room temperature for 24 hours. The reaction mixture was poured into ice water and brine. EtOAc was added. The mixture was stirred at room temperature for 30 minutes, then filtered through a pad of Celite®. The filtrate was extracted with EtOAc. The organic layer was washed with brine, dried over MgSO₄, filtered and evaporated to dryness. The residue was taken-up with Et₂O, the precipitate was filtered and dried to give 14 g (90%) of intermediate 12.

Analogous Preparation of Intermediate 20

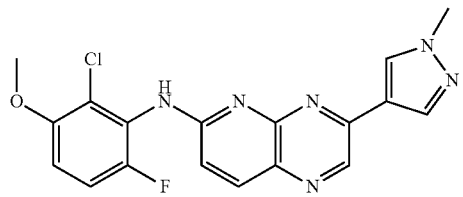 [SMILES: COc1ccc(F)c(Nc2ccc3ncc(-c4cnn(C)c4)nc3n2)c1Cl]

Starting from Intermediate 5

Analogous Preparation of Intermediate 22

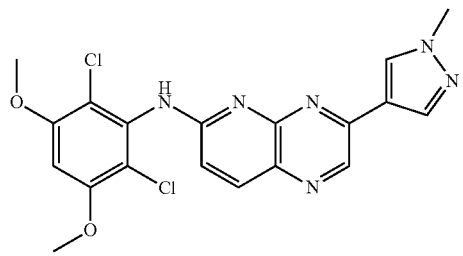 [SMILES: COc1cc(OC)c(Cl)c(Nc2ccc3ncc(-c4cnn(C)c4)nc3n2)c1Cl]

Starting from Intermediate 5
Analogous Preparation of Intermediate 30

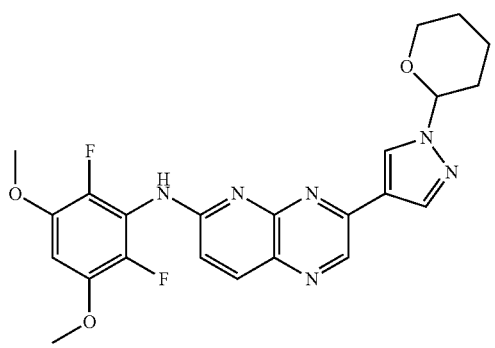 [SMILES: COc1cc(OC)c(F)c(Nc2ccc3ncc(-c4cnn(C5CCCCO5)c4)nc3n2)c1F]

Starting from Intermediate 27
Analogous Preparation of Intermediate 60

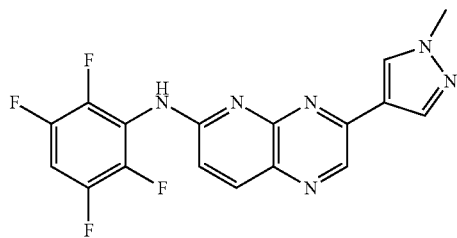 [SMILES: Cn1cc(-c2cnc3ccc(Nc4c(F)c(F)cc(F)c4F)nc3n2)cn1]

Starting from Intermediate 5
Analogous Preparation of Intermediate 89

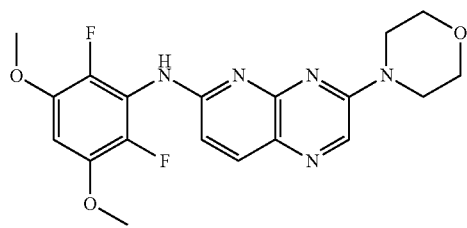 [SMILES: COc1cc(OC)c(F)c(Nc2ccc3ncc(N4CCOCC4)nc3n2)c1F]

Starting from Intermediate 90

Example A8

Preparation of Intermediate 21

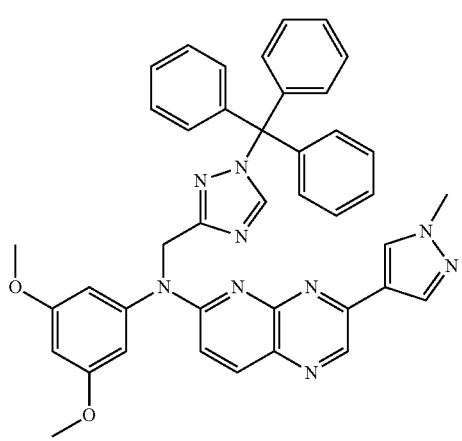 [SMILES: COc1cc(OC)cc(N(Cc2ncn(C(c3ccccc3)(c3ccccc3)c3ccccc3)n2)c2ccc3ncc(-c4cnn(C)c4)nc3n2)c1]

Under $N_2$ at 10° C., NaH (33 mg; 0.83 mmol) was added to a solution of intermediate 6 (300 mg; 0.83 mmol) in DMF (10 mL). The solution was stirred at 10° C. for 30 minutes. Then, a solution of 1H-1,2,4-Triazole-3-methanol, 1-(triphenylmethyl)-, 3-methanesulfonate (CAS: 163009-16-3) (540 mg; 1.29 mmol) in DMF (5 mL) was added drop wise and the solution was allowed to warm to room temperature and stirred overnight. The solution was cooled and the reaction mixture was poured into cooled water and extracted with EtOAc. The organic layer was washed with water, decanted, dried over $MgSO_4$, filtered and evaporated to dryness. The residue was purified by chromatography over silica gel (Irregular SiOH, 20-45 μm, 450 g; mobile phase: 0.3% $NH_4OH$, 97% DCM, 3% MeOH). The product fractions were collected and the solvent was evaporated to give 0.45 g (79%) of intermediate 21

Analogous Preparation of Intermediate 23

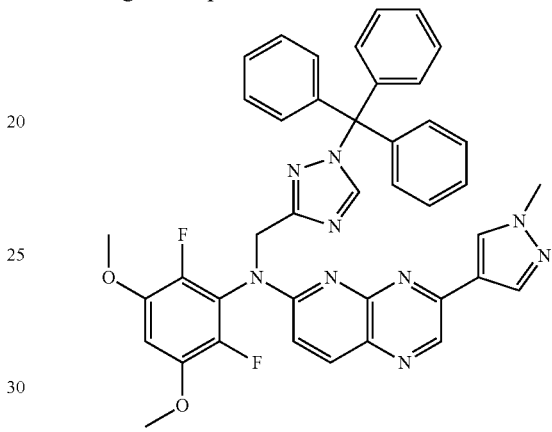

Analogous Preparation of Intermediate 24

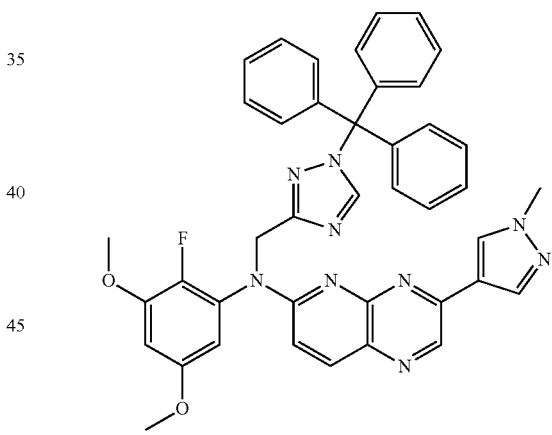

Analogous Preparation of Intermediate 112

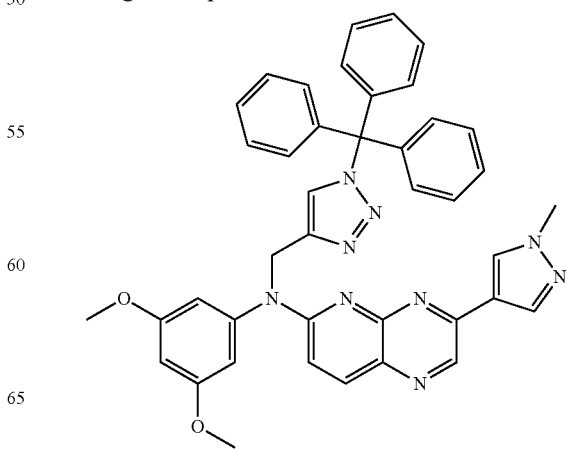

123

Starting from Intermediate 6 and Intermediate 113

Analogous Preparation of Intermediate 116

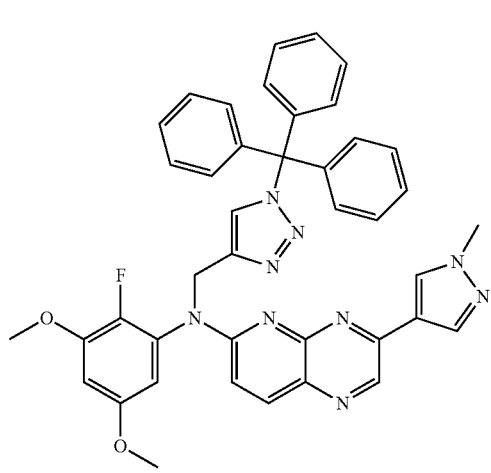 [SMILES: COc1cc(OC)c(F)c(N(Cc2cn(C(c3ccccc3)(c3ccccc3)c3ccccc3)nn2)c2ccc3ncc(-c4cnn(C)c4)nc3n2)c1]

Starting from Intermediate 7 and Intermediate 113

Example A8a

Preparation of Intermediate 70

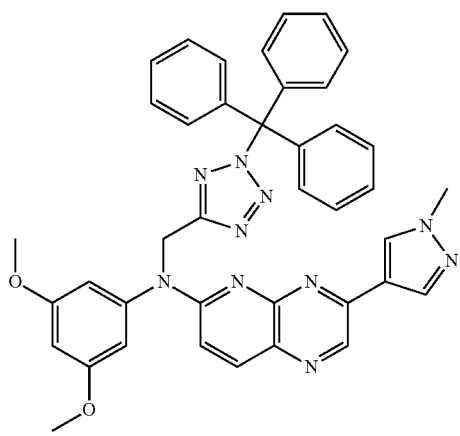 [SMILES: COc1cc(OC)cc(N(Cc2nnn(C(c3ccccc3)(c3ccccc3)c3ccccc3)n2)c2ccc3ncc(-c4cnn(C)c4)nc3n2)c1]

NaH (88 mg; 2.21 mmol) was added under N₂ at 10° C. to a solution of intermediate 6 ((400 mg; 1.1 mmol) in DMF (5 mL). The solution was stirred at 10° C. for 30 minutes. 5-chloromethyl-2-trityl-2H-tetrazole (CAS 160998-59-4) (619 mg; 1.72 mmol) was added portion wise and the solution was allowed to slowly warm to room temperature and stirred overnight. The solution was cooled, poured into cooled water and extracted with EtOAc. The organic layer was decanted, washed with brine, dried over MgSO₄, filtered and evaporated to dryness to give 0.76 g (100%) of intermediate 70.

124

Analogous Preparation of Intermediate 43

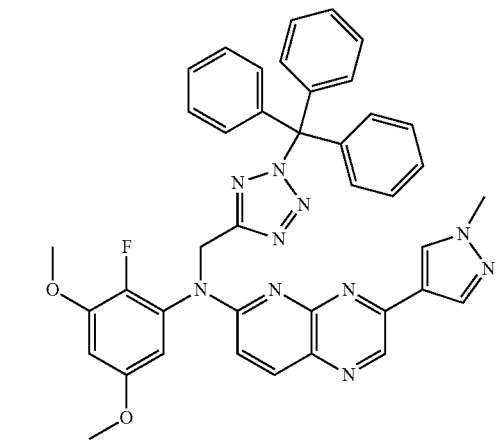 [SMILES: COc1cc(OC)c(F)c(N(Cc2nnn(C(c3ccccc3)(c3ccccc3)c3ccccc3)n2)c2ccc3ncc(-c4cnn(C)c4)nc3n2)c1]

Analogous Preparation of Intermediate 78 Starting

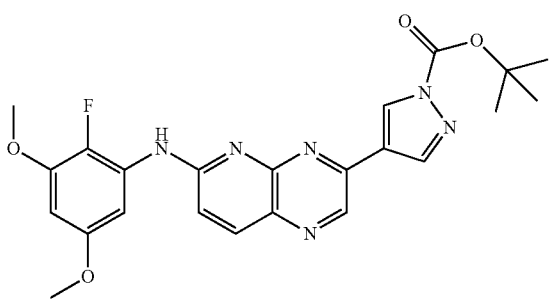 [SMILES: COc1cc(Nc2ccc3ncc(-c4cnn(C(=O)OC(C)(C)C)c4)nc3n2)c(F)c(OC)c1]

From Intermediate 7 and Intermediate 82.

Example A9

Preparation of Intermediate 25

In a round bottom flask, intermediate 26 (1.06 g; 2.89 mmol) was diluted in DCM (30 mL). Then, at room temperature, Et₃N (2.07 mL; 14.48 mmol) followed by Boc₂O (760 mg; 3.4 mmol) were added. The reaction mixture was stirred for 18 hours at room temperature. The reaction mixture was partitioned between water and DCM. The organic layer was separated, dried over MgSO₄, filtered and evaporated to dryness to afford a crude which was taken up with Et₂O to give after filtration 990 mg (82%) of intermediate 25 (orange powder). M.P.: 160° C. (gum, Kofler).

Example A9A

Preparation of Intermediate 140

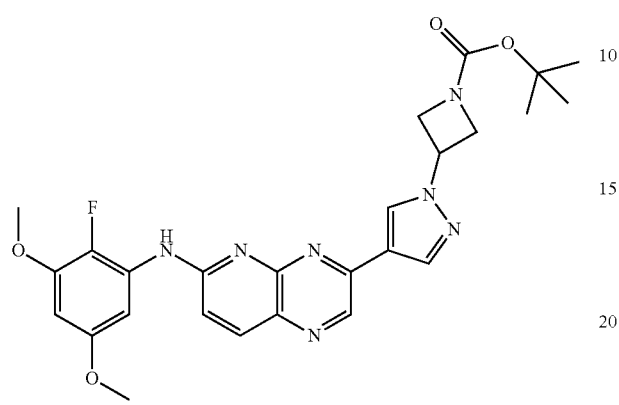

1-(Tert-butoxycarbonyl)-3-(methanesulfonyloxy)azetidine (CAS: 141699-58-3) (850 mg; 3.38 mmol) was added a solution of intermediate 26 (826 mg, 1.86 mmol) and Cs₂CO₃ (1.47 g; 4.51 mmol) in ACN (16 mL). The reaction mixture was stirred in a sealed tube at 100° C. for 6 hours. The reaction mixture was poured into ice water and extracted with EtOAc. The organic layer was washed with brine, dried over MgSO₄, filtered and evaporated to dryness. The residue was purified by chromatography over silica gel (irregular SiOH, 15-45 μm, 12 g; mobile phase: gradient from 99% DCM, 1% MeOH to 97% DCM, 3% MeOH). The product fractions were collected and evaporated to dryness yielding 147 mg (15%) of intermediate 140.

Example A10

Preparation of Intermediate 27

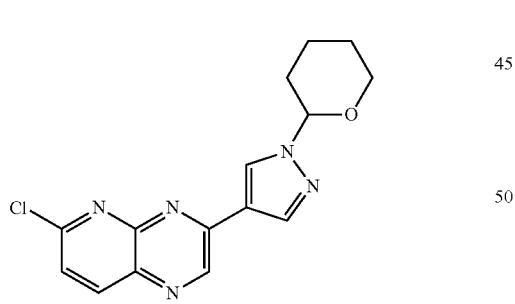

A mixture of intermediate 5a (7.5 g; 30.68 mmol) and 1-(tetrahydro-2H-pyran-2-yl)-4-(4,4,5,5-tetramethyl-1,3,2-dioxaborolan-2-yl)-1H-pyrazole (CAS 1003846-21-6) (9.39 g; 33.75 mmol) in a 2M aqueous solution of sodium carbonate (76 mL; 153.39 mmol) and DME (310 mL) was degassed with N₂ for 15 minutes, then Pd(Ph₃)₄ (1.77 g; 1.53 mmol) was added. The reaction mixture was refluxed overnight, poured into a saturated solution of NaHCO₃ and extracted with AcOEt. The organic layer was washed with brine, dried over MgSO₄, filtered and evaporated to dryness. The residue was crystallized from ACN. The precipitate was filtered, washed with Et₂O and dried yielding 3.06 g (32%) of intermediate 27. The filtrate was purified by chromatography over silica gel (irregular SiOH, 15-45 μm, 120 g; mobile phase: gradient from 100% DCM, 0% MeOH to 99% DCM, 1% MeOH). The fractions were collected and evaporated to dryness yielding 4.21 g (43%) of intermediate 27. (overall yield: 75%).

Analogous Preparation of Intermediate 55

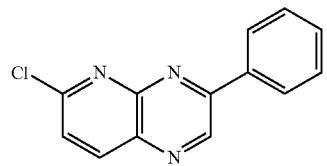 [SMILES: Clc1ccc2ncc(-c3ccccc3)nc2n1]

Starting from Intermediate 5a

Analogous Preparation of Intermediate 72

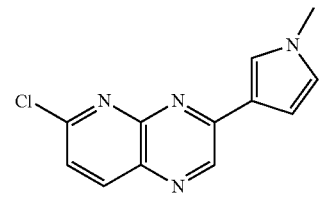 [SMILES: Cn1ccc(-c2cnc3ccc(Cl)nc3n2)c1]

Starting from Intermediate 5a

Example A10 b-1

Preparation of Intermediate 62

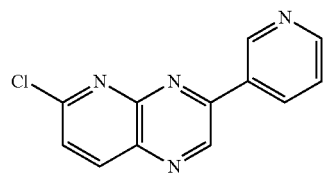 [SMILES: Clc1ccc2ncc(-c3cccnc3)nc2n1]

A solution of intermediate 5a (1.25 g; 5.10 mmol) and 3-(4,4,5,5-tetramethyl-1,3,2-dioxoborolan-2-yl)-pyridine (1.1 g; 5.10 mmol) in Na₂CO₃ 2M (12.7 mL) and DME (51 mL) were degassed with N₂ for 15 minutes. PdCl₂(dppf).DCM (373 mg; 0.51 mmol) was added and the reaction mixture was refluxed for 1 hour. The reaction mixture was cooled to room temperature, poured into water and extracted with EtOAc. The organic layer was decanted, dried over MgSO₄, filtered and the solvent was evaporated. The residue (1.7 g) was purified by chromatography over silica gel (irregular SiOH, 20-45 μm, 30 g; mobile phase: 0.1% NH₄OH, 97% DCM, 3% MeOH). The product fractions were collected and the solvent was evaporated to give 330 mg (27%) of intermediate 62.

Analogous Preparation of Intermediate 75

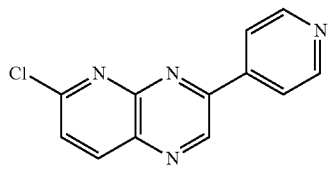 [SMILES: Clc1ccc2ncc(-c3ccncc3)nc2n1]

Starting from Intermediate 5a
Analogous Preparation of Intermediate 96

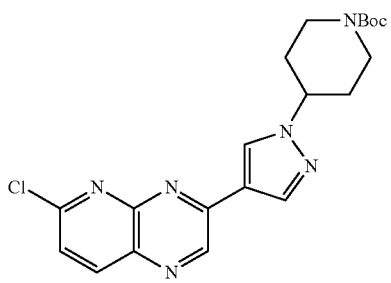 [SMILES: CC(C)(C)OC(=O)N1CCC(n2cc(-c3cnc4ccc(Cl)nc4n3)cn2)CC1]

Starting from Intermediate 5a

Example A11

Preparation of Intermediate 29

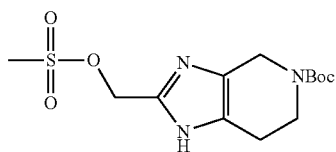 [SMILES: CC(C)(C)OC(=O)N1CCc2[nH]c(COS(C)(=O)=O)nc2C1]

Methanesulfonyl chloride (0.229 mL; 2.96 mmol) was added drop wise to a solution of 2-hydroxymethyl-1,4,6,7-tetrahydro-imidazo[4,5-c]pyridine-5-carboxylicacidtert-butylester (CAS 1251000-69-7) (0.250 g; 0.99 mmol) and Et₃N (0.69 mL; 4.94 mmol) in DCM (10 mL) at 5° C. under N₂ flow. The reaction mixture was stirred at 5° C. for 2 hours. The reaction mixture was poured into iced water and DCM was added. The organic layer was separated, dried over MgSO₄, filtered and the solvent was evaporated to give 0.237 g (72%) of intermediate 29. The product was used without purification in the next step.

Example A11A

Preparation of Intermediate 113

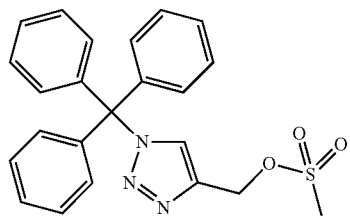 [SMILES: CS(=O)(=O)OCc1cn(C(c2ccccc2)(c2ccccc2)c2ccccc2)nn1]

Methanesulfonyl chloride (0.75 mL; 9.666 mmol) was added dropwise at 5° C. under N₂ flow to a solution of 1-(triphenylmethyl)-1H-1,2,3-triazole-4-methanol (CAS 88529-86-6) (2.2 g; 6.444 mmol) and Et₃N (1.34 ml; 9.666 mmol) in DCM/THF 50/50 (45 mL). The reaction mixture was stirred below 0° C. for 1 hour, poured onto ice and extracted with DCM. The organic layer was decanted, dried over MgSO₄, filtered and evaporated to dryness yielding 2.4 g (89%) of intermediate 113.

Example A12 a) Preparation of Intermediate 331

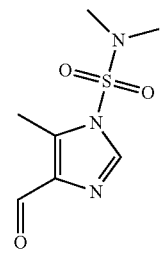

Dimethylsulfamoyl chloride (2.16 mL; 19.98 mmol) was added to a solution of 4-methyl-5-imidazolecarboxaldehyde (CAS 68282-53-1) (2 g; 18.16 mmol) and Et₃N (4.16 mL; 29.06 mmol) in ACN (20 mL). The reaction mixture was stirred at 50° C. overnight. The mixture was poured into water and extracted with EtOAc. The organic layer was washed with brine, dried over MgSO₄, filtered and evaporated to dryness. The residue was purified by chromatography over silica gel (irregular SiOH, 15-40 μm, 80 g; mobile phase: 99% DCM, 1% MeOH). The product fractions were collected and evaporated to dryness yielding 2.35 g (60%) of intermediate 33.

b) Preparation of Intermediate 32

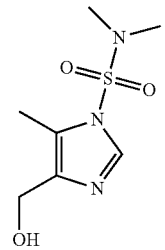

NaBH₄ (491 mg; 12.98 mmol) was added to a solution of intermediate 33 (2.35 g; 10.81 mmol) in MeOH (20 mL) at 5° C. under N₂ flow. The reaction mixture was then stirred at room temperature 2 hours, poured into ice water and extracted with DCM. The organic layer was dried over MgSO₄, filtered and evaporated to dryness. The crude product was taken up in Et₂O then filtered and dried yielding 1.09 g (46%) of intermediate 32.

c) Preparation of Intermediate 31

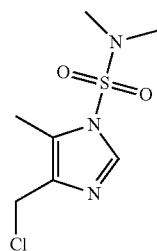

Et₃N (8.24 mL; 57.58 mmol), methanesulfonyl chloride (2.67 mL; 34.55 mmol) and lithium chloride (3.66 g; 86.37 mmol) were added successively to a solution of intermediate 32 (5.91 g; 28.79 mmol) in THF (145 mL) at 5° C. under N₂ flow. The reaction mixture was stirred at room temperature for 4 hours. The reaction mixture was poured into ice water and extracted with EtOAc. The organic layer was washed with brine, dried over MgSO₄, filtered and evaporated to dryness yielding 6.76 g of intermediate 31. The crude mixture was used in the next step without any purification.

Example A13 a) Preparation of Intermediate 34

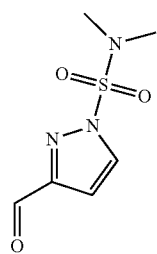

Dimethylsulfamoyl chloride (3.09 mL; 28.62 mmol) was added to a solution of 3-carboxaldehyde pyrazole (2.5 g; 26.02 mmol) and Et₃N (5.96 mL; 41.63 mmol) in ACN (25 mL) and the reaction mixture was stirred at 50° C. overnight. The reaction mixture was poured into ice water and extracted with EtOAc. The organic layer was washed with brine and dried over MgSO₄, filtered and evaporated to dryness. The crude product was purified by chromatography over silica gel (irregular SiOH, 15-45 μm, 80 g; mobile phase: 99% DCM, 1% MeOH). The pure fractions were collected and evaporated to dryness yielding 4.42 g (84%) of intermediate 34.

b) Preparation of Intermediate 35

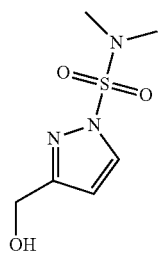

NaBH₄ (987.41 mg; 26.1 mmol) was added portion wise to a solution of intermediate 34 (4.42 g; 21.75 mmol) in MeOH (50 mL) at 5° C. The reaction mixture was then stirred at room temperature 2 hours, poured out into ice water and extracted with DCM. The organic layer was decanted, dried over MgSO₄, filtered and evaporated to dryness. The crude product was taken up with Et₂O; the precipitate was filtered and dried yielding 3.04 g (68%) of intermediate 35.

c) Preparation of Intermediate 36

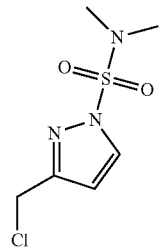

Et₃N (4.24 mL; 29.63 mmol), methanesulfonyl chloride (1.38 mL; 17.78 mmol) and lithium chloride (1.88 g; 44.45 mmol) were added successively to a solution of intermediate 35 (3.04 g; 14.82 mmol) in THF (75 mL) at 5° C. under N₂ flow. The reaction mixture was stirred at room temperature for 4 hours, poured into ice water and extracted with EtOAc. The organic layer was washed with brine, dried over MgSO₄, filtered and evaporated to dryness yielding 3.82 g of intermediate 36 which was used in the next step without any purification.

Example A14 a) Preparation of Intermediate 37

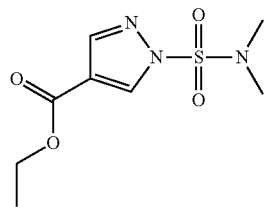 [SMILES: CCOC(=O)c1cnn(S(=O)(=O)N(C)C)c1]

NaH (214 mg; 5.35 mmol) was added portion wise to a solution of ethyl 4-pyrazolecarboxylate (CAS 37622-90-5) (0.5 g; 3.93 mmol) in DMF (5 mL) under N₂ flow at 5° C. The reaction mixture was stirred at 5° C. for 30 minutes, then dimethylsulfamoyl chloride (424 μL; 3.93 mmol) was added. The reaction mixture was allowed to warm to room temperature and stirred at room temperature overnight. The reaction mixture was poured into ice water and extracted with EtOAc. The organic layer was washed with brine, dried over MgSO₄, filtered and evaporated to dryness. The residue was purified by chromatography over silica gel (irregular SiOH, 15-45 μm, 25 g; mobile phase: 99% DCM, 1% MeOH). The product fractions were collected and evaporated to dryness yielding 720 mg (82%) of intermediate 37.

b) Preparation of Intermediate 38

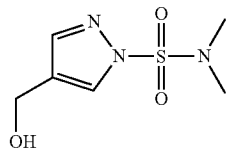

Intermediate 37 (720 mg; 2.91 mmol) in THF (7 mL) was added drop wise to a suspension of LiAlH$_4$ (221 mg; 5.82 mmol) in THF (6 mL) at room temperature and stirred all over the weekend. The reaction mixture was quenched successively with water (220 µL), NaOH (220 µL) and water (660 µL), then extracted with EtOAc. The organic layer was washed with brine, dried over MgSO$_4$, filtered and evaporated to dryness yielding 229 mg (38%) of intermediate 38.

c) Preparation of Intermediate 39

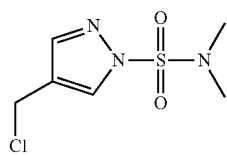

Et$_3$N (0.32 mL; 2.23 mmol), methanesulfonyl chloride (0.104 mL; 1.34 mmol) and lithium chloride (142 mg; 3.35 mmol) were added successively to a solution of intermediate 38 (229 mg; 1.12 mmol) in THF (5 mL) at 5° C. under N$_2$ flow and the reaction mixture was stirred at room temperature for 4 hours. The reaction mixture was poured into ice water and extracted with EtOAc. The organic layer was washed with brine, dried over MgSO$_4$, filtered and evaporated to dryness yielding 245 mg (98%) of intermediate 39. The residue was used in the next step without any purification.

Example A15 a) Preparation of Intermediate 40

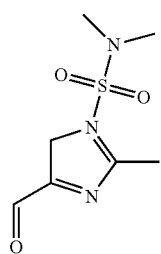

Dimethylsulfamoyl chloride (CAS 13360-57-1) (1.81 mL; 16.78 mmol) was added to a solution of 2-methyl-1H-imidazole-4-carbaldehyde (CAS 35034-22-1) (1.68 g; 15.26 mmol) and Et$_3$N (3.49 mL; 24.41 mmol) in ACN (17 mL) and the reaction mixture was stirred at 50° C. overnight. The reaction mixture was diluted with EtOAc and washed with water. The organic layer was then dried over MgSO$_4$, filtered and evaporated to dryness. The residue was purified by chromatography over silica gel (irregular SiOH, 15-40 µm, 24 g; mobile phase: 100% DCM). The pure fractions were collected and evaporated to dryness yielding 1.36 g (41%) of intermediate 40.

b) Preparation of Intermediate 41

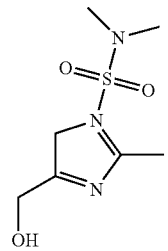

NaBH$_4$ (284 mg; 7.51 mmol) was added portion wise to a solution of intermediate 40 (1.36 g; 6.26 mmol) in MeOH (15 mL) at 5° C. The reaction mixture was stirred at room temperature for 2 hours, poured into ice water, extracted with DCM, dried over MgSO$_4$, filtered and evaporated to dryness. The crude product was taken up with Et$_2$O; the precipitate was filtered and dried yielding 795 mg (58%) of intermediate 41.

c) Preparation of Intermediate 42

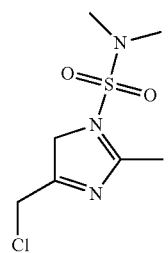

Et$_3$N (1.04 mL; 7.25 mmol), methane sulfonyl chloride (0.337 mL; 4.35 mmol) and LiCl (461.13 mg; 10.9 mmol) were added successively to a solution of intermediate 41 (795 mg; 3.62 mmol) in THF (18 mL) at 5° C. under N$_2$ flow. The reaction mixture was stirred at room temperature for 4 hours, poured into ice water and extracted with EtOAc. The organic layer was washed with brine, dried over MgSO$_4$, filtered and evaporated to dryness yielding 844 mg (98%) of intermediate 42 which was used in the next step without any purification in the preparation of compound 138.

Example A16 a) Preparation of Intermediate 44

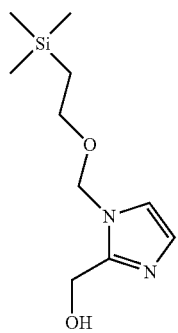

A solution of 1-[[2-(Trimethylsilyl)-ethoxy]-methyl]-1H-imidazole-2-carboxaldehyde (CAS 101226-42-0) (2.25 g;

9.94 mmol) in MeOH (29 mL) was cooled to −20° C. and treated portion wise with NaBH₄ (0.45 g; 11.9 mmol). The reaction mixture was stirred at room temperature for 1 hour, quenched by addition of an aqueous solution of NH₄Cl and extracted with DCM. The organic layer was dried over MgSO₄, filtered and the solvent was evaporated to give 2.13 g (94%) of intermediate 44.

b) Preparation of Intermediate 45

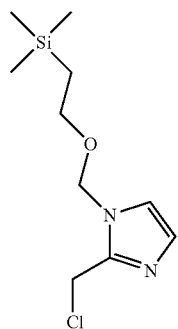

Methanesulfonyl chloride (1.07 mL; 13.8 mmol) was added drop wise to a solution of intermediate 44 (2.1 g; 9.2 mmol) and Et₃N (1.92 mL; 13.8 mmol) in DCM (31 mL) at 0° C. under N₂ flow. The reaction mixture was stirred below 0° C. for 1 hour, poured into ice and extracted with DCM. The organic layer was separated, dried over MgSO₄, filtered and the solvent was evaporated under vacuum at room temperature to give 2.27 g (100%) of intermediate 45 which was used without further purification in the next step.

c) Preparation of Intermediate 46

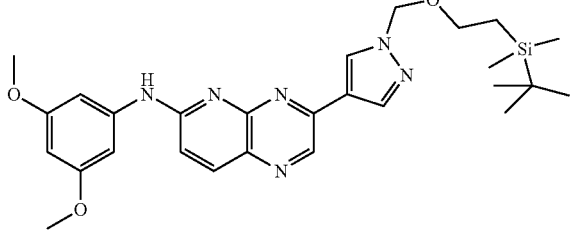

NaH (0.13 g; 3.27 mmol) was added portion wise to intermediate 47 (1.14 g; 3.27 mmol) in DMF (11 mL) under N₂ flow at room temperature. The mixture was stirred for 1.5 hours, then 2-(trimethylsilyl)-ethoxymethyl chloride (0.58 mL; 3.27 mmol) was added drop wise. The reaction mixture was stirred at room temperature overnight, quenched with ice and extracted with EtOAc. The organic layer was washed with brine, dried over MgSO₄, filtered and the solvent was evaporated to dryness. The residue (1.62 g) was purified by chromatography over silica gel (irregular SiOH, 15-40 μm, 80 g; mobile phase: gradient from 100% DCM, 0% MeOH to 96% DCM, 4% MeOH. The product fractions were collected and the solvent was evaporated to give 0.77 g (49%) of intermediate 46.

d) Preparation of Intermediate 48

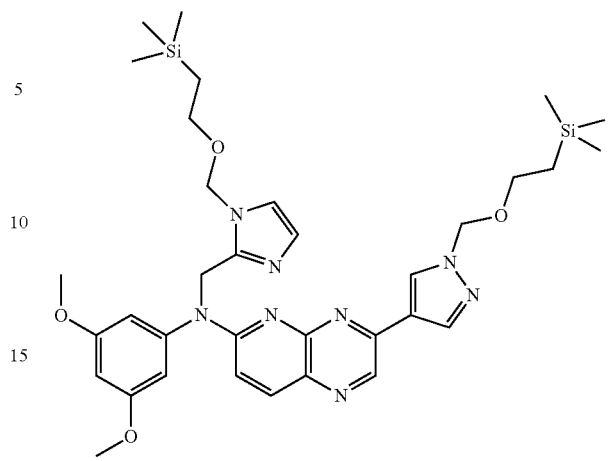

NaH (125 mg; 3.13 mmol) was added under N₂ at 10° C. to a solution of intermediate 46 (750 mg; 1.57 mmol) in DMF (10 mL). The solution was stirred at 10° C. for 30 minutes. Intermediate 45 (601 mg; 2.44 mmol) was added portion wise and, the solution was allowed to slowly warm to room temperature and stirred overnight. The solution was cooled, poured into cooled water and extracted with EtOAc. The organic layer was washed with brine, dried over MgSO₄, filtered and evaporated to dryness. The residue was purified by chromatography over silica gel (irregular SiOH, 15-40 μm, 80 g; mobile phase: gradient from 0% NH4OH, 0% MeOH, 100% DCM to 0.1% NH4OH, 5% MeOH, 95% DCM). The product fractions were collected and the solvent was evaporated to give 0.78 g (72%) of intermediate 48.

Analogous Preparation of Intermediate 66

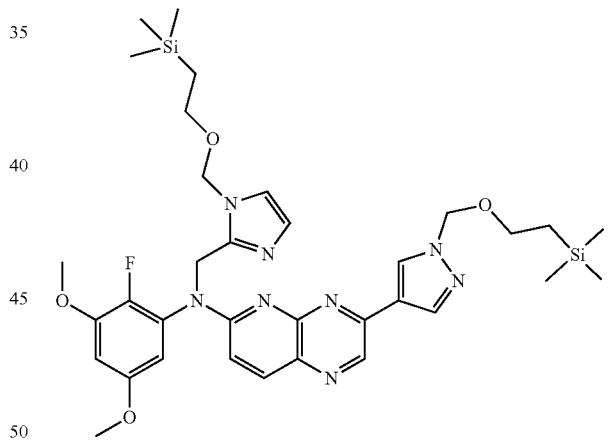

Analogous Preparation of Intermediate 94

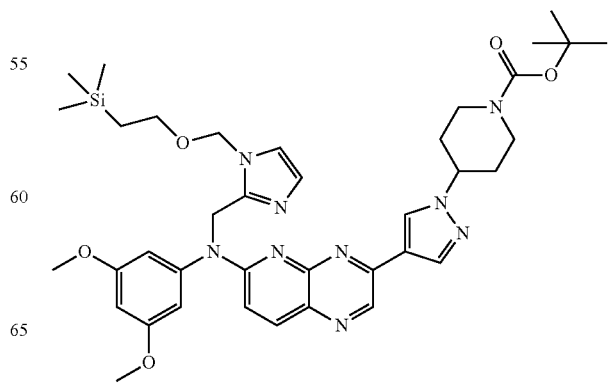

Starting from Intermediate 95 and Intermediate 45
Analogous Preparation of Intermediate 97

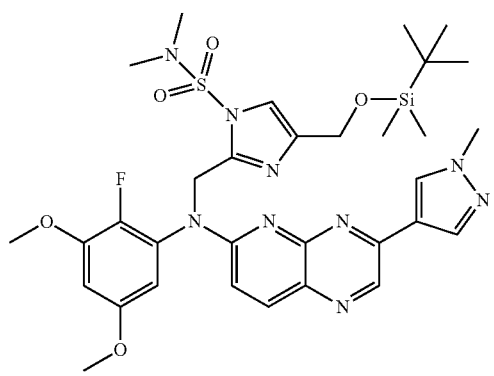 [SMILES: COc1cc(OC)c(F)c(N(Cc2nc(CO[Si](C)(C)C(C)(C)C)cn2S(=O)(=O)N(C)C)c2ccc3ncc(-c4cnn(C)c4)nc3n2)c1]

Starting from Intermediate 7 and Intermediate 102
Analogous Preparation of Intermediate 107

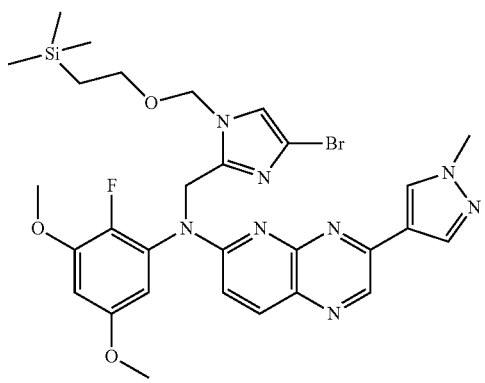 [SMILES: COc1cc(OC)c(F)c(N(Cc2nc(Br)cn2COCC[Si](C)(C)C)c2ccc3ncc(-c4cnn(C)c4)nc3n2)c1]

Starting from Intermediate 7 and from Intermediate 108
Analogous Preparation of Intermediate 115

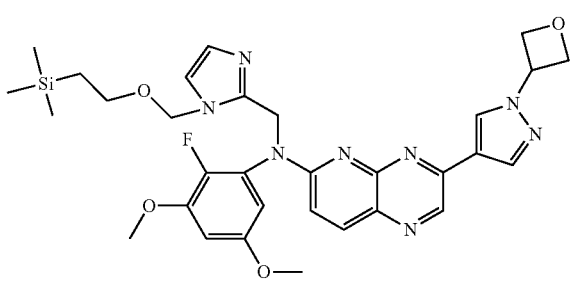 [SMILES: COc1cc(OC)c(F)c(N(Cc2nccn2COCC[Si](C)(C)C)c2ccc3ncc(-c4cnn(C5COC5)c4)nc3n2)c1]

Starting from Intermediate 83 and from Intermediate 45
Analogous Preparation of Intermediate 145 Starting

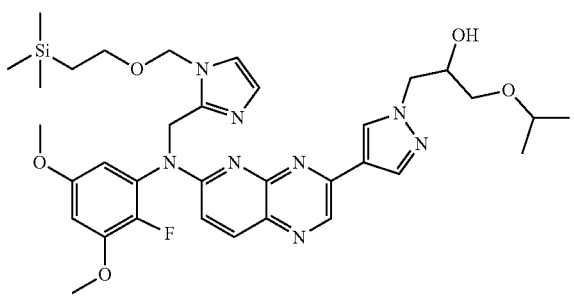 [SMILES: COc1cc(OC)c(F)c(N(Cc2nccn2COCC[Si](C)(C)C)c2ccc3ncc(-c4cnn(CC(O)COC(C)C)c4)nc3n2)c1]

From Intermediate 146 and from Intermediate 45

Example A17

Preparation of Intermediate 49

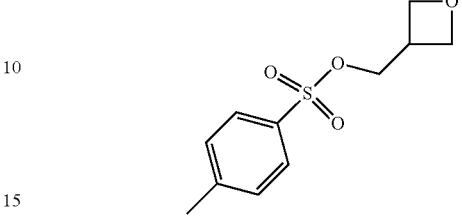

A 30% aqueous solution of NaOH (1.99 mL; 19.9 mmol) was added gradually to a solution of p-toluenesulfonyl chloride (2.6 g; 13.6 mmol) and benzyltriethylammonium chloride (CAS 56-37-1) (0.194 g; 0.85 mmol) in toluene (5 mL) at 5° C. 3-Oxetanemethanol (CAS 6246-06-6) (0.915 mL; 11.35 mmol) was added drop wise below 10° C. The reaction mixture was stirred below 10° C. for 1 hour and at room temperature for 5 hours. The reaction mixture was poured into ice and extracted with DCM (3 times). The organic layer was dried over MgSO$_4$, filtered and the solvent was evaporated to give 2.49 g (91%) of intermediate 49.

Example A18

Preparation of Intermediate 50

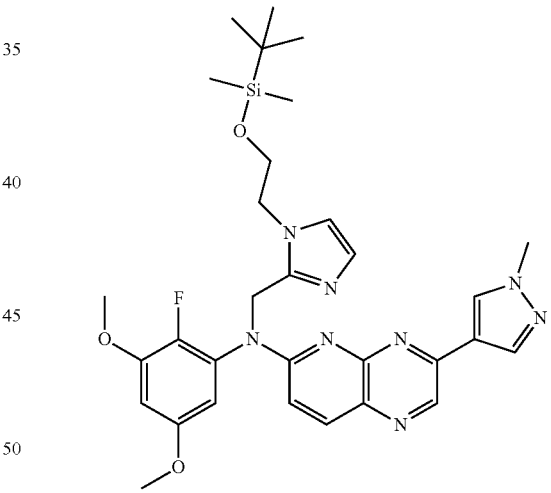

NaH (107 mg; 2.68 mmol) was added to a solution of intermediate 7 (510 mg; 1.34 mmol) in DMF (10 mL) at 5° C. under N$_2$ flow. The reaction was stirred at 5° C. for 30 minutes and a solution of intermediate 53 (554 mg; 2.02 mmol) in DMF (5 mL) was added at 5° C. under N$_2$ flow over a 30 minutes period. The reaction mixture was allowed to warm to room temperature and stirred overnight. The reaction mixture was poured into ice water and extracted with EtOAc. The organic layer was washed with brine, dried over MgSO$_4$, filtered and evaporated to dryness. The crude product was purified by chromatography over silica gel (irregular SiOH, 15-45 µm, 24 g; mobile phase: gradient from DCM 99%, MeOH 1% to DCM 98%, MeOH 2%). The product fractions were collected and evaporated to dryness yielding 200 mg (24%) of intermediate 50.

Example A19 a) Preparation of Intermediate 51

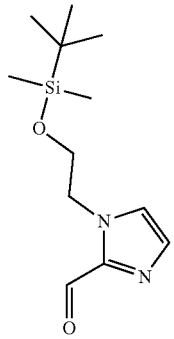 [SMILES: CC(C)(C)[Si](C)(C)OCCn1ccnc1C=O]

NaH (724 mg; 18.11 mmol) was added portion wise to a solution of 2-imidazolecarboxaldehyde (1.16 g; 12.07 mmol) in DMF (58 mL) at 5° C. under N₂ flow. The reaction mixture was stirred at 5° C. for 30 minutes and (2-bromoethoxy)-tert-butyldimethylsilane (3.11 mL; 14.49 mmol) was added. The reaction mixture was allowed to warm to room temperature and stirred all over the weekend. The reaction mixture was poured into ice water and extracted with EtOAc. The organic layer was washed with brine, dried over MgSO₄, filtered and dried. The residue was purified by chromatography over silica gel (irregular SiOH, 15-45 μm, 40 g; mobile phase: DCM 99%, MeOH 1%). The pure fractions were collected and evaporated to dryness yielding 940 mg (31%) of intermediate 51.

b) Preparation of Intermediate 52

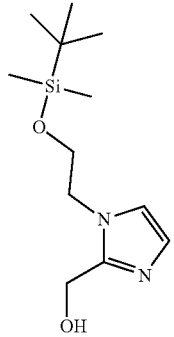 [SMILES: CC(C)(C)[Si](C)(C)OCCn1ccnc1CO]

NaBH₄ (168 mg; 4.43 mmol) was added portion wise to a solution of intermediate 51 (940 mg; 3.70 mmol) in MeOH (10 mL) at 5° C. under N₂ flow. The reaction mixture was stirred at room temperature 2 hours, poured into ice water and extracted with DCM. The organic layer was dried over MgSO₄, filtered and evaporated to dryness. The crude product was taken up with Et₂O. The precipitate was filtered and dried yielding 597 mg (63%) of intermediate 52.

c) Preparation of Intermediate 53

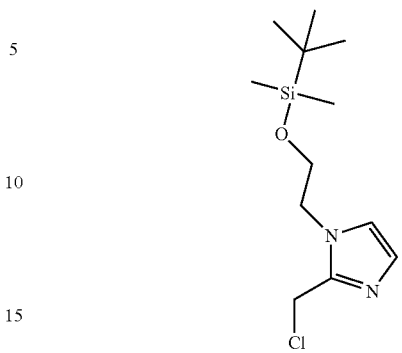

Et₃N (666 μL; 4.66 mmol), methanesulfonyl chloride (216 μL; 2.79 mmol) and LiCl (296 mg; 6.99 mmol) were added successively to a solution of intermediate 52 (597 mg; 2.33 mmol) in THF (12 mL) at 5° C. under N₂ flow and the reaction mixture was stirred at room temperature for 4 hours. The reaction mixture was poured into ice water and extracted with EtOAc. The organic layer was washed with brine, dried over MgSO₄, filtered and evaporated to dryness yielding 554 mg (87%) of intermediate 53 which was used in the next step without any purification.

Example A20

Preparation of Intermediate 56

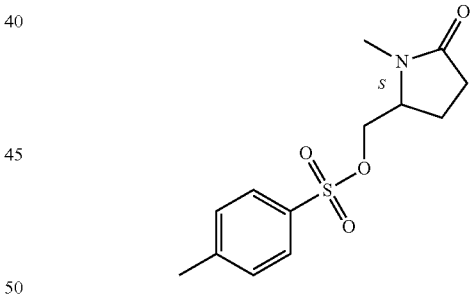

NaH (149 mg; 3.71 mmol) was added portion wise at 5° C. under N₂ to a solution of (S)-5-(Hydroxy-methyl)-2-pyrrolidinone p-toluenesulfonate (CAS 51693-17-5) (1 g; 3.71 mmol) and iodomethane (277 μL; 4.46 mmol) in THF (20 mL). The reaction mixture was allowed to warm to room temperature and stirred overnight. The reaction mixture was quenched with brine and extracted with EtOAc. The organic layer was decanted, washed with water then brine, dried over MgSO₄, filtered and evaporated to dryness. The residue was purified by chromatography over silica gel (irregular SiOH, 30 μm, 30 g; mobile phase: gradient from 100% DCM, 0% MeOH to 98% DCM, 2% MeOH). The product fractions were collected and evaporated to give 390 mg (37%) of intermediate 56.

Example A21

Preparation of Intermediate 57

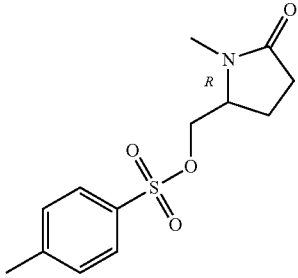

NaH (149 mg; 3.71 mmol) was added portion wise at 5° C. under N$_2$ to a solution of intermediate 18 (1 g; 3.71 mmol) and iodomethane (277 µL; 4.46 mmol) in THF (20 mL). The reaction mixture was allowed to warm to room temperature and stirred overnight. The reaction mixture was quenched with brine and extracted with EtOAc. The organic layer was decanted, washed with water then brine, dried over MgSO$_4$, filtered and evaporated to dryness. The residue was purified by chromatography over silica gel (irregular SiOH, 30 µm, 30 g; mobile phase: gradient from 100% DCM, 0% MeOH to 98% DCM, 2% MeOH). The pure fractions were collected and evaporated to give 377 mg (36%) of intermediate 57.

Example A22 a) Preparation of Intermediate 59

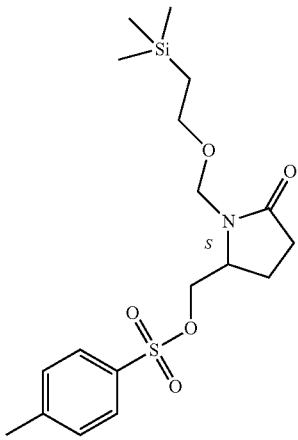

NaH (30 mg; 0.74 mmol) was added at 0° C. to a solution of 2-(trimethylsilyl)-ethoxymethyl chloride (0.13 mL; 0.74 mmol) and (S)-5-(Hydroxy-methyl)-2-pyrrolidinone p-toluenesulfonate (CAS 51693-17-5) (0.2 g; 0.74 mmol) in THF (5 mL). The reaction mixture was stirred 3 hours at 0° C., then partitioned between water and EtOAc. The organic layer was washed with brine, dried over MgSO$_4$, filtered and evaporated to dryness. The residue (0.4 g) was purified by chromatography over silica gel (irregular SiOH, 15-40 µm, 24 g; mobile phase: 98% DCM, 2% MeOH). The product fractions were evaporated to dryness to give 0.142 g (48%, colorless oil) of intermediate 59.

b) Preparation of Intermediates 67 and 58

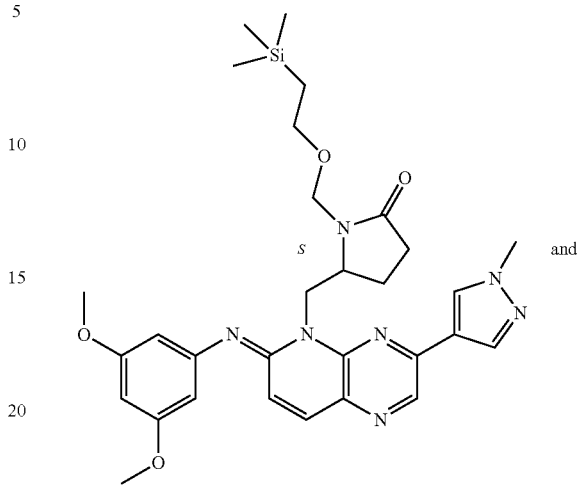

Intermediate 67 and

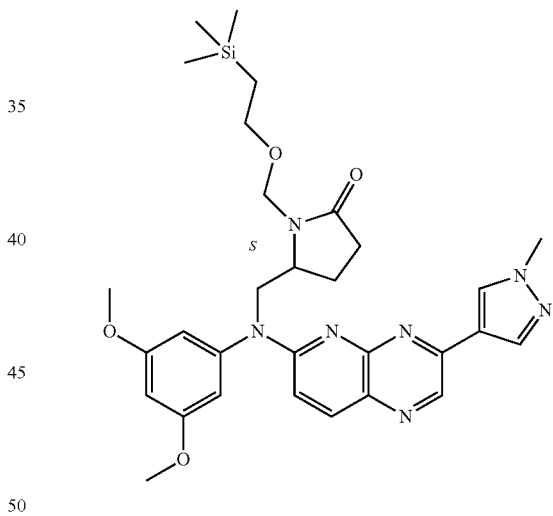

intermediate 58

NaH (14.9 mg; 0.37 mmol) was added to a solution of intermediate 6 0.09 g; 0.25 mmol) in DMF (2.25 mL) at 5° C. under N$_2$ flow. The reaction was stirred at 5° C. for 30 minutes and a solution of intermediate 59 (0.149 g; 0.37 mmol) in DMF (1 mL) was added. The reaction mixture was allowed to warm to room temperature and stirred during 3 days.

The reaction mixture was partitioned between water and EtOAc. The organic layer was washed with brine, dried over MgSO$_4$, filtered and evaporated to dryness. The residue (0.2 g) was purified by chromatography over silica gel (irregular SiOH, 15-40 µm, 24 g; mobile phase: gradient from 98% DCM, 2% MeOH to 95% DCM, 5% MeOH). The product fractions were collected and evaporated to dryness to give 0.076 g (52%, orange oil) of intermediate 67 and 0.05 g (20%, orange oil, purity: 60% based on 1H NMR) of intermediate 58.

Example A23

Preparation of Intermediate 63 and 64

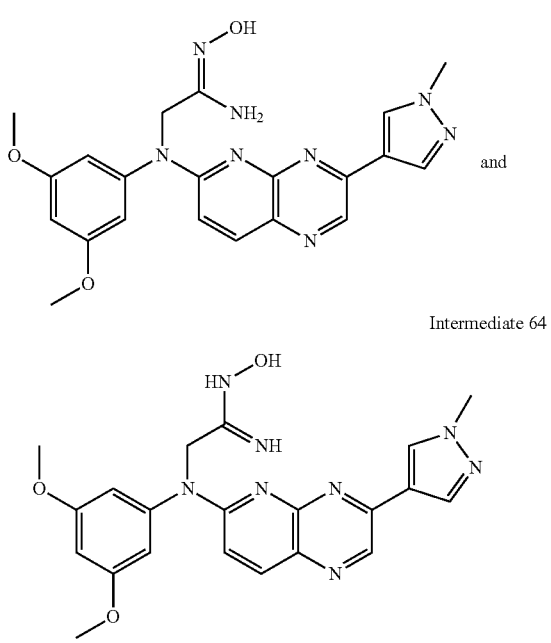

Hydroxylamine hydrochloride (26 mg; 0.37 mmol) was added to a suspension of compound 187 (100 mg; 0.25 mmol) and Et₃N (52 µL; 0.37 mmol) in EtOH (3 mL). The resulting mixture was stirred at 80° C. overnight. The precipitate was filtered and dried to give 0.08 g (74%) of a mixture intermediate 63 and intermediate 64 (70/30 based on 1H NMR).

Analogous Preparation of Intermediate 139

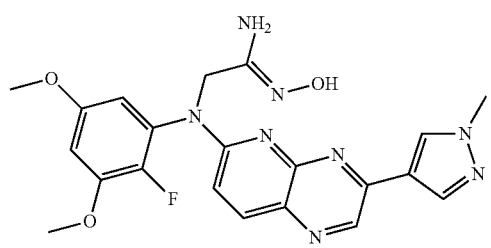

Starting from Compound 298

Example A24

Preparation of Intermediate 65

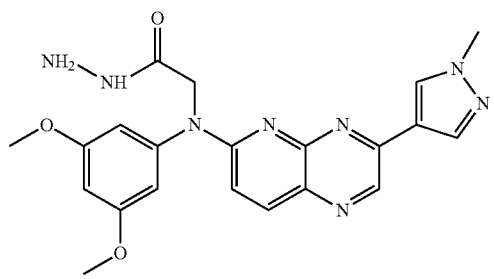 [SMILES: COc1cc(OC)cc(N(CC(=O)NN)c2ccc3ncc(-c4cnn(C)c4)nc3n2)c1]

Hydrazine monohydrate (1.22 ml, 31.2 mol) was added to a solution of compound 189 (0.7 g, 1.56 mmol) in EtOH (70 ml). The mixture was stirred overnight at reflux. After cooling down to room temperature, the precipitate was filtered off, washed with EtOH and dried to give 0.56 g (83%) of intermediate 65, which was used without further purification for the next step.

Analogous Preparation of Intermediate 106

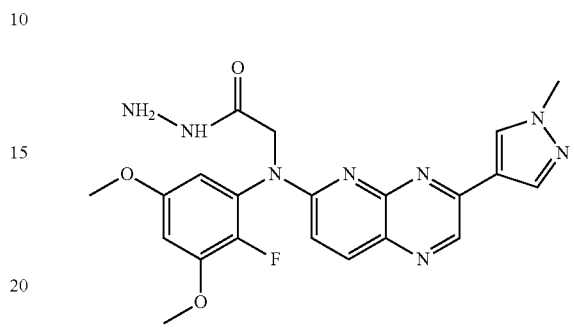

Starting from Compound 234

Example A25

Preparation of Intermediate 76 and 77

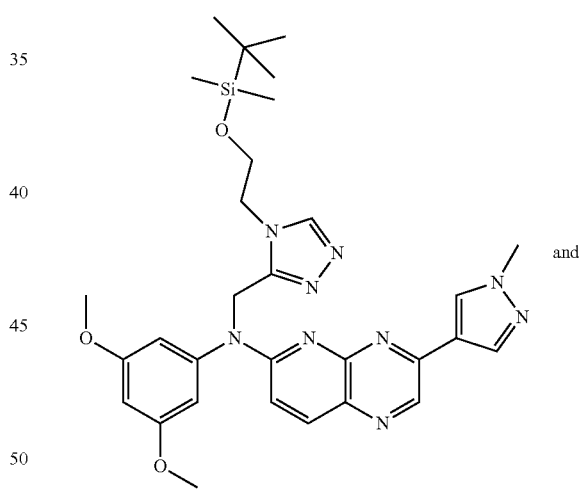

-continued

Intermediate 77

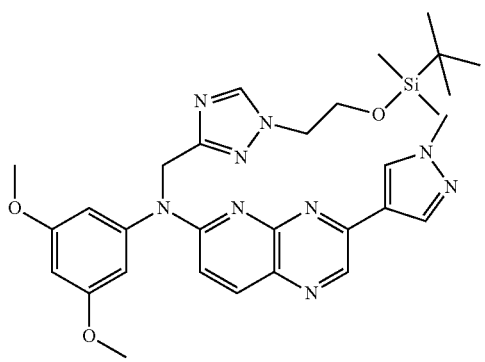

Cs$_2$CO$_3$ (0.3 g; 0.9 mmol) was added to a solution of compound 71 (0.2 g; 0.45 mmol) and (2-Bromoethoxy)-tert-butyldimethylsilane (0.22 mL; 0.99 mmol) in DMF (15 mL) at 5° C. under N$_2$ flow. The reaction mixture was stirred at room temperature for 24 hours, poured into ice water and extracted with EtOAc. The organic layer was washed with water then brine, dried over MgSO$_4$, filtered and evaporated to dryness. The residue (609 mg) was purified by chromatography over silica gel (irregular SiOH, 15-40 µm, 24 g. mobile phase: 0.1% NH$_4$OH, 3% MeOH, 97%). The fractions containing the product were collected and evaporated. The residue (388 mg) was purified again by chromatography over silica gel (Spherical Silica, 5 µm, 150×30.0 mm; mobile phase: gradient from 71% Heptane, 1% MeOH (+10% NH$_4$OH), 28% EtOAc to 0% Heptane, 20% MeOH (+10% NH$_4$OH), 80% EtOAc). The product fractions were collected and the solvent was evaporated to give 0.080 g (29%) of intermediate 76 and 0.175 g (64%) of intermediate 77.

Example A26 a) Preparation of Intermediate 79

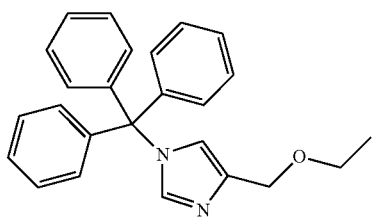 [SMILES: CCOCc1cn(C(c2ccccc2)(c2ccccc2)c2ccccc2)cn1]

NaH (235 mg; 5.88 mmol) was added portion wise to a suspension of 1-Trityl-1H-imidazole-4-methanol (CAS 33769-07-2) (1 g; 2.94 mmol) in DMF (10 mL) at 5° C. under N$_2$ flow. The reaction mixture was stirred at 5° C. for 30 minutes and bromoethane (219 µL; 2.94 mmol) was added drop wise. The reaction mixture was allowed to warm to room temperature and stirred overnight. The reaction mixture was poured into water.

The precipitate was filtered, washed with water, then dissolved in ACN and evaporated to dryness. The residue was taken up twice in EtOH and evaporated to dryness. The crude product was purified by chromatography over silica gel (irregular SiOH, 15-45 µm, 24 g; mobile phase: gradient from 99% DCM, 1% MeOH to 97% DCM, 3% MeOH, 0.1% NH$_4$OH). The product fractions were collected and evaporated to dryness yielding 675 mg (62%) of intermediate 79.

b) Preparation of Intermediate 80

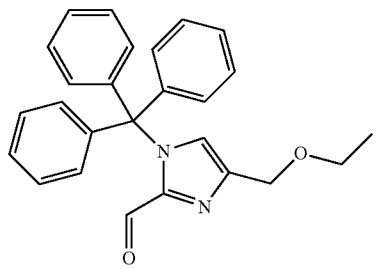 [SMILES: CCOCc1cn(C(c2ccccc2)(c2ccccc2)c2ccccc2)c(C=O)n1]

A solution of nBuLi 1.6M in hexane (1.17 mL; 1.87 mmol) was added drop wise to a solution of intermediate 79 (575 mg; 1.56 mmol) in THF (11 mL) at −78° C. under N$_2$ flow. The reaction mixture was stirred at −78° C. for 10 minutes, then DMF (846 µL; 10.92 mmol) was added drop wise. The reaction mixture was stirred at −78° C. for 30 minutes, allowed to warm to 0° C. over a 3 hour period, quenched with water and extracted with EtOAc. The organic layer was washed with brine, dried over MgSO$_4$, filtered and evaporated to dryness. The residue was purified by chromatography over silica gel (irregular SiOH, 15-45 µm, 12 g; mobile phase: 99% DCM, 1% MeOH). The pure fractions were collected and evaporated to dryness yielding 556 mg (90%) of intermediate 80.

c) Preparation of Intermediate 81

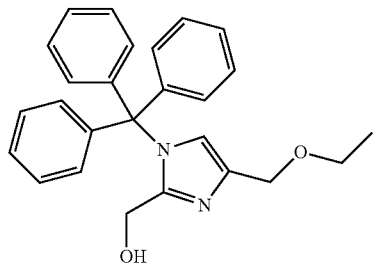 [SMILES: CCOCc1cn(C(c2ccccc2)(c2ccccc2)c2ccccc2)c(CO)n1]

NaBH$_4$ (64 mg; 1.68 mmol) was added portion wise to a solution of intermediate 80 (556 mg; 1.40 mmol) in MeOH (5 mL) at 5° C. The reaction mixture was stirred at room temperature for 2 hours, poured out ice water and extracted with DCM. The organic layer was decanted, dried over MgSO$_4$, filtered and evaporated to dryness. The residue was taken up with Et$_2$O. The precipitate was filtered and dried yielding 530 mg (95%) of intermediate 81 which was used in the next step without any further purification.

d) Preparation of Intermediate 82

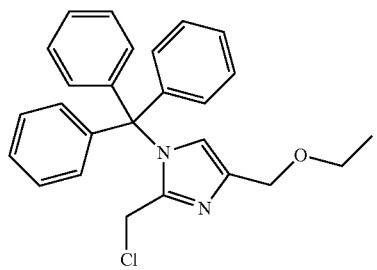 [SMILES: CCOCc1cn(C(c2ccccc2)(c2ccccc2)c2ccccc2)c(CCl)n1]

Et₃N (0.37 mL; 2.66 mmol), methanesulfonyl chloride (124 μL; 1.60 mmol) and LiCl (169.15 mg; 3.99 mmol) were added successively to a solution of intermediate 81 (530 mg; 1.33 mmol) in THF (10 mL) at 5° C. under N₂ flow. The reaction mixture was stirred at room temperature for 4 hours, poured into ice water and extracted with EtOAc. The organic layer was washed with brine, dried over MgSO₄, filtered and evaporated to dryness yielding 610 mg of intermediate 82 which was used in the next step without any further purification.

Example A27

Preparation of Intermediates 83 and 84

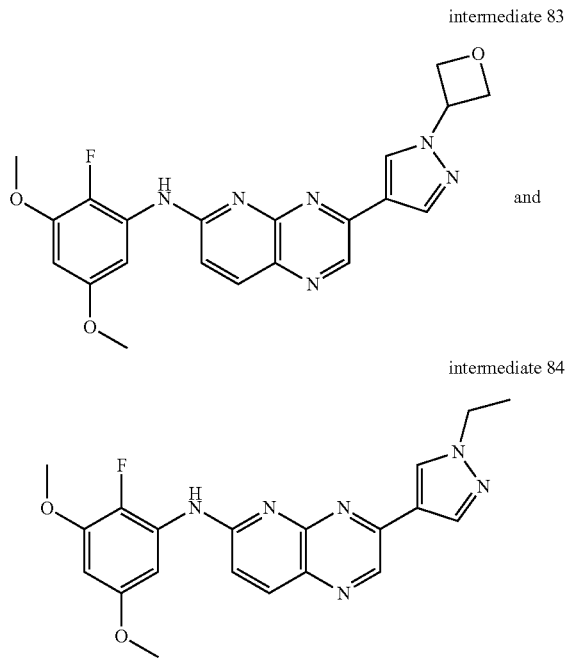

intermediate 83 and intermediate 84

Intermediate 26 (2.08 g, 4.68 mmol), Oxetan-3-yl methanesulfonate (CAS: 148430-81-3) (1.14 g; 7.49 mmol) and cesium carbonate (2.29 g; 7.02 mmol) in DMF (35 mL) were stirred in a sealed tube at 100° C. for 6 hours. The mixture was poured into ice and extracted with EtOAc. The organic layer was washed with brine, dried over MgSO₄, filtered evaporated to dryness. The crude product was purified by chromatography over silica gel (5 g of dry loading irregular SiOH 70-200 μm, irregular SiOH, 15-45 μm, 25 g; mobile phase: gradient from 98% DCM, 2% MeOH to 97% DCM, 3% MeOH). The product fractions were collected and evaporated to dryness yielding 2 fractions Fraction 1: 80 mg of a compound which was dissolved in ACN, crystallized from CAN. The precipitate was filtered, washed with ACN then Et₂O and dried yielding 27 mg (1%) intermediate 84. M.P.: 187-188° C. (Kofler).

Fraction 2: 550 mg of impure intermediate 83 was purified by achiral SFC (AMINO 6 μm 150×21.2 mm; mobile phase 0.3% ISOPROPYLAMINE, 75% CO₂, 25% MeOH). The product fractions were collected and evaporated to dryness yielding 420 mg (21%) of intermediate 83.

Example A28

Preparation of Intermediate 87

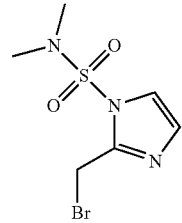

Et₃N (1.4 mL; 9.7 mmol) was added to a solution of 2-(hydroxymethyl)-N,N-dimethyl-1H-imidazole-1-sulfonamide (CAS 935862-80-9) (1 g; 4.87 mmol) in THF (25 mL). The reaction mixture was cooled down to 5° C. under N₂ and methanesulfonyl chloride (0.45 mL; 5.85 mmol) followed by lithium bromide (1.27 g; 14.62 mmol) were added. The reaction mixture was stirred at room temperature for 2 hours, poured into ice water and extracted with EtOAc. The organic layer was washed with brine, dried over MgSO₄, filtered and evaporated to dryness. The residue (1.43 g) was purified by chromatography over silica gel (irregular SiOH, 15-40 μm, 24 g; mobile phase: 99% DCM, 1% MeOH). The product fractions were collected and evaporated to give 0.92 g (70%) intermediate 87.

Example A29

Preparation of Intermediate 90

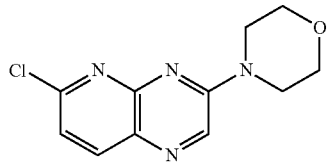 [SMILES: Clc1ccc2ncc(N3CCOCC3)nc2n1]

A solution of 3,6-dichloropyrido[2,3,b]pyrazine (CAS: 1350925-22-2) (14 g; 69.99 mmol), morpholine (12.32 mL; 139.98 mmol), Et₃N (19.4 mL; 139.98 mmol) in DCM (500 mL) was stirred at room temperature for 2 hours. Then, water was added. The organic layer was separated, washed with brine, dried over MgSO₄ and filtered. The filtrate was evaporated to dryness The residue (17 g) was purified by chromatography over silica gel (Irregular SiOH, 20-45 μm, 450 g; Mobile phase: 40% Heptane, 10% MeOH (+10% NH4OH), 50% AcOEt). The product fractions were mixed and the solvent evaporated to give 2 fractions:

Fraction 1: 9.7 g (55%) of intermediate 90

Fraction 2: 4.9 g of impure intermediate 90 which was purified by achiral SFC (Stationary phase: Chiralpak IA 5 μm 250*20 mm; Mobile phase: 55% CO₂, 45% MeOH) to afford additional 3.3 g (19%) of intermediate 90.

Example A30

Preparation of Intermediate 91

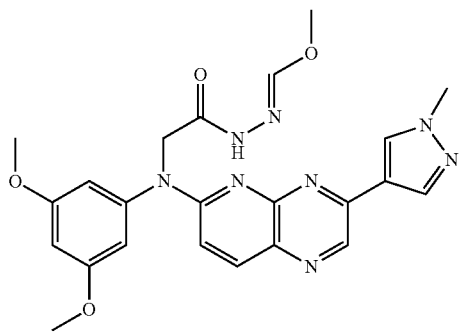 [SMILES: CO/C=N/NC(=O)CN(c1cc(OC)cc(OC)c1)c1ccc2ncc(-c3cnn(C)c3)nc2n1]

A solution of intermediate 65 (316 mg; 0.73 mmol) in trimethyl orthoformate (CAS 149-73-5) (80 mL; 731.24 mmol) was refluxed (100° C.) overnight. The mixture was evaporated until dryness yielding 350 mg of intermediate 91 which was directly used in the next step.

Example A31

Preparation of Intermediates 92 and 93

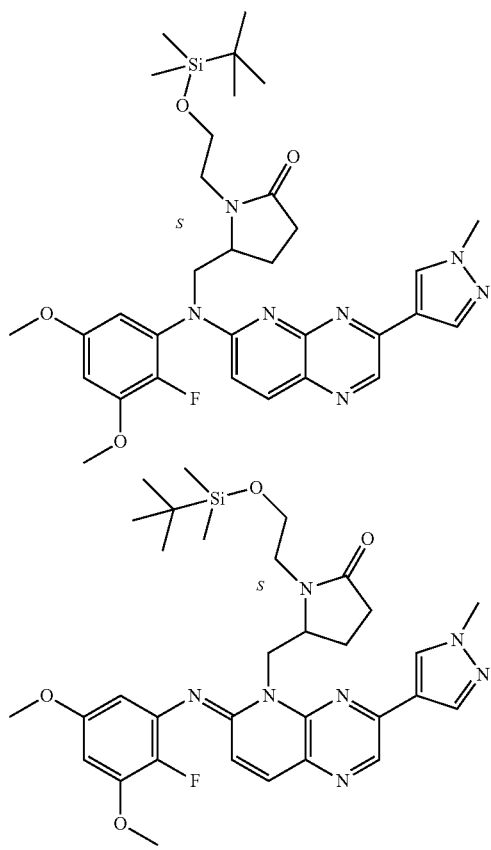

NaH (50.26 mg; 1.26 mmol) was added portionwise to a solution of a 93/7 mixture of compound 46 and compound 45 (400 mg; 0.21 mmol) in DMF (8 mL) at 5° C. under $N_2$ flow. The reaction mixture was stirred at 5° C. for 30 minutes then, (2-bromoethoxy)-tert-butyldimethylsilane (198 µl; 0.92 mmol) was added dropwise and the reaction mixture was stirred at room temperature overnight. The reaction mixture was quenched with iced water and extracted with EtOAc. The organic layer was separated, dried over $MgSO_4$, filtered and evaporated to dryness yielding 415 mg (78%) of a mixture of intermediates 92 and 93 which was used without further purification in the next step. In this mixture, also amounts of compound 218 and 219 were present.

Analogous Preparation of Intermediate 111 (Mixture) Starting from Compound 53

Intermediate 111

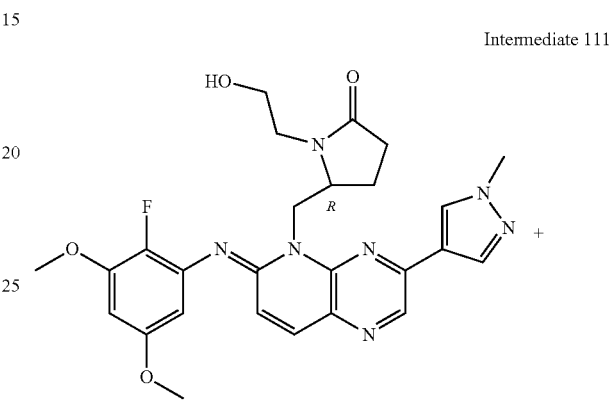

+

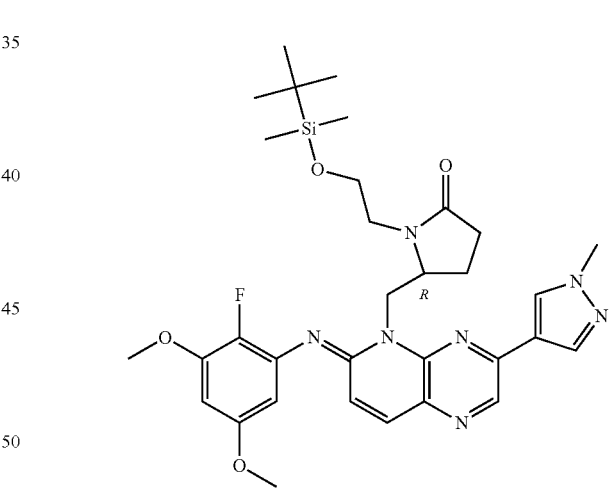

Example A32 a) Preparation of Intermediates 98 and 99 intermediate 98

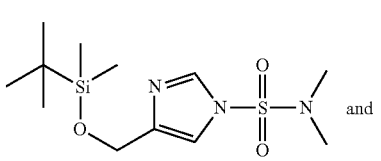

and intermediate 99

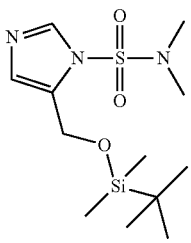

Et₃N (3.75 mL; 26.2 mmol) and dimethylsulfamoyl chloride (CAS 13360-57-1) (2.26 mL; 21 mmol) were added to a solution of 5-[[[(1,1-dimethylethyl)dimethylsilyl]oxy]methyl]-1H-imidazole (CAS 127056-45-5) (3.71 g; 17.5 mmol) in ACN (38 mL). The reaction mixture was stirred at 50° C. overnight. The reaction mixture was cooled to room temperature, poured into water and extracted with EtOAc. The organic layer was washed with water, dried over MgSO₄, filtered and the solvent was evaporated. The residue was eptanes by chromatography over silica gel (irregular SiOH, 15-40 μm, mobile phase: gradient from 100% DCM, 0% MeOH to 99% DCM, 1% MeOH). The product fractions were mixed and the solvent was evaporated yielding 2.52 g (45%) of intermediate 98 and 1.11 g (20%) of intermediate 99.

b) Preparation of Intermediate 100

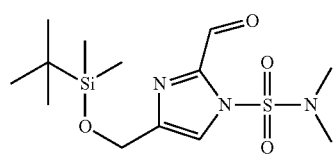 [SMILES: CN(C)S(=O)(=O)n1cc(CO[Si](C)(C)C(C)(C)C)nc1C=O]

nBuLi 1.6M in hexane (5.85 mL; 9.35 mmol) was added dropwise to a solution of intermediate 98 (2.49 g; 7.79 mmol) in THF (52 mL) at −78° C. under N₂ flow. The reaction mixture was stirred for 30 minutes at −78° C. and DMF (3.8 mL; 49.1 mmol) was added. The mixture was stirred for 1 hour at −78° C. allowing the temperature to warm at room temperature. The reaction mixture was neutralized with a 10% aqueous solution of NH₄Cl, then water and EtOAc were added. The organic layer was decanted, dried over MgSO₄, filtered and the solvent was evaporated. The residue was purified by chromatography over silica gel (irregular SiOH, 15-40 μm, 120 g; mobile phase: gradient from 100% DCM, 0% MeOH to 98% DCM, 2% MeOH). The product fractions were mixed and the solvent was evaporated yielding: 1.1 g (41%) of intermediate 100.

c) Preparation of Intermediate 101

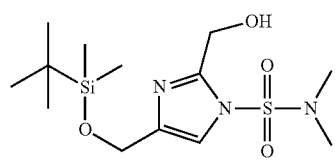 [SMILES: CN(C)S(=O)(=O)n1cc(CO[Si](C)(C)C(C)(C)C)nc1CO]

Sodium borohydride (122 mg; 3.22 mmol) was added to a solution of intermediate 100 (1.12 g; 3.22 mmol) in MeOH (32 mL) at 0° C. and the reaction mixture was stirred for 1 hour. The reaction mixture was poured into ice and extracted with EtOAc. The organic layer was washed with brine, dried over MgSO₄, filtered and the solvent was evaporated. The residue was taken up by DIPE and heptanes, filtered and dried yielding 0.9 g (80%) of intermediate 101.

d) Preparation of Intermediate 102

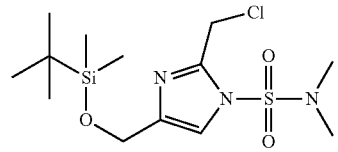

iEt₃N (0.369 mL; 2.58 mmol), methanesulfonyl chloride (0.12 mL; 1.55 mmol) and LiCl (0.164 g; 3.86 mmol) were successively added to a solution of intermediate 101 (0.45 g; 1.29 mmol) in THF (10 mL) at 5° C. under N₂ flow and the reaction mixture was stirred at room temperature overnight. The reaction mixture was poured into water and extracted with EtOAc. The organic layer was washed with brine, dried over MgSO₄, filtered and evaporated to dryness yielding 0.47 g (100%) of intermediate 102 which was used without further purification for the next step.

Example A33

Preparation of Intermediates 103, 104 and 105 intermediate 104

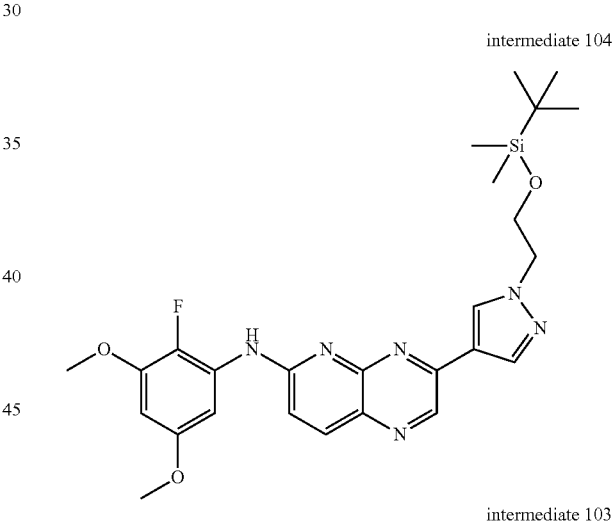

intermediate 103 and

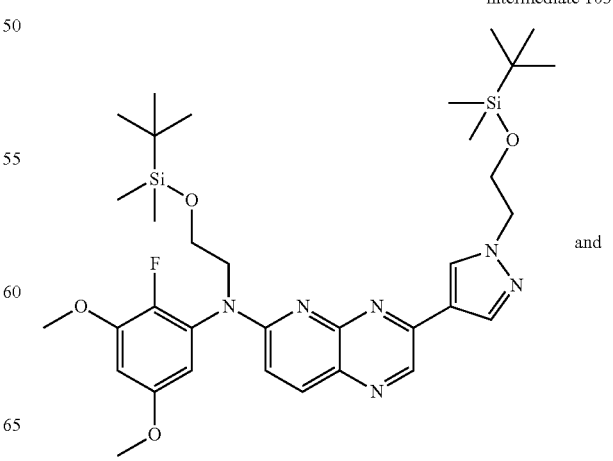

-continued intermediate 105

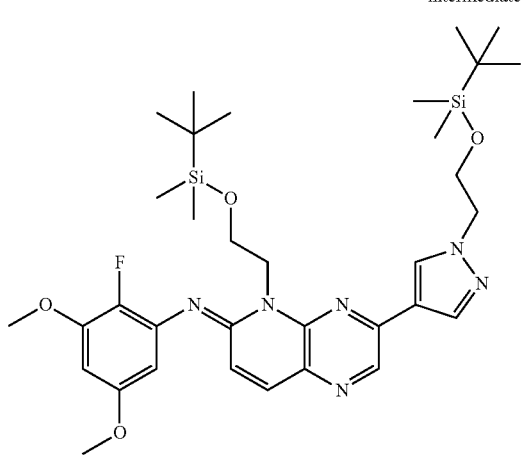

Cs₂CO₃ (533.61 mg; 1.64 mmol), then (2-bromoethoxy)-tert-butyldimethylsilane (211 μL; 0.98 mmol) were added to a solution of intermediate 26 (300 mg; 0.82 mmol) in ACN (6 mL) and the reaction mixture was heated at 100° C. for 6 hours. The reaction mixture was poured into ice water and extracted with EtOAc. The organic layer was washed with brine, dried over MgSO₄, filtered and evaporated to dryness. The crude product was purified by chromatography over silica gel (irregular SiOH, 15-45 μm, 24 g; mobile phase: gradient from 99% DCM, 1% MeOH to 96% DCM, 4% MeOH). The product fractions were collected and evaporated to dryness yielding 10 mg (2%) of intermediate 105, 70 mg (13%) of intermediate 103 and 124 mg (29%) of intermediate 104.

Example A34 a) Preparation of Intermediate 109

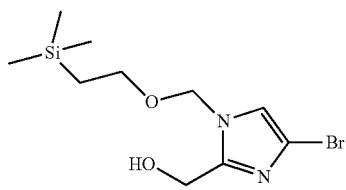 [SMILES: C[Si](C)(C)CCOCn1cc(Br)nc1CO]

Sodium borohydryde (3.2 g; 85.89 mmol) was added portionwise to a solution of 1H-Imidazole-2-carboxylic acid-4-bromo-1-[[2-(trimethylsilyl)ethoxy]methyl]ethyl ester (CAS 954125-17-8) (25 g; 71.57 mmol) in ethanol (500 mL) at 5° C. The reaction was stirred at room temperature overnight, poured into ice water and extracted with DCM. The organic layer was dried over MgSO₄, filtered and evaporated to dryness to give 18.65 g (85%) of intermediate 109.

b) Preparation of Intermediate 108

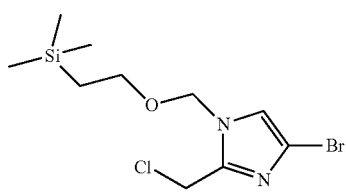 [SMILES: C[Si](C)(C)CCOCn1cc(Br)nc1CCl]

Et₃N (466 μL; 3.255 mmol), methanesulfonylchloride (151 μL; 1.953 mmol) and LiCl (207 mg; 4.882 mmol) were added successively to a solution of intermediate 109 (500 mg; 1.627 mmol) in THF (10 mL) at 5° C. under N₂ flow and the reaction mixture was stirred at room temperature for 2 hours. The reaction mixture was poured into ice water and extracted with EtOAc. The organic layer was washed with brine, dried over MgSO₄, filtered and evaporated to dryness yielding 539 mg (100%) of intermediate 108 which was used in the next step without any further purification.

Example A35

Preparation of Intermediate 110

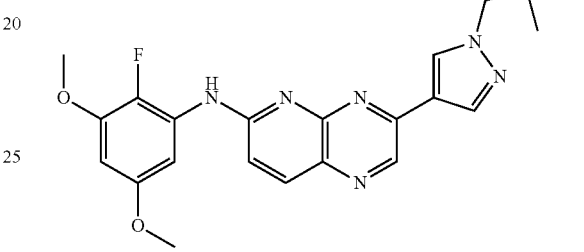

Isobutylene oxide (155 μL; 1.73 mmol) was added to a solution of intermediate 26 (700 mg; 1.58 mmol) and Cs₂CO₃ (1.03 g; 3.15 mmol) in ACN (10.5 mL). The reaction mixture was stirred at 100° C. overnight. The reaction mixture was poured into ice water and extracted with EtOAc. The organic layer was washed with brine, dried over MgSO₄, filtered and evaporated. The crude product was purified by chromatography over silica gel (irregular SiOH, 15-45 μm, 24 g; mobile phase: gradient from 99% DCM, 1% MeOH to 96% DCM, 4% MeOH). The product fractions were collected and evaporated to dryness yielding 192 mg (28%) of intermediate 110.

Example A36 a) Preparation of Intermediate 118 (Cis)

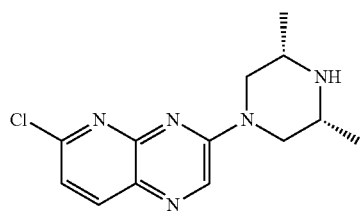 [SMILES: C[C@@H]1CN(c2cnc3ccc(Cl)nc3n2)C[C@H](C)N1]

A solution of 3,6-dichloropyrido[2,3-b]pyrazine (1 g; 5 mmol), 2,6-dimethylpiperazine (0.81 mL; 7 mmol), triethylamine (1.39 mL; 10 mmol) in DCM (86 mL) was stirred at 0° C. for 4 hours then at room temperature for 2 hours. Then, water was added. The organic layer was separated, washed with brine, dried over MgSO₄ and filtered. The filtrate was concentrated under reduced pressure to afford 1.38 g of intermediate 118 (85%) which was used without further purification in the next step.

b) Preparation of Intermediate 119 (Cis)

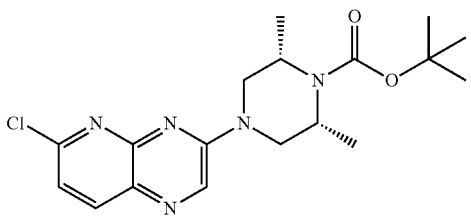 [SMILES: C[C@@H]1CN(c2cnc3ccc(Cl)nc3n2)C[C@H](C)N1C(=O)OC(C)(C)C]

Di-tert-butyl dicarbonate (1.3 g; 5.96 mmol) was added portion wise to a solution of intermediate 118 (1.38 g; 4.97 mmol) and N,N-diisopropylethylamine (2 mL; 11.43 mmol) in dioxane (35 mL) at room temperature. The mixture was heated at 80° C. for 3 hours, then the solution was cooled down to room temperature and poured into iced water, extracted with EtOAc, dried over MgSO$_4$, filtered and evaporated to dryness. The residue (2.41 g) was purified by chromatography over silica gel (irregular 15-40 μm, 40 g, mobile phase: 98% DCM, 2% MeOH). The product fractions were mixed and concentrated under reduced pressure to afford 700 mg (37%) of intermediate 119.

Example A37 a) Preparation of Intermediate 120

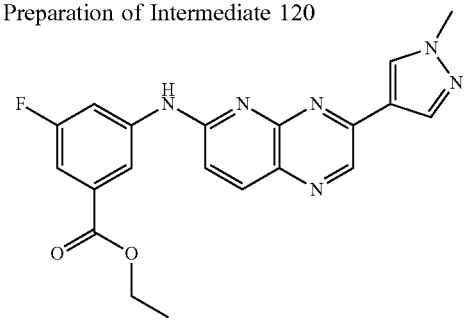

A mixture of intermediate 5 (1.54 g; 6.28 mmol) and 5-amino-3-fluorobenzoic acid ethyl ester (CAS 850807-08-8) (2.3 g; 12.56 mmol) in n-propanol (30 mL) was heated at 100° C. for 1 h. The reaction mixture was cooled down to room temperature, poured into water and extracted with EtOAc. The organic layer was washed with brine, dried over MgSO$_4$, filtered and evaporated to dryness. The residue was crystallized from ACN; the precipitate was filtered, washed with Et$_2$O and dried under vacuum to give 285 mg (12%) of intermediate 120. M.P.: 250-260° C. (Kofler).

b) Preparation of Intermediate 121

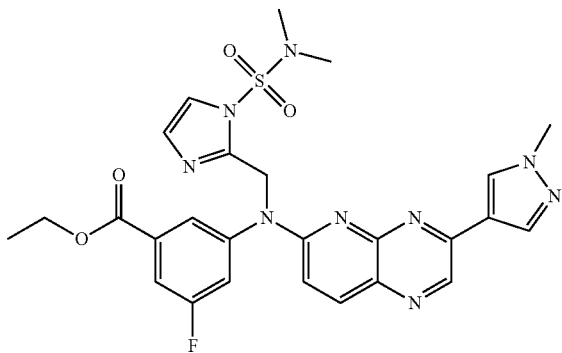 [SMILES: CCOC(=O)c1cc(F)cc(N(Cc2nccn2S(=O)(=O)N(C)C)c2ccc3ncc(-c4cnn(C)c4)nc3n2)c1]

NaH (61 mg; 1.529 mmol) was added at 5° C. under N$_2$ flow to a solution of intermediate 120 (300 mg; 0.765 mmol) in DMF (10 mL). The reaction mixture was stirred at 5° C. for minutes. 2-(chloromethyl)-N,N-dimethyl-1H-imidazole-1-sulfonamide (CAS 935862-81-0) (0.31 g; 1.376 mmol) was added and the mixture was stirred at room temperature for 48 hours. The reaction mixture was poured into cooled water, acidified with a 6N aqueous solution of HCl and extracted with EtOAc. The organic layer was dried over MgSO$_4$, filtered and evaporated to dryness. The residue (500 mg) was purified by chromatography over silica gel (irregular SiOH, 15-40 μm, 24 g; mobile phase: 0.1% NH$_4$OH, 3% MeOH, 97% DCM). The product fractions were collected and evaporated to dryness to give 250 mg (56%) intermediate 121.

c) Preparation of Intermediate 122

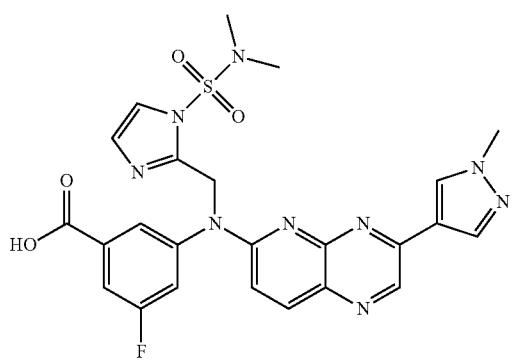 [SMILES: CN(C)S(=O)(=O)n1ccnc1CN(c1cc(F)cc(C(=O)O)c1)c1ccc2ncc(-c3cnn(C)c3)nc2n1]

A mixture of intermediate 121 (200 mg; 0.35 mmol), lithium hydroxide monohydrate (25 mg; 1.04 mmol) in THF (8 mL) and water (2 mL) was stirred at room temperature overnight. The reaction mixture was acidified with a 3N aqueous solution of HCl. The precipitate was filtered, washed with water, then Et$_2$O and dried under vacuum to give 200 mg (quantitative) of intermediate 122.

Example A38 a) Preparation of Intermediate 124

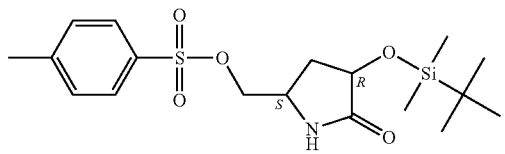

Triethylamine (1.4 mL; 9.78 mmol), p-toluenesulfonyl chloride (1.86 g; 9.78 mmol) and 4-dimethylaminopyridine (99 mg; 0.815 mmol) were added successively to a solution of 3-[[(1,1-dimethylethyl)dimethylsilyl]oxy]-5-(hydroxymethyl)-, (3R,5S)-2-pyrrolidinone (CAS 1311406-99-1) (2 g; 8.15 mmol) in DCM (20 mL) at 5° C. under N$_2$ flow and, the reaction mixture was stirred at room temperature for 18 hours. The reaction mixture was diluted with DCM and washed with a 10% aqueous solution of K$_2$CO$_3$. The organic layer was decanted, dried over MgSO$_4$, filtered and evaporated to dryness. The residue (400 mg) was purified by chromatography over silica gel (irregular SiOH, 15-40 μm, 24 g; mobile phase: gradient from 100% DCM, 0% MeOH to 97% DCM, 3% MeOH). The product fractions were collected and evaporated to dryness yielding 2.48 g of intermediate 124 (76%).

b) Preparation of Intermediates 125 and 126

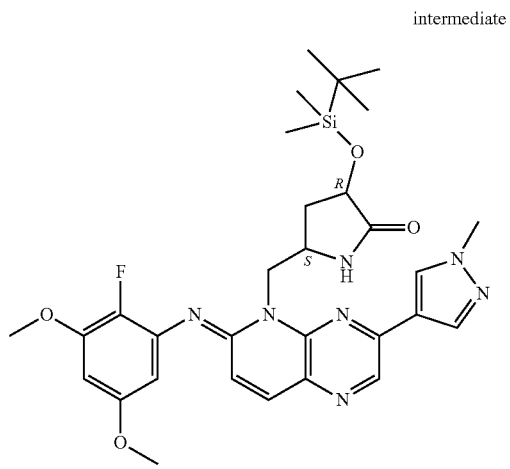

intermediate 125 intermediate 126

NaH (105 mg; 2.629 mmol) was added to a solution of intermediate 7 (500 mg; 1.314 mmol) in DMF (15 mL) at 5° C. under $N_2$ flow. The reaction was stirred at 5° C. for 15 minutes. A solution of intermediate 124 (1 g; 2.629 mmol) in DMF (5 mL) was added over a 2 hours period and the reaction mixture was allowed to warm to room temperature and stirred overnight. The reaction mixture was poured onto iced water and extracted with EtOAc. The organic layer was decanted, washed with brine (twice), dried over $MgSO_4$, filtered and evaporated to dryness. The residue (1.4 g) was purified by chromatography over silica gel (irregular SiOH, 15-40 µm, 300 g; mobile phase: 0.1% $NH_4OH$, 5% iPrOH, 95% DCM). The product fractions were collected and evaporated to dryness yielding 300 mg (37%) of intermediate 125 and 540 mg (56%) of intermediate 126.

Analogous Preparation of Intermediates 127 and 128

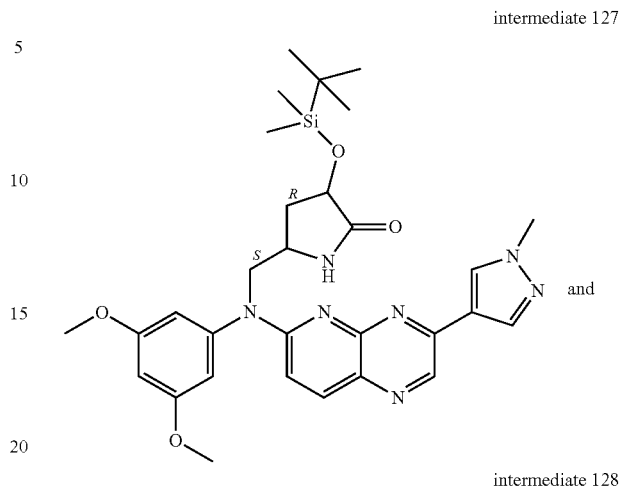

intermediate 127 and intermediate 128

Starting from Intermediate 6 and Intermediate 124

Example A39 a) Preparation of Intermediate 130

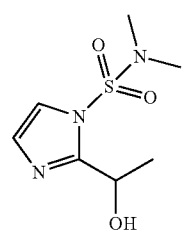

Methylmagnesium bromide (36.91 mL; 36.91 mmol) was added dropwise at 5° C. under $N_2$ flow to a solution of 2-formyl-N,N-dimethyl-1H-imidazole-1-sulfonamide (CAS 167704-98-5) (5 g; 24.60 mmol) in $Et_2O$ (250 mL). The reaction was allowed to raise room temperature and stirred overnight. The reaction mixture was portioned between water and EtOAc. The organic layer was dried over $MgSO_4$, filtered and evaporated to dryness to give 5.09 g (66%) of intermediate 130 (70% of purity based on 1H NMR).

b) Preparation of Intermediate 131

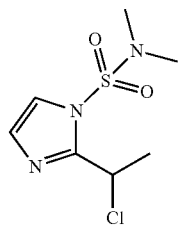

Et₃N (6.65 mL; 46.43 mmol), methanesulfonyl chloride (2.16 mL; 27.86 mmol) and lithium chloride (2.95 g; 69.64 mmol) were added successively at 5° C. under N₂ flow to a solution of intermediate 130 (5.09 g; 23.21 mmol) in THF (127 mL) and the reaction mixture was stirred at room temperature for 4 hours. The reaction mixture was poured into ice water and extracted with EtOAc. The organic layer was washed with brine, dried over MgSO₄, filtered and evaporated to dryness. The residue was purified by chromatography over silica gel (irregular SiOH, 15-45 μm, 80 g; mobile phase: 100% DCM). The product fractions were collected and evaporated to dryness to give 3.26 g (84%) of intermediate 131.

Example A40

Preparation of Intermediate 132°

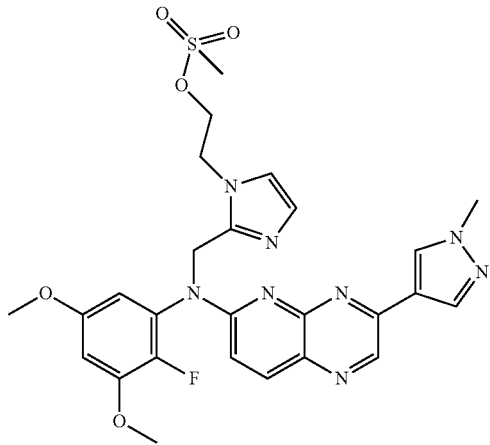 [SMILES: COc1cc(OC)c(F)c(N(Cc2nccn2CCOS(C)(=O)=O)c2ccc3ncc(-c4cnn(C)c4)nc3n2)c1]

Methanesulfonyl chloride (0.13 mL; 1.64 mmol) was added dropwise at 5° C. under N₂ flow to a solution of compound 145 (0.275 g; 0.55 mmol) and triethylamine (0.31 mL; 2.18 mmol) in DCM (5 mL). The reaction mixture was stirred at 5° C. for 2 hours, poured out into iced water and extracted with DCM. The organic layer was separated, dried over MgSO₄, filtered and the solvent was evaporated to dryness at room temperature to give 376 mg of intermediate 132 which was used without purification for the next step.

Example A41 a) Preparation of Intermediate 135

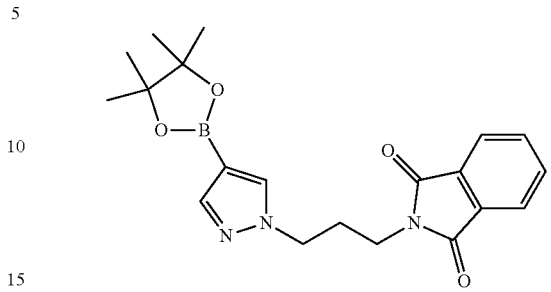

NaH (1.55 g; 38.65 mmol) was added dropwise to at 5° C. under N₂ flow a solution of 4,4,5,5-tetramethyl-2-(1H-pyrazol-4-yl)-1,3,2-dioxaborolane (5 g; 25.77 mmol) in DMF (40 mL). The reaction was stirred at 5° C. for 1 hour, then a solution of N-(3-bromopropyl)-phthalimide (11 g; 41.23 mmol) in DMF (10 mL) was added dropwise. The reaction mixture was stirred at room temperature for 4 hours, poured into iced water and extracted with EtOAc (two times). The organic layer was washed with brine, dried over MgSO₄, filtered and the solvent was evaporated. The residue (11.8 g) was purified by chromatography over silica gel (irregular SiOH, 20-45 μm, 450 g; mobile phase: 62% heptane, 3% MeOH, 35% AcOEt). The product fractions were collected and evaporated to dryness to give 2.8 g (29%) of intermediate 135.

b) Preparation of Intermediate 136

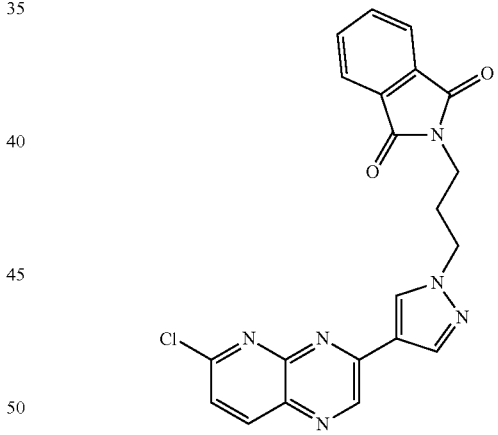

A solution of intermediate 5a (1.6 g; 6.48 mmol), intermediate 135 (2.6 g; 6.48 mmol) in a 2M aqueous solution of sodium carbonate (16 mL; 32.4 mmol) and 1,2-dimethoxyethane (65 mL) was degassed with N₂ for 15 minutes. Then, PdCl₂(dppf).DCM (0.474 g; 0.65 mmol) was added. The reaction mixture was refluxed for 1h30, cooled to room temperature, poured out into water, filtered over a pad of Celite® and extracted with EtOAc. The organic layer was dried over MgSO₄, filtered, and the solvent was evaporated until dryness. The residue (2.6 g) was purified by chromatography over silica gel (irregular SiOH, 20-45 μm, 450 g; mobile phase: gradient from 0.1% NH₄OH, 1% MeOH, 99% DCM to 0.1% NH₄OH, 98% DCM, 2% MeOH). The product fractions were collected and evaporated to dryness to give 1 g (37%) of intermediate 136.

c) Preparation of Intermediate 137

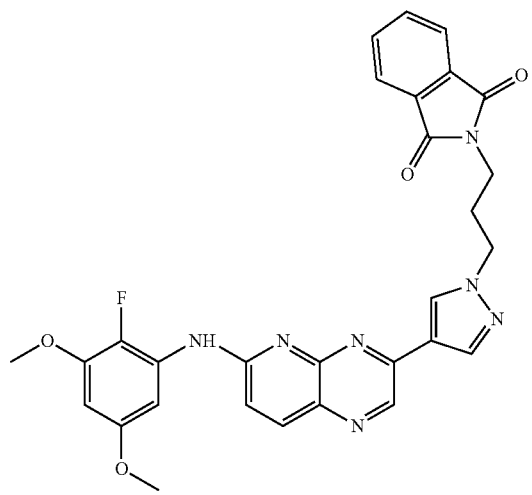 [SMILES: COc1cc(Nc2ccc3ncc(-c4cnn(CCCN5C(=O)c6ccccc6C5=O)c4)nc3n2)c(F)c(OC)c1]

A solution of HCl 4M in 1,4-dioxane (0.06 mL; 0.24 mmol) was added to a solution of intermediate 136 (1 g; 2.39 mmol) in n-propanol (15 mL). 2-fluoro-3,5-dimethoxyaniline (0.82 g; 4.78 mmol) was added and the reaction mixture was heated at 100° C. for 18 hours. The reaction mixture was poured into iced water, basified with an aqueous solution of NH$_4$OH and extracted with DCM. The organic layer was dried over MgSO$_4$, filtered and evaporated till dryness. The residue (1.84 g) was dissolved in DCM. The precipitate was filtered and dried to give 0.81 g (61%) of intermediate 137. The filtrate was concentrated and the resulting residue was purified by chromatography over silica gel (irregular SiOH, 15-40 µm, 40 g; mobile phase: 0.1% NH$_4$OH, 2% MeOH, 98% DCM). The product fractions were collected and evaporated to dryness to give additional 0.479 g (36%) of intermediate 137.

d) Preparation of Intermediate 138

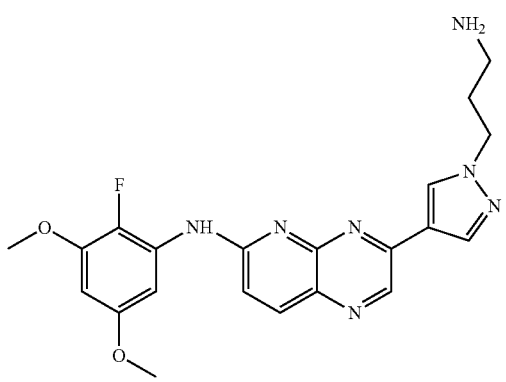 [SMILES: COc1cc(Nc2ccc3ncc(-c4cnn(CCCN)c4)nc3n2)c(F)c(OC)c1]

Intermediate 137 (1.2 g, 2.17 mmol) and hydrazine monohydrate (1 mL, 21.7 mmol) in EtOH (8 mL) were heated at 80° C. for 2 hours. The reaction mixture was cooled down, poured into cooled water and extracted with DCM. The organic layer was dried over MgSO$_4$, filtered and evaporated to dryness to give 1 g of intermediate 138 which was used without further purification in the next step.

Example A42 a) Preparation of Intermediate 141

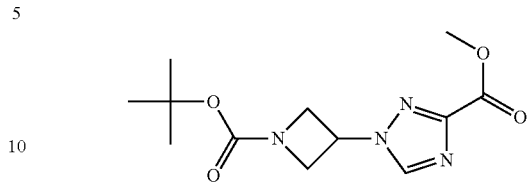

NaH (1.88 g; 47.2 mmol) was added to a solution of 1H-[1,2,4]triazole-3-carboxylic acid methyl ester (5 g; 39.3 mmol) in DMF (60 mL). The reaction mixture was stirred at 25° C. for 20 minutes followed by 1 hour at 70° C. 1-(Tert-butoxycarbonyl)-3-(methanesulfonyloxy)azetidine (CAS: 141699-58-3) was added and the reaction mixture was heated at 70° C. for 48 hours. The solution was cooled to 0° C. and the insoluble material was removed by filtration. The filtrate was diluted with DCM and washed with water, brine, dried over Na$_2$SO$_4$, filtered and evaporated to dryness. The residue was purified by chromatography over silica gel (mobile phase: petroleum ether/ethyl acetate 1/5) to give 2 g (18%) of intermediate 141.

b) Preparation of Intermediate 142

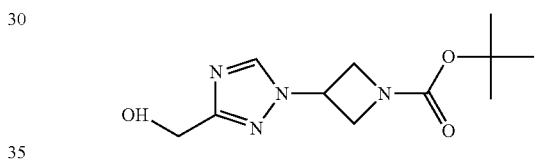

Sodium borohydride (1.07 g; 28.3 mmol) was added at 0° C. to a solution of intermediate 141 (2 g; 7.09 mmol) in MeOH (50 mL). The reaction mixture was stirred at 25° C. for 1 hour, then refluxed for 40 hours. The reaction was cooled to 0° C. and water (50 ml) was slowly added. The solution was extracted with DCM. The organic layer were dried over Na$_2$SO$_4$, filtered and evaporated to dryness. The residue was purified by chromatography over silica gel (mobile phase: DCM/MeOH 30/1) to give 0.781 g (43%) of intermediate 142 c) Preparation of Intermediate 143

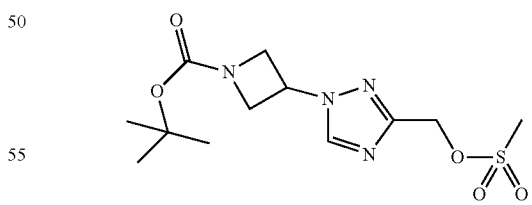

Methanesulfonyl chloride (0.27 mL; 3.461 mmol) was added dropwise at 5° C. under N$_2$ flow to a solution of intermediate 142 (440 mg; 1.73 mmol) and triethylamine (0.72 ml; 5.191 mmol) in DCM (15 mL). The reaction mixture was stirred at room temperature overnight, poured into ice and extracted with DCM. The organic layer was decanted, dried over MgSO$_4$, filtered and evaporated to dryness yielding 500 mg (87%) of intermediate 143 which was used without further purification in the next step.

d) Preparation of Intermediate 144

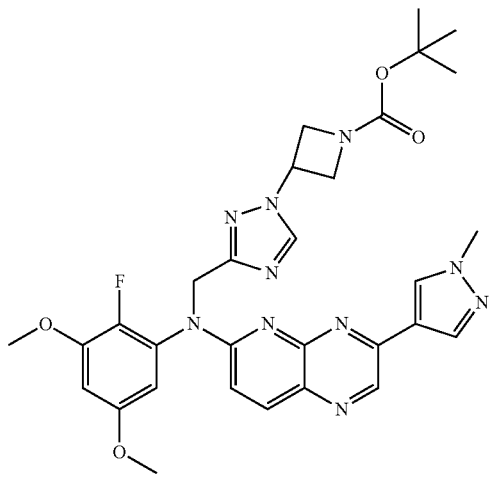 [SMILES: COc1cc(OC)c(F)c(N(Cc2ncn(C3CN(C(=O)OC(C)(C)C)C3)n2)c2ccc3ncc(-c4cnn(C)c4)nc3n2)c1]

NaH (168 mg; 4.2 mmol) was added to a solution of intermediate 7 (798 mg; 2.1 mmol) in DMF (21 mL) at 5° C. under $N_2$ flow. The reaction mixture was stirred at 5° C. for 30 minutes. A solution of intermediate 143 (1.21 g; 3.66 mmol) in DMF (7 mL) was added at 5° C. under $N_2$ flow over a 2 hours period and the reaction mixture was allowed to warm to room temperature and stirred overnight. The reaction mixture was poured onto iced water and extracted with EtOAc. The organic layer was decanted, washed with brine (twice), dried over $MgSO_4$, filtered and evaporated to dryness. The residue was purified by chromatography over silica gel (irregular SiOH, 15-40 µm, 40 g; mobile phase: 0.5% $NH_4OH$, 5% MeOH, 95% DCM). The product fractions were collected and evaporated to dryness yielding 560 mg (60%) of intermediate 144.

Example A43

Preparation of Intermediate 146

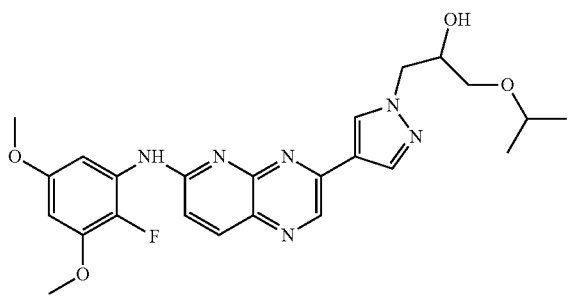 [SMILES: COc1cc(Nc2ccc3ncc(-c4cnn(CC(O)COC(C)C)c4)nc3n2)c(F)c(OC)c1]

Glycidyl isopropyl ether (207 µL; 0.1.64 mmol) was added to a solution of intermediate 26 (500 mg; 1.37 mmol) and cesium carbonate (889.36 mg; 2.73 mmol) in ACN (7.5 mL) and the reaction mixture was stirred at 80° C. overnight. The reaction mixture was poured into an aqueous solution of 10% $K_2CO_3$ and extracted with EtOAc. The organic layer was washed with brine, dried over $MgSO_4$ and evaporated to dryness. The crude product was purified by chromatography over silica gel (irregular SiOH 15-45 µm, 24 g Grace; mobile phase: gradient from 98% DCM, 2% MeOH, 0.2% $NH_4OH$ to 97% DCM, 3% MeOH, 0.3% $NH_4OH$). The product fractions were collected and evaporated to dryness. The residue (200 mg) was crystallized from ACN. The precipitate was filtered, washed with ACN then $Et_2O$ and dried to afford 44 mg of intermediate 146 (7%). M.P.: 150° C. (kofler). The mother liquor was evaporated to give additional 156 mg (24%) of intermediate 146.

B. Preparation of the Compounds

Example B1

Preparation of Compound 1

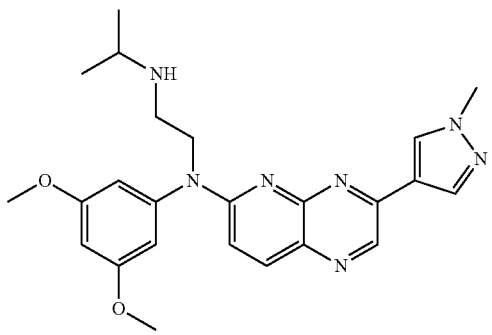 [SMILES: COc1cc(OC)cc(N(CCNC(C)C)c2ccc3ncc(-c4cnn(C)c4)nc3n2)c1]

To a solution of intermediate 6 (498 mg; 1.37 mmol) in 2-methyltetrahydrofuran (15 ml) and water (1 ml) were added at room temperature, 1-butanaminium, N,N,N-tributyl-bromide (1:1) (111 mg; 0.34 mmol) and KOH (1.36 g; 20.6 mmol). The reaction mixture was stirred at 50° C. for 1 hour and N-(2-chloroethyl)-2-propanamine hydrochloride (304 mg; 1.9 mmol) was added. The reaction mixture was stirred at 50° C. for 22 hours. The reaction mixture was cooled down to room temperature, poured out onto water and extracted with EtOAc. The organic layer was washed with brine, dried ($MgSO_4$), filtered and concentrated under reduced pressure. The obtained residue was purified by chromatography over silica gel (5 µm, mobile phase, gradient from 0.2% $NH_4OH$, 98% DCM, 2% MeOH to 1.1% $NH_4OH$, 88% DCM, 11% MeOH). The desired product fraction were collected and evaporated till dryness. The residue was taken up in $Et_2O$ to afford 128 mg (21%) of compound 1.

Analogous Preparation of Compound 2

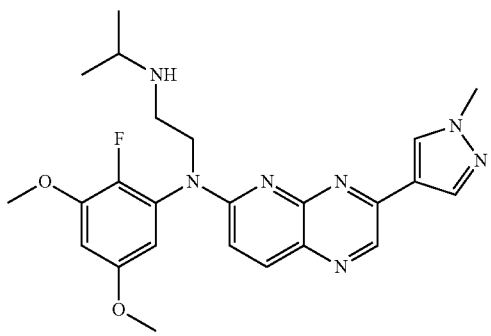 [SMILES: COc1cc(OC)c(F)c(N(CCNC(C)C)c2ccc3ncc(-c4cnn(C)c4)nc3n2)c1]

Example B2

Perpetration of Compound 3

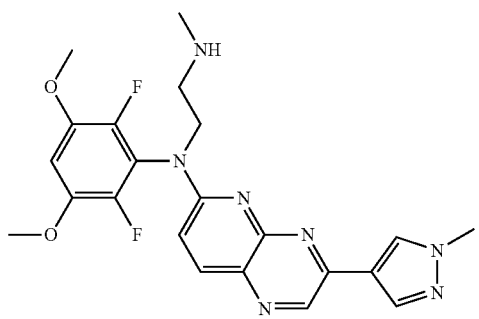

And Compound 4

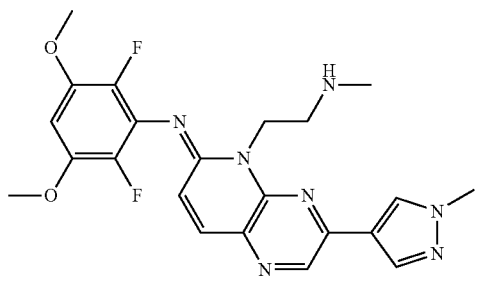

To a solution of intermediate 12 (716 mg; 1.8 mmol) in tetrahydro-2-methylfuran (15 ml) and water (1 ml) were added at room temperature, 1-butanaminium, N,N,N-tributyl-, bromide (290 mg; 2.7 mmol) and KOH (1.8 g; 27 mmol). The reaction mixture was stirred at 50° C. for 1 hour and N-(2-chloroethyl)-methylamine hydrochloride (252 mg; 2.7 mmol) was added. The reaction mixture was stirred for 20 hours at 50° C. The reaction mixture was cooled down to room temperature, poured out onto water and extracted with EtOAc. The organic layer was washed with brine, dried (MgSO$_4$), filtered and concentrated under reduced pressure. The residue was purified by chromatography over silica gel (15-40 μm 300 g; mobile phase, gradient from 0.5% NH$_4$OH, 95% DCM, 5% MeOH to 0.5% NH$_4$OH, 90% DCM, 10% MeOH). The desired product fractions were collected, concentrated and residue (1.3 g) was purified by achiral SFC on (mobile phase 0.3% isopropylamine, 82% CO$_2$, 18% MeOH). The two desired product fractions were collected, evaporated till dryness to provide Fraction 1 (83 mg, 10%) and Fraction 2 (226 mg, 26%).

Fraction 1 (was taken up in Et$_2$O to afford 42 mg of compound 4 (MP: 174° C. (DSC)). Fraction 2 was taken up in Et$_2$O to afford 154 mg of compound 3 (MP: 134° C. (DSC)) C$_{22}$H$_{23}$F$_2$N$_7$O$_2$.0.97H$_2$O.0.027Et$_2$O.

Alternatively, compound 3 and 4 were also prepared as follows:

A solution of KOH (12.4 g; 188 mmol) in 2-methyltetrahydrofuran (200 mL) was stirred for 10 minutes at room temperature. Water (20 mL), intermediate 12 (5 g; 12.6 mmol) followed by tetrabutylammonium bromide (1.62 g; 5 mmol) were added at room temperature. The reaction mixture was stirred at 50° C. for 1 hour and (2-chloroethyl)-methylamine hydrochloride (3.3 g; 25 mmol) was added.

The reaction mixture was stirred for 24 hours at 50° C. The reaction mixture was cooled down to room temperature, poured into water and extracted with EtOAc. The organic layer was washed with brine, dried over MgSO$_4$, filtered and concentrated under reduced pressure.

The residue (5.6 g) was purified by chromatography over silica gel (Irregular SiOH, 20-45 μm, 450 g; mobile phase: gradient from 0.1% NH$_4$OH, 90% DCM, 10% MeOH to 0.5% NH$_4$OH, 90% DCM, 10% MeOH). The product fractions were collected and the solvent was evaporated to dryness affording 0.6 g (10%) of compound 4 and 2 g of an intermediate residue which was crystallized from Et$_2$O to give 1.64 g (29%) of compound 3. M.P.: 159° C. (DSC). C$_{22}$H$_{23}$F$_2$N$_7$O$_2$.0.09 Et$_2$.0.02 DCM.

Analogous Preparation of Compounds 107 and 108 Starting from Intermediate 30 compound 107

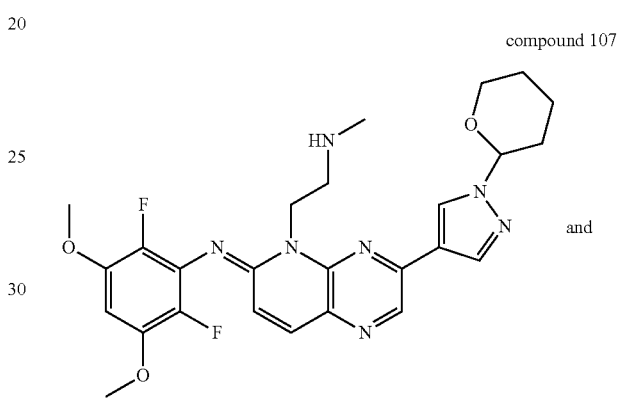

and compound 108

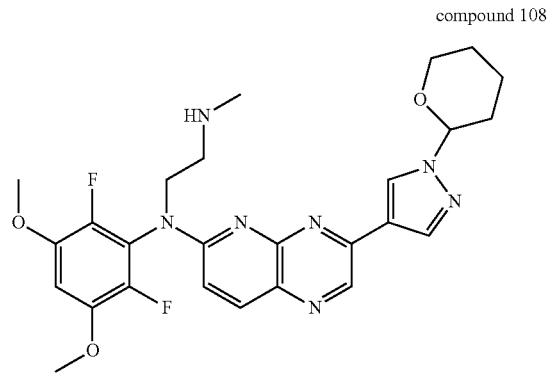

Analogous Preparation of Compound 236 and 237 Starting from Intermediate compound 236

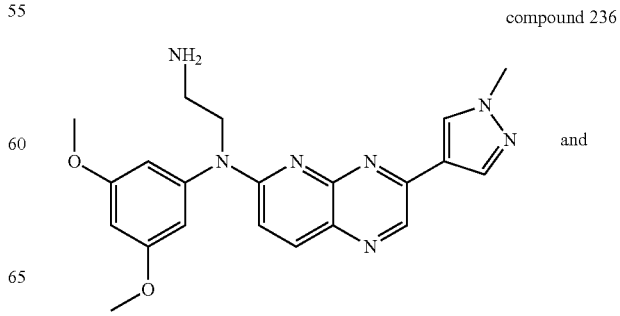

and

-continued compound 237

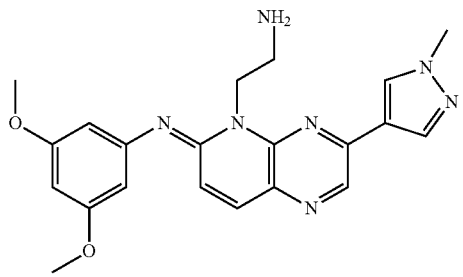

Example B2a

Preparation of Compound 44

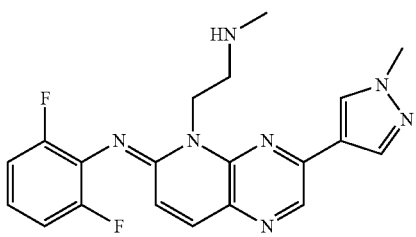 [SMILES: CNCCn1/c(=N/c2c(F)cccc2F)ccc2ncc(-c3cnn(C)c3)nc21]

Water (0.5 mL), intermediate 17 (0.17 g; 0.51 mmol) followed by tetrabutylammonium bromide (41 mg; 0.13 mmol) were added at room temperature to a mixture of potassium hydroxide (0.50 g; 7.63 mmol) in 2-methyltetrahydrofuran (5 mL). The reaction mixture was stirred for 10 minutes at room temperature, then stirred at 50° C. for 1 hour and (2-chloroethyl)-methylamine hydrochloride (CAS 4535-90-4) (0.119 g; 0.92 mmol) was added. The reaction mixture was stirred for 24 hours at 50° C. The reaction mixture was cooled down to room temperature, poured into water and extracted with EtOAc. The organic layer was washed with brine, dried over $MgSO_4$, filtered and evaporated to dryness. The residue was purified by chromatography over silica gel (Spherical SiOH, 10 μm, 60 g; mobile phase: gradient from 0.5% $NH_4OH$, 97% DCM, 3% MeOH to 0.5% $NH_4OH$, 95% DCM, 5% MeOH). The pure fractions were collected and evaporated to give 30 mg (15%) which was taken up $Et_2O$ and evaporated to give 29 mg (14%) of compound 44, M.P.: 80° C. (gum, Kofler).

Example B3

Preparation of Compound 5

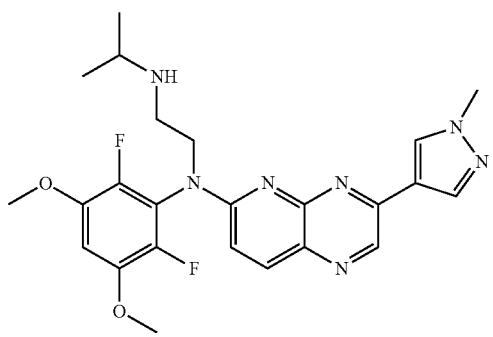

and Compound 6

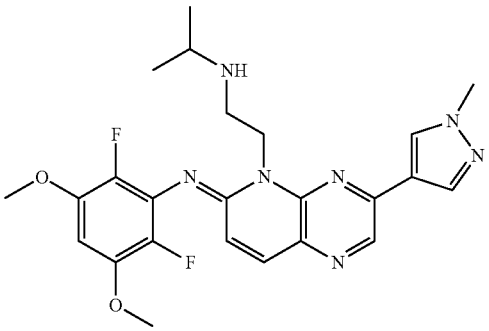 [SMILES: COc1cc(OC)c(F)c(/N=c2\ccc3ncc(-c4cnn(C)c4)nc3n2CCNC(C)C)c1F]

To a solution of intermediate 12 (400 mg; 1.0 mmol) in tetrahydro-2-methylfuran (10 ml) and water (0.66 ml) were added at room temperature, 1-butanaminium, N,N,N-tributyl-bromide (81 mg; 0.25 mmol) and KOH (994 mg; 15.1 mmol). The reaction mixture was stirred at 50° C. for 1 hour and N-(2-chloroethyl)-2-propanamine hydrochloride (222 mg; 1.4 mmol) was added. The reaction mixture was stirred for 22 hours at 50° C. The reaction mixture was cooled down to room temperature, poured out onto water and extracted with EtOAc. The organic layer was washed with brine, dried ($MgSO_4$), filtered and concentrated under reduced pressure. The residue was purified by chromatography over silica gel (15-40 μm 90 g; mobile phase, 0.5% $NH_4OH$, 95% DCM, 5% MeOH). The desired fractions were collected, concentrated and residue (165 mg) was purified by achiral SFC (20 μm 430 g, mobile phase 0.3% isopropylamine, 75% $CO_2$, 25% MeOH). The product fractions were collected and evaporated as Fraction 1 (120 mg) and Fraction 2, yielding 16 mg (3%) of compound 6. Fraction 1 was taken up in $Et_2O$ to afford 107 mg (22%) of compound 5 (MP: 183° C. (DSC)).

Analogous preparation according to procedure B2 or B3 of compounds 37 and 2 starting from intermediate 7

Compound 37

Compound 2

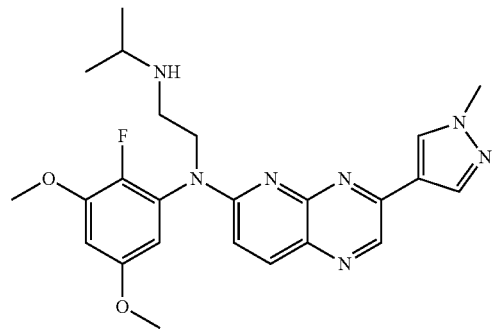

Analogous preparation according to procedure B2 or B3 of compounds 38 and 39 starting from intermediate 7 compound 38

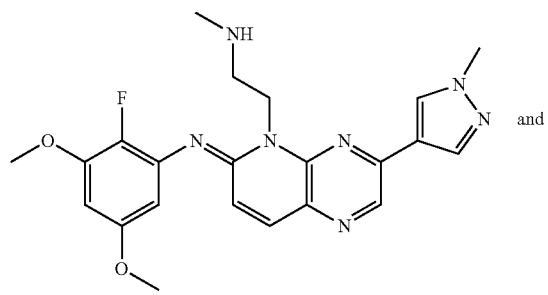

and compound 39

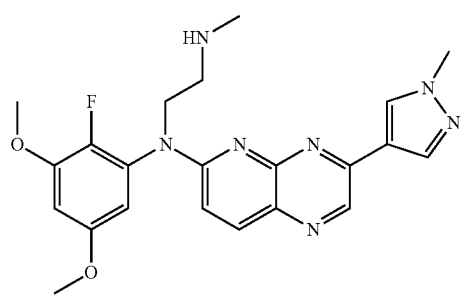

Analogous preparation according to procedure B2 or B3 of compounds 67 and 68 starting from intermediate 12

Compound 67

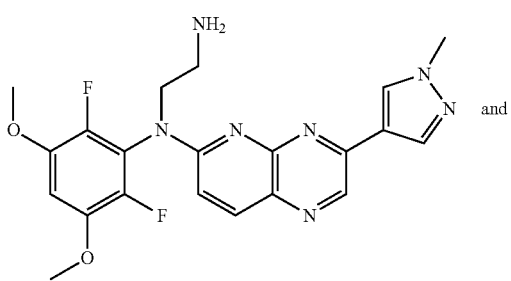

and compound 68

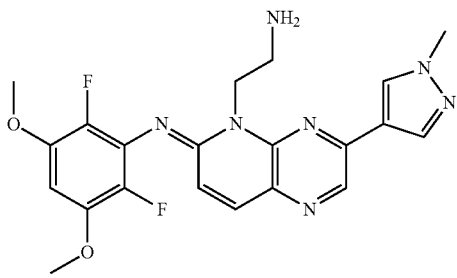

Analogous preparation according to procedure B2 or B3 of compounds 69 and 70 starting from intermediate 20

Compound 69

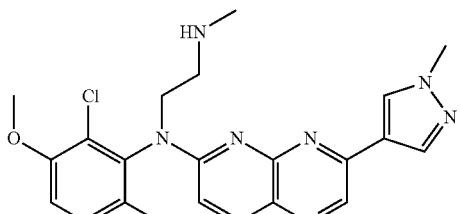

and compound 70

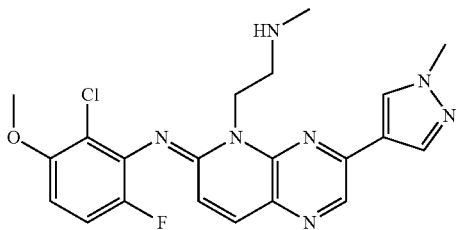

Analogous preparation according to procedure B2 or B3 of compounds 81 and 82 starting from intermediate 22

Compound 81

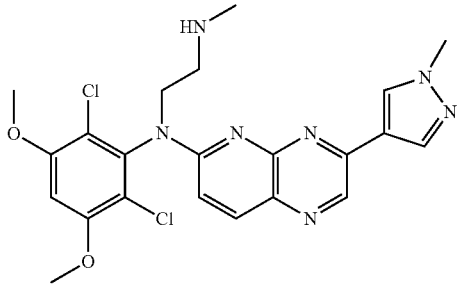

and compound 82

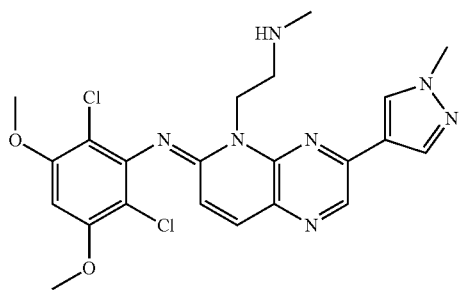

Analogous preparation according to procedure B2 or B3 of compounds 83 and 84 starting from intermediate 19

Compound 83

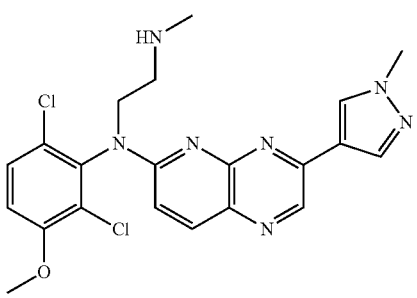

and compound 84

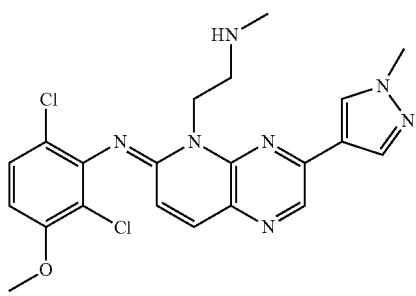

Analogous preparation according to procedure B2 or B3 of compounds 167 and 168 starting from intermediate 7 compound 167

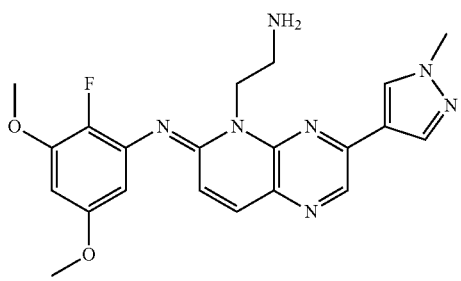

and compound 168

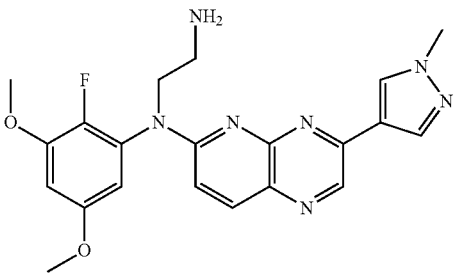

Example B4

Preparation of Compound 7

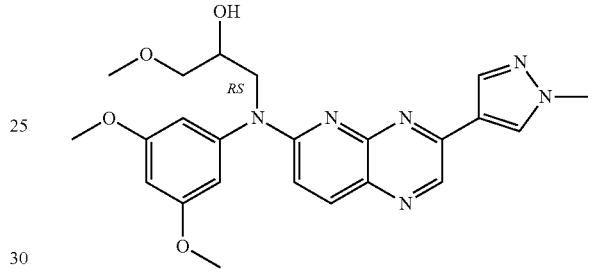

To a solution of intermediate 6 (352 mg; 0.97 mmol) in DMF (10 ml), was added under $N_2$ at 5° C., NaH (39 mg; 0.97 mmol, 60% in mineral oil). The reaction mixture was stirred at 5° C. for 45 minutes then 2-(methoxymethyl)-oxirane (0.082 ml; 0.92 mmol) was added dropwise at 5° C. The reaction mixture was stirred 1 hour at 5° C. then allowed to reach room temperature. The reaction was stirred at 80° C. overnight. The reaction mixture was cooled down, poured out onto ice-water and the reaction mixture was extracted with EtOAc. The organic layer was washed with brine, dried (MgSO$_4$), filtered and concentrated under reduced pressure. The residue was purified by chromatography over silica gel (5 µm; mobile phase, gradient from 100% DCM to 0.8% NH$_4$OH, 92% DCM, 8% MeOH). The desired fractions were collected and were purified by achiral SFC on (2 ethylpyridine 6 µm, mobile phase, 0.3% isopropylamine, 78% CO$_2$, 22% MeOH). The product fraction weres collected and the solvent was evaporated, yielding 46 mg (10%) of compound 7 (MP: 65° C. (Kofler)).

Analogous Preparation of Compound 8

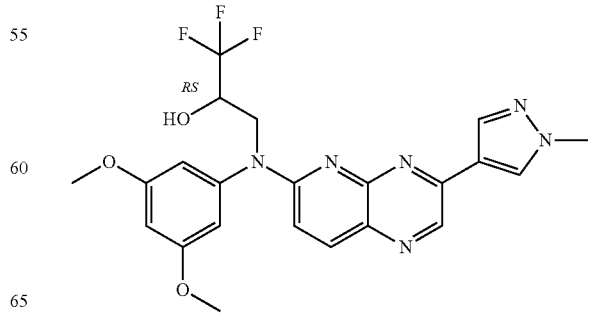

Example B4a

Preparation of Compound 29

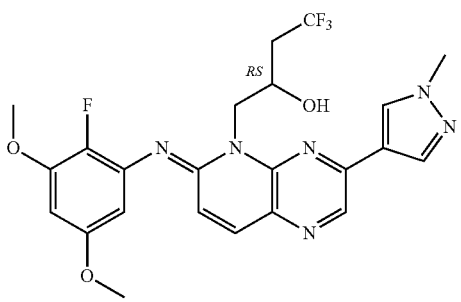 [SMILES: COc1cc(/N=c2\ccc3ncc(-c4cnn(C)c4)nc3n2CC(O)CC(F)(F)F)c(F)c(OC)c1]

and Preparation of Compound 30

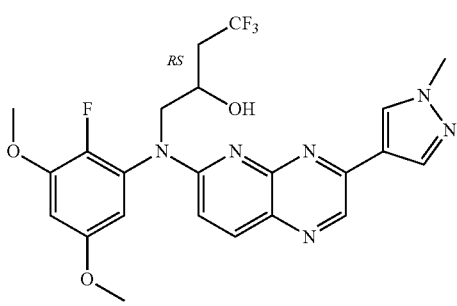 [SMILES: COc1cc(OC)c(F)c(N(CC(O)CC(F)(F)F)c2ccc3ncc(-c4cnn(C)c4)nc3n2)c1]

NaH (56 mg; 1.39 mmol) was added to a solution of intermediate 7 (560 mg; 1.47 mmol) in DMF (25 mL) under N₂ at 5° C. The reaction mixture was stirred at 5° C. for 30 minutes then 1,2-epoxy-3,3,3-trifluoropropane (CAS 359-41-1) (0.12 mL; 1.39 mmol) was added drop wise at 5° C. The reaction mixture was stirred for 1 hour at 5° C., then allowed to reach room temperature and stirred for 6 hours. The reaction mixture was poured into ice water and extracted with EtOAc. The organic layer was washed with brine, dried over MgSO₄, filtered and concentrated. The residue (929 mg) was purified by chromatography over silica gel (Spherical Silica, 5 μm, 150×30.0 mm; mobile phase: gradient from 71% Heptane, 1% MeOH, 28% EtOAc to 0% Heptane, 20% MeOH, 80% EtOAc). The product fractions were collected and the solvent was evaporated to give 23 mg (3%) of compound 29, M.P.: gum at 100° C. (kofler), and 66 mg (9%) of compound 30. M.P.: 202° C. (kofler)

Example B4b

Preparation of Compound 31

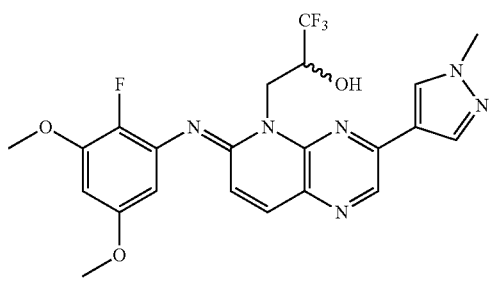 [SMILES: COc1cc(/N=c2\ccc3ncc(-c4cnn(C)c4)nc3n2CC(O)C(F)(F)F)c(F)c(OC)c1]

To a solution of intermediate 7 (1 g; 2.51 mmol) in DMF (25 mL) was added under N₂ at 5° C., NaH 60% in mineral oil (95.4 mg; 2.38 mmol). The reaction mixture was stirred at 5° C. for 45 minutes then 1,2-epoxy-3,3,3-trifluoropropane (0.21 mL; 2.38 mmol) was added drop wise at 5° C. The reaction mixture was stirred for 1 hour at 5° C., overnight at room temperature and 3 hours at 50° C. The reaction mixture was poured into ice water and extracted with EtOAc. The organic layer was washed with brine, dried over MgSO₄, filtered and concentrated under reduced pressure.

The residue (1.69 g) was purified by chromatography over silica gel (irregular SiOH, 15-40 μm, 30 g; Mobile phase: 20% eptanes, 80% EtOAc). The product fractions were mixed and the solvent was concentrated to afford 92 mg of an intermediate fraction which was purified by achiral SFC on (2 ETHYLPYRIDINE 6 μm 150×21.2 mm; Mobile phase: 80% CO₂, 20% MeOH) to give 40 mg of a compound which was was crystallized from Et₂O. The precipitate was filtered and dried to afford 35 mg (3%) of compound 31. M.P.: 200° C. (kofler)

Example B4c

Preparation of Compound 8

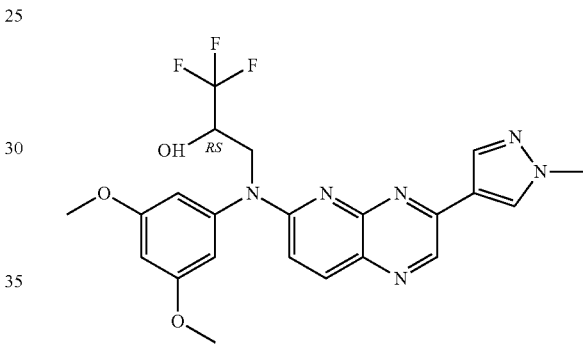

and Preparation of Compound 33

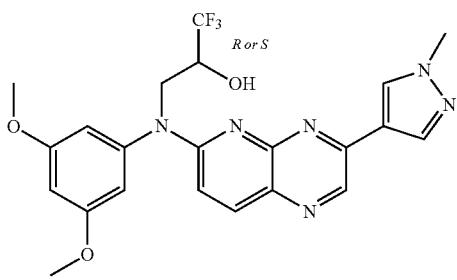 [SMILES: COc1cc(OC)cc(N(CC(O)C(F)(F)F)c2ccc3ncc(-c4cnn(C)c4)nc3n2)c1]

and Compound 34

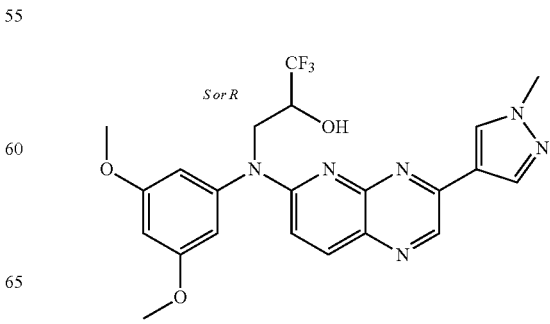

NaH (99 mg; 2.46 mmol) was added to a solution of intermediate 6 (940 mg; 2.59 mmol) in DMF (25 mL) under $N_2$ at 5° C. The reaction mixture was stirred at 5° C. for 30 minutes then 1,2-epoxy-3,3,3-trifluoropropane (0.21 mL; 2.46 mmol) was added drop wise at 5° C. The reaction mixture was stirred for 1 hour at 5° C., then allowed to reach room temperature. The reaction was then stirred at 50° C. for 15 hours. The reaction mixture was poured into ice water and extracted with EtOAc. The organic layer was washed with brine, dried over $MgSO_4$, filtered and evaporated till dryness. The residue (1.41 g) was purified by chromatography over silica gel (irregular SiOH, 15-40 µm; mobile phase 0.1% $NH_4OH$, 98% DCM, 2% MeOH to 0.1% $NH_4OH$, 97% DCM, 3% MeOH). The pure fractions were collected and evaporated to dryness. The residue (0.59 g) was purified by achiral SFC (DIETHYLAMINOPROPYL, 5 µm, 150× 21.2 mm; mobile phase: 93% $CO_2$, 7% MeOH). The product fractions were collected and evaporated to dryness yielding 219 mg (18%) of compound 8.

300 mg of compound 32 (obtained from 7.4 mmol of intermediate 6) were purified by chiral SFC (CHIRALPAK AD-H, 5 µm, 250×20 mm; mobile phase: 60% $CO_2$, 40% MeOH). The product fractions were collected and evaporated to dryness to give 2 fractions:

Fraction A: 135 mg which were crystallized from $Et_2O$ to give 112 mg (3%) of compound 33. M.P.: 208° C. (DSC)

Fraction B: 147 mg which were crystallized from $Et_2O$ to give 127 mg (4%) of compound 34. M.P.: 208° C. (DSC).

NaH (201 mg; 5.02 mmol) was added to a solution of intermediate 12 (2 g; 5.02 mmol) in DMF (35 mL) at 5° C. under $N_2$ flow. The reaction mixture was stirred at 5° C. for 30 minutes, then a solution of glycidyl methyl ether (0.42 mL; 4.77 mmol) in DMF (15 mL) was added drop wise at 5° C. The mixture was stirred at 5° C. for 1 hour, then allowed to warm to room temperature and stirred at 80° C. overnight. The reaction mixture was cooled down, poured into ice-water and extracted with EtOAc. The organic layer was washed with brine, dried over $MgSO_4$, filtered and evaporated to dryness. The crude product was purified by chromatography over silica gel (irregular SiOH, 15-40 µm, 300 g; mobile phase: 0.2% $NH_4OH$, 98% DCM, 2% MeOH). The pure fractions were collected and evaporated to dryness to give 250 mg of fraction 1 (impure) and 60 mg of fraction 2 (impure).

Fraction 1 was purified by achiral SFC (2 ETHYLPYRIDINE, 6 µm, 150×21.2 mm; mobile phase 80% $CO_2$, 20% MeOH). The residue was taken up in ACN and crystallized from ACN. The precipitate was filtered, washed with $Et_2O$ and dried to give 78 mg (3%) of compound 50. M.P.: 162-163° C. (Kofler).

Fraction 2 was purified by achiral SFC (2 ETHYLPYRIDINE, 6 µm, 150×21.2 mm; mobile phase 80% $CO_2$, 20% MeOH). The residue was taken up in ACN and crystallized from ACN. The precipitate was filtered, washed with $Et_2O$ and dried to give 28 mg (1%) of compound 51. M.P.: 180° C. (Kofler).

Example B4d

Preparation of Compound 50

Example B4e

Preparation of Compound 59, 58 and 60

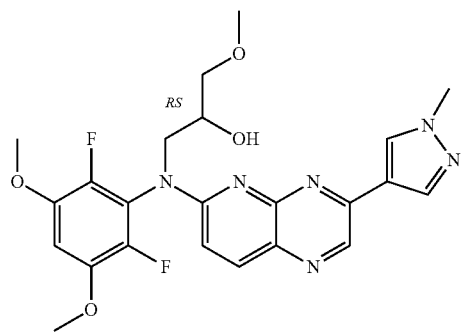 [SMILES: COCC(O)CN(c1ccc2ncc(-c3cnn(C)c3)nc2n1)c1c(F)c(OC)cc(OC)c1F]

and Preparation of Compound 51

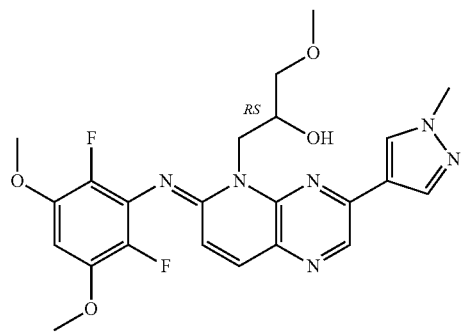 [SMILES: COCC(O)Cn1/c(=N/c2c(F)c(OC)cc(OC)c2F)ccc2ncc(-c3cnn(C)c3)nc21]

compound 59

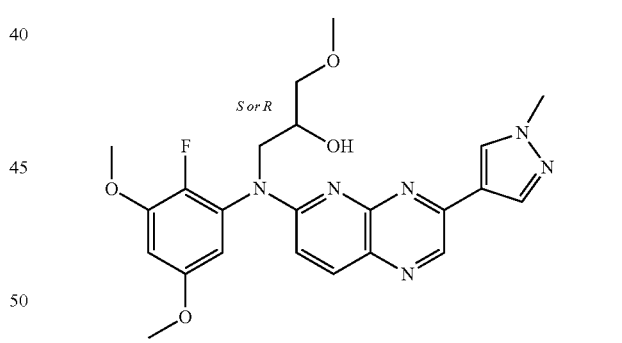

compound 58

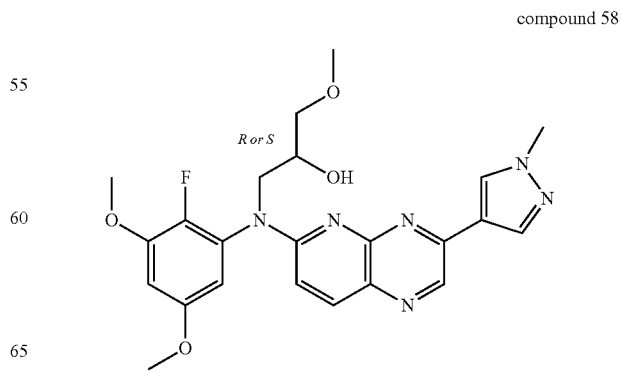

Analogous Preparation of Compounds 61, 62, 63 and 64 Starting from Intermediate 12

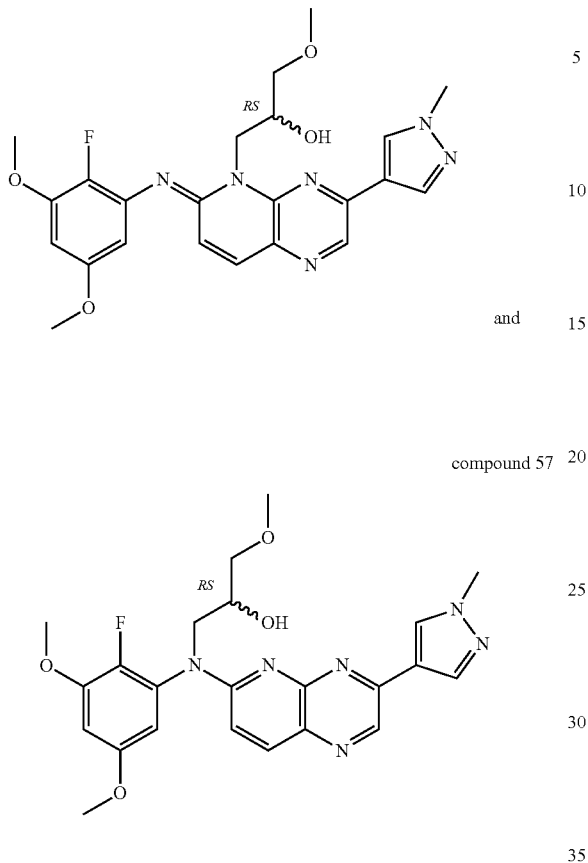

compound 60 compound 57

NaH (105 mg; 2.63 mmol) was added to a solution of intermediate 7 (1 g; 2.63 mmol) in DMF (15 mL) at 5° C. under $N_2$ flow. The reaction mixture was stirred at 5° C. for 30 minutes, then a solution of glycidyl methyl ether (0.22 mL; 2.50 mmol) in DMF (5 mL) was added drop wise at 5° C. The mixture was stirred at 5° C. for 1 hour, then allowed to warm to room temperature and stirred at 80° C. overnight. The reaction mixture was cooled down, poured into ice-water and extracted with EtOAc. The organic layer was washed with brine, dried over $MgSO_4$, filtered and evaporated to dryness. The crude product was purified by chromatography over silica gel (irregular SiOH, 15-40 µm, 300 g; mobile phase: gradient from 0.1% $NH_4OH$, 98% DCM, 2% MeOH to 0.1% $NH_4OH$, 96% DCM, 4% MeOH). The product fractions were collected and evaporated to dryness to give 2 fractions:

Fraction A: 243 mg of compound 57 which was purified by chiral SFC (CHIRALPAK AD-H, 5 µm, 250×20 mm; mobile phase: 60% $CO_2$, 40% iPrOH). The product fractions were collected and evaporated to give 51 mg (4%) of compound 58; M.P.: 94-95° C. (Kofler); and 51 mg (4%) of compound 59; M.P.: 94-95° C. (Kofler).

Fraction B: 227 mg of compound 60 which was purified by achiral SFC (2 ETHYLPYRIDINE 6 µm 150×21.2 mm; mobile phase 85% $CO_2$, 15% MeOH. The product fractions were mixed and the solvent was evaporated. The resulting residue was taken up in $Et_2O$. The precipitate was filtered and dried yielding 76 mg (6%) of compound 60. M.P.: 114° C. (kofler)

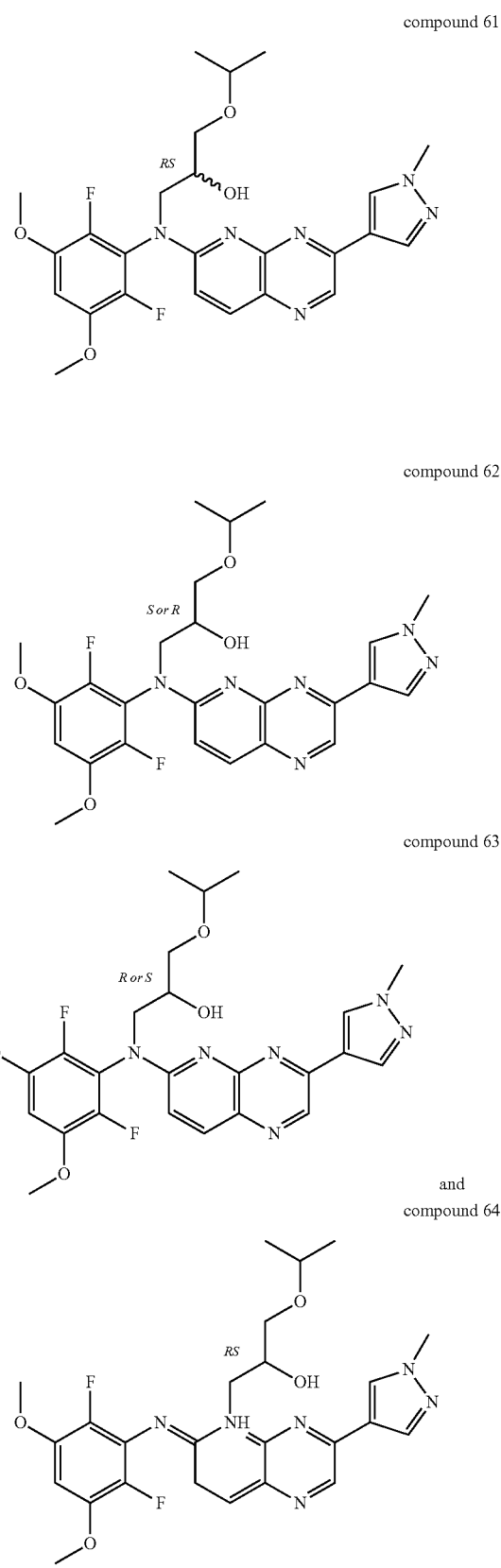

compound 61 compound 62 compound 63 and compound 64

Example B4e1

Preparation of Compound 75, 76, 77, 78 and 79 compound 75
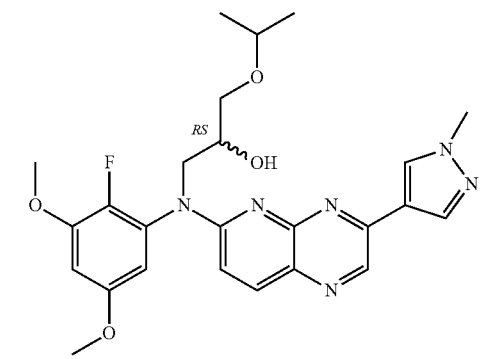

compound 76
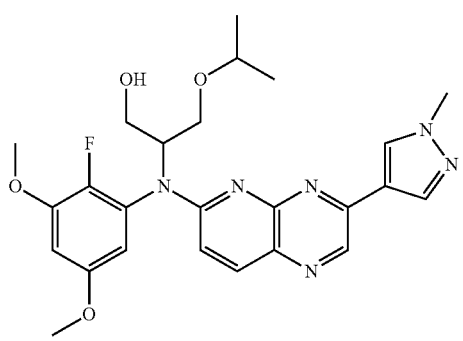

compound 77
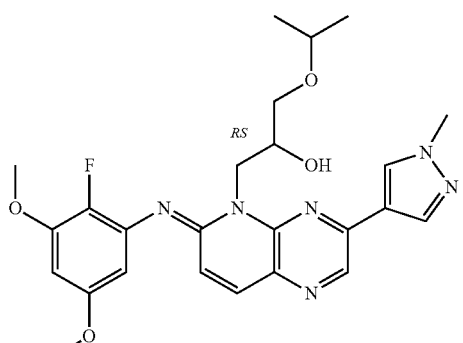

compound 78
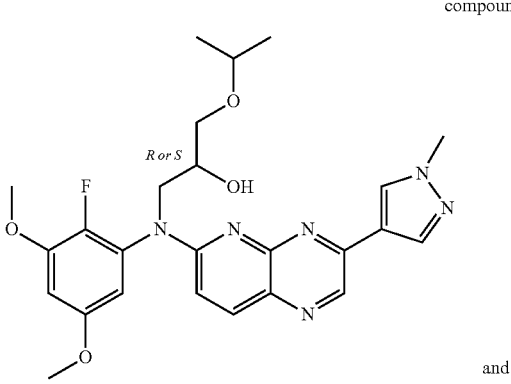

and compound 79
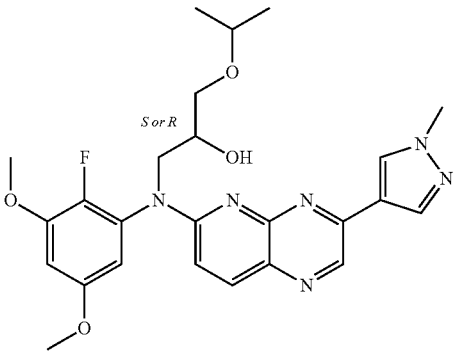

NaH (210 mg; 5.26 mmol) was added to a solution of intermediate 7 (2 g; 5.26 mmol) in DMF (35 mL) at 5° C. under $N_2$ flow. The reaction mixture was stirred at 5° C. for 30 minutes, then, a solution of glycidyl isopropyl ether (0.63 mL; 5.00 mmol) in DMF (15 mL) was added drop wise at 5° C. The mixture was stirred at 5° C. for 1 hour, then allowed to warm to room temperature and stirred at 80° C. overnight. The reaction mixture was cooled down, poured into ice-water and extracted with EtOAc. The organic layer was washed with brine, dried over $MgSO_4$, filtered and evaporated to dryness. The residue was purified by chromatography over silica gel (irregular SiOH, 15-40 μm, 300 g; mobile phase: 0.3% $NH_4OH$, 97% DCM, 3% MeOH). The product fractions were collected and the solvent was evaporated to give 2 fractions:

Fraction 1: 600 mg of an intermediate residue which was purified by achiral SFC (2-ETHYLPYRIDINE, 6 μm, 150×21.2 mm; mobile phase: 90% $CO_2$, 10% MeOH). The product fractions were collected and the solvent was evaporated to give 2 fractions:

Fraction A: 271 mg which were crystallized from ACN to give, after filtration and drying, 171 mg (7%) of compound 77 (M.P.: 96-97° C., Kofler)

Fraction B: 82 mg which were taken up in $Et_2O$ to afford after $Et_2O$ washing, filtration and drying 59 mg (2%) of compound 76. M.P.: 137-138° C. (Kofler).

Fraction 2: 1.35 g of an impure residue which was purified by achiral SFC (2-ETHYLPYRIDINE, 6 μm, 150×21.2 mm; mobile phase: 85% $CO_2$, 15% MeOH). The product fractions were collected and the solvent was evaporated to dryness. The resulting compound (404 mg) was crystallized from ACN. The precipitate was filtered, washed with $Et_2O$ and dried yielding 390 mg (15%) of compound 75 M.P.: 148-149° C. (Kofler).

Compound 75 was purified by chiral SFC (CHIRALPAK AD-H, 5 μm, 250×20 mm; mobile phase: 60% $CO_2$, 40% MeOH). The product fractions were collected and evaporated to give 2 fractions:

Fraction C: 169 mg of a compound which was dissolved in ACN and crystallized from ACN. The precipitate was washed with $Et_2O$ and dried to give 92 (4%) mg of compound 78 (M.P.: 143-144° C., Kofler)

Fraction D: 161 mg of a compound which was dissolved in ACN and crystallized from ACN. The precipitate was washed with $Et_2O$ and dried to give 86 mg (3%) of compound 79 (M.P.: 142° C., Kofler).

Example B5

Preparation of Compound 9

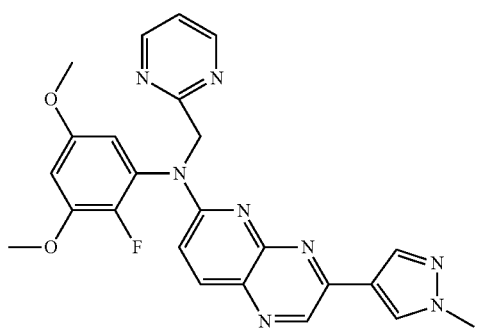

Under N$_2$, NaH (142 mg; 3.55 mmol, 60% in mineral oil) was added to a solution of intermediate 7 (450 mg; 1.2 mmol) in DMF (10 ml) at 5° C. The reaction mixture was stirred 30 minutes at 5° C. and a solution of 2-(chloromethyl)pyrimidine (390.5 mg; 2.4 mmol) in DMF (5 ml) was added. The reaction mixture was allowed to reach room temperature and stirred for 20 hours. The reaction mixture was poured out onto ice water and extracted with EtOAc. The organic layer was washed with brine, dried (MgSO$_4$), filtered and concentrated under reduced pressure. The obtained residue was purified by chromatography over silica gel (15-40 μm 150 g, mobile phase 40% Heptane, 50% EtOAc, 10% MeOH (+10% NH$_4$OH)). The desired fractions were collected, concentrated under reduced pressure to provide 430 mg (77%) of compound 9. This compound was taken up in Et$_2$O, a solid was filtered and dried to afford 305 mg of compound 9 (MP: 227° C. (DSC)).

Analogous Preparation of Compound 10

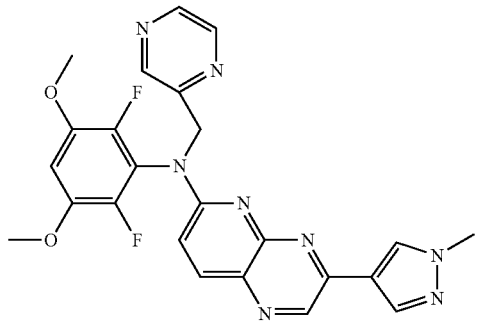

Starting from Intermediate 12
Analogous Preparation of Compound 11

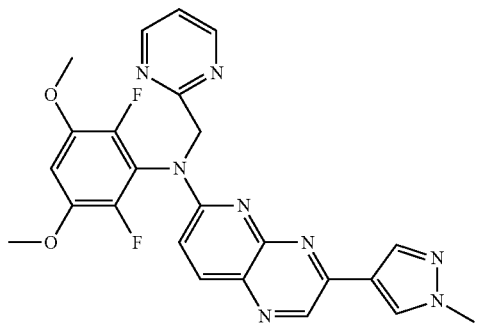

Starting from Intermediate 12
Analogous Preparation of Compound 12

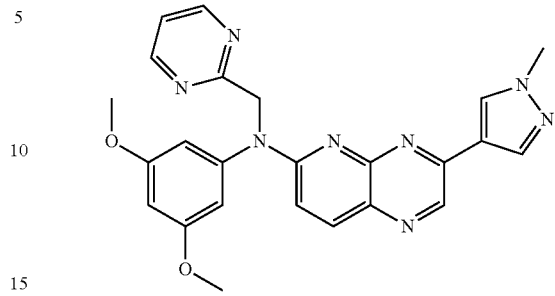

Starting from Intermediate 6
Analogous Preparation of Compound 13

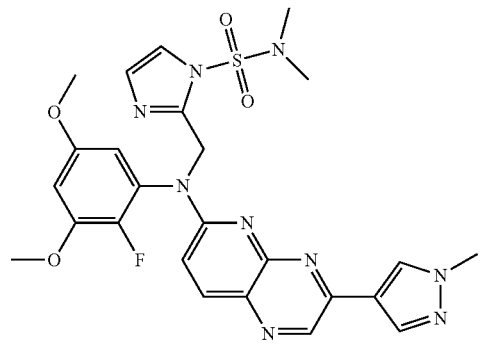

Starting from Intermediate 7
Analogous Preparation of Compound 14

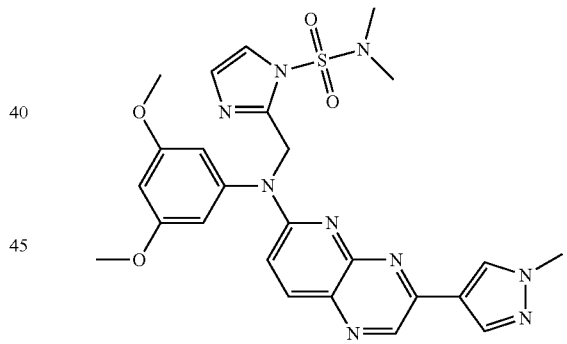

Starting from Intermediate 6
Analogous Preparation of Compound 15

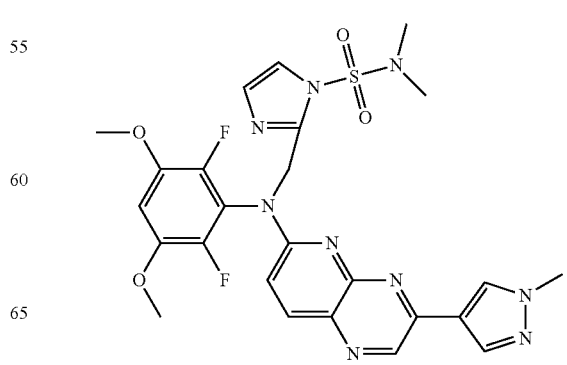

Starting from Intermediate 12
Analogous Preparation of Compound 28

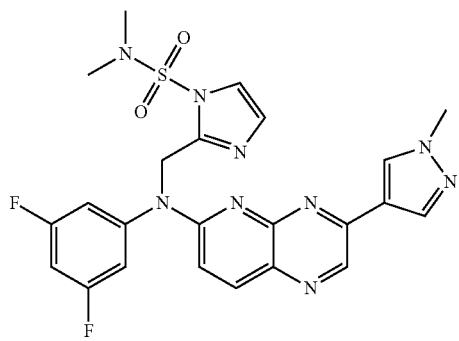 [SMILES: CN(C)S(=O)(=O)n1ccnc1CN(c1cc(F)cc(F)c1)c1ccc2ncc(-c3cnn(C)c3)nc2n1]

Starting from Intermediate 14
Analogous Preparation of Compound 43

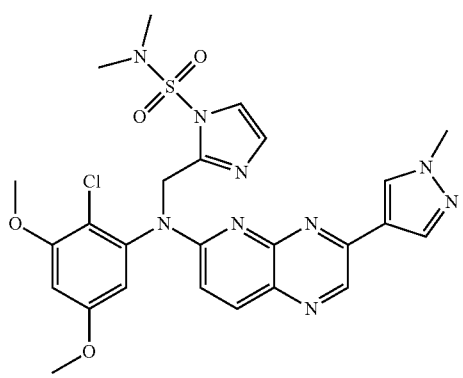 [SMILES: COc1cc(OC)c(Cl)c(N(Cc2nccn2S(=O)(=O)N(C)C)c2ccc3ncc(-c4cnn(C)c4)nc3n2)c1]

Starting from Intermediate 16
Analogous Preparation of Compound 66

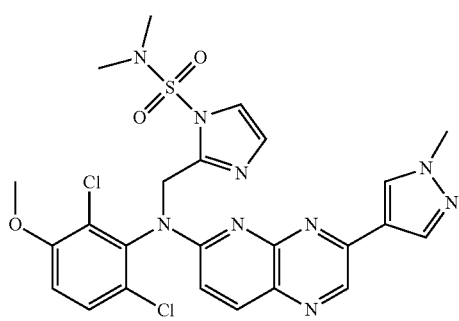 [SMILES: COc1ccc(Cl)c(N(Cc2nccn2S(=O)(=O)N(C)C)c2ccc3ncc(-c4cnn(C)c4)nc3n2)c1Cl]

Starting from Intermediate 19
Analogous Preparation of Compound 72

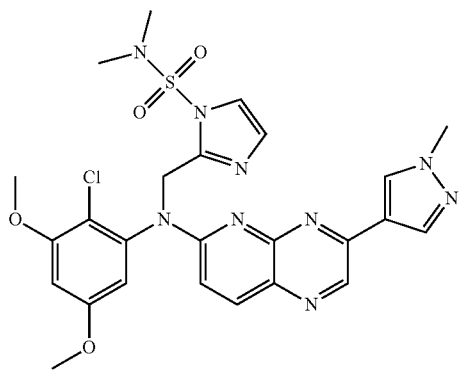 [SMILES: COc1cc(OC)c(Cl)c(N(Cc2nccn2S(=O)(=O)N(C)C)c2ccc3ncc(-c4cnn(C)c4)nc3n2)c1]

Starting from Intermediate 6
Analogous Preparation of Compound 74

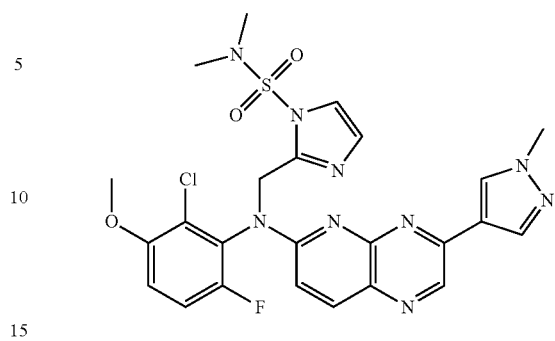

Starting from Intermediate 20
Analogous Preparation of Compound 80

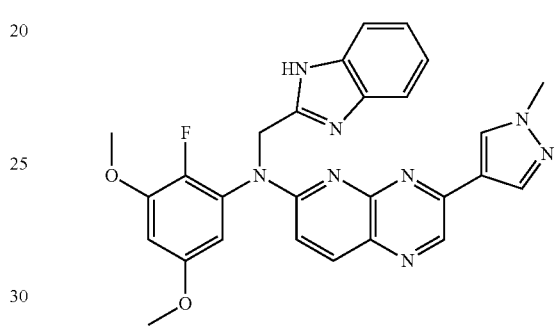

Starting from Intermediate 7
Analogous Preparation of Compound 99

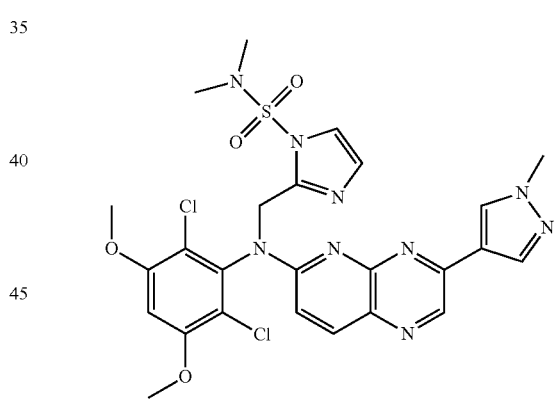

Starting from Intermediate 22
Analogous Preparation of Compound 105

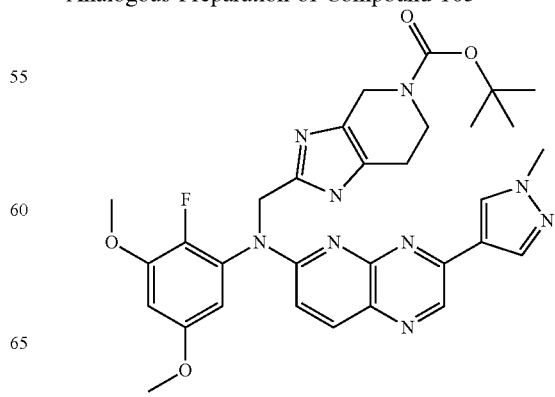

Starting from Intermediate 29
  Analogous Preparation of Compound 110

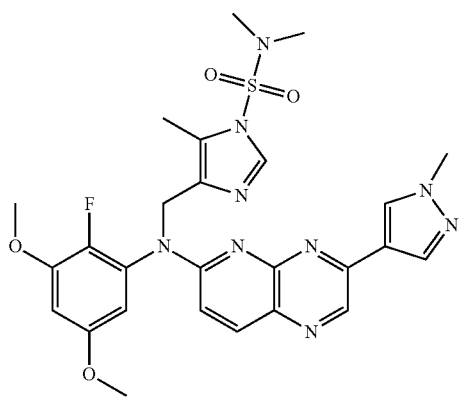 [SMILES: COc1cc(OC)c(F)c(N(Cc2ncn(S(=O)(=O)N(C)C)c2C)c2ccc3ncc(-c4cnn(C)c4)nc3n2)c1]

Starting from Intermediate 7
  Analogous Preparation of Compound 128

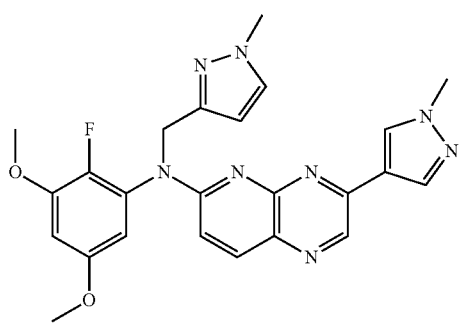 [SMILES: COc1cc(OC)c(F)c(N(Cc2ccn(C)n2)c2ccc3ncc(-c4cnn(C)c4)nc3n2)c1]

Starting from Intermediate 7
  Analogous Preparation of Compound 132

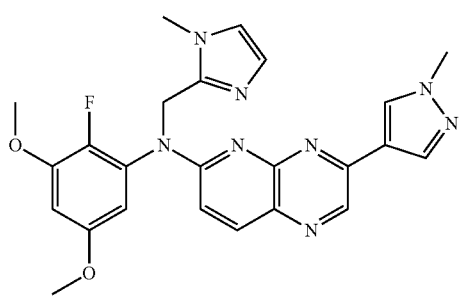 [SMILES: COc1cc(OC)c(F)c(N(Cc2nccn2C)c2ccc3ncc(-c4cnn(C)c4)nc3n2)c1]

Starting from Intermediate 7
  Analogous Preparation of Compound 132

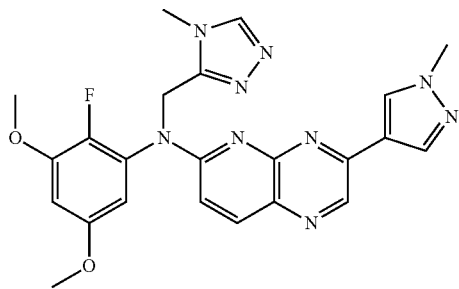 [SMILES: COc1cc(OC)c(F)c(N(Cc2nncn2C)c2ccc3ncc(-c4cnn(C)c4)nc3n2)c1]

Starting from Intermediate 7
  Analogous Preparation of Compound 136

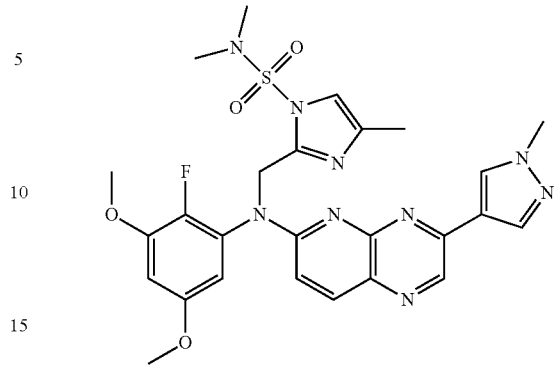

Starting from Intermediate 7
  Analogous Preparation of Compound 138

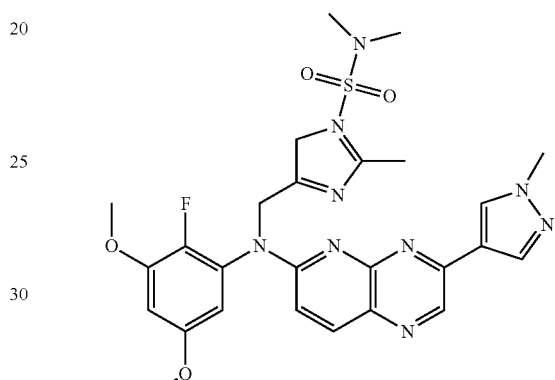

Starting from Intermediate 7
  Analogous Preparation of Compound 153

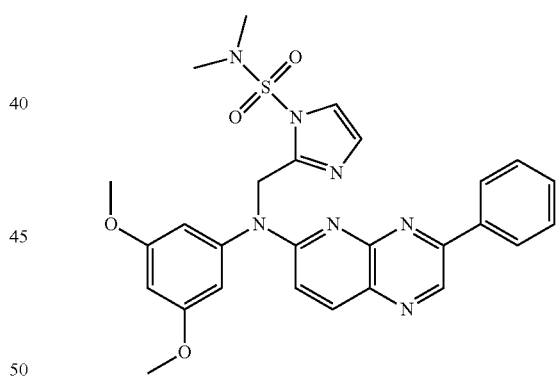

Starting from Intermediate 54
  Analogous Preparation of Compound 174

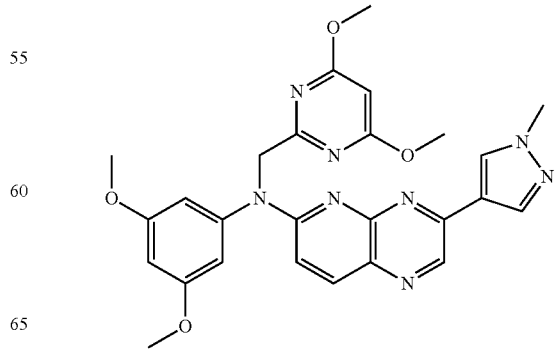

Starting from Intermediate 6.
  Analogous Preparation of Compound 176

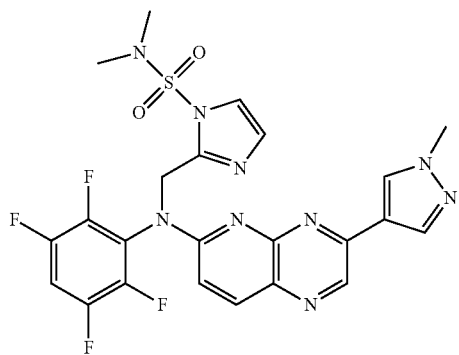 [SMILES: CN(C)S(=O)(=O)n1ccnc1CN(c1ccc2ncc(-c3cnn(C)c3)nc2n1)c1c(F)c(F)cc(F)c1F]

Starting from Intermediate 60
  Analogous Preparation of Compound 177

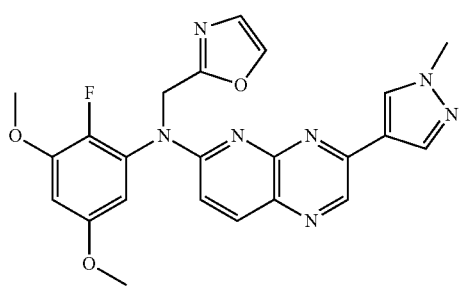 [SMILES: COc1cc(OC)c(F)c(N(Cc2ncco2)c2ccc3ncc(-c4cnn(C)c4)nc3n2)c1]

Starting from Intermediate 7
  Analogous Preparation of Compound 183

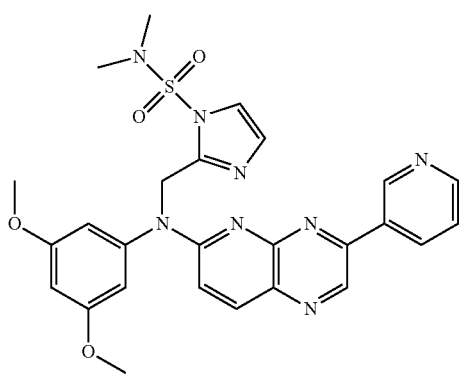 [SMILES: COc1cc(OC)cc(N(Cc2nccn2S(=O)(=O)N(C)C)c2ccc3ncc(-c4cccnc4)nc3n2)c1]

Starting from Intermediate 61
  Analogous Preparation of Compound 191

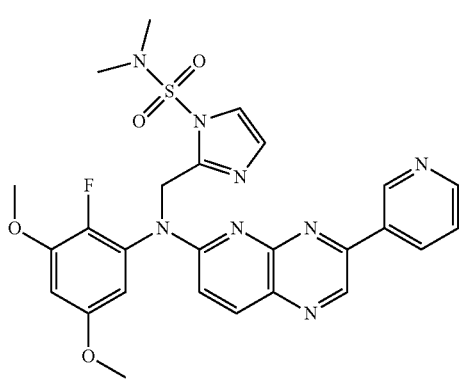 [SMILES: COc1cc(OC)c(F)c(N(Cc2nccn2S(=O)(=O)N(C)C)c2ccc3ncc(-c4ccccc4)nc3n2)c1]

Starting from Intermediate 68
  Analogous Preparation of Compound 199

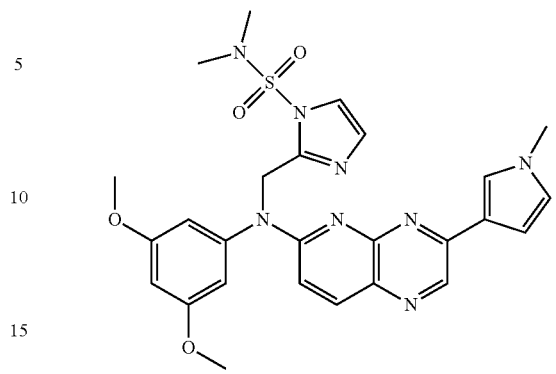

Starting from Intermediate 71
  Analogous Preparation of Compound 201

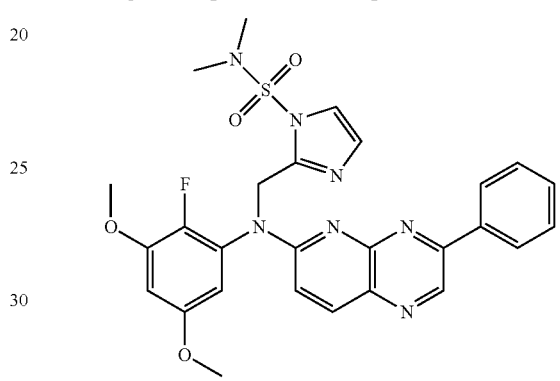

Starting from Intermediate 73
  Analogous Preparation of Compound 203

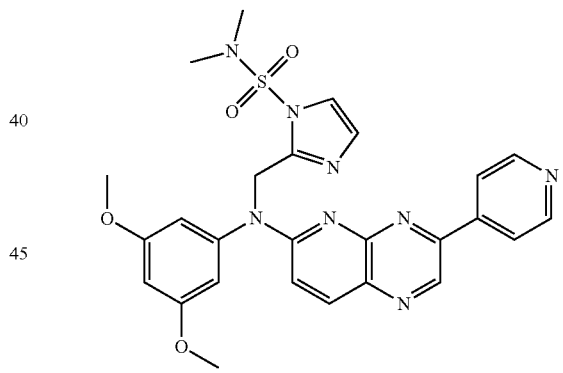

Starting from Intermediate 74
  Analogous Preparation of Compound 210

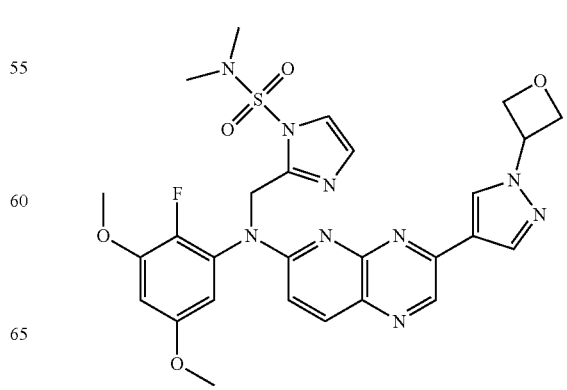

Starting from Intermediate 83
Analogous Preparation of Compound 212

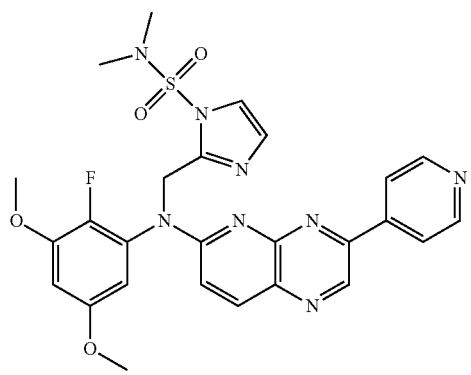 [SMILES: COc1cc(OC)c(F)c(N(Cc2nccn2S(=O)(=O)N(C)C)c2ccc3ncc(-c4ccncc4)nc3n2)c1]

Starting from Intermediate 86 and Intermediate 87
Analogous Preparation of Compound 216

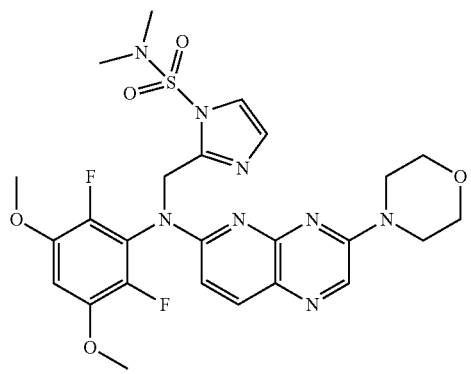 [SMILES: COc1cc(OC)c(F)c(N(Cc2nccn2S(=O)(=O)N(C)C)c2ccc3ncc(N4CCOCC4)nc3n2)c1F]

Starting from Intermediate 89
Analogous Preparation of Compound 220

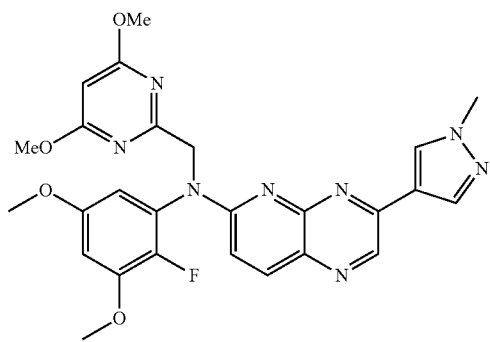 [SMILES: COc1cc(OC)c(F)c(N(Cc2nc(OC)cc(OC)n2)c2ccc3ncc(-c4cnn(C)c4)nc3n2)c1]

Starting from Intermediate 7
Analogous Preparation of Compound 224

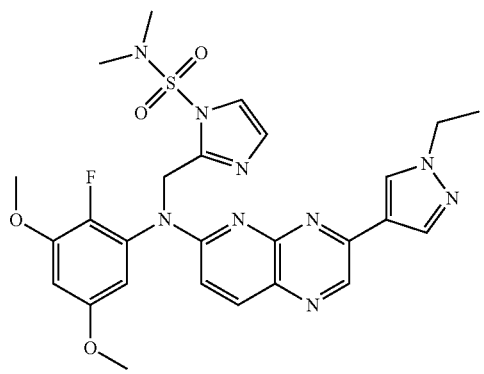 [SMILES: CCn1cc(-c2cnc3ccc(N(Cc4nccn4S(=O)(=O)N(C)C)c4cc(OC)cc(OC)c4F)nc3n2)cn1]

Starting from Intermediate 84
Analogous Preparation of Compound 225

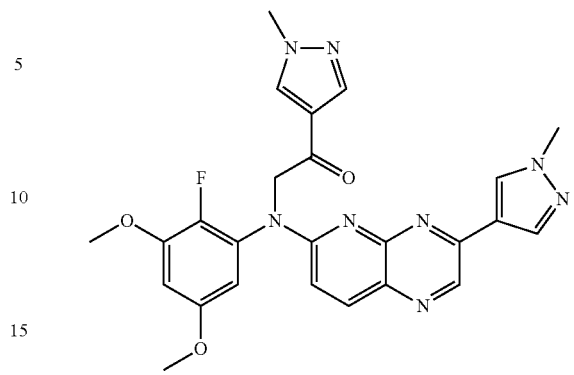

Starting from Intermediate 7
Analogous Preparation of Compound 241

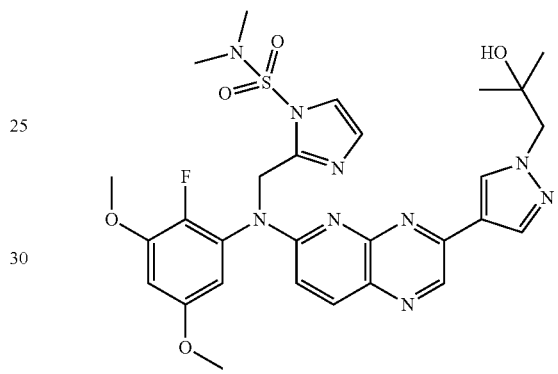

Starting from Intermediate 110
Analogous Preparation of Compound 260

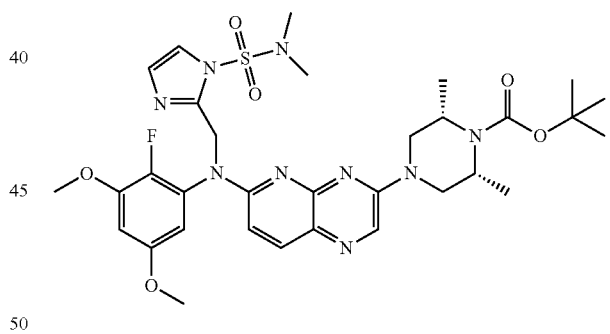

(cis) Starting from Intermediate 117
Analogous Preparation of Compound 274

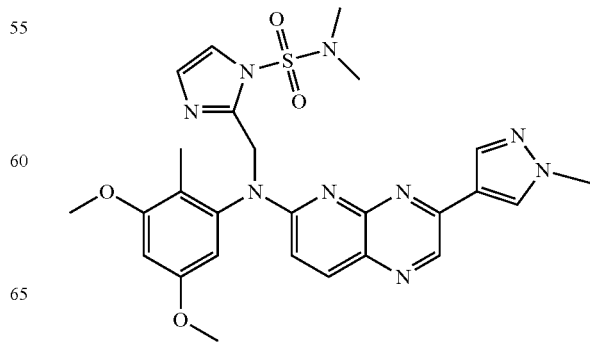

Starting from Intermediate 129
Analogous Preparation of Compound 281

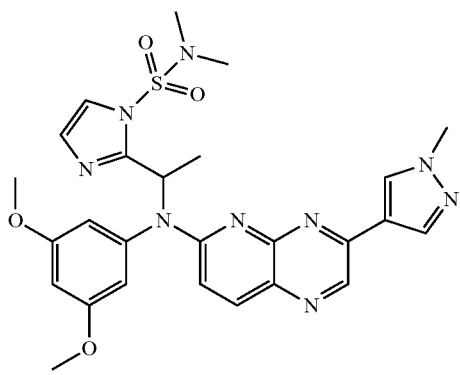 [SMILES: COc1cc(OC)cc(N(c2ccc3ncc(-c4cnn(C)c4)nc3n2)C(C)c2nccn2S(=O)(=O)N(C)C)c1]

Starting from Intermediate 6 and Intermediate 131

Analogous Preparation of Compound 288

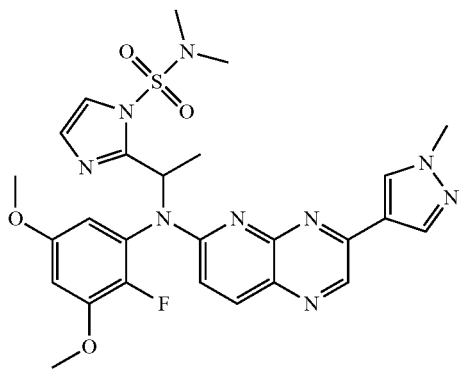 [SMILES: COc1cc(OC)c(F)c(N(c2ccc3ncc(-c4cnn(C)c4)nc3n2)C(C)c2nccn2S(=O)(=O)N(C)C)c1]

Starting from Intermediate 7 and 131

Analogous Preparation of Compound 292

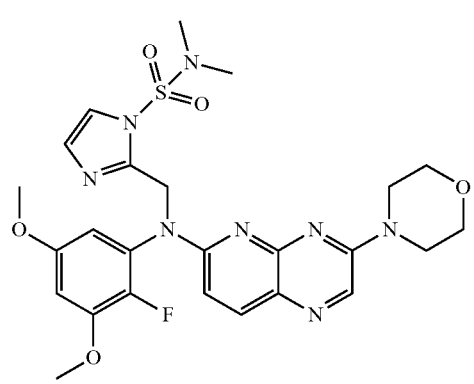 [SMILES: COc1cc(OC)c(F)c(N(Cc2nccn2S(=O)(=O)N(C)C)c2ccc3ncc(N4CCOCC4)nc3n2)c1]

Starting from Intermediate 133
Analogous Preparation of Compound 294

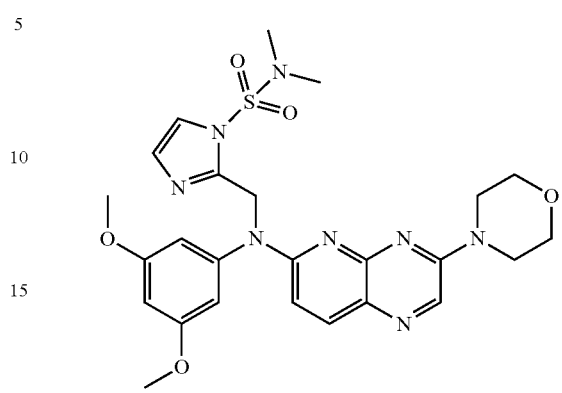

Starting from Intermediate 134
Analogous Preparation of Compound 296

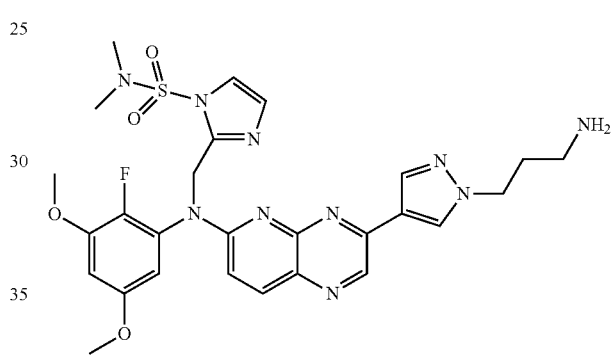

Starting from Intermediate 138

Example B5a

Preparation of Compounds 102 and 101

Compound 102

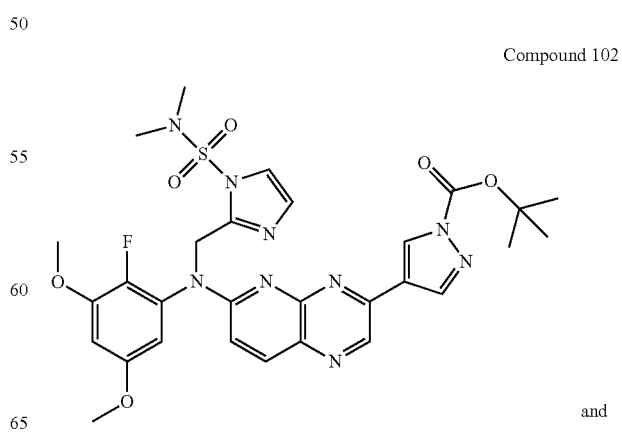

and

-continued compound 101

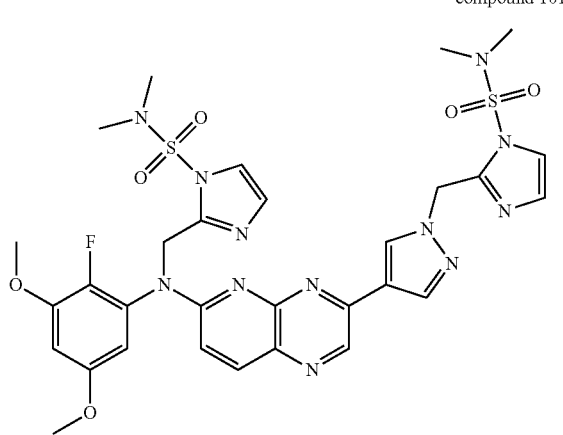

NaH (49 mg; 1.22 mmol) was added to a solution of intermediate 25 (0.38 g; 0.82 mmol) in DMF (8 mL) at 5° C. under $N_2$ flow. The reaction mixture was stirred for 30 minutes at 5° C. and a solution of 2-(chloromethyl)-NN-dimethyl-1H-imidazole-1-sulfonamide (CAS 935862-81-0) (0.219 g; 0.98 mmol) in DMF (2 mL) was added drop wise. The reaction mixture was allowed to warm to room temperature and stirred for 4 hours. The reaction mixture was partitioned between water and EtOAc. The organic layer was washed with brine, dried over $MgSO_4$, filtered and evaporated to dryness. The residue was purified by chromatography over silica gel (Irregular SiOH, 15-40 μm, 40 g; mobile phase: gradient from 99% DCM 1% MeOH 0.1% $NH_4OH$ to 95% DCM 5% MeOH 0.5% $NH_4OH$). The product fractions were collected and the solvent was evaporated to give 0.294 g (55%) of compound 102 (orange oil) and 83 mg (14%) of compound 101 (yellow oil).

Example B5b

Preparation of Compounds 254 and 255 compound 254

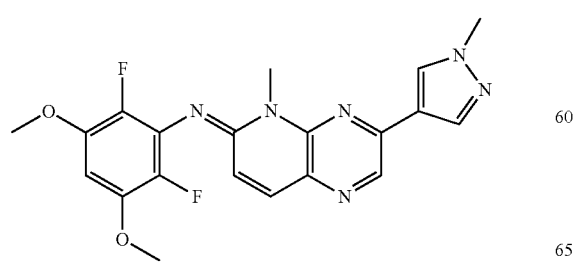

and compound 255

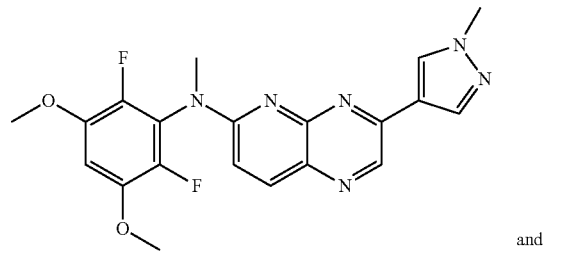

NaH (100 mg; 2.51 mmol) was added to a solution of intermediate 12 (500 mg; 1.255 mmol) in DMF (11 mL) at 5° C. under $N_2$ flow. The reaction mixture was stirred at 5° C. for 30 minutes. Then, a solution of iodomethane (195 μL; 3.138 mmol) in DMF (4 mL) was added at 5° C. under $N_2$ flow over a 2 hours period and the reaction mixture was allowed to warm to room temperature and stirred overnight. The reaction mixture was poured onto iced water and extracted with EtOAc. The organic layer was decanted, washed with brine (twice), dried over $MgSO_4$, filtered and evaporated to dryness. The residue (530 mg) was purified by chromatography over silica gel (spherical silica, 5 μm 150× 30.0 mm; mobile phase: gradient from 98% DCM, 2% MeOH, 0.2% $NH_4OH$ to 92% DCM, 8% MeOH, 0.8% $NH_4OH$). The product fractions were collected and evaporated to dryness yielding 2 fractions:

Fraction 1: 90 mg of a compound which was crystallized from $ACN/Et_2O$. The precipitate was filtered and dried to give 60 mg of compound 255 (11%), MP=199° C. (Kofler).

Fraction 2: 300 mg of a compound which was crystallized from $ACN/Et_2O$. The precipitate was filtered and dried to give 230 mg of compound 254 (44%), MP=210° C. (Kofler).

Analogous Preparation of Compound 256 and 257 Starting from Intermediate 12 compound 256

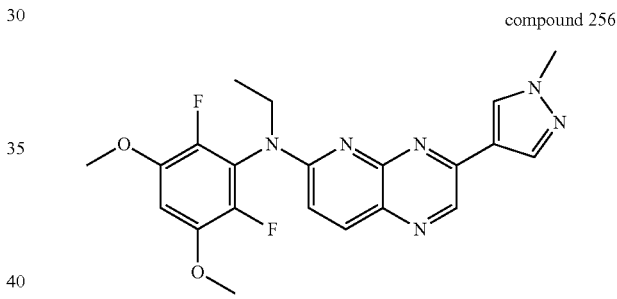

compound 257

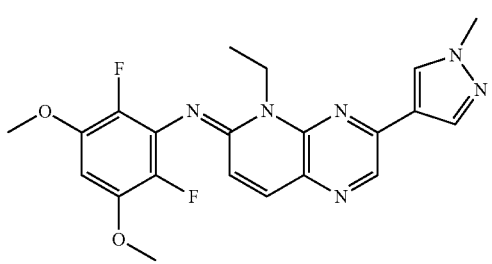

Example B6

Preparation of Compound 16

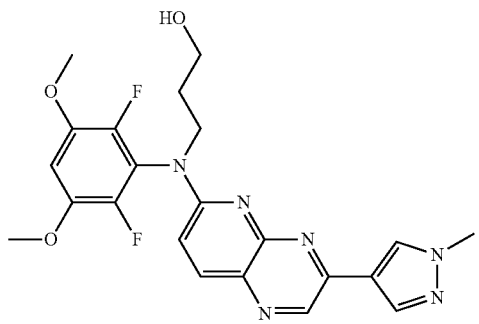

and

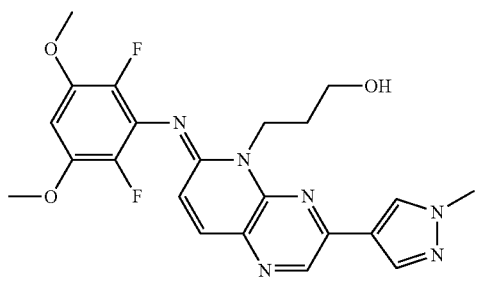

Compound 17

To a solution of a mixture of intermediate 10a and 10b (429 mg; 0.75 mmol) in THF (10 ml) was added dropwise at room temperature, 1-butanaminium, N,N,N-tributyl-fluoride (0.9 ml; 0.90 mmol). The reaction mixture was stirred at room temperature for 3 hours. The mixture was poured out into ice water and EtOAc and the mixture was basified with an aqueous solution of $K_2CO_3$ (10%). The reaction mixture was extracted, the organic layer was washed with brine, dried ($MgSO_4$), filtered and concentrated under reduced pressure. The residue was purified by chromatography over silica gel (5 μm, mobile phase, gradient from, 100% DCM, to 0.8% $NH_4OH$, 92% DCM, 8% MeOH). Two product fractions were collected and concentrated under reduced pressure to afford 91 mg (26%) of compound 17 as Fraction 1 and 117 mg (34%) of compound 16 as Fraction 2. Fraction 1 was taken up in $Et_2O$, triturated, filtered and dried to afford 38 mg of compound 17 (MP: 206° C. (DSC)). Fraction 2 was taken up in $Et_2O$ triturated, filtered and dried to afford 53 mg of compound 16 (MP: 208° C. (DSC)).

Analogous Preparation of Compound 18

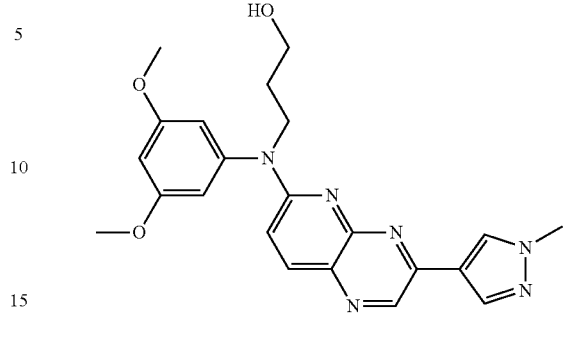

And Compound 19

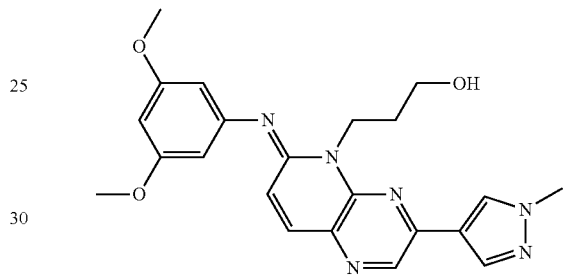

Analogous Preparation of Compound 20

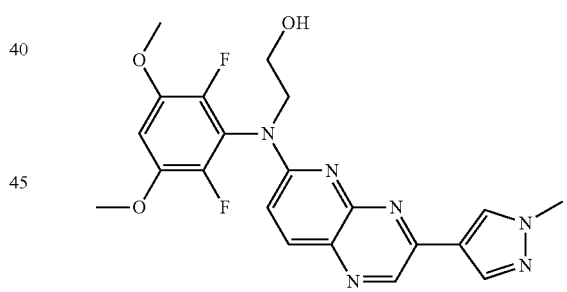

Analogous Preparation of Compound 21

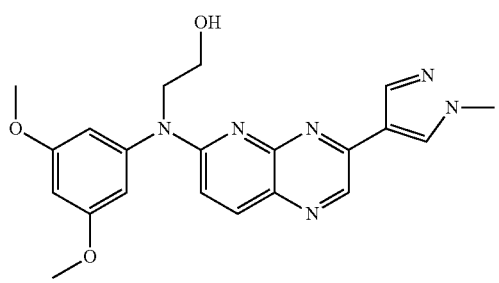 [SMILES: CN/C=C(\C=N)c1cnc2ccc(N(CCO)c3cc(OC)cc(OC)c3)nc2n1]

Analogous Preparation of Compound 40

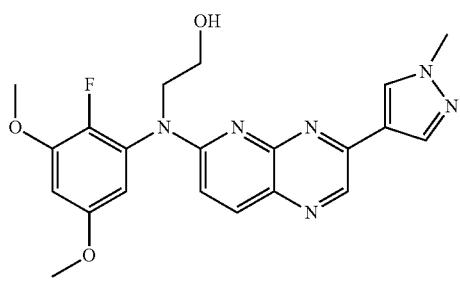 [SMILES: COc1cc(OC)c(F)c(N(CCO)c2ccc3ncc(-c4cnn(C)c4)nc3n2)c1]

Starting from Intermediate 15
Analogous Preparation of Compound 145

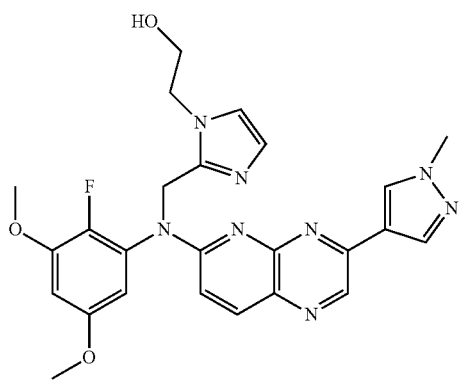 [SMILES: COc1cc(OC)c(F)c(N(Cc2nccn2CCO)c2ccc3ncc(-c4cnn(C)c4)nc3n2)c1]

Starting from Intermediate 50
Analogous Preparation of Compound 213

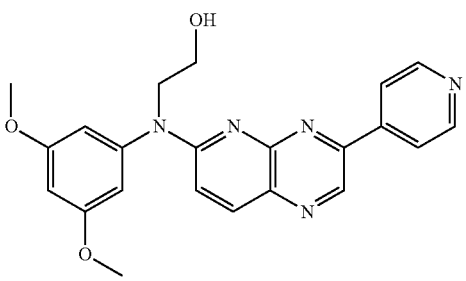 [SMILES: COc1cc(OC)cc(N(CCO)c2ccc3ncc(-c4ccncc4)nc3n2)c1]

Starting from Intermediate 88

Example B6a

Preparation of Compound 204

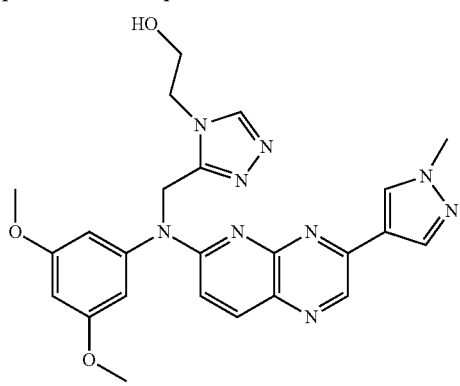

A 1M solution of tetrabutylammonium fluoride in THF (0.31 mL; 1 mmol) was added to a solution of intermediate 76 (0.08 g; 0.13 mmol) in THF (3 mL) at 10° C. The mixture was stirred at room temperature for 2 hours, poured into cold water, basified with a 10% aqueous solution of $K_2CO_3$ and extracted with EtOAc. The organic layer was washed with a 10% aqueous solution of $K_2CO_3$, dried over $MgSO_4$, filtered and evaporated to dryness. The residue (10 mg) was taken up with $Et_2O$ and evaporated to give 0.006 g (9%) of compound 204.

Analogous Preparation of Compound 205 Starting from Intermediate 77

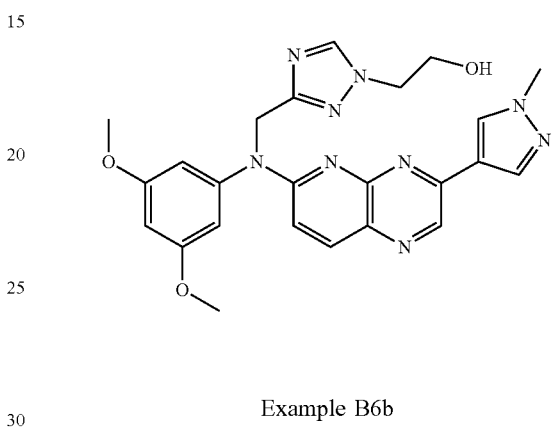

Example B6b

Preparation of Compounds 218 and 219 compound 218

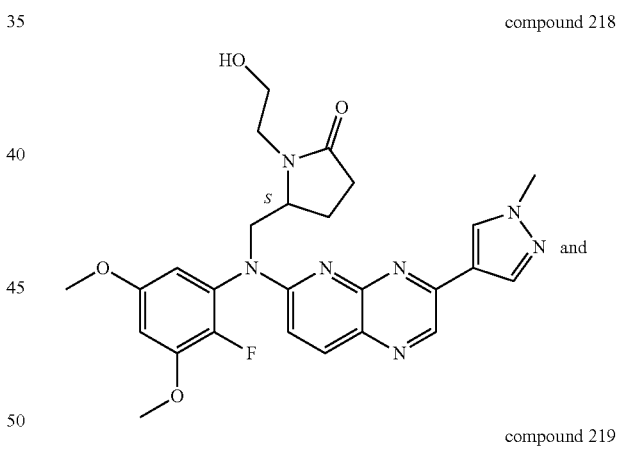

and compound 219

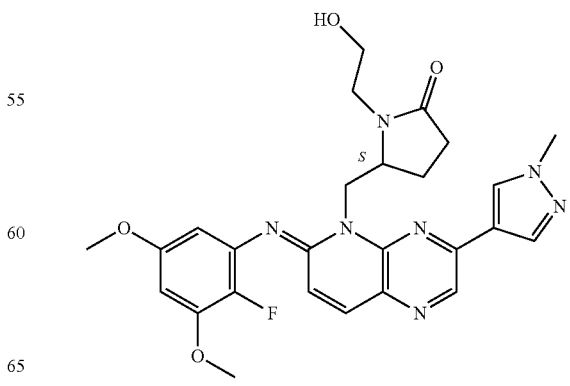

A 1M solution of tetrabutylammonium fluoride in THF (3.26 mL; 3.26 mmol) was added to a solution of intermediates 92 and 93 (415 mg; 0.65 mmol) in THF (20 mL). The reaction mixture was stirred at room temperature overnight, poured into ice water and extracted with EtOAc. The organic layer was washed with brine, dried over $MgSO_4$, filtered and evaporated to dryness. The residue was purified by chromatography over silica gel (irregular SiOH, 15-40 μm, 30 g; mobile phase: 0.1% $NH_4OH$, 3% MeOH, 97% DCM). The product fractions were collected and evaporated to dryness yielding 2 fractions:

Fraction 1: 80 mg (23%) of compound 218; M.P.: 130° C. (gum, Kofler)

Fraction 2: 136 mg of an impure compound which was purified by achiral SFC (2 ETHYLPYRIDINE, 6 μm, 150×21.2 mm; mobile phase: 85% $CO_2$, 15% MeOH). The product fractions were collected and evaporated to dryness yielding 18 mg (5%) of compound 219 M.P.: 112° C. (gum, Kofler).

Analogous Preparation of Compounds 247 and 53 Starting from Intermediate 111 compound 247

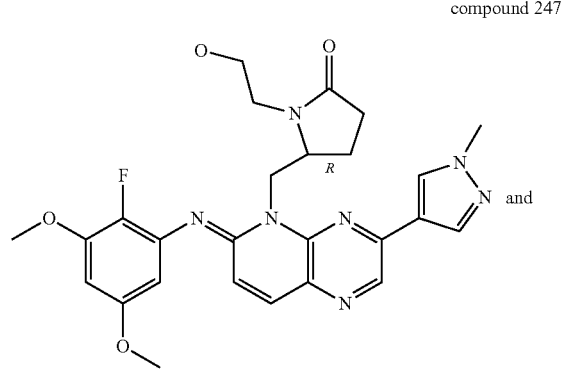

and compound 53

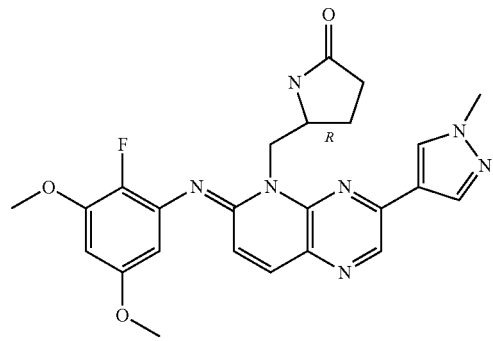

Example B6c

Preparation of Compound 233

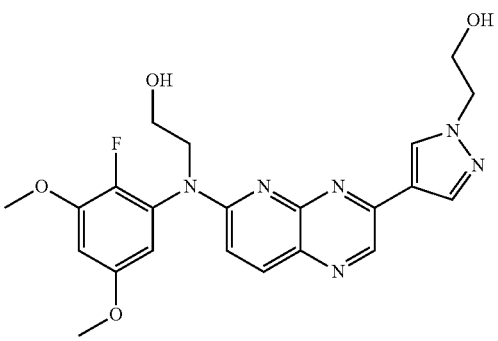 [SMILES: COc1cc(OC)c(F)c(N(CCO)c2ccc3ncc(-c4cnn(CCO)c4)nc3n2)c1]

A 1M solution of tetrabutylammonium fluoride in THF (1.03 mL; 1.03 mmol) was added to a solution of intermediate 103 (70 mg; 0.10 mmol) in tetrahydrofuran (1 mL) and the reaction mixture was refluxed overnight. The reaction mixture was poured into a 10% aqueous solution of $K_2CO_3$ and extracted with EtOAc. The organic layer was washed with brine, dried over $MgSO_4$, filtered and evaporated to dryness. The crude product was purified by chromatography over silica gel (spherical silica, 5 μm, 150×30.0 mm; mobile phase: gradient from 0.2% $NH_4OH$, 2% MeOH, 98% DCM to 1% $NH_4OH$, 10% MeOH, 90% DCM). The product fractions were collected and evaporated to dryness yielding 29 mg (62%) of compound 233. M.P.: 194° C. (Kofler).

Example B6d

Preparation of Compound 269

A mixture of intermediate 126 (450 mg; 0.74 mmol) and a solution of 1M tetrabutylammonium fluoride in THF (3.7 mL; 3.702 mmol) in THF (10 mL) was stirred at room temperature overnight. The reaction mixture was diluted with DCM and quenched with a 10% aqueous solution of $K_2CO_3$. The organic layer was decanted, dried over $MgSO_4$, filtered and evaporated to dryness. The residue (420 mg) was purified by chromatography over silica gel (irregular SiOH, 15-40 μm, 40 g; mobile phase: 95% DCM, 5% MeOH, 0.5% $NH_4OH$). The product fractions were collected and evaporated to dryness. The residue (354 mg) was crystallized from ACN. The precipitate was filtered and dried yielding 324 mg (89%) of compound 269. M.P.: gum at 160° C. (kofler).

Analogous Preparation of Compound 270

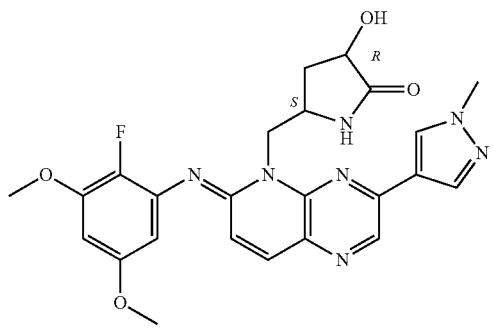

Starting from Intermediate 125
Analogous Preparation of Compound 271

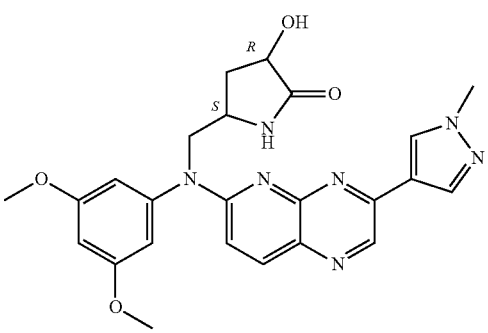

Starting from Intermediate 127
Analogous Preparation of Compound 272

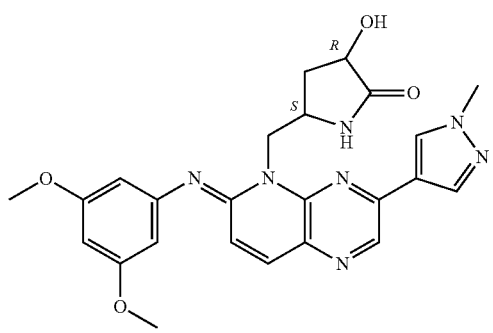

Starting from Intermediate 128

Example B7

Preparation of Intermediate 13 and Compound 22

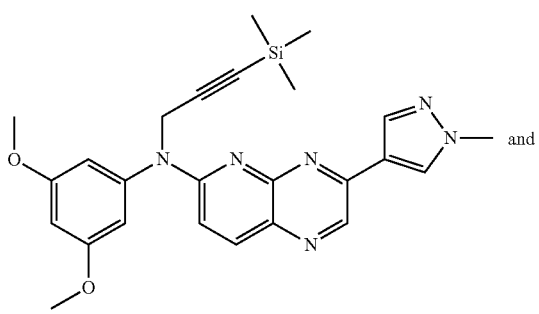

intermediate 13

compound 22

Under $N_2$, to a solution of intermediate 6 (980 mg; 2.7 mmol) in DMF (20 ml) was added at 5° C., NaH (217 mg; 5.4 mmol). The reaction mixture was stirred for 30 minutes at 5° C. and 3-bromo-1-(trimethylsilyl)-1-propyne (0.97 ml; 6.2 mmol) was added dropwise. The reaction mixture was stirred for 1 hour 30 minutes at 5° C. The reaction mixture was poured out into ice water and extracted with EtOAC. The organic layer was washed with brine, dried (MgSO$_4$), filtered and concentrated under reduced pressure. The obtained residue (1.22 g) is a mixture of intermediate 13 and compound 22. The mixture was purified by chromatography over silica gel (15-40 µm 300 g). Mobile phase, 60% Heptane, 5% MeOH, 35% EtOAc). The desired fractions were collected, and evaporated to afford 644 mg (59%) of compound 22.

Example B8a

Preparation of Compounds 45 and 46 compound 45

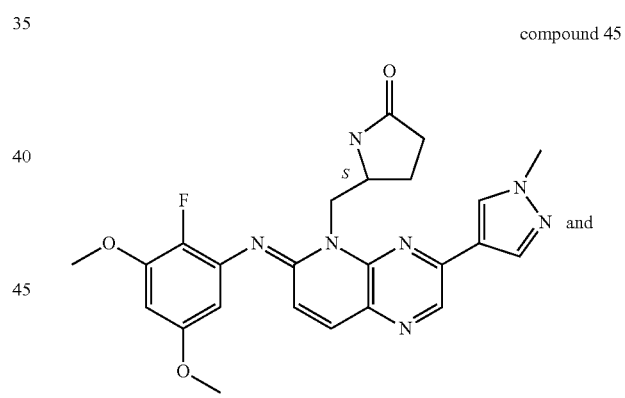

and compound 46

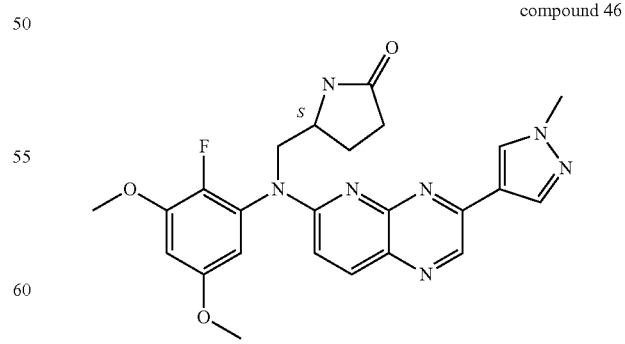

NaH (841 mg; 21.03 mmol) was added to a solution of intermediate 7 (2 g; 5.26 mmol) in DMF (35 mL) at 5° C. under $N_2$ flow. The reaction was stirred at 5° C. for 30 minutes. A solution of (S)-5-(Hydroxy-methyl)-2-pyrrolidinone p-toluenesulfonate (CAS 51693-17-5) (2.1 g; 7.89 mmol) in DMF (15 mL) was added at 5° C. under N₂ flow over a 4 hour period and the reaction mixture was allowed to warm to room temperature and stirred overnight. The reaction mixture was quenched with iced water and extracted with EtOAc. The organic layer was decanted, dried over MgSO₄, filtered and evaporated to dryness. The residue was purified by chromatography over silica gel (irregular SiOH, 15-40 μm, 50 g; mobile phase: gradient from 0.1% NH₄OH, 98% DCM, 2% MeOH to 0.2% NH₄OH, 97% DCM, 3% MeOH). The product fractions were collected and evaporated to give 169 mg (7%) of compound 45, M.P.: 127° C. (gum, Kofler) and 157 mg (6%) of compound 46. M.P.: 131° C. (gum, Kofler).

Analogous Preparation of Compound 158 and 159 Starting from Intermediate 7 and Intermediate 56 compound 193

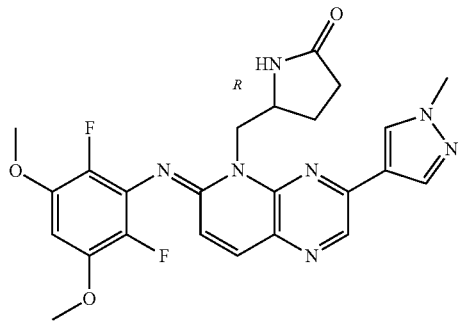

Analogous Preparation of Compound 285 and 286 Starting from Intermediate 110 compound 158

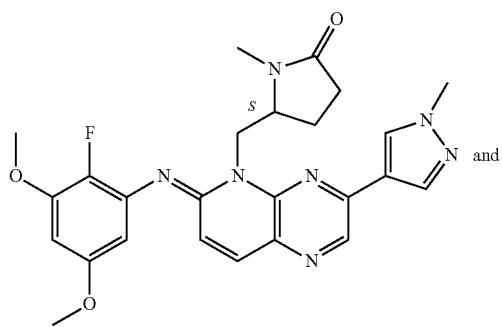

and compound 285

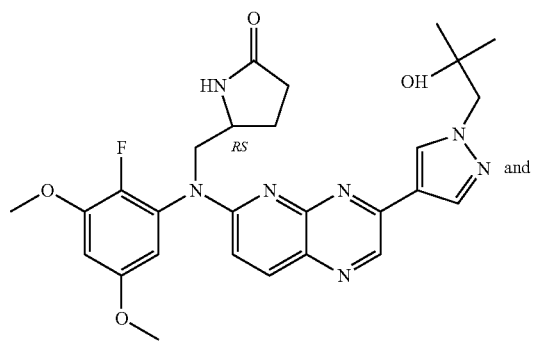

and compound 159

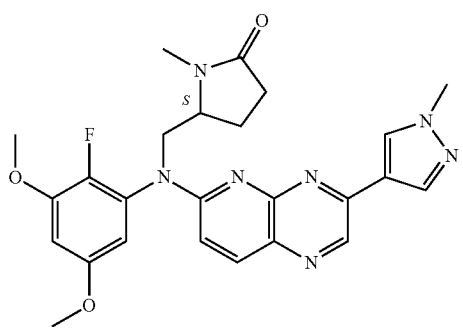

compound 286

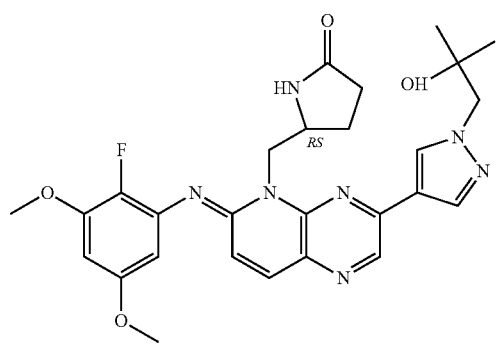

Analogous Preparation of Compound 192 and 193 Starting from Intermediate 12 and Intermediate 18

Example B8a1

Compound 192

Preparation of Compound 49

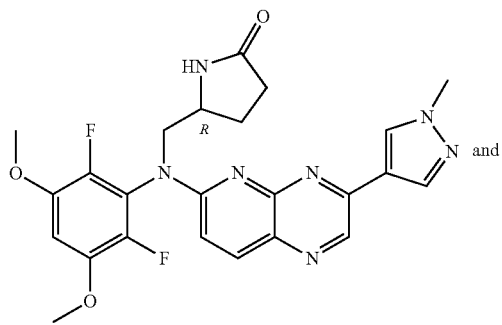

and

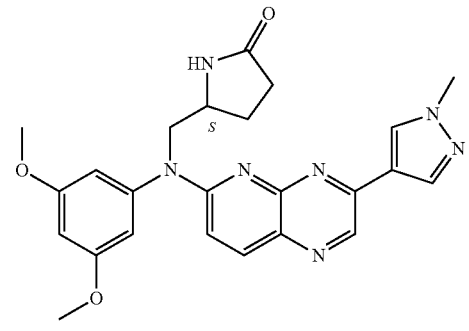

NaH (552 mg; 13.80 mmol) was added to a solution of intermediate 6 (2 g; 5.52 mmol) in DMF (35 mL) at 5° C. under N₂ flow. The reaction was stirred at 5° C. for 30 minutes. A solution of (S)-5-(Hydroxy-methyl)-2-pyrrolidinone p-toluenesulfonate (CAS 51693-17-5) (3.7 g; 13.80 mmol) in DMF (15 mL) was added at 5° C. under N₂ flow over a 2 hour period and the reaction mixture was allowed to warm to room temperature and stirred overnight. The reaction mixture was quenched with iced water and extracted with EtOAc. The organic layer was decanted, dried over MgSO₄, filtered and evaporated to dryness. The residue was purified by chromatography over silica gel (Irregular SiOH, 20-45 µm, 450 g; mobile phase: gradient from 30% Heptane, 15% MeOH, 55% EtOAc to 30% Heptane, 18% MeOH, 52% EtOAc). The product fractions were collected and evaporated to dryness. The residue (375 mg; 15%) was crystallized from ACN/Et₂O to give 302 mg (12%) of compound 49. M.P.: 182° C. (Kofler).

Analogous Preparation of Compound 300

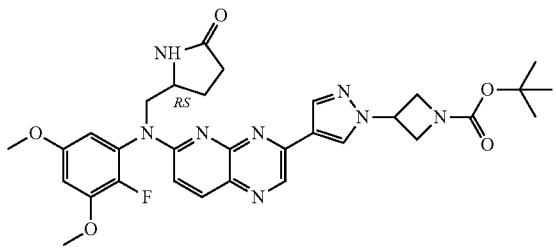

Starting from Intermediate 140

Example B8b

Preparation of Compound 47 and Compound 48 compound 47

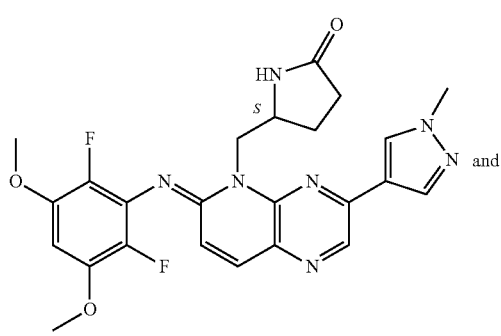

and compound 48

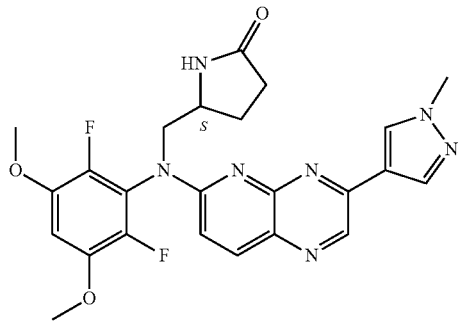

NaH (502 mg; 12.55 mmol) was added to a solution of intermediate 12 (2 g; 5.02 mmol) in DMF (35 mL) at 5° C. under N₂ flow. The reaction was stirred at 5° C. for 30 minutes. A solution of (S)-5-(Hydroxy-methyl)-2-pyrrolidinone p-toluenesulfonate (CAS 51693-17-5) (2 g; 7.53 mmol) in DMF (15 mL) was added at 5° C. under N₂ flow over a 1 hour period and the reaction mixture was allowed to warm to room temperature and stirred overnight. The reaction mixture was quenched with iced water and extracted with EtOAc. The organic layer was decanted, dried over MgSO₄, filtered and evaporated to dryness. The residue was purified by chromatography over silica gel (irregular SiOH, 15-40 µm, 300 g; mobile phase: 0.3% NH₄OH, 97% DCM, 3% MeOH). The product fractions were collected and evaporated to give 478 mg (19%) of compound 47, M.P.: 169° C. (Kofler) and 1 g (40%) of compound 48. M.P.: 134° C. (gum, Kofler).

Example B8c

Preparation of Compound 52 and Compound 53 compound 52

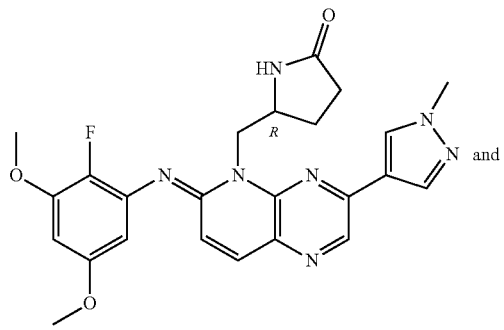

and compound 53

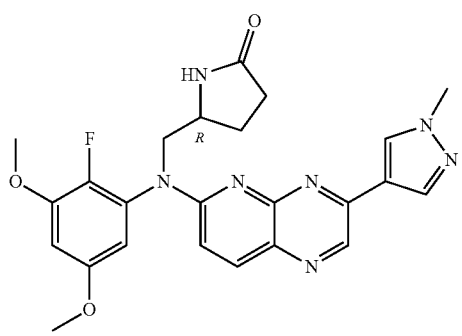

NaH (79 mg; 1.97 mmol) was added to a solution of intermediate 7 (500 mg; 1.31 mmol) in DMF (10 mL) at 5° C. under N$_2$ flow. The reaction was stirred at 5° C. for 30 minutes. A solution of intermediate 18 (531 mg; 1.97 mmol) in DMF (5 mL) was added at 5° C. under N$_2$ flow over a 1 hour period and the reaction mixture was allowed to warm to room temperature and stirred overnight.

The reaction mixture was quenched with iced water and extracted with EtOAc. The organic layer was decanted, dried over MgSO$_4$, filtered and evaporated to dryness. The residue was purified by chromatography over silica gel (Spherical Silica, 5 μm, 150×30.0 mm; mobile phase: gradient from 70% Heptane, 2% MeOH (+10% NH$_4$OH), 28% EtOAc to 0% Heptane, 20% MeOH (+10% NH$_4$OH), 80% EtOAc). The product fractions were collected and evaporated to give 140 mg (22%), which was crystallized from ACN/DiPE, filtered and dried to give 96 mg (15%) of compound 53. M.P.: 176° C. (Kofler) and 208 mg (33%) of compound 52. M.P.: 190° C. (Kofler).

Analogous Preparation of Compounds 160 and 161 Starting from Intermediate 7 and Intermediate 57.

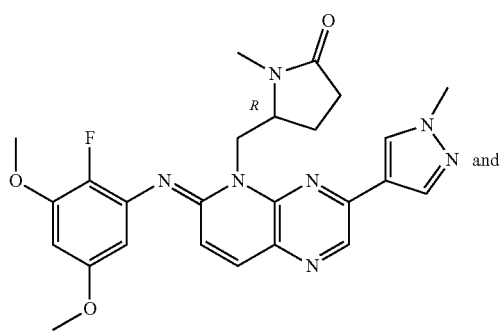

compound 160 compound 161

Example B8c1

Preparation of Compound 54

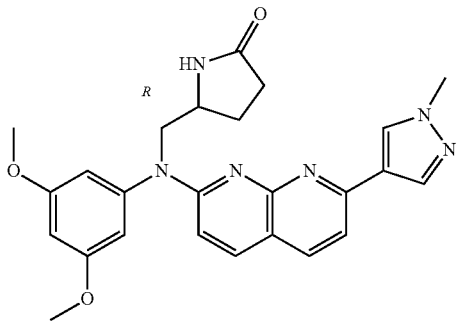

NaH (83 mg; 2.07 mmol) was added to a solution of intermediate 6 (500 mg; 1.38 mmol) in DMF (12 mL) at 5° C. under N$_2$ flow. The reaction was stirred at 5° C. for 30 minutes. A solution of intermediate 18 (557 mg; 2.07 mmol) in DMF (3 mL) was added at 5° C. under N$_2$ flow over a 1 hour period and the reaction mixture was allowed to warm to room temperature and stirred overnight. The reaction mixture was quenched with iced water and extracted with EtOAc. The organic layer was decanted, dried over MgSO$_4$, filtered and evaporated to dryness. The residue was purified by chromatography over silica gel (Spherical Silica, 5 μm, 150×30.0 mm; mobile phase: gradient from 0.2% NH$_4$OH, 98% DCM, 2% MeOH to 1.3% NH$_4$OH, 87% DCM, 13% MeOH). The product fractions were collected and evaporated to dryness yielding 20 mg (3%) of compound 54. M.P.: 125° C. (gum, Kofler).

Example B8d

Preparation of Compounds 55 and 56

Compound 55

-continued compound 56

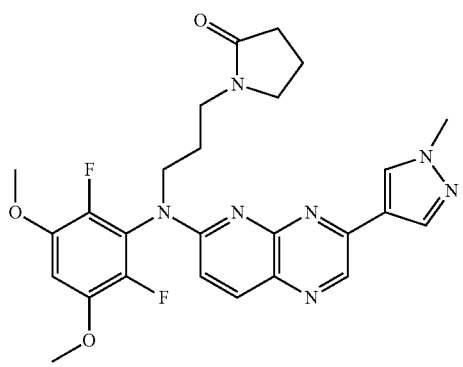

NaH (113 mg; 2.82 mmol) was added to a solution of intermediate 12 (750 mg; 1.88 mmol) in DMF (18 mL) at 5° C. under N₂ flow. The reaction was stirred at 5° C. for 30 minutes. A solution of 1-[3-[(methylsulfonyl)oxy]propyl]-2-pyrrolidinone (625 mg; 2.824 mmol) in DMF (5 mL) was added at 5° C. under N₂ flow over a 1 hour period and the reaction mixture was allowed to warm to room temperature and stirred all over the week end. The reaction mixture was poured onto iced water and extracted with EtOAc. The organic layer was decanted, washed with brine, dried over MgSO₄, filtered and evaporated to dryness. The residue was purified by chromatography over silica gel (Irregular SiOH, 20-45 μm, 450 g; mobile phase: 95% DCM, 5% MeOH). The product fractions were collected and evaporated to dryness yielding 215 mg (22%) which was crystallized from ACN to give 169 mg (17%) of compound 55; M.P.: 227° C. (Kofler) and 207 mg (21%) of compound 56. M.P.: 99° C. (gum, Kofler).

Analogous Preparation of Compounds 119 and 120 Starting from Intermediate 7.

Compound 119

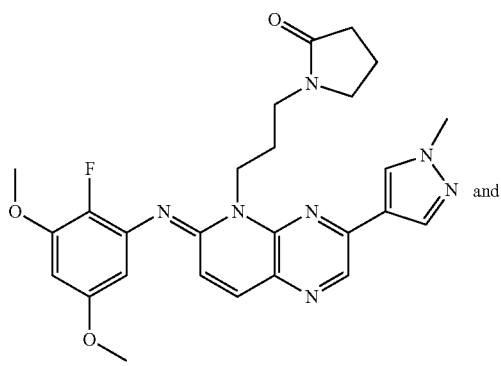

compound 120

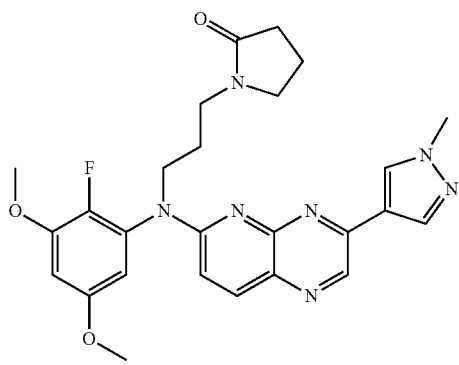

Analogous Preparation of Compounds 133 and 134 Starting from Intermediate 6 compound 133

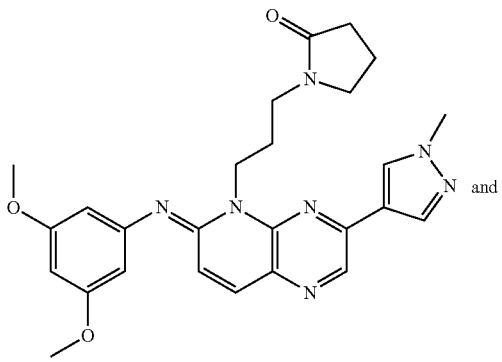 and compound 134

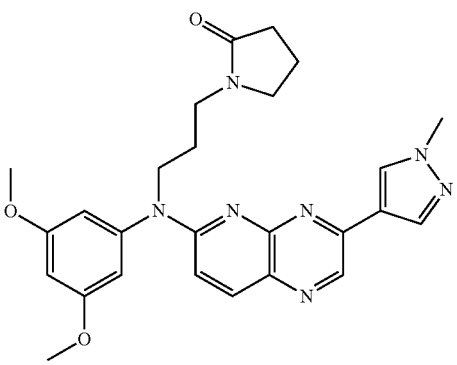

Analogous Preparation of Compounds 150 and 151 Starting from Intermediate 6.

compound 150

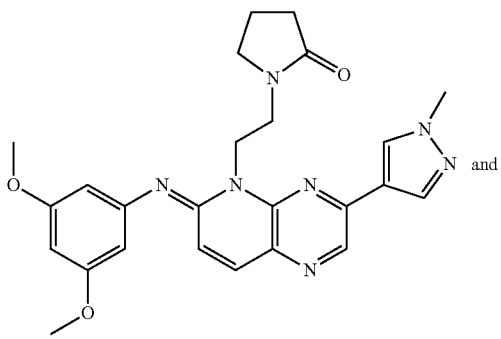 and compound 151

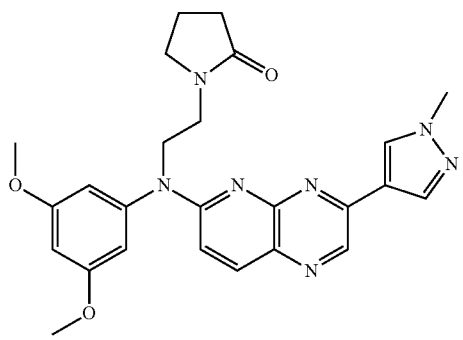

Analogous Preparation of Compounds 156 and 157 Starting from Intermediate 7 compound 156

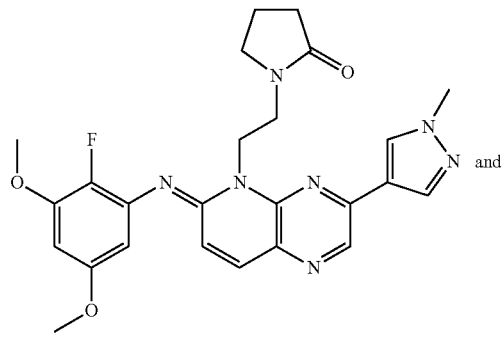

and compound 157

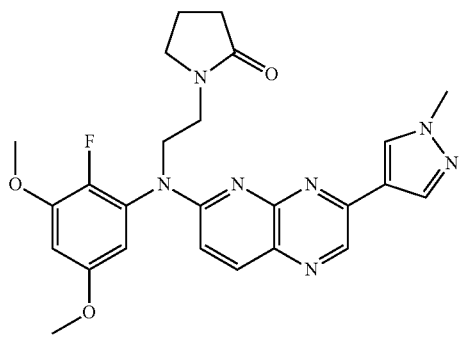

Example B8e

Preparation of Compounds 111 and 112

Compound 111

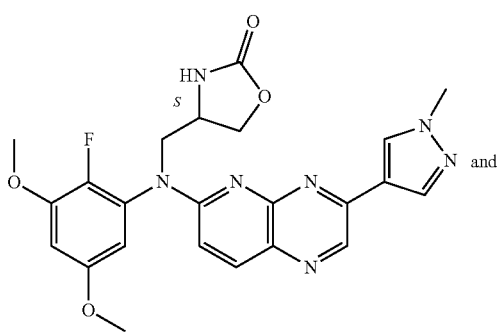

and compound 112

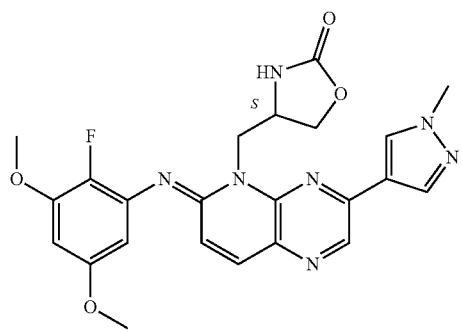

Under N₂, NaH (0.289 g; 7.22 mmol) was added to a solution of intermediate 7 (0.915 g; 2.41 mmol) in DMF (8 mL) at 0° C. and the solution was stirred at room temperature for 30 minutes. (S)-(2-oxooxazolidin-4-yl)methyl 4-methylbenzenesulfonate (CAS 154669-49-5) (0.784 g; 2.89 mmol) was added and the solution was stirred for 18 hours. The reaction mixture was poured into water and extracted with EtOAc. The organic layer was washed with brine, dried over MgSO₄, filtered and concentrated under reduced pressure. The residue (1.1 g) was purified by chromatography over silica gel (irregular SiOH, 15-40 µm, 300 g; mobile phase: 42% Heptane, 8% MeOH, 50% EtOAc). The product fraction were collected and evaporated to give 2 fractions:

Fraction 1: 98 mg of a compound which was taken up with Et₂O. The precipitate was filtered and dried to give 0.093 g (8%) of compound 112. M.P.: 207° C. (DSC).

Fraction 2: 215 mg of an impure compound which was purified by reverse phase chromatography (X-Bridge-C18, 5 µm, 30*150 mm; mobile phase: gradient from 85% NH₄HCO₃ 0.5%, 15% ACN to 0% NH₄HCO₃ 0.5%, 100% ACN). The product fractions were collected and evaporated to dryness. The residue (0.13 g) was crystallized from Et₂O. The precipitate was filtered and dried to give 0.108 g (9%) of compound 111. M.P.: 202° C. (DSC).

Analogous Preparation of Compounds 123 and 124 Starting from Intermediate 7 and (R)-(2-oxooxazolidin-4-yl) methyl 4-methylbenzenesulfonate

211 compound 123

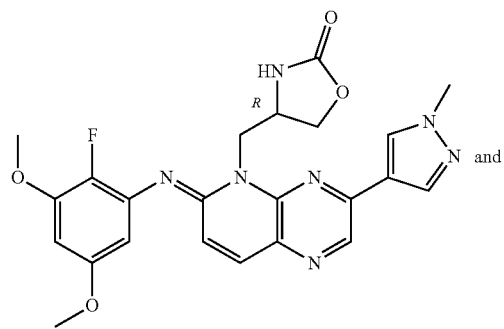

and compounds 124

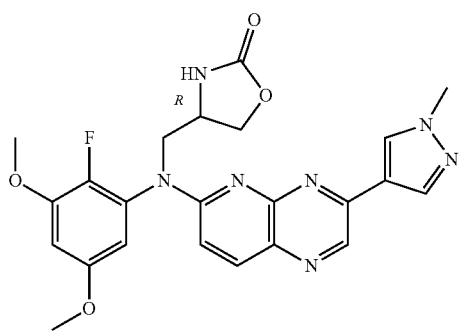

Example B9

Preparation of compound 71

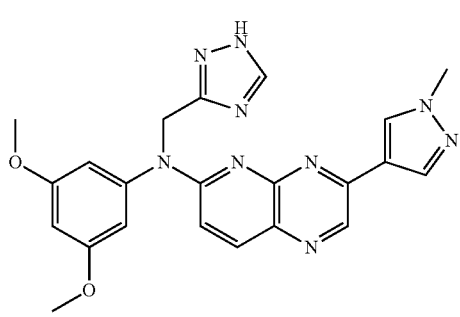 [SMILES: COc1cc(OC)cc(N(Cc2nc[nH]n2)c2ccc3ncc(-c4cnn(C)c4)nc3n2)c1]

TFA (3.3 mL; 43.31 mmol) was added to a solution of intermediate 21 (0.45 g; 0.66 mmol) in DCM (15 mL) and stirred at room temperature for 24 hours. The reaction mixture was poured into ice, basified with a 10% aqueous solution of K$_2$CO$_3$ and extracted with DCM. The organic layer was decanted, dried over MgSO$_4$, filtered and the solvent was evaporated. The residue was purified by chromatography over silica gel (Spherical Silica, 5 μm, 150×30.0 mm; mobile phase: gradient from 0.2% NH$_4$OH, 98% DCM, 2% MeOH to 1% NH$_4$OH, 90% DCM, 10% MeOH). The product fractions were collected and the solvent was evaporated. The residue (185 mg) was crystallized from ACN and Et$_2$O. The precipitate was filtered and dried to give 0.125 g (43%) of compound 71. M.P.: 238° C. (DSC)

212

Analogous Preparation of Compound 85

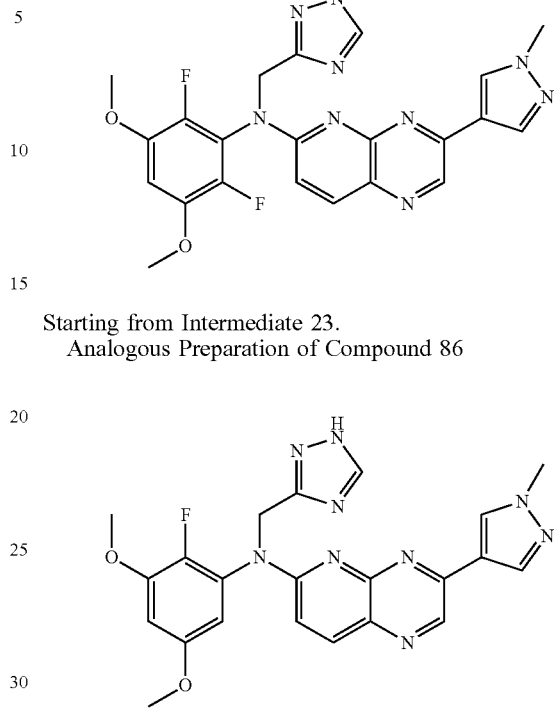

Starting from Intermediate 23.
Analogous Preparation of Compound 86

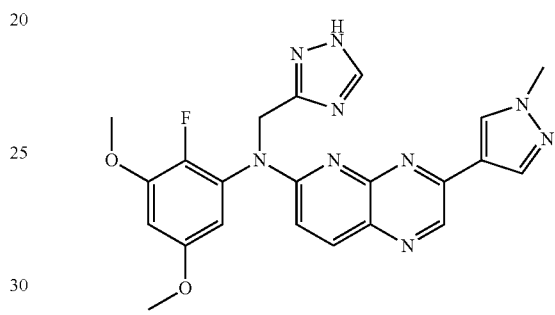

Starting from Intermediate 24.
Analogous Preparation of Compound 206

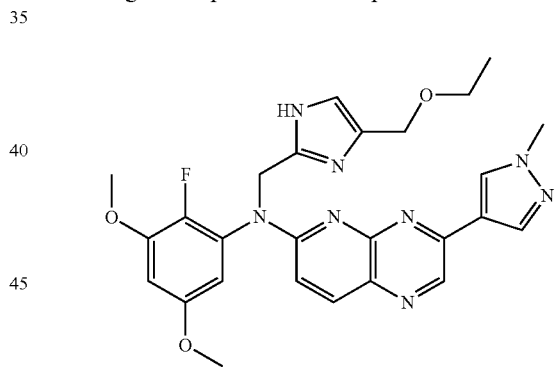

Starting from Intermediate 78

Example B9a

Preparation of Compound 140

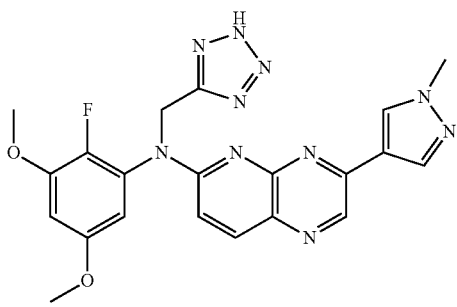 [SMILES: COc1cc(OC)c(F)c(N(Cc2nn[nH]n2)c2ccc3ncc(-c4cnn(C)c4)nc3n2)c1]

A solution of HCl 4M in 1,4-dioxane (2.63 mL; 10.5 mmol) was added to a solution of intermediate 43 (740 mg; 1.05 mmol) in ACN (26 mL). The reaction mixture was heated at 50° C. for 15 hours. The reaction mixture was poured into a saturated aqueous solution of K$_2$CO$_3$ and extracted with DCM. The organic layer was dried over MgSO$_4$, filtered and evaporated to dryness. The residue (0.76 g) was purified by chromatography over silica gel (Spherical Silica, 5 μm, 150×30.0 mm; mobile phase: gradient from 0.5% NH$_4$OH, 95% DCM, 5% MeOH to 1.8% NH$_4$OH, 82% DCM, 18% MeOH). The product fractions were collected and the solvent was evaporated. The residue (0.214 g) was crystallized from MeOH. The precipitate was filtered and dried to give 0.106 g (22%) of compound 140. M.P.: 149° C. (gum, Kofler).

Analogous Preparation of Compound 197

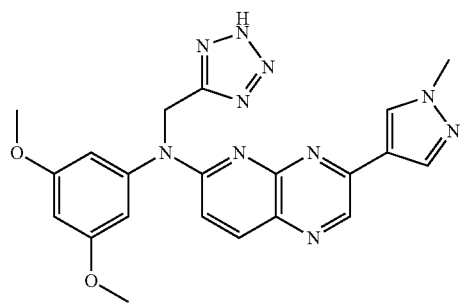 [SMILES: COc1cc(OC)cc(N(Cc2nn[nH]n2)c2ccc3ncc(-c4cnn(C)c4)nc3n2)c1]

Starting from Intermediate 70

Example B10

Preparation of Compounds 87 and 88 compound 87

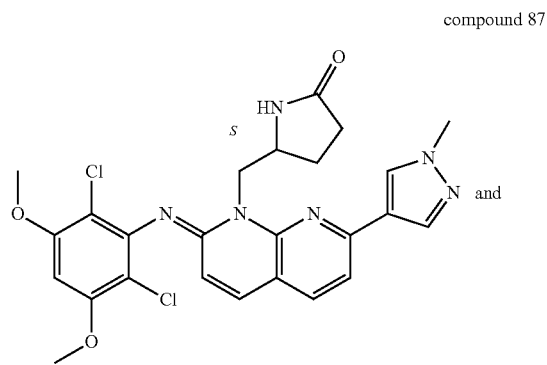

compound 88

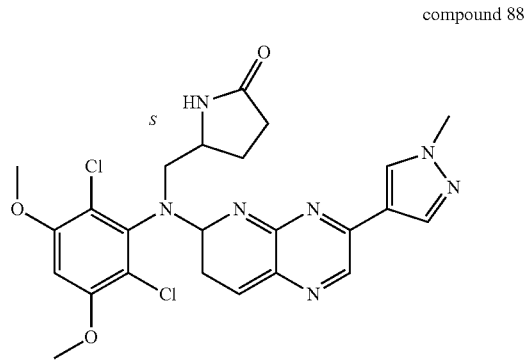

A solution of KOH (2.4 g; 36 mmol) in 2-methyltetrahydrofuran dry (40 mL) and water (4 mL) was stirred for 10 minutes at room temperature. Intermediate 22 (1 g; 2.32 mmol) followed by tetrabutyl ammonium bromide (309 mg; 0.96 mmol) were added. The reaction mixture was stirred at 50° C. for 1 hour and (S)-(+)-5-(hydroxymethyl)-2-pyrrolidinone p-toluenesulfonate (CAS 51693-17-5) (1.3 g; 4.8 mmol) was added. The reaction mixture was stirred for 48 hours at 50° C. The reaction mixture was cooled down to room temperature, poured into water and extracted with EtOAc. The organic layer was washed with brine, dried over MgSO$_4$, filtered and evaporated to dryness. The residue (0.85 g) was purified by chromatography over silica gel (irregular SiOH, 15-40 μm, 300 g; mobile phase: 0.1% NH$_4$OH, 96% DCM, 4% MeOH). The product fractions were collected and the solvent was evaporated to afford 2 fractions:

Fraction 1: 86 mg of an intermediate compound which was crystallized from Et$_2$O to give 50 mg of compound 87. M.P.: 160° C. (kofler).

Fraction 2: 95 mg of an intermediate compound which was crystallized from Et$_2$O to give 75 mg of impure compound 88. The precipitate and the mother layer were dissolved in DCM and the solution was evaporated to dryness. The resulting residue was purified by achiral SFC (DIETHYLAMINOPROPYL, 5 μm, 150× 21.2 mm; mobile phase: 80% CO$_2$, 20% MeOH). The product fractions were collected and evaporated to dryness. The residue (31 mg) was crystallized from Et$_2$O to give 22 mg (2%) of compound 88. M.P.: 175° C.-180° C. (Kofler).

Example B11

Preparation of Compounds 89, 90 and 91 compound 89

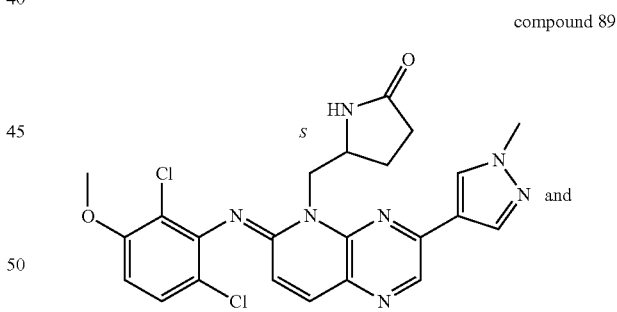

compound 90

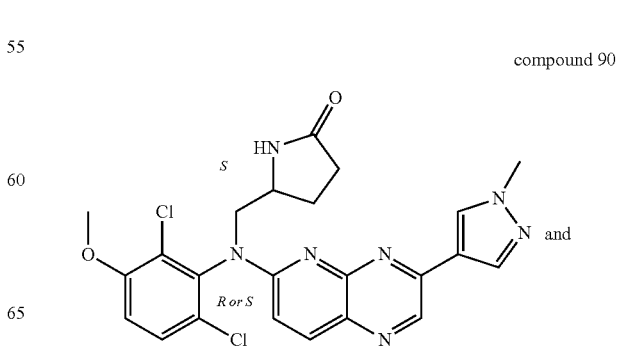

compound 91

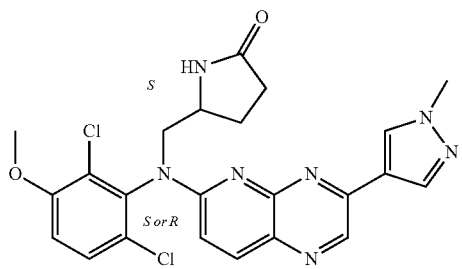

A solution of KOH (1.97 g; 29.91 mmol) in 2-methyltetrahydrofuran dry (40 mL) and water (4 mL) was stirred for 10 minutes at room temperature. Intermediate 19 (800 mg; 1.99 mmol) followed by tetrabutyl ammonium bromide (257 mg; 0.80 mmol) were added at room temperature. The reaction mixture was stirred at 50° C. for 1 hour and (S)-(+)-5-(hydroxymethyl)-2-pyrrolidinone p-toluenesulfonate (CAS 51693-17-5) (1.07 g; 3.99 mmol) was added. The reaction mixture was heated in a sealed reactor at 120° C. using a multimode cavity microwave (CEM MARS system) with a power output ranging from 0 to 400 W for 1h30. The reaction mixture was cooled down to room temperature, poured into water and extracted with EtOAc. The organic layer was washed with brine, dried over MgSO$_4$, filtered and concentrated under reduced pressure. The residue (1.2 g) was purified by chromatography over silica gel (irregular SiOH, 15-40 μm, 300 g; mobile phase: 0.5% NH$_4$OH, 95% DCM, 5% MeOH). The product fractions were collected and evaporated to dryness to give 2 fractions:

Fraction 1: 225 mg of a compound which was crystallized from Et$_2$O to give 168 mg (17%) of compound 89. M.P.: 183° C. (DSC)

Fraction 2: 250 mg of a compound which was crystallized from Et$_2$O. The precipitate was filtered off and dried under vacuum. The resulting residue (0.192 g) was purified by chiral SFC (CHIRALPAK AD-H, 5 m, 250×20 mm; mobile phase: 60% CO$_2$, 40% iPrOH). The product fractions were collected and evaporated to dryness to give 0.072 g (7%) of compound 90 (M.P.: 160° C., gum, Kofler) and 0.075 g (8%) of compound 91 (M.P.: 160° C., gum, Kofler).

Analogous Preparation of Compounds 92, 93 and 94 Starting from Intermediate 19 compound 92

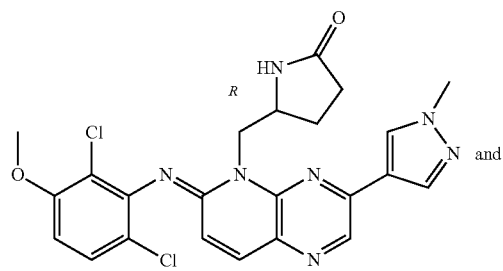

and compound 93

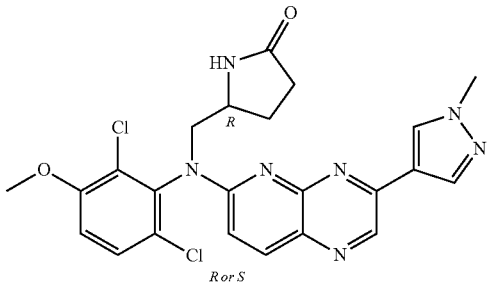

compound 94

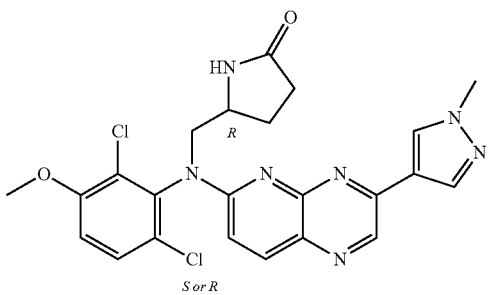

Example B12

Preparation of Compound 97

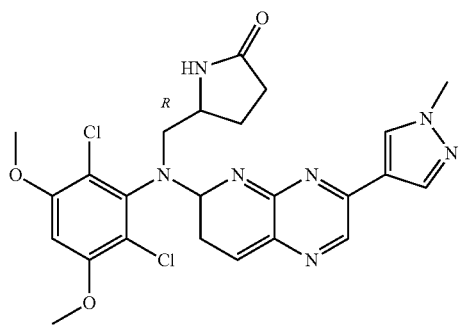

A solution of KOH (1.84 g; 27.82 mmol) in 2-methyltetrahydrofuran dry (25 mL) and water (5 mL) was stirred for 10 minutes at room temperature. Intermediate 22 (800 mg; 1.86 mmol) followed by tetrabutyl ammonium bromide (239 mg; 0.74 mmol) were added. The reaction mixture was stirred at 50° C. for 1 hour and toluene-4-sulfonic acid (R)-5-oxopyrrolidin-2-ylmethyl ester (CAS 128899-31-0) (1 g; 3.71 mmol) was added. The reaction mixture was heated in a sealed reactor at 120° C. using a multimode cavity microwave (CEM MARS system) with a power output ranging from 0 to 400 W for 1 h30. The reaction mixture was cooled down to room temperature, poured into water and extracted with EtOAc. The organic layer was washed with brine, dried over MgSO$_4$, filtered and concentrated under reduced pressure.

The residue (1.2 g) was purified by column chromatography over silica gel (irregular SiOH, 15-40 μm, 40 g; mobile phase: 96% DCM, 4% MEOH, 0.1% NH$_4$OH). The product fractions were collected and the solvent was evaporated to dryness to give 80 mg (8%) of a compound which was crystallized from Et₂O to give, after filtration, 59 mg (6%) of compound 97. M.P.: 150° C. (Kofler).

Example B13

Preparation of Compounds 35 and 36 compound 35 and compound 36

NaH (105 mg; 2.63 mmol) was added to a solution of intermediate 7 (500 mg; 1.31 mmol) in DMF (10 mL) at 5° C. under N₂ flow. The reaction mixture was stirred for 30 minutes at 5° C. and a solution of 4-(chloromethyl)-N,N-dimethyl-1H-imidazole-1-sulfonamide (CAS 161017-64-7) (472 mg; 2.11 mmol) in DMF (3 mL) was added drop wise. The reaction mixture was allowed to warm to room temperature and stirred overnight. The reaction mixture was poured into ice water and extracted with EtOAc. The organic layer was washed with brine, dried over MgSO₄, filtered and evaporated till dryness. The residue was purified by chromatography over silica gel (Irregular SiOH, 20-45 μm; mobile phase: 40% Heptane, 10% MeOH, 50% EtOAc). The pure fractions were collected and concentrated to give 70 mg (9%) of compound 35 and 590 mg (79%) of compound 36. M.P.: 100° C. (gum, Kofler).

Analogous Preparation of Compound 113

And Compound 114

Analogous Preparation of Compound 116

And Compound 117

Using Intermediate 36.
Analogous Preparation of Compound 126
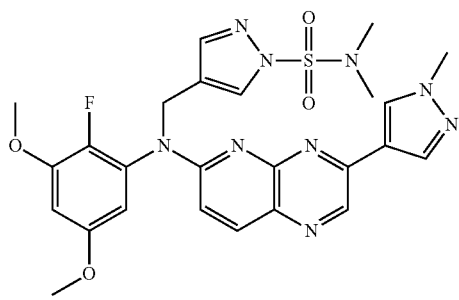 [SMILES: COc1cc(OC)c(F)c(N(Cc2cnn(S(=O)(=O)N(C)C)c2)c2ccc3ncc(-c4cnn(C)c4)nc3n2)c1]
And Compound 127
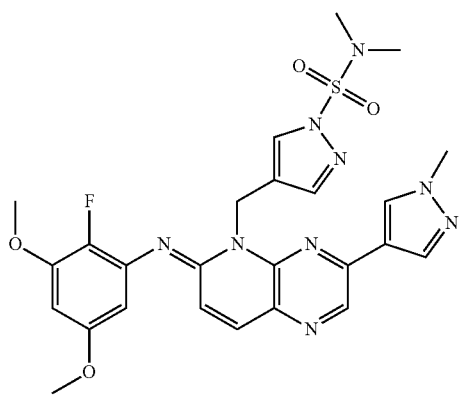 [SMILES: COc1cc(/N=c2\ccc3ncc(-c4cnn(C)c4)nc3n2Cc2cnn(S(=O)(=O)N(C)C)c2)c(F)c(OC)c1]
Starting from Intermediate 7 and Intermediate 39
Analogous Preparation of Compound 178
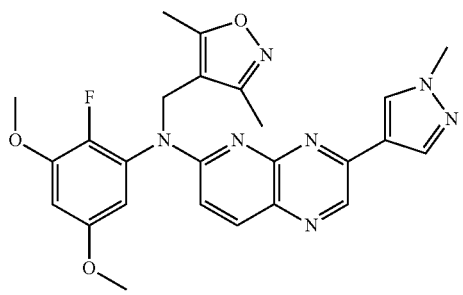 [SMILES: COc1cc(OC)c(F)c(N(Cc2c(C)noc2C)c2ccc3ncc(-c4cnn(C)c4)nc3n2)c1]
And Compound 179
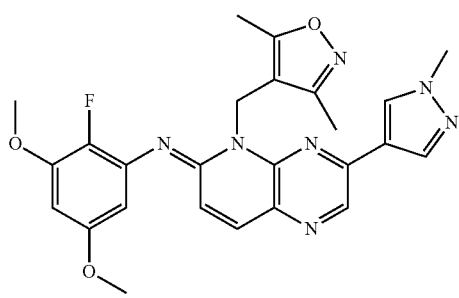 [SMILES: COc1cc(/N=c2\ccc3ncc(-c4cnn(C)c4)nc3n2Cc2c(C)noc2C)c(F)c(OC)c1]
Starting from Intermediate 7
Analogous Preparation of Compound 180
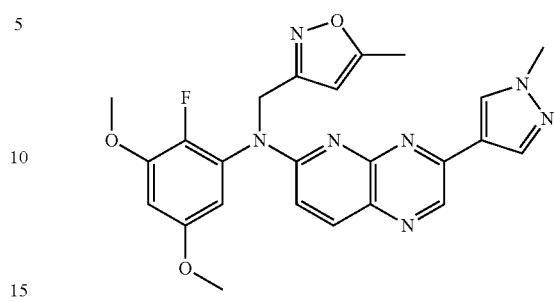
And Compound 181
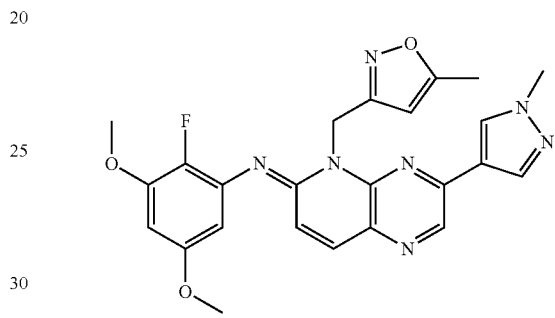
Starting from Intermediate 7
Analogous Preparation of Compound 184
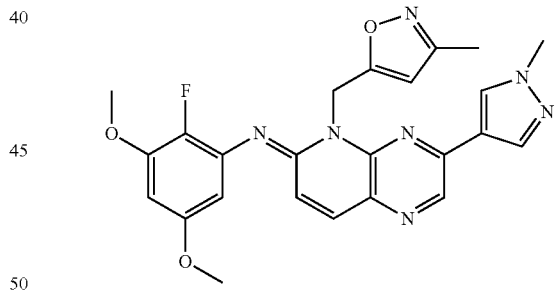
And Compound 185
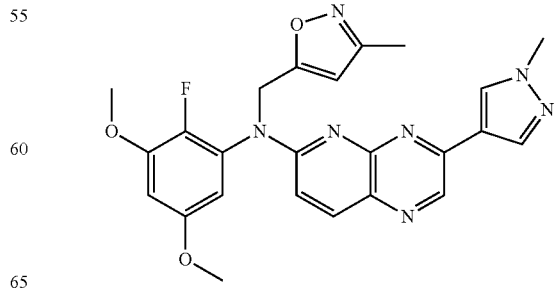

Starting from Intermediate 7
Analogous Preparation of Compound 195

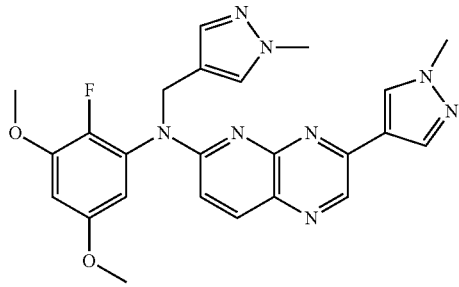 [SMILES: COc1cc(OC)c(F)c(N(Cc2cnn(C)c2)c2ccc3ncc(-c4cnn(C)c4)nc3n2)c1]

And Compound 196

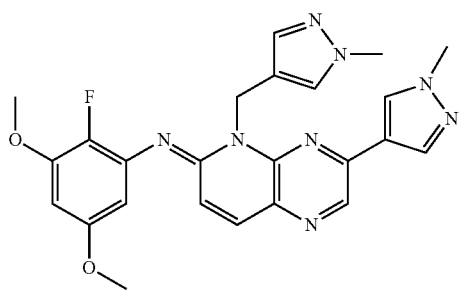 [SMILES: COc1cc(/N=c2\ccc3ncc(-c4cnn(C)c4)nc3n2Cc2cnn(C)c2)c(F)c(OC)c1]

Starting from Intermediate 7

Example B14

Preparation of Compound 129

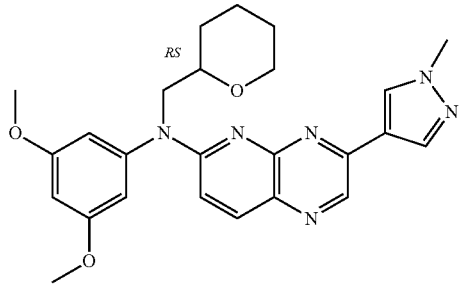 [SMILES: COc1cc(OC)cc(N(CC2CCCCO2)c2ccc3ncc(-c4cnn(C)c4)nc3n2)c1]

and Compound 130

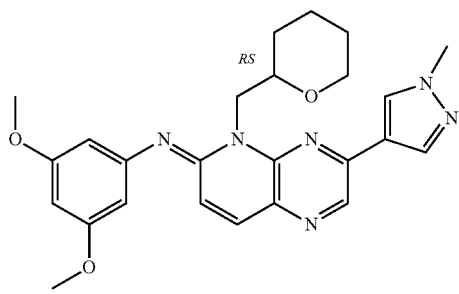 [SMILES: COc1cc(/N=c2\ccc3ncc(-c4cnn(C)c4)nc3n2CC2CCCCO2)cc(OC)c1]

NaH (46 mg; 1.15 mmol) was added to a solution of intermediate 6 (208 mg; 0.57 mmol) in DMF (5 mL) under $N_2$ at 10° C. The solution was stirred at 10° C. for 30 minutes and 2H-Pyran-2-methanol tetrahydro-2-(4-methylbenzenesulfonate) (CAS 75434-63-8) (241 mg; 0.89 mmol) was added portion wise. The solution was allowed to slowly warm to room temperature, overnight, poured into ice and extracted with EtOAc. The organic layer was washed with brine, dried over $MgSO_4$, filtered off and the solvent was evaporated. The residue (0.69 g) was purified by chromatography over silica gel (Spherical Silica, 5 μm, 150×30.0 mm; mobile phase: gradient from 0.2% $NH_4OH$, 98% DCM, 2% MeOH to 0.8% $NH_4OH$, 92% DCM, 8% MeOH). The product fractions were collected and the solvent was evaporated to give 2 fractions:

Fraction 1: 110 mg of a compound which was crystallized from acetone and $Et_2O$. The precipitate was filtered and dried to give 83 mg (31%) of compound 129. M.P.: 137° C. (Kofler).

Fraction 2:12 mg of an impure compound which was purified by achiral SFC (amino, 6 μm, 150×21.2 mm; mobile phase: gradient from 0.3% isopropylamine, 82% $CO_2$, 18% MeOH to 0.3% isopropylamine, 70% $CO_2$, 30% MeOH). The product fractions were collected and the solvent was evaporated to give 8 mg (3%) of compound 130 (94% of purity based on LC/MS).MP: 210° C. (kofler)

Analogous Preparation of Compounds 143 and 144 Starting from Intermediate 7 and Intermediate 49

Compound 143

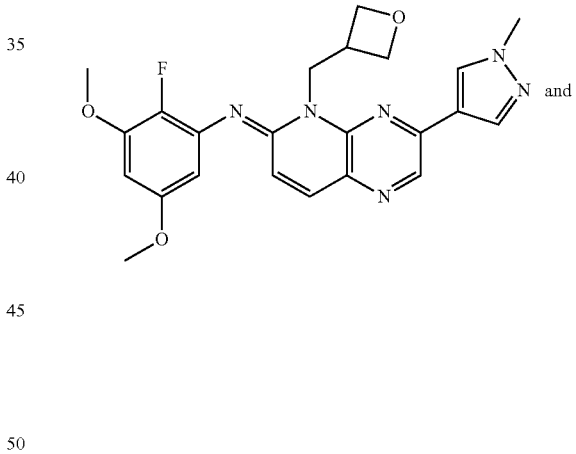

and compound 144

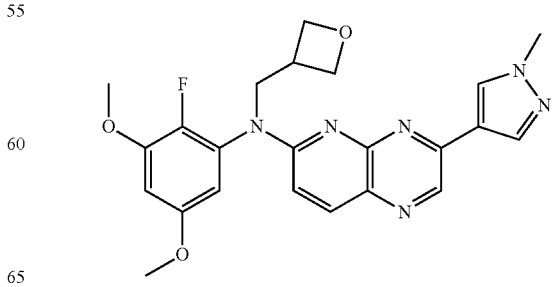

223

Analogous Preparation of Compounds 165 and 166 Starting from Intermediate 6

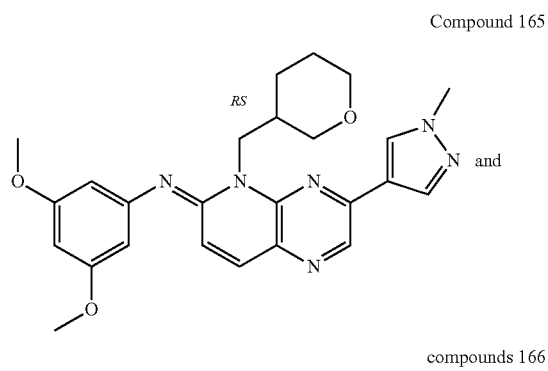

Compound 165 and compounds 166

Example B14a

Preparation of Compound 139

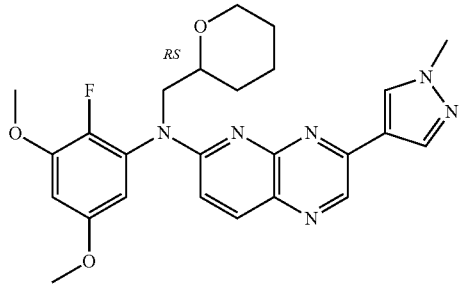 [SMILES: COc1cc(OC)c(F)c(N(CC2CCCCO2)c2ccc3ncc(-c4cnn(C)c4)nc3n2)c1]

NaH (87 mg; 2.19 mmol) was added under N₂ at 10° C. to a solution of intermediate 7 (208 mg; 0.55 mmol) in DMF (5 mL). The solution was stirred at 10° C. for 30 minutes. Tetrahydro-2H-pyran-2-ylmethyl 4-methylbenzenesulfonate (CAS 75434-63-8) (443 mg; 1.64 mmol) was added portion wise and the solution was allowed to slowly warm to room temperature and stirred overnight. The reaction mixture was poured into ice and extracted with EtOAc. The organic layer was washed with brine, dried over MgSO₄, filtered and evaporated to dryness. The residue (0.25 g) was purified by chromatography over silica gel (Spherical Silica, 5 μm, 150×30.0 mm; mobile phase: gradient from 0% NH₄OH, 0% MeOH, 100% DCM to 0.8% NH₄OH, 92% DCM, 8% MeOH). The product fractions were collected and the solvent was evaporated to give 0.024 g (9%) of compound 139. M.P.: 94° C. (Kofler).

224

Analogous Preparation of Compound 142 Starting from Intermediate 6 and 149

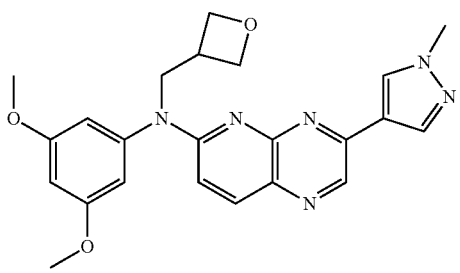 [SMILES: COc1cc(OC)cc(N(CC2COC2)c2ccc3ncc(-c4cnn(C)c4)nc3n2)c1]

Analogous Preparation of Compound 187

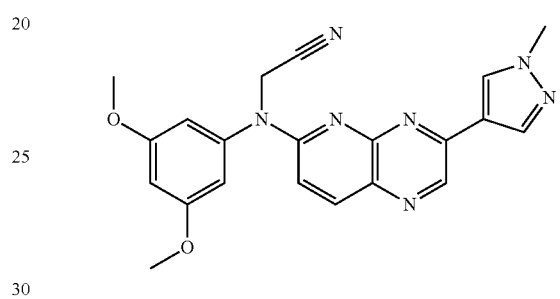

Starting from Intermediate 7
Analogous Preparation of Compound 189

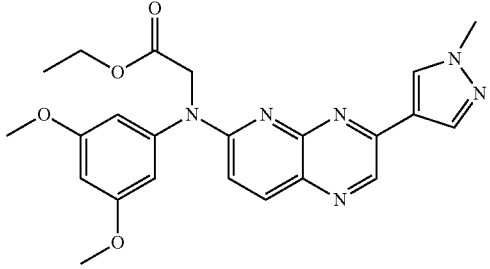 [SMILES: CCOC(=O)CN(c1cc(OC)cc(OC)c1)c1ccc2ncc(-c3cnn(C)c3)nc2n1]

Starting from Intermediate 6
Analogous Preparation of Compound 214

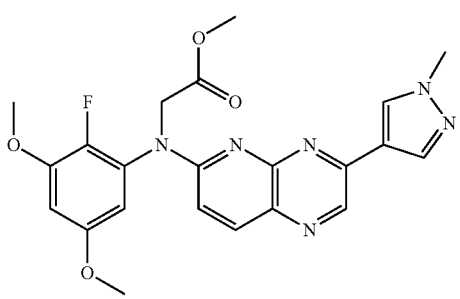 [SMILES: COC(=O)CN(c1ccc2ncc(-c3cnn(C)c3)nc2n1)c1cc(OC)cc(OC)c1F]

Starting from Intermediate 7
  Analogous Preparation of Compound 234

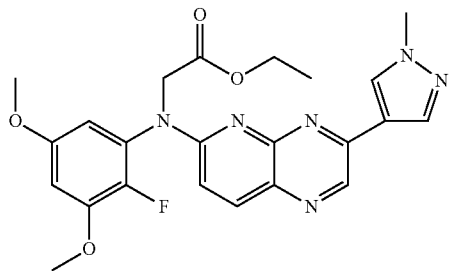 [SMILES: CCOC(=O)CN(c1ccc2ncc(-c3cnn(C)c3)nc2n1)c1cc(OC)cc(OC)c1F]

Starting from Intermediate 7

Example B15

Preparation of Compound 141

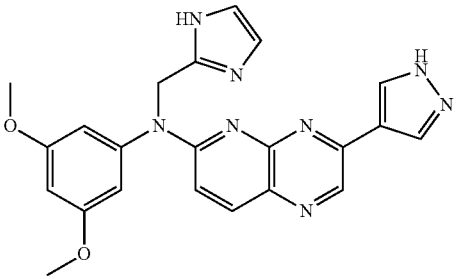 [SMILES: COc1cc(OC)cc(N(Cc2ncc[nH]2)c2ccc3ncc(-c4cn[nH]c4)nc3n2)c1]

A solution of tetrabutylammonium fluoride 1M in THF (6.53 mL; 6.53 mmol) was added to a solution of intermediate 48 (450 mg; 0.65 mmol) in THF (47 mL). The reaction mixture was refluxed for 18 hours, poured into ice and extracted with EtOAc. The organic layer was washed with a saturated solution of NaHCO$_3$, then with brine, dried over MgSO$_4$, filtered and the solvent was evaporated. The residue (1.13 g) was purified by chromatography over silica gel (irregular SiOH, 20-45 μm, 450 g; mobile phase: 0.5% NH$_4$OH, 93% DCM, 7% MeOH). The product fractions were collected and the solvent was evaporated. The residue (0.128 g) was taken up with ACN. The precipitate was filtered and dried to give 0.088 g (31%, yellow solid) of compound 141. M.P.: 285° C. (DSC).

Analogous Preparation of Compound 248

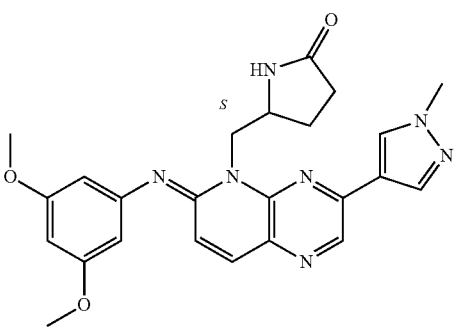

Starting from Intermediate 67.
  Analogous Preparation of Compound 190

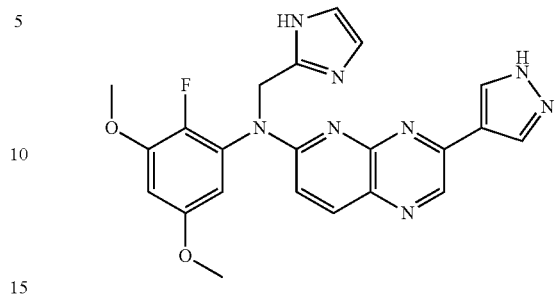

Starting from Intermediate 66
  Analogous Preparation of Compound 228 Starting from Intermediate 94

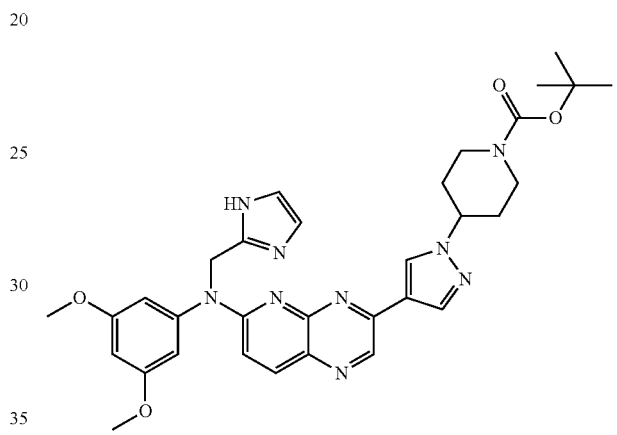

Analogous Preparation of Compound 238

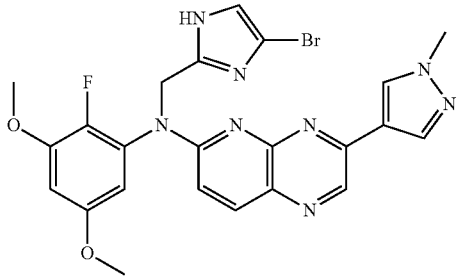 [SMILES: COc1cc(OC)c(F)c(N(Cc2nc(Br)c[nH]2)c2ccc3ncc(-c4cnn(C)c4)nc3n2)c1]

Starting from Intermediate 107
  Analogous Preparation of Compound 253

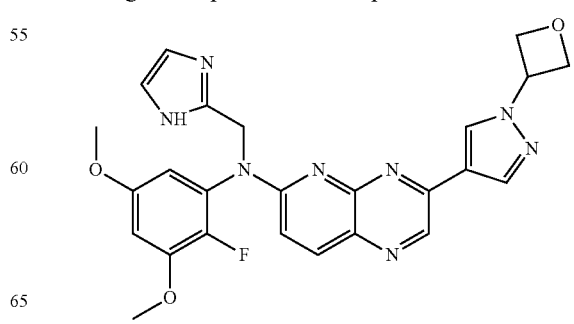

Starting from Intermediate 115

Analogous Preparation of Compound 302

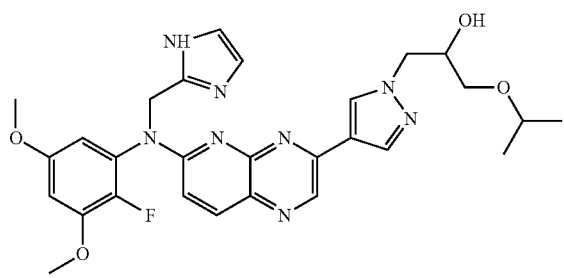 [SMILES: COc1cc(OC)c(F)c(N(Cc2ncc[nH]2)c2ccc3ncc(-c4cnn(CC(O)COC(C)C)c4)nc3n2)c1]

Starting from Intermediate 145 (the Reaction was Performed in the Presence of Tetrabutylammonium Fluoride at Room Temperature)

Example B16

Preparation of Compound 146

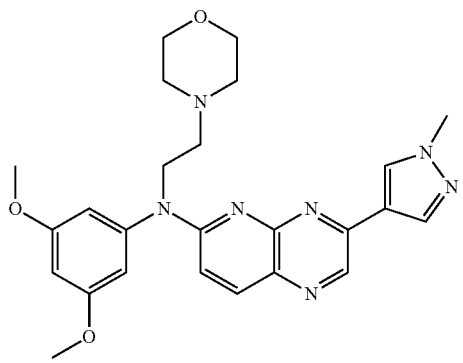 [SMILES: COc1cc(OC)cc(N(CCN2CCOCC2)c2ccc3ncc(-c4cnn(C)c4)nc3n2)c1]

1.66HCl and Compound 147

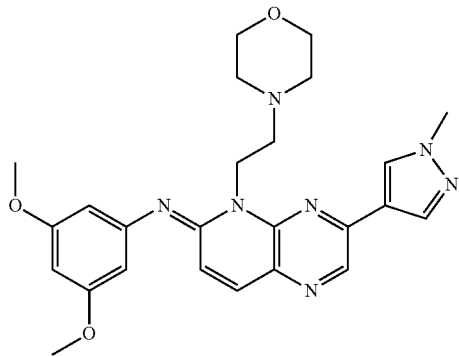 [SMILES: COc1cc(/N=c2\ccc3ncc(-c4cnn(C)c4)nc3n2CCN2CCOCC2)cc(OC)c1]

2.76HCl

NaH (41 mg; 1.04 mmol) was added to a solution of intermediate 6 (250 mg; 0.69 mmol) in DMF (5 mL) at 5° C. under $N_2$ flow and the reaction mixture was stirred at 5° C. for 30 minutes. A solution of 4-(2-chloroethyl)morpholine (CAS 3240-94-6) (155 mg; 1.04 mmol) in DMF (3 mL) was added at 5° C. under $N_2$ flow over a 1 hour period and the reaction mixture was allowed to warm to room temperature and stirred overnight. The reaction mixture was poured onto iced water and extracted with EtOAc. The organic layer was decanted, washed with brine, dried over $MgSO_4$, filtered and evaporated to dryness. The residue (460 mg) was purified by chromatography over silica gel (irregular SiOH, 15-40 µm, 30 g; mobile phase: 0.5% $NH_4OH$, 97% DCM, 3% MeOH). The product fractions were collected and evaporated to dryness yielding 2 fractions:

Fraction 1: 107 mg of a compound which was dissolved in ACN. The solution was cooled in an ice bath and a 4N solution of HCl in 1,4-dioxane was added. The hydrochloride salt was filtered, washed with $Et_2O$ and dried yielding 109 mg (28%) of compound 146. M.P.: 143° C. (gum, Kofler). $C_{25}H_{29}N_7O_3 \cdot 1.66HCl \cdot 2.11H_2O$ Fraction 2: 167 mg of an impure compound which was purified by achiral SFC (CYANO, 6 µm, 150×21.2 mm; mobile phase: 0.3% isopropylamine, 82% $CO_2$, 18% MeOH). The product fractions were collected and evaporated to dryness. The residue was dissolved in ACN. The solution was cooled in an ice bath and a 4N solution of HCl in 1,4-dioxane was added. The hydrochloride salt was filtered, washed with $Et_2O$ and dried yielding 72 mg (17%) of compound 147. M.P.: 162° C. (gum, Kofler). $C_{25}H_{29}N_7O_3 \cdot 2.76HCl \cdot 2.41H_2O$.

Analogous Preparation of Compound 148

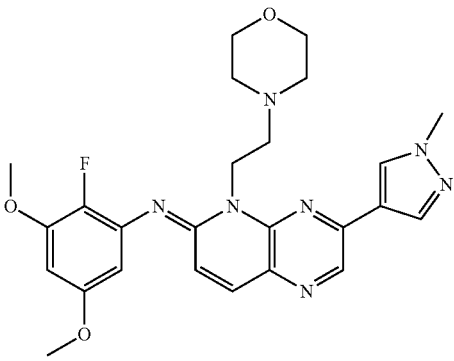 [SMILES: COc1cc(/N=c2\ccc3ncc(-c4cnn(C)c4)nc3n2CCN2CCOCC2)c(F)c(OC)c1]

2.37HCl and Compound 149

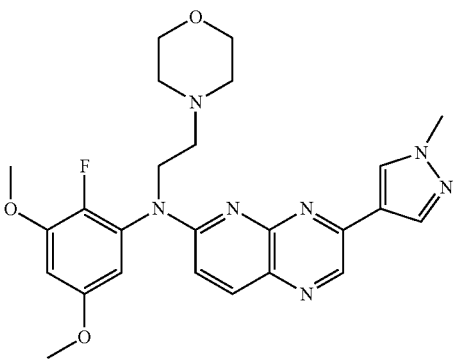 [SMILES: COc1cc(OC)c(F)c(N(CCN2CCOCC2)c2ccc3ncc(-c4cnn(C)c4)nc3n2)c1]

1.71HCl Starting from Intermediate 7

Example B17

Preparation of Compound 154

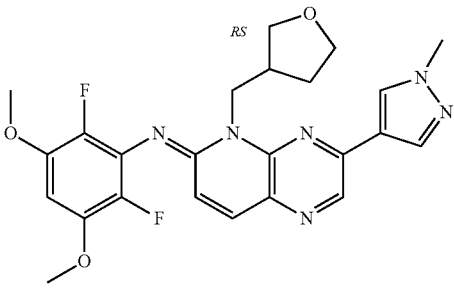 [SMILES: COc1cc(OC)c(F)c(/N=c2\ccc3ncc(-c4cnn(C)c4)nc3n2CC2CCOC2)c1F]

NaH (161 mg; 4.02 mmol) was added portion wise to a solution of intermediate 12 (0.8 g; 2.01 mmol) in DMF (25 mL) under N₂ at 5° C. The reaction mixture was stirred for 30 minutes at 5° C. and a solution of 3-bromomethyl-tetrahydro-furan (484 mg; 4.02 mmol) in DMF (5 mL) was added drop wise. The reaction mixture was allowed to reach room temperature and stirred for 48 hours. The reaction mixture was poured into ice water and extracted with EtOAc. The organic layer was decanted, washed with brine (twice), dried over MgSO₄, filtered and evaporated to dryness. The residue (1 g) was purified by chromatography over silica gel (irregular SiOH, 15-40 µm, 40 g; mobile phase: 0.1% NH₄OH, 3% MeOH, 97% DCM). The product fractions were collected and evaporated to give 0.15 g (15%) of an intermediate compound which was crystallized from Et₂O to give 48 mg (5%) of compound 154. M.P.: 226° C. (Kofler).

Analogous Preparation of Compound 226

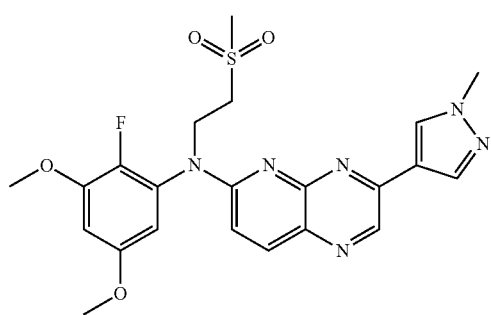 [SMILES: COc1cc(OC)c(F)c(N(CCS(C)(=O)=O)c2ccc3ncc(-c4cnn(C)c4)nc3n2)c1]

Starting from Intermediate 7

Example B17a

Preparation of Compounds 169, 170, 171 and 172 compound 169

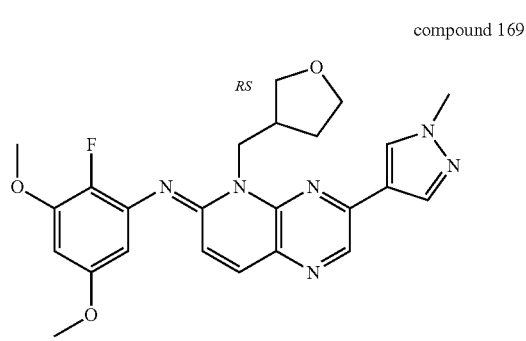

compound 170

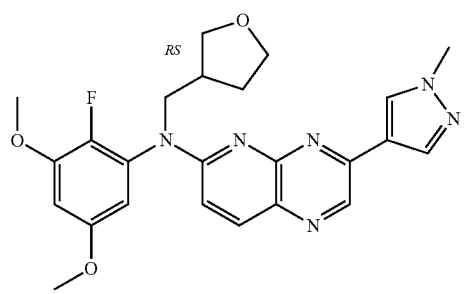

compound 171

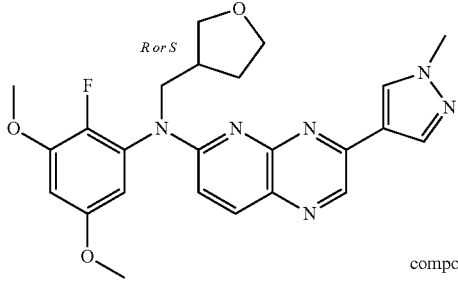

compound 172

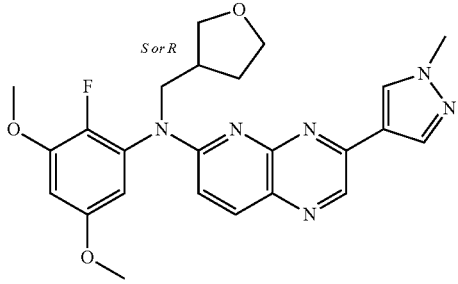

NaH (109 mg; 2.73 mmol) was added portion wise to a solution of intermediate 7 (260 mg; 0.68 mmol) in DMF (5 mL) at 5° C. under N₂. The reaction mixture was stirred for 30 minutes at 5° C. and a solution of 3-bromomethyl-tetrahydro-furan (CAS 165253-29-2) (450 mg; 2.73 mmol) in DMF (3 mL) was added drop wise. The reaction mixture was allowed to reach room temperature and stirred for 48 hours. The reaction mixture was poured into ice water and EtOAc was added. The organic layer was decanted, washed with brine (twice), dried over MgSO₄, filtered and evaporated to dryness. The residue (0.35 g) was purified by chromatography over silica gel (irregular SiOH, 15-40 µm, 30 g; mobile phase: 40% Heptane, 8% MeOH, 52% EtOAc). The product fractions were collected and the solvent was evaporated to give 2 fractions:

Fraction 1: 56 mg (18%) of compound 169 (M.P.: 80° C., gum, kofler)

Fraction 2: 80 mg of a compound which was taken-up with Et₂O to give, after filtration, 70 mg (22%) of compound 170. M.P.: 80° C. (gum, Kofler). 52 mg of compound 170 were purified by chiral SFC (CHIRALPAK AD-H, 5 µm, 250×20 mm; mobile phase: 50% CO₂, 50% MeOH). The product fractions were collected and the solvent was evaporated to give 2 additional fractions:

Fraction 3: 26 mg of compound 171. MP: 172° C. (kofler)

Fraction 4: 26 mg of compound 172. MP: 170° C. (kofler)

Example B18

Preparation of Compound 173

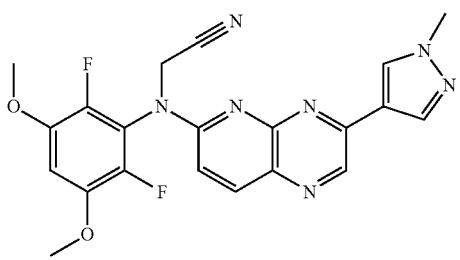 [SMILES: COc1cc(OC)c(F)c(N(CC#N)c2ccc3ncc(-c4cnn(C)c4)nc3n2)c1F]

A solution of KOH (1.74 g; 26.36 mmol) in 2-methyltetrahydrofuran dry (15 mL) was stirred for 10 minutes at room temperature. Water (2.5 mL), intermediate 12 (700 mg; 1.76 mmol) followed by tetrabutylammonium bromide (142 mg; 0.44 mmol) were added. The reaction mixture was stirred at 50° C. for 1 hour and bromoacetonitrile (0.22 mL; 3.16 mmol) was added. The reaction mixture was stirred for 24 hours at 50° C., cooled to room temperature, then poured into ice water and extracted with EtOAc. The organic layer was decanted, washed with brine (twice), dried over MgSO4, filtered and evaporated to dryness. The residue (0.8 g) was purified by chromatography over silica gel (irregular SiOH, 15-40 µm, 50 g; mobile phase: 0.1% NH4OH, 3% MeOH, 97% DCM). The resulting residue (0.4 g) was again purified by chromatography over silica gel (Spherical Silica, 5 µm, 150×30.0 mm; mobile phase: gradient from 0.1% NH4OH, 99% DCM, 1% MeOH to 0.7% NH4OH, 93% DCM, 7% MeOH). The product fractions were collected and evaporated to give 65 mg of a compound which was crystallized from Et2O yielding 44 mg (6%) of compound 173, M.P.: 250° C. (Kofler).

Analogous Preparation of Compound 298

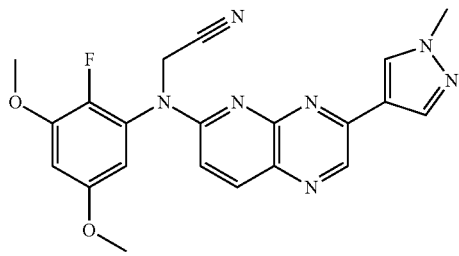 [SMILES: COc1cc(OC)c(F)c(N(CC#N)c2ccc3ncc(-c4cnn(C)c4)nc3n2)c1]

Starting from Intermediate 7

Example B19

Preparation of Compound 217

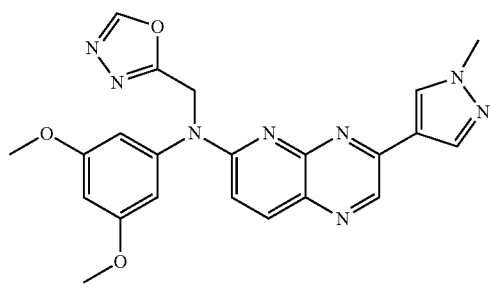 [SMILES: COc1cc(OC)cc(N(Cc2nnco2)c2ccc3ncc(-c4cnn(C)c4)nc3n2)c1]

A solution of intermediate 91 (350 mg; 0.74 mmol) in xylene (40 mL) was refluxed for 36 hours. The reaction mixture was poured into water and extracted with EtOAc. The organic layer was washed with brine, dried over MgSO4, filtered and evaporated to dryness. The residue was purified by chromatography over silica gel (spherical silica, 5 µm, 150×30.0 mm; mobile phase: gradient from 0.1% NH4OH, 1% MeOH, 99% DCM to 0.8% NH4OH, 8% MeOH, 92% DCM). The product fractions were collected and evaporated to dryness. The residue (75 mg) was taken up in ACN. The precipitate was filtered, washed with ACN then Et2O and dried yielding 48 mg (15%) of compound 217. M.P.: 240° C. (Kofler).

Example B20

Preparation of Compound 251

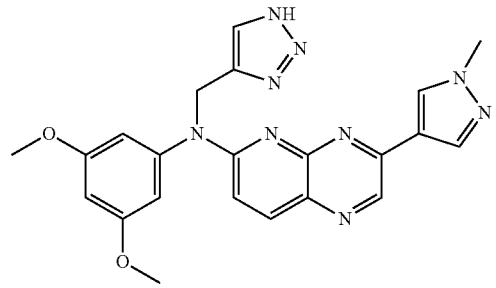 [SMILES: COc1cc(OC)cc(N(Cc2c[nH]nn2)c2ccc3ncc(-c4cnn(C)c4)nc3n2)c1]

A solution of HCl 4N in 1,4-dioxane (0.84 mL; 3.349 mmol) was added to a solution of intermediate 112 (319 mg; 0.335 mmol) in ACN (8 mL) and the reaction mixture was heated at 50° C. for 18 hours. The reaction mixture was poured into a 10% cold aqueous solution of K2CO3 and extracted with EtOAc. The organic layer was decanted, washed with brine, dried over MgSO4, filtered and evaporated to dryness. The residue was purified by chromatography over silica gel (irregular SiOH, 15-40 µm, 24 g; mobile phase: gradient from 95% DCM, 5% MeOH, 0.1% NH4OH to 95% DCM, 5% MeOH, 0.5% NH4OH). The product fractions were collected and evaporated to dryness. The residue (120 mg, 81%) was gathered with 50 mg coming from another batch (performed on 415 mg of intermediate 112). The resulting residue was crystallized from ACN. The precipitate was filtered, washed with Et2O and dried yielding 120 mg (29% based on the 2 batches) of compound 251 (81%), MP=247° C. (Kofler).

Analogous Preparation of Compound 258

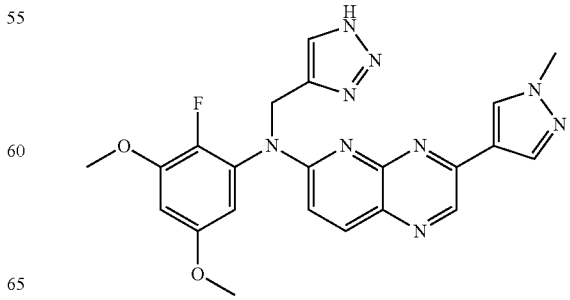

Starting from Intermediate 116

Example B21

Preparation of Compounds 207 and 208 compound 207

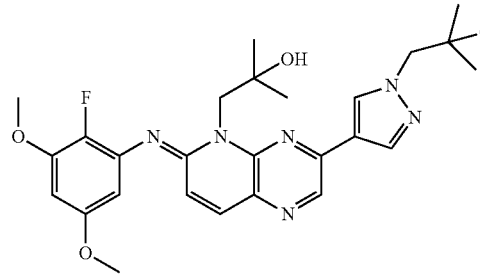

and compound 208

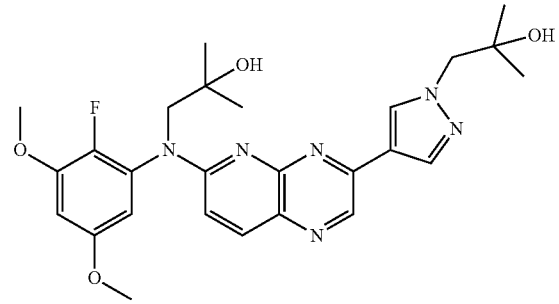

Intermediate 26 (300 mg; 0.82 mmol), isobutylene oxide (3 mL; 33.62 mmol) and $Cs_2CO_3$ (267 mg; 0.82 mmol) were heated at 100° C. in a sealed tube for 5 hours. The reaction mixture was poured into water and extracted with EtOAc. The organic layer was washed with brine, dried over $MgSO_4$, filtered and evaporated to dryness. The residue was purified by chromatography over silica gel (Spherical Silica, 5 μm, 150×30.0 mm; mobile phase: gradient from 0.2% $NH_4OH$, 2% MeOH, 98% DCM to 1% $NH_4OH$, 10% MeOH, 90% DCM). The product fractions were collected and evaporated to dryness yielding 2 fractions:

Fraction 1: 13 mg (3%) of compound 207 (M.P.: 154° C., Kofler)

Fraction 2: 139 mg of a compound which was crystallized from ACN, yielding 98 mg (22%) of compound 208. M.P.: 124° C. (gum, Kofler).

Analogous Preparation of Compounds 245 and 246 Starting from Intermediate 7 compound 245

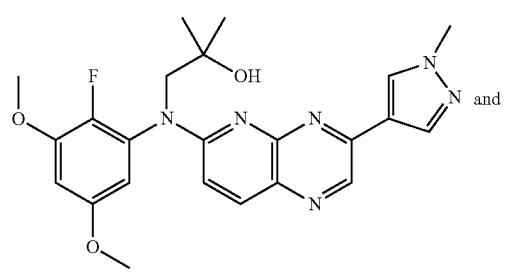

and compound 246

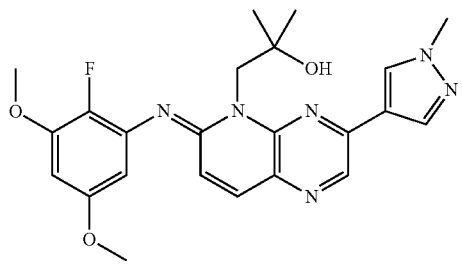

Analogous Preparation of Compounds 276 and 277 Starting from Intermediate 6 compound 276

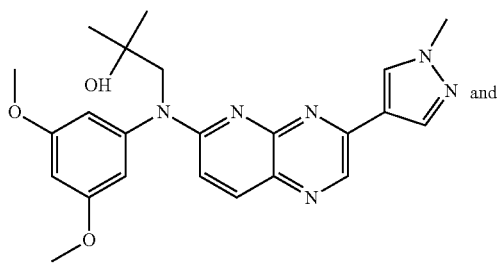

and compound 277

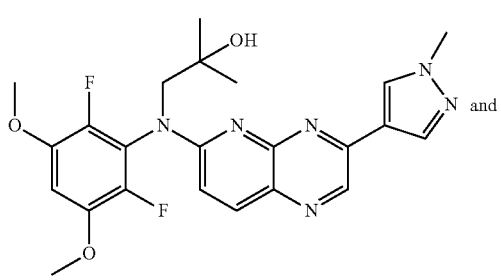

Analogous Preparation of Compounds 278 and 279 Starting from Intermediate 12 compound 278 and compound 279

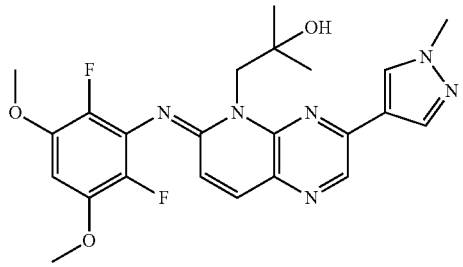

Example B21a

Preparation of Compound 250

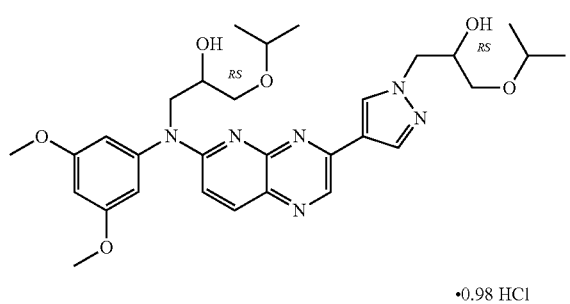 [SMILES: COc1cc(OC)cc(N(CC(O)COC(C)C)c2ccc3ncc(-c4cnn(CC(O)COC(C)C)c4)nc3n2)c1]

•0.98 HCl

Glycidyl isopropyl ether (87 μL; 0.689 mmol) was added to a solution of intermediate 47 (200 mg; 0.574 mmol) and cesium carbonate (299.2 mg; 0.92 mmol) in ACN (3 mL) and the reaction mixture was stirred at 100° C. overnight. The reaction mixture was filtered. The filtrate was extracted with EtOAc. The organic layer was washed with brine, dried over MgSO$_4$, filtered and evaporated to dryness.

The residue (0.25 g) was purified by chromatography over silica gel (stationary phase: stability Silica 5 μm 150×30.0 mm; mobile phase: gradient from 0.2% NH$_4$OH, 98% DCM, 2% MeOH to 1% NH$_4$OH, 90% DCM, 10% MeOH). The product fractions were mixed and the solvent was evaporated affording an intermediate compound which was treated with a solution of HCl 4N in dioxane. The solvent was concentrated to give 48 mg of compound 250, MP: gum at 96° C. (kofler). C$_{30}$H$_4$ON$_6$O$_6$.0.98HCl.0.9H$_2$O.0.05C$_4$H$_8$O$_2$

Example B21b

Preparation of Compound 252 and Intermediate 114 compound 252

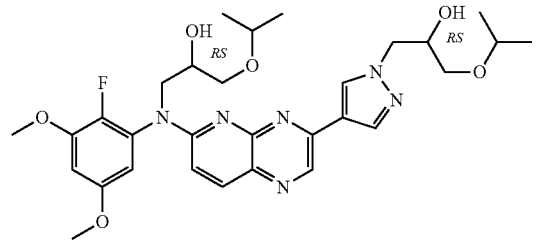

And intermediate 114

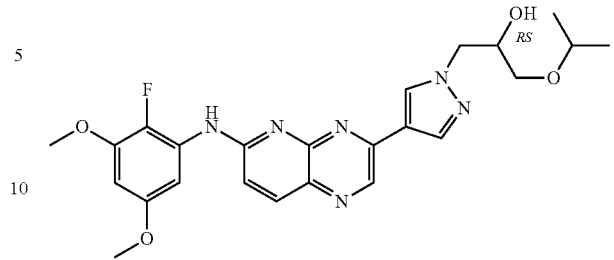

Glycidyl isopropyl ether (51 μL; 0.41 mmol) was added to a solution of intermediate 26 (150 mg; 0.34 mmol) and cesium carbonate (219.9 mg; 0.68 mmol) in ACN (2 mL) and the reaction mixture was stirred at room temperature overnight. Then, the reaction mixture was refluxed for 6 hours, poured into ice water and extracted with AcOEt. The organic layer was washed with brine, dried over MgSO$_4$, filtered and evaporated to dryness. The crude product was purified by chromatography over silica gel (Irregular SiOH, 15-40 μm, 30 g; mobile phase: gradient from 0.1% NH$_4$OH, 99% DCM, 1% MeOH to 0.3% NH$_4$OH, 97% DCM, 3% MeOH). The product fractions were collected and evaporated to dryness yielding to:

Fraction A: 38 mg of an impure intermediate which was crystallized from ACN. The precipitate was filtered, washed with ACN then Et$_2$O and dried to afford 26 mg of (16%) of intermediate 114, MP: gum at 100° C. (kofler)

Fraction B: 32 mg of impure compound 252 which was purified by achiral SFC (Stationary phase: 2 ETHYL-PYRIDINE 6 μm 150×21.2 mm; mobile phase: 80% CO$_2$, 20% MeOH). The product fractions were collected and evaporated to dryness yielding 22 mg (11%) of compound 252, M.P.: 60° C. (kofler), gum.

Example B22

Preparation of Compound 186

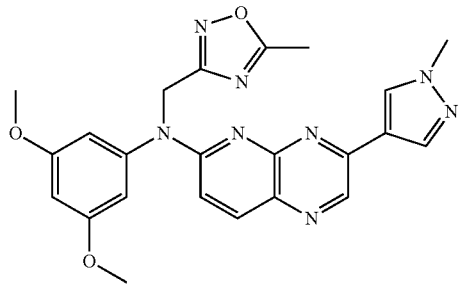 [SMILES: COc1cc(OC)cc(N(Cc2noc(C)n2)c2ccc3ncc(-c4cnn(C)c4)nc3n2)c1]

A 21% solution of sodium ethoxide in EtOH (0.971 mL; 2.6 mmol) was added to a mixture of intermediate 63 and intermediate 64 (0.113 g; 0.26 mmol) in EtOH (10 mL) and EtOAc (0.102 mL). The mixture was refluxed overnight, poured into ice and extracted with EtOAc. The organic layer was washed with brine, dried over MgSO$_4$, filtered and the solvent was evaporated. The residue (0.18 g) was purified by chromatography over silica gel (irregular SiOH, 15-40 μm, 30 g; mobile phase: 0.3% NH$_4$OH, 3% MeOH, 97% DCM). The product fractions were collected and the solvent was evaporated. The residue was crystallized from Et$_2$O and ACN. The precipitate was filtered and dried to give 0.053 g (44%) of compound 186, M.P.: 177° C. (Kofler).

Analogous Preparation of Compound 297

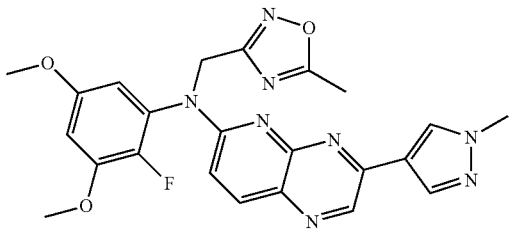

Starting from Intermediate 139

Example B23

Preparation of Compound 188

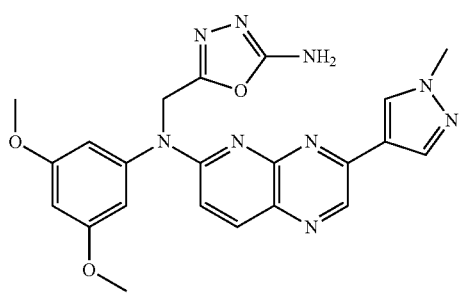 [SMILES: COc1cc(OC)cc(N(Cc2nnc(N)o2)c2ccc3ncc(-c4cnn(C)c4)nc3n2)c1]

Cyanogen bromide (0.012 g; 0.12 mmol) followed by a solution of NaHCO$_3$ (0.01 g; 0.12 mmol) in water (0.6 mL) were added to a mixture of intermediate 65 (0.05 g; 0.12 mmol) in 1,4-dioxane (1 mL) at room temperature. The reaction mixture was stirred for 5 hours and extracted with EtOAc. The organic layer was decanted, dried over MgSO$_4$, filtered and evaporated till dryness. The residue was taken up with Et$_2$O. The precipitate was filtered and dried, then purified by chromatography over silica gel (irregular SiOH, 15-40 µm, 30 g; mobile phase: 0.5% NH$_4$OH, 6% MeOH, 94% DCM). The product fractions were collected and the solvent was evaporated to give 0.033 g of a compound which was crystallized from Et$_2$O and ACN. The precipitate filtered and dried to give 0.025 g (47%) of compound 188, M.P.: 246° C. (Kofler).

Example B23a

Preparation of Compound 229

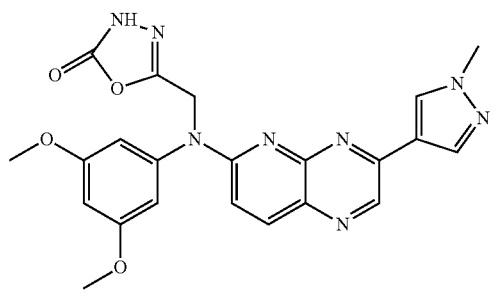 [SMILES: COc1cc(OC)cc(N(Cc2n[nH]c(=O)o2)c2ccc3ncc(-c4cnn(C)c4)nc3n2)c1]

A mixture of intermediate 65 (0.55 g; 1.27 mmol) and 1,1'-carbonyldiimidazole (0.267 g; 1.65 mmol) in 1,4-dioxane (10 mL) was heated at 80° C. overnight. The mixture was poured into ice and the precipitate was filtered, washed with water and dried yielding 0.59 g (99%) of compound 229 which was used without further purification for the next step. M.P.: 232° C. (kofler)

Analogous Preparation of Compound 284

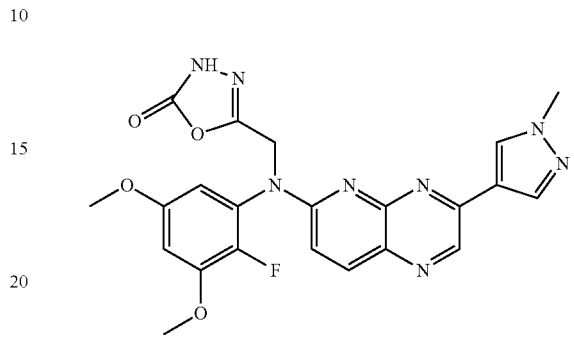

Starting from Intermediate 106

Example B24

Preparation of Compound 239

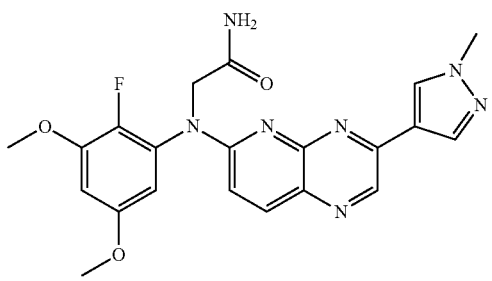

Potassium tert-butoxyde (118 mg; 1.05 mmol) was added to a solution of intermediate 7 (0.2 g; 0.526 mmol) in THF (22 mL) at 5° C. under N$_2$ flow. The reaction mixture was stirred for 30 minutes at 5° C. and 2-bromoacetamide (109 mg; 0.789 mmol) was added portionwise. The reaction mixture was allowed to warm to room temperature and stirred overnight. The reaction mixture was poured into ice and extracted with EtOAc. The organic layer was washed with brine, dried over MgSO$_4$, filtered and the solvent was evaporated. The residue (0.28 g) was purified by chromatography over silica gel (spherical silica, 5 µm, 150×30.0 mm, mobile phase: gradient from 0.2% NH$_4$OH, 2% MeOH, 98% DCM to 1.2% NH$_4$OH, 12% MeOH, 88% DCM). The product fractions were mixed and the solvent was evaporated. The residue was taken up by Et$_2$O. The precipitate was filtered and dried to give 0.114 g (48%) of compound 239. M.P.: gum at 145° C. (kofler).

Example B25

Preparation of Compounds 267 and 268

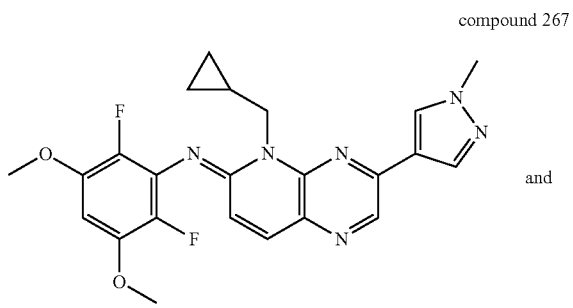

compound 267 and

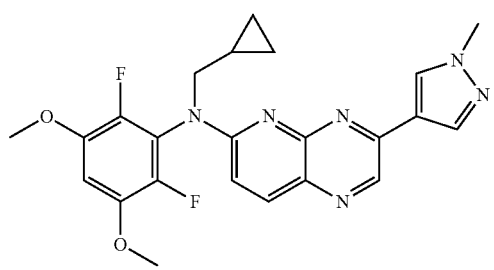

compound 268

NaH (60 mg; 1.506 mmol) was added to a solution of intermediate 12 (300 mg; 0.753 mmol) in DMF (9 mL) at 5° C. under N₂ flow. The reaction was stirred at 5° C. for 30 minutes. A solution of bromomethylcyclopropane (353 mg; 1.311 mmol) in DMF (1 mL) was added over a 2 hours period and the reaction mixture was allowed to warm to room temperature and stirred overnight. The reaction mixture was poured onto iced water and extracted with EtOAc. The organic layer was decanted, washed with brine (twice), dried over MgSO₄, filtered and evaporated to dryness. The residue (410 mg) was purified by chromatography over silica gel (irregular SiOH, 15-40 μm 30 g; mobile phase: 98% DCM, 2% MeOH). The product fractions were collected and evaporated to dryness to give 2 fractions:

Fraction 1: 35 mg of a compound which was crystallized from ACN/DiPE yielding 29 mg of compound 267 (9%) (M.P.: 195° C., kofler)

Fraction 2: 162 mg of a compound which was crystallized from ACN/DiPE yielding 129 mg of compound 268 (38%) M.P.: 212° C. (kofler).

Example B26

Preparation of Compound 261

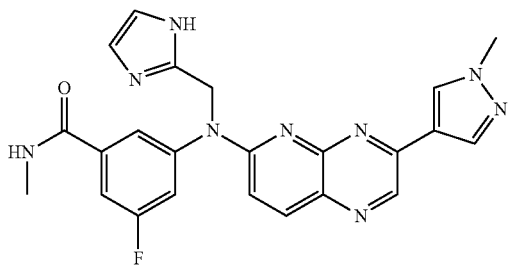 [SMILES: CNC(=O)c1cc(F)cc(N(Cc2ncc[nH]2)c2ccc3ncc(-c4cnn(C)c4)nc3n2)c1]

HOBT (29 mg; 0.218 mmol) then EDCli (41.7 mg; 0.218 mmol) were added portion wise at 10° C. to a solution of intermediate 122 (100 mg; 0.181 mmol) in DMF (10 mL) and Et₃N (51 μL; 0.363 mmol). The reaction mixture was stirred for 10 min. A solution of methylamine 2M in THF (272 μL; 0.544 mmol) was added and the reaction mixture was stirred for 15 hours. Additional HOBT (29 mg; 0.218 mmol), EDCl (41.7 mg; 0.218 mmol), Et₃N (51 μL; 0.363 mmol) and a solution of methylamine 2M in THF (272 μL; 0.544 mmol) were added and the reaction mixture was stirred additional 72 hours. The reaction mixture was poured into water and extracted with EtOAc. The organic layer was washed with brine, dried with MgSO₄, filtered and evaporated to dryness. The residue was purified by chromatography over silica gel (irregular SiOH, 15-40 μm, 30 g; mobile phase: 0.5% NH₄OH, 4% MeOH, 96% DCM) to give 16 mg (19%) of compound 261. M.P. 180° C. (kofler).

Example B27 a) Preparation of Mixture of Intermediate 123 and Compound 266

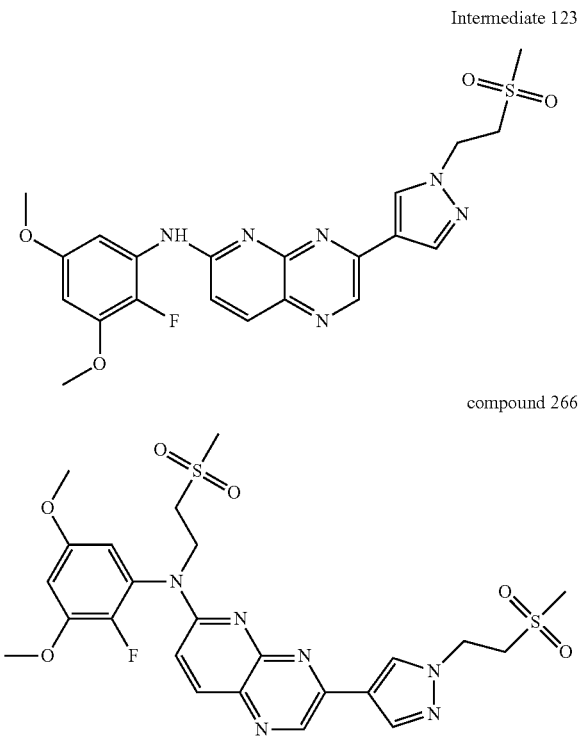 [SMILES: COc1cc(Nc2ccc3ncc(-c4cnn(CCS(C)(=O)=O)c4)nc3n2)c(F)c(OC)c1 ; COc1cc(OC)c(F)c(N(CCS(C)(=O)=O)c2ccc3ncc(-c4cnn(CCS(C)(=O)=O)c4)nc3n2)c1]

Intermediate 123 compound 266

2-bromoethyl-methylsulfone (306 mg; 1.64 mmol) was added to a solution of intermediate 26 (500 mg; 1.37 mmol) and Cs₂CO₃ (667.02 mg; 2.05 mmol) in ACN (8 mL) and the reaction mixture was stirred at room temperature overnight. The reaction mixture was poured into a 10% aqueous solution of K₂CO₃ and extracted with EtOAc. The organic layer was washed with brine, dried over MgSO₄, filtered and evaporated to dryness. The crude product was purified by chromatography over silica gel (irregular SiOH, 15-45 μm, 24 g; mobile phase: 97% CH₂Cl₂, 3% MeOH). The product fractions were collected and evaporated to dryness leading to a 1/1 mixture of intermediate 123 and compound 266 which was used without further purification in the next step.

b) Preparation of Compounds 265 and 266

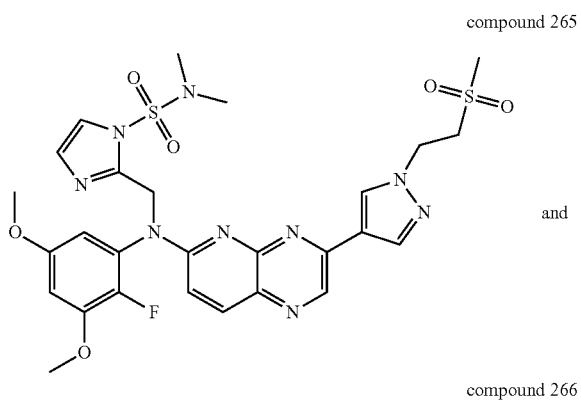

compound 265 and compound 266

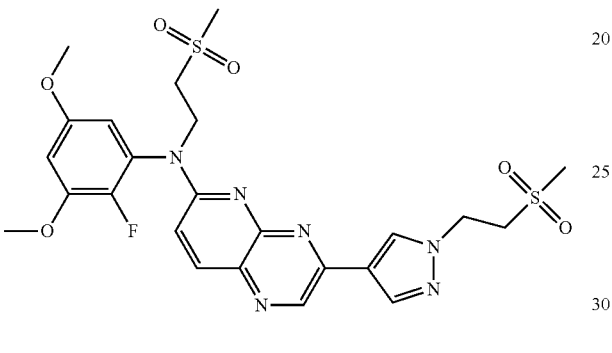

NaH (25.39 mg; 1.06 mmol) was added to a solution of a mixture of intermediate 123 and compound 266 (500 mg; 0.53 mmol) in DMF (15 mL) at 5° C. under $N_2$ flow. The reaction mixture was stirred for 30 minutes at 5° C. and a solution of 2-(chloromethyl)-N,N-dimethyl-1H-imidazole-1-sulfonamide (CAS 935862-81-0) (250 mg; 1.12 mmol) in DMF (10 mL) was added dropwise. The reaction mixture was allowed to warm to room temperature and stirred overnight. The reaction mixture was poured into ice water and extracted with EtOAc. The organic layer was washed with brine, dried over $MgSO_4$, filtered and evaporated to dryness. The residue was purified by chromatography over silica gel (spherical silica, 5 μm, 150×30.0 mm; mobile phase: gradient from 0.2% $NH_4OH$, 2% MeOH, 98% DCM to 1% $NH_4OH$, 10% MeOH, 90% DCM). The product fractions were collected and evaporated to dryness yielding 159 mg (46%) of compound 265 and 115 mg of an intermediate compound which was crystallized from ACN to afford 83 mg of compound 266 (27%). M.P.: 180° C. (kofler).

Example B28

Preparation of Compound 275

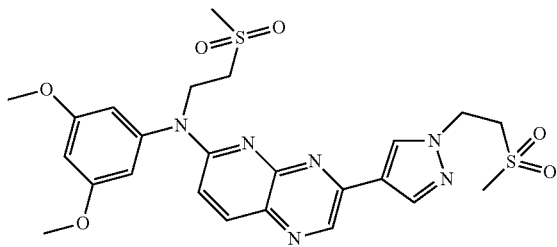 [SMILES: COc1cc(OC)cc(N(CCS(C)(=O)=O)c2ccc3ncc(-c4cnn(CCS(C)(=O)=O)c4)nc3n2)c1]

2-bromoethylmethylsulfone (129 mg; 0.689 mmol) was added to a solution of intermediate 47 (200 mg; 0.574 mmol) and cesium carbonate (374 mg; 1.15 mmol) in ACN (3 mL) and the reaction mixture was stirred at room temperature overnight. The reaction mixture was poured into a 10% aqueous solution of $K_2CO_3$ and extracted with EtOAc. The organic layer was washed with brine, dried over $MgSO_4$, filtered and evaporated to dryness. The residue was purified by chromatography over silica gel (spherical silica, 5 μm, 150×30.0 mm; mobile phase: gradient from 0.2% $NH_4OH$, 2% MeOH, 98% DCM to 1% $NH_4OH$, 10% MeOH, 90% DCM. The product fractions were mixed and the solvent was evaporated to dryness yielding 46 mg of an impure compound which was purified by achiral SFC (2-ethylpyridine, 6 μm, 150×21.2 mm; mobile phase: 82% $CO_2$, 18% MeOH). The product fractions were mixed and the solvent was evaporated to give 0.036 g (11%) of compound 275. M.P.: 172° C. (kofler).

Example B29

Preparation of Compound 289

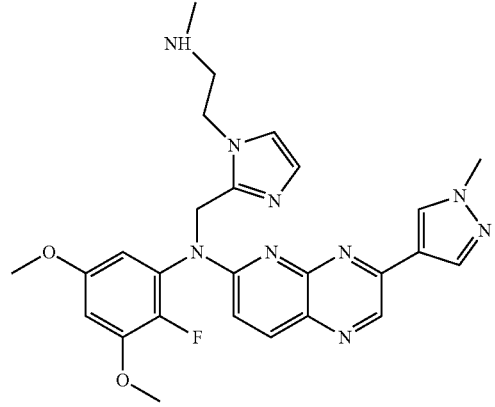 [SMILES: CNCCn1ccnc1CN(c1ccc2ncc(-c3cnn(C)c3)nc2n1)c1cc(OC)cc(OC)c1F]

A mixture of intermediate 132 (0.317 g; 0.55 mmol) and a 2M solution of methylamine in THF (10.9 mL; 21.76 mmol) was heated in a sealed tube at 70° C. for 18 hours. The reaction mixture was cooled down, poured into iced water and extracted with EtOAc. The organic layer was washed with brine, dried over $MgSO_4$, filtered and evaporated to dryness. The residue (0.242 g) was purified by chromatography over silica gel (irregular SiOH, 15-40 μm, 24 g; mobile phase: 0.5% $NH_4OH$, 5% MeOH, 95% DCM). The product fractions were collected and evaporated to dryness. The residue was crystallized from ACN. The precipitate was filtered and dried to give 0.049 g of compound 289 (17%). M.P.: 92° C. (gum, kofler).

Example B30

Preparation of Compound 301

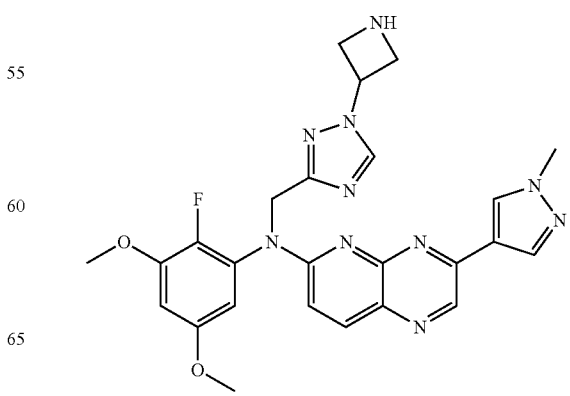

4M HCl in 1,4-dioxane (2.27 mL; 9.08 mmol) was added dropwise to a solution of intermediate 144 (560 mg; 0.908 mmol) in ACN. The reaction mixture was stirred at room temperature for 2 hours, diluted with DCM and poured onto a cold 10% aqueous solution of $K_2CO_3$. The organic layer was decanted, washed with water, dried over $MgSO_4$, filtered and evaporated to dryness. The residue (0.62 g) was purified by chromatography over silica gel (irregular SiOH, 15-40 μm, 40 g; mobile phase: 0.5% $NH_4OH$, 5% MeOH, 95% DCM). The product fractions were collected and evaporated to dryness. The resulting residue (415 mg) was purified by chromatography over silica gel (irregular SiOH, 15-40 μm, 30 g; mobile phase: 1% $NH_4OH$, 92% DCM, 7% MeOH). The product fractions were collected and evaporated to dryness. The residue was taken up with $Et_2O$. The precipitate was filtered and dried yielding 137 mg of (29%) of compound 301 M.P.: 126° C. (kofler)

C. Preparation of the Compounds

Conversion 1

Preparation of Compound 23

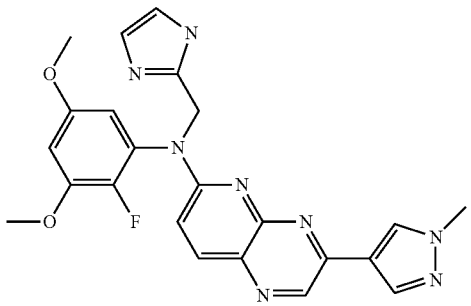

To a solution of compound 13 (350 mg; 0.62 mmol) in ACN (13 ml) was added dropwise at 5° C., HCl (4M in Dioxane) (1.54 ml; 6.2 mmol). The reaction mixture was then heated at 50° C. for 18 hours. The reaction mixture was cooled down to room temperature and then concentrated under reduced pressure. The reaction mixture was taken up with DCM and water and was basified with an aqueous solution of ammonia. The aqueous solution was extracted and the organic layer washed with brine, dried ($MgSO_4$), filtered and concentrated under reduced pressure. The residue was purified by chromatography over silica gel (5 μm, mobile phase, gradient from 0.1% $NH_4OH$, 99% DCM, 1% MeOH to 1% $NH_4OH$, 90% DCM, 10% MeOH). The desired fractions were collected and concentrated under reduced pressure. The residue was triturated in $Et_2O$, filtered and dried to afford 170 mg (60%) of compound 23 (MP: 228° C. (DSC)).

Alternatively, compound 23 was also prepared as follows:

The reaction was performed three times on the same quantities of compound 13 (7.34 g; 12.93 mmol)

HCl 4M in 1,4-dioxane (32.31 mL; 129.25 mmol) was added drop wise at 5° C. to a solution of compound 13 (7.34 g; 12.93 mmol) in ACN (250 mL). The reaction mixture was then heated at 50° C. for 6 hours and cooled down. The 3 batches were mixed; the precipitate was filtered off and stirred in 10% aqueous $K_2CO_3$ overnight. The precipitate was again filtered off, washed with water, then ACN, dissolved in DCM/MeOH (9/1) and evaporated to dryness. The resulting residue (16.28 g) was solubilized by refluxing in ACN (950 mL) and crystallized allowing the temperature to reach room temperature. The precipitate was filtered, washed with ACN, then $Et_2O$ and dried yielding g of 9.3 g (51%) of compound 23. M.P.=226° C. (DSC), $C_{23}H_{21}FN_8O_2.0.13\ CH_3CN$.

The filtrate was evaporated to dryness. The residue (6.7 g) was solubilized by refluxing in ACN (300 mL) and crystallized allowing the temperature to reach room temperature. The precipitate was filtered, washed with ACN, then $Et_2O$ and dried yielding additional 1.92 g (11%) of compound 23. M.P.=226° C. (DSC), $C_{23}H_{21}FN_8O_2.0.1\ CH_3CN$ The filtrate was evaporated to dryness affording 4.67 g of an additional fraction of (impure) compound 23, which was purified by chromatography over silica gel (irregular SiOH, 20-45 μm, 450 g; mobile phase: 96% DCM, 4% MeOH, 0.1% $NH_4OH$). The product fractions were collected and evaporated to dryness yielding 3.35 g of additional compound 23 (18%) which was solubilized by refluxing in ACN (250 mL) and crystallized allowing the temperature to reach room temperature. The precipitate was filtered, washed with CAN, then $Et_2O$ and dried yielding 2.33 g (13%) of additional compound 23 M.P.: 231° C. (DSC)

The filtrate was evaporated to dryness yielding 770 mg of impure compound 23.

Alternatively, compound 23 was also prepared as follows.

The experiment was performed from 2 batches of compound 13 (6.69 g; 11.78 mmol): HCl 4M in 1,4-dioxane (30 mL; 120 mmol) was added drop wise at 5° C. to a solution of compound 13 (6.69 g; 11.78 mmol) in ACN (235 mL). The reaction mixture was heated at 50° C. for 6 hours. The 2 batches were combined. After cooling down, the precipitate was filtered and stirred in a saturated solution of $K_2CO_3$ 10% overnight. The precipitate was filtered, washed with water, then ACN and dissolved in DCM/MeOH (9/1). The solvent was evaporated, and the residue was taken up in ACN, filtered, washed with $Et_2O$ and dried. The resulting residue was dissolved in DCM/MeOH (8/2) (350 mL) and washed twice with water. The organic layer was evaporated until crystallization. The solid was filtered and washed with ACN, then $Et_2O$ and dried to afford 8.94 g (76%) of compound 23 (M.P.: 132° C., DSC). $C_{23}H_{21}FN_8O_2.2.02H_2O$.

The filtrate was purified by chromatography over silica gel (irregular SiOH, 15-40 μm, 300 g; mobile phase: 0.1% $NH_4OH$, 97% DCM, 3% MeOH). The pure fractions were collected and evaporated to dryness yielding additional 740 mg (7%) of compound 23.

Analogous Preparation of Compound 135

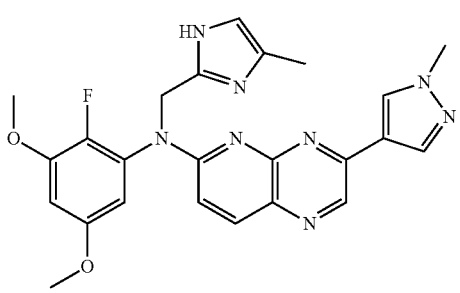 [SMILES: COc1cc(OC)c(F)c(N(Cc2nc(C)c[nH]2)c2ccc3ncc(-c4cnn(C)c4)nc3n2)c1]

Starting from Compound 136
Analogous Preparation of Compound 137

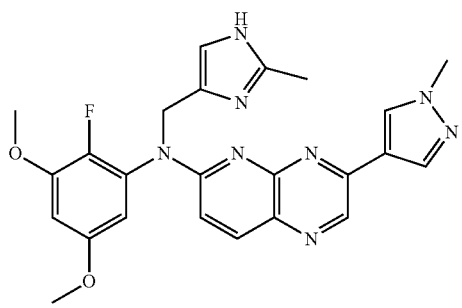 [SMILES: COc1cc(OC)c(F)c(N(Cc2c[nH]c(C)n2)c2ccc3ncc(-c4cnn(C)c4)nc3n2)c1]

Starting from Compound 138

Analogous Preparation of Compound 152

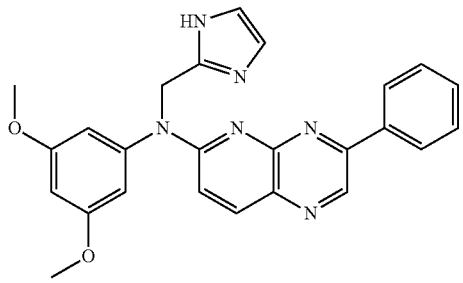 [SMILES: COc1cc(OC)cc(N(Cc2ncc[nH]2)c2ccc3ncc(-c4ccccc4)nc3n2)c1]

Starting from Compound 153

Analogous Preparation of Compound 25

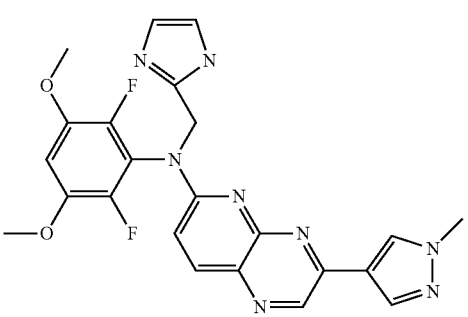

Analogous Preparation of Compound 27

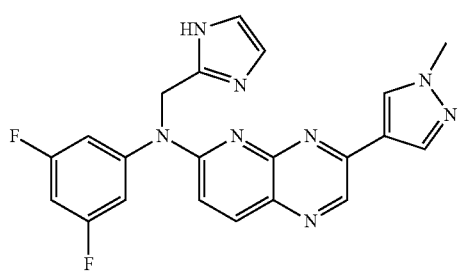 [SMILES: Cn1cc(-c2cnc3ccc(N(Cc4ncc[nH]4)c4cc(F)cc(F)c4)nc3n2)cn1]

Starting from Compound 28.
Analogous Preparation of Compound 41

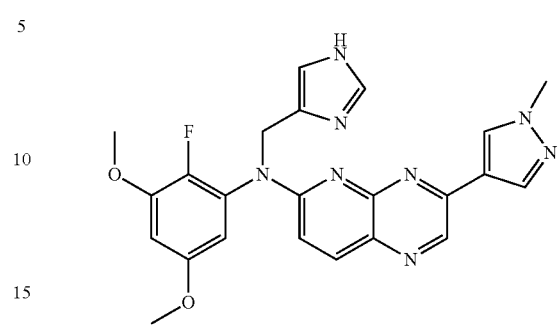

Starting from Compound 36.
Analogous Preparation of Compound 42

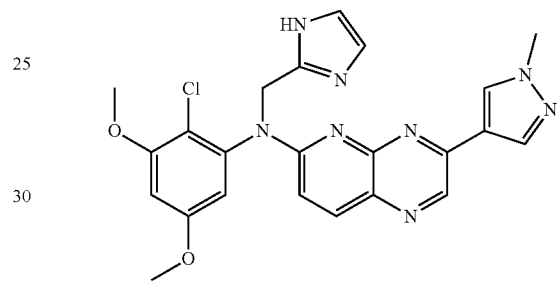

Starting from Compound 43.

Analogous Preparation of Compound 65

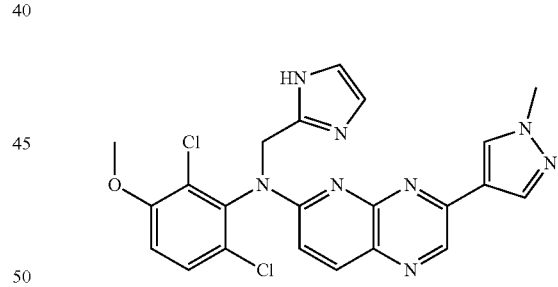

Starting from Compound 66.

Analogous Preparation of Compound 73

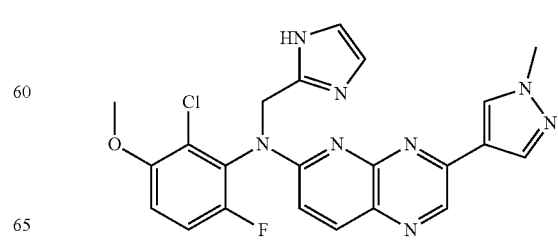

Starting from Compound 74.
  Analogous Preparation of Compound 98

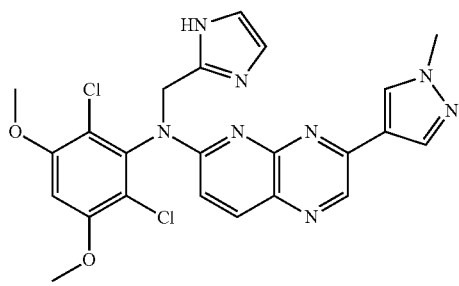 [SMILES: COc1cc(OC)c(Cl)c(N(Cc2ncc[nH]2)c2ccc3ncc(-c4cnn(C)c4)nc3n2)c1Cl]

Starting from Compound 99.
  Analogous Preparation of Compound 100

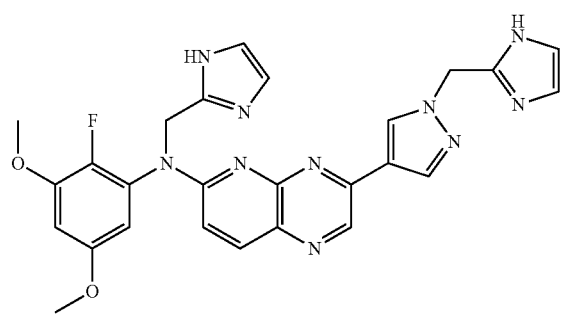 [SMILES: COc1cc(OC)c(F)c(N(Cc2ncc[nH]2)c2ccc3ncc(-c4cnn(Cc5ncc[nH]5)c4)nc3n2)c1]

Starting from Compound 101.
  Analogous Preparation of Compound 109

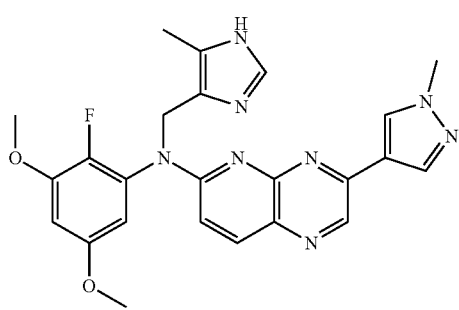 [SMILES: COc1cc(OC)c(F)c(N(Cc2nc[nH]c2C)c2ccc3ncc(-c4cnn(C)c4)nc3n2)c1]

Starting from Compound 110.
  Analogous Preparation of Compound 118

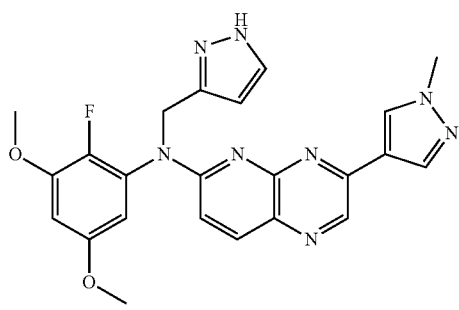 [SMILES: COc1cc(OC)c(F)c(N(Cc2cc[nH]n2)c2ccc3ncc(-c4cnn(C)c4)nc3n2)c1]

Starting from Compound 116
  Analogous Preparation of Compound 125

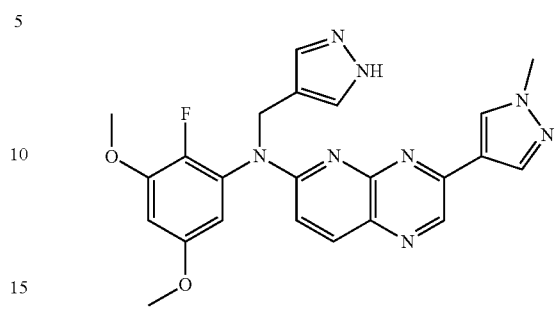

Starting from Compound 126.
  Analogous Preparation of Compound 175

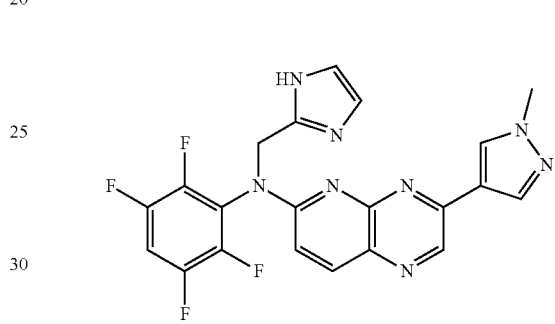

Starting from Compound 176.
  Analogous Preparation of Compound 182

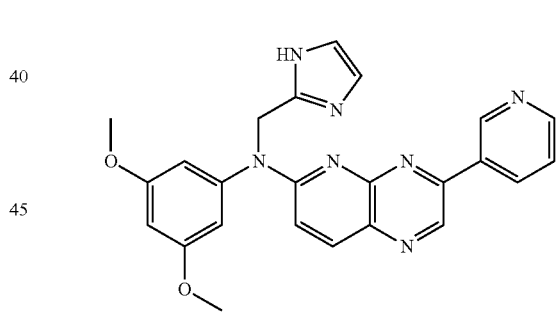

Starting from Compound 183
  Analogous Preparation of Compound 190a

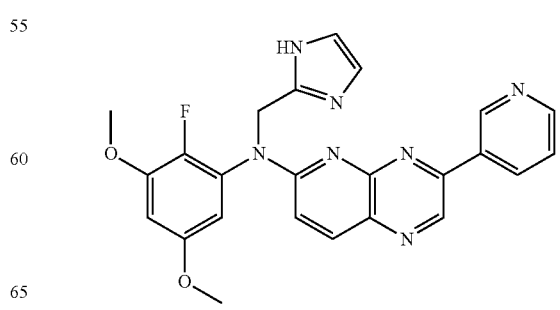

Starting from Compound 191
Analogous Preparation of Compound 198

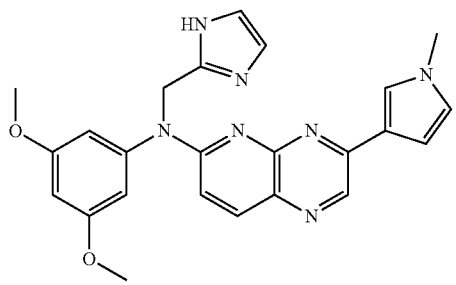 [SMILES: COc1cc(OC)cc(N(Cc2ncc[nH]2)c2ccc3ncc(-c4ccn(C)c4)nc3n2)c1]

Starting from Compound 199
Analogous Preparation of Compound 200

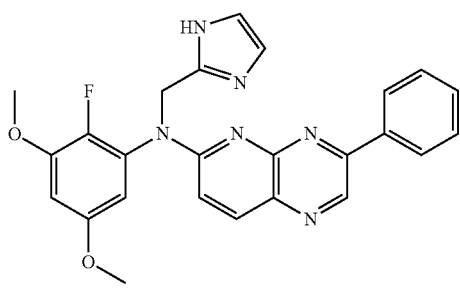 [SMILES: COc1cc(OC)c(F)c(N(Cc2ncc[nH]2)c2ccc3ncc(-c4ccccc4)nc3n2)c1]

Starting from Compound 201
Analogous Preparation of Compound 202

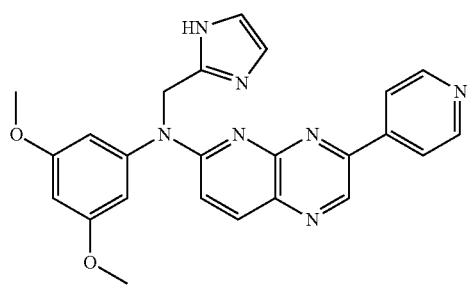 [SMILES: COc1cc(OC)cc(N(Cc2ncc[nH]2)c2ccc3ncc(-c4ccncc4)nc3n2)c1]

Starting from Compound 203
Analogous Preparation of Compound 209

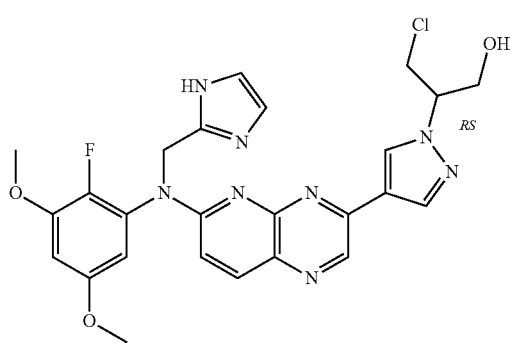 [SMILES: COc1cc(OC)c(F)c(N(Cc2ncc[nH]2)c2ccc3ncc(-c4cnn(C(CO)CCl)c4)nc3n2)c1]

Starting from Compound 210
Analogous Preparation of Compound 211

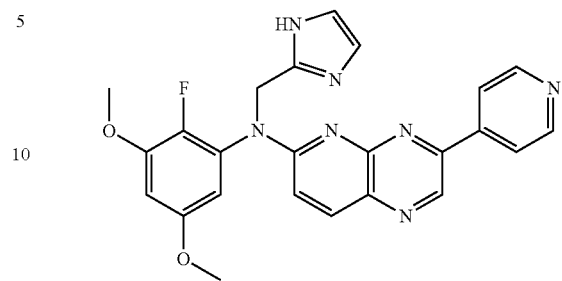

Starting from Compound 212
Analogous Preparation of Compound 223

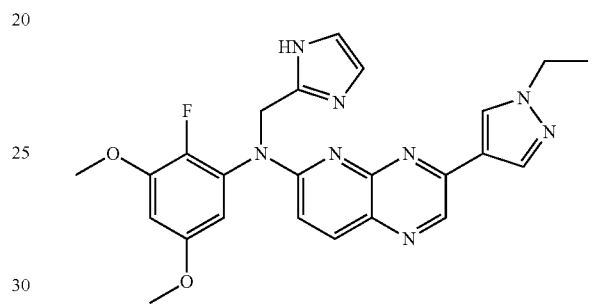

Starting from Compound 224
Analogous Preparation of Compound 240

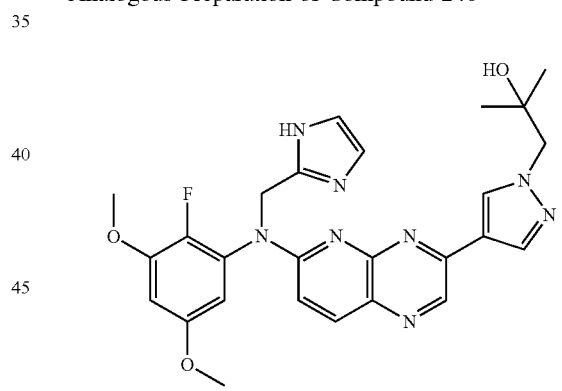

Starting from Compound 241
Analogous Preparation of Compound 232

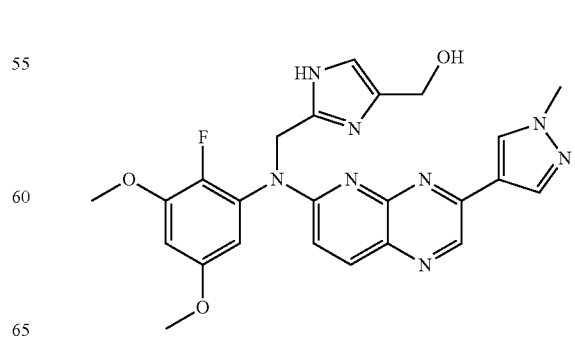

Starting from Intermediate 97
Analogous Preparation of Compound 259

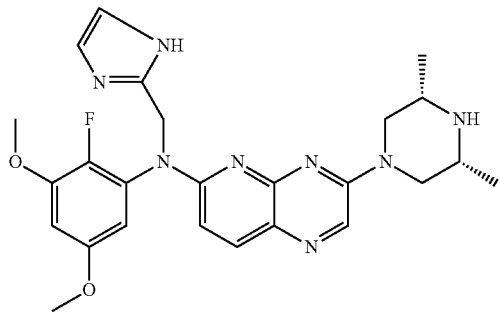

(cis) Starting from Compound 260
Analogous Preparation of Compound 264

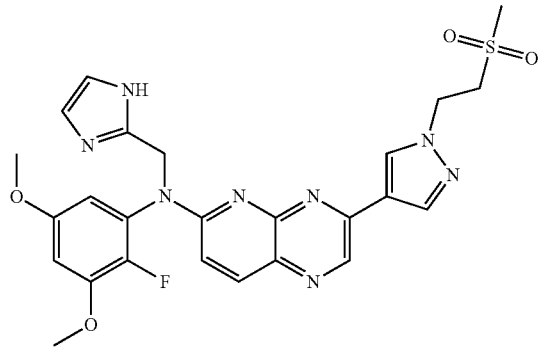 [SMILES: COc1cc(OC)c(F)c(N(Cc2ncc[nH]2)c2ccc3ncc(-c4cnn(CCS(C)(=O)=O)c4)nc3n2)c1]

Starting from Compound 265
Analogous Preparation of Compound 273

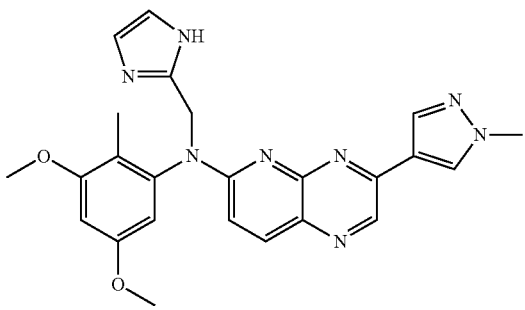

Starting from Compound 274
Analogous Preparation of Compound 280

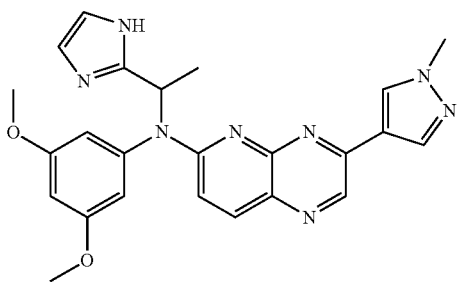 [SMILES: COc1cc(OC)cc(N(c2ccc3ncc(-c4cnn(C)c4)nc3n2)C(C)c2ncc[nH]2)c1]

Starting from Compound 281
Analogous Preparation of Compound 287

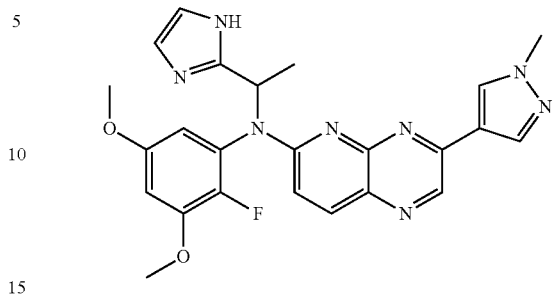

Starting from Compound 288
Analogous Preparation of Compound 293

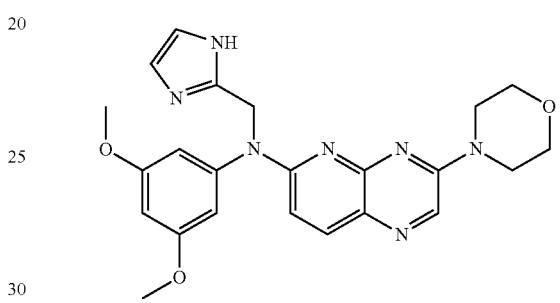

Starting from Compound 294
Compound 24

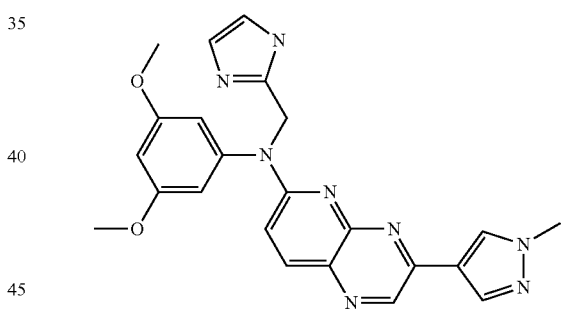

was prepared as follows:

To a solution of compound 14 (545 mg; 0.99 mmol) in ACN (20 mL) was added drop wise, at 5° C., HCl 4M in 1,4-dioxane (2.5 ml; 9.9 mmol). The reaction mixture was heated at 50° C. for 18 hours and then concentrated under reduced pressure. The reaction mixture was taken up with DCM, washed with 10% aqueous $K_2CO_3$ and brine, dried over $MgSO_4$, filtered and concentrated under reduced pressure. The residue (488 mg) was purified by chromatography over silica gel (irregular SiOH, 15-40 μm, 30 g; Mobile phase: 0.1% NH4OH, 97% DCM, 3% MeOH). The product fractions were mixed and concentrated affording 230 mg of an intermediate compound which was taken up in $Et_2O$. The precipitate was filtered, dissolved in DCM and water. The mixture was basified with a 30% ammonia solution. The aqueous layer was extracted and the organic layer washed with brine, dried over $MgSO_4$, filtered and concentrated under reduced pressure to afford 121 mg of an intermediate fraction which was taken up in $Et_2O$. The precipitate was filtered to afford 108 mg (24%) of compound 24. M.P.: 228° C. (Kofler).

Alternatively, compound 24 was prepared as follows:
The experiment was performed from 2 batches of compound 14 (3.55 g; 6.46 mmol):

HCl 4M in 1,4-dioxane (16.1 mL; 64.6 mmol) was added drop wise at 5° C. to a solution of compound 14 (3.55 g; 6.46 mmol) in ACN (140 mL). The reaction mixture was then heated at 50° C. for 18 hours. The two reaction mixtures were combined and cooled down to 40° C., then poured into ice water, basified with a 30% ammonia solution, stirred at room temperature for 30 minutes and allowed to crystallize overnight. The precipitate was filtered, washed with water, ACN and Et$_2$O, then dried under vacuum to give 3.8 g (67%) of compound 24. MP: 246° C. (DSC). The filtrate was also allowed to crystallize overnight. The precipitate was filtered, washed with water, ACN and Et$_2$O affording after drying additional 1.35 g (24%) of compound 24. MP: 244° C. (DSC), $C_{23}H_{22}N_8O_2$.

Alternatively, compound 24 was also prepared as follows.

To a solution of compound 14 (700 mg; 1.27 mmol) in ACN (26 mL) was added drop wise at 5° C., HCl 4M in 1,4-dioxane (3.18 ml; 12.7 mmol). The reaction mixture was heated at 50° C. for 4 hours and then diluted with DCM/MeOH (9/1). The reaction mixture was basified at 0° C. with 10% aqueous solution of K$_2$CO$_3$. The aqueous layer was extracted several times with a mixture of DCM/MeOH (9/1). The organic layers were mixed, dried over MgSO$_4$, filtered and concentrated to afford an intermediate residue (0.7 g, yellow solid) which was taken up with ACN. The precipitate was filtered, dried yielding 0.44 g (78%; yellow solid) of compound 24. M.P.>260° C. (kofler). $C_{23}H_{22}N_8O_2.0.15H_2O.0.015CH_2Cl_2.0.056$ dioxane.

Conversion 1a
Preparation of Compound 115

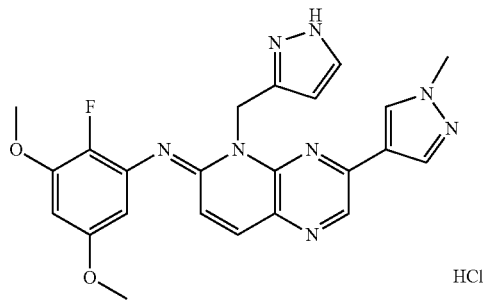 [SMILES: COc1cc(/N=c2\ccc3ncc(-c4cnn(C)c4)nc3n2Cc2cc[nH]n2)c(F)c(OC)c1 ; Cl]

HCl

A solution of HCl 4M in 1,4-dioxane (0.44 mL; 1.74 mmol) was added drop wise at 5° C. to a solution of compound 117 (0.1 g; 0.18 mmol) in ACN (4 mL). The reaction mixture was then heated at 50° C. for 6 hours and cooled to room temperature. The precipitate was filtered, washed with Et$_2$O and dried yielding 70 mg (72%) of compound 115. M.P.: 130° C. (gum, Kofler). $C_{23}H_{21}FN_8O_2.0.65H_2O.2.14HCl$ Analogous Preparation of Compound 155

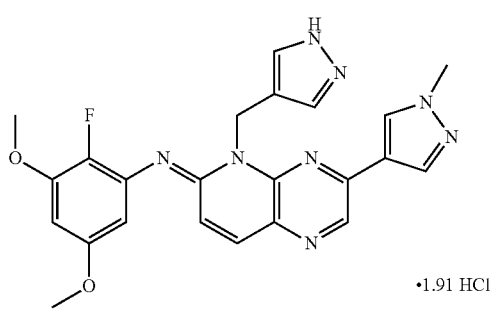 [SMILES: COc1cc(/N=c2\ccc3ncc(-c4cnn(C)c4)nc3n2Cc2cn[nH]c2)c(F)c(OC)c1 ; "·1.91 HCl"]

•1.91 HCl

Conversion 1b
Preparation of Compound 215

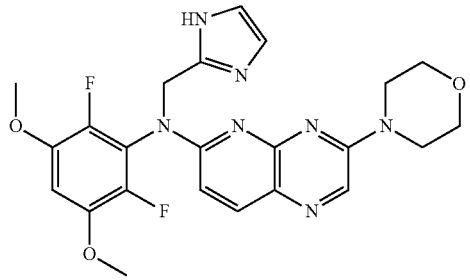 [SMILES: COc1cc(OC)c(F)c(N(Cc2ncc[nH]2)c2ccc3ncc(N4CCOCC4)nc3n2)c1F]

Aqueous HCl 6N (2 mL) was added to a solution of compound 216 (1.1 g; 1.58 mmol) in dioxane (10 mL) at 5° C. The reaction mixture was then heated at 100° C. for 1 hour. The reaction mixture was poured into ice water and basified with NaOH 3N. The product was extracted with EtOAc, washed with brine, dried over MgSO$_4$, filtered and concentrated under reduced pressure. The residue (1 g) was purified by chromatography over silica gel (15-40 µm, 40 g; mobile phase: DCM/MeOH/NH$_4$OH: 97/3/0.1 to 95/5/0.1) The product fractions were collected and evaporated to dryness to give 0.587 g (77%) of an intermediate compound which was crystallized from Et$_2$O. The precipitate was filtered and dried to give 0.517 g (67%) of compound 215. M.P.: gum at 140° C. (kofler).

Analogous Preparation of Compound 291

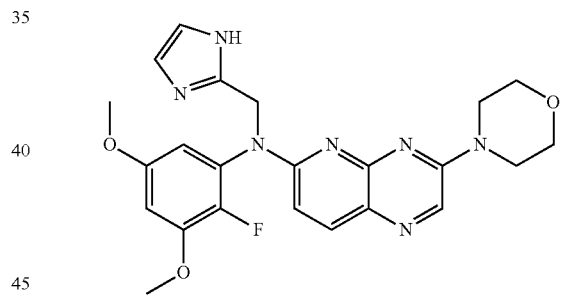

Starting from Compound 292

Analogous Preparation of Compound 295

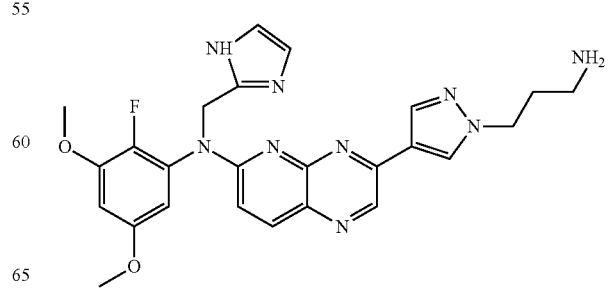

Starting from Compound 296
Conversion 2
Preparation of Compound 2

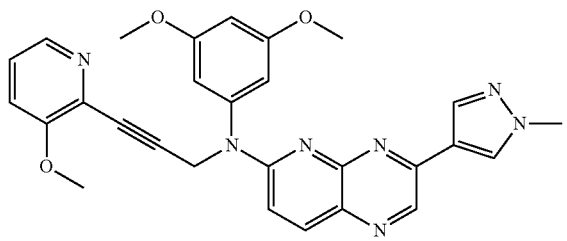 [SMILES: COc1cc(OC)cc(N(CC#Cc2ncccc2OC)c2ccc3ncc(-c4cnn(C)c4)nc3n2)c1]

A solution of compound 22 (422 mg; 1.05 mmol), 2-bromo-3-methoxypyridine (180 mg; 0.95 mmol) and triethylamine (1.6 ml; 11.5 mmol) in DMSO (10 ml) was degassed under $N_2$ for 10 minutes. Then, dichlorobi(triphenylphosphine)palladium (II) (135 mg; 0.19 mmol) and copper(I) iodide (18.3 mg; 0.09 mmol) were added and the reaction mixture was stirred at 90° C. for 40 minutes. The reaction mixture was cooled down to room temperature and poured out onto ice water and EtOAc and filtered through a pad of Celite®. The aqueous layer was extracted with EtOAc and the organic layer was washed with brine, dried (MgSO₄), filtered and concentrated under reduced pressure. The residue was purified by chromatography over silica gel (5 μm, mobile phase, gradient 100% DCM to 0.5% NH₄OH, 95% DCM, 5% MeOH). The desired product fractions were collected, concentrated under reduced pression to provide 116 mg (24%) of compound 26. This compound eptane was triturated in Et₂O, the precipitate was filtered and dried to afford 52.6 mg of compound 26 (MP: 190° C.).
Conversion 3
Preparation of Compound 95

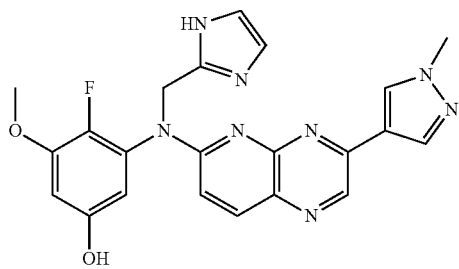 [SMILES: COc1cc(O)cc(N(Cc2ncc[nH]2)c2ccc3ncc(-c4cnn(C)c4)nc3n2)c1F]

And Compound 96

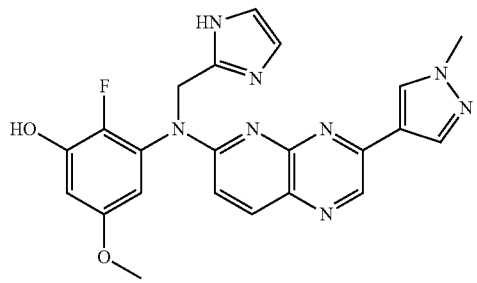 [SMILES: COc1cc(O)c(F)c(N(Cc2ncc[nH]2)c2ccc3ncc(-c4cnn(C)c4)nc3n2)c1]

The reaction was performed twice on the same quantity of compound 23 (1 g; 2.17 mmol) and the batches were mixed for the purification.

A solution of 1M BBr₃ in DCM (11.94 mL; 11.94 mmol) was added dropwise to a solution of compound 23 (1 g; 2.17 mmol) in DCM (55 mL) at 5° C. under $N_2$ flow. The solution was allowed to warm to room temperature and stirred for 1 h30. The reaction mixture was diluted with DCM, an aqueous solution of NaOH 30% was added until basic pH and the reaction mixture was evaporated to dryness. The crude products coming from the 2 batches were mixed and the resulting residue was purified by chromatography over silica gel (Irregular SiOH, 20-45 μm, 450 g; mobile phase: gradient from 0.5% NH₄OH, 97% DCM, 3% MeOH to 0.5% NH₄OH, 93% DCM, 7% MeOH). The product fractions were collected and evaporated to dryness yielding 2 fractions:

Fraction 1: 310 mg of a compound which was taken up in ACN. The precipitate was filtered, washed with Et₂O and dried. The resulting solid (274 mg) was refluxed in 15 mL of ACN and 1.5 mL of MeOH. The solution was cooled down. The precipitate was filtered, washed with ACN then Et₂O and dried to afford 274 mg (13%) of compound 95. M.P.: 218° C. (DSC).

Fraction 2: 105 mg of a compound which was taken up in ACN. The precipitate was filtered, washed with Et₂O and dried yielding 86 mg (4%) of compound 96. M.P.: 192° C. (gum, Kofler).

Analogous Preparation of Compound 122

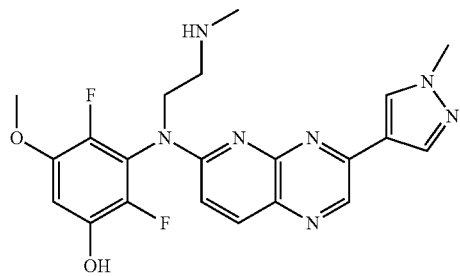 [SMILES: CNCCN(c1ccc2ncc(-c3cnn(C)c3)nc2n1)c1c(F)c(O)cc(OC)c1F]

Starting from Compound 3
Conversion 3a
Preparation of Compound 103

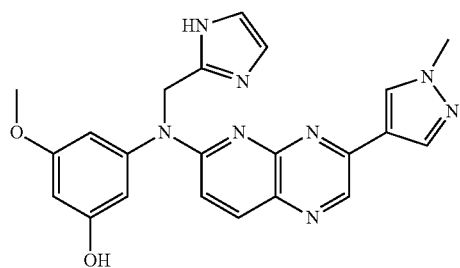 [SMILES: COc1cc(O)cc(N(Cc2ncc[nH]2)c2ccc3ncc(-c4cnn(C)c4)nc3n2)c1]

A solution of 1M BBr₃ in DCM (8.70 mL; 8.70 mmol) was added drop wise to a solution of compound 24 (700 mg; 1.58 mmol) in DCM (40 mL) at 5° C. under $N_2$ flow. The solution was allowed to slowly warm to room temperature and stirred for 1 h30. The reaction mixture was diluted with DCM. A 30% aqueous solution of NaOH was added until basic pH and the reaction mixture was evaporated to dryness. The crude product (10 g) was purified by chromatography over silica gel (Dry loading (70-200 μm, 20 g) irregular SiOH, 15-45 μm, 70 g; mobile phase: 97% DCM, 3% MeOH). The fractions were collected and evaporated to dryness. The impure residue (240 mg) was purified by achiral SFC (2-ETHYLPYRIDINE, 6 μm, 150×21.2 mm; mobile phase: 80% CO$_2$, 20% MeOH). The product fractions were collected and evaporated to dryness. The residue (102 mg) was crystallized from ACN. The precipitate was filtered, washed with Et$_2$O and dried yielding 86 mg (13%) of compound 103. M.P.: 172° C. (gum, Kofler).

Conversion 4

Preparation of compounds 162 and 163 compound 162

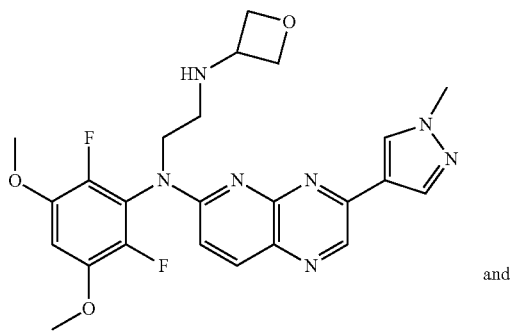

and compound 163

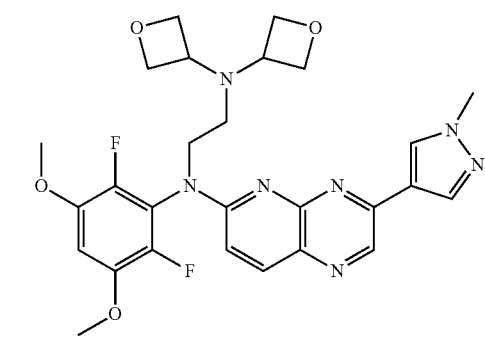

Sodium triacetoxyborohydride (0.204 g; 0.96 mmol) and acetic acid (0.015 mL; 0.25 mmol) were added to a solution of compound 67 (0.265 g; 0.6 mmol) and 3-oxetanone (0.036 mL; 0.6 mmol) in 1,2-dichloroethane (10 mL) at 5° C. under N$_2$ flow. The reaction mixture was stirred at 60° C. overnight, poured into ice water, basified with a 10% aqueous solution of K$_2$CO$_3$ and extracted with DCM. The organic layer was dried over MgSO$_4$, filtered and evaporated to dryness. The residue (268 mg) was purified by chromatography over silica gel (Spherical Silica, a 5 μm, 150×30.0 mm; mobile phase: gradient from 0.2% NH$_4$OH, 98% DCM, 2% MeOH to 1.2% NH$_4$OH, 88% DCM, 12% MeOH). The product fractions were collected and the solvent was evaporated to give 2 fractions:

Fraction 1: 0.033 g of a compound which was crystallized from Et$_2$O to give 51 mg (17%) of compound 162 (M.P.: 183° C., DSC)

Fraction 2: 0.068 g of a compound which was crystallized from Et$_2$O to give 20 mg (6%) of compound 163. M.P.: 182° C. (DSC).

Analogous Preparation of Compound 221

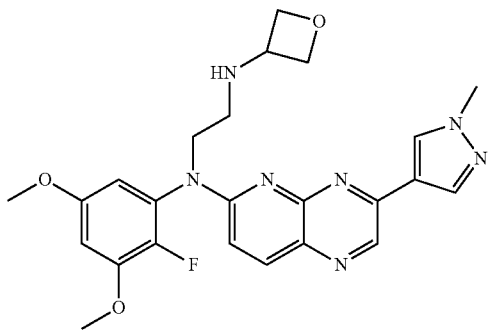 [SMILES: COc1cc(OC)c(F)c(N(CCNC2COC2)c2ccc3ncc(-c4cnn(C)c4)nc3n2)c1]

And Compound 222

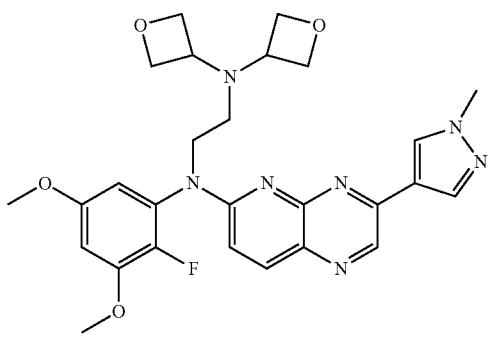 [SMILES: COc1cc(OC)c(F)c(N(CCN(C2COC2)C2COC2)c2ccc3ncc(-c4cnn(C)c4)nc3n2)c1]

Starting from Compound 168
Conversion 4a
Preparation of Compound 164

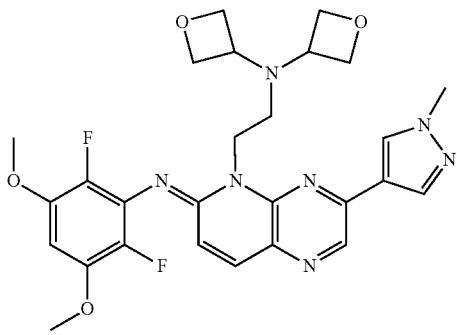 [SMILES: COc1cc(OC)c(F)c(/N=c2\ccc3ncc(-c4cnn(C)c4)nc3n2CCN(C2COC2)C2COC2)c1F]

Sodium triacetoxyborohydride (0.144 g; 0.68 mmol) and acetic acid (0.011 mL; 0.18 mmol) were added to a solution of compound 68 (0.187 g; 0.43 mmol) and 3-oxetanone (0.026 mL; 0.43 mmol) in 1,2-dichloroethane (7 mL) at 5° C. under N$_2$ flow. The reaction mixture was stirred at 60° C. overnight, poured into ice water, basified with a 10% aqueous solution of K$_2$CO$_3$ and extracted with DCM. The organic layer was dried over MgSO$_4$, filtered and evaporated to dryness. The residue (0.154 g) was purified by chromatography over silica gel (Spherical Silica, 5 μm, 150×30.0 mm; mobile phase: gradient from 0.2% NH$_4$OH, 98% DCM, 2% MeOH to 1% NH$_4$OH, 90% DCM, 10% MeOH). The product fractions were collected and the solvent was evaporated to give 0.032 g of a compound which was crystallized from Et$_2$O. The precipitate was filtered and dried to give 0.016 g (7%) of compound 164. M.P.: 218° C. (DSC).

Conversion 4b
Preparation of Compound 290

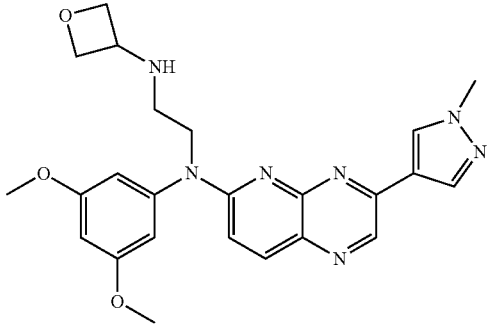 [SMILES: COc1cc(OC)cc(N(CCNC2COC2)c2ccc3ncc(-c4cnn(C)c4)nc3n2)c1]

A solution of compound 236 (280 mg; 0.69 mmol), 3-oxetanone (62 µL; 1.04 mmol) and AcOH (22 µL; 0.38 mmol) in 1,2-dichloroethane (26 mL) was heated at 50° C. for 24 hours. The reaction mixture was cooled to room temperature and sodium triacetoxyborohydride (220 mg; 1.04 mmol) was added. The reaction mixture was heated at 60° C. for 2 hours. The reaction mixture was partitioned between a 10% aqueous solution of K$_2$CO$_3$ and DCM. The aqueous layer was extracted once with DCM. The combined organic layers were dried over MgSO$_4$, filtered and evaporated to dryness. The residue was purified by chromatography over silica gel (spherical silica, 5 µm, 150×30.0 mm; mobile phase: gradient from 70% heptanes, 2% MeOH (+10% NH$_4$OH), 28% EtOAc to 0% eptanes, 20% MeOH (+10% NH$_4$OH), 80% EtOAc). The product fractions were evaporated to dryness to afford 34 mg (21%) of compound 290 M.P.: gum at 66° C. (kofler).

Conversion 5
Preparation of Compound 235

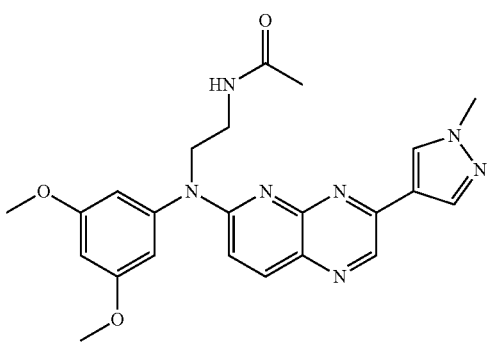 [SMILES: COc1cc(OC)cc(N(CCNC(C)=O)c2ccc3ncc(-c4cnn(C)c4)nc3n2)c1]

Acetylchloride (24 µL; 0.33 mmol) was added to a solution of compound 236 (122 mg; 0.3 mmol) and Et$_3$N (64 µL; 0.45 mmol) in DCM (5 mL) under N$_2$ at 5° C. The reaction mixture was stirred at 10° C. for 3 hours, poured into cooled water and extracted with DCM. The organic layer was dried over MgSO$_4$, filtered and evaporated to dryness. The residue (0.13 g) was purified by chromatography over silica gel (irregular SiOH, 15-40 µm, 12 g; mobile phase: 97% DCM, 3% MEOH). The product fractions were collected and evaporated to dryness. The residue (0.1 g) was crystallized from Et$_2$O. The yellow precipitate was filtered and dried under vacuum to give 87 mg (65%) of compound 235. M.P.: 193° C. (DSC).

Analogous Preparation of Compound 242

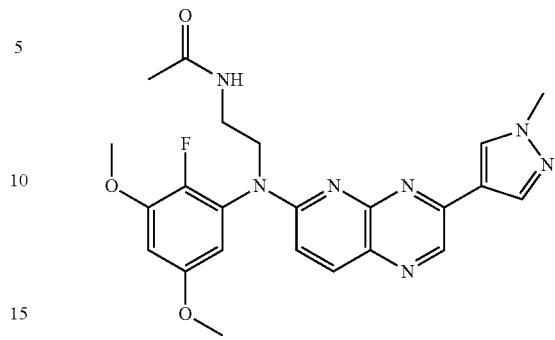

Starting from Compound 168
Analogous Preparation of Compound 243

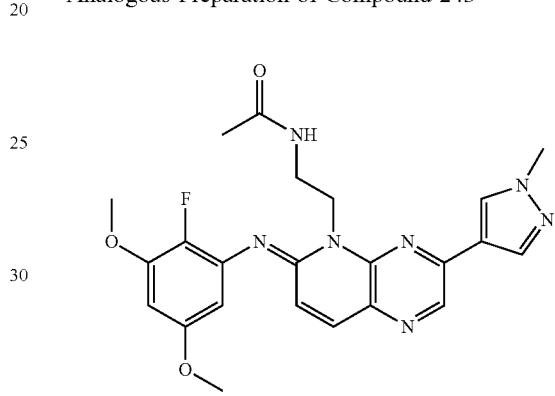

Starting from Compound 167
Conversion 6
Preparation of Compound 104

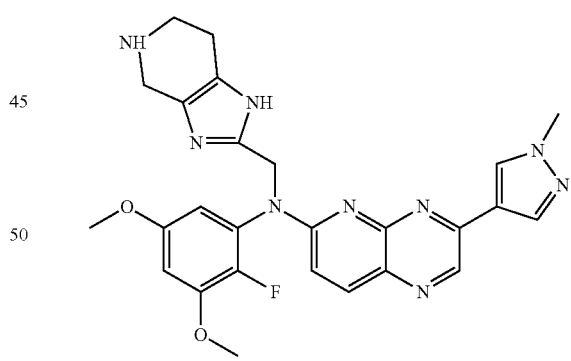

Trifluoroacetic acid (0.49 mL; 6.56 mmol) was added to a solution of compound 105 (0.085 g; 0.14 mmol) in DCM (7 mL) at room temperature. The mixture was stirred at room temperature for 2 hours. The solution was poured into iced water, basified by NH$_4$OH and extracted with DCM. The organic layer was dried over MgSO$_4$, filtered and evaporated till dryness. The residue (70 mg) was purified by chromatography over silica gel (stability Silica 5 µm 150×30.0 mm, mobile phase: gradient from 0.2% NH$_4$OH, 98% DCM, 2% MeOH to 1.3% NH$_4$OH, 87% DCM, 13% MeOH). The product fractions were collected and evaporated to dryness.

The residue (46 mg) was crystallized from Et₂O.
The precipitate was filtered and dried to give 0.027 g of compound 104 (36%). M.P.: gum at 60° C. (Kofler).

Analogous Preparation of Compound 227

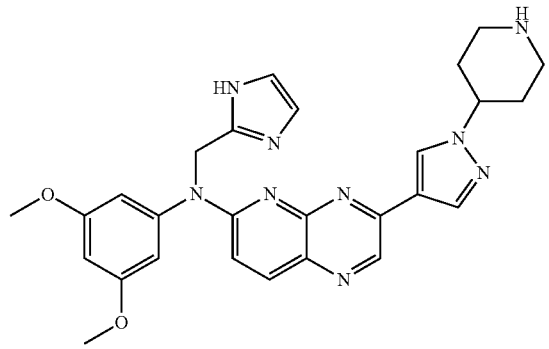 [SMILES: COc1cc(OC)cc(N(Cc2ncc[nH]2)c2ccc3ncc(-c4cnn(C5CCNCC5)c4)nc3n2)c1]

Starting from Compound 228
Analogous Preparation of Compound 262

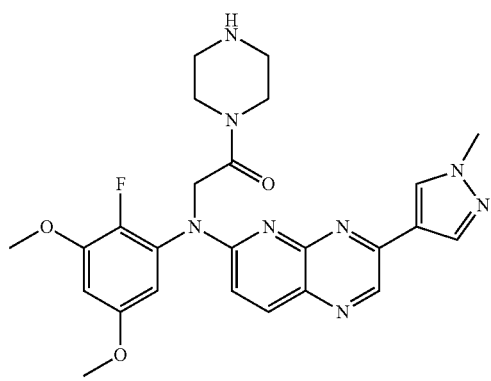 [SMILES: COc1cc(OC)c(F)c(N(CC(=O)N2CCNCC2)c2ccc3ncc(-c4cnn(C)c4)nc3n2)c1]

Starting from Compound 263
Analogous Preparation of Compound 299

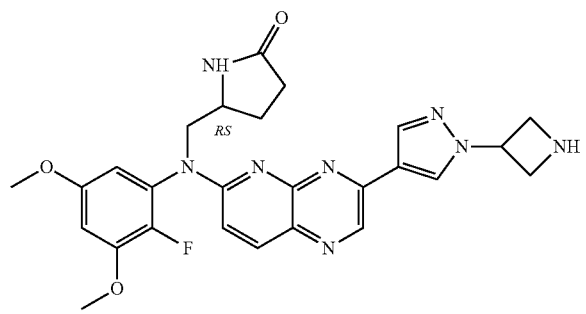 [SMILES: COc1cc(OC)c(F)c(N(CC2CCC(=O)N2)c2ccc3ncc(-c4cnn(C5CNC5)c4)nc3n2)c1]

Starting from Compound 300
Conversion 7
Preparation of Compound 106

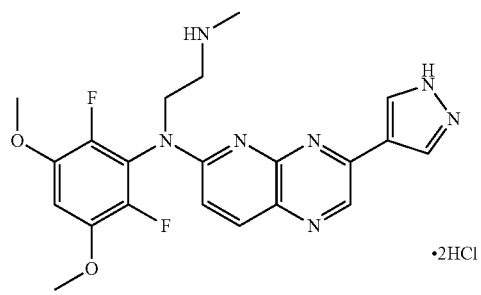 [SMILES: CNCCN(c1ccc2ncc(-c3cn[nH]c3)nc2n1)c1c(F)c(OC)cc(OC)c1F]

At 5° C., a solution of HCl 5/6N in iPrOH (0.88 mL; 4.36 mmol) was added to a solution of compound 108 (0.38 g; 0.73 mmol) in MeOH (6 mL). The reaction mixture was stirred at room temperature for 6 hours. The reaction mixture was concentrated, then the residue was taken-up with Et₂O. The precipitate was filtered and dried under vacuum to give 0.348 g (92%) of compound 106. M.P.: 250° C. (DSC). $C_{21}H_{21}F_2N_7O_2 \cdot 2HCl \cdot 0.39H_2O$ Analogous Preparation of Compound 121 Starting from Compound 107

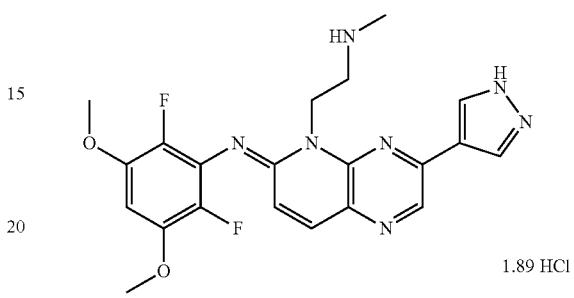

Conversion 8
Preparation of Compound 230

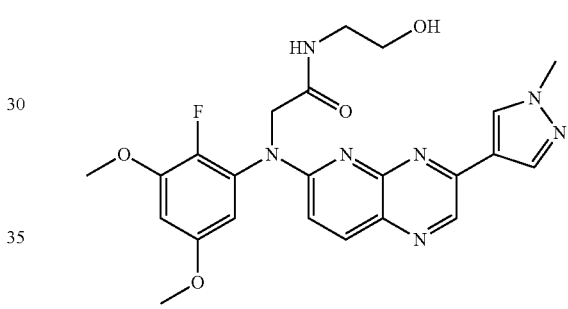

Compound 231 (0.1 g; 0.228 mmol), 1-(3-dimethylaminopropyl)-3-ethylcarbodiimide hydrochloride (0.053 g; 0.342 mmol), DMAP (0.003 g; 0.023 mmol), Et₃N (0.082 mL; 0.57 mmol) and ethanolamine (0.028 mL; 0.456 mmol) were mixed in DCM. The resulting red suspension was stirred overnight at room temperature. The reaction mixture was diluted with DCM. The organic layer was successively washed with a 3N aqueous solution of HCl then, a saturated aqueous of NaHCO₃, dried over MgSO₄, filtered and evaporated to dryness. The residue (0.06 g) was purified by chromatography over silica gel (irregular SiOH, 15-45 µm, 12 g; mobile phase: gradient from 97% DCM, 3% MeOH, 0.3% NH₄OH to 90% DCM, 10% MeOH, 1% NH₄OH). The product fractions were collected and evaporated to dryness yielding 6.6 mg (6%) of compound 230 M.P.: 258° C. (Kofler).

Analogous Preparation of Compound 249

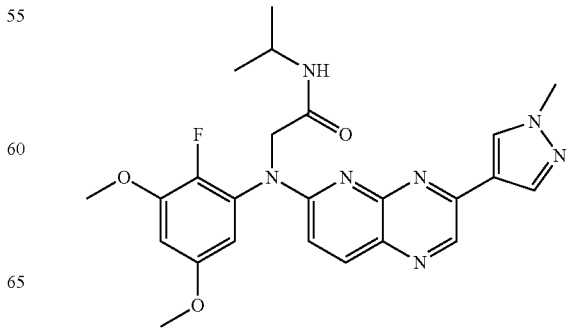

Starting from Compound 231
Analogous Preparation of Compound 263

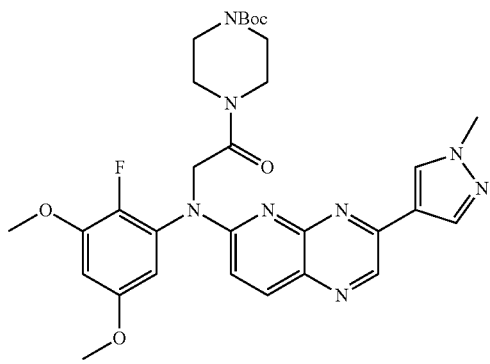 [SMILES: COc1cc(OC)c(F)c(N(CC(=O)N2CCN(C(=O)OC(C)(C)C)CC2)c2ccc3ncc(-c4cnn(C)c4)nc3n2)c1]

Starting from Compound 231
Conversion 9
Preparation of Compound 231

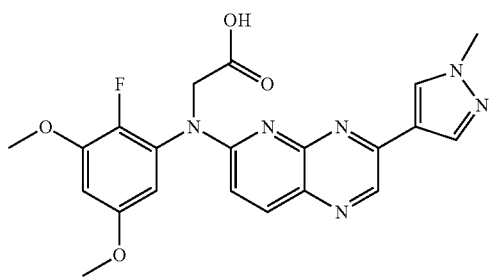

Lithium hydroxide monohydrate (56 mg; 2.34 mmol) was added to a solution of compound 214 (0.212 g; 0.47 mmol) in a mixture of THF (5 mL) and water (2 mL). The reaction mixture was stirred overnight at room temperature and neutralized with an aqueous solution of HCl 3N. The reaction mixture was portioned between water and EtOAc. The organic layer was dried over MgSO₄, filtered and evaporated to dryness. The residue was taken up with ACN to afford 0.188 g (91%) of compound 231. M.P.: >260° C. (Kofler).
Conversion 10
Preparation of Compound 244

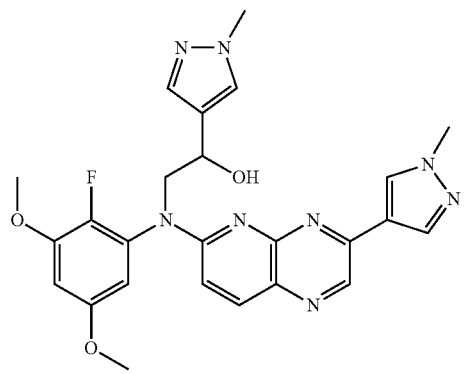 [SMILES: COc1cc(OC)c(F)c(N(CC(O)c2cnn(C)c2)c2ccc3ncc(-c4cnn(C)c4)nc3n2)c1]

Sodium borohydride (60 mg; 1.577 mmol) was added to a suspension of compound 225 (660 mg; 1.314 mmol) in MeOH (30 mL) at room temperature. The reaction mixture was stirred at this temperature for 2 hours, quenched with iced water and extracted with DCM. The organic layer was decanted, dried over MgSO₄, filtered and evaporated to dryness. The residue was purified by chromatography over silica gel (irregular SiOH, 15-40 μm, 24 g; mobile phase: gradient from 100% DCM, 0% MeOH to 95% DCM, 5% MeOH). The product fractions were collected and evaporated to dryness. The resulting residue (0.1 g) was purified by chromatography over silica gel (spherical silica, 5 μm, 150×30.0 mm; mobile phase: gradient from 0.2% NH₄OH, 98% DCM, 2% MeOH to 1.2% NH₄OH, 88% DCM, 12% MeOH). The product fractions were collected and evaporated to dryness. The residue was taken up with Et₂O. The precipitate was filtered and dried yielding 59 mg (9%) of compound 244. M.P.: gum at 101° C. (Kofler).
Conversion 11
Preparation of Compound 282

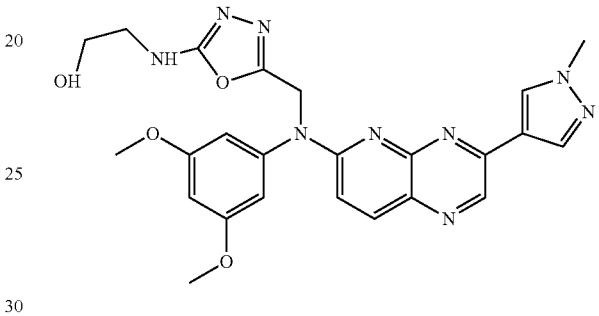

(Benzotriazol-1-yloxy)tris(dimethylamino)phosphonium hexafluorophosphate (454 mg; 1.03 mmol) was added at room temperature to a mixture of compound 229 (0.383 g; 0.789 mmol), ethanolamine (0.115 mL; 1.58 mmol) and DIPEA (0.261 mL; 1.58 mmol) in THF (8 mL). The mixture was stirred overnight, poured into ice and extracted with EtOAc. The organic layer was washed with brine, dried over MgSO₄, filtered and the solvent was evaporated. The residue (0.36 g) was purified by chromatography over silica gel (spherical silica, 5 μm, 150×30.0 mm; mobile phase: gradient from 0.2% NH₄OH, 2% MeOH, 98% DCM to 1.2% NH₄OH, 12% MeOH, 88% DCM). The product fractions were mixed and the solvent was evaporated. The residue was taken up by Et₂O. The precipitate was filtered and dried yielding 0.111 g (28%) of compound 282 (28%). M.P.: 104° C. (gum, kofler).
Analogous Preparation of Compound 283

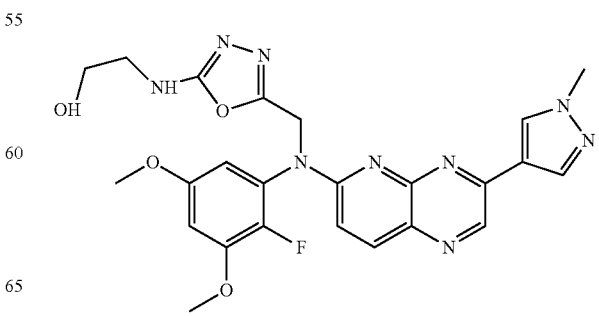

Starting from Compound 284
Conversion 12
Preparation of Compound 194

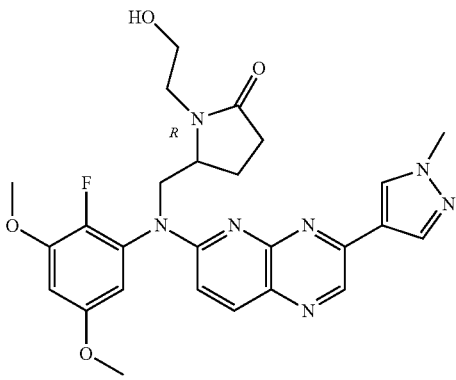

NaH (59 mg; 1.476 mmol) was added portion wise to a solution of compound 53 (470 mg; 0.984 mmol) in DMF (10 mL) at 5° C. under $N_2$ flow. The reaction mixture was stirred at 5° C. for 30 minutes, then (2-bromoethoxy)-tert-butyldimethylsilane (232 μL; 1.08 mmol) was added dropwise. The reaction mixture was stirred at room temperature overnight, quenched with iced water and extracted with EtOAc. The organic layer was decanted, dried over $MgSO_4$, filtered and evaporated to dryness.

A 1M solution of tetrabutylammonium fluoride in THF (4.45 mL; 4.45 mmol) was added to a solution of the residue obtained previously in THF (27 mL). The reaction mixture was stirred at room temperature overnight, poured into ice and extracted with EtOAc. The organic layer was washed with brine, dried over $MgSO_4$, filtered and the solvent was evaporated. The residue was purified by chromatography over silica gel (irregular SiOH, 15-40 μm, 30 g; mobile phase: 0.1% $NH_4OH$, 4% MeOH, 96% DCM). The product fractions were collected and the solvent was evaporated to give 130 mg (26%) of compound 194, M.P.: 102° C. (gum, Kofler).

Conversion 13
Salt Preparation of Compound 23

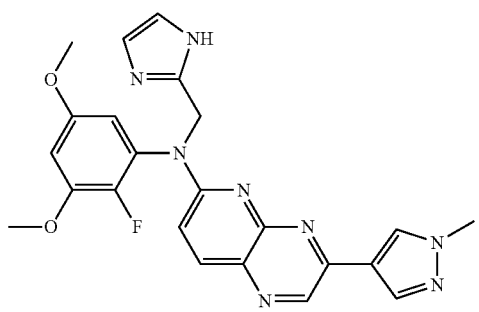

a) Preparation of Sulfate Salt of Compound 23

A solution of concentrated sulfuric acid (24 μL; 0.434 mmol) in ethanol (3.5 mL) was added slowly to a solution of free base of compound 23 (100 mg; 0.217 mmol) in C (6.5 mL) at 50° C. and the resulting solution was allowed to cool to room temperature and stirred overnight. The solution was evaporated to dryness and the residue was crystallized in an ice bath from ACN (2 mL). The precipitate was filtered, washed with $Et_2O$ and dried yielding 69 mg (47%) of compound 23 as a sulfate salt, M.P.: 198° C. (gum, Kofler). $C_{23}H_{21}FN_8O_2.2H_2SO_4.1H_2.0.06\ Et_2O.0.03$ DMF.

b) Preparation of Hydrochloric Acid Salt of Compound 23

A pre-cooled solution of concentrated hydrochloride acid (36 μL; 0.434 mmol) in EtOH (3.5 mL) was added slowly to a solution of free base of compound 23 (100 mg; 0.217 mmol) in ACN (6.5 mL) at 50° C. and the resulting solution was allowed to cool to room temperature and stirred overnight. The solution was evaporated to dryness and the residue was taken up with ACN (2 mL). The precipitate was filtered, washed with $Et_2O$ and dried yielding 92 mg (78%) of compound 23 as a hydrochloric acid salt, M.P.: 216° C. (DSC). $C_{23}H_{21}FN_8O_2.1.76HCl.H_2O$ c) Preparation of Phosphate Salt of Compound 23

A pre-cooled solution of 17M phosphoric acid (26 μL; 0.434 mmol) in EtOH (3.5 mL) was added slowly to a solution of free base of compound 23 (100 mg; 0.217 mmol) in ACN (6.5 mL) at 50° C. and the resulting solution was allowed to cool to room temperature and stirred overnight. The precipitate was filtered, washed with ACN then $Et_2O$ and dried yielding 78 mg (51%) of compound 23 as a phosphate salt, M.P.: 175° C. (gum, Kofler). $C_{23}H_{21}FN_8O_2.2.5H_3PO_4$ d) Preparation of Lactate Salt of Compound 23

A pre-cooled solution of 85% lactic acid (CAS 50-21-5) (41 μL; 0.434 mmol) in EtOH (3.5 mL) was added slowly to a solution of free base of compound 23 (100 mg; 0.217 mmol) in ACN (6.5 mL) at 50° C. and the resulting solution was allowed to cool to room temperature and stirred overnight. The solution was evaporated to dryness and the residue was taken up with ACN (2 mL). The precipitate was filtered, washed with $Et_2O$ and dried yielding 74 mg (60%) of compound 23 as a lactate salt, M.P.: 118° C. (DSC). $C_{23}H_{21}FN_8O_2.C_3H_6O_3.H_2O$.

e) Preparation of Fumarate Salt of Compound 23

A pre-cooled solution of fumaric acid (50 mg; 0.434 mmol) in EtOH (3.5 mL) was added slowly to a solution of free base of compound 23 (100 mg; 0.217 mmol) in ACN (6.5 mL) at 50° C. and the resulting solution was allowed to cool to room temperature and stirred overnight. The precipitate was filtered, washed with ACN then $Et_2O$ and dried yielding 70 mg (60%) of compound 23 as a fumarate salt, M.P.: 186° C. (DSC). $C_{23}H_{21}FN_8O_2.0.5C_4H_4O_4.H_2O$.

Salt Preparation of Compound 24

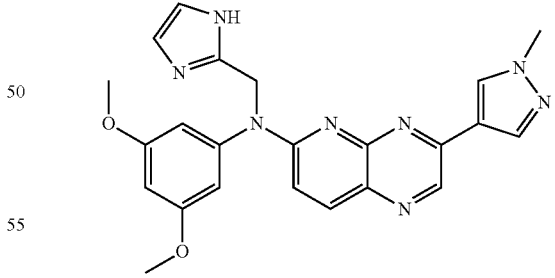

f) Preparation of Sulphate Salt of Compound 24

Free base of compound 24 (150 mg; 0.339 mmol) was diluted in a mixture of EtOH (10 mL) and ACN (5 mL) and the reaction mixture was refluxed until dissolution. The solution was cooled down to 10° C., then a solution of concentrated sulfuric acid (36 μl; 0.68 mmol) in EtOH (150 μl) was added and the reaction mixture was allowed to stand overnight. The precipitate was filtered, washed with $Et_2O$ and dried under vacuum and to give 155 mg (81%) of compound 24 as a sulphate salt. M.P.: 266° C. (DSC). $C_{23}H_{22}N_8O_2.1.03H_2SO_4.1.17H_2O$ g) Preparation of Phosphate Salt of Compound 24

Free base of compound 24 (150 mg; 0.339 mmol) was diluted in EtOH (10 mL) and the reaction mixture was refluxed until dissolution. The solution was cooled down to 10° C., then a solution of phosphoric acid 85% (47 µl; 0.68 mmol) in EtOH (0.5 mL) was added and the mixture was allowed to stand for 4 days. The precipitate was filtered, washed with Et$_2$O and dried under vacuum to give 133 mg (71%) of compound 24 as a phosphate salt. M.P.: 253° C. (DSC). $C_{23}H_{22}N_8O_2.1.13H_3PO_4.0.06\ Et_2O$ h) Preparation of DL-Tartrate Salt of Compound 24

Free base of compound 24 (150 mg; 0.339 mmol) was diluted in EtOH (10 mL) and the reaction mixture was refluxed until dissolution and the solution was cooled down to 10° C. A solution of DL-tartric acid (102 mg; 0.678 mmol) in EtOH (5 mL) at 50° C. was added to the previous solution and the reaction mixture was allowed to stand for 4 days. The precipitate was filtered, washed with Et$_2$O, dried under vacuum and to give 163 mg (70%) of compound 24 as a DL-tartrate salt M.P.: 176° C. (Kofler). $C_{23}H_{22}N_8O_2.1.4C_4H_6O_8.1.8H_2O$ i) Preparation of Fumarate Salt of Compound 24

Free base of compound 24 (150 mg; 0.339 mmol) was diluted in EtOH (10 mL) and the reaction mixture was refluxed until dissolution and the solution was cooled down to 10° C. A solution of fumaric acid (78.7 mg; 0.678 mmol) in EtOH (5 mL) at 50° C. was added to the previous solution and the reaction mixture was allowed to stand for 4 days. The precipitate was filtered, washed with Et$_2$O, dried under vacuum and to give 114 mg (61%) of compound 24 as a fumarate salt. M.P.: 222° C. (DSC). $C_{23}H_{22}N_8O_2.0.9C_4H_4O_4.0.25H_2O$ j) Preparation of Hydrochloric Acid Salt of Compound 24

A 4M solution of hydrochloride acid in 1,4-dioxane (4.6 mL; 18.195 mmol) was added dropwise to a cooled solution of compound 14 (1 g; 1.819 mmol) in ACN (36 mL). The reaction mixture was heated at 50° C. for 18 hours and cooled to room temperature. The precipitate was filtered, washed with Et$_2$O and dried yielding 570 mg (65%) of compound 24 as a hydrochloride salt 100 mg of the residue was recrystallized from MeOH (4 mL).

The solid was filtered and dried under vacuum yielding 68 mg of compound 24 as a hydrochloride salt. M.P.>260° C. (K) $C_{23}H_{22}N_8O_2.1.34HCl.86H_2O$.

The following compounds were prepared according to reaction protocols of one of the above Examples using alternative starting materials as appropriate.

In the table =CoX (or =BX) indicates that the preparation of this compound is described in Conversion X (or Method BX).

In the table ~CoX (or ~BX) indicates that this compound is prepared according to Conversion X (or Method BX).

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

TABLE A1 compounds and physico-chemical data

| Comp No. | Compound Struct. | Method | MP (° C.) Kofler | MP (° C.) DSC | HPLC Rt (min) | MS M+ (H⁺) | LC/ GC/MS Method |
|---|---|---|---|---|---|---|---|
| 23 | | =C1 | | 228° C. | 2.3 | 461 | 1 |
| 7 | | =B4 | 65° C. | | 2.5 | 451 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 9 | | =B5 | | 227° C. | 2.5 | 473 | 1 |
| 16 | | =B6 | | 208° C. | 2.4 | 457 | 1 |
| 5 | | =B3 | | 183° C. | 2.3 | 484 | 1 |
| 10 | | ~B5 | 218° C. | | 2.4 | 91 | 1 |

TABLE A1-continued compounds and physico-chemical data

| Comp No. | Compound Struct. | Method | MP (° C.) Kofler | MP (° C.) DSC | HPLC Rt (min) | MS M+ (H+) | LC/GC/MS Method |
|---|---|---|---|---|---|---|---|
| 24 | | ~C1 | 228° C. | | 2.35 | 443 | 1 |
| 25 | | ~C1 | | 248° C. | 2.3 | 479 | 1 |
| 11 | | ~B5 | | 209° C. | 2.43 | 491 | 1 |
| 26 | | =C2 | 190° C. | | 2.75 | 508 | 1 |
| 20 | | ~B6 | | 220° C. | 2.35 | 443 | 1 |

TABLE A1-continued
compounds and physico-chemical data
| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 1 | 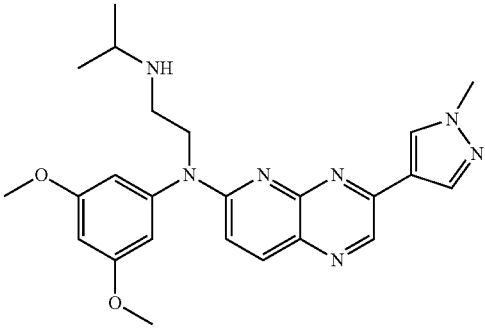 [SMILES: COc1cc(OC)cc(N(CCNC(C)C)c2ccc3ncc(-c4cnn(C)c4)nc3n2)c1] | =B1 | | | 2.31 | 448 | 1 |
| 21 | 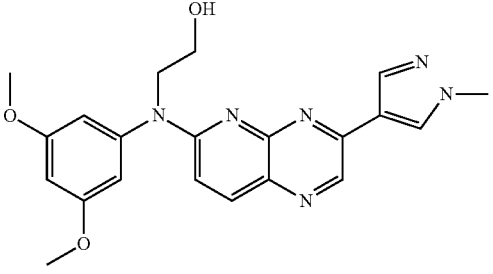 [SMILES: CN/C=C(\C=N)c1cnc2ccc(N(CCO)c3cc(OC)cc(OC)c3)nc2n1] | ~B6 | | | 2.43 | 407 | 1 |
| 19 | 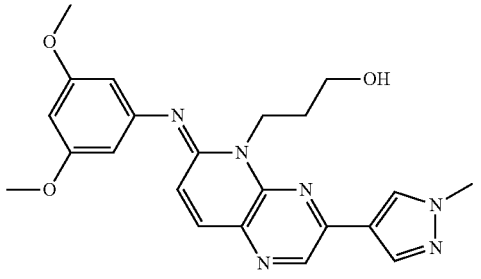 | ~B6 | | 157° C. | 2.71 | 421 | 1 |
| 18 | 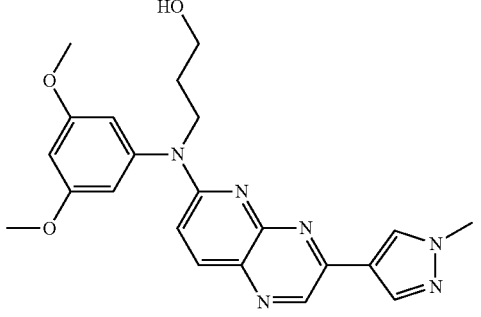 | ~B6 | | 169° C. | 2.54 | 421 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/GC/MS Method |
|---|---|---|---|---|---|---|---|
| 8 | | ~B4 | | 186° C. | 2.89 | 475 | 1 |
| 12 | | ~B5 | | 248° C. | 2.54 | 455 | 1 |
| 17 | | =B6 | | 206° C. | 2.61 | 457 | 1 |
| 2 | | ~B1 | 70° C. | | 2.31 | 466 | 1 |

TABLE A1-continued compounds and physico-chemical data

| Comp No. | Compound Struct. | Method | MP (° C.) Kofler | MP (° C.) DSC | HPLC Rt (min) | MS M+ (H+) | LC/GC/MS Method |
|---|---|---|---|---|---|---|---|
| 6 | | =B3 | 122° C. | | 2.39 | 484 | 1 |
| 4 | | =B2 | | 174° C. | 2.27 | 456 | 1 |
| 3 | | =B2 | | 134° C. | 2.15 | 456 | 1 |
| 3a | | =B2 | | 159° C. | | | |

TABLE A1-continued
compounds and physico-chemical data
| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 13 | 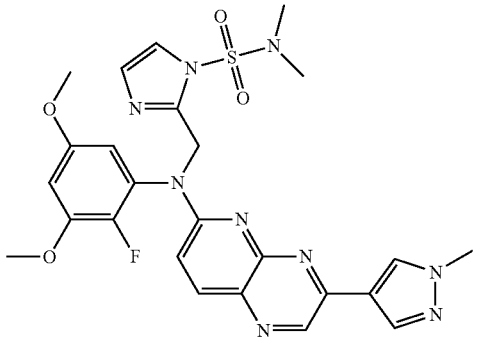 | ~B5 | | | | | |
| 14 | 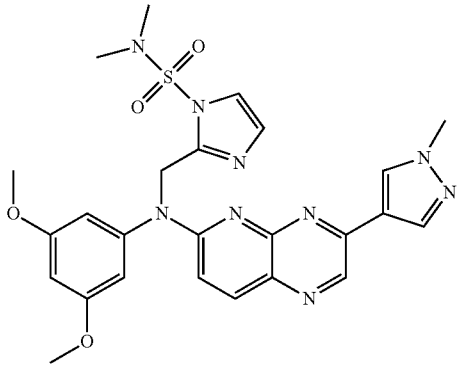 [SMILES: COc1cc(OC)cc(N(Cc2nccn2S(=O)(=O)N(C)C)c2ccc3ncc(-c4cnn(C)c4)nc3n2)c1] | ~B5 | 215 | | 2.81 | 550 | 1 |
| 15 | 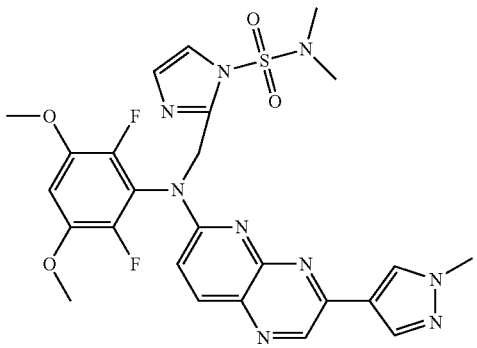 | ~B5 | | | | | |
| 22 | 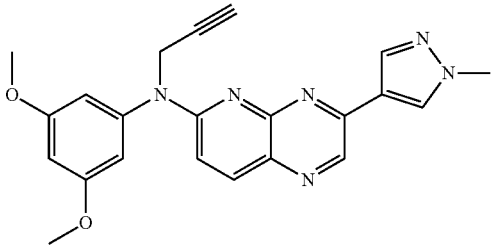 [SMILES: C#CCN(c1cc(OC)cc(OC)c1)c1ccc2ncc(-c3cnn(C)c3)nc2n1] | =B7 | | | | | |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/GC/MS Method |
|---|---|---|---|---|---|---|---|
| 27 | | | 130 | | 2.38 | 419 | 1 |
| 30 | | | 202 | | 2.81 | 493 | 1 |
| 29 | | | Gum at 100 | | 3.04 | 493 | 1 |
| 31 | | | 200 | | 3.00 | 511 | 1 |
| 41 | | | 170 | | 2.28 | 461 | 1 |

TABLE A1-continued
compounds and physico-chemical data
| Comp No. | Compound Struct. | MP Method | MP (° C.) Kofler | MP (° C.) DSC | HPLC Rt (min) | MS M+ (H+) | LC/GC/MS Method |
|---|---|---|---|---|---|---|---|
| 40 | 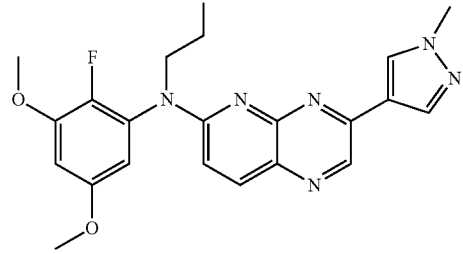 | | | 200 | 2.36 | 425 | 1 |
| 39 | 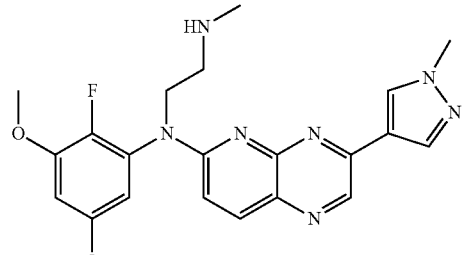 | | | 185 | 2.16 | 438 | 1 |
| 36 | 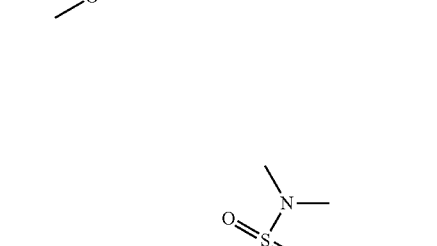 | | | 100 | 2.63 | 568 | 1 |
| 33 | 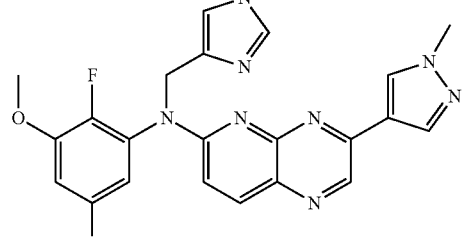 | | | 208 | 2.87 | 475 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/GC/MS Method |
|---|---|---|---|---|---|---|---|
| 34 | | | | 208 | 2.87 | 475 | 1 |
| 42 | | | | 245 | 2.37 | 477 | 1 |
| 52 | | | | 190 | 2.32 | 478 | 1 |
| 53 | | | | 176 | 2.53 | 478 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 50 | | | 162-163 | | 2.42 | 487 | 1 |
| 51 | | | 180 | | 2.66 | 487 | 1 |
| 49 | | | 182 | | 2.36 | 460 | 1 |
| 48 | | | 134 | | 2.29 | 496 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 47 | | | 169 | | 2.52 | 496 | 1 |
| 46 | | | 131 | | 2.32 | 478 | 1 |
| 45 | | | 127 | | 2.53 | 478 | 1 |
| 192 | | | 128 | | 2.29 | 496 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 193 | | | 181 | | 2.52 | 496 | 1 |
| 44 | | | 80 | | 2.23 | 396 | 1 |
| 59 | | | 94-95 | | 2.45 | 469 | 1 |
| 58 | | | 94-95 | | 2.45 | 469 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 56 | | | 99 (gum) | | 2.43 | 524 | 1 |
| 55 | | | 227 | | 2.67 | 524 | 1 |
| 54 | | | 125 (gum) | | 2.36 | 460 | 1 |
| 86 | | | 155 | | 2.24 | 462 | 1 |

TABLE A1-continued compounds and physico-chemical data

| Comp No. | Compound Struct. | Method | MP (° C.) Kofler | MP (° C.) DSC | HPLC Rt (min) | MS M+ (H+) | LC/ GC/MS Method |
|---|---|---|---|---|---|---|---|
| 85 | | | 145 | | 2.22 | 480 | 1 |
| 83 | | | 90 | | 2.21 | 458 | 1 |
| 84 | | | 115 | | 2.41 | 458 | 1 |
| 62 | | | 178 | | 2.67 | 515 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 63 | | | 174 | | 2.66 | 515 | 1 |
| 64 | | | 164 | | 2.93 | 515 | 1 |
| 76 | | | 137-138 | | 2.99 | 497 | 1 |
| 77 | | | 96-97 | | 2.95 | 497 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 81 | | | 80° C. gum | | 2.25 | 488 | 1 |
| 82 | | | 100° C. gum | | 2.38 | 488 | 1 |
| 80 | | | 150° C., >260° C. polymorph | | 2.59 | 511 | 1 |
| 75 | | | 148-149 | | 2.71 | 497 | 1 |
| 73 | | | 174 | | 2.30 | 465 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 72 | | | >260 | | 2.62 | 493 | 1 |
| 71 | | | 234 | | 2.27 | 444 | 1 |
| 69 | | | 130 | | 2.12 | 442 | 1 |
| 70 | | | 138 | | 2.30 | 442 | 1 |
| 67 | | | 169 | | 2.06 | 442 | 1 |

TABLE A1-continued compounds and physico-chemical data

| Comp No. | Compound Struct. | MP (° C.) Method Kofler | MP (° C.) DSC | HPLC Rt (min) | MS M+ (H+) | LC/ GC/MS Method |
|---|---|---|---|---|---|---|
| 68 | | | 198 | 2.17 | 442 | 1 |
| 65 | | | 172 | 2.37 | 481 | 1 |
| 61 | | | 176 | 2.67 | 515 | 1 |
| 78 | | | 143-144 | 2.71 | 497 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 79 | | | | 142 | 2.71 | 497 | 1 |
| 87 | | | | 160 | 2.65 | 528 | 1 |
| 88 | | | | 175-180 | 2.42 | 528 | 1 |
| 89 | | | | 183 | 2.74 | 498 | 1 |

TABLE A1-continued
compounds and physico-chemical data
| Comp No. | Compound Struct. | MP Method | MP (° C.) Kofler | MP (° C.) DSC | HPLC Rt (min) | MS M+ (H+) | LC/GC/MS Method |
|---|---|---|---|---|---|---|---|
| 92 | 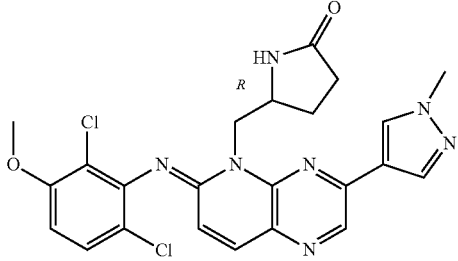 | | | | 2.74 | 498 | 1 |
| 95 | 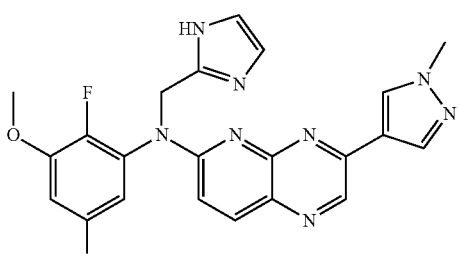 | | 230 | | 2.07 | 447 | 1 |
| 97 | 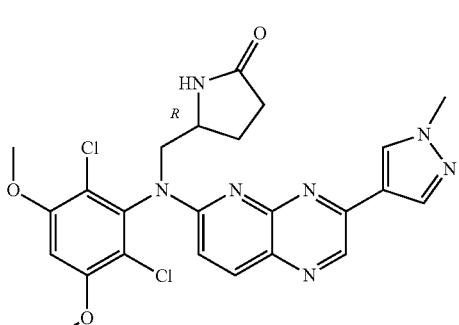 | | 150 | | 2.42 | 528 | 1 |
| 98 | 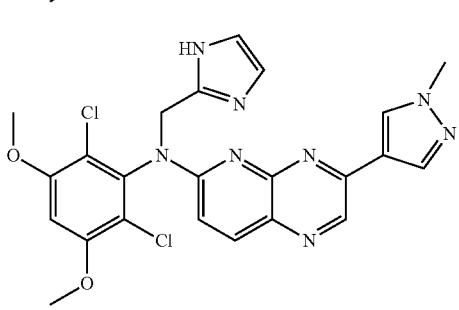 | | 210 | | 2.40 | 511 | 1 |
| 100 | 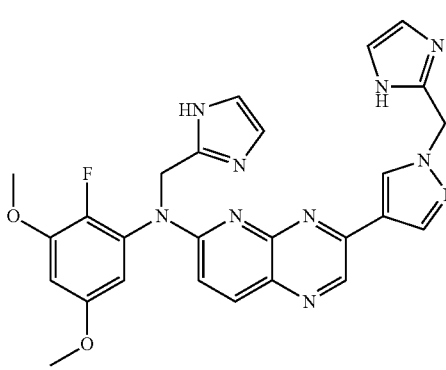 | | 135 (gum) | | 2.19 | 527 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 103 | | | 172 (gum) | | 2.04 | 429 | 1 |
| 106 | | | | 250 | 2.00 | 442 | 1 |
| 109 | | | | 232 | 2.30 | 475 | 1 |
| 111 | | | | 202 | 2.33 | 480 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/GC/MS Method |
|---|---|---|---|---|---|---|---|
| 112 | | | | 207 | 2.54 | 480 | 1 |
| 113 | | | | 212 | 2.48 | 475 | 1 |
| 114 | | | | 222 | 2.73 | 475 | 1 |
| 115 | | | | 130 (gum) | 2.61 | 461 | 1 |
| 118 | | | | 220 | 2.43 | 461 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 119 | | | 226 | | 2.68 | 506 | 1 |
| 120 | | | 80, gum | | 2.45 | 506 | 1 |
| 121 | | | 239 | | 2.13 | 442 | 1 |
| 122 | | | 80 gum | | 1.87 | 442 | 1 |

TABLE A1-continued compounds and physico-chemical data

| Comp No. | Compound Struct. | MP (° C.) Method Kofler | MP (° C.) DSC | HPLC Rt (min) | MS M+ (H+) | LC/ GC/MS Method |
|---|---|---|---|---|---|---|
| 123 | | | 215 | 2.54 | 480 | 1 |
| 124 | | | 197 | 2.33 | 480 | 1 |
| 125 | | | 202 | 2.33 | 461 | 1 |
| 128 | | | 194 | 2.50 | 475 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 129 | | | 137 | | 2.95 | 461 | 1 |
| 131 | | | 236 | | 2.33 | 475 | 1 |
| 132 | | | 235 | | 2.14 | 476 | 1 |
| 133 | | | 230 | | 2.71 | 488 | 1 |

TABLE A1-continued compounds and physico-chemical data

| Comp No. | Compound Struct. | Method | MP (° C.) Kofler | MP (° C.) DSC | HPLC Rt (min) | MS M+ (H+) | LC/ GC/MS Method |
|---|---|---|---|---|---|---|---|
| 134 | | | 142 | | 2.50 | 488 | 1 |
| 135 | | | 145 | 130 | 2.34 | 475 | 1 |
| 137 | | | 185-186 | | 2.27 | 475 | 1 |
| 139 | | | 94 | | 2.88 | 479 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/GC/MS Method |
|---|---|---|---|---|---|---|---|
| 140 | | | 149 (gum) | | 1.90 | 463 | 1 |
| 141 | | | | 285 | 2.21 | 429 | 1 |
| 142 | | | 150 (gum) | | 2.53 | 433 | 1 |
| 143 | | | 174 | | 2.75 | 451 | 1 |
| 144 | | | 213 | | 2.48 | 451 | 1 |

TABLE A1-continued compounds and physico-chemical data

| Comp No. | Compound Struct. | MP Method | MP (° C.) Kofler | MP (° C.) DSC | HPLC Rt (min) | MS M+ (H⁺) | LC/ GC/MS Method |
|---|---|---|---|---|---|---|---|
| 145 | | | | 221 | 2.20 | 505 | 1 |
| 146 | | | | 143 (gum) | 2.53 | 476 | 1 |
| 147 | | | | 162 (gum) | 2.78 | 476 | 1 |
| 148 | | | | 190 (gum) | 2.76 | 494 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 149 | | | 156 (gum) | | 2.48 | 494 | 1 |
| 150 | | | 200 | 202 | 2.63 | 474 | 1 |
| 151 | | | 106 | 113 | 2.41 | 474 | 1 |
| 152 | | | 252 | | 2.82 | 439 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 154 | | | 226 | | 2.87 | 483 | 1 |
| 155 | | | 160 | | 2.62 | 461 | 1 |
| 156 | | | 211 | 207 | 2.61 | 492 | 1 |
| 157 | | | 222 | 224 | 2.38 | 492 | 1 |

TABLE A1-continued compounds and physico-chemical data

| Comp No. | Compound Struct. | MP (° C.) Method Kofler | MP (° C.) DSC | HPLC Rt (min) | MS M+ (H+) | LC/ GC/MS Method |
|---|---|---|---|---|---|---|
| 158 | | | 199 | 2.62 | 492 | 1 |
| 159 | | | 120 | 2.32 | 492 | 1 |
| 160 | | | 198 | 2.62 | 492 | 1 |
| 161 | | | 110 | 2.32 | 492 | 1 |

TABLE A1-continued compounds and physico-chemical data

| Comp No. | Compound Struct. | MP (° C.) Method Kofler | MP (° C.) DSC | HPLC Rt (min) | MS M+ (H+) | LC/ GC/MS Method |
|---|---|---|---|---|---|---|
| 162 | | | 183 | 2.26 | 498 | 1 |
| 163 | | | 182 | 2.39 | 554 | 1 |
| 164 | | | 218 | 2.66 | 554 | 1 |
| 165 | | | 155 | 3.11 | 461 | 1 |

TABLE A1-continued
compounds and physico-chemical data
| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 166 | 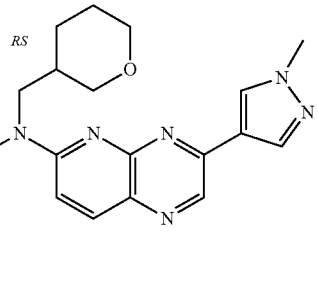 | | | 158 | 2.79 | 461 | 1 |
| 167 | 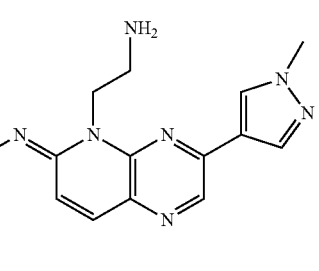 | | | 169 | 2.19 | 424 | 1 |
| 168 | 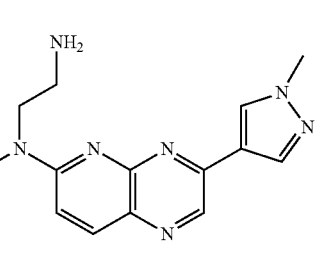 | | | 170 | 2.08 | 424 | 1 |
| 169 | 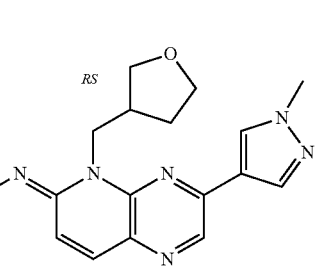 | | | 80 (gum) | 2.91 | 465 | 1 |
| 170 | 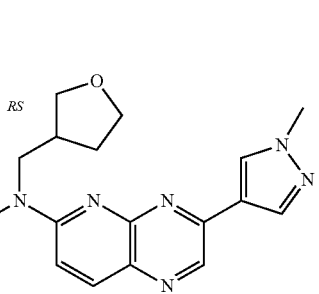 | | | 80 (gum) | 2.61 | 465 | 1 |

TABLE A1-continued
compounds and physico-chemical data
| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 173 | 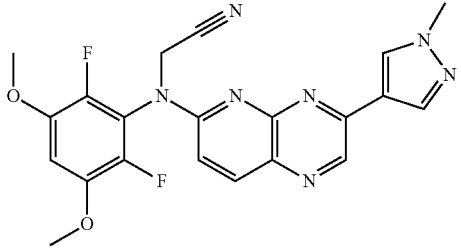 [SMILES: COc1cc(OC)c(F)c(N(CC#N)c2ccc3ncc(-c4cnn(C)c4)nc3n2)c1F] | | 250 | | 2.47 | 438 | 1 |
| 174 | 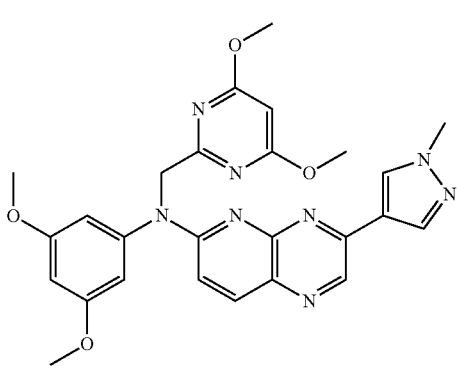 [SMILES: COc1cc(OC)cc(N(Cc2nc(OC)cc(OC)n2)c2ccc3ncc(-c4cnn(C)c4)nc3n2)c1] | | | 148 | 2.93 | 515 | 1 |
| 248 | 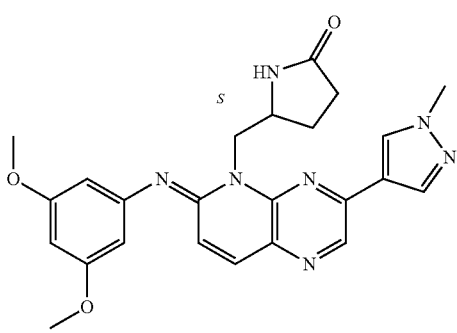 | | | 216 | 2.53 | 460 | 1 |
| 175 | 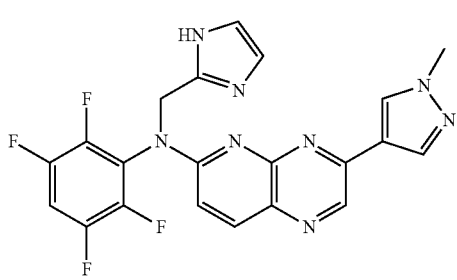 [SMILES: Cn1cc(-c2cnc3ccc(N(Cc4ncc[nH]4)c4c(F)c(F)cc(F)c4F)nc3n2)cn1] | | 210-215 | | 2.33 | 455 | 1 |
| 177 | 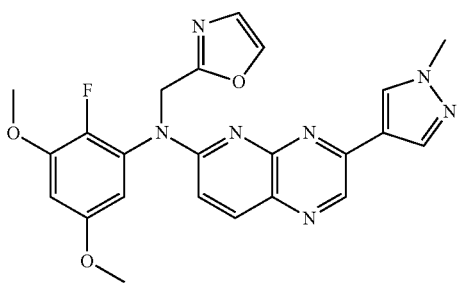 [SMILES: COc1cc(OC)c(F)c(N(Cc2ncco2)c2ccc3ncc(-c4cnn(C)c4)nc3n2)c1] | | | 193 | 2.51 | 462 | 1 |

TABLE A1-continued
compounds and physico-chemical data
| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 178 | 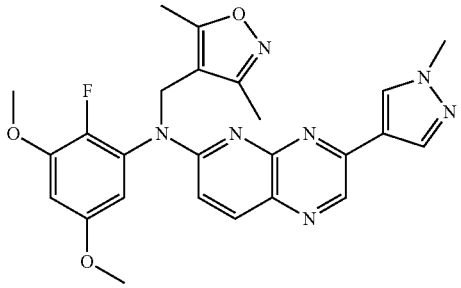 [SMILES: COc1cc(OC)c(F)c(N(Cc2c(C)noc2C)c2ccc3ncc(-c4cnn(C)c4)nc3n2)c1] | | | 185 | 2.65 | 490 | 1 |
| 179 | 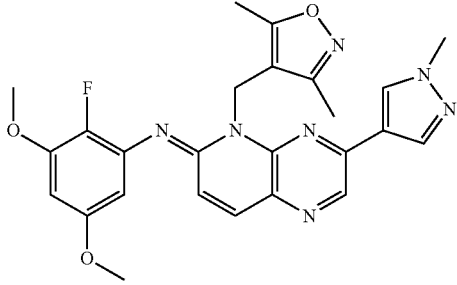 [SMILES: COc1cc(/N=c2\ccc3ncc(-c4cnn(C)c4)nc3n2Cc2c(C)noc2C)c(F)c(OC)c1] | | | 262 | 2.98 | 490 | 1 |
| 180 | 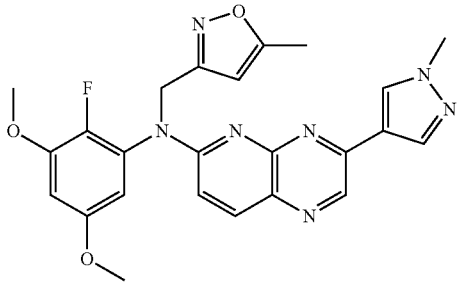 [SMILES: COc1cc(OC)c(F)c(N(Cc2cc(C)on2)c2ccc3ncc(-c4cnn(C)c4)nc3n2)c1] | | | 182 | 2.68 | 476 | 1 |
| 181 | 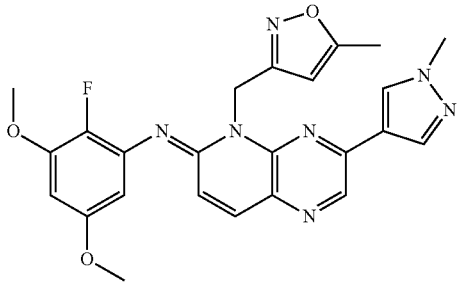 [SMILES: COc1cc(/N=c2\ccc3ncc(-c4cnn(C)c4)nc3n2Cc2cc(C)on2)c(F)c(OC)c1] | | | 190 | 2.94 | 476 | 1 |
| 182 | 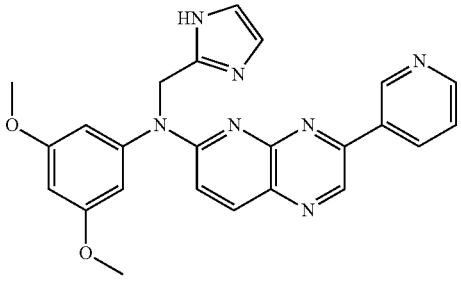 [SMILES: COc1cc(OC)cc(N(Cc2ncc[nH]2)c2ccc3ncc(-c4cccnc4)nc3n2)c1] | | | 250 | 2.36 | 440 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 184 | | | 180 | | 2.92 | 476 | 1 |
| 185 | | | 207 | | 2.64 | 476 | 1 |
| 171 | | | 172 | | 2.62 | 465 | 1 |
| 172 | | | 170 | | 2.62 | 465 | 1 |
| 186 | | | 177 | | 2.62 | 459 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 188 | | | 246 | | 2.23 | 460 | 1 |
| 190 | | | 160, gum | | 2.19 | 447 | 1 |
| 190a | | | | 245 | 2.33 | 458 | 1 |
| 194 | | | 102 gum | | 2.24 | 522 | 1 |
| 195 | | | | 197 | 2.44 | 475 | 1 |

TABLE A1-continued compounds and physico-chemical data

| Comp No. | Compound Struct. | MP (° C.) Method Kofler | MP (° C.) DSC | HPLC Rt (min) | MS M+ (H+) | LC/GC/MS Method |
|---|---|---|---|---|---|---|
| 196 | | | 162 | 2.78 | 475 | 1 |
| 197 | | | 249 | 1.92 | 445 | 1 |
| 198 | | | 232 | 2.60 | 442 | 1 |
| 200 | | | 236 | 2.81 | 457 | 1 |
| 202 | | | | 2.36 | 440 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 204 | | | | | 2.25 | 488 | 1 |
| 205 | | | | | 2.22 | 488 | 1 |
| 206 | | | 104, gum | | 2.42 | 519 | 1 |
| 207 | | | 154 | | 2.77 | 511 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 209 | | | 140, gum | | 2.38 | 539 | 1 |
| 224 | | | | | | | |
| 211 | | | 252 | | 2.34 | 458 | 1 |
| 213 | | | 203 | | 2.46 | 404 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 214 | | | 98, gum | | 2.60 | 453 | 1 |
| 215 | | | 222 | | 2.31 | 484 | 1 |
| 217 | | | 240 | | 2.4 | 445 | 1 |
| 218 | | | 130 | | 2.24 | 522 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/GC/MS Method |
|---|---|---|---|---|---|---|---|
| 219 | | | 112 | | 2.47 | 522 | 1 |
| 208 | | | 124 | 108, 123 | 2.59 | 511 | 1 |
| 96 | | | 192 | | 2.05 | 447 | 1 |
| 220 | | | 153 | | 2.9 | 533 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 221 | | | | 151 | 2.3 | 480 | 1 |
| 222 | | | — | — | 3.01 | 536 | 2 |
| 223 | | | 124, guml | | 3.01 | 475 | 2 |
| 225 | | | 220 | | 2.43 | 503 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/GC/MS Method |
|---|---|---|---|---|---|---|---|
| 226 | | | | 245 | 3.02 | 487 | 2 |
| 90 | | | 160 | | 2.41 | 498 | 1 |
| 91 | | | 176 | | 2.41 | 498 | 1 |
| 93 | | | 160 | | 2.41 | 498 | 1 |
| 94 | | | 176 gum | | 2.41 | 498 | 1 |

TABLE A1-continued compounds and physico-chemical data

| Comp No. | Compound Struct. | MP (° C.) Method Kofler | MP (° C.) DSC | HPLC Rt (min) | MS M+ (H+) | LC/ GC/MS Method |
|---|---|---|---|---|---|---|
| 227 | | | 236 | 2.74 | 512 | 2 |
| 230 | | | 258 | 2.77 | 482 | 2 |
| 232 | | | 147, gum | 2.11 | 491 | 1 |
| 233 | | | 194 | 2.17 | 455 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 231 | | | >260 | | 2.43 | 439 | 2 |
| 235 | | | | 193 | 2.29 | 448 | 1 |
| 238 | | | | 128 | 2.58 | 539 | 1 |
| 239 | | | | 145 | 2.15 | 438 | 1 |
| 240 | | | | 180 | 2.27 | 519 | 1 |

TABLE A1-continued
compounds and physico-chemical data
| Comp No. | Compound Struct. | MP Method | MP (° C.) Kofler | MP (° C.) DSC | HPLC Rt (min) | MS M+ (H+) | LC/GC/MS Method |
|---|---|---|---|---|---|---|---|
| 242 | 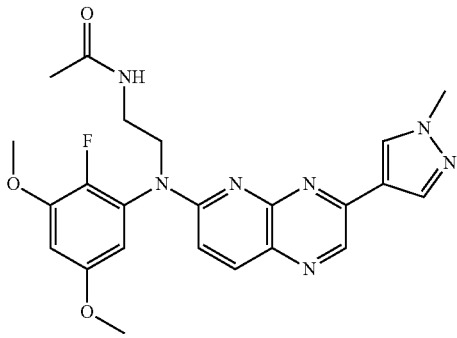 [SMILES: COc1cc(OC)c(F)c(N(CCNC(C)=O)c2ccc3ncc(-c4cnn(C)c4)nc3n2)c1] | | | 131 | 2.26 | 466 | 1 |
| 243 | 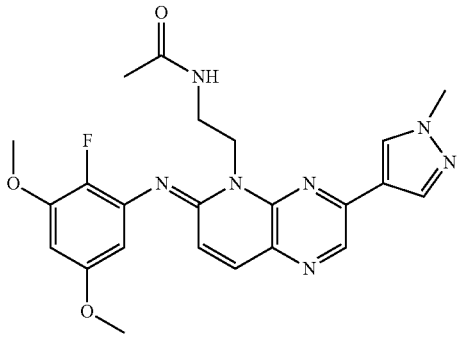 [SMILES: COc1cc(/N=c2\ccc3ncc(-c4cnn(C)c4)nc3n2CCNC(C)=O)c(F)c(OC)c1] | | | 195 | 2.47 | 466 | 1 |
| 244 | 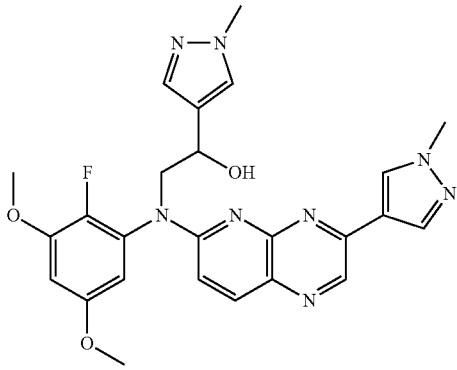 [SMILES: COc1cc(OC)c(F)c(N(CC(O)c2cnn(C)c2)c2ccc3ncc(-c4cnn(C)c4)nc3n2)c1] | | | 101, gum | 2.26 | 505 | 1 |
| 249 | 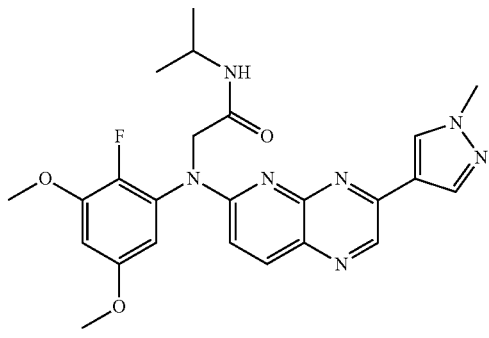 [SMILES: COc1cc(OC)c(F)c(N(CC(=O)NC(C)C)c2ccc3ncc(-c4cnn(C)c4)nc3n2)c1] | | | 208 | 2.46 | 480 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/GC/MS Method |
|---|---|---|---|---|---|---|---|
| 37 | | | 172 | | 2.43 | 466 | 1 |
| 38 | | | 140 | | 2.27 | 438 | 1 |
| 104 | | | 60 gum | | 2.01 | 516 | 1 |
| 284 | | | 252 | | 2.29 | 479 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/GC/MS Method |
|---|---|---|---|---|---|---|---|
| 245 | | | | 200 | 2.57 | 453 | 1 |
| 246 | | | 114-115 | | 2.78 | 453 | 1 |
| 247 | | | 108 gum | | 2.43 | 522 | 1 |
| 250 | | | 96 gum | | 2.85 | 581 | 1 |
| 251 | | | 247 | | 2.33 | 444 | 1 |

TABLE A1-continued compounds and physico-chemical data

| Comp No. | Compound Struct. | MP (° C.) Method | MP (° C.) Kofler | MP (° C.) DSC | HPLC Rt (min) | MS M+ (H+) | LC/ GC/MS Method |
|---|---|---|---|---|---|---|---|
| 252 | | | 60 gum | | 2.79 | 599 | 1 |
| 253 | | | | 235 | 2.26 | 503 | 1 |
| 255 | | | | 199 | 2.8 | 413 | 1 |
| 254 | | | | 210 | 2.54 | 413 | 1 |
| 257 | | | | 205 | 2.99 | 427 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 256 | | | 207 | | 2.67 | 427 | 1 |
| 258 | | | >260 | | 2.29 | 462 | 1 |
| 259 | | | 154 | | 2.08 | 493 | 1 |
| 261 | | | 180 | | 1.97 | 458 | 1 |
| 262 | | | 100 | | 2.03 | 507 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/GC/MS Method |
|---|---|---|---|---|---|---|---|
| 266 | | | 180 | | 2.36 | 579 | 1 |
| 267 | | | 195 | | 3.16 | 453 | 1 |
| 268 | | | 212 | | 2.83 | 453 | 1 |
| 269 | | | 160 gum | | 2.14 | 494 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 270 | | | | 216 | 2.31 | 494 | 1 |
| 271 | | | | 160 gum | 2.16 | 476 | 1 |
| 272 | | | | 135 gum | 2.33 | 476 | 1 |
| 273 | | | | 133 | 2.41 | 457 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 275 | | | 172 | | 2.39 | 561 | 1 |
| 277 | | | 174 | | 2.82 | 435 | 1 |
| 276 | | | 217 | | 2.65 | 435 | 1 |
| 278 | | | 234 | | 2.52 | 471 | 1 |
| 280 | | | 238 | | 2.32 | 457 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 282 | | | 104 gum | | 2.15 | 504 | 1 |
| 283 | | | 162 | 145 | 2.12 | 522 | 1 |
| 285 | | | 114 gum | | 2.28 | 536 | 1 |
| 286 | | | 110 gum | | 2.48 | 536 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 264 | | | 126 gum | | 2.22 | 553 | 1 |
| 287 | | | 213 | | 2.3 | 475 | 1 |
| 289 | | | 92 gum | | 2.02 | 518 | 1 |
| 290 | | | 66 gum | | 2.3 | 462 | 1 |

TABLE A1-continued compounds and physico-chemical data

| Comp No. | Compound Struct. | MP Method | MP (° C.) Kofler | MP (° C.) DSC | HPLC Rt (min) | MS M+ (H+) | LC/ GC/MS Method |
|---|---|---|---|---|---|---|---|
| 291 | | | | 190 | 2.28 | 466 | 1 |
| 293 | | | | 162 | 2.31 | 448 | 1 |
| 295 | | | | 171 | 1.98 | 504 | 1 |
| 297 | | | | 170 gum | 2.53 | 477 | 1 |
| 299 | | | | 133-134 gum | 2.05 | 519 | 1 |

TABLE A1-continued compounds and physico-chemical data

| Comp No. | Compound Struct. | MP Method Kofler | MP (° C.) Kofler | MP (° C.) DSC | HPLC Rt (min) | MS M+ (H+) | LC/ GC/MS Method |
|---|---|---|---|---|---|---|---|
| 301 | | | 126 | | | | 1 |
| 302 | | | Gum at 92 | | 2.41 | 563 | 1 |
| 60 | | | 114 | | 2.68 | 469 | 1 |

Analytical Part

LC/GC/NMR

The LC/GC data reported in Table A1 were determined as follows.

General Procedure A

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method 1

In addition to the general procedure A: Reversed phase UPLC was carried out on a Waters Acquity BEH (bridged ethylsiloxane/silica hybrid) C18 column (1.7 μm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 μl was used. Cone voltage was 20V for positive and negative ionization mode. Mass spectra were acquired by scanning from 100 to 1000 in 0.2 seconds using an interscan delay of 0.1 seconds.

General Procedure B

The LC measurement was performed using a UPLC (Ultra Performance Liquid Chromatography) H-Class (Waters) system comprising a quaternary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3. kV and the source temperature was maintained at 130° C. on the SQD2 (simple quadrupole mass spectrometer from Waters). Nitrogen was used as the nebulizer gas. Data acquisition was performed with a Waters-Micromass MassLynx-Openlynx data system.

Method 2

In addition to the general procedure B: Reversed phase UPLC was carried out on a Waters Acquity BEH (bridged ethylsiloxane/silica hybrid) C18 column (1.7 μm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2□l was used. Cone voltage was 20V for positive and negative ionization mode. Mass spectra were acquired by scanning from 100 to 1000 in 0.15 seconds using an interscan delay of 0.05 seconds.

DSC:

For a number of compounds reported in Table A1, melting points (m.p.) were determined with a DSC1 Star$^e$ System (Mettler-Toledo). Melting points were measured with a temperature gradient of 10° C./minute. Maximum temperature was 350° C. Values are peak values."

OR:

Optical Rotation (OR) was measured with a polarimeter 341 Perkin Elmer.

The polarized light was passed through a sample with a path length of 1 decimeter and a sample concentration of 0.250 to 0.500 gram per 100 milliliters.

$[\alpha]d^T$: (red rotation×100)/(1.000 dm×concentration).

$^d$ is sodium D line (589 nanometer).

T is the temperature (° C.)

Co. 33: $[\alpha]_d$: −10.78° (c 0.306 w/v %, DMF, 20° C.)
Co. 34: $[\alpha]_d$: +8.86° (c 0.271 w/v %, DMF, 20° C.)
Co. 52 $[\alpha]_d$: +48.03° (589 nm, c 0.279 w/v %, DMF, 20° C.)
Co. 53: $[\alpha]_d$: −18.15° (589 nm, c 0.336 w/v %, DMF, 20° C.)
Co. 49: $[\alpha]_d$: −117.78° (589 nm, c 0.343 w/v %, DMF, 20° C.)
Co. 48: $[\alpha]_d$: −27.31° (589 nm, c 0.3735 w/v %, DMF, 20° C.)
Co. 47: $[\alpha]_d$: +82.72° (589 nm, c 0.272 w/v %, DMF, 20° C.)
Co. 46: $[\alpha]_d$: −46.92° (589 nm, c 0.3325 w/v %, DMF, 20° C.)
Co. 45: $[\alpha]_d$: +16.12° (589 nm, c 0.3785 w/v %, DMF, 20° C.)
Co. 192: $[\alpha]_d$: +26.85° (589 nm, c 0.406 w/v %, DMF, 20° C.)
Co. 193: $[\alpha]_d$: −84.89° (589 nm, c 0.2945 w/v %, DMF, 20° C.)
Co. 59: $[\alpha]_d$: precision to low
Co. 58: $[\alpha]_d$: precision to low
Co. 54: $[\alpha]_d$: +108.08° (589 nm, c 0.198 w/v %, DMF, 20° C.)
Co. 62: $[\alpha]_d$: −31, 87° (589 nm, c 0.251 w/v %, DMF, 20° C.)
Co. 63: $[\alpha]_d$: +31° (589 nm, c 0.2645 w/v %, DMF, 20° C.)
Co. 78: $[\alpha]_d$: precision to low
Co. 79: $[\alpha]_d$: precision to low
Co. 87: $[\alpha]_d$: +67.18° (589 nm, c 0.262 w/v %, DMF, 20° C.)
Co. 88: $[\alpha]_d$: −23.68° (589 nm, c 0.228 w/v %, DMF, 20° C.)
Co. 89: $[\alpha]_d$: +67.88° (589 nm, c 0.33 w/v %, DMF, 20° C.)
Co. 92: $[\alpha]_d$: −68.09° (589 nm, c 0.3525 w/v %, DMF, 20° C.)
Co. 97: $[\alpha]_d$: +18.15° (589 nm, c 0.303 w/v %, DMF, 20° C.)
Co. 123: $[\alpha]_d$: −30.89° (589 nm, c 0.3075 w/v %, DMF, 20° C.)
Co. 124 $[\alpha]_d$: +23.82° (589 nm, c 0.319 w/v %, DMF, 20° C.)
Co. 158: $[\alpha]_d$: +23.58° (589 nm, c 0.335 w/v %, DMF, 20° C.)
Co. 159 $[\alpha]_d$: −158.03° (589 nm, c 0.274 w/v %, DMF, 20° C.)
Co. 160: $[\alpha]_d$: −24.04° (589 nm, c 0.312 w/v %, DMF, 20° C.)
Co. 161: $[\alpha]_d$: +147.79° (589 nm, c 0.272 w/v %, DMF, 20° C.)
Co. 218: $[\alpha]_d$: −137.19 (589 nm, c 0.199 w/v %, DMF, 20° C.
Co. 90: $[\alpha]_d$: −20.09° (589 nm, c 0.3185 w/v %, DMF, 20° C.)
Co. 91: $[\alpha]_d$: −34.93° (589 nm, c 0.292 w/v %, DMF, 20° C.)
Co. 93: $[\alpha]_d$: +20.07° (589 nm, c 0.294 w/v %, DMF, 20° C.)
Co. 94: $[\alpha]_d$: +36.67 0 (589 nm, c 0.3 w/v %, DMF, 20° C.)

NMR Data

The below NMR experiments were carried out using a Bruker Avance 500 and a Bruker Avance DRX 400 spectrometers at ambient temperature, using internal deuterium lock and equipped with reverse triple-resonance ($^1$H, $^{13}$C, $^{15}$N TXI) probe head for the 500 MHz and with reverse double-resonance ($^1$H, $^{13}$C, SEI) probe head for the 400 MHz.

Chemical shifts (δ) are reported in parts per million (ppm).

Compound 3

$^1$H NMR (500 MHz, DMSO-d6) δ 9.04 (s, 1H), 8.64 (s, 1H), 8.27 (s, 1H), 8.07 (br.s, 1H), 7.14 (t, J=8.0 Hz, 1H), 6.68 (br.s, 1H), 3.94-4.13 (m, 11H), 2.77 (t, J=7.4 Hz, 2H), 2.29 (s, 3H).

Compound 1

$^1$H NMR (500 MHz, DMSO-d6) δ 8.95 (s, 1H), 8.61 (s, 1H), 8.25 (s, 1H), 7.92 (d, J=9.2 Hz, 1H), 6.78 (d, J=9.2 Hz, 1H), 6.62 (d, J=2.2 Hz, 2H), 6.55 (t, J=2.2 Hz, 1H), 4.12 (t, J=6.9 Hz, 2H), 3.94 (s, 3H), 3.77 (s, 6H), 2.82 (t, J=6.9 Hz, 2H), 2.69 (spt, J=6.2 Hz, 1H), 1.77 (br.s, 1H), 0.95 (d, J=6.2 Hz, 6H).

Compound 2

$^1$H NMR (400 MHz, DMSO-d6) δ 8.98 (s, 1H), 8.61 (s, 1H), 8.25 (s, 1H), 8.00 (d, J=9.2 Hz, 1H), 6.53-6.92 (m, 3H), 4.10 (t, J=7.0 Hz, 2H), 3.94 (s, 3H), 3.89 (s, 3H), 3.79 (s, 3H), 2.81 (t, J=7.0 Hz, 2H), 2.69 (spt, J=6.1 Hz, 1H), 1.62 (br.s, 1H), 0.94 (d, J=6.1 Hz, 6H).

Compound 23

¹H NMR (500 MHz, DMSO-d6) δ 11.82 (br.s, 1H), 9.03 (s, 1H), 8.63 (s, 1H), 8.27 (s, 1H), 8.07 (d, J=9.1 Hz, 1H), 6.80-7.16 (m, 3H), 6.77 (dd, J=6.7, 3.0 Hz, 1H), 6.59 (dd, J=5.5, 3.0 Hz, 1H), 5.27 (br.s, 2H), 3.93 (s, 3H), 3.86 (s, 3H), 3.69 (s, 3H).

Compound 24

¹H NMR (500 MHz, DMSO-d6) δ 12.72 (br.s, 1H), 9.02 (s, 1H), 8.61 (s, 1H), 8.25 (s, 1H), 8.03 (d, J=9.2 Hz, 1H), 7.08 (s, 2H), 6.92 (d, J=9.2 Hz, 1H), 6.66 (d, J=2.2 Hz, 2H), 6.52 (t, J=2.2 Hz, 1H), 5.43 (s, 2H), 3.93 (s, 3H), 3.73 (s, 6H).

Compound 52

¹H NMR (500 MHz, DMSO-$d_6$) δ 9.02 (s, 1H), 8.62 (s, 1H), 8.26 (s, 1H), 8.03 (d, J=9.1 Hz, 1H), 7.81 (s, 1H), 6.82 (br. s., 2H), 6.65-6.78 (m, 1H), 3.72-4.12 (m, 12H), 2.05-2.27 (m, 3H), 1.80 (br. s., 1H)

Compound 53

¹H NMR (500 MHz, DMSO-$d_6$) δ 8.72 (s, 1H), 8.54 (s, 1H), 8.24 (s, 1H), 7.83 (s, 1H), 7.54 (d, J=10.1 Hz, 1H), 6.61 (dd, J=1.58, 10.09 Hz, 1H), 6.37-6.43 (m, 1H), 6.06-6.13 (m, 1H), 4.70 (dd, J=6.9, 12.6 Hz, 1H), 4.56 (dd, J=6.9, 12.6 Hz, 1H), 4.14-4.23 (m, 1H), 3.94 (s, 3H), 3.82 (s, 3H), 3.72 (s, 3H), 2.28-2.40 (m, 1H), 1.95-2.15 (m, 3H)

Compound 47

¹H NMR (500 MHz, DMSO-$d_6$) δ 8.78 (s, 1H), 8.57 (s, 1H), 8.26 (s, 1H), 7.85 (s, 1H), 7.61 (d, J=9.8 Hz, 1H), 6.69 (t, J=7.9 Hz, 1H), 6.57 (d, J=9.8 Hz, 1H), 4.60-4.77 (m, 2H), 4.13-4.24 (m, 1H), 3.94 (s, 3H), 3.86 (s, 6H), 2.27-2.40 (m, 1H), 1.97-2.14 (m, 3H)

Compound 46

¹H NMR (500 MHz, DMSO-$d_6$) δ 9.02 (s, 1H), 8.62 (s, 1H), 8.26 (s, 1H), 8.03 (d, J=9.1 Hz, 1H), 7.81 (s, 1H), 6.79-6.91 (m, 2H), 6.66-6.78 (m, 1H), 3.74-4.16 (m, 12H), 2.05-2.26 (m, 3H), 1.80 (br. s., 1H)

Compound 55

¹H NMR (500 MHz, DMSO-$d_6$) δ 8.78 (s, 1H), 8.57 (s, 1H), 8.24 (s, 1H), 7.60 (d, J=10.1 Hz, 1H), 6.68 (t, J=8.0 Hz, 1H), 6.57 (d, J=10.1 Hz, 1H), 4.50-4.61 (m, 2H), 3.95 (s, 3H), 3.86 (s, 6H), 3.34-3.42 (m, 4H), 2.18 (t, J=8.0 Hz, 2H), 1.92-2.02 (m, 2H), 1.81-1.91 (m, 2H)

Compound 86

¹H NMR (500 MHz, DMSO-$d_6$) δ 13.84 (s, 1H), 9.03 (s, 1H), 8.62 (s, 1H), 8.46 (br. s., 1H), 8.26 (s, 1H), 8.07 (d, J=9.1 Hz, 1H), 6.82-7.03 (m, 1H), 6.78 (d, J=3.5 Hz, 1H), 6.70 (br. s., 1H), 5.36 (br. s., 2H), 3.82-3.97 (m, 6H), 3.72 (s, 3H)

Compound 95

¹H NMR (500 MHz, DMSO-$d_6$) δ 11.80 (br. s., 1H), 9.67 (s, 1H), 9.02 (s, 1H), 8.63 (s, 1H), 8.26 (s, 1H), 8.06 (d, J=9.1 Hz, 1H), 7.02 (s, 1H), 6.71-6.90 (m, 2H), 6.57 (d, J=4.4 Hz, 1H), 6.39 (d, J=2.2 Hz, 1H), 4.22-6.00 (m, 2H), 3.93 (s, 3H), 3.81 (s, 3H)

Compound 111

¹H NMR (500 MHz, DMSO-$d_6$) δ 9.04 (s, 1H), 8.63 (s, 1H), 8.27 (s, 1H), 8.04 (d, J=9.1 Hz, 1H), 7.89 (br. s., 1H), 6.59-6.93 (m, 3H), 4.03-4.57 (m, 5H), 3.95 (s, 3H), 3.89 (s, 3H), 3.79 (s, 3H)

Compound 221

¹H NMR (500 MHz, DMSO-$d_6$) δ 8.99 (s, 1H), 8.62 (s, 1H), 8.26 (s, 1H), 8.00 (d, J=9.1 Hz, 1H), 6.81 (dd, J=2.8, 6.6 Hz, 1H), 6.71-6.77 (m, 2H), 4.60 (t, J=6.6 Hz, 2H), 4.28 (t, J=6.6 Hz, 2H), 4.06 (br. s., 2H), 3.94 (s, 3H), 3.86-3.91 (m, 4H), 3.78 (s, 3H), 2.76 (br. s., 2H), 2.54-2.67 (m, 1H)

Compound 242

¹H NMR (500 MHz, DMSO-$d_6$) δ 9.01 (s, 1H), 8.62 (s, 1H), 8.26 (s, 1H), 8.09 (t, J=5.52 Hz, 1H), 8.03 (d, J=9.14 Hz, 1H), 6.82 (dd, J=3.0, 6.8 Hz, 1H), 6.73-6.80 (m, 1H), 6.70 (dd, J=3.0, 5.2 Hz, 1H), 3.98-4.15 (m, 2H), 3.94 (s, 3H), 3.98 (s, 3H), 3.79 (s, 3H), 3.37-3.47 (m, 2H), 1.74 (s, 3H)

Pharmacological Part

Biological Assays a

FGFR1 (Enzymatic Assay)

In a final reaction volume of 30 μL, FGFR1 (h) (25 ng/ml) was incubated with 50 mM HEPES pH 7.5, 6 mM MnCl$_2$, 1 mM DTT, 0.1 mM Na$_3$VO$_4$, 0.01% Triton-X-100, 500 nM Btn-Flt3 and 5 μM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex 340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an IC$_{50}$ (M) and pIC$_{50}$ (−log IC$_{50}$) value.

FGFR2 (Enzymatic Assay)

In a final reaction volume of 30 μL, FGFR2 (h) (150 ng/ml) was incubated with 50 mM HEPES pH 7.5, 6 mM MnCl$_2$, 1 mM DTT, 0.1 mM Na$_3$VO$_4$, 0.01% Triton-X-100, 500 nM Btn-Flt3 and 0.4 μM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex 340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an IC$_{50}$ (M) and pIC$_{50}$ (−log IC$_{50}$) value.

FGFR3 (Enzymatic Assay)

In a final reaction volume of 30 μL, FGFR3 (h) (40 ng/ml) was incubated with 50 mM HEPES pH 7.5, 6 mM MnCl$_2$, 1 mM DTT, 0.1 mM Na$_3$VO$_4$, 0.01% Triton-X-100, 500 nM Btn-Flt3 and 25 μM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex 340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an IC$_{50}$ (M) and pIC$_{50}$ (−log IC$_{50}$) value.

FGFR4 (enzymatic assay)

In a final reaction volume of 30 μL, FGFR4 (h) (60 ng/ml) was incubated with 50 mM HEPES pH 7.5, 6 mM MnCl$_2$, 1 mM DTT, 0.1 mM Na$_3$VO$_4$, 0.01% Triton-X-100, 500 nM Btn-Flt3 and 5 μM ATP in the presence of compound (1%

DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex 340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an $IC_{50}$ (M) and $pIC_{50}$ (−log $IC_{50}$) value.

KDR (VEGFR2) (Enzymatic Assay)

In a final reaction volume of 30 μL, KDR (h) (150 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 3 μM ATP in the presence of compound (1% DMSO final). After incubation for 120 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex 340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an $IC_{50}$ (M) and $pIC_{50}$ (−log $IC_{50}$) value.

Ba/F3-FGFR1 (Minus IL3 or Plus IL3) (Cellular Proliferation Assay)

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-FGFR1-transfected cells. Cells were put in an incubator at 37° C. and 5% $CO_2$. After 24 hours, 10 μl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 μM to 0.1 nM) was determined and used to calculate an $IC_{50}$ (M) and $pIC_{50}$ (−log $IC_{50}$) value. As a counterscreen the same experiment was performed in the presence of 10 ng/ml murine IL3.

Ba/F3-FGFR3 (Minus IL3 or Plus IL3) (Cellular Proliferation Assay)

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-FGFR3-transfected cells. Cells were put in an incubator at 37° C. and 5% $CO_2$. After 24 hours, 10 μl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 μM to 0.1 nM) was determined and used to calculate an $IC_{50}$ (M) and $pIC_{50}$ (−log $IC_{50}$) value. As a counterscreen the same experiment was performed in the presence of 10 ng/ml murine IL3.

Ba/F3-KDR (Minus IL3 or Plus IL3) (Cellular Proliferation Assay)

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-KDR-transfected cells. Cells were put in an incubator at 37° C. and 5% $CO_2$. After 24 hours, 10 μl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 μM to 0.1 nM) was determined and used to calculate an $IC_{50}$ (M) and $pIC_{50}$ (−log $IC_{50}$) value. As a counterscreen the same experiment was performed in the presence of 10 ng/ml murine IL3.

Ba/F3-Flt3 (Minus IL3 or Plus IL3) (Cellular Proliferation Assay)

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-Flt3-transfected cells. Cells were put in an incubator at 37° C. and 5% $CO_2$. After 24 hours, 10 μl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 μM to 0.1 nM) was determined and used to calculate an $IC_{50}$ (M) and $pIC_{50}$ (−log $IC_{50}$) value. As a counterscreen the same experiment was performed in the presence of 10 ng/ml murine IL3.

Ba/F3-FGFR4 (Cellular Proliferation Assay)

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-FGFR4-transfected cells. Cells were put in an incubator at 37° C. and 5% CO2. After 24 hours, 10 μl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 μM to 0.1 nM) was determined and used to calculate an $IC_{50}$ (M) and $pIC_{50}$ (−log $IC_{50}$) value.

Data for the compounds of the invention in the above assays are provided in Table A2.

TABLE A2

(If data were generated multiple times for a compound or different batches were tested, average values are reported)

| Co. No. | FGFR 1 pIC$_{50}$ | FGFR 2 pIC$_{50}$ | FGFR 3 pIC$_{50}$ | FGFR 4 pIC$_{50}$ | VEGFR 2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FLT3 (MIN IL3) pIC$_{50}$ | BAF3-FLT3 (PLUS IL3) pIC$_{50}$ | BAF3-FGFR 4 pIC$_{50}$ |
|---|---|---|---|---|---|---|---|---|---|---|---|---|---|---|
| 7 | 8.5 | 8.4 | 8.8 | 8.2 | 6.7 | 7.0 | <5 | 7.1 | <5 | 5.1 | <5 | <5 | <5 | 6.53 |
| 9 | 8.25 | 7.9 | 7.8 | 7.6 | 7.3 | 7.4 | <5 | ~7.2 | <5 | 5.95 | <5 | <5 | <5 | 6.79 |
| 16 | 8.0 | 7.8 | 7.6 | 7.6 | 7.0 | 8.0 | <5 | 7.8 | <5 | 6.2 | <5 | 5.18 | <5 | 7.7 |
| 5 | 8.8 | 8.4 | 8.8 | 8.2 | 7.1 | 8.7 | 5.2 | 8.3 | <5 | 6.35 | <5 | 5.66 | <5 | ~8.21 |
| 10 | 7.8 | 7.45 | 7.2 | 7.0 | 7.5 | 8.1 | <5 | 7.85 | <5 | 6.2 | <5 | 5.12 | <5 | 7.57 |
| 25 | 8.1 | 7.85 | 8.6 | 8.45 | 7.1 | 8.8 | 5.2 | 8.5 | <5 | 6.7 | | | | ~8.23 |
| 11 | 7.3 | 7.3 | 8.15 | 7.7 | 6.4 | 7.4 | <5 | 7.2 | <5 | 6.3 | | | | ~7.02 |
| 26 | 7.3 | 7.2 | 7.4 | 7.2 | 6.3 | 6.8 | <5 | ~5.55 | <5 | <5 | <5 | <5 | <5 | <5 |
| 20 | 7.6 | 6.9 | 8.8 | 8.4 | 6.5 | 8.35 | <5 | 8.15 | <5 | 6.53 | <5 | 5.23 | <5 | 7.63 |
| 17 | 9.6 | 8.9 | 9.4 | 9.3 | 8.4 | 8.7 | <5 | 8.6 | <5 | 6.8 | | | | |
| 6 | 9.0 | 8.3 | 8.5 | 8.3 | 7.3 | 8.0 | <5 | 7.6 | <5 | 5.7 | | | | |
| 12 | 8.8 | 8.4 | 8.6 | 7.9 | 7.4 | 7.3 | <5 | 7.1 | <5 | 5.5 | | | | 6.26 |
| 8 | 8.9 | 8.2 | 8.7 | 8.5 | 6.9 | 7.6 | <5 | 7.6 | <5 | 5.3 | | | | 6.66 |
| 18 | 8.7 | 8.4 | 9.0 | 8.5 | 7.3 | 7.4 | <5 | 7.3 | <5 | 5.5 | | | | ~6.64 |
| 21 | 8.7 | 8.4 | 9.1 | 8.3 | 7.2 | 7.3 | <5 | 7.3 | <5 | 5.6 | | | | 6.69 |
| 1 | 8.3 | 7.6 | 8.3 | 7.6 | 6.6 | 8.5 | <5 | 8.1 | <5 | 5.6 | | | | ~7.06 |
| 2 | 8.7 | 8.3 | 8.5 | 8.1 | 7.1 | 8.3 | <5 | 8.0 | <5 | 6.2 | | | | 7.64 |
| 19 | 9.4 | 8.9 | 9.5 | 9.4 | 8.3 | 8.0 | <5 | 8.0 | <5 | 6.4 | | | | |
| 4 | 8.9 | 8.4 | 8.5 | 8.1 | 7.2 | 7.3 | <5 | 6.9 | <5 | 5.4 | | | | |
| 3 | 8.87 | 8.51 | 8.59 | 8.19 | 7.66 | 8.38 | <5 | ~8.04 | <5 | 6.48 | <5 | | | 7.37 |
| 24 | 9.26 | 8.95 | 9.22 | 9.13 | 7.97 | 8.46 | <5 | 8.20 | <5 | 6.22 | <5 | | | 7.77 |
| 24-hydrochloric acid salt | 9.11 | 8.85 | 8.99 | 8.92 | 8.14 | 8.16 | <5 | 7.96 | <5 | 5.92 | <5 | | | 7.77 |
| 24-phosphate salt | 9.15 | 8.91 | 9.08 | 8.99 | 7.84 | 8.42 | <5 | 7.74 | <5 | 6.05 | <5 | | | 7.47 |
| 24-sulphate salt | 9.26 | 8.89 | ~9.04 | 9.12 | 7.88 | 8.29 | <5 | ~8.15 | <5 | 6.15 | <5 | | | 7.57 |
| 24-DL-tartrate salt | 9.45 | 8.88 | 9.13 | 8.95 | 7.93 | 8.47 | <5 | 8.21 | <5 | 6.30 | <5 | | | 7.62 |
| 24-fumarate salt | 9.20 | 8.90 | 9.07 | 8.92 | 7.93 | 8.46 | <5 | ~8.61 | <5 | 6.38 | <5 | | | 7.85 |
| 23 | 9.13 | 8.84 | 8.97 | 9.00 | 8.15 | 8.85 | <5 | ~8.40 | <5 | 6.74 | <5 | | | 8.02 |
| 23-hydrochloric acid salt | 9.36 | 8.85 | 9.11 | 9.07 | 8.17 | 8.81 | <5 | ~8.58 | <5 | 6.68 | <5 | | | 7.98 |
| 23-phosphate salt | 9.33 | 8.72 | 8.96 | 9.01 | 8.10 | 8.83 | <5 | ~8.64 | <5 | 7.03 | <5 | | | 8.15 |
| 23-Sulfate salt | 9.23 | 8.68 | 8.95 | 8.90 | 8.10 | 8.94 | <5 | ~8.64 | <5 | 6.51 | <5 | | | 7.88 |
| 23-fumarate salt | 9.32 | 8.82 | ~9.05 | 9.10 | 8.29 | 8.85 | <5 | ~8.67 | <5 | 6.67 | <5 | | | 7.94 |
| 23-lactate salt | 9.30 | 8.86 | 9.02 | 8.96 | 8.18 | 8.29 | <5 | ~8.14 | <5 | 6.83 | <5 | | | 8.13 |
| 27 | 7.72 | 8.18 | 8.41 | 7.95 | 6.30 | 6.14 | <5 | ~6.54 | <5 | <5 | <5 | <5 | <5 | 6.09 |
| 29 | 9.17 | 8.68 | 9.04 | 8.82 | 7.77 | 7.71 | <5 | ~7.57 | <5 | 5.77 | <5 | <5 | <5 | 7.18 |
| 30 | 8.82 | 8.33 | 8.66 | 8.58 | 7.19 | 7.88 | <5 | 7.80 | <5 | 5.69 | <5 | <5 | <5 | 7.35 |
| 31 | 9.35 | 8.67 | 9.05 | 9.03 | 7.93 | 8.10 | <5 | 8.05 | <5 | 6.05 | <5 | <5 | <5 | 7.55 |
| 33 | 9.06 | 8.69 | 9.15 | 8.85 | 7.12 | 7.60 | <5 | ~7.64 | <5 | 5.26 | <5 | | | ~7.03 |
| 34 | 8.45 | 8.34 | 8.87 | 8.15 | 6.48 | 7.18 | <5 | 6.97 | <5 | <5 | <5 | | | 6.64 |
| 36 | 8.81 | 8.40 | 8.77 | 8.83 | 7.56 | 7.72 | <5 | ~7.57 | <5 | 5.67 | <5 | <5 | <5 | 7.30 |
| 37 | 8.79 | 8.35 | 8.06 | 7.81 | 7.34 | 7.78 | <5 | ~7.65 | <5 | 6.11 | <5 | <5 | <5 | 6.78 |
| 38 | 8.61 | 8.34 | 8.31 | 7.75 | 7.13 | 6.92 | <5 | 6.27 | <5 | 5.13 | <5 | <5 | <5 | 5.74 |
| 39 | 8.66 | 8.27 | 8.40 | 7.96 | 7.33 | 7.97 | <5 | ~7.61 | <5 | ~6.19 | <5 | <5 | <5 | 6.73 |
| 40 | 9.14 | 8.83 | 9.19 | 8.74 | 7.76 | 7.80 | <5 | 7.84 | <5 | 6.00 | <5 | | | 7.04 |
| 41 | 9.44 | 8.88 | 9.23 | 9.12 | 8.27 | 7.99 | <5 | 8.08 | <5 | 6.70 | <5 | | | 7.47 |

TABLE A2-continued (If data were generated multiple times for a compound or different batches were tested, average values are reported)

| Co. No. | FGFR 1 pIC$_{50}$ | FGFR 2 pIC$_{50}$ | FGFR 3 pIC$_{50}$ | FGFR 4 pIC$_{50}$ | VEGFR 2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FLT3 (MIN IL3) pIC$_{50}$ | BAF3-FLT3 (PLUS IL3) pIC$_{50}$ | BAF3-FGFR 4 pIC$_{50}$ |
|---|---|---|---|---|---|---|---|---|---|---|---|---|---|---|
| 42 | 8.86 | 8.69 | 8.67 | 8.52 | 8.05 | 8.57 | <5 | ~8.3 | <5 | 6.89 | <5 | | | 7.35 |
| 44 | 6.31 | 6.66 | ~6.1 | 5.55 | <6 | 5.12 | <5 | <5 | <5 | <5 | <5 | | | <5 |
| 193 | 9.26 | 9.10 | 9.38 | 9.02 | 8.14 | 8.01 | <5 | ~8.06 | <5 | 6.28 | <5 | | | 7.00 |
| 192 | 8.94 | 8.60 | 8.81 | 8.68 | 7.86 | 7.73 | <5 | 7.78 | <5 | 6.11 | <5 | | | 7.01 |
| 45 | 8.83 | 8.72 | 8.87 | 8.40 | 7.87 | 7.14 | <5 | 7.07 | <5 | ~5.96 | <5 | | | 6.59 |
| 46 | 8.74 | 8.61 | 8.82 | 8.41 | 7.38 | 7.33 | <5 | 7.42 | <5 | 5.35 | <5 | | | 6.76 |
| 47 | 9.18 | 8.85 | ~9.03 | 8.84 | 7.90 | 7.86 | <5 | ~7.76 | <5 | 6.28 | <5 | | | 6.70 |
| 48 | 8.90 | 8.49 | 8.77 | 8.66 | 7.61 | 8.00 | <5 | ~7.94 | <5 | 6.03 | <5 | | | 6.89 |
| 49 | 8.49 | 8.71 | 8.79 | 8.20 | 7.22 | 6.78 | <5 | ~6.85 | <5 | 5.16 | <5 | | | 6.24 |
| 51 | 9.23 | 8.89 | 9.30 | 9.28 | 8.11 | 8.48 | <5 | ~8.03 | <5 | 5.93 | <5 | | | 7.77 |
| 50 | 8.76 | 8.41 | 8.44 | 8.49 | 7.66 | 8.10 | <5 | ~8.11 | <5 | 6.23 | <5 | | | 7.66 |
| 53 | 8.92 | 8.79 | 8.96 | 8.48 | 7.91 | 7.47 | <5 | 7.54 | <5 | 5.99 | <5 | | | 6.85 |
| 52 | 8.59 | 8.57 | 8.71 | 8.32 | 7.60 | 7.10 | <5 | 7.10 | <5 | 5.56 | <5 | | | 6.55 |
| 54 | 8.17 | 8.31 | 8.52 | 7.76 | 7.18 | 6.64 | <5 | 6.83 | <5 | 5.39 | <5 | | | 6.05 |
| 55 | 9.22 | 8.90 | 9.31 | 9.35 | 8.55 | 8.12 | 5.11 | 8.19 | <5 | 7.13 | <5 | | | 7.71 |
| 56 | 9.05 | 8.55 | 8.56 | 8.64 | 8.11 | 7.53 | <5 | 7.87 | <5 | 6.60 | <5 | | | 7.41 |
| 58 | 8.87 | 8.71 | 8.90 | 8.67 | 7.46 | 7.51 | <5 | 7.43 | <5 | 5.97 | <5 | | | 7.09 |
| 59 | ~8.75 | 8.74 | 8.91 | 8.66 | 7.60 | 7.60 | <5 | 7.71 | <5 | 5.73 | <5 | | | 7.19 |
| 61 | 8.65 | 8.38 | 8.40 | 8.39 | 7.78 | 7.56 | <5 | 7.87 | <5 | 6.29 | <5 | | | 7.56 |
| 65 | 7.41 | ~7.95 | 7.46 | ~6.45 | 6.72 | 5.97 | <5 | 6.04 | <5 | 5.06 | <5 | | | 5.21 |
| 68 | 9.24 | 8.80 | 8.79 | 8.70 | 7.80 | 7.86 | <5 | 7.70 | <5 | 6.07 | <5 | | | 7.14 |
| 67 | 9.09 | 8.75 | 8.92 | 8.56 | 7.84 | 8.20 | <5 | 7.83 | <5 | 6.59 | <5 | | | 7.37 |
| 69 | 8.52 | 8.37 | 8.19 | 7.41 | 6.38 | 7.06 | <5 | 6.76 | <5 | 5.13 | <5 | | | 6.11 |
| 70 | 7.40 | 7.63 | 7.41 | 7.03 | 6.27 | 5.75 | <5 | 6.31 | <5 | <5 | <5 | | | 5.69 |
| 71 | 8.97 | 8.81 | 9.11 | 8.79 | 7.72 | 7.49 | <5 | 7.71 | <5 | 6.03 | <5 | | | 7.14 |
| 72 | 8.73 | 8.70 | 8.92 | 8.90 | 7.88 | 7.21 | <5 | ~7.64 | <5 | 5.83 | <5 | | | 7.06 |
| 73 | 8.62 | 8.55 | 8.55 | 7.82 | 7.20 | 7.59 | <5 | 7.46 | <5 | 5.55 | <5 | | | 6.50 |
| 75 | 8.67 | 8.58 | 8.71 | 8.65 | 7.63 | 7.76 | <5 | 7.75 | <5 | 6.16 | <5 | | | 7.33 |
| 77 | 8.57 | 8.50 | 8.75 | 8.52 | 7.54 | 7.37 | <5 | 7.38 | <5 | 5.33 | <5 | | | 6.46 |
| 64 | 9.11 | 8.79 | 9.08 | 9.00 | 8.13 | 8.40 | <5 | 8.12 | <5 | 6.31 | <5 | | | 7.52 |
| 80 | 8.87 | 8.58 | 8.74 | 8.81 | 7.99 | 7.76 | <5 | 8.08 | <5 | 5.79 | <5 | | | 7.36 |
| 82 | 7.93 | 7.97 | 7.85 | 6.74 | 6.31 | 6.67 | <5 | ~6.61 | <5 | <5 | <5 | | | 5.43 |
| 81 | 8.23 | 8.04 | 8.09 | 7.15 | 6.71 | 7.04 | <5 | 6.67 | <5 | 5.36 | <5 | | | 5.76 |
| 76 | 6.52 | 6.33 | 6.98 | 6.67 | <6 | 5.55 | <5 | 5.64 | <5 | <5 | <5 | | | 5.20 |
| 63 | 8.43 | 8.21 | 8.20 | 8.22 | 7.80 | 7.90 | <5 | 7.97 | <5 | 6.58 | <5 | | | 7.49 |
| 62 | 8.39 | 8.11 | 8.26 | 8.48 | 7.49 | 8.06 | <5 | 8.10 | <5 | 6.21 | <5 | | | 7.92 |
| 84 | 6.65 | 6.90 | 6.44 | 5.45 | <6 | 5.15 | <5 | ~5.11 | <5 | <5 | <5 | | | <5 |
| 83 | 7.12 | 7.31 | 6.98 | 6.03 | <6 | 5.36 | <5 | ~5.66 | <5 | <5 | <5 | | | <5 |
| 85 | 8.99 | 8.69 | 8.67 | 8.65 | 8.17 | 8.28 | <5 | 8.14 | <5 | 6.43 | <5 | | | 7.66 |
| 86 | 8.90 | 8.85 | 9.00 | 8.95 | 8.12 | 7.74 | <5 | ~7.90 | <5 | 6.24 | <5 | | | 7.33 |
| 78 | 8.62 | 8.56 | 8.63 | 8.60 | 7.82 | 7.59 | <5 | 7.70 | <5 | 6.13 | <5 | | | 7.03 |
| 79 | 8.63 | 8.53 | 8.78 | 8.70 | 7.59 | 7.58 | <5 | 7.63 | <5 | 5.73 | <5 | | | 7.28 |
| 87 | 8.39 | 8.22 | 8.34 | 7.41 | 6.93 | 6.84 | <5.04 | ~6.93 | <5 | 5.45 | <5 | | | 5.89 |
| 89 | 7.03 | 7.15 | 7.01 | ~5.95 | 6.47 | 5.18 | <5 | 5.14 | <5 | <5 | <5 | | | <5 |
| 92 | 7.21 | 7.52 | 7.33 | 6.25 | 6.51 | <5 | <5 | ~5.61 | <5 | <5 | <5 | | | <5 |
| 95 | 9.38 | 9.02 | 9.35 | 9.27 | 8.56 | 8.83 | 5.13 | ~8.46 | <5.03 | 6.85 | <5 | | | 8.03 |
| 88 | 7.89 | 8.04 | 8.17 | 7.37 | 6.99 | 6.68 | <5 | 6.57 | <5 | 5.14 | <5 | | | 5.65 |
| 97 | 8.28 | 8.18 | 8.33 | 7.58 | 7.02 | 6.80 | <5 | ~6.83 | <5 | 5.35 | <5 | | | 5.95 |
| 98 | ~8.41 | 8.36 | 8.57 | 8.11 | 7.78 | 7.72 | <5 | 7.65 | <5 | 6.19 | <5 | | | 6.56 |
| 100 | 8.89 | 8.67 | 8.89 | 8.89 | 8.09 | 8.02 | <5 | 7.56 | <5 | 5.41 | <5 | | | 6.99 |
| 103 | 9.47 | 9.13 | 9.38 | 9.13 | 8.27 | 8.31 | <5.07 | ~8.00 | <5 | 6.40 | <5 | | | ~7.43 |
| 104 | 8.59 | 8.49 | 8.51 | 8.46 | 7.58 | 6.70 | <5 | ~6.01 | <5 | 5.10 | <5 | | | 5.74 |
| 106 | 8.73 | 8.67 | 8.83 | 8.33 | 7.60 | 7.86 | <5 | ~7.12 | <5 | 5.59 | <5 | | | ~6.65 |
| 109 | 8.94 | 8.64 | 8.84 | 8.57 | 7.70 | 7.85 | <5 | ~7.65 | <5 | ~6.01 | <5 | | | ~7.05 |
| 111 | 8.94 | 8.70 | 9.00 | 8.80 | 7.51 | 7.79 | <5 | 7.58 | <5 | 5.61 | <5 | | | 7.27 |
| 112 | 8.90 | 8.78 | 9.11 | 8.69 | 7.77 | 7.23 | <5 | ~7.27 | <5 | 5.65 | <5 | | | 6.67 |
| 113 | 8.70 | 8.66 | 8.86 | 8.48 | 7.29 | 7.19 | <5 | 6.72 | <5 | 5.33 | <5 | | | 6.63 |
| 114 | 9.03 | 8.79 | 9.14 | 9.05 | 8.31 | 7.63 | <5 | ~7.66 | <5 | ~7.05 | <5 | | | 7.14 |
| 115 | 9.15 | 8.80 | 9.07 | 9.03 | 8.23 | ~8.17 | <5 | 7.82 | <5 | 6.58 | <5 | | | ~7.59 |
| 118 | 9.12 | 8.88 | 9.23 | 9.11 | 8.19 | 8.00 | <5 | ~8.04 | <5 | 6.60 | <5 | | | ~7.56 |
| 119 | 8.85 | 8.73 | 9.15 | 9.00 | 8.21 | ~7.92 | <5.4 | ~8.07 | <5.4 | ~6.52 | <5.4 | | | 7.28 |
| 120 | 8.38 | 8.52 | 8.73 | 8.49 | 7.72 | 7.27 | <5 | 7.16 | <5 | 6.10 | <5 | | | 6.84 |
| 121 | 8.79 | 8.59 | 9.00 | 8.53 | 7.57 | 7.38 | <5 | 6.88 | <5 | 5.25 | <5 | | | 6.08 |
| 122 | 8.55 | 8.48 | 8.60 | 8.02 | 7.30 | 6.74 | <5 | 6.09 | <5 | <5 | <5 | | | 5.67 |
| 123 | 8.87 | 8.90 | 9.13 | 8.56 | 7.66 | 7.21 | <5 | 7.16 | <5 | 5.53 | <5 | | | 6.62 |
| 124 | 8.51 | 8.56 | 8.81 | 8.37 | 7.22 | ~7.16 | <5 | ~7.16 | <5 | 5.49 | <5 | | | ~6.64 |
| 125 | 9.07 | 9.10 | 9.14 | 8.80 | 8.06 | 7.61 | <5 | ~7.57 | <5 | 6.21 | <5 | | | ~7.15 |
| 128 | 8.88 | 8.81 | 8.98 | 8.89 | 8.10 | 8.10 | <5 | 8.03 | <5 | 6.34 | <5 | | | 7.12 |
| 129 | 8.46 | 8.62 | 8.57 | 8.11 | 7.23 | ~7.15 | <5 | ~7.15 | <5 | 5.33 | <5 | | | 6.36 |
| 131 | 8.67 | 8.58 | 8.53 | 8.13 | 7.72 | 7.62 | <5 | 7.25 | <5 | 5.50 | <5 | | | 6.62 |
| 132 | 8.25 | 8.52 | 8.37 | 7.76 | 7.37 | 6.62 | <5 | ~6.64 | <5 | 5.38 | <5 | | | ~6.13 |
| 133 | 9.00 | 8.91 | 9.14 | 8.80 | 8.23 | 7.30 | <5 | ~7.58 | <5 | 6.39 | <5 | | | 6.73 |

TABLE A2-continued (If data were generated multiple times for a compound or different batches were tested, average values are reported)

| Co. No. | FGFR 1 pIC$_{50}$ | FGFR 2 pIC$_{50}$ | FGFR 3 pIC$_{50}$ | FGFR 4 pIC$_{50}$ | VEGFR 2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FLT3 (MIN IL3) pIC$_{50}$ | BAF3-FLT3 (PLUS IL3) pIC$_{50}$ | BAF3-FGFR 4 pIC$_{50}$ |
|---|---|---|---|---|---|---|---|---|---|---|---|---|---|---|
| 134 | 8.06 | 8.51 | 8.42 | 7.93 | 7.45 | 6.43 | <5 | ~6.64 | <5 | 5.20 | <5 | | | 5.99 |
| 135 | 8.93 | 8.75 | 8.83 | 8.90 | 8.06 | 8.82 | <5 | 8.25 | <5 | 6.64 | <5 | | | 8.05 |
| 137 | 8.83 | 8.69 | 8.80 | 8.77 | 7.95 | ~8.11 | <5 | 7.64 | <5 | 6.19 | <5 | | | 7.23 |
| 139 | 8.50 | 8.48 | 8.56 | 8.38 | 7.54 | 7.40 | <5 | 7.38 | <5 | 5.33 | <5 | | | 6.61 |
| 140 | 7.93 | 8.35 | 8.25 | 7.93 | 7.25 | <5 | <5 | <5 | <5 | <5 | <5 | | | <5 |
| 141 | 9.22 | 9.03 | 9.34 | 9.22 | 7.92 | 8.27 | <5 | ~8.13 | <5 | 5.87 | <5 | | | 7.40 |
| 142 | 7.79 | 8.10 | 8.24 | 7.52 | 7.13 | 5.49 | <5 | 5.30 | <5 | <5 | <5 | | | 5.10 |
| 143 | 8.90 | 8.82 | 9.12 | 8.99 | 8.30 | 5.48 | <5 | 5.42 | <5 | <5 | <5 | | | 5.29 |
| 144 | 8.41 | 8.55 | 8.76 | 8.28 | 7.64 | 6.44 | <5 | 6.33 | <5 | 5.19 | <5 | | | 6.13 |
| 145 | 8.49 | 8.42 | 8.33 | 7.98 | 7.59 | 7.26 | <5 | 7.04 | <5 | 5.63 | <5 | | | 6.61 |
| 146 | 8.17 | 8.33 | 8.31 | 7.75 | 7.38 | 6.87 | <5 | ~7.14 | <5 | 5.28 | <5 | | | ~6.58 |
| 147 | 8.82 | 8.69 | 8.79 | 8.49 | 8.25 | 7.28 | <5 | 7.23 | <5 | 6.17 | <5 | | | 6.85 |
| 148 | 8.77 | 8.72 | 8.90 | 8.79 | 8.30 | 7.58 | <5 | 7.21 | <5 | 6.26 | <5 | | | 7.21 |
| 149 | 8.61 | 8.51 | 8.58 | 8.29 | 7.81 | 7.45 | <5 | ~7.66 | <5 | 5.89 | <5 | | | 7.12 |
| 150 | 8.42 | 8.60 | 8.45 | 7.83 | 7.51 | 6.80 | <5 | ~7.06 | <5 | 5.34 | <5 | | | 6.18 |
| 151 | 7.41 | 7.82 | 7.97 | 7.04 | 6.90 | 5.56 | <5 | 5.72 | <5 | <5 | <5 | | | 5.49 |
| 152 | 8.97 | 8.83 | 8.94 | 8.85 | 7.82 | 7.96 | <5 | 8.08 | <5 | 5.56 | <5 | | | 7.46 |
| 154 | 9.18 | 8.98 | 9.17 | 9.11 | 8.79 | 7.71 | <5 | 7.59 | <5 | 6.43 | <5 | | | ~7.6 |
| 155 | 9.26 | 8.92 | 9.39 | 9.49 | 8.61 | 8.13 | <5 | 8.07 | <5 | 6.88 | <5 | | | 8.09 |
| 156 | 8.53 | 8.57 | 8.72 | 8.16 | 7.53 | 7.17 | <5 | 7.27 | <5 | 5.52 | <5 | | | 6.68 |
| 157 | 7.98 | 8.20 | 8.25 | 7.58 | 7.33 | 6.17 | <5 | ~6.66 | <5 | 5.30 | <5 | | | 6.08 |
| 158 | 8.76 | 8.73 | 8.89 | 8.60 | 8.18 | 7.18 | <5 | 7.20 | <5 | 6.16 | <5 | | | 6.78 |
| 159 | 8.07 | 8.18 | 8.23 | 7.69 | 7.08 | 6.65 | <5 | 6.30 | <5 | 5.17 | <5 | | | 6.20 |
| 160 | 8.93 | 8.74 | 8.97 | ~8.47 | 8.14 | 7.58 | <5 | 7.20 | <5 | 5.89 | <5 | | | 6.99 |
| 161 | 7.70 | 8.00 | 8.16 | 7.43 | 6.90 | 6.26 | <5 | 6.08 | <5 | <5 | <5 | | | 5.78 |
| 162 | 8.93 | 8.66 | 8.85 | 8.59 | 8.05 | 7.88 | <5 | 7.95 | <5 | 6.61 | <5 | | | ~7.56 |
| 163 | 9.01 | 8.72 | 8.58 | 8.49 | 8.07 | 7.82 | <5 | 7.34 | <5 | 6.21 | <5 | | | 7.32 |
| 164 | 8.99 | 8.74 | 9.03 | 9.01 | 8.47 | 8.01 | <5 | 7.89 | <5 | 6.86 | <5 | | | ~7.66 |
| 165 | 8.94 | 8.62 | 8.95 | 8.69 | 8.20 | 7.38 | <5 | 7.32 | <5 | 6.30 | <5 | | | 7.13 |
| 166 | 8.25 | 8.50 | 8.58 | 8.03 | 7.26 | 6.72 | <5 | 6.65 | <5 | 5.07 | <5 | | | 6.24 |
| 167 | 8.73 | 8.66 | 8.68 | 8.38 | 7.79 | 6.74 | <5 | 6.72 | <5 | 5.63 | <5 | | | 6.31 |
| 168 | 8.77 | 8.69 | 8.50 | 8.34 | 7.80 | 7.48 | <5 | 6.76 | <5 | 5.57 | <5 | | | 6.72 |
| 169 | ~9.03 | 8.79 | 8.99 | 9.01 | 8.37 | 7.68 | <5 | 7.44 | <5 | 6.40 | <5 | | | 7.20 |
| 170 | 8.63 | 8.67 | 8.66 | 8.31 | 7.87 | 6.92 | <5 | 6.78 | <5 | 5.56 | <5 | | | 6.49 |
| 173 | ~9.01 | 8.96 | 9.36 | 9.14 | 8.05 | 8.00 | <5 | ~8.04 | <5 | 5.78 | <5 | | | 7.61 |
| 174 | ~7.4 | 8.16 | 7.44 | 7.11 | 7.05 | 5.68 | <5 | 5.57 | <5 | <5 | <5 | | | 5.45 |
| 248 | 8.29 | 8.44 | 8.74 | 8.09 | 7.70 | 6.70 | <5 | 6.67 | <5 | 5.76 | <5 | | | 6.25 |
| 175 | 8.39 | 8.72 | 8.70 | 8.32 | 6.66 | 6.87 | <5 | 6.86 | <5 | <5 | <5 | | | 6.75 |
| 177 | 8.75 | 8.79 | 8.97 | 8.61 | 7.98 | 7.22 | <5 | 7.10 | <5 | 5.67 | <5 | | | 6.79 |
| 178 | 7.95 | 8.13 | 8.45 | 7.71 | 7.21 | 6.20 | <5 | 6.29 | <5 | <5 | <5 | | | 5.83 |
| 179 | 8.53 | 8.59 | 8.90 | 8.46 | 7.91 | <5.52 | <5.52 | <5.52 | <5.52 | <5.52 | <5.52 | | | <5.52 |
| 180 | 8.96 | 8.79 | 8.97 | 8.78 | 8.02 | 7.43 | <5 | 7.36 | <5 | 5.58 | <5 | | | 7.10 |
| 181 | 8.82 | 8.66 | 8.81 | 8.98 | 8.17 | 7.76 | <5 | 8.05 | <5 | 5.97 | <5 | | | 7.55 |
| 182 | 8.77 | 8.69 | 8.94 | 8.63 | 7.19 | 7.60 | <5 | ~7.76 | <5 | 5.48 | <5 | | | 7.17 |
| 184 | 9.01 | 8.66 | 8.87 | 8.93 | 8.32 | ~8.34 | <5 | ~8.15 | <5 | 6.71 | <5 | | | 8.03 |
| 185 | 9.07 | 8.82 | 9.04 | 9.01 | 7.75 | 7.59 | <5 | 7.64 | <5 | 5.51 | <5 | | | 7.39 |
| 171 | 8.45 | 8.59 | 8.81 | 8.43 | ~7.84 | 7.10 | <5 | 7.28 | <5 | 5.63 | <5 | | | 6.55 |
| 172 | 8.43 | 8.35 | 8.52 | ~7.8 | 7.34 | 6.54 | <5 | ~7.06 | <5 | 5.35 | <5 | | | 6.33 |
| 186 | 8.61 | 8.59 | 8.57 | 7.92 | 7.34 | 7.03 | <5 | ~7.11 | <5 | 5.20 | <5 | | | 6.36 |
| 188 | 8.78 | 8.87 | 9.03 | 8.79 | 7.47 | 6.78 | <5 | ~7.15 | <5 | 5.63 | <5 | | | 6.62 |
| 190 | 9.21 | 8.89 | 8.91 | 8.95 | 8.10 | 8.19 | <5 | ~8.15 | <5 | 6.46 | <5 | | | 8.08 |
| 190a | 8.99 | 8.69 | 8.70 | 8.53 | 7.54 | 7.94 | <5 | 7.72 | <5 | 5.82 | <5 | | | 7.11 |
| 194 | 7.95 | 7.92 | 8.07 | 7.35 | 6.90 | 6.30 | <5 | 6.16 | <5 | 5.18 | <5 | | | 5.50 |
| 195 | 9.23 | 8.69 | 9.06 | 9.06 | 7.94 | 8.08 | <5 | 8.09 | <5 | 5.79 | <5 | | | 7.33 |
| 196 | 9.39 | 8.67 | 9.04 | ~9.05 | 8.40 | 8.95 | <5 | ~8.66 | <5 | 7.41 | <5 | | | ~8.62 |
| 197 | 7.65 | 7.95 | 7.84 | 7.46 | 6.84 | <5 | <5 | <5 | <5 | <5 | <5 | | | <5 |
| 198 | 9.51 | 8.97 | 9.19 | 9.18 | 8.34 | 8.48 | <5 | ~8.15 | <5 | 6.68 | <5 | | | 8.05 |
| 200 | 9.27 | 8.77 | 8.84 | 8.83 | ~8.02 | 8.37 | <5 | ~8.13 | <5 | 5.99 | <5 | | | 7.33 |
| 202 | 8.95 | 8.76 | 8.79 | 8.55 | 7.21 | 7.47 | <5 | ~7.67 | <5 | 5.24 | <5 | | | 6.81 |
| 204 | 7.95 | 7.96 | 7.82 | 7.22 | 6.52 | 6.15 | <5 | 6.09 | <5 | <5 | <5 | | | 5.49 |
| 205 | 8.41 | 8.29 | 7.84 | 7.32 | 7.41 | 6.31 | <5 | 6.20 | <5 | 5.45 | <5 | | | 5.62 |
| 206 | 8.86 | 8.38 | 8.60 | 8.53 | 7.56 | 7.89 | <5 | ~8.12 | <5 | 5.84 | <5 | | | 7.34 |
| 207 | 9.09 | 8.60 | 8.93 | 8.50 | 8.08 | 7.45 | <5 | ~7.57 | <5 | 6.11 | <5 | | | 6.69 |
| 209 | 9.11 | 8.62 | 8.88 | 8.95 | 8.12 | 8.71 | <5 | 8.25 | <5 | 6.57 | <5 | | | 7.92 |
| 211 | 9.00 | ~8.63 | 8.82 | 8.64 | 7.44 | 8.08 | <5 | ~8.11 | <5 | 5.82 | <5 | | | 7.29 |
| 213 | 8.37 | 8.25 | 8.42 | 7.60 | 6.61 | 6.57 | <5 | ~6.7 | <5 | 5.01 | <5 | | | 6.15 |
| 214 | 8.62 | 8.59 | 8.62 | 7.95 | 6.84 | 7.08 | <5 | ~7.18 | <5 | 5.31 | <5 | | | 6.52 |
| 215 | 9.13 | 8.68 | ~8.90 | 8.67 | 7.28 | 8.25 | <5 | 8.18 | <5 | 5.91 | <5 | | | 7.54 |
| 217 | 8.10 | 8.23 | 8.41 | 7.63 | 6.79 | 6.59 | <5 | ~6.68 | <5 | 5.18 | <5 | | | 6.03 |
| 218 | 8.49 | 8.26 | 8.38 | 8.41 | 7.37 | 7.51 | <5 | ~7.64 | <5 | 5.64 | <5 | | | 6.99 |
| 219 | 9.09 | 8.65 | 8.89 | 8.72 | 8.10 | 7.77 | <5 | 7.66 | <5 | 6.38 | <5 | | | 6.78 |
| 208 | 8.44 | 8.28 | 8.43 | 7.73 | 7.11 | 6.84 | <5 | ~7.15 | <5 | 5.57 | <5 | | | 6.16 |

TABLE A2-continued (If data were generated multiple times for a compound or different batches were tested, average values are reported)

| Co. No. | FGFR 1 pIC$_{50}$ | FGFR 2 pIC$_{50}$ | FGFR 3 pIC$_{50}$ | FGFR 4 pIC$_{50}$ | VEGFR 2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FLT3 (MIN IL3) pIC$_{50}$ | BAF3-FLT3 (PLUS IL3) pIC$_{50}$ | BAF3-FGFR 4 pIC$_{50}$ |
|---|---|---|---|---|---|---|---|---|---|---|---|---|---|---|
| 96 | 9.13 | 8.80 | 8.97 | 8.75 | 7.94 | 8.08 | <5 | ~8.09 | <5 | 5.89 | <5 | | | 7.16 |
| 220 | 8.38 | 8.16 | 8.03 | 7.53 | 7.30 | 6.32 | <5 | 5.91 | <5 | 5.22 | <5 | | | 5.83 |
| 221 | 8.82 | 8.51 | 9.05 | 8.18 | ~7.53 | 7.53 | <5 | ~7.67 | <5 | 6.11 | <5 | | | 6.98 |
| 222 | 8.65 | 8.28 | 8.41 | 7.81 | 7.39 | 7.12 | <5 | ~7.19 | <5 | 5.68 | <5 | | | 6.55 |
| 223 | 9.26 | 8.80 | 8.91 | 8.89 | 8.15 | 8.85 | <5 | ~8.58 | <5 | 6.81 | <5 | | | 7.95 |
| 225 | 8.18 | ~8.15 | 8.11 | 7.44 | 6.70 | 6.41 | <5 | 6.29 | <5 | 5.17 | <5 | | | 5.96 |
| 226 | 9.04 | 8.66 | 8.95 | 8.52 | 7.58 | 7.32 | <5 | ~7.54 | <5 | 5.92 | <5 | | | 6.60 |
| 90 | 6.78 | 6.89 | 6.90 | ~6.04 | <6 | 5.04 | <5 | 5.19 | <5 | <5 | <5 | | | <5 |
| 91 | 6.66 | 6.84 | 6.86 | <6 | 6.13 | 5.13 | <5 | 5.17 | <5 | <5 | <5 | | | <5 |
| 93 | 7.18 | 7.22 | 7.11 | 6.10 | <6 | 5.59 | <5 | ~5.59 | <5 | <5 | <5 | | | 5.02 |
| 94 | 7.01 | 7.31 | 7.09 | 6.17 | <6 | 5.52 | <5 | ~5.56 | <5 | <5 | <5 | | | <5 |
| 227 | 9.25 | 8.84 | 9.05 | 8.74 | 7.92 | 7.73 | <5 | 7.63 | <5 | 5.79 | <5 | | | 6.91 |
| 229 | 8.31 | 8.25 | 8.39 | 7.65 | 6.74 | 5.97 | <5 | 6.05 | <5 | <5 | <5 | | | 5.45 |
| 230 | 8.12 | 8.13 | 8.10 | 7.37 | 6.44 | 6.09 | <5 | 6.18 | <5 | 5.04 | <5 | | | 5.73 |
| 232 | 9.09 | ~8.56 | 8.89 | 8.73 | 7.65 | 7.45 | <5 | 7.81 | <5 | 5.83 | <5 | | | 6.96 |
| 233 | 9.12 | 8.77 | 9.11 | 8.54 | 7.59 | 7.49 | <5 | 7.40 | <5 | 5.90 | <5 | | | 6.91 |
| 231 | 8.32 | 8.20 | 8.40 | 7.75 | 6.70 | 5.27 | <5 | 5.75 | <5 | <5 | <5 | | | 5.02 |
| 284 | 8.80 | 8.67 | 8.98 | 8.26 | 7.20 | 6.37 | <5 | 6.42 | <5 | <5 | <5 | | | 6.01 |
| 235 | 8.78 | 8.59 | 8.92 | 8.69 | 7.10 | 6.93 | <5 | ~7.63 | <5 | 5.62 | <5 | | | 6.84 |
| 238 | 9.32 | 8.67 | 8.93 | 8.95 | 7.95 | ~8.32 | <5 | ~8.45 | <5 | 6.46 | <5 | | | 8.06 |
| 239 | 8.27 | 8.10 | 8.28 | 7.45 | 6.83 | 6.44 | <5 | 6.51 | <5 | 5.27 | <5 | | | 5.87 |
| 240 | 9.04 | 8.59 | 8.74 | 8.72 | 7.81 | 8.57 | <5 | ~8.52 | <5 | 6.89 | <5 | | | 7.87 |
| 242 | 8.93 | 8.53 | 8.73 | 8.65 | 7.55 | 7.35 | <5 | ~8.11 | <5 | 5.49 | <5 | | | 7.22 |
| 243 | 9.01 | 8.79 | 8.88 | 8.71 | 7.82 | 7.85 | <5 | ~8.13 | <5 | 6.00 | <5 | | | 7.14 |
| 244 | 8.23 | 8.30 | 8.39 | 7.79 | 6.89 | 6.76 | <5 | 6.73 | <5 | 5.03 | <5 | | | 6.11 |
| 245 | 8.44 | 8.35 | 8.48 | 7.80 | 7.22 | 6.86 | <5 | 7.07 | <5 | 5.33 | <5 | | | 6.34 |
| 246 | 9.22 | 8.82 | 9.10 | 8.68 | 8.12 | 7.25 | <5 | 7.53 | <5 | 5.83 | <5 | | | 6.71 |
| 247 | 9.22 | 8.63 | 8.88 | 8.74 | 7.92 | 7.51 | <5 | ~7.7 | <5 | 5.63 | <5 | | | 6.87 |
| 249 | 8.41 | 8.32 | 8.12 | 7.48 | 6.65 | 6.70 | <5 | 6.83 | <5 | 5.09 | <5 | | | 6.00 |
| 250 | 8.38 | 8.22 | 8.32 | 8.06 | 6.92 | 6.45 | <5 | ~7.09 | <5 | 5.16 | <5 | | | 6.37 |
| 251 | 8.88 | 8.85 | 9.18 | 8.57 | 7.58 | 6.99 | <5 | ~7.6 | <5 | 5.53 | <5 | | | 6.57 |
| 252 | 8.71 | 8.27 | 8.39 | 8.29 | 7.31 | 7.14 | <5 | 7.42 | <5 | 5.67 | <5 | | | 6.95 |
| 253 | 9.22 | 8.74 | 8.87 | 8.72 | 7.92 | 8.61 | <5 | ~8.63 | <5 | 6.32 | <5 | | | 7.90 |
| 255 | 9.67 | 9.11 | 9.44 | 9.29 | 8.51 | 7.93 | <5 | 8.38 | <5 | 6.22 | <5 | | | 7.34 |
| 254 | 9.33 | 8.98 | 9.36 | 9.00 | 7.85 | 7.67 | <5 | 8.08 | <5 | 5.98 | <5 | | | 7.15 |
| 257 | 9.48 | 8.87 | 9.16 | 9.34 | 8.50 | 8.58 | <5 | ~8.66 | <5 | 6.80 | <5 | | | 7.98 |
| 256 | 9.31 | 8.78 | 9.15 | 8.99 | 8.06 | 8.05 | <5 | 8.16 | <5 | 6.16 | <5 | | | 7.36 |
| 258 | 9.26 | 8.84 | 9.17 | 8.88 | 7.91 | 7.38 | <5 | 7.91 | <5 | 6.02 | <5 | | | 7.03 |
| 259 | 8.68 | 8.54 | 8.34 | 7.55 | 6.51 | 7.33 | <5 | 7.18 | <5 | 5.13 | <5 | | | 6.19 |
| 261 | 8.83 | ~8.55 | 8.72 | 8.22 | 7.99 | 7.61 | <5 | ~7.74 | <5 | 6.01 | <5 | | | 6.77 |
| 262 | 8.14 | 8.14 | 7.76 | 7.26 | 6.62 | 6.51 | <5 | ~6.17 | <5 | 5.06 | <5 | | | 5.63 |
| 266 | 8.84 | 8.65 | 8.77 | 8.37 | 7.46 | 6.29 | <5 | 6.35 | <5 | <5 | <5 | | | 5.78 |
| 267 | 9.01 | 8.37 | 8.62 | 8.83 | 7.90 | 7.98 | <5 | 8.16 | <5 | 6.37 | <5 | | | 7.55 |
| 268 | 9.04 | 8.55 | 8.73 | 8.59 | 7.92 | 7.44 | <5 | 7.74 | <5 | 5.55 | <5 | | | 6.90 |
| 269 | 8.79 | 8.49 | 8.67 | 8.51 | 7.13 | 6.72 | <5 | ~7.1 | <5 | 5.12 | <5 | | | 6.29 |
| 270 | 9.11 | 8.68 | 8.96 | 8.64 | 8.19 | 7.12 | <5 | 7.00 | <5 | 5.56 | <5 | | | 6.40 |
| 271 | 8.34 | 8.40 | 8.61 | 8.11 | 6.76 | 6.02 | <5 | 6.27 | <5 | <5 | <5 | | | 5.80 |
| 272 | 9.01 | 8.59 | 8.84 | 8.28 | 8.00 | 6.54 | <5 | 6.73 | <5 | 5.68 | <5 | | | 5.97 |
| 273 | 8.94 | 8.42 | 8.50 | 8.55 | 7.69 | 8.44 | <5 | ~8.60 | <5 | 6.44 | <5 | | | 7.60 |
| 275 | 8.23 | 8.46 | 8.47 | 7.92 | 6.85 | 5.64 | <5 | 5.80 | <5 | <5 | <5 | | | 5.13 |
| 277 | 9.06 | 8.68 | 8.97 | 8.33 | 7.82 | 6.91 | <5 | 7.16 | <5 | 5.49 | <5 | | | 6.37 |
| 276 | 7.84 | 8.04 | 8.08 | 7.16 | 6.85 | 6.28 | <5 | 6.41 | <5 | 5.02 | <5 | | | 5.82 |
| 278 | 8.79 | 8.38 | 8.53 | 8.31 | 7.80 | 7.45 | <5 | 7.73 | <5 | 5.92 | <5 | | | 7.11 |
| 280 | 9.07 | 8.69 | 8.73 | 8.63 | 7.50 | 8.64 | <5 | ~8.63 | <5 | 6.03 | <5 | | | 7.97 |
| 282 | 7.48 | 7.72 | 7.59 | 6.98 | 6.18 | <5 | <5 | <5 | <5 | <5 | <5 | | | <5 |
| 283 | ~8.15 | 8.29 | 8.29 | 7.67 | 6.98 | 5.18 | <5 | 5.26 | <5 | <5 | <5 | | | <5 |
| 285 | 8.63 | 8.39 | 8.56 | 8.14 | 7.45 | 6.38 | <5 | 6.84 | <5 | 5.36 | <5 | | | 6.12 |
| 286 | ~8.81 | 8.69 | 8.87 | 8.41 | 7.96 | 7.07 | <5 | 7.66 | <5 | 6.23 | <5 | | | 6.69 |
| 264 | 9.26 | 8.73 | 8.85 | 8.86 | 8.03 | 7.66 | <5 | 8.09 | <5 | 5.58 | <5 | | | 7.18 |
| 287 | 9.07 | 8.51 | 8.67 | 8.67 | 7.76 | 8.87 | <5 | ~8.54 | <5 | 6.62 | <5 | | | 8.08 |
| 289 | 8.36 | 8.07 | 7.89 | 7.24 | 7.01 | 6.66 | <5 | 6.92 | <5 | 5.28 | <5 | | | 6.07 |
| 290 | 8.45 | 8.35 | 8.35 | 7.89 | 7.26 | 7.09 | <5 | 7.06 | <5 | 5.81 | <5 | | | 6.32 |
| 291 | 9.06 | 8.81 | 8.92 | 8.47 | 7.05 | 8.03 | <5 | 7.73 | <5 | 5.68 | <5 | | | 7.08 |
| 293 | 8.79 | 8.74 | 8.80 | 8.32 | 6.63 | 7.59 | <5 | 7.59 | <5 | 5.31 | <5 | | | 6.82 |
| 295 | 9.25 | 8.76 | 8.89 | 8.62 | 8.03 | 8.47 | <5 | 8.17 | <5 | 6.45 | <5 | | | 7.61 |
| 297 | 9.10 | 8.75 | 8.77 | 8.52 | 7.79 | 7.70 | <5 | 7.69 | <5 | 6.08 | <5 | | | 6.99 |
| 299 | 8.75 | 8.33 | 8.45 | 8.05 | 6.92 | 6.05 | <5 | 5.94 | <5 | <5 | <5 | | | 5.32 |
| 60 | 9.13 | 9.00 | 9.28 | 9.14 | 8.05 | 8.43 | <5 | 8.15 | <5 | 6.58 | <5 | | | 7.76 |

The invention claimed is:

1. A method for inhibiting fibroblast growth factor receptor (FGFR) kinase activity in a subject suffering from, or being at risk of suffering from a disease state or condition mediated by a fibroblast growth factor receptor kinase, said method comprising administering to the subject a compound selected from the group consisting of a compound of formula (I-A) or formula (I-B):

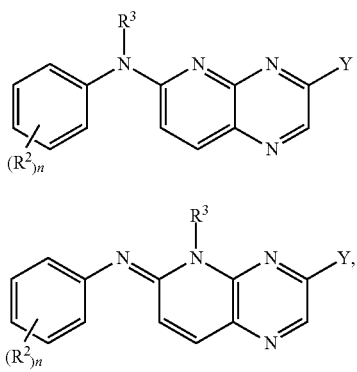

a tautomeric form, stereochemically isomeric form, and isotopic form thereof, wherein each $R^2$ independently represents hydroxyl, halogen, cyano, $C_{1-4}$alkyl, $C_{2-4}$alkenyl, $C_{2-4}$alkynyl, $C_{1-4}$alkoxy, hydroxy$C_{1-4}$alkyl, hydroxy$C_{1-4}$alkoxy, halo$C_{1-4}$alkyl, halo$C_{1-4}$alkoxy, hydroxyhalo$C_{1-4}$alkyl, hydroxyhalo$C_{1-4}$alkoxy, $C_{1-4}$alkoxy$C_{1-4}$alkyl, halo$C_{1-4}$alkoxy$C_{1-4}$ alkyl, $C_{1-4}$alkoxy$C_{1-4}$alkyl wherein each $C_{1-4}$alkyl may optionally be substituted with one or two hydroxyl groups, hydroxyhalo$C_{1-4}$alkoxy$C_{1-4}$alkyl, $R^{13}$, $C_{1-4}$alkyl substituted with $R^{13}$, $C_{1-4}$alkyl substituted with —C(=O)—$R^{13}$, $C_{1-4}$alkoxy substituted with $R^{13}$, $C_{1-4}$alkoxy substituted with —C(=O)—$R^{13}$, —C(=O)—$R^{13}$, $C_{1-4}$alkyl substituted with —$NR^7R^8$, $C_{1-4}$alkyl substituted with —C(=O)—$NR^7R^8$, $C_{1-4}$alkoxy substituted with —$NR^7R^8$, $C_{1-4}$alkoxy substituted with —C(=O)—$NR^7R^8$, —$NR^7R^8$ or —C(=O)—$NR^7R^8$; or when two $R^2$ groups are attached to adjacent carbon atoms they may be taken together to form a radical of formula:

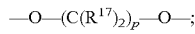

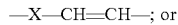

wherein $R^{17}$ represents hydrogen or fluoro, p represents 1 or 2 and X represents O or S;

Y represents —C$R^{18}$=N—O$R^{19}$ or -E-D;

D represents a 3 to 12 ring membered monocyclic or bicyclic carbocyclyl or a 3 to 12 ring membered monocyclic or bicyclic heterocyclyl containing at least one heteroatom selected from N, O and S, wherein said carbocyclyl and heterocyclyl may each be optionally substituted by one or more $R^1$ groups;

E represents a bond, —(C$R^{22}R^{23}$)$_n$—, $C_{2-4}$alkenediyl optionally substituted with $R^{22}$, $C_{2-4}$alkynediyl optionally substituted with $R^{22}$, —CO—(C$R^{22}R^{23}$)$_s$—, —(C$R^{22}R^{23}$)$_s$—CO—, —$NR^{22}$—(C$R^{22}R^{23}$)$_s$—, —(C$R^{22}R^{23}$)$_s$—$NR^{22}$—, —O—(C$R^{22}R^{23}$)$_s$—, —(C$R^{22}R^{23}$)$_s$—O—, —S(O)$_m$—(C$R^{22}R^{23}$)$_s$—, —(C$R^{22}R^{23}$)$_s$—S(O)$_m$—, —(C$R^{22}R^{23}$)$_s$—CO—$NR^{22}$—(C$R^{22}R^{23}$)$_s$— or —(C$R^{22}R^{23}$)$_s$—$NR^{22}$—CO—(C$R^{22}R^{23}$)$_s$—;

$R^1$ represents hydrogen, halo, cyano, $C_{1-6}$alkyl, $C_{1-6}$alkoxy, —C(=O)—O—$C_{1-6}$alkyl, $C_{2-4}$alkenyl, hydroxy$C_{1-6}$alkyl, halo$C_{1-6}$alkyl, hydroxyhalo$C_{1-6}$ alkyl, cyano$C_{1-4}$alkyl, $C_{1-6}$alkoxy$C_{1-6}$alkyl wherein each $C_{1-6}$alkyl may optionally be substituted with one or two hydroxyl groups, —$NR^4R^5$, $C_{1-6}$alkyl substituted with —O—C(=O)— $C_{1-6}$alkyl, $C_{1-6}$alkyl substituted with —$NR^4R^5$, —C(=O)—$NR^4R^5$, —C(=O)—$C_{1-6}$alkyl-$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, —C(=O)—$R^6$, $C_{1-6}$alkyl substituted with —C(=O)—$R^6$, hydroxy$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$;

$R^3$ represents hydroxyl, $C_{1-6}$alkoxy, hydroxy$C_{1-6}$alkoxy, $C_{1-6}$alkoxy substituted with —$NR^{10}R^{11}$, $C_{1-6}$alkyl, $C_{2-6}$alkenyl, $C_{2-6}$alkynyl, halo$C_{1-6}$alkyl optionally substituted with —O—C(=O)—$C_{1-6}$alkyl, hydroxy$C_{1-6}$ alkyl optionally substituted with —O—C(=O)—$C_{1-6}$ alkyl, hydroxy$C_{2-6}$alkenyl, hydroxy$C_{2-6}$alkynyl, hydroxyhalo$C_{1-6}$alkyl, cyano$C_{1-6}$alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy$C_{1-6}$alkyl-C(=O)—, $C_{1-6}$alkyl substituted with —O—C(=O)—$C_{1-6}$alkyl, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{2-6}$alkenyl substituted with $C_{1-6}$alkoxy, $C_{2-6}$alkynyl substituted with $C_{1-6}$alkoxy, $C_{1-6}$alkyl substituted with $R^9$ and optionally substituted with —O—C(=O)—$C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$, $C_{2-6}$alkynyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —O—C(=O)—$NR^{10}R^{11}$, —S(=O)$_2$—$C_{1-6}$alkyl, —S(=O)$_2$-halo$C_{1-6}$ alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —$NR^{12}$—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^{13}$, $C_{1-6}$alkyl substituted with —P(=O)(OH)$_2$ or $C_{1-6}$alkyl substituted with —P(=O)(O$C_{1-6}$alkyl)$_2$;

$R^4$ and $R^5$ each independently represent hydrogen, $C_{1-6}$alkyl, $C_{1-6}$alkyl substituted with —$NR^{14}R^{15}$, hydroxyC$_{1-6}$alkyl, haloC$_{1-6}$alkyl, hydroxyhaloC$_{1-6}$alkyl, C$_{1-6}$alkoxyC$_{1-6}$alkyl wherein each C$_{1-6}$alkyl may optionally be substituted with one or two hydroxyl groups, —S(=O)$_2$—C$_{1-6}$alkyl, —S(=O)$_2$-haloC$_{1-6}$alkyl, —S(=O)$_2$—NR$^{14}$R$^{15}$, —C(=O)—NR$^{14}$R$^{15}$, —C(=O)—O—C$_{1-6}$alkyl, —C(=O)—R$^{13}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl, C$_{1-6}$alkyl substituted with —NH—S(=O)$_2$—NR$^{14}$R$^{15}$, R$^{13}$ or C$_{1-6}$alkyl substituted with R$^{13}$;

R$^6$ represents C$_{3-8}$cycloalkyl, C$_{3-8}$cycloalkenyl, phenyl, 4 to 7-membered monocyclic heterocyclyl containing at least one heteroatom selected from N, O and S; said C$_{3-8}$cycloalkyl, C$_{3-8}$cycloalkenyl, phenyl, 4 to 7-membered monocyclic heterocyclyl, optionally and each independently being substituted by 1, 2, 3, 4 or 5 substituents, each substituent independently being selected from cyano, C$_{1-6}$alkyl, cyanoC$_{1-6}$alkyl, hydroxyl, carboxyl, hydroxyC$_{1-6}$alkyl, halogen, haloC$_{1-6}$alkyl, hydroxyhaloC$_{1-6}$alkyl, C$_{1-6}$alkoxy, C$_{1-6}$alkoxyC$_{1-6}$alkyl, C$_{1-6}$alkyl-O—C(=O)—, —NR$^{14}$R$^{15}$, —C(=O)—NR$^{14}$R$^{15}$, C$_{1-6}$alkyl substituted with —NR$^{14}$R$^{15}$, C$_{1-6}$alkyl substituted with —C(=O)—NR$^{14}$R$^{15}$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl and C$_{1-6}$alkyl substituted with —NH—S(=O)$_2$—NR$^{14}$R$^{15}$;

R$^7$ and R$^8$ each independently represent hydrogen, C$_{1-6}$alkyl, hydroxyC$_{1-6}$alkyl, haloC$_{1-6}$alkyl, hydroxyhaloC$_{1-6}$alkyl or C$_{1-6}$alkoxyC$_{1-6}$alkyl;

R$^9$ represents C$_{3-8}$cycloalkyl, C$_{3-8}$cycloalkenyl, phenyl, naphthyl, or 3 to 12 membered monocyclic or bicyclic heterocyclyl containing at least one heteroatom selected from N, O and S, said C$_{3-8}$cycloalkyl, C$_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, C$_{1-4}$alkyl, hydroxyl, carboxyl, hydroxyC$_{1-4}$alkyl, cyano, cyanoC$_{1-4}$alkyl, C$_{1-4}$alkyl-O—C(=O)—, C$_{1-4}$alkyl substituted with C$_{1-4}$alkyl-O—C(=O)—, C$_{1-4}$alkyl-C(=O)—, C$_{1-4}$alkoxyC$_{1-4}$alkyl wherein each C$_{1-4}$alkyl may optionally be substituted with one or two hydroxyl groups, halogen, haloC$_{1-4}$alkyl, hydroxyhaloC$_{1-4}$alkyl, —NR$^{14}$R$^{15}$, —C(=O)—NR$^{14}$R$^{15}$, C$_{1-4}$alkyl substituted with —NR$^{14}$R$^{15}$, C$_{1-4}$alkyl substituted with —C(=O)—NR$^{14}$R$^{15}$, C$_{1-4}$alkoxy, —S(=O)$_2$—C$_{1-4}$alkyl, —S(=O)$_2$-haloC$_{1-4}$alkyl, —S(=O)$_2$—NR$^{14}$R$^{15}$, C$_{1-4}$alkyl substituted with —S(=O)$_2$—NR$^{14}$R$^{15}$, C$_{1-4}$alkyl substituted with —NH—S(=O)$_2$—C$_{1-4}$alkyl, C$_{1-4}$alkyl substituted with —NH—S(=O)$_2$-haloC$_{1-4}$alkyl, C$_{1-4}$alkyl substituted with —NH—S(=O)$_2$—NR$^{14}$R$^{15}$, R$^{13}$, —C(=O)—R$^{13}$, C$_{1-4}$alkyl substituted with R$^{13}$, phenyl optionally substituted with R$^{16}$, phenylC$_{1-4}$alkyl wherein the phenyl is optionally substituted with R$^{16}$, a 5 or 6-membered aromatic monocyclic heterocyclyl containing at least one heteroatom selected from N, O and S wherein said heterocyclyl is optionally substituted with R$^{16}$;

or when two of the substituents of R$^9$ are attached to the same atom, they may be taken together to form a 4 to 7-membered saturated monocyclic heterocyclyl containing at least one heteroatom selected from N, O and S;

R$^{10}$ and R$^{11}$ each independently represent hydrogen, carboxyl, C$_{1-6}$alkyl, cyanoC$_{1-6}$alkyl, C$_{1-6}$alkyl substituted with —NR$^{14}$R$^{15}$, C$_{1-6}$alkyl substituted with —C(=O)—NR$^{14}$R$^{15}$, haloC$_{1-6}$alkyl, hydroxyC$_{1-6}$alkyl, hydroxyhaloC$_{1-6}$alkyl, C$_{1-6}$alkoxy, C$_{1-6}$alkoxyC$_{1-6}$alkyl wherein each C$_{1-6}$alkyl may optionally be substituted with one or two hydroxyl groups, R$^6$, C$_{1-6}$alkyl substituted with R$^6$, —C(=O)—R$^6$, —C(=O)—C$_{1-6}$alkyl, —C(=O)-hydroxyC$_{1-6}$alkyl, —C(=O)-haloC$_{1-6}$alkyl, —C(=O)-hydroxyhaloC$_{1-6}$alkyl, C$_{1-6}$alkyl substituted with —Si(CH$_3$)$_3$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl, C$_{1-6}$alkyl substituted with carboxyl, or C$_{1-6}$alkyl substituted with —NH—S(=O)$_2$—NR$^{14}$R$^{15}$;

R$^{12}$ represents hydrogen or C$_{1-4}$alkyl optionally substituted with C$_{1-4}$alkoxy;

R$^{13}$ represents C$_{3-8}$cycloalkyl or a saturated 4 to 6-membered monocyclic heterocyclyl containing at least one heteroatom selected from N, O and S, wherein said C$_{3-8}$cycloalkyl or monocyclic heterocyclyl is optionally substituted with 1, 2 or 3 substituents each independently selected from halogen, hydroxyl, C$_{1-6}$alkyl, haloC$_{1-6}$alkyl, =O, cyano, —C(=O)—C$_{1-6}$alkyl, C$_{1-6}$alkoxy, and —NR$^{14}$R$^{15}$;

R$^{14}$ and R$^{15}$ each independently represent hydrogen, or haloC$_{1-4}$alkyl, or C$_{1-4}$alkyl optionally substituted with a substituent selected from hydroxyl, C$_{1-4}$alkoxy, amino and mono- or di(C$_{1-4}$alkyl)amino;

R$^{16}$ represents hydroxyl, halogen, cyano, C$_{1-4}$alkyl, C$_{1-4}$alkoxy, —NR$^{14}$R$^{15}$ or —C(=O)NR$^{14}$R$^{15}$;

R$^{18}$ represents hydrogen, C$_{1-6}$ alkyl, C$_{3-8}$ cycloalkyl, C$_{1-4}$alkyl substituted with C$_{3-8}$ cycloalkyl;

R$^{19}$ represents hydrogen; C$_{1-6}$ alkyl; C$_{3-8}$ cycloalkyl; C$_{1-6}$alkyl substituted with —O—R$^{20}$; —(CH$_2$)$_r$—CN; —(CH$_2$)$_r$—CONR$^{20}$R$^{21}$; —(CH$_2$)$_{r1}$—NR$^{20}$R$^{21}$; —(CH$_2$)$_{r1}$—NR$^{20}$COR$^{21}$; —(CH$_2$)$_{r1}$—NR$^{20}$—(CH$_2$)$_s$—SO$_2$—R$^{21}$; —(CH$_2$)$_{r1}$—NH—SO$_2$—NR$^{20}$R$^{21}$; —(CH$_2$)$_{r1}$—NR$^{20}$CO$_2$R$^{21}$; —(CH$_2$)$_r$—SO$_2$NR$^{20}$R$^{21}$; phenyl optionally substituted with 1, 2, 3, 4 or 5 substituents each independently selected from halogen, C$_{1-4}$alkyl, C$_{1-4}$alkyloxy, cyano and amino; a 5- or 6-membered aromatic monocyclic heterocycle containing at least one heteroatom selected from N, O and S, said heterocycle being optionally substituted with 1, 2, 3 or 4 substituents each independently selected from halogen, C$_{1-4}$alkyl, C$_{1-4}$alkyloxy, cyano and amino; wherein said C$_{1-6}$ alkyl and C$_{3-8}$ cycloalkyl, may be optionally substituted by one or more R$^{20}$ groups;

R$^{20}$ and R$^{21}$ independently represent hydrogen, C$_{1-6}$ alkyl, C$_{1-6}$ alkanol —(CH$_2$)$_n$—O—C$_{1-6}$alkyl, or when attached to a nitrogen atom R$^{20}$ and R$^{21}$ can be taken together to form with the nitrogen atom to which they are attached a monocyclic saturated 4, 5 or 6-membered ring which optionally contains a further heteroatom selected from O, S and N;

$R^{22}$ and $R^{23}$ independently represent hydrogen, $C_{1-6}$ alkyl, or hydroxy$C_{1-6}$alkyl;

m independently represents 0, 1 or 2;

n independently represents 0, 1, 2, 3 or 4;

s independently represents 0, 1, 2, 3 or 4;

r independently represents 1, 2, 3, or 4;

r1 independently represents 2, 3 or 4;

or an N-oxide thereof, a pharmaceutically acceptable salt thereof or a solvate thereof.

2. The method according to claim 1, wherein the compound is selected from the group consisting of a compound of formula (I-A), a tautomeric form, stereochemically isomeric form, and isotopic form thereof, or an N-oxide thereof, a pharmaceutically acceptable salt thereof or a solvate thereof.

3. The method according to claim 1, wherein the compound is selected from the group consisting of a compound of formula (I-B), a tautomeric form, stereochemically isomeric form, and isotopic form thereof, or an N-oxide thereof, a pharmaceutically acceptable salt thereof or a solvate thereof.

4. The method according to claim 1, wherein the compound is selected from the group consisting of a compound of formula (I-A) or formula (I-B), a tautomeric form, stereochemically isomeric form, and isotopic form thereof, wherein Y represents —$CR^{18}$=N—$OR^{19}$, or an N-oxide thereof, a pharmaceutically acceptable salt thereof or a solvate thereof.

5. The method according to claim 1, wherein the compound is selected from the group consisting of a compound of formula (I-A) or formula (I-B), a tautomeric form, stereochemically isomeric form, and isotopic form thereof, wherein Y is -E-D, or an N-oxide thereof, a pharmaceutically acceptable salt thereof or a solvate thereof.

6. The method according to claim 5, wherein the compound is selected from the group consisting of a compound of formula (I-A) or formula (I-B), a tautomeric form, stereochemically isomeric form, and isotopic form thereof, wherein E represents a bond, $C_{2-4}$alkenediyl, —CO—$(CR^{22}R^{23})_s$—, —$(CR^{22}R^{23})_s$—CO—, —$NR^{22}$—$(CR^{22}R^{23})_s$—, —$(CR^{22}R^{23})_s$—$NR^{22}$—, —$(CR^{22}R^{23})_s$—CO—$NR^{22}$—$(CR^{22}R^{23})_s$—, or —$(CR^{22}R^{23})_s$—$NR^{22}$—CO—$(CR^{22}R^{23})_s$—, or an N-oxide thereof, a pharmaceutically acceptable salt thereof or a solvate thereof.

7. The method according to claim 5, wherein the compound is selected from the group consisting of a compound of formula (I-A) or formula (I-B), a tautomeric form, stereochemically isomeric form, and isotopic form thereof, wherein D is optionally substituted pyrazolyl, or an N-oxide thereof, a pharmaceutically acceptable salt thereof or a solvate thereof.

8. The method according to claim 1, wherein the compound is selected from the group consisting of a compound of formula (I-A) or formula (I-B), a tautomeric form, stereochemically isomeric form, and isotopic form thereof, wherein each $R^2$ independently represents hydroxyl, halogen, cyano, $C_{1-4}$alkyl, $C_{2-4}$alkenyl, $C_{1-4}$alkoxy, hydroxy$C_{1-4}$akyl, hydroxy$C_{1-4}$alkoxy, halo$C_{1-4}$alkoxy, $C_{1-4}$alkoxy$C_{1-4}$alkyl, $R^{13}$, $C_{1-4}$alkoxy substituted with $R^{13}$, —C(=O)—$R^{13}$, $C_{1-4}$alkyl substituted with $NR^7R^8$, $C_{1-4}$alkoxy substituted with $NR^7R^8$, —$NR^7R^8$ or —C(=O)—$NR^7R^8$, or an N-oxide thereof, a pharmaceutically acceptable salt thereof or a solvate thereof.

9. The method according to claim 1, wherein the compound is selected from the group consisting of a compound of formula (I-A) or formula (I-B), a tautomeric form, stereochemically isomeric form, and isotopic form thereof, wherein $R^3$ represents $C_{1-6}$alkyl, hydroxy$C_{1-6}$alkyl, hydroxyhalo$C_{1-6}$alkyl, halo$C_{1-6}$alkyl, $C_{1-6}$alkyl substituted with —C(=O)—$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with $R^9$, $C_{1-6}$alkyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, $C_{1-6}$alkyl substituted with —C(=O)—O—$C_{1-6}$alkyl, $C_{1-6}$alkyl substituted with —O—C(=O)—$NR^{10}R^{11}$, $C_{1-6}$alkyl substituted with carboxyl, $C_{1-6}$alkyl substituted with —$NR^{12}$—S(=O)$_2$—$C_{1-6}$alkyl, $C_{1-6}$alkyl substituted with —$NR^{12}$—S(=O)$_2$—$NR^{14}R^{15}$, $C_{1-6}$alkyl substituted with hydroxyl and $R^9$, —$C_{1-6}$ alkyl-C($R^{12}$)=N—O—$R^{12}$, $C_{1-6}$alkyl substituted with —C(=O)—$NR^{10}R^{11}$, $C_{1-6}$alkyl substituted with —C(=O)—$R^9$, $C_{2-6}$alkynyl substituted with $R^9$, hydroxy$C_{1-6}$alkoxy, $C_{2-6}$alkenyl, $C_{2-6}$alkynyl or $R^{13}$, or an N-oxide thereof, a pharmaceutically acceptable salt thereof or a solvate thereof.

10. The method according to claim 1, wherein the compound is selected from the group consisting of a compound of formula (I-A) or formula (I-B), a tautomeric form, stereochemically isomeric form, and isotopic form thereof, wherein:

(i) n represents 2, 3 or 4; and each $R^2$ represents $C_{1-4}$alkoxy or halogen; $R^3$ represents hydroxy$C_{1-6}$ alkyl, hydroxyhalo$C_{1-6}$alkyl, $C_{1-6}$alkyl substituted with $R^9$, $C_{1-6}$alkyl substituted with —$NR^{10}R^{11}$, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{2-6}$alkynyl substituted with $R^9$, $C_{2-6}$alkynyl; Y represents -E-D wherein E represents a bond and D represents pyrazolyl substituted with $C_{1-6}$alkyl; $R^{10}$ and $R^{11}$ represent hydrogen or $C_{1-6}$alkyl; and $R^9$ represents an optionally substituted 5 membered aromatic heterocycle or an optionally substituted 6 membered aromatic heterocycle; or (ii) n represents 2, 3 or 4; and each $R^2$ represents $C_{1-4}$alkoxy, halogen, hydroxyl, $C_{1-4}$alkyl, or —C(=O)—$NR^7R^8$; $R^3$ represents $C_{1-6}$alkyl, hydroxy$C_{1-6}$alkyl, hydroxyhalo$C_{1-6}$alkyl, cyano$C_{1-6}$ alkyl, $C_{1-6}$alkyl substituted with carboxyl, $C_{1-6}$alkyl substituted with —C(=O)—O—$C_{1-6}$alkyl, $C_{1-6}$alkyl substituted with $R^9$, $C_{1-6}$alkyl substituted with —C(=O)—$R^9$, $C_{1-6}$alkyl substituted with hydroxyl and $R^9$, $C_{1-6}$alkyl substituted with —$NR^{10}R^{11}$, $C_{1-6}$alkyl substituted with —C(=O)—$NR^{10}R^{11}$, $C_{1-6}$alkyl substituted with —S(=O)$_2$—$C_{1-6}$alkyl, $C_{1-6}$alkoxy$C_{1-6}$alkyl wherein each $C_{1-6}$alkyl may optionally be substituted with one or two hydroxyl groups or with —O—C(=O)—$C_{1-6}$ alkyl, $C_{2-6}$alkynyl substituted with $R^9$, $C_{2-6}$alkynyl; Y represents -E-D wherein E represents a bond and D represents an optionally substituted monocyclic 6 membered carbocyclyl, or an optionally substituted 5 or 6 membered monocyclic heterocyclyl, or an N-oxide thereof, a pharmaceutically acceptable salt thereof or a solvate thereof.

11. The method according to claim 1, wherein the compound is selected from the group consisting of a compound of formula (I-A) or formula (I-B), a tautomeric form, stereochemically isomeric form, and isotopic form thereof, wherein n represents 2, 3 or 4; and each $R^2$ represents $C_{1-4}$alkoxy, halogen, hydroxyl, $C_{1-4}$alkyl, or —C(=O)—$NR^7R^8$; $R^3$ represents $C_{1-6}$alkyl, hydroxy$C_{1-6}$alkyl, hydroxyhalo$C_{1-6}$alkyl, cyano$C_{1-6}$alkyl, $C_{1-6}$alkyl substituted with carboxyl, $C_{1-6}$alkyl substituted with —C(=O)—O—$C_{1-6}$alkyl, $C_{1-6}$alkyl substituted with $R^9$, $C_{1-6}$alkyl substituted with —C(=O)—$R^9$, $C_{1-6}$alkyl substituted with hydroxyl and $R^9$, $C_{1-6}$alkyl substituted with —$NR^{10}R^{11}$, $C_{1-6}$alkyl substituted with —C(=O)—$NR^{10}R^{11}$, $C_{1-6}$alkyl substituted with —S(=O)$_2$—$C_{1-6}$alkyl, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{2-6}$alkynyl substituted with $R^9$, $C_{2-6}$alkynyl; Y represents -E-D wherein E represents a bond and D represents an optionally substituted monocyclic 6 membered carbocyclyl, or an optionally substituted 5 or 6 membered monocyclic heterocyclyl, and $R^1$ represents $C_{1-6}$alkyl, hydroxy$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —S(=O)$_2$—$C_{1-6}$alkyl, $R^6$, $C_{1-6}$alkyl substituted with $R^6$; $R^9$ represents an optionally substituted 4 membered saturated heterocycle, an optionally substituted 5 membered saturated heterocycle, an optionally substituted 5 membered aromatic heterocycle, an optionally substituted 6 membered saturated heterocycle, an optionally substituted 6 membered aromatic heterocycle, an optionally substituted bicyclic heterocycle, or $C_{3-6}$cycloalkyl; $R^{10}$ and $R^{11}$ represent hydrogen, $C_{1-6}$alkyl, hydroxy$C_{1-6}$alkyl, —C(=O)—$C_{1-6}$alkyl, or $R^6$; $R^6$ represents a 4 membered monocyclic saturated heterocycle, or a 6-membered monocyclic saturated heterocyclyl, or a 5-membered monocyclic aromatic heterocycle; $R^4$ and $R^5$ represent hydrogen; $R^7$ and $R^8$ each independently represent hydrogen or $C_{1-6}$alkyl, $R^{14}$ and $R^{15}$ each independently represent hydrogen or $C_{1-4}$alkyl optionally substituted with hydroxyl, or an N-oxide thereof, a pharmaceutically acceptable salt thereof or a solvate thereof.

12. The method according to claim 1, wherein the compound is selected from the group consisting of a compound of formula (I-A) or formula (I-B), a tautomeric form, stereochemically isomeric form, and isotopic form thereof, or a pharmaceutically acceptable salt or solvate thereof.

13. The method according to claim 1, wherein the compound is selected from the group consisting of a compound of formula (I-C) or formula (I-D)

(I-C)

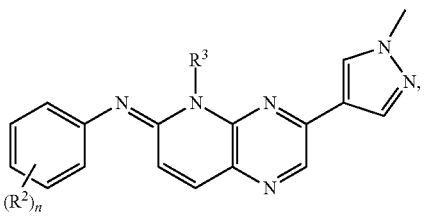

(I-D)

a tautomeric form, stereochemically isomeric form, and isotopic form thereof;

or an N-oxide thereof, a pharmaceutically acceptable salt thereof or a solvate thereof.

14. The method according to claim 13, wherein the compound is selected from the group consisting of a compound of formula (I-C) or formula (I-D), a tautomeric form, stereochemically isomeric form, and isotopic form thereof, wherein $R^2$ represents $C_{1-4}$alkoxy or halogen or hydroxyl; $R^3$ represents $C_{1-4}$alkyl substituted with $R^9$ or $R^3$ represents $C_{1-4}$alkyl substituted with —$NR^{10}R^{11}$ wherein one of $R^{10}$ and $R^{11}$ represents hydrogen and the other represents $C_{1-6}$alkyl, or —C(=O)—$C_{1-6}$alkyl, or $R^6$; n is 2, 3, or 4, or an N-oxide thereof, a pharmaceutically acceptable salt thereof or a solvate thereof.

15. The method according to claim 1, wherein the subject is a subject suffering from, or being at risk of suffering from cancer.

16. The method according to claim 15, wherein the cancer is a tumor with a mutant of FGFR1, FGFR2, FGFR3 or FGFR4.

17. The method according to claim 15, wherein the cancer is a tumor with a gain-of-function mutant of FGFR2 and FGFR3.

18. The method according to claim 15, wherein the cancer is a tumor with over-expression of FGFR1.

19. The method according to claim 15, wherein the cancer is selected from lung cancer, squamous cell carcinoma, liver cancer, kidney cancer, breast cancer, colon cancer, colorectal cancer, and prostate cancer.

20. The method according to claim 15, wherein the cancer is urothelial carcinoma.

21. The method according to claim 20, wherein the compound is

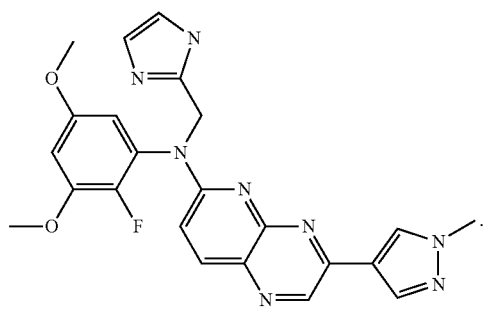

22. The method according to claim 15, wherein the cancer is selected from multiple myeloma, myeloproliferative disorders, endometrial cancer, prostate cancer, bladder cancer, lung cancer, ovarian cancer, breast cancer, gastric cancer, colorectal cancer, and oral squamous cell carcinoma.

23. The method according to claim 22, wherein the cancer is multiple myeloma.

24. The method according to claim 22, wherein the cancer is bladder cancer.

25. The method according to claim 24, wherein the cancer is bladder cancer with a FGFR3 chromosomal translocation.

26. The method according to claim 24, wherein the cancer is bladder cancer with a FGFR3 point mutation.

27. The method according to claim 22, wherein the compound is

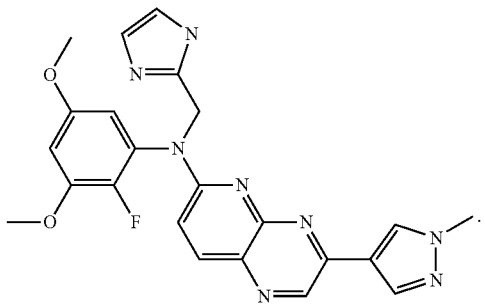

28. The method according to claim 1, wherein the subject is a subject suffering from, or being at risk of suffering from a carcinoma, wherein the carcinoma is selected from a carcinoma of the bladder, breast, colon, kidney, epidermis, liver, lung, oesophagus, head and neck, gall bladder, ovary, pancreas, stomach, gastrointestinal cancer, cervix, endometrium, thyroid, prostate, or skin, a hematopoietic tumour of lymphoid lineage; a hematopoietic tumour of myeloid lineage; multiple myeloma; thyroid follicular cancer; a tumour of mesenchymal origin; a tumour of the central or peripheral nervous system; melanoma; seminoma; teratocarcinoma; osteosarcoma; xeroderma pigmentosum; keratoctanthoma; or Kaposi's sarcoma.

29. The method according to claim 28, wherein the carcinoma is glioblastoma multiforme.

30. The method according to claim 28, wherein the compound is

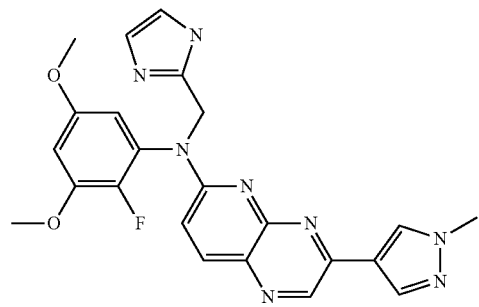

or an N-oxide thereof, a pharmaceutically acceptable salt thereof or a solvate thereof.

31. The method according to claim 1, wherein the compound is

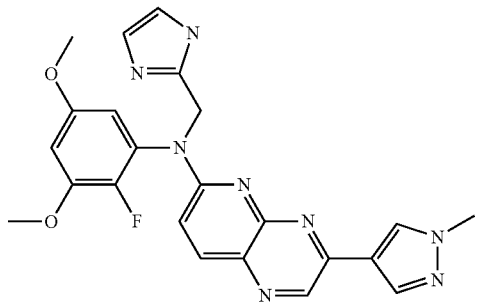

or an N-oxide thereof, a pharmaceutically acceptable salt thereof or a solvate thereof.

32. The method according to claim 1, wherein the compound is

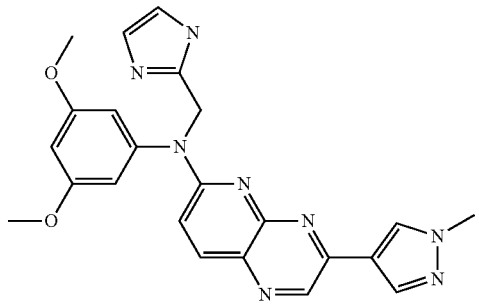

or an N-oxide thereof, a pharmaceutically acceptable salt thereof or a solvate thereof.

33. The method according to claim 1, wherein the compound is

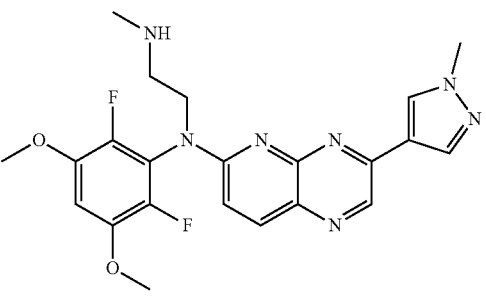 [SMILES: CNCCN(c1ccc2ncc(-c3cnn(C)c3)nc2n1)c1c(F)c(OC)cc(OC)c1F]

or an N-oxide thereof, a pharmaceutically acceptable salt thereof or a solvate thereof.

* * * * *